US010370722B2

(12) United States Patent
Kawauchi et al.

(10) Patent No.: US 10,370,722 B2
(45) Date of Patent: Aug. 6, 2019

(54) PANCREATIC CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Junpei Kawauchi, Kamakura (JP); Hitoshi Nobumasa, Kamakura (JP); Satoko Kozono, Kamakura (JP); Satoshi Kondou, Kamakura (JP); Hiroko Sudo, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 21 days.

(21) Appl. No.: 15/314,859

(22) PCT Filed: May 29, 2015

(86) PCT No.: PCT/JP2015/065696
§ 371 (c)(1),
(2) Date: Jun. 5, 2017

(87) PCT Pub. No.: WO2015/182781
PCT Pub. Date: Dec. 3, 2015

(65) Prior Publication Data
US 2017/0275699 A1    Sep. 28, 2017

(30) Foreign Application Priority Data

May 30, 2014 (JP) .................. 2014-113523
Sep. 11, 2014 (JP) .................. 2014-185730

(51) Int. Cl.
| C07H 21/02 | (2006.01) |
| C07H 21/04 | (2006.01) |
| C12Q 1/6886 | (2018.01) |
| C12M 1/00 | (2006.01) |
| C12M 1/34 | (2006.01) |
| C12N 15/09 | (2006.01) |
| G01N 37/00 | (2006.01) |
| G01N 33/53 | (2006.01) |
| G01N 33/574 | (2006.01) |

(52) U.S. Cl.
CPC .......... *C12Q 1/6886* (2013.01); *C12M 1/00* (2013.01); *C12M 1/34* (2013.01); *C12N 15/09* (2013.01); *G01N 33/53* (2013.01); *G01N 33/574* (2013.01); *G01N 37/00* (2013.01); *C12Q 2600/158* (2013.01); *C12Q 2600/178* (2013.01)

(58) Field of Classification Search
CPC ........................ C12N 15/111; C12N 15/113
See application file for complete search history.

(56) References Cited

U.S. PATENT DOCUMENTS

| 9,416,369 B2 * | 8/2016 | Ruohola-Baker et al. ................. |
| | | C12N 15/85 |
| 2008/0306018 A1 | 12/2008 | Croce et al. |
| 2010/0286232 A1 | 11/2010 | Schmittgen et al. |
| 2013/0072393 A1 | 3/2013 | Zhang et al. |
| 2013/0310276 A1 | 11/2013 | Johansen et al. |
| 2015/0184248 A1 | 7/2015 | Tsuchiya et al. |

FOREIGN PATENT DOCUMENTS

| EP | 2518158 A1 | 10/2012 |
| EP | 2 522 750 A1 | 11/2012 |
| EP | 3159398 A1 | 4/2017 |
| JP | 2012-507300 A | 3/2012 |
| WO | WO 2007/103808 A2 | 9/2007 |
| WO | WO 2010/062706 A2 | 6/2010 |
| WO | WO 2011/075873 A1 | 6/2011 |
| WO | WO 2013/107459 A2 | 7/2013 |
| WO | WO 2014/003053 A1 | 1/2014 |

OTHER PUBLICATIONS

Ali et al., "Differentially expressed miRNAs in the plasma may provide a molecular signature for aggressive pancreatic cancer", Am J Transl Res, 2011, vol. 3, (1), p. 28-47.
Eto et al., "Prospect of microRNA toward laboratory medicine Gastrointestinal Cancer and microRNA", Clinical Chemistry, vol. 43, p. 99-105, 2014.
Ganepola et al., "Novel blood-based microRNA biomarker panel for early diagnosis of pancreatic cancer", World J Gastrointest Oncol, 2014, Jan. 15, vol. 6(1), p. 22-33.
International Search Report, issued in PCT/JP2015/065696, PCT/ISA/210, dated Aug. 18, 2015.
Japan Pancreas Society, "2009 Scientific evidence based clinical practice guidelines for pancreatic cancer", http://www.suizou.org/PCMG2009/cq1/cq1-3.html. CQ1 diagnosis methods.
Kozomara et al., "miRBase: annotating high confidence microRNAs using deep sequencing data", Nucleic Acids Research, 2013, vol. 42, Database issue, p. D68-D73.
Kurokawa et al., LAB Data, 2013, p. 633, 636 (Igaku-Shoin Ltd., Tokyo, Japan).
Li et al., "MicroRNA Array Analysis Finds Elevated Serum miR-1290 Accurately Distinguishes Patients with Low-Stage Pancreatic Cancer from Healthy and Disease Controls", Clin Cancer Res, 2013, vol. 19, (13), p. 3600-3610.

(Continued)

*Primary Examiner* — Amy H Bowman
(74) *Attorney, Agent, or Firm* — Birch, Stewart, Kolasch & Birch, LLP

(57) ABSTRACT

This invention provides a kit or a device for the detection of pancreatic cancer, comprising a nucleic acid(s) capable of specifically binding to a miRNA(s) in a sample from a subject, and a method for detecting pancreatic cancer, comprising measuring the miRNA(s) in vitro.

6 Claims, 4 Drawing Sheets
Specification includes a Sequence Listing.

(56) References Cited

OTHER PUBLICATIONS

Liu et al., "Serum MicroRNA Expression Profile as a Biomarker in the Diagnosis and Prognosis of Pancreatic Cancer", Clinical Chemistry, 2012, vol. 58, No. 3, p. 610-618.
Takizawa et al., "Abstract 5294: The difference of serum RNA profile: RNA extraction and detection method", Cancer Res, Apr. 15, 2013, vol. 73, Abstract No. 5294.
Takizawa et al., "Simultaneous Profiling of Multiple miRNAs in FFPE or Serum Samples Using DNA Chip 3D-Gene®", Bio Clinica, 2013, vol. 28, No. 9, p. 872-873.
Tetsuya Mine, "Suizo (Pancreas), Journal of the Japan Pancreas Society", Japan Pancreas Society, 2007, vol. 22, p. 105-113.
Written Opinion of the International Searching Authority, issued in PCT/JP2015/065696, PCT/ISA/237, dated Aug. 18, 2015.
Zhang et al., "Upregulation of miR-194 contributes to tumor growth and ProgresSion in pancreatic ductal adenocarcinoma", Oncology Reports, vol. 31, (3), p. 1157-1164.
Author Unknown, "Mature sequence hsa-miR-6836-3p," miRBase, Accession No. MIMAT0027575, http://www.mirbase.org/cgi-bin/mature.pl?mature_acc=MIMAT0027575, Sep. 1, 2012, 1 page.
Partial Supplmentary European Search Report issued in European Application No. 15800550.4 dated Dec. 15, 2017.
Kojima et al., "Micro RNA markers for the diagnosis of pancreatic and bile duct cancers," E-2020, Digital abstract for the 73rd Annual Meeting of the Japanese Cancer Association, published online Sep. 19, 2014, 3 pages.
Kojima et al., "Micro RNA markers for the diagnosis of pancreatic and bile duct cancers," E-2020, English oral session at the 73rd Annual Meeting of the Japanese Cancer Association, Sep. 26, 2014, 22 pages.
Kojima et al., "MicroRNA Markers for the Diagnosis of Pancreatic and Biliary-Tract Cancers," PLOS One, vol. 10, No. 2, Feb. 23, 2015, pp. 1-22.
Hua et al., "The Expression Level of miRNAs in Pancreatic Cancer Cell Lines and Pancreatic Cancer Tissues", Progress in Modern Biomedicine, vol. 13, No. 17, Jun. 2013, pp. 3238-3242, Abstract only, article is not in English.
Author Unknown, "Mature sequence hsa-miR-6836-3p", miRBase, Accession number: MI0022682, http://www.mirbase.org/cgi-bin/mima_entry.pl?acc=MIMAT0027575, 2 pages.
Ladewig et al., "Discovery of hundreds of mirtrons in mouse and human small RNA data", PN 163620, Genome Research, 2012, vol. 22, pp. 1634-1645.

\* cited by examiner

PANCREATIC CANCER DETECTION KIT OR DEVICE, AND DETECTION METHOD

REFERENCE TO SEQUENCE LISTING SUBMITTED VIA EFS-WEB

This application includes an electronically submitted sequence listing in .txt format. The .txt file contains a sequence listing entitled "2018_05_30_1254_0585PUS1_ST25.txt" created on May 30, 2018 and is 87,437 bytes in size. The sequence listing contained in this .txt file is part of the specification and is hereby incorporated by reference herein in its entirety.

TECHNICAL FIELD

The present invention relates to a kit or a device for the detection of pancreatic cancer, comprising a nucleic acid capable of specifically binding to a particular miRNA, which is used for examining the presence or absence of pancreatic cancer in a subject, and a method for detecting pancreatic cancer, comprising measuring an expression level of the miRNA using the nucleic acid.

BACKGROUND ART

The pancreas serves as an exocrine gland that secretes pancreatic juice as a digestive juice and sends the juice into the digestive tract through the pancreatic duct, while also functioning as an endocrine gland that secretes hormones such as insulin and glucagon into blood.

Since the pancreas is surrounded by many organs such as the stomach, the duodenum, the small intestine, the liver, and the gallbladder, pancreatic cancer is not only difficult to detect early but has properties such as a lack of subjective symptoms, very rapid progression, and metastasis to other organs and thus has very poor prognosis as compared with other cancers. According to the 2011 statistics of cancer type-specific mortality in Japan disclosed by the Center for Cancer Control and Information Services, National Cancer Center (Tokyo, Japan), the number of pancreatic cancer deaths climbed to 28,829 people, and 5-year relative survival rates by cancer type in 2003 to 2005 were lowest in pancreatic cancer with 7.1% for males and 6.9% for females.

As described in Non-Patent Literature 1, the basic therapy of pancreatic cancer is practiced by surgery, systemic chemotherapy, radiotherapy, or a combination thereof depending on a stage of progression. Although 15 to 20% pancreatic cancer patients undergo surgery for potential cure, the great majority of patients who do not undergo surgery are considered to have local progression or metastasis. The median survival time is reportedly 8 to 12 months for locally advanced cancer and 3 to 6 months for metastatic cancer, which are very poor as compared with other cancers.

The UICC (Unio Internationalis Contra Cancrum) stages of progression of pancreatic cancer are defined in General Rules for the Study of Pancreatic Cancer, the 5th edition (edited by Japan Pancreas Society, KANEHARA & Co., LTD., 2013, p. 55) and classified into stages 0, IA, IB, IIA, IIB, III, IVa, and IVb according to the size of primary tumor, lymph node metastasis, distant metastasis, etc. Stages I to III occupy half or more of the number of 5-year survivals, and stages IVa and IVb occupy 70% or more of the progressed stages at the time of diagnosis. Also, pancreatic cancer differs in symptoms among sites of origin. Carcinoma of the head of the pancreas often manifests jaundice, whereas carcinoma of the tail of the pancreas has few symptoms. Therefore, the carcinoma of the tail of the pancreas tends to result in delayed diagnosis as compared with the carcinoma of the head of the pancreas.

As described in Non-Patent Literature 2, abdominal ultrasonography is very useful as convenient and limitedly invasive examination in outpatient settings or medical examination for the diagnosis of pancreatic cancer. However, it is often difficult to visualize pancreatic cancer having a small tumor size or a lesion on the pancreatic tail side. In ordinary medical checkup, the prevalence of pancreatic cancer found in pancreatic images by abdominal ultrasonography is approximately 1%, and the detection rate of pancreatic cancer is approximately 0.06% or lower. For example, CA19-9, Span-1, CA50, CA242, Dupan-2, TAG-72, and urinary fucose as carbohydrate antigens, and CEA, POA, and TPS as non-carbohydrate antigens are known as tumor markers for the detection of pancreatic cancer. As for how to use these tumor markers, a subject is suspected of having a cancer when their concentrations in blood are higher or lower than predetermined reference values. For example, as described in Non-Patent Literature 3, the reference value of CEA is set to 5 ng/mL, and the reference value of CA19-9 is set to 37 U/mL. A subject is suspected of having a cancer including pancreatic cancer when their concentrations exhibit these values or higher. However, the evaluation of tumor markers often examines advanced pancreatic cancer and does not show abnormal values for early pancreatic cancer in many cases. Even combinatorial use of tumor markers and abdominal ultrasonography in medical examination results in low rates of detection of pancreatic cancer. The implementation of such medical examinations for the detection of pancreatic cancer is controversial from the viewpoint of cost effectiveness.

As shown in Patent Literatures 1 to 4, there are reports, albeit at a research stage, on the determination of pancreatic cancer using the expression levels of microRNAs (miRNAs), or combinations of the expression levels of miRNAs and the expression levels of additional protein markers in biological samples including blood.

Patent Literature 1 discloses a method for detecting pancreatic cancer by combining hsa-miR-125a-3p with dozens of other miRNAs in blood.

Patent Literature 2 discloses a method for detecting pancreatic cancer by combining a hsa-miR-204-3p precursor, a hsa-miR-423-5p precursor, or a hsa-miR-328-5p precursor with several hundreds of other miRNAs in blood or tissues.

Patent Literature 3 discloses a method for detecting pancreatic cancer by combining hsa-miR-575, hsa-miR-16-5p, or hsa-miR-24-3p with several hundreds of other miRNAs in blood.

Patent Literature 4 discloses a method for detecting pancreatic cancer by combining hsa-miR-451a with dozens of other miRNAs in blood or tissues.

Patent Literature 5 discloses a method for detecting pancreatic cancer by combining a hsa-miR-150-3p precursor or a hsa-miR-187-5p precursor with several hundreds of other miRNAs in blood or tissues.

Non-Patent Literature 4 discloses hsa-miR-423-5p, hsa-miR-1246, hsa-miR-150-3p, hsa-miR-550a-5p, hsa-miR-371a-5p, hsa-miR-1469, hsa-miR-575, hsa-miR-564, hsa-miR-125a-3p, hsa-miR-451a, hsa-miR-1908-5p and the like in plasma as miRNAs that have significant difference in their expression levels between pancreatic cancer patients and healthy subjects.

Non-Patent Literature 5 discloses miR-3188, miR-16-5p, and the like in plasma as miRNAs that have significant difference in their expression levels between pancreatic cancer patients and healthy subjects.

Non-Patent Literature 6 discloses miR-550a-5p, miR-1290, miR-24-3p, miR-486-3p, miR-423-5p, miR-125a-3p, and the like in serum as miRNAs that have significant difference in their expression levels between pancreatic cancer patients and healthy subjects.

Non-Patent Literature 7 discloses miR-602 in tissues as a miRNA that have significant difference in its expression level between pancreatic cancer patients and healthy subjects.

PRIOR ART LITERATURE

Patent Literature

Patent Literature 1: JP Patent Publication (Kohyo) No. 2012-507300 A (2012)
Patent Literature 2: Published U.S. Patent Application No. 2010/0286232
Patent Literature 3: International Publication No. WO 2013/107459
Patent Literature 4: Published U.S. Patent Application No. 2013/0310276
Patent literature 5: Published U.S. Patent Application No. 2008/0306018

Non-Patent Literature

Non-Patent Literature 1: Tetsuya Mine, "Suizo (Pancreas), Journal of the Japan Pancreas Society", Japan Pancreas Society, 2007, Vol. 22, p. 10-13 Non-Patent Literature 2: Japan Pancreas Society, "2009 Scientific evidence based clinical practice guidelines for pancreatic cancer" CQ1 diagnosis methods http://www.suizou.org/PCMG2009/cq1/cq1-3.html
Non-Patent Literature 3: Kiyoshi Kurokawa et al. ed., LAB DATA, 2013, p. 633, 636 (Igaku-Shoin Ltd., Tokyo, Japan)
Non-Patent Literature 4: Ali S. et al, 2011, American Journal of Translational Research, Vol. 3, (1), p. 28-47
Non-Patent Literature 5: Ganepola G A. et al., 2014, World Journal of Gastrointestinal Oncology, Vol. 6, (1), p. 22-33
Non-Patent Literature 6: Li A. et al., 2013, Clinical Cancer Research, Vol. 19, (13), p. 3600-3610
Non-Patent Literature 7: Zhang J. et al., 2014, Oncology Reports, Vol. 31, (3), p. 1157-1164

SUMMARY OF INVENTION

Problem to be Solved by Invention

An object of the present invention is to find novel tumor markers for pancreatic cancer and to provide a method that can effectively detect pancreatic cancer using nucleic acids capable of specifically binding to the markers. As described in Non-Patent Literature 2, for example, CA19-9, Span-1, CA50, CA242, Dupan-2, TAG-72, and urinary fucose as carbohydrate antigens and CEA, POA, and TPS as non-carbohydrate antigens are known as tumor markers for the detection of pancreatic cancer. The pancreatic cancer detection sensitivity of these tumor markers is 70 to 80% for CA19-9, 70 to 80% for Span-1, 50 to 60% for Dupan-2, 30 to 60% for CEA, and 60% for CA50. In addition, their specificity is not much high, and their false positive rates are as high as 20 to 30%. Therefore, there may be the possibility of false detection of other cancers and/or benign tumors and/or benign diseases of the pancreas and/or peripancreatic organs, etc. Particularly, the detection sensitivity of early pancreatic cancer is generally low, and the positive rate of CA19-9 is merely ½ (52%) for pancreatic cancer having a tumor size of 2 cm or smaller. Therefore, these tumor markers are not useful for the detection of early pancreatic cancer. Furthermore, the tumor markers based on carbohydrate antigens exhibit false negatives in Lewis blood type negative cases, in which the subjects do not produce the antigens. Therefore, this examination is unsuitable for some subjects.

As described below, there are reports, albeit at a research stage, on the determination of pancreatic cancer using the expression levels of microRNAs (miRNAs) in biological samples including blood, none of which, however, have yet been brought into practical use.

Patent Literature 1 describes a method for diagnosing various cancers including pancreatic cancer by combining hsa-miR-125a-3p with a large number (dozens) of other miRNAs in blood. This literature, however, neither describes specific detection performance thereof such as accuracy, sensitivity, or specificity nor describes a specific method for diagnosing pancreatic cancer using blood.

Patent Literature 2 describes a method for detecting pancreatic cancer by combining a hsa-miR-204-3p precursor, a hsa-miR-423-5p precursor, or a hsa-miR-328-5p precursor with several hundreds of other miRNAs in blood or tissues. This literature, however, neither describes specific detection performance thereof such as accuracy, sensitivity, or specificity nor describes a specific method for diagnosing pancreatic cancer using blood.

The method described in Patent Literature 3 diagnoses pancreatic cancer by combining hsa-miR-575, hsa-miR-16-5p, or hsa-miR-24-3p with several hundreds of other miRNAs and does not state that diagnosis can be conducted by combining several miRNAs.

Patent Literature 4 employs hsa-miR-451a in combination with dozens or more of other miRNAs in pancreatic cancer tissues for the diagnosis of pancreatic cancer. This literature, however, does not describe a specific method for diagnosing pancreatic cancer using blood.

Patent Literature 5 employs a hsa-miR-150-3p precursor or a hsa-miR-187-5p precursor in combination with several hundreds or more of other miRNAs in pancreatic cancer tissues for the diagnosis of pancreatic cancer. This literature, however, neither describes specific detection performance thereof such as accuracy, sensitivity, or specificity nor describes a specific method for diagnosing pancreatic cancer using blood.

In Non-Patent Literature 4, examples of the miRNAs that have significant difference in their expression levels in plasma between pancreatic cancer patients and healthy subjects include miR-423-5p, miR-1246, miR-150-3p, miR-550a-5p, miR-371a-5p, miR-1469, miR-575, miR-564, miR-125a-3p, miR-451a, and miR-1908-5p. This literature, however, does not describe specific detection performance thereof such as accuracy, sensitivity, or specificity.

In Non-Patent Literature 5, examples of the miRNAs that have significant difference in their expression levels in plasma between pancreatic cancer patients and healthy subjects include miR-3188 and miR-16-5p. However, as a result of validation, these miRNAs were excluded from the analytes due to their low reliability.

In Non-Patent Literature 6, examples of the miRNAs that have significant difference in their expression levels in serum between pancreatic cancer patients and healthy subjects include miR-550a-5p, miR-1290, miR-24-3p, miR-486-3p, miR-423-5p, and miR-125a-3p. This literature, however, neither describes the specific detection performance, such as accuracy, sensitivity, or specificity, of miR-550a-5p, miR-24-3p, miR-486-3p, miR-423-5p, and miR-125a-3p nor validated the detection performance of miR-1290 in an independent sample group.

In Non-Patent Literature 7, examples of the miRNA that have significant difference in its expression level in pancreatic tissues between pancreatic cancer patients and healthy subjects include miR-602. This literature, however, neither describes specific detection performance thereof such as accuracy, sensitivity, or specificity nor describes a specific method for diagnosing pancreatic cancer using blood.

As mentioned above, the existing tumor markers exhibit low performance in the detection of pancreatic cancer, or neither performance nor detection methods are specifically shown as to the markers at a research stage. Therefore, use of these markers might require carrying out needless extra examination due to the false detection of healthy subjects as being pancreatic cancer patients, or might waste therapeutic opportunity because of overlooking pancreatic cancer patients. In addition, the measurement of dozens to several hundreds of miRNAs increases examination costs and is therefore difficult to use in large-scale screening such as medical checkup. Furthermore, the collection of pancreatic tissues for measuring the tumor markers is highly invasive to patients and is not favorable. Hence, there is a demand for a highly accurate pancreatic cancer marker that is detectable from blood, which can be collected in less invasive manner, and is capable of correctly determining a pancreatic cancer patient as a pancreatic cancer patient and a healthy subject as a healthy subject. Particularly, a highly sensitive pancreatic cancer marker is desired because tumor resection based on early detection is only radical cure for pancreatic cancer.

Means for Solution of Problem

The present inventors have conducted diligent studies to attain the object and consequently completed the present invention by finding several genes usable as markers for the detection of pancreatic cancer from blood, which can be collected with limited invasiveness, and finding that pancreatic cancer can be significantly detected by using nucleic acids capable of specifically binding to any of these markers.

SUMMARY OF INVENTION

The present invention has the following features:

(1) A kit for the detection of pancreatic cancer, comprising a nucleic acid(s) capable of specifically binding to at least one or more polynucleotides selected from the group consisting of the following pancreatic cancer markers: miR-6893-5p, miR-6075, miR-6820-5p, miR-4294, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231, miR-4665-5p, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, ma-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, ma-4508, miR-940, miR-4327, miR-4665-3p, miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p.

(2) The kit according to (1), wherein miR-6893-5p is hsa-miR-6893-5p, miR-6075 is miR-6820-5p is hsa-miR-6820-5p, miR-4294 is hsa-miR-4294, miR-6729-5p is hsa-miR-6729-5p, miR-4476 is hsa-miR-4476, miR-6836-3p is hsa-miR-6836-3p, miR-6765-3p is hsa-miR-6765-3p, miR-6799-5p is hsa-miR-6799-5p, miR-4530 is hsa-miR-4530, miR-7641 is hsa-miR-7641, miR-4454 is hsa-miR-4454, miR-615-5p is hsa-miR-615-5p, miR-8073 is hsa-miR-8073, miR-663a is hsa-miR-663a, miR-4634 is hsa-miR-4634, miR-4450 is hsa-miR-4450, miR-4792 is hsa-miR-4792, miR-665 is hsa-miR-665, miR-7975 is hsa-miR-7975, miR-7109-5p is hsa-miR-7109-5p, miR-6789-5p is hsa-miR-6789-5p, miR-4497 is hsa-miR-4497, miR-6877-5p is hsa-miR-6877-5p, miR-6880-5p is hsa-miR-6880-5p, miR-7977 is hsa-miR-7977, miR-4734 is hsa-miR-4734, miR-6821-5p is hsa-miR-6821-5p, miR-8089 is hsa-miR-8089, miR-5585-3p is hsa-miR-5585-3p, miR-6085 is hsa-miR-6085, miR-6845-5p is hsa-miR-6845-5p, miR-4651 is hsa-miR-4651, miR-4433-3p is hsa-miR-4433-3p, miR-1231 is hsa-miR-1231, miR-4665-5p is hsa-miR-4665-5p, miR-7114-5p is hsa-miR-7114-5p, miR-1238-5p is hsa-miR-1238-5p, miR-8069 is hsa-miR-8069, miR-4732-5p is hsa-milt-4732-5p, miR-619-5p is hsa-miR-619-5p, miR-3622a-5p is hsa-miR-3622a-5p, miR-1260a is hsa-miR-1260a, miR-6741-5p is hsa-miR-6741-5p, miR-6781-5p is hsa-miR-6781-5p, miR-6125 is hsa-miR-6125, miR-6805-5p is hsa-miR-6805-5p, miR-6132 is hsa-miR-6132, miR-6872-3p is hsa-miR-6872-3p, miR-6875-5p is hsa-miR-6875-5p, miR-1908-3p is hsa-miR-1908-3p, miR-4433b-3p is hsa-miR-4433b-3p, miR-4736 is hsa-miR-4736, miR-5100 is hsa-miR-5100, miR-6724-5p is hsa-miR-6724-5p, miR-7107-5p is hsa-miR-7107-5p, miR-6726-5p is hsa-miR-6726-5p, miR-3185 is hsa-miR-3185, miR-4638-5p is hsa-miR-4638-5p, miR-1273g-3p is hsa-miR-1273g-3p, miR-6778-5p is hsa-miR-6778-5p, miR-328-5p is hsa-miR-328-5p, miR-3679-3p is hsa-miR-3679-3p, miR-1228-3p is hsa-miR-1228-3p, miR-6779-5p is hsa-miR-6779-5p, miR-4723-5p is hsa-miR-4723-5p, miR-6850-5p is hsa-miR-6850-5p, miR-760 is hsa-miR-760, miR-7704 is hsa-miR-7704, miR-8072 is hsa-miR-8072, miR-4486 is hsa-miR-4486, miR-1913 is hsa-miR-1913, miR-4656 is hsa-miR-4656, miR-1260b is hsa-miR-1260b, miR-7106-5p is hsa-miR-7106-5p, miR-6889-5p is hsa-miR-6889-5p, miR-6780b-5p is hsa-miR-6780b-5p, miR-6090 is hsa-miR-6090, miR-4534 is hsa-miR-4534, miR-4449 is hsa-miR-4449, miR-5195-3p is hsa-miR-5195-3p, miR-1202 is hsa-miR-1202, miR-4467 is hsa-miR-4467, miR-6515-3p is hsa-miR-6515-3p, miR-4281 is hsa-miR-4281, miR-4505 is hsa-miR-4505, miR-4484 is hsa-miR-4484, miR-6805-3p is hsa-miR-6805-3p, miR-3135b is hsa-miR-3135h, miR-3162-5p is hsa-miR-3162-5p, miR-6768-5p is hsa-miR-6768-5p, miR-6721-5p is hsa-miR-6721-5p, miR-1227-5p is hsa-miR-1227-5p, miR-6722-3p is hsa-miR-6722-3p, miR-4286 is hsa-miR-4286, miR-4746-3p is hsa-miR-4746-3p, miR-6727-5p is hsa-miR-6727-5p, miR-6816-5p is hsa-miR-6816-5p, miR-4741 is hsa-miR-4741, miR-4508 is hsa-miR- 4508, miR-940 is hsa-miR-940, miR-4327 is lisa-miR-4327, miR-4665-3p is hsa-miR-4665-3p, miR-718 is hsa-miR-718, miR-1203 is hsa-miR-1203, miR-663b is hsa-miR-663b, miR-4258 is hsa-miR-4258, miR-4649-5p is hsa-miR-4649-5p, miR-4516 is hsa-miR-4516, miR-3619-3p is hsa-miR-3619-3p, miR-6826-5p is hsa-miR-6826-5p, miR-6757-5p ishsa-miR-6757-5p, miR-3131 is hsa-miR-3131, miR-1343-3p is hsa-miR-1343-3p, miR-6775-5p is hsa-miR-6775-5p, miR-6813-5p is hsa-miR-6813-5p, and miR-3940-5p is hsa-miR-3940-5p.

(3) The kit according to (1) or (2), wherein the nucleic acid(s) is a polynucleotide(s) selected from the group consisting of the following polynucleotides (a) to (e):
(a) a polynucleotide consisting of a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 104, 464 to 473, and 492 to 494;
(c) a polynucleotide consisting of a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(d) a polynucleotide comprising a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t; and
(e) a polynucleotide hybridizing under stringent conditions to any of the polynucleotides (a) to (d).

(4) The kit according to any of (1) to (3), further comprising, in addition to the nucleic acid(s), a nucleic acid(s) capable of specifically binding to at least one or more polynucleotides selected from the group consisting of miR-125a-3p, miR-204-3p, miR-1469, miR-575, miR-150-3p, miR-423-5p, miR-564, miR-3188, miR-1246, miR-602, miR-1290, miR-16-5p, miR-451a, miR-24-3p, miR-187-5p, miR-1908-5p, miR-371a-5p, and miR-550a-5p.

(5) The kit according to (4), wherein miR-125a-3p is hsa-miR-125a-3p, miR-204-3p is hsa-miR-204-3p, miR-1469 is hsa-miR-1469, miR-575 is hsa-miR-575, miR-150-3p is hsa-miR-150-3p, miR-423-5p is hsa-miR-423-5p, miR-564 is hsa-miR-564, miR-3188 is hsa-miR-3188, miR-1246 is hsa-miR-1246, miR-602 is hsa-miR-602, miR-1290 is hsa-miR-1290, miR-16-5p is hsa-miR-16-5p, miR-451a is hsa-miR-451a, miR-24-3p is hsa-miR-24-3p, miR-187-5p is hsa-miR-187-5p, miR-1908-5p is hsa-miR-1908-5p, miR-371a-5p is hsa-miR-371a-5p, and miR-550a-5p is hsa-miR-550a-5p.

(6) The kit according to (4) or (5), wherein the nucleic acid(s) further comprise a polynucleotide(s) selected from the group consisting of the following polynucleotides (f) to (j):
(f) a polynucleotide consisting of a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(g) a polynucleotide comprising a nucleotide sequence represented by any of SEQ ID NOs: 105 to 122;
(h) a polynucleotide consisting of a nucleotide sequence complementary to a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 105 to 122 or a nucleotide sequence derived from the nucleotide sequence by the replacement of u with t; and
(j) a polynucleotide hybridizing under stringent conditions to any of the polynucleotides (f) to (i).

(7) The kit according to any of (1) to (6), further comprising, in addition to the nucleic acid(s), a nucleic acid(s) capable of specifically binding to at least one or more polynucleotides selected from the group consisting of miR-4417, miR-4707-5p, miR-7847-3p, miR-2861, miR-4513, miR-7111-5p, miR-6777-5p, miR-7113-3p, miR-4648, miR-3184-5p, miR-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92b-5p, miR-6774-5p, miR-486-3p, miR-6806-5p, miR-6842-5p, miR-6716-5p, miR-557, miR-4673, miR-4674, miR-4442, miR-1915-3p, miR-4687-3p, and miR-92b-3p.

(8) The kit according to claim 7), wherein miR-4417 is hsa-miR-4417, miR-4707-5p is hsa-miR-4707-5p, miR-7847-3p is hsa-miR-7847-3p, miR-2861 is hsa-miR-2861, miR-4513 is hsa-miR-4513, miR-7111-5p is hsa-miR-7111-5p, miR-6777-5p is hsa-miR-6777-5p, miR-7113-3p is hsa-miR-7113-3p, miR-4648 is hsa-miR-4648, miR-3184-5p is hsa-miR-3184-5p, miR-4271 is hsa-miR-4271, miR-6791-5p is hsa-miR-6791-5p, miR-642a-3p is hsa-miR-642a-3p, miR-7108-5p is hsa-miR-7108-5p, miR-128-1-5p is hsa-miR-128-1-5p, miR-5196-5p is hsa-miR-5196-5p, miR-3178 is hsa-miR-3178, miR-3656 is hsa-miR-3656, miR-92a-2-5p is hsa-miR-92a-2-5p, miR-6769b-5p is hsa-miR-6769b-5p, miR-4689 is hsa-miR-4689, miR-6076 is hsa-miR-6076, miR-92b-5p is hsa-miR-92h-5p, miR-6774-5p is hsa-miR-6774-5p, miR-486-3p is hsa-miR-486-3p, miR-6806-5p is hsa-miR-6806-5p, miR-6842-5p is hsa-miR-6842-5p, miR-6716-5p is hsa-miR-6716-5p, miR-557 is hsa-miR-557, miR-4673 is hsa-miR-4673, miR-4674 is hsa-miR-4674, miR-4442 is hsa-miR-4442, miR-1915-3p is hsa-miR-1915-3p, miR-4687-3p is hsa-miR-4687-3p, and miR-92b-3p is hsa-miR-92b-3p.

(9) The kit according to (7) or (8), wherein the nucleic acid(s) is a polynucleotide(s) selected from the group consisting of the following polynucleotides (k) to (o):
(k) a polynucleotide consisting of a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;
(l) a polynucleotide comprising a nucleotide sequence represented by any of SEQ ID NOs: 349 to 383;
(m) a polynucleotide consisting of a nucleotide sequence complementary to a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;
(n) a polynucleotide comprising a nucleotide sequence complementary to a nucleotide sequence represented by any of SEQ ID NOs: 349 to 383 or a nucleotide sequence derived from the nucleotide sequence by the replacement of u with t; and
(o) a polynucleotide hybridizing under stringent conditions to any of the polynucleotides (k) to (n).

(10) The kit according to any one of (1) to (9), wherein the kit comprises at least two or more nucleic acids capable of specifically binding to at least two or more polynucleotides, respectively, selected from all of the pancreatic cancer markers according to (1) or (2).

(11) A device for the detection of pancreatic cancer, comprising a nucleic acid(s) capable of specifically binding to at least one or more polynucleotides selected from the group consisting of pancreatic cancer markers miR-6893-5p, miR-6075, miR-6820-5p, miR-4294, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231, miR-4665-5p, miR-7114-5p, miR-1238-5p, miR-8069, miR-4732-5p, ma-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-4508, miR-940, miR-4327, miR-4665-3p, miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p.

(12) The device according to (11), wherein miR-6893-5p is hsa-miR-6893-5p, miR-6075 is hsa-miR-6075, miR-6820-5p is hsa-miR-6820-5p, miR-4294 is hsa-miR-4294, miR-6729-5p is hsa-miR-6729-5p, miR-4476 is hsa-miR-4476, miR-6836-3p is hsa-miR-6836-3p, miR-6765-3p is hsa-miR-6765-3p, miR-6799-5p is hsa-miR-6799-5p, miR-4530 is hsa-miR-4530, miR-7641 is hsa-miR-7641, miR-4454 is hsa-miR-4454, miR-615-5p is hsa-miR-615-5p, miR-8073 is hsa-miR-8073, miR-663a is hsa-miR-663a, miR-4634 is hsa-miR-4634, miR-4450 is hsa-miR-4450, miR-4792 is hsa-miR-4792, miR-665 is hsa-miR-665, miR-7975 is hsa-miR-7975, miR-7109-5p is hsa-miR-7109-5p, ma-6789-5p is hsa-miR-6789-5p, miR-4497 is hsa-miR-4497, miR-6877-5p is hsa-miR-6877-5p, miR-6880-5p is hsa-miR-6880-5p, miR-7977 is hsa-miR-7977, miR-4734 is hsa-miR-4734, miR-6821-5p is hsa-miR-6821-5p, miR-8089 is hsa-miR-8089, miR-5585-3p is hsa-miR-5585-3p, miR-6085 is hsa-miR-6085, miR-6845-5p is hsa-miR-6845-5p, miR-4651 is hsa-miR-4651, miR-4433-3p is hsa-miR-4433-3p, miR-1231 is hsa-miR-1231, miR-4665-5p is hsa-miR-4665-5p, miR-7114-5p is hsa-miR-7114-5p, miR-1238-5p is hsa-miR-1238-5p, miR-8069 is hsa-miR-8069, miR-4732-5p is hsa-miR-4732-5p, miR-619-5p is hsa-miR-619-5p, miR-3622a-5p is hsa-miR-3622a-5p, miR-1260a is hsa-miR-1260a, miR-6741-5p is hsa-miR-6741-5p, miR-6781-5p is hsa-miR-6781-5p, miR-6125 is hsa-miR-6125, miR-6805-5p is hsa-miR-6805-5p, miR-6132 is hsa-miR-6132, miR-6872-3p is hsa-miR-6872-3p, miR-6875-5p is hsa-miR-6875-5p, miR-1908-3p is hsa-miR-1908-3p, miR-4433b-3p is hsa-miR-4433b-3p, miR-4736 is hsa-miR-4736, miR-5100 is hsa-miR-5100, miR-6724-5p is hsa-miR-6724-5p, miR-7107-5p is hsa-miR-7107-5p, miR-6726-5p is hsa-miR-6726-5p, miR-3185 is hsa-miR-3185, miR-4638-5p is hsa-miR-4638-5p, miR-1273g-3p is hsa-miR-1273g-3p, miR-6778-5p is hsa-miR-6778-5p, miR-328-5p is hsa-miR-328-5p, miR-3679-3p is hsa-miR-3679-3p, miR-1228-3p is hsa-miR-1228-3p, miR-6779-5p is hsa-miR-6779-5p, miR-4723-5p is hsa-miR-4723-5p, miR-6850-5p is hsa-miR-6850-5p, miR-760 is hsa-miR-760, miR-7704 is hsa-miR-7704, miR-8072 is hsa-miR-8072, miR-4486 is hsa-miR-4486, miR-1913 is hsa-miR-1913, miR-4656 is hsa-miR-4656, miR-1260b is hsa-miR-1260b, miR-7106-5p is hsa-miR-7106-5p, miR-6889-5p is hsa-miR-6889-5p, miR-6780b-5p is hsa-miR-6780b-5p, miR-6090 is hsa-miR-6090, miR-4534 is hsa-miR-4534, miR-4449 is hsa-miR-4449, miR-5195-3p is hsa-miR-5195-3p, miR-1202 is hsa-miR-1202, miR-4467 is hsa-miR-4467, miR-6515-3p is hsa-miR-6515-3p, miR-4281 is hsa-miR-4281, miR-4505 is hsa-miR-4505, miR-4484 is hsa-miR-4484, miR-6805-3p is hsa-miR-6805-3p, miR-3135b is hsa-miR-3135b, miR-3162-5p is hsa-miR-3162-5p, miR-6768-5p is hsa-miR-6768-5p, miR-6721-5p is hsa-miR-6721-5p, miR-1227-5p is hsa-miR-1227-5p, miR-6722-3p is hsa-miR-6722-3p, miR-4286 is hsa-miR-4286, miR-4746-3p is hsa-miR-4746-3p, miR-6727-5p is hsa-miR-6727-5p, miR-6816-5p is hsa-miR-6816-5p, miR-4741 is hsa-miR-4741, miR-4508 is hsa-miR-4508, miR-940 is hsa-miR-940, miR-4327 is hsa-miR-4327, miR-4665-3p is hsa-miR-4665-3p, miR-718 is hsa-miR-718, miR-1203 is hsa-miR-1203, miR-663b is hsa-miR-663b, miR-4258 is hsa-miR-4258, miR-4649-5p is hsa-miR-4649-5p, miR-4516 is hsa-miR-4516, miR-3619-3p is hsa-miR-3619-3p, miR-6826-5p is hsa-miR-6826-5p, miR-6757-5p is hsa-miR-6757-5p, miR-3131 is hsa-miR-3131, miR-1343-3p is hsa-miR-1343-3p, miR-6775-5p is hsa-miR-6775-5p, miR-6813-5p is hsa-miR-6813-5p, and miR-3940-5p is hsa-miR-3940-5p.

(13) The device according to (11) or (12), wherein the nucleic acid(s) is a polynucleotide(s) selected from the group consisting of the following polynucleotides (a) to (e):
(a) a polynucleotide consisting of a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 104, 464 to 473, and 492 to 494;
(c) a polynucleotide consisting of a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(d) a polynucleotide comprising a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t; and
(e) a polynucleotide hybridizing under stringent conditions to any of the polynucleotides (a) to (d).

The device according to any one of (11) to (13), wherein the device further comprises a nucleic acid(s) capable of specifically binding to at least one or more polynucleotides selected from the group consisting of other pancreatic cancer markers miR-125a-3p, miR-204-3p, miR-1469, miR-575, miR-150-3p, miR-423-5p, miR-564, miR-3188, miR-1246, miR-602, miR-1290, miR-16-5p, miR-451a, miR-24-3p, miR-87-5p, miR-1908-5p, miR-371a-5p, and miR-550a-5p.

(15) The device according to (14), wherein miR-125a-3p is hsa-miR-125a-3p, miR-204-3p is hsa-miR-204-3p, miR-1469 is hsa-miR-1469, miR-575 is hsa-miR-575, miR-150-3p is hsa-miR-150-3p, miR-423-5p is hsa-miR-423-5p, miR-564 is hsa-miR-564, miR-3188 is hsa-miR-3188, miR-1246 is hsa-miR-1246, miR-602 is hsa-miR-602, miR-1290 is hsa-miR-1290, miR-16-5p is hsa-miR-16-5p, miR-451a is hsa-miR-451a, miR-24-3p is hsa-miR-24-3p, miR-187-5p is hsa-miR-187-5p, miR-1908-5p is hsa-miR-1908-5p, miR-371a-5p is hsa-miR-371a-5p, and miR-550a-5p is hsa-miR-550a-5p.

(16) The device according to (14) or (15), wherein the nucleic acid(s) is a polynucleotide(s) selected from the group consisting of the following polynucleotides (f) to (j):
(f) a polynucleotide consisting of a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(g) a polynucleotide comprising a nucleotide sequence represented by any of SEQ ID NOs: 105 to 122;
(h) a polynucleotide consisting of a nucleotide sequence complementary to a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 105 to 122 or a nucleotide sequence derived from the nucleotide sequence by the replacement of u with t; and
(j) a polynucleotide hybridizing under stringent conditions to any of the polynucleotides (f) to (i).

(17) The device according to any one of (11) to (16), wherein the device further comprises a nucleic acid(s) capable of specifically binding to at least one or more polynucleotides selected from the group consisting of other pancreatic cancer markers miR-4417, miR-4707-5p, miR-7847-3p, miR-2861, miR-4513, miR-7111-5p, miR-6777-5p, miR-7113-3p, miR-4648, miR-3184-5p, miR-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92b-5p, miR-6774-5p, miR-486-3p, miR-6806-5p, miR-6842-5p, miR-6716-5p, miR-557, miR-4673, miR-4674, miR-444 miR-1915-3p, miR-4687-3p and miR-92b-3p.

(18) The device according to (17), wherein miR-4417 is hsa-miR-4417, miR-4707-5p is hsa-miR-4707-5p, miR-7847-3p is hsa-miR-7847-3p, miR-2861 is hsa-miR-2861, miR-4513 is hsa-miR-4513, miR-7111-5p is hsa-miR-7111-5p, miR-6777-5p is hsa-miR-6777-5p, miR-7113-3p is hsa-miR-7113-3p, miR-4648 is hsa-miR-4648, miR-3184-5p is hsa-miR-3184-5p, miR-4271 is hsa-miR-4271, miR-6791-5p is hsa-miR-6791-5p, miR-642a-3p is hsa-miR-642a-3p, miR-7108-5p is hsa-miR-7108-5p, miR-128-1-5p is hsa-miR-128-1-5p, miR-5196-5p is hsa-miR-5196-5p, miR-3178 is hsa-miR-3178, miR-3656 is hsa-miR-3656, miR-92a-2-5p is hsa-miR-92a-2-5p, miR-6769b-5p is hsa-miR-6769b-5p, miR-4689 is hsa-miR-4689, miR-6076 is hsa-miR-6076, miR-92b-5p is hsa-miR-92b-5p, miR-6774-5p is hsa-miR-6774-5p, miR-486-3p is hsa-miR-486-3p, miR-6806-5p is hsa-miR-6806-5p, miR-6842-5p is hsa-miR-6842-5p, miR-6716-5p is hsa-miR-6716-5p, miR-557 is hsa-miR-557, miR-4673 is hsa-miR-4673, miR-4674 is hsa-miR-4674, miR-4442 is hsa-miR-4442, miR-1915-3p is hsa-miR-1915-3p, miR-4687-3p is hsa-miR-4687-3p, and miR-92b-3p is hsa-miR-92b-3p.

(19) The device according to (17) or (18), wherein the nucleic acid(s) is a polynucleotide(s) selected from the group consisting of the following polynucleotides (k) to (o):
(k) a polynucleotide consisting of a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;
(l) a polynucleotide comprising a nucleotide sequence represented by any of SEQ ID NOs: 349 to 383;
(m) a polynucleotide consisting of a nucleotide sequence complementary to a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;
(n) a polynucleotide comprising a nucleotide sequence complementary to a nucleotide sequence represented by any of SEQ ID NOs: 349 to 383 or a nucleotide sequence derived from the nucleotide sequence by the replacement of u with t; and
(o) a polynucleotide hybridizing under stringent conditions to any of the polynucleotides (k) to (n).

(20) The device according to any one of (11) to (19), wherein the device is for measurement based on a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the pancreatic cancer markers according to (11) or (12).

(23) A method for detecting pancreatic cancer, comprising: measuring an expression level(s) of a target nucleic acid(s) in a sample from a subject using a kit according to any one of (1) to (10) or a device according to any one of (11) to (22); and evaluating in vitro whether or not the subject has pancreatic cancer using both of the measured expression level(s) and a control expression level(s) in a sample from a healthy subject measured in the same way.

(24) The method according to (23), wherein the subject is a human.

(25) The method according to (23) or (24), wherein the sample is blood, serum, or plasma.

<Definition of Terms>

The terms used herein are defined as described below.

The term "pancreatic cancer" used herein refers to any malignant tumor formed in the pancreas. Specifically, the "pancreatic cancer" includes serous cystadenoma, mucinous cystadenocarcinoma, intraductal papillary-mucinous carcinoma, invasive ductal carcinoma, acinar cell carcinoma, neuroendocrine cancer, and the like ("General Rules for the Study of Pancreatic Cancer", the 6th edition, revised version, 2013, Japan Pancreas Society, KANEHARA & Co., LTD., p. 21-22).

The term "benign tumors and/or benign diseases of the pancreas and/or peripancreatic organs" used herein refers to diseases with nonmalignant tumors in the pancreas, the liver, and the bile duct.

Abbreviations or terms such as "nucleotide", "polynucleotide", "DNA", and "RNA" used herein abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Here the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotides (i.e., a variant sequence) and a sequence comprising one or more modified nucleotides (i.e., a modified sequence), which are different from the natural sequence. Herein, the term "polynucleotide" is used interchangeably with the term "nucleic acid."

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus(+) strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand) including cDNA, microRNA (miRNA), and their fragments, and their transcripts, unless otherwise specified. The "gene" includes not only a "gene" represented by a particular nucleotide sequence (or SEQ ID NO) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 499 or a nucleotide sequence derived from the nucleotide sequence by the replacement of u with t. Regardless whether or not there is a difference in functional region, the "gene" can comprise, for example, expression control regions, coding region, exons, or introns. The "gene" may be contained in a cell or may exist alone after being released from a cell. Alternatively, the "gene" may be in a state enclosed in a vesicle called exosome.

The term "exosome" used herein is a vesicle that is encapsulated by lipid bilayer and secreted from a cell. The exosome is derived from a multivesicular endosome and may incorporate biomaterials such as "genes" (e.g., RNA or DNA) or proteins when released into an extracellular environment. The exosome is known to be contained in a body fluid such as blood, serum, plasma, or lymph.

The term "transcript" used herein refers to an RNA synthesized from the DNA sequence of a gene as a template. RNA polymerase binds to a site called promoter located upstream of the gene and adds ribonucleotides complementary to the nucleotide sequence of the DNA to the 3' end to synthesize an RNA. This RNA contains not only the gene itself but the whole sequence from a transcription initiation site to the end of a polyA sequence, including expression control regions, coding region, exons, or introns.

Unless otherwise specified, the term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, and integrated into a protein complex called RISC, and that is involved in the suppression of translation of snRNA. The term "miRNA" used herein includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 499. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes a polynucleotide that specifically recognizes and amplifies an RNA resulting from the expression of a gene or a polynucleotide derived from the RNA, and/or a polynucleotide complementary thereto.

In this context, the complementary polynucleotide (complementary strand or reverse strand) means a polynucleotide in a complementary relationship based on A:T (U) and G:C base pairs with the full-length sequence of a polynucleotide consisting of a nucleotide sequence defined by any of SEQ IIS NOs: 1 to 499 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a detectably larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 499 or a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant as used herein can be prepared by use of a well-known technique such as site-directed mutagenesis or mutagenesis using PCR.

The term "percent (%) identity" used herein can be determined with or without an introduced gap, using a protein or gene search system based on BLAST or FASTA (Zheng Zhang et al., 2000, J. Comput. Biol., Vol. 7, p. 203-214; Altschul, S. F, et al., 1990, Journal of Molecular Biology, Vol. 215, p. 403-410; and Pearson, W. R. et al., 1988, Proc. Natl. Acad. Sci. U.S.A., Vol. 85, p. 2444-2448).

The term "derivative" used herein is meant to include unlimitedly a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404).

As used herein, the "nucleic acid" capable of specifically binding to a polynucleotide selected from the pancreatic cancer marker miRNAs described above is a synthesized or prepared nucleic acid and specifically includes a "nucleic acid probe" or a "primer". The "nucleic acid" is utilized directly or indirectly for detecting the presence or absence of pancreatic cancer in a subject, for diagnosing the presence or absence or the severity of pancreatic cancer, the presence or absence or the degree of amelioration of pancreatic cancer, or the therapeutic sensitivity of pancreatic cancer, or for screening for a candidate substance useful in the prevention, amelioration, or treatment of pancreatic cancer. The "nucleic acid" includes a nucleotide, an oligonucleotide, and a polynucleotide capable of specifically recognizing and binding to a transcript represented by any of SEQ ID NOs: 1 to 499 or a synthetic cDNA nucleic acid thereof in vivo, particularly, in a sample such as a body fluid (e.g., blood or urine), in relation to the development of pancreatic cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". As used herein, the term "evaluation" is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that actually calculated from data under null hypothesis is observed in a statistical test. Thus, smaller "P" or "P value" is regarded as being a more significant difference between subjects to be compared.

The term "sensitivity" used herein means a value of (the number of true positives)/(the number of true positives+the number of false negatives). High sensitivity allows pancreatic cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being pancreatic cancer patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

As used herein, the "sample" that is subject to determination, detection, or diagnosis refers to a tissue and a biological material in which the expression of the gene of the present invention varies as pancreatic cancer develops, as pancreatic cancer progresses, or as therapeutic effects on pancreatic cancer are exerted. Specifically, the "sample" refers to a pancreatic tissue, a peripancreatic vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-6893-5p gene" or "hsa-miR-6893-5p" used herein includes the hsa-miR-6893-5p gene (miRBase Accession No. MIMAT0027686) described in SEQ ID NO: 1, a homolog or an ortholog of a different organism species, and the like. The hsa-miR-6893-5p gene can be obtained by a method described in Ladewig E et al., 2012, Genome Res., Vol. 22, p. 1634-1645. Also, "hsa-mir-6893" (miRBase Accession No. MI0022740, SEQ ID NO: 123) having a hairpin-like structure is known as a precursor of "hsa-miR-6893-5p".

The term "hsa-miR-6075 gene" or "hsa-miR-6075" used herein includes the hsa-miR-6075 gene (miRBase Accession No. MIMAT0023700) described in SEQ ID NO: 2, a homolog or an ortholog of a different organism species, and the like. The hsa-miR-6075 gene can be obtained by a method described in Voellenkle C et al., 2012, RNA., Vol. 18, p. 472-484. Also, "hsa-mir-6075" (miRBase Accession No. MI0020352, SEQ ID NO: 124) having a hairpin-like structure is known as a precursor of "hsa-miR-6075".

The term "hsa-miR-6820-5p gene" or "hsa-miR-6820-5p" used herein includes the hsa-miR-6820-5p gene (miRBase Accession No. MIMAT0027540) described in SEQ ID NO: 3, a homolog or an ortholog of a different organism species, and the like. The hsa-miR-6820-5p gene can be obtained by a method described in Ladewig E et al., 2012, Genome Res., Vol. 22, p. 1634-1645. Also, "hsa-mir-6820" (miRBase Accession No. MI0022665, SEQ ID NO: 125) having a hairpin-like structure is known as a precursor of "hsa-miR-6820-5p".

The term "hsa-miR-4294 gene" or "hsa-miR-4294" used herein includes the hsa-miR-4294 gene (miRBase Accession No. MIMAT0016849) described in SEQ ID NO: 4, a homolog or an ortholog of a different organism species, and the like. The hsa-miR-4294 gene can be obtained by a method described in Goff L A et al., 2009, PLoS One., Vol. 4, e7192. Also, "hsa-mir-4294" (miRBase Accession No. MI0015827, SEQ ID NO: 126) having a hairpin-like structure is known as a precursor of "hsa-miR-4294".

The term "hsa-miR-6729-5p gene" or "hsa-miR-6729-5p" used herein includes the hsa-miR-6729-5p gene (miRBase Accession No. MIMAT0027359) described in SEQ ID NO: 5, a homolog or an ortholog of a different organism species, and the like. The hsa-miR-6729-5p gene can be obtained by a method described in Ladewig E et al., 2012, Genome Res., Vol. 22, p. 1634-1645. Also, "hsa-mir-6729" (miRBase Accession No. MI0022574, SEQ ID NO: 127) having a hairpin-like structure is known as a precursor of "hsa-miR-6729-5p".

The term "hsa-miR-4476 gene" or "hsa-miR-4476" used herein includes the hsa-miR-4476 gene (miRBase Accession No. MIMAT0019003) described in SEQ ID NO: 6, a homolog or an ortholog of a different organism species, and the like. The hsa-miR-4476 gene can be obtained by a method described in Jima D D et al., 2010, Blood., Vol. 116, e118-e127. Also, "hsa-mir-4476" (miRBase Accession No. MI0016828, SEQ ID NO: 128) having a hairpin-like structure is known as a precursor of "hsa-miR-4476".

The term "hsa-miR-6836-3p gene" or "hsa-miR-6836-3p" used herein includes the hsa-miR-6836-3p gene (miRBase Accession No. MIMAT0027575) described in SEQ ID NO: 7, a homolog or an ortholog of a different organism species, and the like. The hsa-miR-6836-3p gene can be obtained by a method described in Ladewig E et al., 2012, Genome Res., Vol. 22, p. 1634-1645. Also, "hsa-mir-6836" (miRBase Accession No. MI0022682, SEQ ID NO: 129) having a hairpin-like structure is known as a precursor of "hsa-miR-6836-3p".

The term "hsa-miR-6765-3p gene" or "hsa-miR-6765-3p" used herein includes the hsa-miR-6765-3p gene (miRBase Accession No. MIMAT0027431) described in SEQ ID NO: 8, a homolog or an ortholog of a different organism species, and the like. The hsa-miR-6765-3p gene can be obtained by a method described in Ladewig E et al., 2012, Genome Res., Vol. 22, p. 1634-1645. Also, "hsa-mir-6765" (miRBase Accession No. MI0022610, SEQ ID NO: 130) having a hairpin-like structure is known as a precursor of "hsa-miR-6765-3p".

The term "hsa-miR-6799-5p gene" or "hsa-miR-6799-5p" used herein includes the hsa-miR-6799-5p gene (miRBase Accession No. MIMAT0027498) described in SEQ ID NO: 9, a homolog or an ortholog of a different organism species, and the like. The hsa-miR-6799-5p gene can be obtained by a method described in Ladewig E et al., 2012, Genome Res., Vol. 22, p. 1634-1645. Also, "hsa-mir-6799" (miRBase Accession No. MI0022644, SEQ ID NO: 131) having a hairpin-like structure is known as a precursor of "hsa-miR-6799-5p".

The term "hsa-miR-4530 gene" or "hsa-miR-4530" used herein includes the hsa-miR-4530 gene (miRBase Accession No. MIMAT0019069) described in SEQ ID NO: 10, a homolog or an ortholog of a different organism species, and the like. The hsa-miR-4530 gene can be obtained by a method described in n Jima D D et al., 2010, Blood., Vol. 116, e118-e127. Also, "hsa-mir-4530" (miRBase Accession No. MI0016897, SEQ ID NO: 132) having a hairpin-like structure is known as a precursor of "hsa-miR-4530".

The term "hsa-miR-7641 gene" or "hsa-miR-7641" used herein includes the hsa-miR-7641 gene (miRBase Accession No. MIMAT0029782) described in SEQ ID NO: 11, a homolog or an ortholog of a different organism species, and the like. The hsa-miR-7641 gene can be obtained by a method described in Yoo J K et al., 2013, Arch Pharm Res., Vol. 36, p. 353-358. Also, "hsa-mir-7641-1 and hsa-mir-7641-2" (miRBase Accession Nos. MI0024975 and MI0024976, SEQ ID NOs: 133 and 134) a hairpin-like structure are known as precursors of "hsa-miR-7641".

The term "hsa-miR-4454 gene" or "hsa-miR-4454" used herein includes the hsa-miR-4454 gene (miRBase Accession No. MIMAT0018976) described in SEQ ID NO: 12, a homoloe or an ortholog of a different organism species, and the like. The hsa-miR-4454 gene can be obtained by a method described in Jima D D et al., 2010, Blood., Vol. 116, e118-e127. Also, "hsa-mir-4454" (miRBase Accession No. MI0016800, SEQ ID NO: 135) having a hairpin-like structure is known as a precursor of "hsa-miR-4454".

The term "hsa-miR-615-5p gene" or "hsa-miR-615-5p" used in the present specification includes the hsa-miR-615-5p gene (miRBase Accession No. MIMAT0004804) described in SEQ ID NO: 13, a homolog or an ortholog of a different organism species, and the like. The hsa-miR-615-5p gene can be obtained by a method described in Cummins J M, 2006, Proc Natl Acad Sci, Vol. 103, p. 3687-3692. Also, "hsa-mir-615" (miRBase Accession No. MI0003628, SEQ ID NO: 136) having a hairpin-like structure is known as a precursor of "hsa-miR-615-5p".

The term "hsa-miR-8073 gene" or "hsa-miR-8073" used herein includes the hsa-miR-8073 gene (miRBase Accession No. MIMAT0031000) described in SEQ ID NO: 14, a homolog or an ortholog of a different organism species, and the like. The hsa-miR-8073 gene can be obtained by a method described in Wang H J et al., 2013, Shock., Vol. 39, p. 480-487. Also, "hsa-mir-8073" (miRBase Accession No. MI0025909, SEQ ID NO: 137) having a hairpin-like structure is known as a precursor of "hsa-miR-8073".

The term "hsa-miR-663a gene" or "hsa-miR-663a" used herein includes the hsa-miR-663a gene (miRBase Accession No. MIMAT0003326) described in SEQ ID NO: 15, a homolog or an ortholog of a different organism species, and the like. The hsa-miR-663a gene can be obtained by a method described in Cummins J M, 2006, Proc Natl Acad Sci, Vol: 103, p. 3687-3692. Also, "hsa-mir-663a" (miRBase Accession No. MI0003672, SEQ ID NO: 138) having a hairpin-like structure is known as a precursor of "hsa-miR-663a".

The term "hsa-miR-4634 gene" or "hsa-miR-4634" used herein includes the hsa-miR-4634 gene (miRBase Accession No. MIMAT0019691) described in SEQ ID NO: 16, a homolog or an ortholog of a different organism species, and the like. The hsa-miR-4634 gene can be obtained by a method described in Persson H et al., 2011. Cancer Res., Vol. 71, p. 78-86. Also, "hsa-mir-4634" (miRBase Accession No. MI0017261, SEQ ID NO: 139) having a hairpin-like structure is known as a precursor of "hsa-miR-4634".

The term "hsa-miR-4450 gene" or "hsa-miR-4450" used herein includes the hsa-miR-4450 gene (miRBase Accession No. MIMAT001.8971) described in SEQ ID NO: 17, a homolog or an ortholog of a different organism species, and the like. The hsa-miR-4450 gene can be obtained by a method described in Jima D D et al., 2010, Blood., Vol. 116, e118-e127. Also, "hsa-mir-4450" (miRBase Accession No. MI0016795, SEQ ID NO: 140) having a hairpin-like structure is known as a precursor of "hsa-miR-4450".

The term "hsa-miR-4792 gene" or "hsa-miR-4792" used herein includes the hsa-miR-4792 gene (miRBase Accession No. MIMAT0019964) described in SEQ ID NO: 18, a homolog or an ortholog of a different organism species, and the like. The hsa-miR-4792 gene can be obtained by a method described in Persson H et al., 2011, Cancer Res., Vol. 71, p. 78-86. Also, "hsa-mir-4792" (miRBase Accession No. MI10017439, SEQ ID NO: 141) having a hairpin-like structure is known as a precursor of "hsa-miR-4792".

The term "hsa-miR-665 gene" or "hsa-miR-665" used herein includes the hsa-miR-665 gene (miRBase Accession No. MIMAT0004952) described in SEQ ID NO: 19, a homolog or art ortholog of a different organism species, and the like. The hsa-miR-665 gene can be obtained by a method described in Berezikov E et al., 2006, Genome Res., Vol. 16, p. 1289-1298. Also, "hsa-mir-665" (miRBase Accession No. MI0005563, SEQ ID NO: 142) having a hairpin-like structure is known as a precursor of "hsa-miR-665".

The term "hsa-miR-7975 gene" or "hsa-miR-7975" used herein includes the hsa-miR-7975 gene (miRBase Accession No. MIMAT0031178) described in SEQ ID NO: 20, a homolog or an ortholog of a different organism species, and the like. The hsa-miR-7975 gene can be obtained by a method described in Velthut-Meikas A et al., 2013, Mol Endocrinol, [Epub prior to print]. Also, "hsa-mir-7975" (miRBase Accession No. MI0025751, SEQ ID NO: 143) having a hairpin-like structure is known as a precursor of "hsa-miR-7975".

The term "hsa-miR-7109-5p gene" or "hsa-miR-7109-5p" used herein includes the hsa-miR-7109-5p gene (miRBase Accession No. MEMAT0028115) described in SEQ ID NO: 21, a homolog or an ortholog of a different organism species, and the like. The lisa-miR-7109-5p gene can be obtained by a method described in Ladewig E et al., 2012, Genome Res., Vol. 22, p. 1634-1645. Also, "hsa-mir-7109" (miRBase Accession No. MI0022960, SEQ ID NO: 144) having a hairpin-like structure is known as a precursor of "hsa-miR-7109-5p".

The term "hsa-miR-6789-5p gene" or "hsa-miR-6789-5p" used herein includes the hsa-miR-6789-5p gene (miRBase Accession No. MIMAT0027478) described in SEQ ID NO: 22, a homolog or an ortholog of a different organism species, and the like. The hsa-miR-6789-5p gene can be obtained by a method described in Ladewig E et al., 2012, Genome Res., Vol. 22, p. 1634-1645. Also, "hsa-mir-6789" (miRBase Accession No. MI0022634, SEQ ID NO: 145) having a hairpin-like structure is known as a precursor of "hsa-miR-6789-5p".

The term "hsa-miR-4497 gene" or "hsa-miR-4497" used herein includes the hsa-miR-4497 gene (miRBase Accession No. MIMAT0019032) described in SEQ ID NO: 23, a homolog or an ortholog of a different organism species, and the like. The hsa-miR-4497 gene can be obtained by a method described in Jima D D et al., 2010, Blood., Vol. 116, e118-e127. Also, "hsa-mir-4497" (miRBase Accession No. MI0016859, SEQ ID NO: 146) having a hairpin-like structure is known as a precursor of "hsa-miR-4497".

The term "hsa-miR-6877-5p gene" or "hsa-miR-6877-5p" used herein includes the hsa-miR-6877-5p gene (miRBase Accession No. MIMAT0027654) described in SEQ ID NO: 24, a homolog or an ortholog of a different organism species, and the like. The hsa-miR-6877-5p gene can be obtained by a method described in Ladewig E et al., 2012, Genome Res., Vol. 22, p. 1634-1645. Also, "hsa-mir-6877" (miRBase Accession No. MI0022724, SEQ ID NO: 147) having a hairpin-like structure is known as a precursor of "hsa-miR-6877-5p".

The term "hsa-miR-6880-5p gene" or "hsa-miR-6880-5p" used herein includes the hsa-miR-6880-5p gene (iniRBase Accession No. MEMAT0027660) described in SEQ ID NO: 25, a homolog or an ortholog of a different organism species, and the like. The lisa-miR-6880-5p gene can be obtained by a method described in Ladewig E et al., 2012, Genome Res., Vol. 22, p. 1634-1645. Also, "hsa-mir-6880" (miRBase Accession No. MI0022727, SEQ ID NO: 148) having a hairpin-like structure is known as a precursor of "hsa-miR-6880-5p".

The term "hsa-miR-7977 gene" or "hsa-miR-7977" used herein includes the lisa-miR-7977 gene (miRBase Accession No. MIMAT0031180) described in SEQ ID NO: 26, a homolog or an ortholog of a different organism species, and the like. The hsa-miR-7977 gene can be obtained by a method described in Velthut-Meikas A et al., 2013, Mol Endocrinol. [Epub prior to print]. Also, "hsa-mir-7977" (mIRBase Accession No. MI0025753, SEQ ID NO: 149) having a hairpin-like structure is known as a precursor of "hsa-miR-7977".

The term "hsa-miR-4734 gene" or "hsa-miR-4734" used herein includes the hsa-miR-4734 gene (miRBase Accession No. MIMAT0019859) described in SEQ ID NO: 27, a homolog or an ortholog of a different organism species, and the like. The hsa-miR-4734 gene can be obtained by a method described in Persson H et al., 2011, Cancer Res., Vol. 71, p. 78-86. Also, "hsa-mir-4734" (miRBase Accession No. MI0017371, SEQ ID NO: 150) having a hairpin-like structure is known as a precursor of "hsa-miR-4734".

The term "hsa-miR-6821-5p gene" or "hsa-miR-6821-5p" used herein includes the hsa-miR-6821-5p gene (miRBase Accession No. MIMAT0027542) described in SEQ ID NO: 28, a homolog or an ortholog of a different organism species, and the like. The hsa-miR-6821-5p gene can be obtained by a method described in Ladewig E et al., 2012, Genome Res., Vol. 22, p. 1634-1645. Also, "hsa-mir-6821" (miRBase Accession No. MI0022666, SEQ ID NO: 151) having a hairpin-like structure is known as a precursor of "hsa-miR-6821-5p".

The term "hsa-miR-8089 gene" or "hsa-miR-8089" used herein includes the hsa-miR-8089 gene (miRBase Accession No. MIMAT0031016) described in SEQ ID NO: 29, a homolog or an ortholog of a different organism species, and the like. The hsa-miR-8089 gene can be obtained by a method described in Wang H J et al., 2013, Shock., Vol. 39, p. 480-487. Also, "hsa-mir-8089" (miRBase Accession No. MI0025925, SEQ ID NO: 152) having a hairpin-like structure is known as a precursor of "hsa-miR-8089".

The tem "hsa-miR-5585-3p gene" or "hsa-miR-5585-3p" used herein includes the hsa-miR-5585-3p gene (miRBase Accession No. MIMAT0022286) described in SEQ ID NO: 30, a homolog or an ortholog of a different organism species, and the like. The hsa-miR-5585-3p gene can be obtained by a method described in Friedlander M R et al., 2012, Nucleic Acids Res., Vol. 40, p. 37-52. Also "hsa-mir-5585" (miRBase Accession No. MI0019142, SEQ ID NO: 153) having a hairpin-like structure is known as a precursor of "hsa-miR-5585-3p".

The term "hsa-miR-6085 gene" or "hsa-miR-6085" used herein includes the hsa-miR-6085 gene (miRBase Accession No. MIMAT0023710) described in SEQ ID NO: 31, a homolog or an ortholog of a different organism species, and the like. The hsa-miR-6085 gene can be obtained by a method described in Voellencle C et al., 2012, RNA., Vol. 18, p. 472-484. Also, "hsa-mir-6085" (miRBase Accession No. MI0020362, SEQ ID NO: 154) having a hairpin-like structure is known as a precursor of "hsa-miR-6085".

The term "hsa-miR-6845-5p gene" or "hsa-miR-6845-5p" used herein includes the hsa-miR-6845-5p gene (miRBase Accession No. MIMAT0027590) described in SEQ ID NO: 32, a homolog or an ortholog of a different organism species, and the like. The hsa-miR-6845-5p gene can be obtained by a method described in Ladewig E et al., 2012, Genome Res., Vol. 22, p. 1634-1645. Also, "hsa-mir-6845" (miRBase Accession No. MI0022691, SEQ ID NO: 155) having a hairpin-like structure is known as a precursor of "hsa-miR-6845-5p".

The term "hsa-miR-4651 gene" or "hsa-miR-4651" used herein includes the hsa-miR-4651 gene (miRBase Accession No. MIMAT001.9715) described in SEQ ID NO: 33, a homolog or an ortholog of a different organism species, and the like. The hsa-miR-4651 gene can be obtained by a method described in Persson H et al., 2011, Cancer Res., Vol. 71, p. 78-86. Also, "hsa-mir-4651" (miRBase Accession No. MI0017279, SEQ ID NO: 156) having a hairpin-like structure is known as a precursor of "hsa-miR-4651".

The term "hsa-miR-4433-3p gene" or "hsa-miR-4433-3p" used herein includes the hsa-miR-4433-3p gene (miRBase Accession No. MIMAT0018949) described in SEQ ID NO: 34, a homolog or an ortholog of a different organism species, and the like. The hsa-miR-4433-3p gene can be obtained by a method described in Jima D D et al., 2010, Blood., Vol. 116, e118-e127. Also, "hsa-mir-4433" (miRBase Accession No. MI0016773, SEQ ID NO: 157) having a hairpin-like structure is known as a precursor of "hsa-miR-4433-3p".

The term "hsa-miR-1231 gene" or "hsa-miR-1231" used herein includes the hsa-miR-1231 gene (miRBase Accession No. MIMAT0005586) described in SEQ ID NO: 35, a homolog or an ortholog of a different organism species, and the like. The hsa-miR-1231 gene can be obtained by a method described in Berezikov E et al., 2007, Mol Cell., Vol. 28, p. 328-336. Also, "hsa-mir-1231" (miRBase Accession No. MI0006321, SEQ ID NO: 158) having a hairpin-like structure is known as a precursor of "hsa-miR-1231".

The term "hsa-miR-4665-5p gene" or "hsa-miR-4665-5p" used herein includes the hsa-miR-4665-5p gene (miRBase Accession No. MIMAT0019739) described in SEQ ID NO: 36, a homolog or an ortholog of a different organism species, and the like. The hsa-miR-4665-5p gene can be obtained by a method described in Persson H et al., 2011, Cancer Res., Vol. 71, p. 78-86. Also, "hsa-mir-4665" (miRBase Accession No. MI0017295, SEQ ID NO: 159) having a hairpin-like structure is known as a precursor of "hsa-miR-4665-5p".

The term "hsa-miR-7114-5p gene" or "hsa-miR-7114-5p" used herein includes the hsa-miR-7114-5p gene (miRBase Accession No. MIMAT0028125) described in SEQ ID NO: 37, a homolog or an ortholog of a different organism species, and the like. The hsa-miR-7114-5p gene can be obtained by a method described in Ladewig E et al., 2012, Genome Res., Vol. 22, p. 1634-1645. Also, "hsa-mir-7114" (miRBase Accession No. MI0022965, SEQ ID NO: 160) having a hairpin-like structure is known as a precursor of "hsa-miR-7114-5p".

The term "hsa-miR-1238-5p gene" or "hsa-miR-1238-5p" used herein includes the hsa-miR-1238-5p gene (miRBase Accession No. MIMAT0022947) described in SEQ ID NO: 38, a homolog or an ortholog of a different organism species, and the like. The hsa-miR-1238-5p gene can be obtained by a method described in Berezikov E et al., 2007, Mol Cell., Vol. 28, p. 328-336. Also, "hsa-mir-1238" (miRBase Accession No. MI0006328, SEQ ID NO: 161) having a hairpin-like structure is known as a precursor of "hsa-miR-1238-5p".

The term "hsa-miR-8069 gene" or "hsa-miR-8069" used herein includes the hsa-miR-8069 gene (miRBase Accession No. MIMAT0030996) described in SEQ ID NO: 39, a homolog or an ortholog of a different organism species, and the like. The hsa-miR-8069 gene can be obtained by a method described in Wang H J et al., 2013, Shock., Vol. 39, p. 480-487. Also, "hsa-mir-8069" (miRBase Accession No. MI0025905, SEQ ID NO: 162) having a hairpin-like structure is known as a precursor of "hsa-miR-8069".

The term "hsa-miR-4732-5p gene" or "hsa-miR-4732-5p" used herein includes the hsa-miR-4732-5p gene (miRBase Accession No. MIMAT0019855) described in SEQ ID NO: 40, a homolog or an ortholog of a different organism species, and the like. The hsa-miR-4732-5p gene can be obtained by a method described in Persson 14 et al., 2011. Cancer Res., Vol. 71, p. 78-86. Also, "hsa-mir-4732" (miRBase Accession No. MI0017369, SEQ ID NO: 163) having a hairpin-like structure is known as a precursor of "hsa-miR-4732-5p".

The term "hsa-miR-619-5p gene" or "hsa-miR-619-5p" used herein includes the hsa-miR-619-5p gene (miRBase Accession No. MIMAT0026622) described in SEQ ID NO: 41, a homolog or an ortholog of a different organism species, and the like. The hsa-miR-619-5p gene can be obtained by a method described in Cummins J M, 2006, Proc Natl. Acad Sci, Vol. 103, p. 3687-3692. Also, "hsa-mir-619" (miRBase Accession No. MI0003633, SEQ ID NO: 164) having a hairpin-like structure is known as a precursor of "hsa-miR-619-5p".

The term "hsa-miR-3622a-5p gene" or "hsa-miR-3622a-5p" used herein includes the hsa-miR-3622a-5p gene (miRBase Accession No. MIMAT001.8003) described in SEQ ID NO: 42, a homolog or an ortholog of a different organism species, and the like. The hsa-miR-3622a-5p gene can be obtained by a method described in Witten D et al., 2010. BMC Biol., Vol. 8, p. 58. Also, "hsa-mir-3622a" (miRBase Accession No. MI0016013, SEQ ID NO: 165) having a hairpin-like structure is known as a precursor of "hsa-miR-3622a-5p".

The term "hsa-miR-1260a gene" or "hsa-miR-1260a" used herein includes the hsa-miR-1260a gene (miRBase Accession No. MIMAT0005911) described in SEQ ID NO: 43, a homolog or an ortholog of a different organism species, and the like. The hsa-miR-1260a gene can be obtained by a method described in Morin R D et al., 2008. Genome Res., Vol. 18, p. 610-621. Also, "hsa-mir-1260a" (miRBase Accession No. MI0006394, SEQ ID NO: 166) having a hairpin-like structure is known as a precursor of "hsa-miR-1260a".

The term "hsa-miR-6741-5p gene" or "hsa-miR-6741-5p" used herein includes the hsa-miR-6741-5p gene (miRBase Accession No. MIMAT0027383) described in SEQ ID NO: 44, a homolog or an ortholog of a different organism species, and the like. The hsa-miR-6741-5p gene can be obtained by a method described in Ladewig E et al., 2012, Genome Res., Vol. 22, p. 1634-1645. Also, "hsa-mir-6741" (miRBase Accession No. MI0022586, SEQ ID NO: 167) having a hairpin-like structure is known as a precursor of "hsa-miR-6741-5p".

The term "hsa-miR-6781-5p gene" or "hsa-miR-6781-5p" used herein includes the hsa-miR-6781-5p gene (miRBase Accession No. MIMAT0027462) described in SEQ ID NO: 45, a homolog or an ortholog of a different organism species, and the like. The lisa-miR-6781-5p gene can be obtained by a method described in Ladewig E et al., 2012, Genome Res., Vol. 22, p. 1634-1645. Also, "hsa-mir-6781" (miRBase Accession No. MI0022626, SEQ ID NO: 168) having a hairpin-like structure is known as a precursor of "hsa-miR-6781-5p".

The term "hsa-miR-6125 gene" or "hsa-miR-6125" used herein includes the hsa-miR-6125 gene (miRBase Accession No. MIMAT0024598) described in SEQ ID NO: 46, a homolog or an ortholog of a different organism species, and the like. The hsa-miR-6125 gene can be obtained by a method described in Smith J L et al., 2012, J Virol., Vol. 86, p. 5278-5287. Also, "hsa-mir-6125" (miRBase Accession No. MI0021259, SEQ ID NO: 169) having a hairpin-like structure is known as a precursor of "hsa-miR-6125".

The term "hsa-miR-6805-5p gene" or "hsa-miR-6805-5p" used herein includes the hsa-miR-6805-5p gene (miRBase Accession No. MIMAT0027510) described in SEQ ID NO: 47, a homolog or an ortholog of a different organism species, and the like. The hsa-miR-6805-5p gene can be obtained by a method described in Ladewig E et al., 2012, Genome Res., Vol. 22, p. 1634-1645. Also, "hsa-mir-6805" (miRBase Accession No. MI0022650, SEQ ID NO: 170) having a hairpin-like structure is known as a precursor of "hsa-miR-6805-5p".

The term "hsa-miR-6132 gene" or "hsa-miR-6132" used herein includes the hsa-miR-6132 gene (miRBase Accession No. MIMAT0024616) described in SEQ ID NO: 48, a homolog or an ortholog of a different organism species, and the like. The hsa-miR-6132 gene can be obtained by a method described in Dannemann M, 2012, Genome Biol Evol., Vol. 4, p. 552-564. Also, "hsa-mir-6132" (miRBase Accession No. MI0021277, SEQ ID NO: 171) having a hairpin-like structure is known as a precursor of "hsa-miR-6132".

The term "hsa-miR-6872-3p gene" or "hsa-miR-6872-3p" used herein includes the hsa-miR-6872-3p gene (miRBase Accession No. MIMAT0027645) described in SEQ ID NO: 49, a homolog or an ortholog of a different organism species, and the like. The hsa-miR-6872-3p gene can be obtained by a method described in Ladewig E et al., 2012, Genome Res., Vol. 22, p. 1634-1645. Also, "hsa-mir-6872" (miRBase Accession No. MI0022719, SEQ ID NO: 172) having a hairpin-like structure is known as a precursor of "hsa-miR-6872-3p".

The tem "hsa-miR-6875-5p gene" or "hsa-miR-6875-5p" used herein includes the hsa-miR-6875-5p gene (miRBase Accession No. MIMAT0027650) described in SEQ ID NO: 50, a homolog or an ortholog of a different organism species, and the like. The hsa-miR-6875-5p gene can be obtained by a method described in Ladewig E et al., 2012, Genome Res., Vol. 22, p. 1634-1645. Also, "hsa-mir-6875" (miRBase Accession No. MI0022722, SEQ ID NO: 173) having a hairpin-like structure is known as a precursor of "hsa-miR-6875-5p".

The term "hsa-miR-1908-3p gene" or "hsa-miR-1908-3p" used herein includes the hsa-miR-1908-3p gene (miRBase Accession No. MIMAT0026916) described in SEQ ID NO: 51, a homolog or an ortholog of a different organism species, and the like. The hsa-miR-1908-3p gene can be obtained by a method described in Bar M et al., 2008, Stem Cells., Vol. 26, p. 2496-2505. Also, "hsa-mir-1908" (miRBase Accession No. MI0008329, SEQ ID NO: 174) having a hairpin-like structure is known as a precursor of "hsa-miR-1908-3p".

The term "hsa-miR-4433b-3p gene" or "hsa-miR-4433b-3p" used herein includes the hsa-miR-4433b-3p gene (miRBase Accession No. MIMAT0030414) described in SEQ ID NO: 52, a homolog or an ortholog of a different organism species, and the like. The hsa-miR-4433b-3p gene can be obtained by a method described in Ple H et al., 2012, PLoS One., Vol. 7, e50746. Also, "hsa-mir-4433h" (miRBase Accession No. MI0025511, SEQ ID NO: 175) having a hairpin-like structure is known as a precursor of "hsa-miR-4433b-3p".

The term "hsa-miR-4736 gene" or "hsa-miR-4736" used herein includes the hsa-miR-4736 gene (miRBase Accession No. MIMAT001.9862) described in SEQ ID NO: 53, a homolog or an ortholog of a different organism species, and the like. The hsa-miR-4736 gene can be obtained by a method described in Persson H et al., 2011, Cancer Res., Vol. 71, p. 78-86. Also, "hsa-mir-4736" (miRBase Accession No. MI0017373, SEQ ID NO: 176) having a hairpin-like structure is known as a precursor of "hsa-miR-4736".

The term "hsa-miR-5100 gene" or "hsa-miR-5100" used herein includes the hsa-miR-5100 gene (miRBase Accession No. MIMAT0022259) described in SEQ ID NO: 54, a homolog or an ortholog of a different organism species, and the like. The hsa-miR-5100 gene can be obtained by a method described in Tandon M et al., 2012, Oral Dis., Vol. 18, p. 127-131. Also, "hsa-mir-5100" (miRBase Accession No. MI0019116, SEQ ID NO: 177) having a hairpin-like structure is known as a precursor of "hsa-miR-5100".

The term "hsa-miR-6724-5p gene" or "hsa-miR-6724-5p" used herein includes the hsa-miR-6724-5p gene (miRBase Accession No. MIMAT0025856) described in SEQ ID NO: 55 a homolog or an ortholog of a different organism species, and the like. The hsa-miR-6724-5p gene can be obtained by a method described in Li Y et al., 2012, Gene., Vol. 497, p. 330-335. Also, "hsa-mir-6724" (miRBase Accession No. MI0022559, SEQ ID NO: 178) having a hairpin-like structure is known as a precursor of "hsa-miR-6724-5p".

The term "hsa-miR-7107-5p gene" or "hsa-miR-7107-5p" used herein includes the hsa-miR-7107-5p gene (miRBase Accession No. MIMAT0028111) described in SEQ ID NO: 56, a homolog or an ortholog of a different organism species, and the like. The hsa-miR-7107-5p gene can be obtained by a method described in Ladewig E et al., 2012, Genome Res., Vol. 22, p. 1634-1645. Also, "hsa-mir-7107" (miRBase Accession No. MI0022958, SEQ ID NO: 179) having a hairpin-like structure is known as a precursor of "hsa-miR-7107-5p".

The term "hsa-miR-6726-5p gene" or "hsa-miR-6726-5p" used herein includes the hsa-miR-6726-5p gene (miRBase Accession No. MIMAT0027353) described in SEQ ID NO: 57, a homolog or an ortholog of a different organism species, and the like. The hsa-miR-6726-5p gene can be obtained by a method described in Ladewig E et al., 2012, Genome Res., Vol. 22, p. 1634-1645. Also, "hsa-mir-6726" (miRBase Accession No. MI0022571, SEQ ID NO: 180) having a hairpin-like structure is known as a precursor of "hsa-miR-6726-5p".

The term "hsa-miR-3185 gene" or "hsa-miR-3185" used herein includes the hsa-miR-3185 gene (miRBase Accession No. MIMAT0015065) described in SEQ ID NO: 58, a homolog or an ortholog of a different organism species, and the like. The hsa-miR-3185 gene can be obtained by a method described in Stark M S et al., 2010, PLoS One., Vol. 5, e9685. Also, "hsa-mir-3185" (miRBase Accession No. MI0014227, SEQ ID NO: 181) having a hairpin-like structure is known as a precursor of "hsa-miR-3185".

The term "hsa-miR-4638-5p gene" or "hsa-miR-4638-5p" used herein includes the hsa-miR-4638-5p gene (miRBase Accession No. MIMAT0019695) described in SEQ ID NO: 59, a homolog or an ortholog of a different organism species, and the like. The hsa-miR-4638-5p gene can be obtained by a method described in Persson H et al., 2011, Cancer Res., Vol. 71, p. 78-86. Also, "hsa-mir-4638" (miRBase Accession No. MI0017265, SEQ ID NO: 182) having a hairpin-like structure is known as a precursor of "hsa-miR-4638-5p".

The term "hsa-miR-1273g-3p gene" or "hsa-miR-1273g-3p" used herein includes the hsa-miR-1273g-3p gene (miRBase Accession No. MIMAT0022742) described in SEQ ID NO: 60, a homolog or an ortholog of a different organism species, and the like. The hsa-miR-1273g-3p gene can be obtained by a method described in Reshmi G et al., 2011, Genomics., Vol. 97, p. 333-340. Also, "hsa-mir-1273g" (miRBase Accession No. MI0018003, SEQ ID NO: 183) having a hairpin-like structure is known as a precursor of "hsa-miR-1273g-3p".

The term "hsa-miR-6778-5p gene" or "hsa-miR-6778-5p" used herein includes the hsa-miR-6778-5p gene (miRBase Accession No. MIMAT0027456) described in SEQ ID NO: 61, a homolog or an ortholog of a different organism species, and the like. The hsa-miR-6778-5p gene can be obtained by a method described in Ladewig E et al., 2012, Genome Res., Vol. 22, p. 1634-1645. Also, "hsa-mir-6778" (miRBase Accession No. MI0022623, SEQ ID NO: 184) having a hairpin-like structure is known as a precursor of "hsa-miR-6778-5p".

The term "hsa-miR-328-5p gene" or "hsa-miR-328-5p" used herein includes the hsa-miR-328-5p gene (miRBase Accession No. MIMAT0026486) described in SEQ ID NO: 62, a homolog or an ortholog of a different organism species, and the like. The hsa-miR-328-5p gene can be obtained by a method described in Kim J et al., 2004, Proc Natl Acad Sci, Vol. 101, p. 360-365. Also, "hsa-mir-328" (miRBase Accession No. MI0000804, SEQ ID NO: 185) having a hairpin-like structure is known as a precursor of "hsa-miR-328-5p".

The term "hsa-miR-3679-3p gene" or "hsa-miR-3679-3p" used herein includes the hsa-miR-3679-3p gene (miRBase Accession No. MIMAT0018105) described in SEQ ID NO: 63, a homolog or an ortholog of a different organism species, and the like. The hsa-miR-3679-3p gene can be obtained by a method described in Creighton C J et al., 2010, PLoS One., Vol. 5, e9637. Also, "hsa-mir-3679" (miRBase Accession No. MI0016080, SEQ ID NO: 186) having a hairpin-like structure is known as a precursor of "hsa-miR-3679-3".

The term "hsa-miR-1228-3p gene" or "hsa-miR-1228-3p" used herein includes the hsa-miR-1228-3p gene (miRBase Accession No. MIMAT0005583) described in SEQ ID NO: 64, a homolog or an ortholog of a different organism species, and the like. The hsa-miR-1228-3p gene can be obtained by a method described in Berezikov E et al., 2007, Mol Cell., Vol. 28, p. 328-336. Also, "hsa-mir-1228" (miRBase Accession No. MI0006318, SEQ ID NO: 187) having a hairpin-like structure is known as a precursor of "hsa-miR-1228-3p".

The term "hsa-miR-6779-5p gene" or "hsa-miR-6779-5p" used herein includes the hsa-miR-6779-5p gene (miRBase Accession No. MIMAT0027458) described in SEQ ID NO: 65, a homolog or an ortholog of a different organism species, and the like. The hsa-miR-6779-5p gene can be obtained by a method described in Ladewig E et al., 2012, Genome Res., Vol. 22, p. 1634-1645. Also, "hsa-mir-6779" (miRBase Accession No. MI0022624, SEQ ID NO: 188) having a hairpin-like structure is known as a precursor of "hsa-miR-6779-5p".

The term "hsa-miR-4723-5p gene" or "hsa-miR-4723-5p" used herein includes the hsa-miR-4723-5p gene (miRBase Accession No. MIMAT0019838) described in SEQ ID NO: 66, a homolog or an ortholog of a different organism species, and the like. The hsa-miR-4723-5p gene can be obtained by a method described in Persson H et al., 2011, Cancer Res., Vol. 71, p. 78-86. Also, "hsa-mir-4723" (miRBase Accession No. MI0017359, SEQ ID NO: 189) having a hairpin-like structure is known as a precursor of "hsa-miR-4723-5p".

The term "hsa-miR-6850-5p gene" or "hsa-miR-6850-5p" used herein includes the hsa-miR-6850-5p gene (miRBase Accession No. MIMAT0027600) described in SEQ ID NO: 67, a homolog or an ortholog of a different organism species, and the like. The hsa-miR-6850-5p gene can be obtained by a method described in Ladewig E et al., 2012, Genome Res., Vol. 22, p. 1634-1645. Also, "hsa-mir-6850" (miRBase Accession No. MI0022696, SEQ ID NO: 190) having a hairpin-like structure is known as a precursor of "hsa-miR-6850-5p".

The term "hsa-miR-760 gene" or "hsa-miR-760" used herein includes the hsa-miR-760 gene ase Accession No. MIMAT0004957) described in SEQ ID NO: 68, a homolog or an ortholog of a different organism species, and the like. The hsa-miR-760 gene can be obtained by a method described in Berezikov E et al., 2006, Genome Res., Vol. 16, p. 1289-1298. Also, "hsa-tnir-760" (miRBase Accession No. MI0005567, SEQ ID NO: 191) having a hairpin-like structure is known as a precursor of "hsa-miR-760".

The term "hsa-miR-7704 gene" or "hsa-miR-7704" used herein includes the hsa-miR-7704 gene (miRBase Accession No. MIMAT0030019) described in SEQ ID NO: 69, a homolog or an ortholog of a different organism species, and the like. The hsa-miR-7704 gene can be obtained by a method described in Swaminathan S et al., 2013, Biochem Biophvs Res Commun., Vol. 434, p. 228-234. Also, "hsa-mir-7704" (miRBase Accession No. MI0025240, SEQ ID NO: 192) having a hairpin-like structure is known as a precursor of "hsa-miR-7704".

The term "hsa-miR-8072 gene" or "hsa-miR-8072" used herein includes the hsa-miR-8072 gene (miRBase Accession No. MIMAT0030999) described in SEQ ID NO: 70, a homolog or an ortholog of a different organism species, and the like. The hsa-miR-8072 gene can be obtained by a method described in Wang H J et al., 2013, Shock., Vol. 39, p. 480-487. Also, "hsa-mir-8072" (miRBase Accession No. MI0025908, SEQ ID NO: 193) having a hairpin-like structure is known as a precursor of "hsa-miR-8072".

The term "hsa-miR-4486 gene" or "hsa-miR-4486" used herein includes the hsa-miR-4486 gene (miRBase Accession No. MIMAT0019020) described in SEQ ID NO: 71, a homolog or an ortholog of a different organism species, and the like. The hsa-miR-4486 gene can be obtained by a method described in Jima D D et al., 2010, Blood., Vol. 116, e118-e127. Also, "hsa-mir-4486" (miRBase Accession No.

MI0016847, SEQ ID NO: 194) ming a hairpin-like structure is known as a precursor of "hsa-miR-4486".

The term "hsa-miR-1913 gene" or "hsa-miR-1913" used herein includes the hsa-miR-1913 gene (miRBase Accession No. MIMAT0007888) described in SEQ ID NO: 72, a homolog or an ortholog of a different organism species, and the like. The hsa-miR-1913 gene can be obtained by a method described in Bar M et al., 2008, Stem Cells., Vol. 26, p. 2496-2505. Also, "hsa-mir-1913" (miRBase Accession No. MI0008334, SEQ ID NO: 195) having a hairpin-like structure is known as a precursor of "hsa-miR-1913".

The term "hsa-miR-4656 gene" or "hsa-miR-4656" used herein includes the hsa-miR-4656 gene (miRBase Accession No. MIMAT001.9723) described in SEQ ID NO: 73, a homolog or an ortholog of a different organism species, and the like. The hsa-miR-4656 gene can be obtained by a method described in Persson H et al., 2011, Cancer Res., Vol. 71, p. 78-86. Also, "hsa-mir-4656" (iniRBase Accession No. MI0017284, SEQ ID NO: 196) having a hairpin-like structure is known as a precursor of "hsa-miR-4656".

The term "hsa-miR-1260b gene" or "hsa-miR-1260b" used herein includes the hsa-miR-1260b gene (miRBase Accession No. MIMAT0015041) described in SEQ ID NO: 74, a homolog or an ortholog of a different organism species, and the like. The hsa-miR-1260b gene can be obtained by a method described in Stark M S et al., 2010, PLoS One., Vol. 5, e9685. Also, "hsa-mir-1260b" (miRBase Accession No. MI0014197, SEQ ID NO: 197) having a hairpin-like structure is known as a precursor of "hsa-miR-1260b".

The term "hsa-miR-7106-5p gene" or "hsa-miR-7106-5p" used herein includes the hsa-miR-7106-5p gene (miRBase Accession No. MIMAT0028109) described in SEQ ID NO: 75, a homolog or an ortholog of a different organism species, and the like. The hsa-miR-7106-5p gene can be obtained by a method described in Ladewig E et al., 2012, Genome Res., Vol. 22, p. 1634-1645. Also, "hsa-mir-7106" (miRBase Accession No. MI0022957, SEQ ID NO: 198) having a hairpin-like structure is known as a precursor of "hsa-miR-7106-5p".

The term "hsa-miR-6889-5p gene" or "hsa-miR-6889-5p" used herein includes the hsa-miR-6889-5p gene (miRBase Accession No. MIMAT0027678) described in SEQ ID NO: 76, a homolog or an ortholog of a different organism species, and the like. The hsa-miR-6889-5p gene can be obtained by a method described in Ladewig E et al., 2012, Genome Res., Vol. 22, p. 1634-1645. Also, "hsa-mir-6889" (miRBase Accession No. MI0022736, SEQ ID NO: 199) having a hairpin-like structure is known as a precursor of "hsa-miR-6889-5p".

The term "sa-miR-6780b-5p gene" or "hsa-miR-6780b-5p" used herein includes the hsa-miR-6780b-5p gene (miRBase Accession No. MIMAT0027572) described in SEQ ID NO: 77, a homolog or an ortholog of a different organism species, and the like. The hsa-miR-6780b-5p gene can be obtained by a method described in Ladewig E et al., 2012, Genome Res., Vol. 22, p. 1634-1645. Also, "hsa-mir-6780b" (miRBase Accession No. MI0022681, SEQ ID NO: 200) having a hairpin-like structure is known as a precursor of "hsa-miR-6780b-5p".

The term "hsa-miR-6090 gene" or "hsa-miR-6090" used herein includes the hsa-miR-6090 gene (miRBase Accession No. MIMAT0023715) described in SEQ ID NO: 78, a homolog or an ortholog of a different organism species, and the like. The hsa-miR-6090 gene can be obtained by a method described in Yoo J K et al., 2013, Arch Pharm Res., Vol. 36, p. 353-358. Also, "hsa-mir-6090" (miRBase Accession No. MI0020367, SEQ ID NO: 201) having a hairpin-like structure is known as a precursor of "hsa-miR-6090".

The term "hsa-miR-4534 gene" or "hsa-miR-4534" used herein includes the hsa-miR-4534 gene (miRBase Accession No. MIMAT0019073) described in SEQ ID NO: 79, a homolog or an ortholog of a different organism species, and the like. The hsa-miR-4534 gene can be obtained by a method described in Jima D D et al., 2010, Blood., Vol. 116, e118-e127. Also, "hsa-mir-4534" (miRBase Accession No. MI0016901, SEQ ID NO: 202) having a hairpin-like structure is known as a precursor of "hsa-miR-4534".

The term "hsa-miR-4449 gene" or "hsa-miR-4449" used herein includes the hsa-miR-4449 gene (miRBase Accession No. MIMAT0018968) described in SEQ ID NO: 80, a homolog or an ortholog of a different organism species, and the like. The hsa-miR-4449 gene can be obtained by a method described in Jima D D et al., 2010, Blood., Vol. 116, e118-e127. Also, "hsa-mir-4449" (miRBase Accession No. MI0016792, SEQ ID NO: 203) having a hairpin-like structure is known as a precursor of "hsa-miR-4449".

The term "hsa-miR-5195-3p gene" or "hsa-miR-5195-3p" used herein includes the hsa-miR-5195-3p gene (miRBase Accession No. MIMAT0021127) described in SEQ ID NO: 81, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 204) having a hairpin-like structure is known as a precursor of "hsa-miR-5195-3p".

The term "hsa-miR-1202 gene" or "hsa-miR-1202" used herein includes the hsa-miR-1202 gene (miRBase Accession No. MIMAT0005865) described in SEQ ID NO: 82, a homolog or an ortholog of a different organism species, and the like. The hsa-miR-1202 gene can be obtained by a method described in Marton S et al., 2008, Leukemia, Vol. 22, p. 330-338. Also, "hsa-mir-1202" (miRBase Accession No. MI0006334, SEQ ID NO: 205) having a hairpin-like structure is known as a precursor of "hsa-miR-1202".

The term "hsa-miR-4467 gene" or "hsa-miR-4467" used herein includes the hsa-miR-4467 gene (miRBase Accession No. MIMAT0018994) described in SEQ ID NO: 83, a homolog or an ortholog of a different organism species, and the like. The hsa-miR-4467 gene can be obtained by a method described in Jima D D et al., 2010, Blood., Vol. 116, e118-e127. Also, "hsa-mir-4467" (miRBase Accession No. MI0016818, SEQ ID NO: 06) having a hairpin-like structure is known as a precursor of "hsa-miR-4467".

The term "hsa-miR-6515-3p gene" or "hsa-miR-6515-3p" used herein includes the hsa-miR-6515-3p gene (miRBase Accession No. MIMAT0025487) described in SEQ ID NO: 84, a homolog or an ortholog of a different organism species, and the like. The hsa-miR-6515-3p gene can be obtained by a method described in Joyce C E et al., 2011, Hum Mol Genet., Vol. 20, p. 4025-4040. Also, "hsa-mir-6515" (miRBase Accession No. MI0022227, SEQ ID NO: 207) having a hairpin-like structure is known as a precursor of "hsa-miR-6515-3p".

The term "hsa-miR-4281 gene" or "hsa-miR-4281" used herein includes the hsa-miR-4281 gene (miRBase Accession No. MIMAT001.6907) described in SEQ ID NO: 85, a homolog or an ortholog of a different organism species, and the like. The hsa-miR-4281 gene can be obtained by a method described in Goff L A et al., 2009, PLoS One., Vol. 4, e7192. Also, "hsa-mir-4281" (miRBase Accession No. MI0015885, SEQ ID NO: 208) having a hairpin-like structure is known as a precursor of "hsa-miR-4281".

The term "hsa-miR-4505 gene" or "hsa-miR-4505" used herein includes the hsa-miR-4505 gene (miRBase Accession No. MIMAT0019041) described in SEQ ID NO: 86, a homolog or an ortholog of a different organism species, and the like. The hsa-miR-4505 gene can be obtained by a method described in Jima D D et al., 2010, Blood., Vol. 116, e118-e127. Also, "hsa-mir-4505" (miRBase Accession No. NI10016868, SEQ ID NO: 209) having a hairpin-like structure is known as a precursor of "hsa-miR-4505".

The term "hsa-miR-4484 gene" or "hsa-miR-4484" used herein includes the hsa-miR-4484 gene (miRBase Accession No. MIMAT0019018) described in SEQ ID NO: 87, a homolog or an ortholog of a different organism species, and the like. The hsa-miR-4484 gene can be obtained by a method described in Jima D D et al., 2010, Blood., Vol. 116, e118-e127. Also, "hsa-mir-4484" (miRBase Accession No. MI0016845, SEQ ID NO: 210) having a hairpin-like structure is known as a precursor of "hsa-miR-4484".

The term "hsa-miR-6805-3p gene" or "hsa-miR-6805-3p" used herein includes the hsa-miR-6805-3p gene (miRBase Accession No. MIMAT0027511) described in SEQ ID NO: 88, a homolog or an ortholog of a different organism species, and the like. The hsa-miR-6805-3p gene can be obtained by a method described in Ladewig E et al., 2012, Genome Res., Vol. 22, p. 1634-1645. Also, "hsa-mir-6805" (miRBase Accession No. MI0022650, SEQ ID NO: 211) having a hairpin-like structure is known as a precursor of "hsa-miR-6805-3p".

The term "hsa-miR-3135b gene" or "hsa-miR-3135b" used herein includes the hsa-miR-3135b gene (miRBase Accession No. MIMAT0018985) described in SEQ ID NO: 89, a homolog or an ortholog of a different organism species, and the like. The hsa-miR-3135b gene can be obtained by a method described in Jima D D et al., 2010, Blood., Vol. 116, e118-e127. Also, "hsa-mir-3135b" (miRBase Accession No. MI0016809, SEQ ID NO: 212) having a hairpin-like structure is known as a precursor of "hsa-miR-3135b".

The term "hsa-miR-3162-5p gene" or "hsa-miR-3162-5p" used herein includes the hsa-miR-3162-5p gene (miRBase Accession No. MIMAT0015036) described in SEQ ID NO: 90, a homolog or an ortholog of a different organism species, and the like. The hsa-miR-3162-5p gene can be obtained by a method described in Stark M S et al., 2010, PLoS One., Vol. 5, e9685. Also, "hsa-mir-3162" (miRBase Accession No. MI0014192, SEQ ID NO: 213) having a hairpin-like structure is known as a precursor of "hsa-miR-3162-5p".

The term "hsa-miR-6768-5p gene" or "hsa-miR-6768-5p" used herein includes the hsa-miR-6768-5p gene (miRBase Accession No. MIMAT0027436) described in SEQ ID NO: 91, a homolog or an ortholog of a different organism species, and the like. The hsa-miR-6768-5p gene can be obtained by a method described in Ladewig E et al., 2012, Genome Res., Vol. 22, p. 1634-1645. Also, "hsa-mir-6768" (miRBase Accession No. MI0022613, SEQ ID NO: 214) having a hairpin-like structure is known as a precursor of "hsa-miR-6768-5p".

The term "hsa-miR-6721-5p gene" or "hsa-miR-6721-5p" used herein includes the hsa-miR-6721-5p gene (miRBase Accession No. MIMAT0025852) described in SEQ ID NO: 92, a homolog or an ortholog of a different organism species, and the like. The hsa-miR-6721-5p gene can be obtained by a method described in Li Y et al., 2012, Gene., Vol. 497, p. 330-335. Also, "hsa-mir-6721" (miRBase Accession No. MI0022556, SEQ ID NO: 215) having a hairpin-like structure is known as a precursor of "hsa-miR-6721-5p".

The term "hsa-miR-1227-5p gene" or "hsa-miR-1227-5p" used herein includes the hsa-miR-1227-5p gene (miRBase Accession No. MIMAT0022941) described in SEQ ID NO: 93, a hotnolog or an ortholog of a different organism species, and the like. The lisa-miR-1227-5p gene can be obtained by a method described in Berezikov E et al., 2007. Mol Cell., Vol. 28, p. 328-336. Also, "hsa-mir-1227" (miRBase Accession No. MI0006316, SEQ ID NO: 216) having a hairpin-like structure is known as a precursor of "hsa-miR-1227-5p".

The term "hsa-miR-6722-3p gene" or "hsa-miR-6722-3p" used herein includes the hsa-miR-6722-3p gene (miRBase Accession No. MIMAT0025854) described in SEQ ID NO: 94, a homolog or an ortholog of a different organism species, and the like. The hsa-miR-6722-3p gene can be obtained by a method described in Li Y et al., 2012, Gene., Vol. 497, p. 330-335. Also, "hsa-mir-6722" (miRBase Accession No. MI0022557, SEQ ID NO: 217) having a hairpin-like structure is known as a precursor of "hsa-miR-6722-3p".

The term "hsa-miR-4286 gene" or "hsa-miR-4286" used herein includes the hsa-miR-4286 gene (miRBase Accession No. MIMAT0016916) described in SEQ ID NO: 95, a homolog or an ortholog of a different organism species, and the like. The hsa-miR-4286 gene can be obtained by a method described in Goff L A et al., 2009, PLoS One., Vol. 4, e7192. Also, "hsa-mir-4286" (miRBase Accession No. MI0015894, SEQ ID NO: 218) having a hairpin-like structure is known as a precursor of "hsa-miR-4286".

The term "hsa-miR-4746-3p gene" or "hsa-miR-4746-3p" used herein includes the hsa-miR-4746-3p gene (miRBase Accession No. MIMAT0019881) described in SEQ ID NO: 96, a homolog or an ortholog of a different organism species, and the like. The hsa-miR-4746-3p gene can be obtained by a method described in Persson H et al., 2011, Cancer Res., Vol. 71, p. 78-86. Also, "hsa-mir-4746" (miRBase Accession No. MI0017385, SEQ ID NO: 219) having a hairpin-like structure is known as a precursor of "hsa-miR-4746-3p".

The term "hsa-miR-6727-5p gene" or "hsa-miR-6727-5p" used herein includes the hsa-miR-6727-5p gene (miRBase Accession No. MLMAT0027355) described in SEQ ID NO: 97, a homolog or an ortholog of a different organism species, and the like. The hsa-miR-6727-5p gene can be obtained by a method described in Ladewig E et al., 2012, Genome Res., Vol. 22, p. 1634-1645. Also, "hsa-mir-6727" (miRBase Accession No. MI0022572, SEQ ID NO: 220) having a hairpin-like structure is known as a precursor of "hsa-miR-6727-5p".

The tem "hsa-miR-6816-5p gene" or "hsa-miR-6816-5p" used herein includes the hsa-miR-6816-5p gene (miRBase Accession No. MIMAT0027532) described in SEQ ID NO: 98, a homolog or an ortholog of a different organism species, and the like. The hsa-miR-6816-5p gene can be obtained by a method described in Ladewig E et al., 2012, Genome Res., Vol. 22, p. 1634-1645. Also, "hsa-mir-6816" (miRBase Accession No. MI0022661, SEQ ID NO: 221) having a hairpin-like structure is known as a precursor of "hsa-miR-6816-5p".

The term "hsa-miR-4741 gene" or "hsa-miR-4741" used herein includes the hsa-miR-4741 gene (miRBase Accession No. MIMATOO19871) described in SEQ ID NO: 99, a homolog or an ortholog of a different organism species, and the like. The hsa-miR-4741 gene can be obtained by a method described in Persson H et al., 2011, Cancer Res., Vol. 71, p. 78-86. Also, "hsa-mir-4741" (miRBase Accession No. MI0017379, SEQ ID NO: 222) having a hairpin-like structure is known as a precursor of "hsa-miR-4741".

The term "hsa-miR-4508 gene" or "hsa-miR-4508" used herein includes the hsa-miR-4508 gene (miRBase Accession No. MIMAT0019045) described in SEQ ID NO: 100, a homolog or an ortholog of a different organism species, and the like. The hsa-miR-4508 gene can be obtained by a method described in Jima D D et al., 2010, Blood., Vol. 116, e118-e127. Also, "hsa-mir-4508" (miRBase Accession No. MI0016872, SEQ ID NO: 223) having a hairpin-like structure is known as a precursor of "hsa-miR-4508".

The term "hsa-miR-940 gene" or "hsa-miR-940" used herein includes the hsa-miR-940 gene miRBase Accession No. MIMAT0004983) described in SEQ ID NO: 101, a homolog or an ortholog of a different organism species, and the like. The hsa-miR-940 gene can be obtained by a method described in Lui W O et al., 2007, A Cancer Res., Vol. 67, p. 6031-6043. Also, "hsa-mir-940" (miRBase Accession No. MI0005762, SEQ ID NO: 224) having a hairpin-like structure is known as a precursor of "hsa-miR-940".

The term "hsa-miR-4327 gene" or "hsa-miR-4327" used herein includes the hsa-miR-4327 gene (miRBase Accession No. MIMAT0016889) described in SEQ ID NO: 102, a homolog or an ortholog of a different organism species, and the like. The hsa-miR-4327 gene can be obtained by a method described in Golf L A et al., 2009, PLoS One., Vol. 4, e7192. Also, "hsa-mir-4327" (miRBase Accession No. MI0015867, SEQ ID NO: 225) having a hairpin-like structure is known as a precursor of "hsa-miR-4327".

The term "hsa-miR-4665-3p gene" or "hsa-miR-4665-3p" used herein includes the hsa-miR-4665-3p gene (miRBase Accession No. MIMAT0019740) described in SEQ ID NO: 103, a homolog or an ortholog of a different organism species, and the like. The hsa-miR-4665-3p gene can be obtained by a method described in Persson H et al., 2011, Cancer Res., Vol. 71, p. 78-86. Also, "hsa-mir-4665" (miRBase Accession No. MI0017295, SEQ ID NO: 159) having a hairpin-like structure is known as a precursor of "hsa-miR-4665-3p".

The term "hsa-miR-718 gene" or "hsa-miR-718" used herein includes the hsa-miR-718 gene (miRBase Accession No. MIMAT0012735) described in SEQ ID NO: 104, a homolog or an ortholog of a different organism species, and the like. The hsa-miR-718 gene can be obtained by a method described in Artzi S et al., 2008, BMC Bioinformatics., Vol. 9, p. 39. Also, "hsa-mir-718" (miRBase Accession No. MI0012489, SEQ ID NO: 226) having a hairpin-like structure is known as a precursor of "hsa-miR-718".

The term "hsa-miR-125a-3p gene" or "hsa-miR-125a-3p" used herein includes the hsa-miR-125a-3p gene (miRBase Accession No. MIMAT0004602) described in SEQ ID NO: 105, a homolog or an ortholog of a different organism species, and the like. The hsa-miR-125a-3p gene can be obtained by a method described in Lagos-Quintana M et al., 2002. Curr Biol., Vol. 12, p. 735-739. Also, "hsa-mir-125a" (miRBase Accession No. MI0000469, SEQ ID NO: 227) having a hairpin-like structure is known as a precursor of "hsa-miR-125a-3p".

The term "hsa-miR-204-3p gene" or "hsa-miR-204-3p" used herein includes the hsa-miR-204-3p gene (miRBase Accession No. MIMAT0022693) described in SEQ ID NO: 106, a homolog or an ortholog of a different organism species, and the like. The hsa-miR-204-3p gene can be obtained by a method described in Lim L P et al., 2003, Science., Vol. 299, p. 1540. Also, "hsa-mir-204" (miRBase Accession No. MI0000284, SEQ ID NO: 228) having a hairpin-like structure is known as a precursor of "hsa-miR-204-3p".

The term "hsa-miR-1469 gene" or "hsa-miR-1469" used herein includes the hsa-miR-1469 gene (miRBase Accession No. MIMAT0007347) described in SEQ ID NO: 107, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 229) having a hairpin-like structure is known as a precursor of "hsa-miR-1469".

The term "hsa-miR-575 gene" or "hsa-miR-575" used herein includes the hsa-miR-575 gene (miRBase Accession No. MIMAT0003240) described in SEQ ID NO: 108, a homolog or an ortholog of a different organism species, and the like. The hsa-miR-575 gene can be obtained by a method described in Cummins J M, 2006, Proc Natl Acad Sci, Vol. 103, p. 3687-3692. Also, "hsa-mir-575" (miRBase Accession No. MI0003582, SEQ ID NO: 230) having a hairpin-like structure is known as a precursor of "hsa-miR-575".

The term "hsa-miR-150-3p gene" or "hsa-miR-150-3p" used herein includes the hsa-miR-150-3p gene (miRBase Accession No. MIMAT0004610) described in SEQ ID NO: 109, a homolog or an ortholog of a different organism species, and the like. The hsa-miR-150-3p gene can be obtained by a method described in Lagos-Quintana M et al., 2002. Curr Biol., Vol. 12, p. 735-739. Also, "hsa-mir-150" (miRBase Accession No. MI0000479, SEQ ID NO: 231) having a hairpin-like structure is known as a precursor of "hsa-miR-150-3p".

The term "hsa-miR-423-5p gene" or "hsa-miR-423-5p" used herein includes the hsa-miR-423-5p gene (miRBase Accession No. MIMAT0004748) described in SEQ ID NO: 110, a homolog or an ortholog of a different organism species, and the like. The hsa-miR-423-5p gene can be obtained by a method described in Kasashima K et al., 2004, Biochem Biophys Res Commun., Vol. 322, p. 403-410. Also, "hsa-mir-423" (miRBase Accession No. MI0001445, SEQ ID NO: 232) having a hairpin-like structure is known as a precursor of "hsa-miR-423-5p".

The term "hsa-miR-564 gene" or "hsa-miR-564" used herein includes the hsa-miR-564 gene miRBase Accession No. MIMAT0003228) described in SEQ ID NO: 111, a homolog or art ortholog of a different organism species, and the like. The hsa-miR-564 gene can be obtained by a method described in Cummins J M, 2006, Proc Natl Acad Sci, Vol. 103, p. 3687-3692. Also, "hsa-mir-564" (miRBase Accession No. MI0003570, SEQ ID NO: 233) having a hairpin-like structure is known as a precursor of "hsa-miR-564".

The term "hsa-miR-3188 gene" or "hsa-miR-3188" used herein includes the hsa-miR-3188 gene (miRBase Accession No. MIMAT0015070) described in SEQ ID NO: 112, a homolog or an ortholog of a different organism species, and the like. The hsa-miR-3188 gene can be obtained by a method described in Stark M S et al., 2010, PLoS One., Vol. 5, e9685. Also, "hsa-mir-3188" (miRBase Accession No. MI0014232, SEQ ID NO: 234) having a hairpin-like structure is known as a precursor of "hsa-miR-3188".

The term "hsa-miR-1246 gene" or "hsa-miR-1246" used herein includes the hsa-miR-1246 gene (miRBase Accession No. MIMAT0005898) described in SEQ ID NO: 113, a homolog or an ortholog of a different organism species, and the like. The hsa-miR-1246 gene can be obtained by a method described in Morin R D et al., 2008, Genome Res., Vol. 18, p. 610-621. Also, "hsa-mir-1246" (miRBase Accession No. MI0006381, SEQ ID NO: 235) having a hairpin-like structure is known as a precursor of "hsa-miR-1246".

The term "hsa-miR-602 gene" or "hsa-miR-602" used herein includes the hsa-miR-602 gene (miRBase Accession No. MIMAT0003270) described in SEQ ID NO: 114, a homolog or an ortholog of a different organism species, and the like. The hsa-miR-602 gene can be obtained by a method described in Cummins J M, 2006, Proc Natl Acad Sci, Vol.

103, p. 3687-3692. Also, "hsa-mir-602" (miRBase Accession No. MI0003615, SEQ ID NO: 236) having a hairpin-like structure is known as a precursor of "hsa-miR-602".

The term "hsa-miR-1290 gene" or "hsa-miR-1290" used herein includes the hsa-miR-1290 gene (miRBase Accession No. MIMAT0005880) described in SEQ ID NO: 115, a homolog or an ortholog of a different organism species, and the like. The hsa-miR-1290 gene can be obtained by a method described in Morin R D et al., 2008. Genome Res., Vol. 18, p. 610-621. Also, "hsa-mir-1290" (miRBase Accession No. MI0006352, SEQ ID NO: 237) having a hairpin-like structure is known as a precursor of "hsa-miR-1290".

The term "hsa-miR-16-5p gene" or "hsa-miR-16-5p" used herein includes the hsa-miR-16-5p gene (miRBase Accession No. MiMAT0000069) described in SEQ ID NO: 116, a homolog or an ortholog of a different organism species, and the like. The hsa-miR-16-5p gene can be obtained by a method described in Lagos-Quintana M et al., 2002, Curr Biol., Vol. 12, p. 735-739. Also, "hsa-mir-16-1 and hsa-mir-16-2" (miRBase Accession Nos. MI0000070 and MI0000115, SEQ ID NOs: 238 and 239) having a hairpin-like structure are known as precursors of "hsa-miR-16-5p".

The term "hsa-miR-451a gene" or "hsa-miR-451a" used herein includes the hsa-miR-451a gene (miRBase Accession No. MINLAT0001631) described in SEQ ID NO: 117, a homolog or an ortholog of a different organism species, and the like. The hsa-miR-451a gene can be obtained by a method described in Alluvia Y et al., 2005, Nucleic Acids Res., Vol. 33, p. 2697-2706. Also, "hsa-mir-451a" (miRBase Accession No. MI0001729, SEQ ID NO: 240) having a hairpin-like structure are known as precursors of "hsa-miR-451a".

The term "hsa-miR-24-3p gene" or "hsa-miR-24-3p" used herein includes the hsa-miR-24-3p gene (miRBase Accession No. MIMAT0000080) described in SEQ ID NO: 118, a homolog or an ortholog of a different organism species, and the like. The hsa-miR-24-3p gene can be obtained by a method described in Lagos-Quintana M et al., 2001, Science., Vol. 294, p. 853-858. Also, "hsa-mir-24-1 and hsa-mir-24-2" (miRBase Accession Nos. MI0000080 and MI0000081, SEQ ID NOs: 241 and 242) having a hairpin-like structure are known as precursors of "hsa-miR-24-3p".

The term "hsa-miR-5p gene" "hsa-miR-187-5p" used herein includes the hsa-miR-187-5p gene (miRBase Accession No. MIMAT0004561) described in SEQ ID NO: 119, a homolog or an ortholog of a different organism species, and the like. The hsa-miR-187-5p gene can be obtained by a method described in Lim L P et al., 2003, Science., Vol. 299, p. 1540. Also, "hsa-mir-187" (miRBase Accession No. MI0000274, SEQ ID NO: 243) having a hairpin-like structure are known as precursors of "hsa-miR-187-5p".

The term "hsa-miR-1908-5p gene" or "hsa-miR-1908-5p" used herein includes the hsa-miR-1908-5p gene (miRBase Accession No. MIMAT0007881) described in SEQ ID NO: 120, a homolog or an ortholog of a different organism species, and the like. The hsa-miR-1908-5p gene can be obtained by a method described in Bar M et al., 2008, Stem Cells., Vol. 26, p. 2496-2505. Also, "hsa-mir-1908" (miRBase Accession No. MI0008329, SEQ ID NO: 244) having a hairpin-like structure are known as precursors of "hsa-miR-1908-5p".

The term "hsa-miR-371a-5p gene" or "hsa-miR-371a-5p" used herein includes the hsa-miR-371a-5p gene (miRBase Accession No. MIMAT0004687) described in SEQ ID NO: 121, a homolog or an ortholog of a different organism species, and the like. The hsa-miR-371a-5p gene can be obtained by a method described in Suh M R et al., 2004, Dev Biol., Vol. 270, p. 488-498. Also, "hsa-mir-371a" (miRBase Accession No. MI0000779, SEQ ID NO: 245) having a hairpin-like structure are known as precursors of "hsa-miR-371a-5p".

The term "hsa-miR-550a-5p gene" or "hsa-miR-550a-5p" used herein includes the hsa-miR-550a-5p gene (miRBase Accession No. MIMAT0004800) described in SEQ ID NO: 122, a homolog or an ortholog of a different organism species, and the like. The hsa-miR-550a-5p gene can be obtained by a method described in Cummins J M, 2006, Proc Natl Acad Sci, Vol. 103, p. 3687-3692. Also, "hsa-mir-550a-1 and hsa-mir-550a-2" (miRBase Accession Nos. MI0003600 and MI0003601, SEQ ID NOs: 246 and 247) having a hairpin-like structure are known as precursors of "hsa-miR-550a-5p".

The term "hsa-miR-4417 gene" or "hsa-miR-4417" used herein includes the hsa-miR-4417 gene (miRBase Accession No. MIMAT0018929) described in SEQ ID NO: 349, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 384) having a hairpin-like structure are known as precursors of "hsa-miR-4417".

The term "hsa-miR-4707-5p gene" or "hsa-miR-4707-5p" used herein includes the hsa-miR-4707-5p gene (miRBase Accession No. MIMAT0019807) described in SEQ ID NO: 350, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 385) having a hairpin-like structure are known as precursors of "hsa-miR-4707-5p".

The term "hsa-miR-7847-3p gene" or "hsa-miR-7847-3p" used herein includes the hsa-miR-7847-3p gene (miRBase Accession No. MIMAT0030422) described in SEQ ID NO: 351, a homolog or an ortholog of a different organism species, and the like. The hsa-miR-7847-3p gene can be obtained by a method described in Pie H et al., 2012, PLoS One, Vol. 7, e50746. Also, "hsa-mir-7847" (miRBase Accession No. MI0025517, SEQ ID NO: 386) having a hairpin-like structure are known as precursors of "hsa-miR-7847-3p".

The term "hsa-miR-2861 gene" or "hsa-miR-2861" used herein includes the hsa-miR-2861 gene (miRBase Accession No. MIMAT0013802) described in SEQ ID NO: 352, a homolog or an ortholog of a different organism species, and the like. The hsa-miR-2861 gene can be obtained by a method described in Li H et al., 2009, J Clin Invest, Vol. 119, p. 3666-3677. Also, "hsa-mir-2861" (miRBase Accession No. MI0013006, SEQ ID NO: 387) having a hairpin-like structure are known as precursors of "hsa-miR-2861".

The term "hsa-miR-4513 gene" or "hsa-miR-4513" used herein includes the hsa-miR-4513 gene (miRBase Accession No. MIMAT0019050) described in SEQ ID NO: 353, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 388) having a hairpin-like structure are known as precursors of "hsa-miR-4513".

The term "hsa-miR-7111-5p gene" or "hsa-miR-7111-5p" used herein includes the hsa-miR-7111-5p gene (miRBase Accession No. MIMAT0028119) described in SEQ ID NO:

354, a homolog or an ortholog of a different organism species, and the like. The hsa-miR-7111-5p gene can be obtained by a method described in Ladewig E et al., 2012, Genome Res, Vol. 22, p. 1634-1645. Also, "hsa-mir-7111" (miRBase Accession No. MI0022962, SEQ ID NO: 389) having a hairpin-like structure are known as precursors of "hsa-miR-7111-5p".

The term "hsa-miR-6777-5p gene" or "hsa-miR-6777-5p" used herein includes the hsa-miR-6777-5p gene (miRBase Accession No. MIMAT0027454) described in SEQ ID NO: 355, a homolog or an ortholog of a different organism species, and the like. The lisa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 390) having a hairpin-like structure are known as precursors of "hsa-miR-6777-5p".

The tem "hsa-miR-7113-3p gene" or "hsa-miR-7113-3p" used herein includes the hsa-miR-7113-3p gene (miRBase Accession No. MIMAT0028124) described in SEQ ID NO: 356, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 391) having a hairpin-like structure are known as precursors of "hsa-miR-7113-3p".

The term "hsa-miR-4648 gene" or "hsa-miR-4648" used herein includes the hsa-miR-4648 gene (miRBase Accession No. MIMAT0019710) described in SEQ ID NO: 357, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 392) having a hairpin-like structure are known as precursors of "hsa-miR-4648".

The term "hsa-miR-3184-5p gene" or "hsa-miR-3184-5p" used herein includes the hsa-miR-3184-5p gene (miRBase Accession No. MIMAT0015064) described in SEQ ID NO: 358, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 393) having a hairpin-like structure are known as precursors of "hsa-miR-3184-5p".

The term "hsa-miR-4271 gene" or "hsa-miR-4271" used herein includes the hsa-miR-4271 gene (miRBase Accession No. MIMAT0016901) described in SEQ ID NO: 359, a homolog or an ortholog of a different organism species, and the like. The hsa-miR-4271 gene can be obtained by a method described in Goff L A. et al., 2009, PLoS One, Vol. 4, e7192. Also, "hsa-mir-4271" (miRBase Accession No. MI0015879, SEQ ID NO: 394) having a hairpin-like structure are known as precursors of "hsa-miR-4271".

The tem "hsa-miR-6791-5p gene" or "hsa-miR-6791-5p" used herein includes the hsa-miR-6791-5p gene (miRBase Accession No. MIMAT0027482) described in SEQ ID NO: 360, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 395) having a hairpin-like structure are known as precursors of "hsa-miR-6791-5p".

The term "hsa-miR-642a-3p gene" or "hsa-miR-642a-3p" used herein includes the hsa-miR-642a-3p gene (miRBase Accession No. MIMAT0020924) described in SEQ ID NO: 361, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692, Landgraf P et al., 2007, Cell, Vol. 129, p. 1401-1414, Zaragosi L E et al., 2011, Genome Biol, Vol. 12, R64, etc. Also, "hsa-mir-642a" (miRBase Accession No. MI0003657, SEQ ID NO: 396) having a hairpin-like structure is known as a precursor of "hsa-miR-642a-3p".

The term "hsa-miR-7108-5p gene" or "hsa-miR-7108-5p" used herein includes the hsa-miR-7108-5p gene (miRBase Accession No. MIMAT0028113) described in SEQ ID NO: 362, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 397) having a hairpin-like structure is known as a precursor of "hsa-miR-7108-5p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 363, a homolog or an ortholog of a different organism species, and the like. The hsa-miR-128-1-5p gene can be obtained by a method described in Lagos-Quintana M et al., 2002, Curr Biol, Vol. 12, p. 735-739, Kasashima K et al., 2004, Biochem Biophys Res Commun, Vol. 322, p. 403-410, Landgraf P et al., 2007, Cell, Vol. 129, p. 1401-1414, Meunier J et al., 2013, Genome Res, Vol. 23, p. 34-45, etc. Also, "hsa-mir-128-1" (miRBase Accession No. MI0000447, SEQ ID NO: 398) having a hairpin-like structure is known as a precursor of "hsa-miR-128-1-5p".

The term "hsa-miR-5196-5p gene" or "hsa-miR-5196-5p" used herein includes the hsa-miR-5196-5p gene miRBase Accession No. MIMAT00211281) described in SEQ ID NO: 364, a homolog or an ortholog of a different organism species, and the like. The hsa-miR-5196-5p gene can be obtained by a method described in Schotte D et al., 2011, Leukemia, Vol. 25, p. 1389-1399. Also, "hsa-mir-5196" (miRBase Accession No. MI0018175, SEQ ID NO: 399) having a hairpin-like structure is known as a precursor of "hsa-miR-5196-5p".

The term "hsa-miR-3178 gene" or "hsa-miR-3178" used herein includes the hsa-miR-3178 gene (miRBase Accession No. MIMAT0015055) described in SEQ ID NO: 365, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212, SEQ ID NO: 400) having a hairpin-like structure is known as a precursor of "hsa-miR-3178".

The term "hsa-miR-3656 gene" or "hsa-miR-3656" used herein includes the hsa-miR-3656 gene (miRBase Accession No. MIMAT0018076) described in SEQ ID NO: 366, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 401) having a hairpin-like structure is known as a precursor of "hsa-miR-3656".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 367, a homolog or an ortholog of a different organism species, and the like. The hsa-miR-92a-2-5p gene can be obtained by a method described in Mourelatos Z et al., 2002, Genes Dev, Vol. 16, p. 0-728, Dostie J et al., 2003, RNA, Vol. 9, p. 180-186, Houbaviy H E et al., 2003, Dev Cell, Vol. 5, p. 351-358, Suh M R et al., 2004, Dev Biol, Vol. 270, p. 488-498, Kasashima K et al., 2004, Biochem Biophys Res Commun, Vol. 322, p. 403-410, Fu et al., 2005, FEBS Lett, Vol. 579, p. 3849-3854, Landgraf P et al., 2007, Cell, Vol. 129, p. 1401-1414, Lui W O et al., 2007, Cancer Res, Vol. 67, p. 6031-6043, etc. Also, "hsa-mir-92a-2" (miRBase Accession No. MI0000094, SEQ ID NO: 402) having a hairpin-like structure is known as a precursor of "hsa-miR-92a-2-5p".

The term "hsa-miR-6769h-5p gene" or "hsa-miR-6769b-5p" used herein includes the hsa-miR-6769b-5p gene (miRBase Accession No. MIMAT0027620) described in SEQ ID NO: 368, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 403) having a hairpin-like structure is known as a precursor of "hsa-miR-6769b-5p".

The term "hsa-miR-4689 gene" or "hsa-miR-4689" used herein includes the hsa-miR-4689 gene (miRBase Accession No. MIMAT0019778) described in SEQ ID NO: 369, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 404) having a hairpin-like structure is known as a precursor of "hsa-miR-4689".

The term "hsa-miR-6076 gene" or "hsa-miR-6076" used herein includes the hsa-miR-6076 gene (miRBase Accession No. MIMAT0023701) described in SEQ ID NO: 370, a homolog or an ortholog of a different organism species, and the like. The hsa-miR-6076 gene can be obtained by a method described in Voellenkle C et al., 2012, RNA, Vol. 18, p. 472-484. Also, "hsa-mir-6076" (miRBase Accession No. MI0020353, SEQ ID NO: 405) having a hairpin-like structure is known as a precursor of "hsa-miR-6076".

The term "hsa-miR-92b-5p gene" or "hsa-miR-92b-5p" used herein includes the hsa-miR-92b-5p gene (miRBase Accession No. MIMAT0004792) described in SEQ ID NO: 371, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692, Landgraf P et al., 2007, Cell, Vol. 129, p. 1401-1414. Lui W O et al., 2007, Cancer Res, Vol. 67, p. 6031-6043, etc. Also, "hsa-mir-92b" (miRBase Accession No. MI0003560, SEQ ID NO: 406) having a hairpin-like structure is known as a precursor of "hsa-miR-92b-5p".

The term "hsa-miR-6774-5p gene" or "hsa-miR-6774-5p" used herein includes the hsa-miR-6774-5p gene (miRBase Accession No. MIMAT0027448) described in SEQ ID NO: 372, a homolog or an ortholog of a different organism species, and the like. The hsa-miR-6774-5p gene can be obtained by a method described in Ladewig E et al., 2012, Genome Res, Vol. 22, p. 1634-1645. Also, "hsa-mir-6774" (miRBase Accession No. MI0022619, SEQ ID NO: 407) having a hairpin-like structure is known as a precursor of "hsa-miR-6774-5p".

The term "hsa-miR-486-3p gene" or "hsa-miR-486-3p" used herein includes the hsa-miR-486-3p gene (miRBase Accession No. MIMAT0004762) described in SEQ ID NO: 373, a homolog or an ortholog of a different organism species, and the like. The hsa-miR-486-3p gene can be obtained by a method described in Fu H et al., 2005, FEBS Lett, Vol. 579, p. 3849-3854, Landgraf P et al., 2007, Cell, Vol. 129, p. 1401-1414, Meunier J et al., 2013, Genome Res. Vol. 23, p, 34-45, etc. Also, "hsa-mir-486 and hsa-mir-486-2" (miRBase Accession Nos. MI0002470 and MI0023622, SEQ ID NOs: 408 and 409) having a hairpin-like structure are known as precursors of "hsa-miR-486-3p".

The term "hsa-miR-6806-5p gene" or "hsa-miR-6806-5p" used herein includes the hsa-miR-6806-5p gene (miRBase Accession No. MIMAT0027512) described in SEQ ID NO: 374, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 410) having a hairpin-like structure is known as a precursor of "hsa-miR-6806-5p".

The term "hsa-miR-6842-5p gene" or "hsa-miR-6842-5p" used herein includes the hsa-miR-6842-5p gene (miRBase Accession No. MIMAT0027586) described in SEQ ID NO: 375, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 411) having a hairpin-like structure is known as a precursor of "hsa-miR-6842-5p".

The term "hsa-miR-6716-5p gene" or "hsa-miR-6716-5p" used herein includes the hsa-miR-6716-5p gene (miRBase Accession No. MIMA10025844) described in SEQ ID NO: 376, a homolog or an ortholog of a different organism species, and the like. The hsa-miR-6716-5p gene can be obtained by a method described in Li Y et al., 2012, Gene., Vol. 497, p. 330-335. Also, "hsa-mir-6716" (miRBase Accession No. MI0022550, SEQ ID NO: 412) having a hairpin-like structure is known as a precursor of "hsa-miR-6716-5p".

The term "hsa-miR-557 gene" or "hsa-miR-557" used herein includes the hsa-miR-557 gene (miRBase Accession No. MIMAT0003221) described in SEQ ID NO: 377, a homolog or an ortholog of a different organism species, and the like. The hsa-miR-557 gene can be obtained by a method described in Cummins J M et al., 2006, Proc Natl Acad Sci USA, Vol. 103, p. 3687-3692. Also, "hsa-mir-557" (miRBase Accession No. MI0003563, SEQ ID NO: 413) having a hairpin-like structure is known as a precursor of "hsa-miR-557".

The term "hsa-miR-4673 gene" or "hsa-miR-4673" used herein includes the hsa-miR-4673 gene (miRBase Accession No. MIMAT0019755) described in SEQ ID NO: 378, a homolog or an ortholog of a different organism species, and the like. The hsa-miR-4673 gene can be obtained by a method described in Persson H et al., 2011, Cancer Res, Vol. 71, p. 78-86. Also, "hsa-mir-4673" (miRBase Accession No. MI0017304, SEQ ID NO: 414) having a hairpin-like structure is known as a precursor of "hsa-miR-4673".

The term "hsa-miR-4674 gene" or "hsa-miR-4674" used herein includes the hsa-miR-4674 gene (miRBase Accession No. MIMAT0019756) described in SEQ ID NO: 379, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 4151) having a hairpin-like structure is known as a precursor of "hsa-miR-4674".

The term "hsa-miR-4442 gene" or "hsa-miR-4442" used herein includes the hsa-miR-4442 gene (miRBase Accession No. MIMAT0018960) described in SEQ ID NO: 380, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 416) having a hairpin-like structure is known as a precursor of "hsa-miR-4442".

The tem "hsa-miR-1915-3p gene" or "hsa-miR-1915-3p" used herein includes the hsa-miR-1915-3p gene (miRBase Accession No. MIMAT0007892) described in SEQ ID NO: 381, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 417) having a hairpin-like structure is known as a precursor of "hsa-miR-1915-3p".

The term "hsa-miR-4687-3p gene" or "hsa-miR-4687-3p" used herein includes the hsa-miR-4687-3p gene (miRBase Accession No. MIMAT0019775) described in SEQ ID NO: 382, a homolog or an ortholog of a different organism species, and the like. The hsa-miR-4687-3p gene can be obtained by a method described in Persson H et al., 2011, Cancer Res, Vol. 71, p. 78-86. Also, "hsa-mir-4687" (miRBase Accession No. MI0017319, SEQ ID NO: 418) having a hairpin-like structure is known as a precursor of "hsa-miR-4687-3p".

The term "hsa-miR-92b-3p gene" or "hsa-miR-92h-3p" used herein includes the hsa-miR-92b-3p gene (miRBase Accession No. MIMAT0003218) described in SEQ ID NO: 383, a homolog or an ortholog of a different organism species, and the like. The hsa-miR-92b-3p gene can be obtained by a method described in Cummins J M et al., 2006, Proc Natl Acad Sci USA, Vol. 103, p. 3687-3692, Landgraf P et al., 2007, Cell, Vol. 129, p. 1401-1414, Lui W O et al., 2007, Cancer Res, Vol. 67, p. 6031-6043. Also, "hsa-mir-92b" (miRBase Accession No. MI0003560, SEQ ID NO: 419) having a hairpin-like structure is known as a precursor of "hsa-miR-92b-3p".

The term "hsa-miR-1203 gene" or "hsa-miR-1203" used herein includes the hsa-miR-1203 gene (miRBase Accession No. MIMAT0005866) described in SEQ ID NO: 464, a homolog or an ortholog of a different organism species, and the like. The hsa-miR-1203 gene can be obtained by a method described in Marton S et al., 2008, Leukemia, Vol. 22, p. 330-338. Also, "hsa-mir-1203" (miRBase Accession No. MI0006335, SEQ ID NO: 467) having a hairpin-like structure is known as a precursor of "hsa-miR-1203".

The term "hsa-miR-663b gene" or "hsa-miR-663b" used herein includes the hsa-miR-663b gene (miRBase Accession No. MIMAT0005867) described in SEQ ID NO: 465, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 475) having a hairpin-like structure is known as a precursor of "hsa-miR-663b".

The term "hsa-miR-4258 gene" or "hsa-miR-4258" used herein includes the hsa-miR-4258 gene (miRBase Accession No. NIIMAT0016879) described in SEQ ID NO: 466, a homolog or an ortholog of a different organism species, and the like. The hsa-miR-4258 gene can be obtained by a method described in Goff L A et al., 2009, PLoS One., Vol. 4, e7192. Also, "hsa-mir-4258" (miRBase Accession No. MI0015857, SEQ ID NO: 476) having a hairpin-like structure is known as a precursor of "hsa-miR-4258".

The term "hsa-miR-4649-5p gene" or "hsa-miR-4649-5p" used herein includes the hsa-miR-4649-5p gene (miRBase Accession No. MIMAT0019711) described in SEQ ID NO: 467, a homolog or an ortholog of a different organism species, and the like. The hsa-miR-4649-5p gene can be obtained by a method described in Persson H et al., 2011, Cancer Res., Vol. 71, p. 78-86. Also, "hsa-mir-4649" (miRBase Accession No. MI0017276, SEQ ID NO: 4771) having a hairpin-like structure is known as a precursor of "hsa-miR-4649-5p".

The term "hsa-miR-4516 gene" or "hsa-miR-4516" used herein includes the hsa-miR-4516 gene (miRBase Accession No. MIMAT0019053) described in SEQ ID NO: 468, a homolog or an ortholog of a different organism species, and the like. The hsa-miR-4516 gene can be obtained by a method described in Jima D D et al., 2010, Blood., Vol. 116, e118-e127. Also, "hsa-mir-4516" (miRBase Accession No. MI0016882, SEQ ID NO: 478) having a hairpin-like structure is known as a precursor of "hsa-miR-4516".

The term "hsa-miR-3619-3p gene" or "hsa-miR-3619-3p" used herein includes the hsa-miR-3619-3p gene (miRBase Accession No. MIMAT0019219) described in SEQ ID NO: 469, a homolog or an ortholog of a different organism species, and the like. The hsa-miR-3619-3p gene can be obtained by a method described in Witten D et al., 2010, BMC Biol., Vol. 8, p. 58. Also, "hsa-mir-3619" (miRBase Accession No. MI0016009, SEQ ID NO: 479) having a hairpin-like structure is known as a precursor of "hsa-miR-3619-3p".

The term "hsa-miR-6826-5p gene" or "hsa-miR-6826-5p" used herein includes the hsa-miR-6826-5p gene (miRBase Accession No. MIMAT0027552) described in SEQ ID NO: 470, a homolog or an ortholog of a different organism species, and the like. The hsa-miR-6826-5p gene can be obtained by a method described in Ladewig E et al., 2012, Genome Res., Vol. 22, p. 1634-1645. Also, "hsa-mir-6826" (miRBase Accession No. MI0022671, SEQ ID NO: 480) having a hairpin-like structure is known as a precursor of "hsa-miR-6826-5p".

The term "hsa-miR-6757-5p gene" or "hsa-miR-6757-5p" used herein includes the hsa-miR-6757-5p gene miRBase Accession No. MIMAT0027414) described in SEQ ID NO: 471, a homolog or an ortholog of a different organism species, and the like. The hsa-miR-6757-5p gene can be obtained by a method described in Ladewig E et al., 2012, Genome Res., Vol. 22, p. 1634-1645. Also, "hsa-mir-6757" (miRBase Accession No. MI0022602, SEQ ID NO: 481) having a hairpin-like structure is known as a precursor of "hsa-miR-6757-5p".

The term "hsa-miR-3131 gene" or "hsa-miR-3131" used herein includes the hsa-miR-3131 gene (miRBase Accession No. MIMAT0014996) described in SEQ ID NO: 472, a homolog or an ortholog of a different organism species, and the like. The hsa-miR-3131 gene can be obtained by a method described in Stark M S et al., 2010, PLoS One., Vol. 5, e9685. Also, "hsa-mir-3131" (miRBase Accession No. MI0014151, SEQ ID NO: 482) having a hairpin-like structure is known as a precursor of "hsa-miR-3131".

The tem "hsa-miR-1343-3p gene" or "hsa-miR-1343-3p" used herein includes the hsa-miR-1343-3p gene (miRBase Accession No. MIMAT0019776) described in SEQ ID NO: 473, a homolog or an ortholog of a different organism species, and the like. The hsa-miR-1343-3p gene can be obtained by a method described in Persson H et al., 2011, Cancer Res., Vol. 71, p. 78-86. Also, "hsa-mir-1343" (miR- Base Accession No. MI0017320, SEQ ID NO: 483) having a hairpin-like structure is known as a precursor of "hsa-miR-1343-3p".

The term "hsa-miR-6775-5p gene" or "hsa-miR-6775-5p" used herein includes the hsa-miR-6775-5p gene (miRBase Accession No. MIMAT0027450) described in SEQ ID NO: 492, a homolog or an ortholog of a different organism species, and the like. The hsa-miR-6775-5p gene can be obtained by a method described in Ladewig E et al., 2012, Genome Res, Vol. 22, p. 1634-1645. Also, "hsa-mir-6775" (miRBase Accession No. MI0022620, SEQ ID NO: 495) having a hairpin-like structure is known as a precursor of "hsa-miR-6775-5p".

The term "hsa-miR-6813-5p gene" or "hsa-miR-6813-5p" used herein includes the hsa-miR-6813-5p gene (miRBase Accession No. MIMAT0027526) described in SEQ ID NO: 493, a homolog or an ortholog of a different organism species, and the like. The hsa-miR-6813-5p gene can be obtained by a method described in Ladewig E et al., 2012, Genome Res, Vol. 22, p. 1634-1645. Also, "hsa-mir-6813" (miRBase Accession No. MI0022658, SEQ ID NO: 496) having a hairpin-like structure is known as a precursor of "lisa-miR-6813-5p".

The term "hsa-miR-3940-5p gene" or "hsa-miR-3940-5p" used herein includes the hsa-miR-3940-5p gene miRBase Accession No. MIMAT0019229) described in SEQ ID NO: 494, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 497) having a hairpin-like structure is known as a precursor of "hsa-miR-3940-5p".

A mature miRNA may become a variant due to the sequence cleaved shorter or longer by one to several flanking nucleotides, or due to substitution of nucleotides, when cut out as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 122, 349 to 383, 464 to 473, and 492 to 494 as well as a large number of the nucleotide sequence variants and fragments represented by SEQ ID NOs: 248 to 348, 420 to 463, 484 to 491, and 498 to 499, called isomiRs. These variants can also be obtained as miRNAs having a nucleotide sequence represented by any of SEQ ID NOs: 1 to 122, 349 to 383, 464 to 473, and 492 to 494. Specifically, among the variants of polynucleotides consisting of the nucleotide sequence represented by any of SEQ ID NOs: 6, 10, 12, 13, 15, 18, 19, 23, 30, 33, 34, 41, 43, 46, 48, 51, 55, 59, 60, 62, 63, 64, 66, 68, 71, 74, 80, 83, 86, 87, 89, 90, 92, 95, 99, 100, 101, 105, 106, 109, 110, 112, 113, 115, 116, 117, 118, 119, 121, 349, 350, 352, 353, 357, 359, 361, 363, 364, 365, 366, 367, 369, 371, 373, 376, 378, 379, 380, 381, 382, 383, 465, 468, 472, 473, and 492 or a nucleotide sequence derived from the nucleotide sequence by the replacement of u with t according to the present invention, examples of the longest variants registered in miRBase Release 20 include polynucleotides represented by SEQ ID NOs: 248, 250, 251, 253, 255, 257, 259, 262, 265, 267, 268, 272, 275, 277, 278, 279, 282, 285, 287, 289, 291, 292, 294, 296, 298, 300, 302, 305, 306, 307, 309, 310, 312, 314, 316, 318, 320, 322, 324, 326, 328, 330, 332, 334, 336, 337, 339, 341, 342, 344, 346, 420, 422, 424, 426, 428, 430, 432, 434, 436, 438, 440, 442, 444, 446, 448, 450, 452, 454, 456, 458, 460, 462, 484, 486, 488, 490, and 498, respectively. Also, among the variants of polynucleotides consisting of a nucleotide sequence represented by any of SEQ ID NOs: 6, 10, 12, 13, 15, 18, 19, 23, 30, 33, 34, 41, 43, 46, 48, 51, 55, 59, 60, 62, 63, 64, 66, 68, 71, 74, 80, 83, 86, 87, 89, 90, 92, 95, 99, 100, 101, 105, 106, 109, 110, 112, 113, 115, 116, 117, 118, 119, 121, 349, 350, 352, 353, 357, 359, 361, 363, 364, 365, 366, 367, 369, 371, 373, 376, 378, 379, 380, 381, 382, 383, 465, 468, 472, 473 and 492 or a nucleotide sequence derived from the nucleotide sequence by the replacement of u with t according to the present invention, examples of shortest variants registered in the miRBase Release 20 include polynucleotides having sequences represented by SEQ ID NOs: 249, 252, 254, 256, 258, 260, 261, 263, 264, 266, 269, 270, 271, 273, 274, 276, 280, 281, 283, 284, 286, 288, 290, 293, 295, 297, 299, 301, 303, 304, 308, 311, 313, 315, 317, 319, 321, 323, 325, 327, 329, 331, 333, 335, 338, 340, 343, 345, 347, 348, 421, 423, 425, 427, 429, 431, 433, 435, 437, 439, 441, 443, 445, 447, 449, 451, 453, 455, 457, 459, 461, 463, 485, 487, 489, 491, and 499, respectively. In addition to these variants and fragments, examples thereof include a large number of isomiR polynucleotides of SEQ ID NOs: 6, 10, 12, 13, 15, 18, 19, 23, 30, 33, 34, 41, 43, 46, 48, 51, 55, 59, 60, 62, 63, 64, 66, 68, 71, 74, 80, 83, 86, 87, 89, 90, 92, 95, 99, 100, 101, 105, 106, 109, 110, 112, 113, 115, 116, 117, 118, 119, 121, 349, 350, 352, 353, 357, 359, 361, 363, 364, 365, 366, 367, 369, 371, 373, 376, 378, 379, 380, 381, 382, 383, 465, 468, 472, 473 and 492 registered in the miRBase. Examples of the polynucleotide comprising a nucleotide sequence represented by any of SEQ ID NOs: 1 to 122, 349 to 383, 464 to 473 and 492 to 494 include a polynucleotide represented by any of SEQ ID NOs: 123 to 247, 384 to 419, 474 to 483, and 495 to 497, which are their respective precursors.

The names and miRBase Accession Nos. (registration numbers) of the genes represented by SEQ ID NOs: 1 to 499 are shown n Table 1.

As used herein_ the term "capable of specifically binding" means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-6893-5p | MIMAT0027686 |
| 2 | hsa-miR-6075 | MIMAT0023700 |
| 3 | hsa-miR-6820-5p | MIMAT0027540 |
| 4 | hsa-miR-4294 | MIMAT0016849 |
| 5 | hsa-miR-6729-5p | MIMAT0027359 |
| 6 | hsa-miR-4476 | MIMAT0019003 |
| 7 | hsa-miR-6836-3p | MIMAT0027575 |
| 8 | hsa-miR-6765-3p | MIMAT0027431 |
| 9 | hsa-miR-6799-5p | MIMAT0027498 |
| 10 | hsa-miR-4530 | MIMAT0019069 |
| 11 | hsa-miR-7641 | MIMAT0029782 |
| 12 | hsa-miR-4454 | MIMAT0018976 |
| 13 | hsa-miR-615-5p | MIMAT0004804 |
| 14 | hsa-miR-8073 | MIMAT0031000 |
| 15 | hsa-miR-663a | MIMAT0003326 |
| 16 | hsa-miR-4634 | MIMAT0019691 |
| 17 | hsa-miR-4450 | MIMAT0018971 |
| 18 | hsa-miR-4792 | MIMAT0019964 |
| 19 | hsa-miR-665 | MIMAT0004952 |
| 20 | hsa-miR-7975 | MIMAT0031178 |
| 21 | hsa-miR-7109-5p | MIMAT0028115 |
| 22 | hsa-miR-6789-5p | MIMAT0027478 |
| 23 | hsa-miR-4497 | MIMAT0019032 |
| 24 | hsa-miR-6877-5p | MIMAT0027654 |
| 25 | hsa-miR-6880-5p | MIMAT0027660 |
| 26 | hsa-miR-7977 | MIMAT0031180 |
| 27 | hsa-miR-4734 | MIMAT0019859 |

TABLE 1-continued

| SEQ ID NO: | Gene name | miRBase registration No. |
|---|---|---|
| 28 | hsa-miR-6821-5p | MIMAT0027542 |
| 29 | hsa-miR-8089 | MIMAT0031016 |
| 30 | hsa-miR-5585-3p | MIMAT0022286 |
| 31 | hsa-miR-6085 | MIMAT0023710 |
| 32 | hsa-miR-6845-5p | MIMAT0027590 |
| 33 | hsa-miR-4651 | MIMAT0019715 |
| 34 | hsa-miR-4433-3p | MIMAT0018949 |
| 35 | hsa-miR-1231 | MIMAT0005586 |
| 36 | hsa-miR-4665-5p | MIMAT0019739 |
| 37 | hsa-miR-7114-5p | MIMAT0028125 |
| 38 | hsa-miR-1238-5p | MIMAT0022947 |
| 39 | hsa-miR-8069 | MIMAT0030996 |
| 40 | hsa-miR-4732-5p | MIMAT0019855 |
| 41 | hsa-miR-619-5p | MIMAT0026622 |
| 42 | hsa-miR-3622a-5p | MIMAT0018003 |
| 43 | hsa-miR-1260a | MIMAT0005911 |
| 44 | hsa-miR-6741-5p | MIMAT0027383 |
| 45 | hsa-miR-6781-5p | MIMAT0027462 |
| 46 | hsa-miR-6125 | MIMAT0024598 |
| 47 | hsa-miR-6805-5p | MIMAT0027510 |
| 48 | hsa-miR-6132 | MIMAT0024616 |
| 49 | hsa-miR-6872-3p | MIMAT0027645 |
| 50 | hsa-miR-6875-5p | MIMAT0027650 |
| 51 | hsa-miR-1908-3p | MIMAT0026916 |
| 52 | hsa-miR-4433b-3p | MIMAT0030414 |
| 53 | hsa-miR-4736 | MIMAT0019862 |
| 54 | hsa-miR-5100 | MIMAT0022259 |
| 55 | hsa-miR-6724-5p | MIMAT0025856 |
| 56 | hsa-miR-7107-5p | MIMAT0028111 |
| 57 | hsa-miR-6726-5p | MIMAT0027353 |
| 58 | hsa-miR-3185 | MIMAT0015065 |
| 59 | hsa-miR-4638-5p | MIMAT0019695 |
| 60 | hsa-miR-1273g-3p | MIMAT0022742 |
| 61 | hsa-miR-6778-5p | MIMAT0027456 |
| 62 | hsa-miR-328-5p | MIMAT0026486 |
| 63 | hsa-miR-3679-3p | MIMAT0018105 |
| 64 | hsa-miR-1228-3p | MIMAT0005583 |
| 65 | hsa-miR-6779-5p | MIMAT0027458 |
| 66 | hsa-miR-4723-5p | MIMAT0019838 |
| 67 | hsa-miR-6850-5p | MIMAT0027600 |
| 68 | hsa-miR-760 | MIMAT0004957 |
| 69 | hsa-miR-7704 | MIMAT0030019 |
| 70 | hsa-miR-8072 | MIMAT0030999 |
| 71 | hsa-miR-4486 | MIMAT0019020 |
| 72 | hsa-miR-1913 | MIMAT0007888 |
| 73 | hsa-miR-4656 | MIMAT0019723 |
| 74 | hsa-miR-1260b | MIMAT0015041 |
| 75 | hsa-miR-7106-5p | MIMAT0028109 |
| 76 | hsa-miR-6889-5p | MIMAT0027678 |
| 77 | hsa-miR-6780b-5p | MIMAT0027572 |
| 78 | hsa-miR-6090 | MIMAT0023715 |
| 79 | hsa-miR-4534 | MIMAT0019073 |
| 80 | hsa-miR-4449 | MIMAT0018968 |
| 81 | hsa-miR-5195-3p | MIMAT0021127 |
| 82 | hsa-miR-1202 | MIMAT0005865 |
| 83 | hsa-miR-4467 | MIMAT0018994 |
| 84 | hsa-miR-6515-3p | MIMAT0025487 |
| 85 | hsa-miR-4281 | MIMAT0016907 |
| 86 | hsa-miR-4505 | MIMAT0019041 |
| 87 | hsa-miR-4484 | MIMAT0019018 |
| 88 | hsa-miR-6805-3p | MIMAT0027511 |
| 89 | hsa-miR-3135b | MIMAT0018985 |
| 90 | hsa-miR-3162-5p | MIMAT0015036 |
| 91 | hsa-miR-6768-5p | MIMAT0027436 |
| 92 | hsa-miR-6721-5p | MIMAT0025852 |
| 93 | hsa-miR-1227-5p | MIMAT0022941 |
| 94 | hsa-miR-6722-3p | MIMAT0025854 |
| 95 | hsa-miR-4286 | MIMAT0016916 |
| 96 | hsa-miR-4746-3p | MIMAT0019881 |
| 97 | hsa-miR-6727-5p | MIMAT0027355 |
| 98 | hsa-miR-6816-5p | MIMAT0027532 |
| 99 | hsa-miR-4741 | MIMAT0019871 |
| 100 | hsa-miR-4508 | MIMAT0019045 |
| 101 | hsa-miR-940 | MIMAT0004983 |
| 102 | hsa-miR-4327 | MIMAT0016889 |
| 103 | hsa-miR-4665-3p | MIMAT0019740 |
| 104 | hsa-miR-718 | MIMAT0012735 |
| 105 | hsa-miR-125a-3p | MIMAT0004602 |
| 106 | hsa-miR-204-3p | MIMAT0022693 |
| 107 | hsa-miR-1469 | MIMAT0007347 |
| 108 | hsa-miR-575 | MIMAT0003240 |
| 109 | hsa-miR-150-3p | MIMAT0004610 |
| 110 | hsa-miR-423-5p | MIMAT0004748 |
| 111 | hsa-miR-564 | MIMAT0003228 |
| 112 | hsa-miR-3188 | MIMAT0015070 |
| 113 | hsa-miR-1246 | MIMAT0005898 |
| 114 | hsa-miR-602 | MIMAT0003270 |
| 115 | hsa-miR-1290 | MIMAT0005880 |
| 116 | hsa-miR-16-5p | MIMAT0000069 |
| 117 | hsa-miR-451a | MIMAT0001631 |
| 118 | hsa-miR-24-3p | MIMAT0000080 |
| 119 | hsa-miR-187-5p | MIMAT0004561 |
| 120 | hsa-miR-1908-5p | MIMAT0007881 |
| 121 | hsa-miR-371a-5p | MIMAT0004687 |
| 122 | hsa-miR-550a-5p | MIMAT0004800 |
| 123 | hsa-mir-6893 | MI0022740 |
| 124 | hsa-mir-6075 | MI0020352 |
| 125 | hsa-mir-6820 | MI0022665 |
| 126 | hsa-mir-4294 | MI0015827 |
| 127 | hsa-mir-6729 | MI0022574 |
| 128 | hsa-mir-4476 | MI0016828 |
| 129 | hsa-mir-6836 | MI0022682 |
| 130 | hsa-mir-6765 | MI0022610 |
| 131 | hsa-mir-6799 | MI0022644 |
| 132 | hsa-mir-4530 | MI0016897 |
| 133 | hsa-mir-7641-1 | MI0024975 |
| 134 | hsa-mir-7641-2 | MI0024976 |
| 135 | hsa-mir-4454 | MI0016800 |
| 136 | hsa-mir-615 | MI0003628 |
| 137 | hsa-mir-8073 | MI0025909 |
| 138 | hsa-mir-663a | MI0003672 |
| 139 | hsa-mir-4634 | MI0017261 |
| 140 | hsa-mir-4450 | MI0016795 |
| 141 | hsa-mir-4792 | MI0017439 |
| 142 | hsa-mir-665 | MI0005563 |
| 143 | hsa-mir-7975 | MI0025751 |
| 144 | hsa-mir-7109 | MI0022960 |
| 145 | hsa-mir-6789 | MI0022634 |
| 146 | hsa-mir-4497 | MI0016859 |
| 147 | hsa-mir-6877 | MI0022724 |
| 148 | hsa-mir-6880 | MI0022727 |
| 149 | hsa-mir-7977 | MI0025753 |
| 150 | hsa-mir-4734 | MI0017371 |
| 151 | hsa-mir-6821 | MI0022666 |
| 152 | hsa-mir-8089 | MI0025925 |
| 153 | hsa-mir-5585 | MI0019142 |
| 154 | hsa-mir-6085 | MI0020362 |
| 155 | hsa-mir-6845 | MI0022691 |
| 156 | hsa-mir-4651 | MI0017279 |
| 157 | hsa-mir-4433 | MI0016773 |
| 158 | hsa-mir-1231 | MI0006321 |
| 159 | hsa-mir-4665 | MI0017295 |
| 160 | hsa-mir-7114 | MI0022965 |
| 161 | hsa-mir-1238 | MI0006328 |
| 162 | hsa-mir-8069 | MI0025905 |
| 163 | hsa-mir-4732 | MI0017369 |
| 164 | hsa-mir-619 | MI0003633 |
| 165 | hsa-mir-3622a | MI0016013 |
| 166 | hsa-mir-1260a | MI0006394 |
| 167 | hsa-mir-6741 | MI0022586 |
| 168 | hsa-mir-6781 | MI0022626 |
| 169 | hsa-mir-6125 | MI0021259 |
| 170 | hsa-mir-6805 | MI0022650 |
| 171 | hsa-mir-6132 | MI0021277 |
| 172 | hsa-mir-6872 | MI0022719 |
| 173 | hsa-mir-6875 | MI0022722 |
| 174 | hsa-mir-1908 | MI0008329 |
| 175 | hsa-mir-4433b | MI0025511 |
| 176 | hsa-mir-4736 | MI0017373 |
| 177 | hsa-mir-5100 | MI0019116 |
| 178 | hsa-mir-6724 | MI0022559 |
| 179 | hsa-mir-7107 | MI0022958 |
| 180 | hsa-mir-6726 | MI0022571 |
| 181 | hsa-mir-3185 | MI0014227 |

TABLE 1-continued

| SEQ ID NO: | Gene name | miRBase registration No. |
|---|---|---|
| 182 | hsa-mir-4638 | MI0017265 |
| 183 | hsa-mir-1273g | MI0018003 |
| 184 | hsa-mir-6778 | MI0022623 |
| 185 | hsa-mir-328 | MI0000804 |
| 186 | hsa-mir-3679 | MI0016080 |
| 187 | hsa-mir-1228 | MI0006318 |
| 188 | hsa-mir-6779 | MI0022624 |
| 189 | hsa-mir-4723 | MI0017359 |
| 190 | hsa-mir-6850 | MI0022696 |
| 191 | hsa-mir-760 | MI0005567 |
| 192 | hsa-mir-7704 | MI0025240 |
| 193 | hsa-mir-8072 | MI0025908 |
| 194 | hsa-mir-4486 | MI0016847 |
| 195 | hsa-mir-1913 | MI0008334 |
| 196 | hsa-mir-4656 | MI0017284 |
| 197 | hsa-mir-1260b | MI0014197 |
| 198 | hsa-mir-7106 | MI0022957 |
| 199 | hsa-mir-6889 | MI0022736 |
| 200 | hsa-mir-6780b | MI0022681 |
| 201 | hsa-mir-6090 | MI0020367 |
| 202 | hsa-mir-4534 | MI0016901 |
| 203 | hsa-mir-4449 | MI0016792 |
| 204 | hsa-mir-5195 | MI0018174 |
| 205 | hsa-mir-1202 | MI0006334 |
| 206 | hsa-mir-4467 | MI0016818 |
| 207 | hsa-mir-6515 | MI0022227 |
| 208 | hsa-mir-4281 | MI0015885 |
| 209 | hsa-mir-4505 | MI0016868 |
| 210 | hsa-mir-4484 | MI0016845 |
| 211 | hsa-mir-6805 | MI0022650 |
| 212 | hsa-mir-3135b | MI0016809 |
| 213 | hsa-mir-3162 | MI0014192 |
| 214 | hsa-mir-6768 | MI0022613 |
| 215 | hsa-mir-6721 | MI0022556 |
| 216 | hsa-mir-1227 | MI0006316 |
| 217 | hsa-mir-6722 | MI0022557 |
| 218 | hsa-mir-4286 | MI0015894 |
| 219 | hsa-mir-4746 | MI0017385 |
| 220 | hsa-mir-6727 | MI0022572 |
| 221 | hsa-mir-6816 | MI0022661 |
| 222 | hsa-mir-4741 | MI0017379 |
| 223 | hsa-mir-4508 | MI0016872 |
| 224 | hsa-mir-940 | MI0005762 |
| 225 | hsa-mir-4327 | MI0015867 |
| 226 | hsa-mir-718 | MI0012489 |
| 227 | hsa-mir-125a | MI0000469 |
| 228 | hsa-mir-204 | MI0000284 |
| 229 | hsa-mir-1469 | MI0007074 |
| 230 | hsa-mir-575 | MI0003582 |
| 231 | hsa-mir-150 | MI0000479 |
| 232 | hsa-mir-423 | MI0001445 |
| 233 | hsa-mir-564 | MI0003570 |
| 234 | hsa-mir-3188 | MI0014232 |
| 235 | hsa-mir-1246 | MI0006381 |
| 236 | hsa-mir-602 | MI0003615 |
| 237 | hsa-mir-1290 | MI0006352 |
| 238 | hsa-mir-16-1 | MI0000070 |
| 239 | hsa-mir-16-2 | MI0000115 |
| 240 | hsa-mir-451a | MI0001729 |
| 241 | hsa-mir-24-1 | MI0000080 |
| 242 | hsa-mir-24-2 | MI0000081 |
| 243 | hsa-mir-187 | MI0000274 |
| 244 | hsa-mir-1908 | MI0008329 |
| 245 | hsa-mir-371a | MI0000779 |
| 246 | hsa-mir-550a-1 | MI0003600 |
| 247 | hsa-mir-550a-2 | MI0003601 |
| 248 | isomiR example 1 of SEQ ID NO: 6 | — |
| 249 | isomiR example 2 of SEQ ID NO: 6 | — |
| 250 | isomiR example 1 of SEQ ID NO: 10 | — |
| 251 | isomiR example 1 of SEQ ID NO: 12 | — |
| 252 | isomiR example 2 of SEQ ID NO: 12 | — |
| 253 | isomiR example 1 of SEQ ID NO: 13 | — |
| 254 | isomiR example 2 of SEQ ID NO: 13 | — |
| 255 | isomiR example 1 of SEQ ID NO: 15 | — |
| 256 | isomiR example 2 of SEQ ID NO: 15 | — |
| 257 | isomiR example 1 of SEQ ID NO: 18 | — |
| 258 | isomiR example 2 of SEQ ID NO: 18 | — |
| 259 | isomiR example 1 of SEQ ID NO: 19 | — |
| 260 | isomiR example 2 of SEQ ID NO: 19 | — |
| 261 | isomiR example 1 of SEQ ID NO: 20 | — |
| 262 | isomiR example 1 of SEQ ID NO: 23 | — |
| 263 | isomiR example 2 of SEQ ID NO: 23 | — |
| 264 | isomiR example 1 of SEQ ID NO: 27 | — |
| 265 | isomiR example 1 of SEQ ID NO: 30 | — |
| 266 | isomiR example 2 of SEQ ID NO: 30 | — |
| 267 | isomiR example 1 of SEQ ID NO: 33 | — |
| 268 | isomiR example 1 of SEQ ID NO: 34 | — |
| 269 | isomiR example 2 of SEQ ID NO: 34 | — |
| 270 | isomiR example 1 of SEQ ID NO: 36 | — |
| 271 | isomiR example 1 of SEQ ID NO: 40 | — |
| 272 | isomiR example 1 of SEQ ID NO: 41 | — |
| 273 | isomiR example 2 of SEQ ID NO: 41 | — |
| 274 | isomiR example 1 of SEQ ID NO: 42 | — |
| 275 | isomiR example 1 of SEQ ID NO: 43 | — |
| 276 | isomiR example 2 of SEQ ID NO: 43 | — |
| 277 | isomiR example 1 of SEQ ID NO: 46 | — |
| 278 | isomiR example 1 of SEQ ID NO: 48 | — |
| 279 | isomiR example 1 of SEQ ID NO: 51 | — |
| 280 | isomiR example 2 of SEQ ID NO: 51 | — |
| 281 | isomiR example 1 of SEQ ID NO: 54 | — |
| 282 | isomiR example 1 of SEQ ID NO: 55 | — |
| 283 | isomiR example 2 of SEQ ID NO: 55 | — |
| 284 | isomiR example 1 of SEQ ID NO: 58 | — |
| 285 | isomiR example 1 of SEQ ID NO: 59 | — |
| 286 | isomiR example 2 of SEQ ID NO: 59 | — |
| 287 | isomiR example 1 of SEQ ID NO: 60 | — |
| 288 | isomiR example 2 of SEQ ID NO: 60 | — |
| 289 | isomiR example 1 of SEQ ID NO: 62 | — |
| 290 | isomiR example 2 of SEQ ID NO: 62 | — |
| 291 | isomiR example 1 of SEQ ID NO: 63 | — |
| 292 | isomiR example 1 of SEQ ID NO: 64 | — |
| 293 | isomiR example 2 of SEQ ID NO: 64 | — |
| 294 | isomiR example 1 of SEQ ID NO: 66 | — |
| 295 | isomiR example 2 of SEQ ID NO: 66 | — |
| 296 | isomiR example 1 of SEQ ID NO: 68 | — |
| 297 | isomiR example 2 of SEQ ID NO: 68 | — |
| 298 | isomiR example 1 of SEQ ID NO: 71 | — |
| 299 | isomiR example 1 of SEQ ID NO: 72 | — |
| 300 | isomiR example 1 of SEQ ID NO: 74 | — |
| 301 | isomiR example 2 of SEQ ID NO: 74 | — |
| 302 | isomiR example 1 of SEQ ID NO: 80 | — |
| 303 | isomiR example 2 of SEQ ID NO: 80 | — |
| 304 | isomiR example 1 of SEQ ID NO: 82 | — |
| 305 | isomiR example 1 of SEQ ID NO: 83 | — |
| 306 | isomiR example 1 of SEQ ID NO: 86 | — |
| 307 | isomiR example 1 of SEQ ID NO: 87 | — |
| 308 | isomiR example 2 of SEQ ID NO: 87 | — |
| 309 | isomiR example 1 of SEQ ID NO: 89 | — |
| 310 | isomiR example 1 of SEQ ID NO: 90 | — |
| 311 | isomiR example 2 of SEQ ID NO: 90 | — |
| 312 | isomiR example 1 of SEQ ID NO: 92 | — |
| 313 | isomiR example 2 of SEQ ID NO: 92 | — |
| 314 | isomiR example 1 of SEQ ID NO: 95 | — |
| 315 | isomiR example 2 of SEQ ID NO: 95 | — |
| 316 | isomiR example 1 of SEQ ID NO: 99 | — |
| 317 | isomiR example 2 of SEQ ID NO: 99 | — |
| 318 | isomiR example 1 of SEQ ID NO: 100 | — |
| 319 | isomiR example 2 of SEQ ID NO: 100 | — |
| 320 | isomiR example 1 of SEQ ID NO: 101 | — |
| 321 | isomiR example 2 of SEQ ID NO: 101 | — |
| 322 | isomiR example 1 of SEQ ID NO: 105 | — |
| 323 | isomiR example 2 of SEQ ID NO: 105 | — |
| 324 | isomiR example 1 of SEQ ID NO: 106 | — |
| 325 | isomiR example 2 of SEQ ID NO: 106 | — |
| 326 | isomiR example 1 of SEQ ID NO: 109 | — |
| 327 | isomiR example 2 of SEQ ID NO: 109 | — |
| 328 | isomiR example 1 of SEQ ID NO: 110 | — |
| 329 | isomiR example 2 of SEQ ID NO: 110 | — |
| 330 | isomiR example 1 of SEQ ID NO: 112 | — |
| 331 | isomiR example 2 of SEQ ID NO: 112 | — |
| 332 | isomiR example 1 of SEQ ID NO: 113 | — |
| 333 | isomiR example 2 of SEQ ID NO: 113 | — |
| 334 | isomiR example 1 of SEQ ID NO: 115 | — |
| 335 | isomiR example 2 of SEQ ID NO: 115 | — |

TABLE 1-continued

| SEQ ID NO: | Gene name | miRBase registration No. |
|---|---|---|
| 336 | isomiR example 1 of SEQ ID NO: 116 | — |
| 337 | isomiR example 2 of SEQ ID NO: 116 | — |
| 338 | isomiR example 3 of SEQ ID NO: 116 | — |
| 339 | isomiR example 1 of SEQ ID NO: 117 | — |
| 340 | isomiR example 2 of SEQ ID NO: 117 | — |
| 341 | isomiR example 1 of SEQ ID NO: 118 | — |
| 342 | isomiR example 2 of SEQ ID NO: 118 | — |
| 343 | isomiR example 3 of SEQ ID NO: 118 | — |
| 344 | isomiR example 1 of SEQ ID NO: 119 | — |
| 345 | isomiR example 2 of SEQ ID NO: 119 | — |
| 346 | isomiR example 1 of SEQ ID NO: 121 | — |
| 347 | isomiR example 2 of SEQ ID NO: 121 | — |
| 348 | isomiR example 1 of SEQ ID NO: 122 | — |
| 349 | hsa-miR-4417 | MIMAT0018929 |
| 350 | hsa-miR-4707-5p | MIMAT0019807 |
| 351 | hsa-miR-7847-3p | MIMAT0030422 |
| 352 | hsa-miR-2861 | MIMAT0013802 |
| 353 | hsa-miR-4513 | MIMAT0019050 |
| 354 | hsa-miR-7111-5p | MIMAT0028119 |
| 355 | hsa-miR-6777-5p | MIMAT0027454 |
| 356 | hsa-miR-7113-3p | MIMAT0028124 |
| 357 | hsa-miR-4648 | MIMAT0019710 |
| 358 | hsa-miR-3184-5p | MIMAT0015064 |
| 359 | hsa-miR-4271 | MIMAT0016901 |
| 360 | hsa-miR-6791-5p | MIMAT0027482 |
| 361 | hsa-miR-642a-3p | MIMAT0020924 |
| 362 | hsa-miR-7108-5p | MIMAT0028113 |
| 363 | hsa-miR-128-1-5p | MIMAT0026477 |
| 364 | hsa-miR-5196-5p | MIMAT0021128 |
| 365 | hsa-miR-3178 | MIMAT0015055 |
| 366 | hsa-miR-3656 | MIMAT0018076 |
| 367 | hsa-miR-92a-2-5p | MIMAT0004508 |
| 368 | hsa-miR-6769b-5p | MIMAT0027620 |
| 369 | hsa-miR-4689 | MIMAT0019778 |
| 370 | hsa-miR-6076 | MIMAT0023701 |
| 371 | hsa-miR-92b-5p | MIMAT0004792 |
| 372 | hsa-miR-6774-5p | MIMAT0027448 |
| 373 | hsa-miR-486-3p | MIMAT0004762 |
| 374 | hsa-miR-6806-5p | MIMAT0027512 |
| 375 | hsa-miR-6842-5p | MIMAT0027586 |
| 376 | hsa-miR-6716-5p | MIMAT0025844 |
| 377 | hsa-miR-557 | MIMAT0003221 |
| 378 | hsa-miR-4673 | MIMAT0019755 |
| 379 | hsa-miR-4674 | MIMAT0019756 |
| 380 | hsa-miR-4442 | MIMAT0018960 |
| 381 | hsa-miR-1915-3p | MIMAT0007892 |
| 382 | hsa-miR-4687-3p | MIMAT0019775 |
| 383 | hsa-miR-92b-3p | MIMAT0003218 |
| 384 | hsa-mir-4417 | MI0016753 |
| 385 | hsa-mir-4707 | MI0017340 |
| 386 | hsa-mir-7847 | MI0025517 |
| 387 | hsa-mir-2861 | MI0013006 |
| 388 | hsa-mir-4513 | MI0016879 |
| 389 | hsa-mir-7111 | MI0022962 |
| 390 | hsa-mir-6777 | MI0022622 |
| 391 | hsa-mir-7113 | MI0022964 |
| 392 | hsa-mir-4648 | MI0017275 |
| 393 | hsa-mir-3184 | MI0014226 |
| 394 | hsa-mir-4271 | MI0015879 |
| 395 | hsa-mir-6791 | MI0022636 |
| 396 | hsa-mir-642a | MI0003657 |
| 397 | hsa-mir-7108 | MI0022959 |
| 398 | hsa-mir-128-1 | MI0000447 |
| 399 | hsa-mir-5196 | MI0018175 |
| 400 | hsa-mir-3178 | MI0014212 |
| 401 | hsa-mir-3656 | MI0016056 |
| 402 | hsa-mir-92a-2 | MI0000094 |
| 403 | hsa-mir-6769b | MI0022706 |
| 404 | hsa-mir-4689 | MI0017322 |
| 405 | hsa-mir-6076 | MI0020353 |
| 406 | hsa-mir-92b | MI0003560 |
| 407 | hsa-mir-6774 | MI0022619 |
| 408 | hsa-mir-486 | MI0002470 |
| 409 | hsa-mir-486-2 | MI0023622 |
| 410 | hsa-mir-6806 | MI0022651 |
| 411 | hsa-mir-6842 | MI0022688 |
| 412 | hsa-mir-6716 | MI0022550 |
| 413 | hsa-mir-557 | MI0003563 |
| 414 | hsa-mir-4673 | MI0017304 |
| 415 | hsa-mir-4674 | MI0017305 |
| 416 | hsa-mir-4442 | MI0016785 |
| 417 | hsa-mir-1915 | MI0008336 |
| 418 | hsa-mir-4687 | MI0017319 |
| 419 | hsa-mir-92b | MI0003560 |
| 420 | isomiR example 1 of SEQ ID NO: 349 | — |
| 421 | isomiR example 2 of SEQ ID NO: 349 | — |
| 422 | isomiR example 1 of SEQ ID NO: 350 | — |
| 423 | isomiR example 2 of SEQ ID NO: 350 | — |
| 424 | isomiR example 1 of SEQ ID NO: 352 | — |
| 425 | isomiR example 2 of SEQ ID NO: 352 | — |
| 426 | isomiR example 1 of SEQ ID NO: 353 | — |
| 427 | isomiR example 2 of SEQ ID NO: 353 | — |
| 428 | isomiR example 1 of SEQ ID NO: 357 | — |
| 429 | isomiR example 2 of SEQ ID NO: 357 | — |
| 430 | isomiR example 1 of SEQ ID NO: 359 | — |
| 431 | isomiR example 2 of SEQ ID NO: 359 | — |
| 432 | isomiR example 1 of SEQ ID NO: 361 | — |
| 433 | isomiR example 2 of SEQ ID NO: 361 | — |
| 434 | isomiR example 1 of SEQ ID NO: 363 | — |
| 435 | isomiR example 2 of SEQ ID NO: 363 | — |
| 436 | isomiR example 1 of SEQ ID NO: 364 | — |
| 437 | isomiR example 2 of SEQ ID NO: 364 | — |
| 438 | isomiR example 1 of SEQ ID NO: 365 | — |
| 439 | isomiR example 2 of SEQ ID NO: 365 | — |
| 440 | isomiR example 1 of SEQ ID NO: 366 | — |
| 441 | isomiR example 2 of SEQ ID NO: 366 | — |
| 442 | isomiR example 1 of SEQ ID NO: 367 | — |
| 443 | isomiR example 2 of SEQ ID NO: 367 | — |
| 444 | isomiR example 1 of SEQ ID NO: 369 | — |
| 445 | isomiR example 2 of SEQ ID NO: 369 | — |
| 446 | isomiR example 1 of SEQ ID NO: 371 | — |
| 447 | isomiR example 2 of SEQ ID NO: 371 | — |
| 448 | isomiR example 1 of SEQ ID NO: 373 | — |
| 449 | isomiR example 2 of SEQ ID NO: 373 | — |
| 450 | isomiR example 1 of SEQ ID NO: 376 | — |
| 451 | isomiR example 2 of SEQ ID NO: 376 | — |
| 452 | isomiR example 1 of SEQ ID NO: 378 | — |
| 453 | isomiR example 2 of SEQ ID NO: 378 | — |
| 454 | isomiR example 1 of SEQ ID NO: 379 | — |
| 455 | isomiR example 2 of SEQ ID NO: 379 | — |
| 456 | isomiR example 1 of SEQ ID NO: 380 | — |
| 457 | isomiR example 2 of SEQ ID NO: 380 | — |
| 458 | isomiR example 1 of SEQ ID NO: 381 | — |
| 459 | isomiR example 2 of SEQ ID NO: 381 | — |
| 460 | isomiR example 1 of SEQ ID NO: 382 | — |
| 461 | isomiR example 2 of SEQ ID NO: 382 | — |
| 462 | isomiR example 1 of SEQ ID NO: 383 | — |
| 463 | isomiR example 2 of SEQ ID NO: 383 | — |
| 464 | hsa-miR-1203 | MIMAT0005866 |
| 465 | hsa-miR-663b | MIMAT0005867 |
| 466 | hsa-miR-4258 | MIMAT0016879 |
| 467 | hsa-miR-4649-5p | MIMAT0019711 |
| 468 | hsa-miR-4516 | MIMAT0019053 |
| 469 | hsa-miR-3619-3p | MIMAT0019219 |
| 470 | hsa-miR-6826-5p | MIMAT0027552 |
| 471 | hsa-miR-6757-5p | MIMAT0027414 |
| 472 | hsa-miR-3131 | MIMAT0014996 |
| 473 | hsa-miR-1343-3p | MIMAT0019776 |
| 474 | hsa-mir-1203 | MI0006335 |
| 475 | hsa-mir-663b | MI0006336 |
| 476 | hsa-mir-4258 | MI0015857 |
| 477 | hsa-mir-4649 | MI0017276 |
| 478 | hsa-mir-4516 | MI0016882 |
| 479 | hsa-mir-3619 | MI0016009 |
| 480 | hsa-mir-6826 | MI0022671 |
| 481 | hsa-mir-6757 | MI0022602 |
| 482 | hsa-mir-3131 | MI0014151 |
| 483 | hsa-mir-1343 | MI0017320 |
| 484 | isomiR example 1 of SEQ ID NO: 465 | — |
| 485 | isomiR example 2 of SEQ ID NO: 465 | — |
| 486 | isomiR example 1 of SEQ ID NO: 468 | — |
| 487 | isomiR example 2 of SEQ ID NO: 468 | — |
| 488 | isomiR example 1 of SEQ ID NO: 472 | — |
| 489 | isomiR example 2 of SEQ ID NO: 472 | — |

TABLE 1-continued

| SEQ ID NO: | Gene name | miRBase registration No. |
|---|---|---|
| 490 | isomiR example 1 of SEQ ID NO: 473 | — |
| 491 | isomiR example 2 of SEQ ID NO: 473 | — |
| 492 | hsa-miR-6775-5p | MIMAT0027450 |
| 493 | hsa-miR-6813-5p | MIMAT0027526 |
| 494 | hsa-miR-3940-5p | MIMAT0019229 |
| 495 | hsa-mir-6775 | MI0022620 |
| 496 | hsa-mir-6813 | MI0022658 |
| 497 | hsa-mir-3940 | MI0016597 |
| 498 | isomiR example 1 of SEQ ID NO: 494 | — |
| 499 | isomiR example 2 of SEQ ID NO: 494 | — |

The present specification encompasses the contents described in the specifications and/or drawings of Japanese Patent Application No. 2014-113523 and No. 2014-185730 from which the present application claims priorities.

Advantageous Effect of Invention

According to the present invention, pancreatic cancer can be detected easily and in high accuracy.

For example, the presence or absence of pancreatic cancer in patients can be easily detected by using, as indicators, the determined expression levels of several miRNAs in blood, serum, and/or plasma of the patients, which can be collected with limited invasiveness.

MODES FOR CARRYING OUT THE INVENTION

Figure 1:
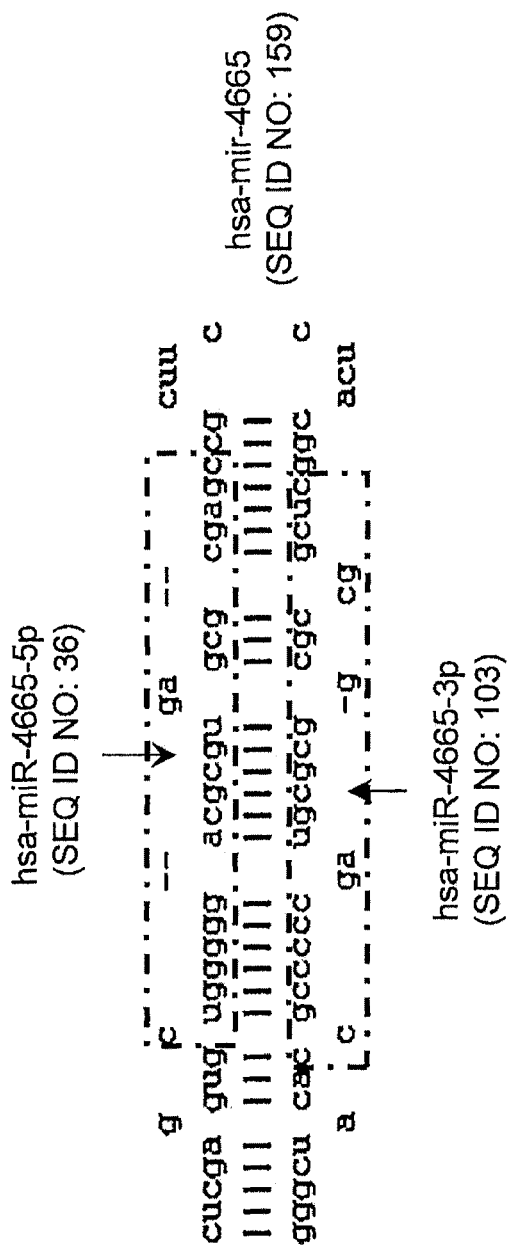
FIG. 1 This figure shows the relationship between the nucleotide sequences of hsa-miR-4665-5p represented by SEQ ID NO: 36 and hsa-miR-4665-3p represented by SEQ ID NO: 103, which are produced from a precursor hsa-mir-4665 represented by SEQ ID NO: 159.

Hereinafter, the present invention will be further described in detail.

1. Target Nucleic Acid for Pancreatic Cancer

Primary target nucleic acids, as pancreatic cancer markers, for detecting the presence and/or absence of pancreatic cancer or pancreatic cancer cells using the nucleic acid probes or the primers for the detection of pancreatic cancer defined above according to the present invention comprise at least one or more miRNAs selected from the group consisting of the following miRNAs: hsa-miR-6893-5p, hsa-miR-6075, hsa-miR-6820-5p, hsa-miR-4294, hsa-miR-6729-5p, hsa-miR-4476, hsa-miR-6836-3p, hsa-miR-6765-3p, hsa-miR-6799-5p, hsa-miR-4530, hsa-miR-7641, hsa-miR-4454, hsa-miR-615-5p, hsa-miR-8073, hsa-miR-663a, hsa-miR-4634, hsa-miR-4450, hsa-miR-4792, hsa-miR-665, hsa-miR-7975, hsa-miR-7109-5p, hsa-miR-6789-5p, hsa-miR-4497, hsa-miR-6877-5p, hsa-miR-6880-5p, hsa-miR-7977, hsa-miR-4734, hsa-miR-6821-5p, hsa-miR-8089, hsa-miR-5585-3p, hsa-miR-6085, hsa-miR-6845-5p, hsa-miR-4651., hsa-miR-4433-3p, hsa-miR-1231., hsa-miR-4665-5p, hsa-miR-71.1.4-5p, hsa-miR-1238-5p, hsa-miR-8069, hsa-miR-4732-5p, hsa-miR-619-5p, hsa-miR-3622a-5p, hsa-miR-1260a, hsa-miR-6741-5p, hsa-miR-6781-5p, hsa-miR-6125, hsa-miR-6805-5p, hsa-miR-6132, hsa-miR-6872-3p, hsa-miR-6875-5p, hsa-miR-1908-3p, hsa-miR-4433b-3p, hsa-miR-4736, hsa-miR-5100, hsa-miR-6724-5p, hsa-miR-7107-5p, hsa-miR-6726-5p, hsa-miR-3185, hsa-miR-4638-5p, hsa-miR-1273g-3p, hsa-miR-6778-5p, hsa-miR-328-5p, hsa-miR-3679-3p, hsa-miR-1228-3p, hsa-miR-6779-5p, hsa-miR-4723-5p, hsa-miR-6850-5p, hsa-miR-760, hsa-miR-7704, hsa-miR-8072, hsa-miR-4486, hsa-miR-1913, hsa-miR-4656, hsa-miR-12601), hsa-miR-7106-5p, hsamiR-6889-5p, hsa-miR-6780b-5p, hsa-miR-6090, hsa-miR-4534, hsa-miR-4449, hsa-miR-5195-3p, hsa-miR-1202, hsa-miR-4467, hsa-miR-6515-3p, hsa-miR-4281, hsa-miR-4505, hsa-miR-4484, hsa-miR-6805-3p, hsa-miR-3135b, hsa-miR-3162-5p, hsa-miR-6768-5p, hsa-miR-6721-5p, hsa-miR-1227-5p, hsa-miR-6722-3p, hsa-miR-4286, hsa-miR-4746-3p, hsa-miR-6727-5p, hsa-miR-6816-5p, hsa-miR-4741, hsa-miR-4508, hsa-miR-940, hsa-miR-4327, hsa-miR-4665-3p, hsa-miR-718, hsa-miR-1203, hsa-miR-663b, hsa-miR-4258, hsa-miR-4649-5p, hsa-miR-4516, hsa-miR-3619-3p, hsa-miR-6826-5p, hsa-miR-6757-5p, hsa-miR-3131, hsa-miR-1343-3p, hsa-miR-6775-5p, hsa-miR-6813-5p and hsa-miR-3940-5p. Furthermore, at least one or more miRNAs selected from the group consisting of the following other pancreatic cancer markers that can be combined with these miRNAs, i.e., hsa-miR-125a-3p, hsa-miR-204-3p, hsa-miR-1469, hsa-miR-575, hsa-miR-150-3p, hsa-miR-423-5p, hsa-miR-564, hsa-miR-3188, hsa-miR-1246, hsa-miR-602, hsa-miR-1290, hsa-miR-16-5p, hsa-miR-451a, hsa-miR-24-3p, hsa-miR-187-5p, hsa-miR-1908-5p, hsa-miR-371a-5p and hsa-miR-550a-5p can also be preferably used as target nucleic acids. Moreover, at least one or more miRNAs selected from the group consisting of the following other pancreatic cancer markers that can be combined with these miRNAs, i.e., hsa-miR-4417, hsa-miR-4707-5p, hsa-miR-7847-3p, hsa-miR-2861, hsa-miR-4513, hsa-miR-7111-5p, hsa-miR-6777-5p, hsa-miR-7113-3p, hsa-miR-4648, hsa-miR-3184-5p, hsa-miR-4271, hsa-miR-6791-5p, hsa-miR-642a-3p, hsa-miR-7108-5p, hsa-miR-128-1-5p, hsa-miR-5196-5p, hsa-miR-3178, hsa-miR-3656, hsa-miR-92a-2-5p, hsa-miR-6769b-5p, hsa-miR-4689, hsa-miR-6076, hsa-miR-92b-5p, hsa-miR-6774-5p, hsa-miR-486-3p, hsa-miR-6806-5p, hsa-miR-6842-5p, hsa-ma-6716-5p, hsa-miR-557, hsa-miR-4673, hsa-miR-4674, hsa-miR-4442, hsa-miR-1915-3p, hsa-miR-4687-3p and hsa-miR-92b-3p can also be preferably used as target nucleic acids.

These miRNAs include, for example, a human gene comprising a nucleotide sequence represented by any of SEQ ID NOs: 1 to 122 and 349 to 383, 464 to 473, and 492 to 494 (i.e., hsa-miR-6893-5p, hsa-miR-6075, hsa-miR-682.0-5p, hsa-miR-4294, hsa-miR-6729-5p, hsa-miR-4476, hsa-miR-6836-3p, hsa-miR-6765-3p, hsa-miR-6799-5p, hsa-miR-4530, hsa-miR-7641, hsa-miR-4454, hsa-miR-615-5p, hsa-miR-8073, hsa-miR-663a, hsa-miR-4634, hsa-miR-4450, hsa-miR-4792, hsa-miR-665, hsa-miR-7975, hsa-miR-7109-5p, hsa-miR-6789-5p, hsa-miR-4497, hsa-miR-6877-5p, hsa-miR-6880-5p, hsa-miR-7977, hsa-miR-4734, hsa-miR-6821-5p, hsa-miR-8089, hsa-miR-5585-3p, hsa-miR-6085, hsa-miR-6845-5p, hsa-miR-4651, hsa-miR-4433-3p, hsa-miR-1231, hsa-miR-4665-5p, hsa-miR-7114-5p, hsa-miR-1238-5p, hsa-miR-8069, hsa-miR-4732-5p, hsa-miR-619-5p, hsa-miR-3622a-5p, hsa-miR-1260a, hsa-miR-6741-5p, hsa-miR-6781-5p, hsa-miR-6125, hsa-miR-6805-5p, hsa-miR-6132, hsa-miR-6872-3p, hsa-miR-6875-5p, hsa-miR-1908-3p, hsa-miR-4433b-3p, hsa-miR-4736, hsa-miR-5100, hsa-miR-6724-5p, hsa-miR-7107-5p, hsa-miR-6726-5p, hsa-miR-3185, hsa-miR-4638-5p, hsa-miR-1273g-3p, hsa-miR-6778-5p, hsa-miR-328-5p, hsa-miR-3679-3p, hsa-miR-1228-3p, hsa-miR-6779-5p, hsa-miR-4723-5p, hsa-miR-6850-5p, hsa-miR-760, hsa-miR-7704, hsa-miR-8072, hsa-miR-4486, hsa-miR-1913, hsa-miR-4656, hsa-miR-1260b, hsa-miR-7106-5p, hsa-miR-6889-5p, hsa-miR-6780b-5p, hsa-miR-6090, hsa-miR-4534, hsa-miR-4449, hsa-miR-5195-3p, hsa-miR-1202, hsa-miR-4467, hsa-miR-6515-3p, hsa-miR-4281, hsa-miR-4505, hsa-miR-4484, hsa-miR-6805-3p, hsa-miR-3135b, hsa-miR-3162-5p, hsa-miR-6768-5p, hsa-miR-6721-5p, hsa-miR-1227-5p, hsa-miR-6722-3p, hsa-miR-4286, hsa-miR-4746-3p, hsa-miR-6727-5p, hsa-miR-6816-5p, hsa-miR-4741, hsa-miR-4508, hsa-miR-940, hsa-miR-4327, hsa-miR-4665-3p, hsa-miR-718, hsa-miR-125a-3p, hsa-miR-204-3p, hsa-miR-1469, hsa-miR-575, hsa-miR-150-3p, hsa-miR-423-5p, hsa-miR-564, hsa-miR-3188, hsa-miR-1246, hsa-miR-602, hsa-miR-1290, hsa-miR-16-5p, hsa-miR-451a, hsa-miR-24-3p, hsa-miR-187-5p, hsa-miR-1908-5p, hsa-miR-371a-5p, hsa-miR-550a-5p, hsa-miR-4417, hsa-miR-4707-5p, hsa-ma-7847-3p, hsa-miR-2861, hsa-miR-4513, hsa-miR-7111-5p, hsa-miR-6777-5p, hsa-miR-7113-3p, hsa-miR-4648, hsa-miR-3184-5p, hsa-miR-4271, hsa-miR-6791-5p, hsa-miR-642a-3p, hsa-miR-7108-5p, hsa-miR-128-1-5p, hsa-miR-5196-5p, hsa-miR-3178, hsa-miR-3656, hsa-miR-92a-2-5p, hsa-miR-6769b-5p, hsa-miR-4689, hsa-miR-6076, hsa-miR-92b-5p, hsa-miR-6774-5p, hsa-miR-486-3p, hsa-miR-6806-5p, hsa-miR-6842-5p, hsa-miR-6716-5p, 557, hsa-miR-4673, hsa-miR-4674, hsa-miR-4442, hsa-miR-1915-3p, hsa-miR-4687-3p, hsa-miR-92b-3p, hsa-miR-1203, hsa-miR-663b, hsa-miR-4258, hsa-miR-4649-5p, hsa-miR-4516, hsa-miR-3619-3p, hsa-miR-6826-5p, hsa-miR-6757-5p, hsa-miR-3131, hsa-miR-1343-3p, hsa-miR-6775-5p, hsa-miR-6813-5p and hsa-miR-3940-5p, respectively), a congener, a transcript thereof, or/and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 499 or a transcript thereof, more preferably the transcript, i.e., a miRNA or its precursor RNA (pri-miRNA or pre-miRNA).

The first target gene is the hsa-miR-6893-5p gene, a congener thereof, a transcript thereof, or a variant or a derivative thereof. None of the previously known reports show that change in the expression of the gene or the transcript thereof can serve as a marker for pancreatic cancer.

The second target gene is the hsa-miR-6075 gene, a congener thereof, a transcript thereof, or a variant or a derivative thereof. None of the previously known reports show that change in the expression of the gene or the transcript thereof can serve as a marker for pancreatic cancer.

The third target gene is the hsa-miR-6820-5p gene, a congener thereof, a transcript thereof, or a variant or a derivative thereof. None of the previously known reports show that change in the expression of the gene or the transcript thereof can serve as a marker for pancreatic cancer.

The fourth target gene is the hsa-miR-4294 gene, a congener thereof, a transcript thereof, or a variant or a derivative thereof. None of the previously known reports show that change in the expression of the gene or the transcript thereof can serve as a marker for pancreatic cancer.

The fifth target gene is the hsa-miR-6729-5p gene, a congener thereof, a transcript thereof, or a variant or a derivative thereof. None of the previously known reports show that change in the expression of the gene or the transcript thereof can serve as a marker for pancreatic cancer.

The sixth target gene is the 1 sa-miR-4476 gene, a congener thereof, a transcript thereof, or a variant or a derivative thereof. None of the previously known reports show that change in the expression of the gene or the transcript thereof can serve as a marker for pancreatic cancer.

The seventh target gene is the hsa-miR-6836-3p gene, a congener thereof, a transcript thereof, or a variant or a derivative thereof. None of the previously known reports show that change in the expression of the gene or the transcript thereof can serve as a marker for pancreatic cancer.

The eighth target gene is the hsa-miR-6765-3p gene, a congener thereof, a transcript thereof, or a variant or a derivative thereof. None of the previously known reports show that change in the expression of the gene or the transcript thereof can serve as a marker for pancreatic cancer.

The ninth target gene is the hsa-miR-6799-5p gene, a congener thereof, a transcript thereof, or a variant or a derivative thereof. None of the previously known reports show that change in the expression of the gene or the transcript thereof can serve as a marker for pancreatic cancer.

The 10th target gene is the hsa-miR-4530 gene, a congener thereof, a transcript thereof, or a variant or a derivative thereof. None of the previously known reports show that change in the expression of the gene or the transcript thereof can serve as a marker for pancreatic cancer.

The 11th target gene is the hsa-miR-7641 gene, a congener thereof, a transcript thereof, or a variant or a derivative thereof. None of the previously known reports show that change in the expression of the gene or the transcript thereof can serve as a marker for pancreatic cancer.

The 12th target gene is the hsa-miR-4454 gene, a congener thereof, a transcript thereof, or a variant or a derivative thereof. None of the previously known reports show that change in the expression of the gene or the transcript thereof can serve as a marker for pancreatic cancer.

The 13th target gene is the hsa-miR-615-5p gene, a congener thereof, a transcript thereof, or a variant or a derivative thereof. None of the previously known reports show that change in the expression of the gene or the transcript thereof can serve as a marker for pancreatic cancer.

The 14th target gene is the hsa-miR-8073 gene, a congener thereof, a transcript thereof, or a variant or a derivative thereof. None of the previously known reports show that change in the expression of the gene or the transcript thereof can serve as a marker for pancreatic cancer.

The 15th target gene is the hsa-miR-663a gene, a congener thereof, a transcript thereof, or a variant or a derivative thereof. None of the previously known reports show that change in the expression of the gene or the transcript thereof can serve as a marker for pancreatic cancer.

The 16th target gene is the hsa-miR-4634 gene, a congener thereof, a transcript thereof, or a variant or a derivative thereof. None of the previously known reports show that change in the expression of the gene or the transcript thereof can serve as a marker for pancreatic cancer.

The 17th target gene is the hsa-miR-4450 gene, a congener thereof, a transcript thereof, or a variant or a derivative thereof. None of the previously known reports show that change in the expression of the gene or the transcript thereof can serve as a marker for pancreatic cancer.

The 18th target gene is the hsa-miR-4792 gene, a congener thereof a transcript thereof, or a variant or a derivative thereof. None of the previously known reports show that change in the expression of the gene or the transcript thereof can serve as a marker for pancreatic cancer.

The 19th target gene is the hsa-miR-665 gene, a congener thereof, a transcript thereof or a variant or a derivative thereof. None of the previously known reports show that change in the expression of the gene or the transcript thereof can serve as a marker for pancreatic cancer.

The 20th target gene is the hsa-miR-7975 gene, a congener thereof a transcript thereof, or a variant or a derivative thereof. None of the previously known reports show that change in the expression of the gene or the transcript thereof can serve as a marker for pancreatic cancer.

The 21st target gene is the hsa-miR-7109-5p gene, a congener thereof a transcript thereof, or a variant or a derivative thereof. None of the previously known reports show that change in the expression of the gene or the transcript thereof can serve as a marker for pancreatic cancer.

The 22nd target gene is the hsa-miR-6789-5p gene, a congener thereof a transcript thereof, or a variant or a derivative thereof. None of the previously known reports show that change in the expression of the gene or the transcript thereof can serve as a marker for pancreatic cancer.

The 23rd target gene is the hsa-miR-4497 gene, a congener thereof, a transcript thereof, or a variant or a derivative thereof. None of the previously known reports show that change in the expression of the gene or the transcript thereof can serve as a marker for pancreatic cancer.

The 24th target gene is the hsa-miR-6877-5p gene, a congener thereof, a transcript thereof, or a variant or a derivative thereof. None of the previously known reports show that change in the expression of the gene or the transcript thereof can serve as a marker for pancreatic cancer.

The 25th target gene is the hsa-miR-6880-5p gene, a congener thereof, a transcript thereof, or a variant or a derivative thereof. None of the previously known reports show that change in the expression of the gene or the transcript thereof can serve as a marker for pancreatic cancer.

The 26th target gene is the hsa-miR-7977 gene, a congener thereof, a transcript thereof, or a variant or a derivative thereof. None of the previously known reports show that change in the expression of the gene or the transcript thereof can serve as a marker for pancreatic cancer.

The 27th target gene is the hsa-miR-4734 gene, a congener thereof, a transcript thereof, or a variant or a derivative thereof. None of the previously known reports show that change in the expression of the gene or the transcript thereof can serve as a marker for pancreatic cancer.

The 28th target gene is the hsa-miR-6821-5p gene, a congener thereof, a transcript thereof, or a variant or a derivative thereof. None of the previously known reports show that change in the expression of the gene or the transcript thereof can serve as a marker for pancreatic cancer.

The 29th target gene is the hsa-miR-8089 gene, a congener thereof, a transcript thereof, or a variant or a derivative thereof. None of the previously known reports show that change in the expression of the gene or the transcript thereof can serve as a marker for pancreatic cancer.

The 30th target gene is the hsa-miR-5585-3p gene, a congener thereof, a transcript thereof, or a variant or a derivative thereof. None of the previously known reports show that change in the expression of the gene or the transcript thereof can serve as a marker for pancreatic cancer.

The 31st target gene is the hsa-miR-6085 gene, a congener thereof, a transcript thereof, or a variant or a derivative thereof. None of the previously known reports show that change in the expression of the gene or the transcript thereof can serve as a marker for pancreatic cancer.

The 32nd target gene is the hsa-miR-6845-5p gene, a congener thereof, a transcript thereof, or a variant or a derivative thereof. None of the previously known reports show that change in the expression of the gene or the transcript thereof can serve as a marker for pancreatic cancer.

The 33rd target gene is the hsa-miR-4651 gene, a congener thereof, a transcript thereof, or a variant or a derivative thereof. None of the previously known reports show that change in the expression of the gene or the transcript thereof can serve as a marker for pancreatic cancer.

The 34th target gene is the hsa-miR-4433-3p gene, a congener thereof, a transcript thereof, or a variant or a derivative thereof. None of the previously known reports show that change in the expression of the gene or the transcript thereof can serve as a marker for pancreatic cancer.

The 35th target gene is the hsa-miR-1231 gene, a congener thereof, a transcript thereof, or a variant or a derivative thereof. None of the previously known reports show that change in the expression of the gene or the transcript thereof can serve as a marker for pancreatic cancer.

The 36th target gene is the hsa-miR-4665-5p gene, a congener thereof, a transcript thereof, or a variant or a derivative thereof. None of the previously known reports show that change in the expression of the gene or the transcript thereof can serve as a marker for pancreatic cancer.

The 37th target gene is the hsa-miR-7114-5p gene, a congener thereof, a transcript thereof, or a variant or a derivative thereof. None of the previously known reports show that change in the expression of the gene or the transcript thereof can serve as a marker for pancreatic cancer.

The 38th target gene is the hsa-miR-1238-5p gene, a congener thereof, a transcript thereof, or a variant or a derivative thereof. None of the previously known reports show that change in the expression of the gene or the transcript thereof can serve as a marker for pancreatic cancer.

The 39th target gene is the hsa-miR-8069 gene, a congener thereof, a transcript thereof, or a variant or a derivative thereof. None of the previously known reports show that change in the expression of the gene or the transcript thereof can serve as a marker for pancreatic cancer.

The 40th target gene is the hsa-miR-4732-5p gene, a congener thereof, a transcript thereof, or a variant or a derivative thereof. None of the previously known reports show that change in the expression of the gene or the transcript thereof can serve as a marker for pancreatic cancer.

The 41st target gene is the hsa-miR-619-5p gene, a congener thereof, a transcript thereof, or a variant or a derivative thereof. None of the previously known reports show that change in the expression of the gene or the transcript thereof can serve as a marker for pancreatic cancer.

The 42nd target gene is the hsa-miR-3622a-5p gene, a congener thereof, a transcript thereof, or a variant or a derivative thereof. None of the previously known reports show that change in the expression of the gene or the transcript thereof can serve as a marker for pancreatic cancer.

The 43rd target gene is the hsa-miR-1260a gene, a congener thereof, a transcript thereof, or a variant or a derivative thereof. None of the previously known reports show that change in the expression of the gene or the transcript thereof can serve as a marker for pancreatic cancer.

The 44th target gene is the hsa-miR-6741-5p gene, a congener thereof, a transcript thereof, or a variant or a derivative thereof. None of the previously known reports show that change in the expression of the gene or the transcript thereof can serve as a marker for pancreatic cancer.

The 45th target gene is the hsa-miR-6781-5p gene, a congener thereof a transcript thereof, or a variant or a derivative thereof. None of the previously known reports show that change in the expression of the gene or the transcript thereof can serve as a marker for pancreatic cancer.

The 46th target gene is the hsa-miR-6125 gene, a congener thereof, a transcript thereof, or a variant or a derivative thereof. None of the previously known reports show that change in the expression of the gene or the transcript thereof can serve as a marker for pancreatic cancer.

The 47th target gene is the hsa-miR-6805-5p gene, a congener thereof, a transcript thereof, or a variant or a derivative thereof. None of the previously known reports show that change in the expression of the gene or the transcript thereof can serve as a marker for pancreatic cancer.

The 48th target gene is the hsa-miR-6132 gene, a congener thereof, a transcript thereof, or a variant or a derivative thereof. None of the previously known reports show that change in the expression of the gene or the transcript thereof can serve as a marker for pancreatic cancer.

The 49th target gene is the hsa-miR-6872-3p gene, a congener thereof, a transcript thereof, or a variant or a derivative thereof. None of the previously known reports show that change in the expression of the gene or the transcript thereof can serve as a marker for pancreatic cancer.

The 50th target gene is the hsa-miR-6875-5p gene, a congener thereof, a transcript thereof, or a variant or a derivative thereof. None of the previously known reports show that change in the expression of the gene or the transcript thereof can serve as a marker for pancreatic cancer.

The 51st target gene is the hsa-miR-1908-3p gene, a congener thereof, a transcript thereof, or a variant or a derivative thereof. None of the previously known reports show that change in the expression of the gene or the transcript thereof can serve as a marker for pancreatic cancer.

The 52nd target gene is the hsa-miR-4433b-3p gene, a congener thereof, a transcript thereof, or a variant or a derivative thereof. None of the previously known reports show that change in the expression of the gene or the transcript thereof can serve as a marker for pancreatic cancer.

The 53rd target gene is the hsa-miR-4736 gene, a congener thereof, a transcript thereof, or a variant or a derivative thereof. None of the previously known reports show that change in the expression of the gene or the transcript thereof can serve as a marker for pancreatic cancer.

The 54th target gene is the hsa-miR-5100 gene, a congener thereof, a transcript thereof, or a variant or a derivative thereof. None of the previously known reports show that change in the expression of the gene or the transcript thereof can serve as a marker for pancreatic cancer.

The 55th target gene is the hsa-miR-6724-5p gene, a congener thereof, a transcript thereof, or a variant or a derivative thereof. None of the previously known reports show that change in the expression of the gene or the transcript thereof can serve as a marker for pancreatic cancer.

The 56th target gene is the hsa-miR-7107-5p gene, a congener thereof, a transcript thereof, or a variant or a derivative thereof. None of the previously known reports show that change in the expression of the gene or the transcript thereof can serve as a marker for pancreatic cancer.

The 57th target gene is the hsa-miR-6726-5p gene, a congener thereof, a transcript thereof, or a variant or a derivative thereof. None of the previously known reports show that change in the expression of the gene or the transcript thereof can serve as a marker for pancreatic cancer.

The 58th target gene is the hsa-miR-3185 gene, a congener thereof, a transcript thereof, or a variant or a derivative thereof. None of the previously known reports show that change in the expression of the gene or the transcript thereof can serve as a marker for pancreatic cancer.

The 59th target gene is the hsa-miR-4638-5p gene, a congener thereof, a transcript thereof, or a variant or a derivative thereof. None of the previously known reports show that change in the expression of the gene or the transcript thereof can serve as a marker for pancreatic cancer.

The 60th target gene is the hsa-miR-1273g-3p gene, a congener thereof, a transcript thereof, or a variant or a derivative thereof. None of the previously known reports show that change in the expression of the gene or the transcript thereof can serve as a marker for pancreatic cancer.

The 61st target gene is the hsa-miR-6778-5p gene, a congener thereof, a transcript thereof, or a variant or a derivative thereof. None of the previously known reports show that change in the expression of the gene or the transcript thereof can serve as a marker for pancreatic cancer.

The 62nd target gene is the hsa-miR-328-5p gene, a congener thereof, a transcript thereof, or a variant or a derivative thereof. None of the previously known reports show that change in the expression of the gene or the transcript thereof can serve as a marker for pancreatic cancer.

The 63rd target gene is the hsa-miR-3679-3p gene, a congener thereof, a transcript thereof, or a variant or a derivative thereof. None of the previously known reports show that change in the expression of the gene or the transcript thereof can serve as a marker for pancreatic cancer.

The 64th target gene is the hsa-miR-1228-3p gene, a congener thereof, a transcript thereof, or a variant or a derivative thereof. None of the previously known reports show that change in the expression of the gene or the transcript thereof can serve as a marker for pancreatic cancer.

The 65th target gene is the hsa-miR-6779-5p gene, a congener thereof, a transcript thereof, or a variant or a derivative thereof. None of the previously known reports show that change in the expression of the gene or the transcript thereof can serve as a marker for pancreatic cancer.

The 66th target gene is the hsa-miR-4723-5p gene, a congener thereof, a transcript thereof, or a variant or a derivative thereof. None of the previously known reports show that change in the expression of the gene or the transcript thereof can serve as a marker for pancreatic cancer.

The 67th target gene is the hsa-miR-6850-5p gene, a congener thereof, a transcript thereof, or a variant or a derivative thereof. None of the previously known reports show that change in the expression of the gene or the transcript thereof can serve as a marker for pancreatic cancer.

The 68th target gene is the hsa-miR-760 gene, a congener thereof, a transcript thereof, or a variant or a derivative thereof. None of the previously known reports show that change in the expression of the gene or the transcript thereof can serve as a marker for pancreatic cancer.

The 69th target gene is the hsa-miR-7704 gene, a congener thereof, a transcript thereof, or a variant or a derivative thereof. None of the previously known reports show that change in the expression of the gene or the transcript thereof can serve as a marker for pancreatic cancer.

The 70th target gene is the hsa-miR-8072 gene, a congener thereof, a transcript thereof, or a variant or a derivative thereof. None of the previously known reports show that change in the expression of the gene or the transcript thereof can serve as a marker for pancreatic cancer.

The 71st target gene is the hsa-miR-4486 gene, a congener thereof, a transcript thereof, or a variant or a derivative thereof. None of the previously known reports show that change in the expression of the gene or the transcript thereof can serve as a marker for pancreatic cancer.

The 72nd target gene is the hsa-miR-1913 gene, a congener thereof, a transcript thereof, or a variant or a derivative thereof. None of the previously known reports show that change in the expression of the gene or the transcript thereof can serve as a marker for pancreatic cancer.

The 73rd target gene is the hsa-miR-4656 gene, a congener thereof, a transcript thereof, or a variant or a derivative thereof. None of the previously known reports show that change in the expression of the gene or the transcript thereof can serve as a marker for pancreatic cancer.

The 74th target gene is the hsa-miR-1260b gene, a congener thereof, a transcript thereof, or a variant or a derivative thereof. None of the previously known reports show that change in the expression of the gene or the transcript thereof can serve as a marker for pancreatic cancer.

The 75th target gene is the hsa-miR-7106-5p gene, a congener thereof, a transcript thereof, or a variant or a derivative thereof. None of the previously known reports show that change in the expression of the gene or the transcript thereof can serve as a marker for pancreatic cancer.

The 76th target gene is the hsa-miR-6889-5p gene, a congener thereof, a transcript thereof, or a variant or a derivative thereof. None of the previously known reports show that change in the expression of the gene or the transcript thereof can serve as a marker for pancreatic cancer.

The 77th target gene is the hsa-miR-6780b-5p gene, a congener thereof, a transcript thereof, or a variant or a derivative thereof. None of the previously known reports show that change in the expression of the gene or the transcript thereof can serve as a marker for pancreatic cancer.

The 78th target gene is the hsa-miR-6090 gene, a congener thereof, a transcript thereof, or a variant or a derivative thereof. None of the previously known reports show that change in the expression of the gene or the transcript thereof can serve as a marker for pancreatic cancer.

The 79th target gene is the hsa-miR-4534 gene, a congener thereof, a transcript thereof, or a variant or a derivative thereof. None of the previously known reports show that change in the expression of the gene or the transcript thereof can serve as a marker for pancreatic cancer.

The 80th target gene is the hsa-miR-4449 gene, a congener thereof, a transcript thereof, or a variant or a derivative thereof. None of the previously known reports show that change in the expression of the gene or the transcript thereof can serve as a marker for pancreatic cancer.

The 81st target gene is the hsa-miR-5195-3p gene, a congener thereof, a transcript thereof, or a variant or a derivative thereof. None of the previously known reports show that change in the expression of the gene or the transcript thereof can serve as a marker for pancreatic cancer.

The 82nd target gene is the hsa-miR-1202 gene, a congener thereof, a transcript thereof, or a variant or a derivative thereof. None of the previously known reports show that change in the expression of the gene or the transcript thereof can serve as a marker for pancreatic cancer.

The 83rd target gene is the hsa-miR-4467 gene, a congener thereof, a transcript thereof, or a variant or a derivative thereof. None of the previously known reports show that change in the expression of the gene or the transcript thereof can serve as a marker for pancreatic cancer.

The 84th target gene is the hsa-miR-6515-3p gene, a congener thereof, a transcript thereof, or a variant or a derivative thereof. None of the previously known reports show that change in the expression of the gene or the transcript thereof can serve as a marker for pancreatic cancer.

The 85th target gene is the hsa-miR-4281 gene, a congener thereof, a transcript thereof, or a variant or a derivative thereof. None of the previously known reports show that change in the expression of the gene or the transcript thereof can serve as a marker for pancreatic cancer.

The 86th target gene is the hsa-miR-4505 gene, a congener thereof, a transcript thereof, or a variant or a derivative thereof. None of the previously known reports show that change in the expression of the gene or the transcript thereof can serve as a marker for pancreatic cancer.

The 87th target gene is the hsa-miR-4484 gene, a congener thereof, a transcript thereof, or a variant or a derivative thereof. None of the previously known reports show that change in the expression of the gene or the transcript thereof can serve as a marker for pancreatic cancer.

The 88th target gene is the hsa-miR-6805-3p gene, a congener thereof, a transcript thereof, or a variant or a derivative thereof. None of the previously known reports show that change in the expression of the gene or the transcript thereof can serve as a marker for pancreatic cancer.

The 89th target gene is the hsa-miR-3135b gene, a congener thereof, a transcript thereof, or a variant or a derivative thereof. None of the previously known reports show that change in the expression of the gene or the transcript thereof can serve as a marker for pancreatic cancer.

The 90th target gene is the hsa-miR-3162-5p gene, a congener thereof, a transcript thereof, or a variant or a derivative thereof. None of the previously known reports show that change in the expression of the gene or the transcript thereof can serve as a marker for pancreatic cancer.

The 91st target gene is the hsa-miR-6768-5p gene, a congener thereof, a transcript thereof, or a variant or a derivative thereof. None of the previously known reports show that change in the expression of the gene or the transcript thereof can serve as a marker for pancreatic cancer.

The 92nd target gene is the hsa-miR-6721-5p gene, a congener thereof, a transcript thereof, or a variant or a derivative thereof. None of the previously known reports show that change in the expression of the gene or the transcript thereof can serve as a marker for pancreatic cancer.

The 93rd target gene is the hsa-miR-1227-5p gene, a congener thereof, a transcript thereof, or a variant or a derivative thereof. None of the previously known reports show that change in the expression of the gene or the transcript thereof can serve as a marker for pancreatic cancer.

The 94th target gene is the hsa-miR-6722-3p gene, a congener thereof a transcript thereof, or a variant or a derivative thereof. None of the previously known reports show that change in the expression of the gene or the transcript thereof can serve as a marker for pancreatic cancer.

The 95th target gene is the hsa-miR-4286 gene, a congener thereof, a transcript thereof, or a variant or a derivative thereof. None of the previously known reports show that change in the expression of the gene or the transcript thereof can serve as a marker for pancreatic cancer.

The 96th target gene is the hsa-miR-4746-3p gene, a congener thereof a transcript thereof, or a variant or a derivative thereof. None of the previously known reports show that change in the expression of the gene or the transcript thereof can serve as a marker for pancreatic cancer.

The 97th target gene is the hsa-miR-6727-5p gene, a congener thereof, a transcript thereof, or a variant or a derivative thereof. None of the previously known reports show that change in the expression of the gene or the transcript thereof can serve as a marker for pancreatic cancer.

The 98th target gene is the hsa-miR-6816-5p gene, a congener thereof, a transcript thereof, or a variant or a derivative thereof. None of the previously known reports show that change in the expression of the gene or the transcript thereof can serve as a marker for pancreatic cancer.

The 99th target gene is the hsa-miR-4741 gene, a congener thereof, a transcript thereof, or a variant or a derivative thereof. None of the previously known reports show that change in the expression of the gene or the transcript thereof can serve as a marker for pancreatic cancer.

The 100th target gene is the hsa-miR-4508 gene, a congener thereof, a transcript thereof, or a variant or a derivative thereof. None of the previously known reports show that change in the expression of the gene or the transcript thereof can serve as a marker for pancreatic cancer.

The 101st target gene is the hsa-miR-940 gene, a congener thereof, a transcript thereof, or a variant or a derivative thereof. None of the previously known reports show that change in the expression of the gene or the transcript thereof can serve as a marker for pancreatic cancer.

The 102nd target gene is the hsa-miR-4327 gene, a congener thereof, a transcript thereof, or a variant or a derivative thereof. None of the previously known reports show that change in the expression of the gene or the transcript thereof can serve as a marker for pancreatic cancer.

The 103rd target gene is the hsa-miR-4665-3p gene, a congener thereof, a transcript thereof, or a variant or a derivative thereof. None of the previously known reports show that change in the expression of the gene or the transcript thereof can serve as a marker for pancreatic cancer.

The 104th target gene is the hsa-atiR-718 gene, a congener thereof, a transcript thereof, or a variant or a derivative thereof. None of the previously known reports show that change in the expression of the gene or the transcript thereof can serve as a marker for pancreatic cancer.

The 105th target gene is the hsa-miR-125a-3p gene, a congener thereof, a transcript thereof, or a variant or a derivative thereof. The previously known report shows that change in the expression of the gene or the transcript thereof can serve as a marker for pancreatic cancer (Patent Literature 1 described above).

The 106th target gene is the hsa-miR-204-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 107th target gene is the hsa-miR-1469 gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 108th target gene is the hsa-miR-575 gene, a congener thereof, a transcript thereof, or a variant or a derivative thereof. The previously known report shows that change in the expression of the gene or the transcript thereof can serve as a marker for pancreatic cancer (Patent Literature 3 described above).

The 109th target gene is the hsa-miR-150-3p gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 110th target gene is the hsa-miR-423-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 111th target gene is the hsa-miR-564 gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 112th target gene is the hsa-miR-3188 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 113th target gene is the hsa-miR-1246 gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 114th target gene is the hsa-miR-602 gene, a congener thereof, a transcript thereof, or a variant or a derivative thereof. The previously known report shows that change in the expression of the gene or the transcript thereof can serve as a marker for pancreatic cancer (Non-Patent Literature 7 described above).

The 115th target gene is the hsa-miR-1290 gene, a congener thereof, a transcript thereof, or a variant or a derivative thereof. The previously known report shows that change in the expression of the gene or the transcript thereof can serve as a marker for pancreatic cancer (Non-Patent Literature 6 described above).

The 116th target gene is the hsa-miR-16-5p gene, a congener thereof, a transcript thereof, or a variant or a derivative thereof. The previously known report shows that change in the expression of the gene or the transcript thereof can serve as a marker for pancreatic cancer (Patent Literature 3 described above).

The 117th target gene is the hsa-miR-451a gene, a congener thereof, a transcript thereof, or a variant or a derivative thereof. The previously known report shows that change in the expression of the gene or the transcript thereof can serve as a marker for pancreatic cancer (Patent Literature 4 described above).

The 118th target gene is the hsa-miR-24-3p gene, a congener thereof, a transcript thereof, or a variant or a derivative thereof. The previously known report shows that change in the expression of the gene or the transcript thereof can serve as a marker for pancreatic cancer (Patent Literature 3 described above).

The 119th target gene is the hsa-miR-187-5p gene, a congener thereof, a transcript thereof, or a variant or a derivative thereof. The previously known report shows that change in the expression of the gene or the transcript thereof can serve as a marker for pancreatic cancer (Patent Literature 5 described above).

The 120th target gene is the hsa-miR-1908-5p gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 121st target gene is the hsa-miR-371a-5p gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 122nd target gene is the hsa-miR-550a-5p gene, a congener thereof, a transcript thereof, or a variant or a derivative thereof. The previously known report shows that change in the expression of the gene or the transcript thereof can serve as a marker for pancreatic cancer (Non-Patent Literature 6 described above).

The 123rd target gene is the hsa-miR-4417 gene, a congener thereof, a transcript thereof, or a variant or a derivative thereof. None of the previously known reports show that change in the expression of the gene or the transcript thereof can serve as a marker for pancreatic cancer.

The 124th target gene is the hsa-miR-4707-5p gene, a congener thereof, a transcript thereof, or a variant or a derivative thereof. None of the previously known reports show that change in the expression of the gene or the transcript thereof can serve as a marker for pancreatic cancer.

The 125th target gene is the hsa-miR-7847-3p gene, a congener thereof, a transcript thereof, or a variant or a derivative thereof. None of the previously known reports show that change in the expression of the gene or the transcript thereof can serve as a marker for pancreatic cancer.

The 126th target gene is the hsa-miR-2861 gene, a congener thereof, a transcript thereof, or a variant or a derivative thereof. None of the previously known reports show that change in the expression of the gene or the transcript thereof can serve as a marker for pancreatic cancer.

The 127th target gene is the hsa-miR-4513 gene, a congener thereof, a transcript thereof, or a variant or a derivative thereof. None of the previously known reports show that change in the expression of the gene or the transcript thereof can serve as a marker for pancreatic cancer.

The 128th target gene is the hsa-miR-7111-5p gene, a congener thereof, a transcript thereof, or a variant or a derivative thereof. None of the previously known reports show that change in the expression of the gene or the transcript thereof can serve as a marker for pancreatic cancer.

The 129th target gene is the hsa-miR-6777-5p gene, a congener thereof, a transcript thereof, or a variant or a derivative thereof. None of the previously known reports show that change in the expression of the gene or the transcript thereof can serve as a marker for pancreatic cancer.

The 130th target gene is the hsa-miR-7113-3p gene, a congener thereof, a transcript thereof, or a variant or a derivative thereof. None of the previously known reports show that change in the expression of the gene or the transcript thereof can serve as a marker for pancreatic cancer.

The 131st target gene is the hsa-miR-4648 gene, a congener thereof, a transcript thereof, or a variant or a derivative thereof. None of the previously known reports show that change in the expression of the gene or the transcript thereof can serve as a marker for pancreatic cancer.

The 132nd target gene is the hsa-miR-3184-5p gene, a congener thereof, a transcript thereof, or a variant or a derivative thereof. None of the previously known reports show that change in the expression of the gene or the transcript thereof can serve as a marker for pancreatic cancer.

The 133rd target gene is the hsa-miR-4271 gene, a congener thereof, a transcript thereof, or a variant or a derivative thereof. None of the previously known reports show that change in the expression of the gene or the transcript thereof can serve as a marker for pancreatic cancer.

The 134th target gene is the hsa-miR-6791-5p gene, a congener thereof, a transcript thereof, or a variant or a derivative thereof. None of the previously known reports show that change in the expression of the gene or the transcript thereof can serve as a marker for pancreatic cancer.

The 135th target gene is the hsa-miR-642a-3p gene, a congener thereof, a transcript thereof, or a variant or a derivative thereof. None of the previously known reports show that change in the expression of the gene or the transcript thereof can serve as a marker for pancreatic cancer.

The 136th target gene is the hsa-miR-7108-5p gene, a congener thereof, a transcript thereof, or a variant or a derivative thereof. None of the previously known reports show that change in the expression of the gene or the transcript thereof can serve as a marker for pancreatic cancer.

The 137th target gene is the hsa-miR-128-1-5p gene, a congener thereof, a transcript thereof, or a variant or a derivative thereof. None of the previously known reports show that change in the expression of the gene or the transcript thereof can serve as a marker for pancreatic cancer.

The 138th target gene is the hsa-miR-5196-5p gene, a congener thereof, a transcript thereof, or a variant or a derivative thereof. None of the previously known reports show that change in the expression of the gene or the transcript thereof can serve as a marker for pancreatic cancer.

The 139th target gene is the hsa-miR-3178 gene, a congener thereof, a transcript thereof, or a variant or a derivative thereof. None of the previously known reports show that change in the expression of the gene or the transcript thereof can serve as a marker for pancreatic cancer.

The 140th target gene is the hsa-miR-3656 gene, a congener thereof, a transcript thereof, or a variant or a derivative thereof. None of the previously known reports show that change in the expression of the gene or the transcript thereof can serve as a marker for pancreatic cancer.

The 141st target gene is the hsa-miR-92a-2-5p gene, a congener thereof, a transcript thereof, or a variant or a derivative thereof. None of the previously known reports show that change in the expression of the gene or the transcript thereof can serve as a marker for pancreatic cancer.

The 142nd target gene is the hsa-miR-6769b-5p gene, a congener thereof, a transcript thereof, or a variant or a derivative thereof. None of the previously known reports show that change in the expression of the gene or the transcript thereof can serve as a marker for pancreatic cancer.

The 143rd target gene is the hsa-miR-4689 gene, a congener thereof, a transcript thereof, or a variant or a derivative thereof. None of the previously known reports show that change in the expression of the gene or the transcript thereof can serve as a marker for pancreatic cancer.

The 144th target gene is the hsa-miR-6076 gene, a congener thereof, a transcript thereof, or a variant or a derivative thereof. None of the previously known reports show that change in the expression of the gene or the transcript thereof can serve as a marker for pancreatic cancer.

The 145th target gene is the hsa-miR-92b-5p gene, a congener thereof, a transcript thereof, or a variant or a derivative thereof. None of the previously known reports show that change in the expression of the gene or the transcript thereof can serve as a marker for pancreatic cancer.

The 146th target gene is the hsa-miR-6774-5p gene, a congener thereof, a transcript thereof, or a variant or a derivative thereof. None of the previously known reports show that change in the expression of the gene or the transcript thereof can serve as a marker for pancreatic cancer.

The 147th target gene is the hsa-miR-486-3p gene, a congener thereof, a transcript thereof, or a variant or a derivative thereof. None of the previously known reports show that change in the expression of the gene or the transcript thereof can serve as a marker for pancreatic cancer.

The 148th target gene is the hsa-miR-6806-5p gene, a congener thereof, a transcript thereof, or a variant or a derivative thereof. None of the previously known reports show that change in the expression of the gene or the transcript thereof can serve as a marker for pancreatic cancer.

The 149th target gene is the hsa-miR-6842-5p gene, a congener thereof, a transcript thereof, or a variant or a derivative thereof. None of the previously known reports show that change in the expression of the gene or the transcript thereof can serve as a marker for pancreatic cancer.

The 150th target gene is the hsa-miR-6716-5p gene, a congener thereof, a transcript thereof, or a variant or a derivative thereof. None of the previously known reports show that change in the expression of the gene or the transcript thereof can serve as a marker for pancreatic cancer.

The 151st target gene is the hsa-miR-557 gene, a congener thereof, a transcript thereof, or a variant or a derivative thereof. None of the previously known reports show that change in the expression of the gene or the transcript thereof can serve as a marker for pancreatic cancer.

The 152nd target gene is the hsa-miR-4673 gene, a congener thereof, a transcript thereof, or a variant or a derivative thereof. None of the previously known reports show that change in the expression of the gene or the transcript thereof can serve as a marker for pancreatic cancer.

The 153rd target gene is the hsa-miR-4674 gene, a congener thereof, a transcript thereof, or a variant or a derivative thereof. None of the previously known reports show that change in the expression of the gene or the transcript thereof can serve as a marker for pancreatic cancer.

The 154th target gene is the hsa-miR-4442 gene, a congener thereof, a transcript thereof, or a variant or a derivative thereof. None of the previously known reports show that change in the expression of the gene or the transcript thereof can serve as a marker for pancreatic cancer.

The 155th target gene is the hsa-miR-1915-3p gene, a congener thereof, a transcript thereof, or a variant or a derivative thereof. None of the previously known reports show that change in the expression of the gene or the transcript thereof can serve as a marker for pancreatic cancer.

The 156th target gene is the hsa-miR-4687-3p gene, a congener thereof, a transcript thereof, or a variant or a derivative thereof. None of the previously known reports show that change in the expression of the gene or the transcript thereof can serve as a marker for pancreatic cancer.

The 157th target gene is the hsa-miR-92b-3p gene, a congener thereof, a transcript thereof, or a variant or a derivative thereof. None of the previously known reports show that change in the expression of the gene or the transcript thereof can serve as a marker for pancreatic cancer.

The 158th target gene is the hsa-miR-1203 gene, a congener thereof, a transcript thereof, or a variant or a derivative thereof. None of the previously known reports show that change in the expression of the gene or the transcript thereof can serve as a marker for pancreatic cancer.

The 159th target gene is the hsa-mir-663b gene, a congener thereof, a transcript thereof, or a variant or a derivative thereof. None of the previously known reports show that change in the expression of the gene or the transcript thereof can serve as a marker for pancreatic cancer.

The 160th target gene is the hsa-mir-4258 gene, a congener thereof, a transcript thereof, or a variant or a derivative thereof. None of the previously known reports show that change in the expression of the gene or the transcript thereof can serve as a marker for pancreatic cancer.

The 161st target gene is the hsa-mir-4649 gene, a congener thereof, a transcript thereof, or a variant or a derivative thereof. None of the previously known reports show that change in the expression of the gene or the transcript thereof can serve as a marker for pancreatic cancer.

The 162nd target gene is the hsa-mir-4516 gene, a congener thereof, a transcript thereof, or a variant or a derivative thereof. None of the previously known reports show that change in the expression of the gene or the transcript thereof can serve as a marker for pancreatic cancer.

The 163rd target gene is the hsa-mir-3619 gene, a congener thereof, a transcript thereof, or a variant or a derivative thereof. None of the previously known reports show that change in the expression of the gene or the transcript thereof can serve as a marker for pancreatic cancer.

The 164th target gene is the hsa-mir-6826 gene, a congener thereof, a transcript thereof, or a variant or a derivative thereof. None of the previously known reports show that change in the expression of the gene or the transcript thereof can serve as a marker for pancreatic cancer.

The 165th target gene is the hsa-mir-6757 gene, a congener thereof, a transcript thereof, or a variant or a derivative thereof. None of the previously known reports show that change in the expression of the gene or the transcript thereof can serve as a marker for pancreatic cancer.

The 166th target gene is the hsa-mir-3131 gene, a congener thereof, a transcript thereof, or a variant or a derivative thereof. None of the previously known reports show that change in the expression of the gene or the transcript thereof can serve as a marker for pancreatic cancer.

The 167th target gene is the hsa-mir-1343 gene, a congener thereof, a transcript thereof, or a variant or a derivative thereof. None of the previously known reports show that change in the expression of the gene or the transcript thereof can serve as a marker for pancreatic cancer.

The 168th target gene is the hsa-miR-6775-5p gene, a congener thereof, a transcript thereof, or a variant or a derivative thereof. None of the previously known reports show that change in the expression of the gene or the transcript thereof can serve as a marker for pancreatic cancer.

The 169th target gene is the hsa-miR-6813-5p gene, a congener thereof, a transcript thereof, or a variant or a derivative thereof. None of the previously known reports show that change in the expression of the gene or the transcript thereof can serve as a marker for pancreatic cancer.

The 170th target gene is the hsa-miR-3940-5p gene, a congener thereof, a transcript thereof, or a variant or a derivative thereof. None of the previously known reports show that change in the expression of the gene or the transcript thereof can serve as a marker for pancreatic cancer.

2. Nucleic Acid Probe or Primer for Detection of Pancreatic Cancer

In the present invention, a nucleic acid capable of specifically binding to any of the target nucleic acids as the pancreatic cancer markers described above can be used as a nucleic acid, for example, a nucleic acid probe or a primer, for the detection or diagnosis of pancreatic cancer.

In the present invention, the nucleic acid probes or the primers that can be used for detecting pancreatic cancer or for diagnosing pancreatic cancer enable qualitative and/or quantitative measurement of the presence, expression level, or existing amount (abundance) of: any of human-derived hsa-miR-6893-5p, hsa-miR-6075, hsa-miR-6820-5p, hsa-miR-4294, hsa-miR-6729-5p, hsa-miR-4476, hsa-miR-6836-3p, hsa-miR-6765-3p, hsa-miR-6799-5p, hsa-miR-4530, hsa-miR-7641, hsa-miR-4454, hsa-miR-615-5p, hsa-miR-8073, hsa-miR-663a, hsa-miR-4634, hsa-miR-4450, hsa-miR-4792, hsa-miR-665, hsa-miR-7975, hsa-miR-7109-5p, hsa-miR-6789-5p, hsa-miR-4497, hsa-miR-6877-5p, hsa-miR-6880-5p, hsa-miR-7977, hsa-miR-4734, hsa-miR-6821-5p, hsa-miR-8089, hsa-miR-5585-3p, hsa-miR-6085, hsa-miR-6845-5p, hsa-miR-4651, hsa-miR-4433-3p, hsa-miR-1231, hsa-miR-4665-5p, hsa-miR-7114-5p, hsa-miR-1238-5p, hsa-miR-8069, hsa-miR-4732-5p, hsa-miR-619-5p, hsa-miR-3622a-5p, hsa-miR-1260a, hsa-miR-6741-5p, hsa-miR-6781-5p, hsa-miR-6125, hsa-miR-6805-5p, hsa-miR-6132, hsa-miR-6872-3p, hsa-miR-6875-5p, hsa-miR-1908-3p, hsa-miR-4433b-3p, hsa-miR-4736, hsa-miR-5100, hsa-miR-7107-5p, hsa-miR-6726-5p, hsa-miR-3185, hsa-miR-4638-5p, hsa-miR-1273g-3p, hsa-miR-6778-5p, hsa-miR-328-5p, hsa-miR-3679-3p, hsa-miR-1228-3p, hsa-miR-6779-5p, hsa-miR-4723-5p, hsa-miR-6850-5p, hsa-miR-760, hsa-miR-7704, hsa-miR-8072, hsa-miR-4486, hsa-miR-1913, hsa-miR-4656, hsa-miR-1260b, hsa-miR-7106-5p, hsa-miR-6889-5p, hsa-miR-6780b-5p, hsa-miR-6090, hsa-miR-4534, hsa-miR-4449, hsa-miR-5195-3p, hsa-miR-1202, hsa-miR-4467, hsa-miR-6515-3p, hsa-miR-4281, hsa-miR-4505, hsa-miR-4484, hsa-miR-6805-3p, hsa-miR-3135b, hsa-miR-3162-5p, hsa-miR-6768-5p, hsa-miR-6721-5p, hsa-miR-1227-5p, hsa-miR-6722-3p, hsa-miR-4286, hsa-miR-6727-5p, hsa-miR-6816-5p, hsa-miR-4741, hsa-miR-4508, hsa-miR-940, hsa-miR-4327, hsa-miR-4665-3p, hsa-miR-718, hsa-miR-1203, hsa-miR-663b, hsa-miR-4258, hsa-miR-4649-5p, hsa-miR-4516, hsa-ntiR-3619-3p, hsa-miR-6826-5p, hsa-miR-6757-5p, hsa-miR-3131, hsa-miR-1343-3p, hsa-miR-6775-5p, hsa-miR-6813-5p, and hsa-miR-3940-5p, as target nucleic acids for pancreatic cancer, or a combination thereof; and hsa-miR-125a-3p, hsa-miR-204-3p, hsa-miR-1469, hsa-miR-575, hsa-miR-150-3p, hsa-miR-423-5p, hsa-miR-564, hsa-miR-3188, hsa-miR-1246, hsa-miR-602, hsa-miR-1290, hsa-miR-16-5p, hsa-miR-451a, hsa-miR-24-3p, hsa-miR-187-5p, hsa-miR-1908-5p, hsa-miR-371a-5p, and hsa-miR-550a-5p, that can be further optionally combined therewith or a combination thereof; and hsa-miR-4417, hsa-miR-4707-5p, hsa-miR-7847-3p, hsa-miR-2861, hsa-miR-4513, hsa-miR-7111-5p, hsa-miR-6777-5p, hsa-miR-7113-3p, hsa-miR-4648, hsa-miR-3184-5p, hsa-miR-4271, hsa-miR-6791-5p, hsa-miR-642a-3p, hsa-miR-7108-5p, hsa-miR-128-1-5p, hsa-miR-5196-5p, hsa-miR-3178, hsa-miR-3656, hsa-miR-92a-2-5p, hsa-miR-6769b-5p, hsa-miR-4689, hsa-miR-6076, hsa-miR-92b-5p, hsa-miR-6774-5p, hsa-miR-486-3p, hsa-miR-6806-5p, hsa-miR-6842-5p, hsa-miR-6716-5p, hsa-miR-557, hsa-miR-4673, hsa-miR-4674, hsa-miR-4442, hsa-miR-1915-3p, hsa-miR-4687-3p and hsa-miR-92b-3p, that can be further optionally combined therewith or a combination thereof; congeners thereof: transcripts thereof: or variants or derivatives thereof.

The expression levels of the target nucleic acids described above are increased or decreased (hereinafter, referred to as "increased/decreased") depending on the types of the target nucleic acids in subjects having pancreatic cancer as compared with healthy subjects. Hence, the composition of the present invention can be effectively used for measuring expression levels of the target nucleic acids in body fluids from subjects (e.g., humans) suspected of having pancreatic cancer and body fluids from healthy subjects and thereby detecting pancreatic cancer through the comparison thereof. The composition of the invention can also be effectively used for measuring expression levels of the target nucleic acids in body fluids from subjects (e.g., humans) suspected of having pancreatic cancer and body fluids from colorectal cancer patients, stomach cancer patients, esophageal cancer patients, liver cancer patients, and benign pancreaticobiliary disease patients and thereby specifically detecting pancreatic cancer while distinguished from other cancers, benign diseases or the like, through the comparison thereof.

The nucleic acid probe or the primer that can be used in the present invention is a nucleic acid probe capable of specifically binding to a polynucleotide consisting of a nucleotide sequence represented by at least one of SEQ If3 NOs: 1 to 104, 464 to 473, and 492 to 494, or a primer for amplifying a polynucleotide consisting of a nucleotide sequence represented by at least one of SEQ ID NOs: 1 to 104, 464 to 473, and 492 to 494.

The nucleic acid probe or the primer that can be used in the present invention may further comprise a nucleic acid probe capable of specifically binding to a polynucleotide consisting of a nucleotide sequence represented by at least one of SEQ ID NOs: 105 to 122, or a primer for amplifying a polynucleotide consisting of a nucleotide sequence represented by at least one of SEQ ID NOs: 105 to 122.

The nucleic acid probe or the primer that can be used in the present invention may further comprise a nucleic acid probe capable of specifically binding to a polynucleotide consisting of a nucleotide sequence represented by at least one of SEQ ID NOs: 349 to 383, or a primer for amplifying a polynucleotide consisting of a nucleotide sequence represented by at least one of SEQ ID NOs: 349 to 383.

Specifically, these nucleic acid probes or primers comprise a combination of one or more polynucleotides selected from: a group of polynucleotides comprising nucleotide sequences represented by any of SEQ ID NOs: 1 to 122, 349 to 383, 464 to 473, and 492 to 494 or nucleotide sequences derived from the nucleotide sequences by the replacement of u with t, and a group of complementary polynucleotides thereof; a group of polynucleotides respectively hybridizing under stringent conditions (mentioned later) to DNAs consisting of nucleotide sequences complementary to these nucleotide sequences, and a group of complementary polynucleotides thereof; and a group of polynucleotides comprising 15 or more, preferably 17 or more consecutive nucleotides and being from the nucleotide sequences of these polynucleotide groups. These polynucleotides can be used as nucleic acid probes and primers for detecting the pancreatic cancer markers as target nucleic acids.

More specifically, examples of the nucleic acid probes or the primers that can be used in the present invention include one or more polynucleotides selected from the group consisting of the following polynucleotides (a) to (e):

(a) a polynucleotide consisting of a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 104, 464 to 473, and 492 to 494;
(c) a polynucleotide consisting of a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(d) a polynucleotide comprising a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t; and
(e) a polynucleotide hybridizing under stringent conditions to any of the polynucleotides (a) to (d).

In addition to at least one or more polynucleotides selected from any of the polynucleotides (a) to (e), the nucleic acid probes or the primers that can be used in the present invention may further comprise any of the following polynucleotides (1) to (i):
(f) a polynucleotide consisting of a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(g) a polynucleotide comprising a nucleotide sequence represented by any of SEQ ID NOs: 105 to 122;
(h) a polynucleotide consisting of a nucleotide sequence complementary to a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 105 to 122 or a nucleotide sequence derived from the nucleotide sequence by the replacement of u with t; and
(j) a polynucleotide hybridizing under stringent conditions to any of the polynucleotides (f) to (i).

In addition to at least one or more polynucleotides selected from any of the polynucleotides (a) to (j), the nucleic acid probes or the primers that can be used in the present invention may further comprise any of the following polynucleotides (k) to (o):
(k) a polynucleotide consisting of a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;
(l) a polynucleotide comprising a nucleotide sequence represented by any of SEQ ID NOs: 349 to 383;
(m) a polynucleotide consisting of a nucleotide sequence complementary to a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;
(n) a polynucleotide comprising a nucleotide sequence complementary to a nucleotide sequence represented by any of SEQ ID NOs: 349 to 383 or a nucleotide sequence derived from the nucleotide sequence by the replacement of u with t; and
(o) a polynucleotide hybridizing under stringent conditions to any of the polynucleotides (k) to (n).

For the above-mentioned polynucleotides, the "fragment thereof comprising 15 or more consecutive nucleotides" can comprise, but is not limited to, the number of nucleotides in the range of, for example, from 15 consecutive nucleotides to less than the total number of nucleotides of the sequence, from 17 consecutive nucleotides to less than the total number of nucleotides of the sequence, from 19 consecutive nucleotides to less than the total number of nucleotides of the sequence, or the like, and is from the nucleotide sequence of each polynucleotide.

These polynucleotides or fragments thereof used in the present invention may each be DNA or may each be RNA.

The polynucleotides that can be used in the present invention can be prepared by use of a general technique such as a DNA recombination technique, a PCR method, or a method using an automatic DNA/RNA synthesizer.

The DNA recombination technique and the PCR method may employ techniques described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-6893-5p, hsa-miR-6075, hsa-miR-6820-5p, hsa-miR-4294, hsa-miR-6729-5p, hsa-miR-4476, hsa-miR-6836-3p, hsa-miR-6765-3p, hsa-miR-6799-5p, hsa-miR-4530, hsa-miR-7641, hsa-miR-7-1454, hsa-miR-615-5p, hsa-miR-8073, hsa-miR-663a, hsa-miR-4634, hsa-miR-4450, hsa-miR-4792, hsa-miR-665, hsa-miR-7975, hsa-miR-7109-5p, hsa-miR-6789-5p, hsa-miR-4497, hsa-miR-6877-5p, hsa-miR-6880-5p, hsa-miR-7977, hsa-miR-4734, hsa-miR-6821-5p, hsa-miR-8089, hsa-miR-5585-3p, hsa-miR-6085, hsa-miR-6845-5p, hsa-miR-4651, hsa-miR-4433-3p, hsa-miR-1231, hsa-miR-4665-5p, hsa-miR-7114-5p, hsa-miR-1238-5p, hsa-miR-8069, hsa-miR-4732-5p, hsa-miR-619-5p, hsa-miR-3622a-5p, hsa-miR-1260a, hsa-miR-6741-5p, hsa-miR-6781-5p, hsa-miR-6125, hsa-miR-6805-5p, hsa-miR-6132, hsa-miR-6872-3p, hsa-miR-6875-5p, hsa-miR-1908-3p, hsa-miR-4433b-3p, hsa-miR-4736, hsa-miR-5100, hsa-miR-6724-5p, hsa-miR-7107-5p, hsa-miR-6726-5p, hsa-miR-3185, hsa-miR-4638-5p, hsa-miR-1273g-3p, hsa-miR-6778-5p, hsa-miR-328-5p, hsa-miR-3679-3p, hsa-miR-1228-3p, hsa-miR-6779-5p, hsa-miR-4723-5p, hsa-miR-6850-5p, 760, hsa-miR-7704, hsa-miR-8072, hsa-miR-4486, hsa-miR-1913, hsa-miR-4656, hsa-miR-1260b, hsa-miR-7106-5p, hsa-miR-6889-5p, hsa-miR-6780b-5p, hsa-miR-6090, hsa-miR-4534, hsa-miR-4449, hsa-miR-5195-3p, hsa-miR-1202, hsa-miR-4467, hsa-miR-6515-3p, hsa-miR-4281, hsa-miR-4505, hsa-miR-4484, hsa-miR-6805-3p, hsa-miR-3135b, hsa-miR-3162-5p, hsa-miR-6768-5p, hsa-miR-6721-5p, hsa-miR-1227-5p, hsa-miR-6722-3p, hsa-miR-4286, hsa-miR-4746-3p, hsa-miR-6727-5p, hsa-miR-6816-5p, hsa-miR-4741, hsa-miR-4508, hsa-miR-940, hsa-miR-4327, hsa-miR-4665-3p, hsa-miR-718, hsa-miR-125a-3p, hsa-miR-204-3p, hsa-miR-1469, hsa-miR-575, hsa-miR-150-3p, hsa-miR-423-5p, hsa-miR-564, hsa-miR-3188, hsa-miR-1246, hsa-miR-602, hsa-miR-1290, hsa-miR-16-5p, hsa-miR-451a, hsa-miR-24-3p, hsa-miR-187-5p, hsa-miR-1908-5p, hsa-miR-371a-5p, hsa-miR-550a-5p, hsa-miR-4417, hsa-miR-4707-5p, hsa-miR-7847-3p, hsa-miR-2861, hsa-miR-4513, hsa-miR-7111-5p, hsa-miR-6777-5p, hsa-miR-7113-3p, hsa-miR-4648, hsa-miR-3184-5p, hsa-miR-4271, hsa-miR- 6791-5p, hsa-miR-642a-3p, hsa-miR-7108-5p, hsa-miR-128-1-5p, hsa-miR-5196-5p, hsa-miR-3178, hsa-miR-3656, hsa-miR-92a-2-5p, hsa-miR-6769b-5p, hsa-miR-4689, hsa-miR-6076, hsa-miR-92b-5p, hsa-miR-6774-5p, hsa-miR-486-3p, hsa-miR-6806-5p, hsa-miR-6842-5p, hsa-miR-6716-5p, hsa-miR-557, hsa-miR-4673, hsa-miR-4674, hsa-miR-4442, hsa-miR-1915-3p, hsa-miR-4687-3p, hsa-miR-92h-3p, hsa-miR-1203, hsa-miR-663h, hsa-miR-4258, hsa-miR-4649-5p, hsa-miR-4516, hsa-miR-3619-3p, hsa-miR-6826-5p, hsa-miR-6757-5p, hsa-miR-3131, hsa-miR-1343-3p, hsa-miR-6775-5p, hsa-miR-6813-5p and hsa-miR-3940-5p represented by SEQ ID NOs: 1 to 122, 349 to 383, 464 to 473, and 492 to 494 are known in the art, and their obtainment methods are also known as mentioned above. Therefore, each polynucleotide that can be used as a nucleic acid probe or a primer in the present invention can be prepared by cloning the gene.

Such nucleic acid probes or primers can be chemically synthesized using an automatic DNA synthesizer. In general, the phosphoramidite method is used in this synthesis, and single-stranded DNA up to approximately 100 nucleotides can be automatically synthesized by this method. The automatic DNA synthesizer is commercially available from, for example, Polygen GmbH, ABI, or Applied Biosystems, Inc.

Alternatively, the polynucleotides of the present invention can also be prepared by cDNA cloning methods. The cDNA cloning technique may employ, for example, microRNA Cloning Kit Wako.

In this context, the sequences of the nucleic acid probes and the primers for detecting the polynucleotide consisting of a nucleotide sequence represented by any of SEQ ID NOs: 1 to 122, 349 to 383, 464 to 473, and 492 to 494 do not exist as miRNAs or precursors thereof in the living body or in vivo. For example, the nucleotide sequences represented by SEQ NO: 36 and SEQ ID NO: 103 are produced from the precursor represented by SEQ ID NO: 159. This precursor has a hairpin-like structure as shown in FIG. 1, and the nucleotide sequences represented by SEQ ID NO: 36 and SEQ ID NO: 103 have mismatch sequences with each other. As such, a nucleotide sequence completely complementary to the nucleotide sequence represented by SEQ ID NO: 36 or SEQ ID NO: 103 does not naturally occur in vivo. Therefore, the nucleic acid probes and the primers for detecting the nucleotide sequence represented by any of SEQ ID NOs: 1 to 122, 349 to 383, 464 to 473, and 492 to 494 have artificial nucleotide sequences that do not exist in the living body or in vivo.

3. Kit or Device for Detection of Pancreatic Cancer

The present invention also provides a hit or a device for the detection of pancreatic cancer, comprising one or more polynucleotides (which may include a variant, a fragment, or a derivative thereof) that can be used as nucleic acid probes or primers in the present invention for measuring target nucleic acids as pancreatic cancer markers.

The target nucleic acids as pancreatic cancer markers according to the present invention are at least one nucleic acid selected from the following group A:

Group A:
miR-6893-5p, miR-6075, miR-6820-5p, miR-4294, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231 miR-4665-5p, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, ma-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-4508, miR-940, miR-4327, miR-4665-3p, miR-718, miR-1203, miR-663h, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p.

Additional target nucleic acids that may be optionally used in the measurement are at least one nucleic acid selected from the following group B:

Group B:
miR-125a-3p, miR-204-3p, miR-1469, miR-575, miR-150-3p, miR-423-5p, miR-564, miR-3188, miR-1246, miR-602, miR-1290, miR-16-5p, miR-451a, miR-24-3p, miR-187-5p, miR-1908-5p, miR-371a-5p, and miR-550a-5p.

Additional target nucleic acids that may be further optionally used in the measurement are at least one nucleic acid selected from the following group C:

Group C:
miR-4417, miR-4707-5p, miR-7847-3p, miR-2861., miR-4513, miR-71.11-5p, miR-6777-5p, miR-711.3-3p, miR-4648, miR-3184-5p, miR-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92h-5p, miR-6774-5p, miR-486-3p, miR-6806-5p, miR-6842-5p, miR-6716-5p, miR-557, miR-4673, miR-4674, miR-4442, miR-1915-3p, miR-4687-3p, and miR-92b-3p.

The kit or the device of the present invention comprises one or more nucleic acids capable of specifically binding to any of the target nucleic acids as the pancreatic cancer markers described above, preferably one or more polynucleotides selected from the polynucleotides described in the preceding Section 2, or variants thereof.

Specifically, the kit or the device of the present invention can comprise at least one or more polynucleotides comprising (or consisting of) a nucleotide sequence represented by any of SEQ ID NOs: 1 to 104, 464 to 473, and 492 to 494 or a nucleotide sequence derived from the nucleotide sequence by the replacement of u with t, polynucleotide(s) comprising (or consisting of) a complementary sequence thereof, a polynucleotide(s) hybridizing under stringent conditions to any of these polynucleotides, or a variant(s) or a fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 105 to 122 or a nucleotide sequence derived from the nucleotide sequence by the replacement of u with t, a polynucleotide(s) comprising (or consisting of) a complementary sequence thereof, a polynucleotide(s) hybridizing under stringent conditions to any of these polynucleotides, a variant(s) or a fragment(s) comprising 1.5 or more consecutive nucleotides of any of these polynucleotide sequences.

The kit or the device of the present invention can further comprise one or more polynucleotides comprising (or consisting of) a nucleotide sequence represented by any of SEQ ID NOs: 349 to 383 or a nucleotide sequence derived from the nucleotide sequence by the replacement of u with t, polynucleotide(s) comprising (or consisting of) a complementary sequence thereof, a polynucleotide(s) hybridizing under stringent conditions to any of these polynucleotides, a variant(s) or a fragments) comprising 15 or more consecutive nucleotides of any of these polynucleotide sequences.

The fragment or fragments that can be comprised in the kit or the device of the present invention is/are, for example, one or more polynucleotides, preferably two or more polynucleotides, selected from the group consisting of the following polynucleotides (1) to (3):
(1) a polynucleotide comprising 15 or more consecutive nucleotides that are from a nucleotide sequence derived from a nucleotide sequence represented by any of SEQ ID NOs: 1 to 104, 464 to 473, and 492 to 494 by the replacement of u with t, or a complementary sequence thereof;
(2) a polynucleotide comprising 15 or more consecutive nucleotides that are from a nucleotide sequence derived from a nucleotide sequence represented by any of SEQ ID NOs: 105 to 122 by the replacement of u with t, or a complementary sequence thereof; and
(3) a polynucleotide comprising 15 or more consecutive nucleotides that are from a nucleotide sequence derived from a nucleotide sequence represented by any of SEQ ID NOs: 349 to 383 by the replacement of u with t, or a complementary sequence thereof.

In a preferred embodiment, the polynucleotide is a polynucleotide consisting of a nucleotide sequence represented by any of SEQ ID NOs: 1 to 104, 464 to 473, and 492 to 494 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 105 to 122 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ IO NOs: 349 to 383 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

Specific examples of the aforementioned combination constituting the kit or the device of the present invention can include the above-mentioned polynucleotides relevant to the combinations of SEQ ID NOs shown in Table 1 (i.e., SEQ ID NOs: 1 to 122, 349 to 383, 464 to 473, and 492 to 494 corresponding to the miRNA markers in Table 1). However, these are given merely for illustrative purposes, and all of various other possible combinations are included in the present invention.

The combination constituting the kit or the device for discriminating a pancreatic cancer patient from a healthy subject according to the present invention is desirably, for example, a combination of two or more polynucleotides consisting of the nucleotide sequences represented by SEQ ID NOs shown in Table 1. Usually, a combination of two of these polynucleotides can produce adequate performance.

The specific combination of two polynucleotides that consist of the above-mentioned nucleotide sequences or the complementary sequences thereof for discriminating a pancreatic cancer patient from a healthy subject is preferably a combination comprising at least one or more polynucleotides of the newly found polynucleotides consisting of the nucleotide sequences represented by SEQ ID NOs: 1 to 104, 349 to 383, 464 to 473, and 492 to 494, among the combinations constituted by two polynucleotides of the polynucleotides consisting of the nucleotide sequences represented by SEQ IO NOs: 1 to 122, 349 to 383, 464 to 473, and 492 to 494.

The combination of two polynucleotides that consist of the above-mentioned nucleotide sequences or the complementary sequences thereof for discriminating a pancreatic cancer patient from a healthy subject is preferably a combination of two polynucleotides comprising at least one polynucleotide selected from the group consisting of polynucleotides consisting of the nucleotide sequences represented by SEQ ID NOs: 1, 2, 4, 7, 15, 24, 105, 107, and 108 or complementary sequences thereof, with any of the polynucleotides of the other SEQ ID NOs.

Non-limiting examples of the combination comprising a polynucleotide consisting of the nucleotide sequence represented by SEQ ID NO: 1 or a complementary sequence thereof among the combinations constituted by two polynucleotides of the polynucleotides consisting of the nucleotide sequences represented by SEQ ID NOs: 1 to 122, 349 to 383, 464 to 473, and 492 to 494 for discriminating a pancreatic cancer patient from a healthy subject are listed below:
(1) a combination of SEQ ID NOs: 1 and 77 (markers: hsa-miR-6893-5p and hsa-miR-6780b-5p);
(2) a combination of SEQ ID NOs: 1 and 119 (markers: hsa-miR-6893-5p and hsa-miR-187-5p); and
(3) a combination of SEQ ID NOs: 1 and 20 (markers: hsa-miR-6893-5p and hsa-miR-7975).

Non-limiting examples of the combination comprising a polynucleotide consisting of the nucleotide sequence represented by SEQ ID NO: 2 or a complementary sequence thereof among the combinations constituted by two polynucleotides of the polynucleotides consisting of the nucleotide sequences represented by SEQ ID NOs: 1 to 122, 349 to 383, 464 to 473, and 492 to 494 for discriminating a pancreatic cancer patient from a healthy subject are further listed below:
(1) a combination of SEQ ID NOs: 2 and 105 (markers: hsa-miR-6075 and hsa-miR-125a-3p);

(2) a combination of SEQ ID NOs: 2 and 16 (markers: hsa-miR-6075 and hsa-miR-4634); and
(3) a combination of SEQ ID NOs: 2 and 10 (markers: hsa-miR-6075 and hsa-miR-4530).

Non-limiting examples of the combination comprising a polynucleotide consisting of the nucleotide sequence represented by SEQ ID NO: 4 or a complementary sequence thereof among the combinations constituted by two polynucleotides of the polynucleotides consisting of the nucleotide sequences represented by SEQ ID NOs: 1 to 122, 349 to 383, 464 to 473, and 492 to 494 for discriminating a pancreatic cancer patient from a healthy subject are further listed below:
(1) a combination of SEQ ID NOs: 4 and 105 (markers: hsa-miR-4294 and hsa-miR-125a-3p);
(2) a combination of SEQ ID NOs: 4 and 119 (markers: hsa-miR-4294 and hsa-miR-187-5p); and
(3) a combination of SEQ ID NOs: 4 and 45 (markers: hsa-miR-4294 and hsa-miR-6781-5p).

Non-limiting examples of the combination comprising a polynucleotide consisting of the nucleotide sequence represented by SEQ ID NO: 7 or a complementary sequence thereof among the combinations constituted by two polynucleotides of the polynucleotides consisting of the nucleotide sequences represented by SEQ ID NOs: 1 to 122, 349 to 383, 464 to 473, and 492 to 494 for discriminating a pancreatic cancer patient from a healthy subject are further listed below:
(1) a combination of SEQ ID NOs: 7 and 105 (markers: hsa-miR-6836-3p and hsa-miR-125a-30;
(2) a combination of SEQ ID NOs: 7 and 34 (markers: hsa-miR-6836-3p and hsa-miR-4433-3p); and
(3) a combination of SEQ ID NOs: 7 and 12 (markers: hsa-miR-6836-3p and hsa-miR-4454).

Non-limiting examples of the combination comprising a polynucleotide consisting of the nucleotide sequence represented by SEQ ID NO: 105 or a complementary sequence thereof among the combinations constituted by two polynucleotides of the polynucleotides consisting of the nucleotide sequences represented by SEQ ID NOs: 1 to 122, 349 to 383, 464 to 473, and 492 to 494 for discriminating a pancreatic cancer patient from a healthy subject are further listed below:
(1) a combination of SEQ ID NOs: 18 and 105 (markers: hsa-miR-4792 and hsa-miR-125a-3p);
(2) a combination of SEQ ID NOs: 46 and 105 (markers: hsa-miR-6125 and hsa-miR-125a-3p); and
(3) a combination of SEQ ID NOs: 105 and 494 (markers: hsa-miR-125a-3p and hsa-miR-3940-5p).

The combination of polynucleotides with cancer type specificity capable of discriminating a pancreatic cancer patient not only from a healthy subject but also from other cancer patients is preferably, for example, a combination of multiple polynucleotides comprising: at least one polynucleotide selected from the group consisting of polynucleotides consisting of the nucleotide sequences represented by SEQ ID NOs: 2, 4, 6, 7, 9, 10, 25, 28, 30, 31, 38, 48, 82, 103, 105, 108, and 464 or complementary sequences thereof (hereinafter, this group is referred to as "cancer type-specific polynucleotide group 1"); and any of the polynucleotides of the other SEQ ID NOs.

The combination of polynucleotides with cancer type specificity capable of discriminating a pancreatic cancer patient not only from a healthy subject but also from other cancer patients is more preferably a combination of multiple polynucleotides selected from the cancer type-specific polynucleotide group 1.

The combination of polynucleotides with cancer type specificity capable of discriminating a pancreatic cancer patient not only from a healthy subject but also from other cancer patients is more preferably a combination comprising at least one or more polynucleotides selected from the group consisting of polynucleotides consisting of the nucleotide sequences represented by SEQ ID NOs: 2, 4, 7, 10, and 25 or complementary sequences thereof (hereinafter, this group is referred to as "cancer type-specific polynucleotide group 2") included in the cancer type-specific polynucleotide group 1, among the combinations of multiple polynucleotides selected from the cancer type-specific polynucleotide group 1. The number of the polynucleotides with cancer type specificity may be 1, 2, 3, 4, 5, 6, 7, 8, 9, 10 or more in the combination and is more preferably 4 or more in the combination. Usually, the combination of 4 polynucleotides of these polynucleotides can produce adequate performance.

Non limiting examples of the combination of the polynucleotide consisting of the nucleotide sequence represented by SEQ ID NO: 2 or a complementary sequence thereof, with polynucleotides consisting of nucleotide sequences represented by SEQ ID NOs of three polynucleotides selected from the cancer type-specific polynucleotide group 1 or complementary sequences thereof are listed below:
(1) a combination of SEQ ID NOs: 2, 9, 105, and 7 (markers: hsa-miR-6075, hsa-miR-6799-5p, hsa-miR-125a-3p, and hsa-miR-6836-3p);
(2) a combination of SEQ ID NOs: 2, 7, 108, and 464 (markers: hsa-miR-6075, hsa-miR-6836-3p, hsa-miR-575, and hsa-miR-1203);
(3) a combination of SEQ ID NOs: 2, 31, 48, and 38 (markers: hsa-miR-6075, hsa-miR-6085, hsa-miR-6132, and hsa-miR-1238-5p),
(4) a combination of SEQ ID NOs: 2, 31, 28, and 48 (markers: hsa-miR-6075, hsa-miR-6085, hsa-miR-6821-5p, and hsa-miR-6132); and
(5) a combination of SEQ ID NOs: 2, 25, 105, and 10 (markers: hsa-miR-6075, hsa-miR-6880-5p, hsa-miR-125a-3p, and hsa-miR-4530).

Non-limiting examples of the combination of the polynucleotide consisting of the nucleotide sequence represented by SEQ ID NO: 4 or a complementary sequence thereof, with polynucleotides consisting of nucleotide sequences represented by SEQ ID NOs of three polynucleotides selected from the cancer type-specific polynucleotide group 1 or complementary sequences thereof are further listed below:
(1) a combination of SEQ ID NOs: 4, 31, 7, and 82 (markers: hsa-miR-4294, hsa-miR-6085, hsa-miR-6836-3p, and hsa-miR-1202);
(2) a combination of SEQ ID NOs: 4, 31, 28, and 82 (markers: hsa-miR-4294, hsa-miR-6085, hsa-miR-6821-5p, and hsa-miR-1202);
(3) a combination of SEQ ID NOs: 4, 10, 7, and 82 (markers: hsa-miR-4294, hsa-miR-4530, hsa-miR-6836-3p, and hsa-miR-1202);
(4) a combination of SEQ ID NOs: 4, 7, 82, and 103 (markers: hsa-miR-4294, hsa-miR-6836-3p, hsa-miR-1202, and hsa-miR-4665-3p); and
(5) a combination of SEQ ID NOs: 4, 105, 10, and 6 arkers: hsa-miR-4294, hsa-miR-125a-3p, hsa-miR-4530, and hsa-miR-4476).

Non-limiting examples of the combination of the polynucleotide consisting of the nucleotide sequence represented by SEQ ID NO: 7 or a complementary sequence thereof, with polynucleotides consisting of nucleotide sequences represented by SEQ ID NOs of three polynucleotides selected from the cancer type-specific polynucleotide group 1 or complementary sequences thereof are further listed below:
- (1) a combination of SEQ ID NOs: 4, 7, 82, and 101 (markers: hsa-miR-4294, hsa-miR-6836-3p, hsa-miR-1202, and hsa-miR-940);
- (2) a combination of SEQ ID NOs: 4, 7, 38, and 82 (markers: hsa-miR-4294, hsa-miR-6836-3p, hsa-miR-1238-5p, and hsa-miR-1202);
- (3) a combination of SEQ ID NOs: 6, 7, 61, and 68 (markers: hsa-miR-4476, hsa-miR-6836-3p, hsa-miR-6778-5p, and hsa-miR-760);
- (4) a combination of SEQ ID NOs: 4, 7, 47, and 82 (markers: hsa-miR-4294, hsa-miR-6836-3p, hsa-miR-6805-5p, and hsa-miR-1202); and
- (5) a combination of SEQ ID NOs: 4, 7, 82, and 103 (markers: hsa-miR-4294, hsa-miR-6836-3p, hsa-miR-1202, and hsa-miR-4665-3p).

Non-limiting examples of the combination of the polynucleotide consisting of the nucleotide sequence represented by SEQ ID NO: 10 or a complementary sequence thereof, with polynucleotides consisting of nucleotide sequences represented by SEQ ID NOs of three polynucleotides selected from the cancer type-specific polynucleotide group 1 or complementary sequences thereof are further listed below:
- (1) a combination of SEQ ID NOs: 10, 47, 90, and 101 (markers: hsa-miR-4530, hsa-miR-6805-5p, hsa-miR-3162-5p, and hsa-miR-940);
- (2) a combination of SEQ ID NOs: 10, 30, 103, and 365 (markers: hsa-miR-4530, hsa-miR-5585-3p, hsa-miR-4665-3p, and phsa-miR-3178);
- (3) a combination of SEQ ID NOs: 9, 10, 61, and 68 (markers: hsa-miR-6799-5p, hsa-miR-4530, hsa-miR-6778-5p, and hsa-miR-760);
- (4) a combination of SEQ ID NOs: 10, 48, 68, and 90 (markers: hsa-miR-4530, hsa-miR-6132, hsa-miR-760, and hsa-miR-3162-5p); and
- (5) a combination of SEQ ID NOs: 10, 30, 68, and 365 (markers: hsa-miR-4530, hsa-miR-5585-3p, hsa-miR-760, and hsa-miR-3178).

Non-limiting examples of the combination of the polynucleotide consisting of the nucleotide sequence represented by SEQ ID NO: 25 or a complementary sequence thereof, with polynucleotides consisting of nucleotide sequences represented by SEQ ID NOs of three polynucleotides selected from the cancer type-specific polynucleotide group 1 or complementary sequences thereof are further listed below:
- (1) a combination of SEQ ID NOs: 7, 25, 466, and 47 (markers: hsa-miR-6836-3p, hsa-miR-6880-5p, hsa-miR-4258, and hsa-miR-6805-5p);
- (2) a combination of SEQ ID NOs: 7, 25, 48, and 466 (markers: hsa-miR-6836-3p, hsa-miR-6880-5p, hsa-miR-6132, and hsa-miR-4258);
- (3) a combination of SEQ ID NOs: 7, 25, 28, and 466 (markers: hsa-miR-6836-3p, hsa-miR-6880-5p, hsa-miR-6821-5p, and hsa-miR-4258);
- (4) a combination of SEQ ID NOs: 7, 25, 30, and 466 (markers: hsa-miR-6836-3p, hsa-miR-5585-3p, and hsa-miR-4258); and
- (5) a combination of SEQ ID NOs: 7, 25, 31, and 47 (markers: hsa-miR-6836-3p, hsa-miR-6880-5p, hsa-miR-6085, and hsa-miR-6805-5p).

The kit or the device of the present invention can also comprise a known polynucleotide(s) that enables detection of pancreatic cancer, or a polynucleotide(s) that will be found in the future, in addition to the polynucleotide(s) (which may include a variant(s), a fragment(s), and a derivative(s)) as described above according to the present invention.

The kit of the present invention can also comprise an antibody for measuring a marker or markers for pancreatic cancer examination known in the art, such as CEA, CA19-9, SPan-1, DUPAN-2, CA50, CA242, TAG-72, urinary fucose, POA, and TPS, in addition to the polynucleotide(s) according to the present invention as described above, and a variant or variants thereof or a fragment or fragments thereof.

These polynucleotides and variants thereof or fragments thereof contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above, variants thereof, derivatives thereof, or fragments thereof are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one or more, preferably at least two or more, more preferably at least three or more, most preferably at least five or more to all of the pancreatic cancer marker miRNAs, respectively, of the group 1 described above. The kit or the device of the present invention can optionally further comprise nucleic acids capable of specifically binding to the polynucleotides of at least one or more, preferably at least two or more, more preferably at least three or more, most preferably at least five or more to all of the pancreatic cancer marker miRNAs, respectively, of the group 2 described above. The kit or the device of the present invention can optionally further comprise nucleic acids capable of specifically binding to the polynucleotides of at least one or more, preferably at least two or more, more preferably at least three or more, most preferably at least five or more to all of the pancreatic cancer marker miRNAs, respectively, of the group 3 described above.

The kit or the device of the present invention can be used for detecting pancreatic cancer as described in Section 4 below.

4. Method for Detecting Pancreatic Cancer

The present invention further provides a method for detecting pancreatic cancer, comprising using the kit or the device of the present invention (comprising the above-mentioned nucleic acid(s) that can be used in the present invention) as described in Section 3 above to measure expression levels of one or more pancreatic cancer-derived genes represented by: an expression level(s) of pancreatic cancer-derived gene(s) selected from the following group of miRNAs, i.e., miR-6893-5p, miR-6075, miR-6820-5p, miR-4294, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, ntiR-6821-5p, miR-8089, miR-5585-3p, miR-6085, miR-6845-5p, miR-4651, miR-4433-3p, miR-1231, miR-4665-5p, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-44508, miR-940, miR-4327, miR-4665-3p and miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p; and optionally an expression level(s) of pancreatic cancer-derived gene(s) selected from the following group of miRNA: miR-125a-3p, miR-204-3p, ma-1469, miR-575, miR-150-3p, ma-423-5p, miR-564, miR-3188, miR-1246, miR-602, miR-1290, ma-16-5p, miR-451a, miR-24-3p, miR-187-5p, miR-1908-5p, miR-371a-5p, and miR-550a-5p; and optionally an expression level(s) of pancreatic cancer-derived gene(s) selected from the following group of miRNAs, i.e., miR-4417, miR-4707-5p, miR-7847-3p, miR-2861, miR-4513, miR-7111-5p, ma-6777-5p, miR-7113-3p, miR-4648, miR-3184-5p, ma-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92b-5p, miR-6774-5p, miR-486-3p, miR-6806-5p, miR-6842-5p, miR-6716-5p, miR-557, miR-4673, miR-4674, miR-4442, miR-1915-3p, miR-4687-3p, and miR-92b-3p, in a sample in vitro, further comparing, for example, the expression level(s) of the gene(s) in the sample (e.g., blood, serum, or plasma) collected from a subject suspected of having pancreatic cancer, with a control expression level(s) in the sample(s) collected from a healthy subject(s) (including a non-pancreatic cancer patient(s)), and evaluating the subject as having pancreatic cancer when the expression level(s) of the target nucleic acid(s) is statistically significantly different between the samples.

This method of the present invention enables a limitedly invasive, early diagnosis of the cancer with high sensitivity and high specificity and thereby brings about early treatment and improved prognosis. In addition, exacerbation of the disease or the effectiveness of surgical, radiotherapeutic, and chemotherapeutic treatments can be monitored.

The method for extracting the pancreatic cancer-derived gene(s) from the sample such as blood, serum, or plasma according to the present invention is particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol™ (Life Technologies Corp.) may be used. The pancreatic cancer-derived gene(s) may be prepared by the addition of a reagent for RNA extraction containing acidic phenol, such as Trizol (Life Technologies Corp.) or Isogen (Nippon Gene Co., Ltd., Japan). Alternatively, a kit such as miRNeasy™ Mini Kit (Qiagen N.V.) may be used, though the method is not limited thereto.

The present invention also provides use of the kit or the device of the present invention for detecting in vitro an expression product(s) of a pancreatic cancer-derived miRNA gene(s) in a sample derived from a subject.

In the method of the present invention, the kit or the device described above comprises a single polynucleotide or any possible combination of polynucleotides that can be used in the present invention as described above.

In the detection or (genetic) diagnosis of pancreatic cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of pancreatic cancer or the detection of the presence or absence of pancreatic cancer. Specifically, the detection of pancreatic cancer using the kit or the device can be performed by detecting in vitro an expression level(s) of a gene(s) using the nucleic acid probe(s) or the primer(s) contained in the kit or the device, in a sample such as blood, serum, plasma, or urine from a subject suspected of having pancreatic cancer. The subject suspected of having pancreatic cancer can be evaluated as having pancreatic cancer when the expression level(s) of a target miRNA marker(s) measured using polynucleotide(s) (including a variant(s), a fragment(s), and a derivative(s) thereof) consisting of a nucleotide sequence(s) represented by at least one or more of SEQ ID NOs: 1 to 104, 464 to 473, and 492 to 494 or a complementary sequence(s) thereof, and optionally a nucleotide sequence(s) represented by one or more of SEQ ID NOs: 105 to 122 or a complementary sequence(s) thereof, and optionally a nucleotide sequences) represented by one or more of SEQ ID NOs: 349 to 383 or a complementary sequence(s) thereof, in the sample such as blood, serum, plasma, or urine of the subject, has a statistically significant difference compared to an expression level(s) thereof in the sample such as blood, serum, or plasma, or urine of a healthy subject.

The method of the present invention can be combined with a diagnostic imaging method such as abdominal ultrasonography, CT scanning, endoscopic retrograde cholangiopancreatography, or endoscopic ultrasonography. The method of the present invention is capable of specifically detecting pancreatic cancer and can substantially discriminate pancreatic cancer from the other cancers. Particularly, for bile duct cancer, some miRNA markers for pancreatic cancer can be commonly used. However, pancreatic cancer can be discriminated from bile duct cancer by a way of determining a discriminant boundary according to a discriminant. Alternatively, pancreatic cancer can be discriminated therefrom by combination with an additional diagnostic method such as the diagnostic imaging method as described above.

The method for detecting the absence of an expression product(s) of a pancreatic cancer-derived gene(s) or the presence of the expression product(s) of a pancreatic cancer-derived gene(s) in a sample using the kit or the device of the present invention comprises collecting a body fluid such as blood, serum, plasma, or urine of a subject, and measuring the expression level(s) of the target gene(s) contained therein using one or more polynucleotides (including a variant(s), a fragment(s), or a derivative(s)) selected from the groups of polynucleotides of the present invention, to evaluate the presence or absence of pancreatic cancer or to detect pancreatic cancer. The method for detecting pancreatic cancer according to the present invention can also evaluate or diagnose, for example, the presence or absence of amelioration of the disease or the degree of amelioration thereof in a pancreatic cancer patient in the case that a therapeutic drug is administered to the patient for amelioration of the disease.

The method of the present invention can comprise, for example, the following steps (a), (b), and (c):

(a) a step of contacting in vitro a sample from a subject with a polynucleotide(s) contained in the kit or the device of the present invention;

(b) a step of measuring an expression level(s) of the target nucleic acid(s) in the sample using the polynucleotide(s) as a nucleic acid probe(s) or primer(s); and (c) a step of evaluating the presence or absence of pancreatic cancer (cells) in the subject on the basis of the measurement results in the step (b).

Specifically, the present invention provides a method for detecting pancreatic cancer, comprising: measuring an expression level(s) of a target nucleic acid(s) in a sample of a subject using a nucleic acid(s) capable of specifically binding to at least one or more (preferably at least two or more) polynucleotides selected from the following miRNAs: miR-6893-5p, miR-6075, miR-6820-5p, miR-4294, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231, miR-4665-5p, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433h-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-4508, miR-940, miR-4327, miR-4665-3p and miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p; and evaluating in yin?) whether or not the subject has pancreatic cancer subject using the above-measured expression levels and control expression levels of a healthy subject(s) measured in the same way as above.

As used herein, the term "evaluation" is evaluation support based on results of in vitro examination, not physician's judgment.

As described above, in the method of the present invention, specifically, miR-6893-5p is hsa-miR-6893-5p, miR-6075 is hsa-miR-6075, miR-6820-5p is hsa-miR-6820-5p, miR-4294 is hsa-miR-4294, miR-6729-5p is hsa-miR-6729-5p, miR-4476 is hsa-miR-4476, miR-6836-3p is hsa-miR-6836-3p, miR-6765-3p is hsa-miR-6765-3p, miR-6799-5p is hsa-miR-6799-5p, miR-4530 is hsa-miR-4530, miR-7641 is hsa-miR-7641, miR-4454 is hsa-miR-4454, miR-615-5p is hsa-miR-615-5p, miR-8073 is hsa-miR-8073, miR-663a is hsa-miR-663a, miR-4634 is hsa-miR-4634, miR-4450 is hsa-miR-4450, miR-4792 is hsa-miR-4792, miR-665 is hsa-miR-665, miR-7975 is hsa-miR-7975, miR-7109-5p is hsa-miR-7109-5p, miR-6789-5p is hsa-miR-6789-5p, miR-4497 is hsa-miR-4497, miR-6877-5p is hsa-miR-6877-5p, miR-6880-5p is hsa-miR-6880-5p, miR-7977 is hsa-miR-7977, miR-4734 is hsa-miR-4734, miR-6821-5p is hsa-miR-6821-5p, miR-8089 is hsa-miR-89, miR-5585-3p is hsa-miR-5585-3p, miR-6085 is hsa-miR-6085, miR-6845-5p is hsa-miR-6845-5p, miR-4651 is hsa-miR-4651, miR-4433-3p is hsa-miR-4433-3p, miR-1231 is hsa-miR-1231, miR-4665-5p is hsa-miR-4665-5p, miR-7114-5p is hsa-miR-7114-5p, miR-1238-5p is hsa-miR-1238-5p, miR-8069 is hsa-miR-8069, miR-4732-5p is hsa-miR-4732-5p, miR-619-5p is hsa-miR-619-5p, miR-3622a-5p is hsa-miR-3622a-5p, miR-1260a is hsa-miR-1260a, miR-6741-5p is hsa-miR-6741-5p, miR-6781-5p is hsa-miR-6781-5p, miR-6125 is hsa-miR-6125, miR-6805-5p is hsa-miR-6805-5p, miR-6132 is hsa-miR-6132, miR-6872-3p is hsa-miR-6872-3p, miR-6875-5p is hsa-miR-6875-5p, miR-1908-3p is hsa-miR-1908-3p, miR-4433b-3p is hsa-miR-4433b-3p, miR-4736 is hsa-miR-4736, miR-5100 is hsa-miR-5100, miR-6724-5p is hsa-miR-6724-5p, miR-7107-5p is hsa-miR-7107-5p, miR-6726-5p is hsa-miR-6726-5p, miR-3185 is hsa-miR-3185, miR-4638-5p is hsa-miR-4638-5p, miR-1273g-3p is hsa-miR-1273g-3p, miR-6778-5p is hsa-miR-6778-5p, miR-328-5p is hsa-miR-328-5p, miR-3679-3p is hsa-miR-3679-3p, miR-1228-3p is hsa-miR-1228-3p, miR-6779-5p is hsa-miR-6779-5p, miR-4723-5p is hsa-miR-4723-5p, miR-6850-5p is hsa-miR-6850-5p, miR-760 is hsa-miR-760, miR-7704 is hsa-miR-7704, miR-8072 is hsa-miR-8072, miR-4486 is hsa-miR-4486, miR-1913 is hsa-miR-1913, miR-4656 is hsa-miR-4656, miR-1260b is hsa-miR-1260b, miR-7106-5p is hsa-miR-7106-5p, miR-6889-5p is hsa-miR-6889-5p, miR-6780b-5p is hsa-miR-6780b-5p, miR-6090 is hsa-miR-6090, miR-4534 is hsa-miR-4534, miR-4449 is hsa-miR-4449, miR-5195-3p is hsa-miR-5195-3p, miR-1202 is hsa-miR-1202, miR-4467 is hsa-miR-4467, miR-6515-3p is hsa-miR-6515-3p, miR-4281 is hsa-miR-4281, miR-4505 is hsa-miR-4505, miR-4484 is hsa-miR-4484, miR-6805-3p is hsa-miR-6805-3p, miR-3135b is hsa-miR-3135b, miR-3162-5p is hsa-miR-3162-5p, miR-6768-5p is hsa-miR-6768-5p, miR-6721-5p is hsa-miR-6721-5p, miR-1227-5p is lisa-miR-1227-5p, miR-6722-3p is hsa-miR-6722-3p, miR-4286 is hsa-miR-4286, miR-4746-3p is hsa-miR-4746-3p, miR-6727-5p is hsa-miR-6727-5p, miR-6816-5p is hsa-miR-6816-5p, miR-4741 is hsa-miR-4741, miR-4508 is hsa-miR-4508, miR-940 is hsa-miR-940, miR-4327 is hsa-miR-4327, miR-4665-3p is hsa-miR-4665-3p, miR-718 is hsa-miR-718, miR-1203 is hsa-miR-1203, miR-663b is hsa-miR-663b, miR-4258 is hsa-miR-4258, miR-4649-5p is lisa-miR-4649-5p, miR-4516 is hsa-miR-4516, miR-3619-3p is hsa-miR-3619-3p, miR-6826-5p is hsa-miR-6826-5p, miR-6757-5p is hsa-miR-6757-5p, miR-3131 is hsa-miR-3131., miR-1343-3p is hsa-miR-1343-3p, miR-6775-5p is hsa-miR-6775-5p, miR-6813-5p is hsa-miR-6813-5p, and miR-3940-5p is hsa-miR-3940-5p.

In the method of the present invention, specifically, the nucleic acid(s) (specifically, probe(s) or primer(s)) is selected from the group consisting of the following polynucleotides (a) to (e):

(a) a polynucleotide consisting of a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 104, 464 to 473, and 492 to 494;
(c) a polynucleotide consisting of a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(d) a polynucleotide comprising a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t; and
(e) a polynucleotide hybridizing under stringent conditions to any of the polynucleotides (a) to (d).

The nucleic acid(s) further used in the method of the present invention can comprise a nucleic acid(s) capable of specifically binding to at least one or more polynucleotides selected from the following miRNM: miR-125a-3p, miR-204-3p, miR-1469, miR-575, miR-150-3p, miR-423-5p, miR-564, miR-3188, miR-1246, miR-602, miR-1290, miR-16-5p, miR-451a, miR-187-5p, miR-1908-5p, miR-371a-5p, and miR-550a-5p Specifically, miR-125a-3p is hsa-miR-125a-3p, miR-204-3p is hsa-miR-204-3p, miR-1469 is hsa-miR-1469, miR-575 is hsa-miR-575, miR-150-3p is hsa-miR-150-3p, miR-423-5p is hsa-miR-423-5p, miR-564 is hsa-miR-564, miR-3188 is hsa-miR-3188, miR-1246 is hsa-miR-1246, miR-602 is hsa-miR-602, miR-1290 is hsa-miR-1290, miR-16-5p is hsa-miR-16-5p, miR-451a is hsa-miR-451a, miR-24-3p is hsa-miR-24-3p, miR-187-5p is hsa-miR-187-5p, miR-1908-5p is hsa-miR-1908-5p, miR-371a-5p is hsa-miR-371a-5p, and miR-550a-5p is hsa-miR-550a-5p.

Specifically, the nucleic acid(s) is further selected from the group consisting of the following polynucleotides (f) to (j):

(f) a polynucleotide consisting of a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(g) a polynucleotide comprisimg a nucleotide sequence represented by any of SEQ ID NOs: 105 to 122;
(h) a polynucleotide consisting of a nucleotide sequence complementary to a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 105 to 122 or a nucleotide sequence derived from the nucleotide sequence by the replacement of u with t; and
(j) a polynucleotide hybridizimg under stringent conditions to any of the polynucleotides (1) to (i).

The nucleic acid(s) further used can comprise a nucleic acid capable of specifically binding to at least one or more polynucleotides selected from the following miRNAs: miR-4417, miR-4707-5p, miR-7847-3p, miR-2861, miR-4513, miR-7111-5p, miR-6777-5p, miR-7113-3p, miR-4648, miR-3184-5p, miR-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92b-5p, miR-6774-5p, miR-486-3p, miR-6806-5p, miR-6842-5p, miR-6716-5p, miR-557, miR-4673, miR-4674, ma-4442, miR-1915-3p, miR-4687-3p, and miR-92h-3p.

Specifically, miR-4417 is hsa-miR-4417, miR-4707-5p is hsa-miR-4707-5p, miR-7847-3p is hsa-miR-7847-3p, miR-2861 is hsa-miR-2861, miR-4513 is hsa-miR-4513, miR-7111-5p is hsa-ma-7111-5p, ma-6777-5p is hsa-miR-6777-5p, ma-7113-3p is hsa-miR-7113-3p, miR-4648 is hsa-miR-4648, miR-3184-5p is hsa-miR-3184-5p, miR-4271 is hsa-miR-4271, miR-6791-5p is hsa-miR-6791-5p, ma-642a-3p is hsa-miR-642a-3p, miR-7108-5p is hsa-miR-7108-5p, miR-128-1-5p is hsa-miR-128-1-5p, miR-5196-5p is hsa-miR-5196-5p, miR-3178 is hsa-miR-3178, miR-3656 is hsa-miR-3656, miR-92a-2-5p is hsa-miR-92a-2-5p, ma-67696-5p is hsa-miR-6769b-5p, miR-4689 is hsa-miR-4689, miR-6076 is hsa-miR-6076, miR-92h-5p is hsa-miR-92h-5p, miR-6774-5p is hsa-miR-6774-5p, miR-486-3p is hsa-miR-486-3p, miR-6806-5p is hsa-miR-6806-5p, miR-6842-5p is hsa-miR-6842-5p, miR-6716-5p is hsa-miR-6716-5p, miR-557 is hsa-miR-557, ma-4673 is hsa-ma-4673, miR-4674 is hsa-miR-4674, miR-4442 is hsa-miR-4442, miR-1915-3p is hsa-miR-1915-3p, miR-4687-3p is hsa-miR-4687-3p, and miR-92b-3p is hsa-miR-92b-3p.

Specifically, the nucleic acid(s) further used is a polynucleotide(s) selected from the group consisting of the following polynucleotides (k) to (o):

(k) a polynucleotide consisting of a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;
(l) a polynucleotide comprising a nucleotide sequence represented by any of SEQ ID NOs: 349 to 383;

(m) a polynucleotide consisting of a nucleotide sequence complementary to a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;

(n) a polynucleotide comprising a nucleotide sequence complementary to a nucleotide sequence represented by any of SEQ ID NOs: 349 to 383 or a nucleotide sequence derived from the nucleotide sequence by the replacement of u with t; and (o) a polynucleotide hybridizing under stringent conditions to any of the polynucleotides (k) to (n).

Examples of the sample used in the method of the present invention can include samples prepared from living tissues (preferably pancreatic tissues) or body fluids such as blood, serum, plasma, and urine from subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a primate such as a human or a monkey, a rodent such as a mouse or a rat, a pet animal such as a dog or a cat, and an athletic animal such as a horse without any limitation, and is preferably a human.

The steps of the method of the present invention can be changed according to the type of the sample to be assayed.

In the case of using RNA as an analyte, the detection of pancreatic cancer can comprise, for example, the following steps (a), (b), and (c):

(a) a step of binding RNA prepared from a sample from a subject or complementary polynucleotides (cDNAs) transcribed from the RNA to a polynucleotide(s) in the kit or the device of the present invention;

(b) a step of measuring the sample-derived RNA or the cDNAs synthesized from the RNA, which is/are bound to the polynucleotide(s), by hybridization using the polynucleotide(s) as a nucleic acid probe(s) or by quantitative RT-PCR using the polynucleotide(s) as a primer(s); and (c) a step of evaluating the presence or absence of pancreatic cancer (or pancreatic cancer-derived gene expression) on the basis of the measurement results of the step (b).

For example, various hybridization methods can be used for detecting, examining, evaluating, or diagnosing pancreatic cancer (or pancreatic cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe(s) that can be used in the present invention. Specific examples thereof can include a method which comprises labeling the nucleic acid probe (or a complementary strand) with a radioisotope ($^{32}P$, $^{33}P$, $^{35}S$, etc.), a fluorescent material, or the like, hybridizing the labeled product with the tissue-derived RNA from a subject, which is transferred to a nylon membrane or the like according to a routine method, and then detecting and measuring a signal derived from the label (radioisotope or fluorescent material) on the formed. DNA/RNA duplex using a radiation detector (examples thereof can include BAS-1800 II (Fujifilm Corp., Japan)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises preparing cDNAs from the tissue-derived RNA of a subject according to a routine method, hybridizing a pair of primers (consisting of a plus strand and a reverse strand binding to the cDNA) prepared from the composition for detection of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the composition for detection of the present invention is attached as nucleic acid probes (single-stranded or double-stranded) to a substrate (solid phase) is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. In the present specification, the term "chip" includes these arrays. 3D-Gene™ Human miRNA Oligo chip (foray Industries, Inc.) can be used as the DNA chip, though the DNA chip is not limited thereto.

Examples of the measurement using the DNA chip can include, but are not limited to, a method of detecting and measuring a signal derived from the label on the composition for detection using an image detector (examples thereof can include Typhoon 9410 (GE Healthcare) and 3D-Gene™ scanner (Toray Industries, Inc.)).

The "stringent conditions" used herein are, as mentioned above, conditions under which a nucleic acid probe hybridizes to its target sequence to a detectably larger extent (e.g., a measurement value equal to or larger than "(a mean of background measurement values)+(a standard deviation of the background measurement values)×2") than that for other sequences.

The stringent conditions are defined by hybridization and subsequent washing. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.), LNA™-based MicroRNA PCR (Exiqon), or Ncode™ miRNA qRT-PCT kit (Invitrogen Corp.) may be used.

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring target genes or gene expression levels in a sample from a subject using the polynucleotides, the kit, or the device (e.g., chip) for diagnosis of the present invention, or a combination thereof, preparing a discriminant (discriminant function) with gene expression levels in a sample from a pancreatic cancer patient and a sample from a healthy subject as supervising samples, and determining or evaluating the presence and/or absence of the pancreatic cancer-derived genes in the sample.

Specifically, the present invention further provides the method comprising: a first step of measuring in vitro expression levels of target genes in a plurality of samples known to determine or evaluate the presence and/or absence of the pancreatic cancer-derived genes in the samples, using the polynucleotides, the kit, or the device (e.g., chip) for diagnosis of the present invention, or a combination thereof; a second step of preparing a discriminant with the measurement values of the expression levels of the target genes obtained in the first step as supervising samples; a third step of measuring in vitro expression levels of the target genes in a sample derived from a subject in the same way as in the first step; and a fourth step of assigning the measurement values of the expression levels of the target genes obtained in the third step to the discriminant obtained in the second step, and determining or evaluating the presence and/or absence of the pancreatic cancer-derived genes in the sample on the basis of the results obtained from the discriminant, wherein the target genes can be detected using the polynucleotides or using polynucleotides, variants thereof, or fragments thereof contained in the kit or the device (e.g., chip). In this context, the discriminant can be prepared by use of Fisher's discriminant analysis, nonlinear discriminant analysis based on Mahalanobis' distance, neural network, Support Vector Machine TM or the like, though the method is not limited thereto.

When a clustering boundary is a straight line or a hyperplane, the linear discriminant analysis is a method for determining the belonging of a cluster using Formula 1 as a discriminant. In Formula 1, x represents an explanatory variable, w represents a coefficient of the explanatory variable, and $w_0$ represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, one type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer, 2002). In the Fisher's discriminant analysis, direction w of projection is determined so as to maximize Formula 2. In this formula, μ, represents an average input, ng represents the number of data belonging to class g, and μg represents an average input of the data belonging to class g. The numerator and the denominator are the interclass variance and the intraclass variance, respectively, when each data is projected in the direction of the vector w. Discriminant coefficient $w_i$ is determined by maximizing this ratio (Takafumi Kariamori et al., "Pattern Recognition", Kyoritsu Shuppan Co., Ltd., Tokyo, Japan (2009); and Richard O. et al., Pattern Classification Second Edition, Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i: y_i = g} (w^T x_i - w^T \mu_g)(w^T x_i - w^T \mu_g)} \quad \text{Formula 2}$$

$$\text{subject to } \mu = \sum_{i=1}^{n} \frac{x_i}{n}, \quad \mu_g = \sum_{i: u_i = g}^{n} \frac{x_i}{n_g}$$

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, $\mu$ represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x,\mu) = \{(x-\mu)^t S^{-1} (x-\mu)\}^{1/2} \quad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers, Tokyo. Japan (2004); Nello Cristianini et al., Introduction to SVM, Kyoritsu Shuppan Co., Ltd., Tokyo, Japan (2008)).

C-support vector classification (C-SVC), one type of SVM, comprises preparing a hyperplane by supervising a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a pancreatic cancer patient group and a healthy subject group. For example, pancreatic tissue examination can be used for a reference under which each subject is confirmed either as a pancreatic cancer patient or as a healthy subject. Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and this grouping as objective variables (e.g., -1 and +1). An optimizing objective function is represented by Formula 4 wherein e represents all input vectors, v represents an objective variable, a represents a Lagrange's undetermined multiplier vector, Q represents a positive definite matrix, and C represents a parameter for adjusting constrained conditions.

$$\min_a \frac{1}{2} a^T Q a - e^T a \quad \text{Formula 4}$$

$$\text{subject to } y^T a = 0, \quad 0 \le a_i \le C, \quad i = 1, \ldots, l,$$

Formula 5 is a finally obtained discriminant, and a group in which the data point belongs to can be determined on the basis of the sign of a value obtained according to the discriminant. In this formula, x represents a support vector, y represents a label indicating the belonging of a group, a represents the corresponding coefficient, b represents a constant term, and K represents a kernel function.

$$f(x) = \text{sgn}\left(\sum_{i=1}^{l} y_i a_i K(x_i, x) + b\right) \quad \text{Formula 5}$$

For example, a RBF kernel defined by Formula 6 can be used as the kernel function. In this formula x represents a support vector, and y represents a kernel parameter for adjusting the complexity of the hyperplane.

$$K(x_i, x_j) = \exp(-r\|x_i - x_j\|^2), \quad r<0 \quad \text{Formula 6}$$

In addition, an approach such as neural network, k-nearest neighbor algorithms, decision trees, or logistic regression analysis can be selected as a method for determining or evaluating the presence and/or absence of expression of a pancreatic cancer-derived target genets) in a sample derived from a subject, or for evaluating the expression level thereof by comparison with a control derived from a healthy subject.

The method of the present invention can comprise, for example, the following steps (a), (b), and (c):

(a) a step of measuring an expression level(s) of a target gene(s) in tissues containing pancreatic cancer-derived genes derived from pancreatic cancer patients andlor samples already known to be tissues containing no pancreatic cancer-derived gene(s) derived from healthy subjects, using the polynucleotide(s), the kit, or the device (e.g., DNA chip) for detection according to the present invention;

(b) a step of preparing the discriminants of Formulas 1 to 3, 5, and 6 described above from the measurement values of the expression level measured in the step (a); and (c) a step of measuring an expression level(s) of the target gene(s) in a sample derived from a subject using the polynucleotide(s), the kit, or the device (e.g., DNA chip) for diagnosis (detection) according to the present invention, assigning the obtained measurement value(s) to the discriminants prepared in the step (b), and determining or evaluating the presence and/or absence of expression of the pancreatic cancer-derived target genes in the sample, or evaluating the expression levels thereof by comparison with a healthy subject-derived control, on the basis of the obtained results.

In this context, in the discriminants of Formulas 1 to 3, 5, and 6, x represents an explanatory variable and includes a value obtained by measuring a polynucleotide(s) selected from the polynucleotides described in Section 2 above, or any fragment thereof. Specifically, the explanatory variable for discriminating a pancreatic cancer patient from a healthy subject according to the present invention is a gene expression levels) selected from, for example, the following expression levels (1) to (3):

(1) a gene expression level(s) in the serum of a pancreatic cancer patient or a healthy subject measured by any RNA or DNA comprising 15 or more consecutive nucleotides in a nucleotide sequence represented by any of SEQ ID NOs: 1 to 104, 464 to 473, and 492 to 494 or a complementary sequence thereof, or nucleotides derived from the nucleotides by the replacement of u with t;

(2) a gene expression level(s) in the serum of a pancreatic cancer patient or a healthy subject measured by any RNA or DNA comprising 15 or more consecutive nucleotides in a nucleotide sequence represented by any of SEQ ID NOs: 105 to 122 or a complementary sequence thereof, or nucleotides derived from the nucleotides by the replacement of u with t; and (3) a gene expression level(s) in the serum of a pancreatic cancer patient or a healthy subject measured by any RNA or DNA comprising 15 or more consecutive nucleotides in a nucleotide sequence represented by any of SEQ ID NOs: 349 to 383 or a complementary sequence thereof, or nucleotides derived from the nucleotides by the replacement of u with t.

As described above, for the method for determining or evaluating the presence and/or absence of a pancreatic cancer-derived gene(s) in a sample derived from a subject, the preparation of a discriminant requires a discriminant prepared from a training cohort. For enhancing the accuracy of the discriminant, it is necessary to use genes having clear difference between two groups in the training cohort when preparing the discriminant.

Each gene that is used for an explanatory variable in a discriminant is preferably determined as follows. First, comprehensive gene expression levels of a pancreatic cancer patient group and comprehensive gene expression levels of a healthy subject group, both of which are in a training cohort, are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the test, the absolute value (fold change) of an expression ratio of a median value of each gene expression level between gene expression levels of a pancreatic cancer patient group and gene expression levels of a healthy stibject Effoup may be calculated to select a gene that is used for an explanatory variable in a discriminant. Alternatively, ROC curves may be prepared using gene expression levels of a pancreatic cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discrimination accuracy include a method of constructing a discriminant in every combination of genes that satisfy the significance level being P value, and a method of repetitively evaluating the genes for use in the preparation of a discriminant while increasing the number of genes one by one in a descending order of difference in gene expression level (Furey T S, et al., 2000, Bioinformatics., Vol. 16, p. 906-14). A gene expression level of another independent pancreatic cancer patient or healthy subject is assigned as an explanatory variable to this discriminant to calculate discrimination results of the group to which this independent pancreatic cancer patient or healthy subject belongs. Specifically, the found gene set for diagnosis and the discriminant constructed using the gene set for diagnosis can be evaluated in an independent sample cohort to find a more universal gene set for diagnosis capable of detecting pancreatic cancer and a more universal method for discriminating pancreatic cancer.

Split-sample method is preferably used for evaluating the performance (generality) of the discriminant. Specifically, a data set is divided into a training cohort and a validation cohort, and gene selection by a statistical test and discriminant preparation are performed using the training cohort. Accuracy, sensitivity, and specificity are calculated using a result of discriminating a validation cohort according to the discriminant, and a true group to which the validation cohort belongs, to evaluate the performance of the discriminant. On the other hand, instead of dividing a data set, the gene selection by a statistical test and discriminant preparation may be performed using all of samples, and accuracy, sensitivity, and specificity can be calculated by the discriminat anaylsis using a newly prepared sample cohort for evaluation of the performance of the discriminant.

The present invention provides polynucleotides for disease diagnosis useful in the diagnosis and treatment of pancreatic cancer, a method for detecting pancreatic cancer using the polynucleotide(s), and a kit and a device for the detection of pancreatic cancer, comprising the polynucleotide(s). Particularly, in order to select a gene(s) for diagnosis and prepare a discriminant so as to exhibit accuracy beyond the pancreatic cancer diagnosis methods using the existing tumor markers CEA and CA19-9, a gene set for diagnosis and a discriminant for the method of the present invention can be constructed, which exhibit accuracy beyond CEA and CA19-9, for example, by comparing expressed genes in serum from a patient confirmed to be negative using CEA and CA19-9 but finally found to have pancreatic cancer by detailed examination such as computed tomography using a contrast medium, with genes expressed in serum from a patient having no pancreatic cancer.

For example, the gene set for diagnosis is set to any combination selected from one or two or more of the polynucleotides based on a nucleotide sequence represented by any of SEQ NOs: 1 to 104, 464 to 473, and 492 to 494 or a nucleotide sequence derived from the nucleotide sequence by the replacement of u with t, or a complementary sequence thereof as described above; and optionally one or two or more of the polynucleotides based on a nucleotide sequence represented by any of SEQ ID NOs: 105 to 122 or a nucleotide sequence derived from the nucleotide sequence by the replacement of u with t, or a complementary sequence thereof; and optionally one or two or more of the polynucleotides based on a nucleotide sequence represented by any of SEQ ID NOs: 349 to 383 or a nucleotide sequence derived from the nucleotide sequence by the replacement of u with t, or a complementary sequence thereof. Further, a discriminant is constructed using expression levels of the gene set for diagnosis in samples from class I pancreatic cancer patients as a result of tissue diagnosis and samples from class II healthy subjects as a result of tissue diagnosis. As a result, the presence or absence of pancreatic cancer-derived genes in an unknown sample can be determined with 100% accuracy at the maximum by measuring expression levels of the gene set for diagnosis in an unknown sample.

EXAMPLES

Hereinafter, the present invention will be described further specifically with reference to Examples below. However, the scope of the present invention is not intended to be limited by these Examples.

Reference Example 1

<Collection of Samples of Pancreatic Cancer Patient and Healthy Subject>

Sera were collected using VENOJECT II vacuum blood collecting tube VP-AS109K60 (Terumo Corp., Japan) from 100 healthy subjects and 67 pancreatic cancer patients (1 case with stage IB, 10 cases with stage IIB, 17 cases with stage III, and 39 cases with stage IV) confirmed to have no cancer in organs other than the pancreas after obtainment of informed consent, and used as a training cohort. Likewise, sera were collected using VENOJECT II vacuum blood collecting tube VP-AS109K60 (Terumo Corp.) from 50 healthy subjects and 33 pancreatic cancer patients (1 case with stage IB, 2 cases with stage IIA, 4 cases with stage IIB, 11 cases with stage III, and 15 cases with stage IV) confirmed to have no cancer in organs other than the pancreas after obtainment of informed consent, and used as a validation cohort.

<Extraction of Total RNA>

Total RNA was obtained using a reagent for RNA extraction in 3D-Gene™ RNA extraction reagent from liquid sample kit (foray Industries, Inc., Japan) according to the protocol provided by the manufacturer from 300 µL the serum sample obtained from each of 250 persons in total of 150 healthy subjects and 100 pancreatic cancer patients included in the training cohort and the validation cohort.

<Measurement of Gene Expression Level> miRNAs in the total RNA obtained from the serum samples of each of 250 persons in total of 150 healthy subjects and 100 pancreatic cancer patients included in the training cohort and the validation cohort were fluorescently labeled using 3D-Gene™ miRNA Labeling kit (foray Industries, Inc.) according to the protocol (ver 2.20) provided by the manufacturer. The oligo DNA chip used was 3D-Gene™ Human miRNA Oligo chip (foray Industries, Inc.) with attached probes having sequences complementary to 2,555 miRNAs among the miRNAs registered in miRBase Release 20. Hybridization under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained for the 100 pancreatic cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples of Other Cancers and Benign Diseases>

Sera were collected using VENOJECT II vacuwn blood collecting tube VP-AS109K60 (Terumo Corp.) from each of 35 colorectal cancer patients, 37 stomach cancer patients, 32 esophageal cancer patients, 38 liver cancer patients, and 13 benign pancreaticohiliary disease patients confirmed to have no cancer in other organs after obtainment of informed consent, and used as a training cohort together with the samples of 67 pancreatic cancer patients (1 case with stage IIA, 11 cases with stage IIB, 17 cases with stage III, and 38 cases with stage IV) and 93 healthy subjects of Reference Example 1. Likewise, sera were collected using VENOJECT II vacuum blood collecting tube VP-AS109K60 (Terumo Corp.) from each of 15 colorectal cancer patients, 13 stomach cancer patients, 18 esophageal cancer patients, 12 liver cancer patients, and 8 benign pancreaticobiliary disease patients confirmed to have no cancer in other organs after obtainment of informed consent, and used as a validation cohort together with the samples of 33 pancreatic cancer patients (2 cases with stage IB, 1 case with stage 3 cases with stage IIB, 11 cases with stage III, and 16 cases with stage IV) and 57 healthy subjects of Reference Example 1. Subsequent extraction of total RNA and measurement and analysis of gene expression levels were conducted in the same way as in Reference Example 1.

Example 1

<Selection of Gene Markers Using the Training Cohort, and Method for Evaluating Pancreatic Cancer Descriminant Performance of the Single Gene Marker Using the Validation Cohort>

In this Example, a gene marker for discriminating a pancreatic cancer patient from a healthy subject was selected from the training cohort and studied in the validation cohort independent of the training cohort.

Specifically, first, the miRNA expression levels of the training cohort and the validation cohort obtained in the preceding Reference Examples were combined and normalized by quantile normalization.

Next, genes for diagnosis were selected using the training cohort. Here, in order to acquire diagnostic markers with higher reliability, only genes having the expression level of $2^6$ or higher in 50% or more of the samples in either of the pancreatic cancer patient group of the training cohort or the healthy subject group of the training cohort were selected. In order to further acquire statistically significant genes for discriminating a pancreatic cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant and described in Table 2.

In this way, hsa-miR-6893-5p, hsa-miR-6075, hsa-miR-6820-5p, hsa-miR-4294, hsa-miR-6729-5p, hsa-miR-4476, hsa-miR-6836-3p, hsa-miR-6765-3p, hsa-miR-6799-5p, hsa-miR-4530, hsa-miR-7641, hsa-miR-4454, hsa-miR-615-5p, hsa-miR-8073, hsa-miR-663a, hsa-miR-4634, hsa-miR-4450, hsa-miR-4792, hsa-miR-665, hsa-miR-7975, hsa-miR-7109-5p, hsa-miR-6789-5p, hsa-miR-4497, hsa-miR-6877-5p, hsa-miR-6880-5p, hsa-miR-7977, hsa-miR-4734, hsa-miR-6821-5p, hsa-miR-8089, hsa-miR-5585-3p, hsa-miR-6085, hsa-miR-6845-5p, hsa-miR-4651, hsa-miR-4433-3p, hsa-miR-1231, hsa-miR-4665-5p, hsa-miR-7114-5p, hsa-miR-1238-5p, hsa-miR-8069, hsa-miR-4732-5p, hsa-miR-619-5p, hsa-miR-3622a-5p, hsa-miR-1260a, hsa-miR-6741-5p, hsa-miR-6781-5p, hsa-miR-6125, hsa-miR-6805-5p, hsa-miR-6132, hsa-miR-6872-3p, hsa-miR-6875-5p, hsa-miR-1908-3p, hsa-miR-4433h-3p, hsa-miR-4736, hsa-miR-5100, hsa-miR-6724-5p, hsa-miR-7107-5p, hsa-miR-6726-5p, hsa-miR-3185, hsa-miR-4638-5p, hsa-miR-1273g-3p, hsa-miR-6778-5p, hsa-miR-328-5p, hsa-miR-3679-3p, hsa-miR-1228-3p, hsa-miR-6779-5p, hsa-miR-4723-5p, hsa-miR-6850-5p, hsa-miR-760, hsa-miR-7704, hsa-miR-8072, hsa-miR-4486, hsa-miR-1913, hsa-miR-4656, hsa-miR-1260h, hsa-miR-7106-5p, hsa-miR-6889-5p, hsa-miR-6780h-5p, hsa-miR-6090, hsa-miR-4534, hsa-miR-4449, hsa-miR-5195-3p, hsa-miR-1202, hsa-miR-4467, hsa-miR-6515-3p, hsa-miR-4281, hsa-miR-4505, hsa-miR-4484, hsa-miR-6805-3p, hsa-miR-3135b, hsa-miR-3162-5p, hsa-miR-6768-5p, hsa-miR-6721-5p, hsa-miR-1227-5p, hsa-miR-6722-3p, hsa-miR-4286, hsa-miR-4746-3p, hsa-miR-6727-5p, hsa-miR-6816-5p, hsa-miR-4741, hsa-miR-4508, hsa-miR-940, hsa-miR-4327, hsa-miR-4665-3p, hsa-miR-718, hsa-miR-125a-3p, hsa-miR-204-3p, hsa-miR-1469, hsa-miR-575, hsa-miR-150-3p, hsa-miR-423-5p, hsa-miR-564, hsa-miR-3188, hsa-miR-1246, hsa-miR-602, hsa-miR-1290, hsa-miR-16-5p, hsa-miR-451a, hsa-miR-24-3p, hsa-miR-187-5p, hsa-miR-1908-5p, hsa-miR-371a-5p, and hsa-miR-550a-5p genes, and the nucleotide sequences of SEQ ID NOs: 1 to 122 related thereto were found.

A discriminant for determining the presence or absence of pancreatic cancer was further prepared by Fisher's discriminant analysis with the expression levels of these genes as indicators. Specifically, any newly found polynucleotide consisting of a nucleotide sequence represented by any of SEQ ID NOs: 1 to 104 among the 122 genes selected in the training cohort was input to Formula 2 above to prepare a discriminant. Calculated accuracy, sensitivity, and specificity are shown in Table 3. In this respect, a discriminant coefficient and a constant term are shown in Table 4.

Figure 2:
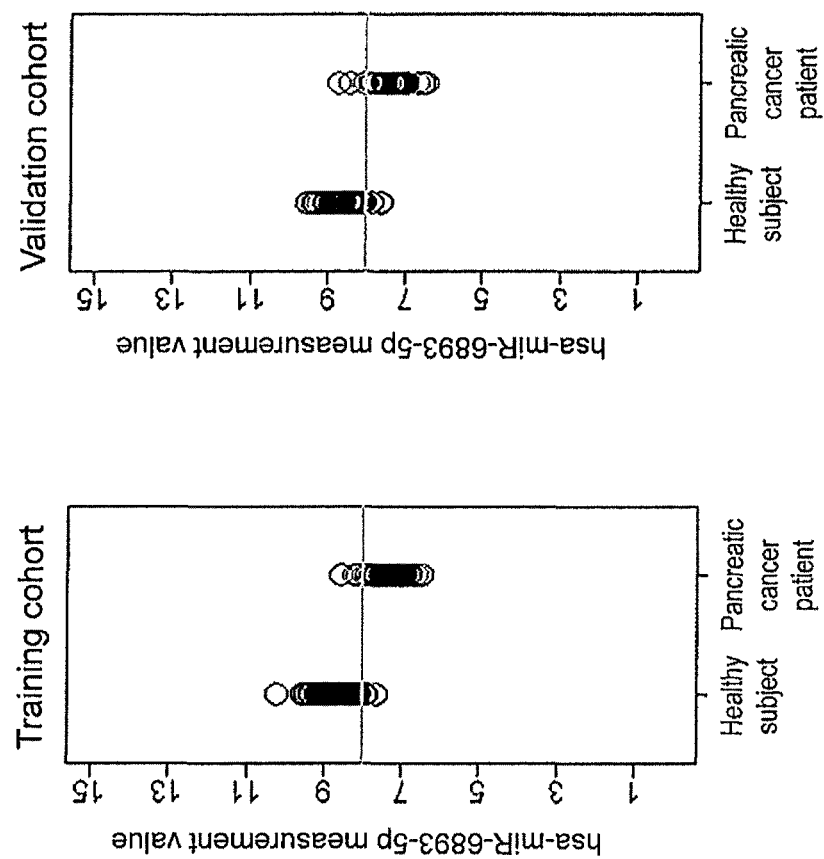
FIG. 2 Left diagram: the expression level measurement values of hsa-miR-6893-5p (SEQ ID NO: 1) in healthy subjects (100 persons) and pancreatic cancer patients (67 persons) selected as a training cohort were each plotted on the ordinate. The horizontal line in the diagram depicts a threshold (8.02) that was optimized by Fisher's discriminant analysis and discriminated between the two groups. Right diagram: the expression level measurement values of hsa-miR-6893-5p (SEQ ID NO: 1) in healthy subjects (50 persons) and pancreatic cancer patients (33 persons) selected as a validation cohort were each plotted on the ordinate. The horizontal line in the diagram depicts the threshold (8.02) that was set in the training cohort and discriminated between the two groups.

Next, accuracy, sensitivity, and specificity in the validation cohort were calculated using the discriminant thus prepared, and the discriminant performance of the selected polynucleotides was validated using independent samples (Table 3). For example, the expression level measurement value of the nucleotide sequence represented by SEQ ID NO: 1 was compared between the healthy subjects (50 persons) and the pancreatic cancer patients (33 persons) in the validation cohort. As a result, the gene expression level measurement values in the training cohort were found to be significantly lower in the pancreatic cancer patient group than in the healthy subject group (see the left diagram of FIG. 2). These results were also reproducible in the validation cohort (see the right diagram of FIG. 2). Likewise, the results obtained about the other polynucleotides shown in SEQ ID NOs: 1 to 122 showed that the gene expression level measurement values were significantly lower (−) or higher (+) in the pancreatic cancer patient group than in the healthy subject group (Table 2). These results were able to be validated in the validation cohort. For example, as for this nucleotide sequence represented by SEQ ID NO: 1, the number of correctly or incorrectly identified samples in the detection of pancreatic cancer was calculated using the threshold (8.02) that was set in the training cohort and discriminated between the two groups. As a result, 30 true positives, 49 true negatives, 1 false positive, and 3 false negatives were obtained. From these values, 95% accuracy, 91% sensitivity, and 98% specificity were obtained as the detection performance. In this way, the detection performance was calculated as to all of the polynucleotides shown in SEQ ID NOs: 1 to 122, and described in Table 3. Among the polynucleotides consisting of the nucleotide sequences represented by SEQ ID NOs: 1 to 104 shown in Table 2, for example, 14 polynucleotides consisting of the nucleotide sequences represented by SEQ ID NOs: 1, 2, 4, 5, 7, 9, 11, 18, 21, 22, 24, 25, 35, and 46 exhibited sensitivity of 87.9%, 90.9%, 87.9%, 81.8%, 90.9%, 78.8%, 78.8%, 78.8%, 84.8%, 78.8%, 81.8%, 81.8%, 93.9%, and 81.8%, respectively, in the validation cohort (Table 3). Also, these polynucleotides were able to correctly identify one stage 1 pancreatic cancer sample contained in the validation cohort as a pancreatic cancer sample. Furthermore, these polynucleotides were able to correctly discriminate pancreatic cancer as to any of the tumors occupying the head, the body, and the tail of the pancreas in the validation cohort, and, particularly, were able to detect tumors even in the tail of the pancreas, which are prone to delayed diagnosis. As seen from Comparative Example mentioned later, the existing markers CEA and CA19-9 had sensitivity of 45.5% and 75.8%, respectively, in the validation cohort (Table 5), demonstrating that, for example, the 14 polynucleotides consisting of the nucleotide sequences represented by SEQ ID Nos: 1, 2, 4, 5, 7, 9, 11, 18, 21, 22, 24, 25, 35, and 46 can discriminate, each alone, pancreatic cancer in the validation cohort with sensitivity beyond CA19-9.

Example 2

<Method A for Evaluating Pancreatic Cancer Discriminant Performance by Cotribination of Plurality of Gene Markers Using Samples in the Validation Cohort>

In this Example, a method for evaluating pancreatic cancer discriminant performance by a combination of the gene markers selected in Example 1 was studied.

Figure 3:
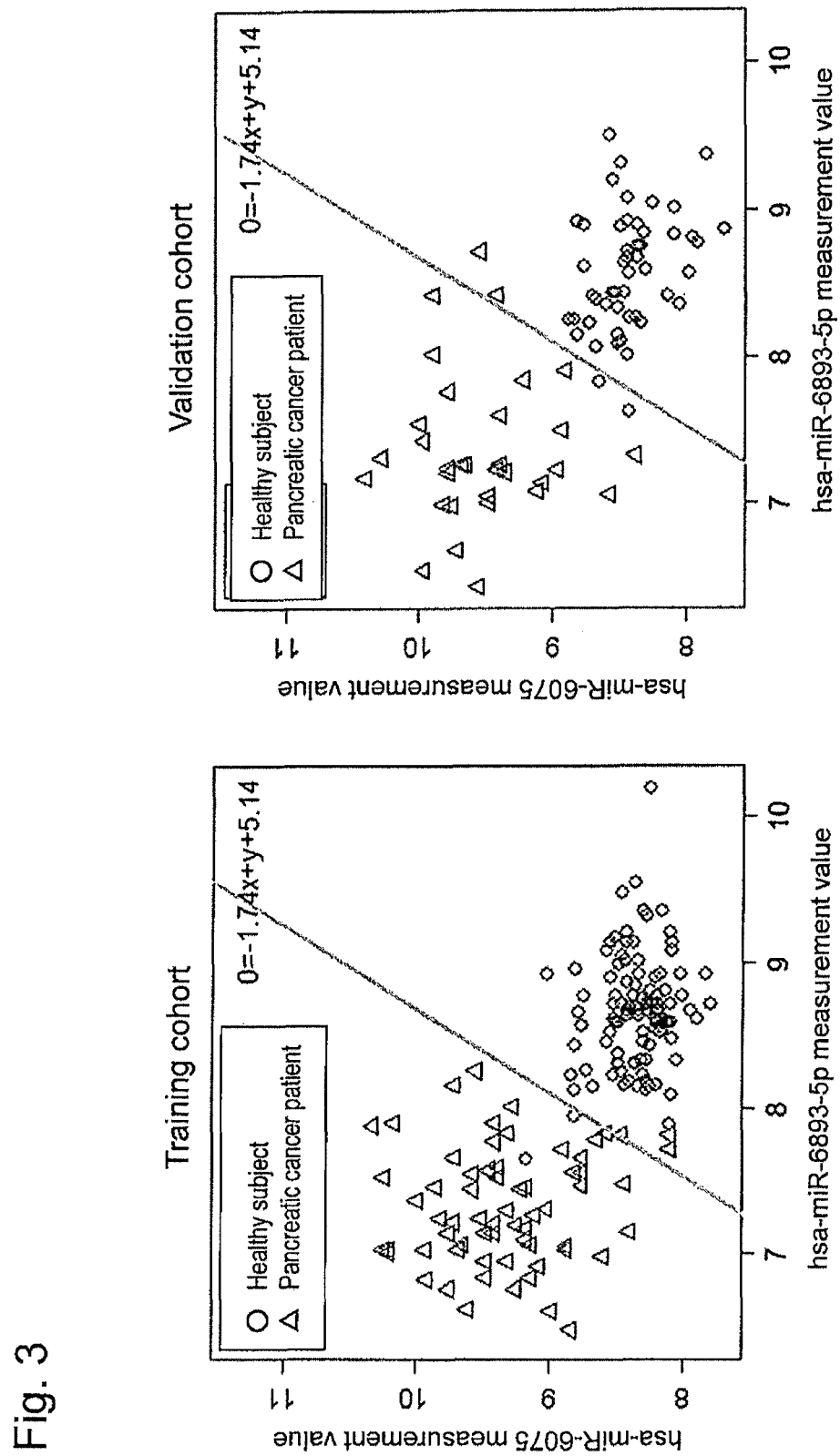
FIG. 3 Left diagram: the expression level measurement values of hsa-miR-6893-5p (SEQ ID NO: 1) in healthy subjects (100 persons, circles) and pancreatic cancer patients (67 persons, triangles) selected as a training cohort were each plotted on the abscissa against their expression level measurement values of hsa-miR-6075 (SEQ ID NO: 2) on the ordinate. The line in the diagram depicts a discriminant function (0=1.74x+y+5.14) that was optimized by Fisher's discriminant analysis and discriminated between the two groups. Right diagram: the expression level measurement values of hsa-miR-6893-5p (SEQ ID NO: 1) in healthy subjects (50 persons, circles) and pancreatic cancer patients (33 persons, triangles) selected as a validation cohort were each plotted on the abscissa against their expression level measurement values of hsa-miR-6075 (SEQ ID NO: 2) on the ordinate. The line in the diagram depicts the threshold (0=1.74x+v+5.14) that was set in the training cohort and discriminated between the two groups.

Specifically, Fisher's discriminant analysis was conducted as to 7,228 combinations of two expression level measurement values comprising at least one or more of the expression level measurement values of the newly found polynucleotides consisting of the nucleotide sequences represented by SEQ ID NOs: 1 to 104 among the polynucleotides consisting of the nucleotide sequences represented by SEQ ID NOs: 1 to 122 selected in Example 1, to construct a discriminant for determining the presence or absence of pancreatic cancer. Next, accuracy, sensitivity, and specificity in the validation cohort were calculated using the discriminant thus prepared, and the discriminant performance of the selected polynucleotides was validated using independent samples. For example, the expression level measurement values of the nucleotide sequences represented by SEQ ID NO: 1 and SEQ ID NO: 2 were compared between the healthy subjects (50 persons) and the pancreatic cancer patients (33 persons) in the validation cohort. As a result, a scatter diagram that significantly separated the expression level measurement values of the pancreatic cancer patient group from those of the healthy subject group was obtained in the training cohort (see the left diagram of FIG. 3). These results were also reproducible in the validation cohort (see the right diagram of FIG. 3). Likewise, a scatter diagram that significantly separated the gene expression level measurement values of the pancreatic cancer patient group from those of the healthy subject group was also obtained as to the other combinations of two expression level measurement values comprising at least one or more of the expression level measurement values of the newly found polynucleotides consisting of the nucleotide sequences represented by SEQ ID NOs: 1 to 104 among the polynucleotides consisting of the nucleotide sequences represented by SEQ ID NOs: 1 to 122. These results were able to be validated in the validation cohort. For example, as for these nucleotide sequences represented by SEQ ID NO: 1 and SEQ NO: 2, the number of samples that were correctly or incorrectly identified pancreatic cancer was calculated using the threshold (0=1.74x+y+5.14) that was set in the training cohort and discriminated between the two groups. As a result, 30 true positives, 49 true negatives, 1 false positive, and 3 false negatives were obtained. From these values, 95% accuracy, 91% sensitivity, and 98% specificity were obtained as the detection performance. In this way, the detection performance was calculated for the combinations of two expression level measurement values comprising at least one or more of the expression level measurement values of the newly found polynucleotides consisting of the nucleotide sequences represented by SEQ ID NOs: 1 to 104 among the polynucleotides consisting of the nucleotide sequences represented by SEQ ID NOs: 1 to 122, and the 2,619 combinations that showed sensitivity better than the sensitivity (75.8%) of the existing marker in the validation cohort, were described in Table 6.

The discriminant analysis for pancreatic cancer in the validation cohort was performed using the 7,228 combinations of the expression level measurement values of the polynucleotides. As a result, for example, the combinations of the expression level measurement values of the polynucleotides consisting of the nucleotide sequences represented by SEQ ID NOs: 2 and 105, SEQ ID NOs: 18 and 105, SEQ ID NOs: 46 and 105, and SEQ ID NOs: 55 and 105 exhibited sensitivity of 100%, 100%, and 100%, respectively, in the validation cohort. In this way, the 2,691 combinations of the expression level measurement values of the polynucleotides having sensitivity beyond the existing marker CA19-9 (Table 5) were obtained in the validation cohort. All of the nucleotide sequences 1 to 122 described in Table 2 obtained in Example 1 were employed at least once in these combinations. These results demonstrated that the combinations of two expression level measurement values comprising at least one or more of the expression level measurement values of the polynucleotides consisting of the nucleotide sequences represented by SEQ ID NOs: 1 to 122 can detect pancreatic cancer with sensitivity beyond CA19-9 in the validation cohort.

Thus, markers capable of detecting pancreatic cancer with excellent sensitivity are obtained even if 3, 4, 5, 6, 7, 8, 9, 10 or more of the expression level measurement values of the polynucleotides consisting of the nucleotide sequences represented by SEQ ID NOs: 1 to 122 are combined. For example, the polynucleotides consisting of the nucleotide sequences represented by SEQ ID NOs: 1 to 122 selected in Example 1 were ranked in the descending order of their P values which indicate statistical significance, and detection performance was calculated using combinations of one or more miRNAs to which the miRNAs were added one by one from the top to the bottom according to the rank. As a result, the sensitivity in the validation cohort was 87.9% for 2 miRNAs, 90.9% for 3 miRNAs, 100% for 5 miRNAs, 100% for 10 miRNAs, 100% for 20 miRNAs, 100% for 50 miRNAs, 100% for 100 miRNAs, and 100% for 122 miRNAs. These values of the sensitivity were higher than the sensitivity of the existing tumor marker in blood, demonstrating that even combinations of a plurality of the miRNAs can serve as excellent markers for the detection of pancreatic cancer. In this context, the combinations of a plurality of the miRNAs are not limited to the combinations of the miRNAs added in the order of statistically significant difference as described above, and any combination of a plurality of the miRNAs can be used in the detection of pancreatic cancer.

From these results, it can be concluded that all of the polynucleotides consisting of the nucleotide sequences represented by SEQ ID NOs: 1 to 122 serve as excellent diagnostic markers.

Tables 2, 3, 4, 5, and 6 mentioned above are as follows.

TABLE 2

| SEQ ID NO: | Gene name | P value after Bonferroni correction | Expression level in pancreatic cancer patient relative to healthy subject |
|---|---|---|---|
| 1 | hsa-miR-6893-5p | 7.19E−46 | − |
| 2 | hsa-miR-6075 | 1.91E−29 | + |
| 3 | hsa-miR-6820-5p | 1.78E−27 | − |
| 4 | hsa-miR-4294 | 3.27E−27 | − |
| 5 | hsa-miR-6729-5p | 6.76E−26 | + |
| 6 | hsa-miR-4476 | 8.49E−25 | − |
| 7 | hsa-miR-6836-3p | 1.97E−22 | + |
| 8 | hsa-miR-6765-3p | 4.75E−22 | − |
| 9 | hsa-miR-6799-5p | 5.00E−19 | − |
| 10 | hsa-miR-4530 | 9.09E−19 | − |
| 11 | hsa-miR-7641 | 7.84E−18 | − |
| 12 | hsa-miR-4454 | 1.29E−17 | − |
| 13 | hsa-miR-615-5p | 3.14E−17 | − |
| 14 | hsa-miR-8073 | 3.61E−17 | + |
| 15 | hsa-miR-663a | 1.72E−16 | + |
| 16 | hsa-miR-4634 | 2.55E−16 | + |
| 17 | hsa-miR-4450 | 3.14E−16 | − |
| 18 | hsa-miR-4792 | 3.80E−16 | + |
| 19 | hsa-miR-665 | 7.86E−16 | + |
| 20 | hsa-miR-7975 | 8.48E−15 | − |
| 21 | hsa-miR-7109-5p | 3.23E−14 | − |

TABLE 2-continued

| SEQ ID NO: | Gene name | P value after Bonferroni correction | Expression level in pancreatic cancer patient relative to healthy subject |
|---|---|---|---|
| 22 | hsa-miR-6789-5p | 4.58E−13 | + |
| 23 | hsa-miR-4497 | 5.38E−13 | − |
| 24 | hsa-miR-6877-5p | 5.58E−13 | − |
| 25 | hsa-miR-6880-5p | 6.14E−13 | − |
| 26 | hsa-miR-7977 | 6.28E−13 | − |
| 27 | hsa-miR-4734 | 6.79E−13 | + |
| 28 | hsa-miR-6821-5p | 8.22E−13 | − |
| 29 | hsa-miR-8089 | 9.61E−13 | − |
| 30 | hsa-miR-5585-3p | 1.38E−12 | + |
| 31 | hsa-miR-6085 | 4.32E−12 | − |
| 32 | hsa-miR-6845-5p | 1.41E−11 | + |
| 33 | hsa-miR-4651 | 1.53E−11 | − |
| 34 | hsa-miR-4433-3p | 5.65E−11 | + |
| 35 | hsa-miR-1231 | 1.38E−10 | + |
| 36 | hsa-miR-4665-5p | 2.54E−10 | − |
| 37 | hsa-miR-7114-5p | 5.73E−10 | − |
| 38 | hsa-miR-1238-5p | 6.26E−10 | + |
| 39 | hsa-miR-8069 | 7.39E−10 | + |
| 40 | hsa-miR-4732-5p | 8.03E−10 | + |
| 41 | hsa-miR-619-5p | 2.23E−09 | + |
| 42 | hsa-miR-3622a-5p | 2.53E−09 | − |
| 43 | hsa-miR-1260a | 3.84E−09 | − |
| 44 | hsa-miR-6741-5p | 6.57E−09 | − |
| 45 | hsa-miR-6781-5p | 6.86E−09 | + |
| 46 | hsa-miR-6125 | 7.51E−09 | + |
| 47 | hsa-miR-6805-5p | 8.71E−09 | + |
| 48 | hsa-miR-6132 | 1.71E−08 | − |
| 49 | hsa-miR-6872-3p | 1.74E−08 | − |
| 50 | hsa-miR-6875-5p | 2.76E−08 | + |
| 51 | hsa-miR-1908-3p | 2.77E−08 | + |
| 52 | hsa-miR-4433b-3p | 5.12E−08 | + |
| 53 | hsa-miR-4736 | 5.45E−08 | + |
| 54 | hsa-miR-5100 | 7.94E−08 | − |
| 55 | hsa-miR-6724-5p | 9.14E−08 | + |
| 56 | hsa-miR-7107-5p | 9.80E−08 | − |
| 57 | hsa-miR-6726-5p | 2.49E−07 | − |
| 58 | hsa-miR-3185 | 2.57E−07 | + |
| 59 | hsa-miR-4638-5p | 6.78E−07 | − |
| 60 | hsa-miR-1273g-3p | 6.87E−07 | + |
| 61 | hsa-miR-6778-5p | 6.95E−07 | + |
| 62 | hsa-miR-328-5p | 7.01E−07 | − |
| 63 | hsa-miR-3679-3p | 7.68E−07 | + |
| 64 | hsa-miR-1228-3p | 9.27E−07 | + |
| 65 | hsa-miR-6779-5p | 1.28E−06 | − |
| 66 | hsa-miR-4723-5p | 1.35E−06 | − |
| 67 | hsa-miR-6850-5p | 1.68E−06 | + |
| 68 | hsa-miR-760 | 1.69E−06 | − |
| 69 | hsa-miR-7704 | 1.82E−06 | − |
| 70 | hsa-miR-8072 | 5.28E−06 | + |
| 71 | hsa-miR-4486 | 8.48E−06 | + |
| 72 | hsa-miR-1913 | 1.02E−05 | + |
| 73 | hsa-miR-4656 | 1.36E−05 | + |
| 74 | hsa-miR-1260b | 3.21E−05 | − |
| 75 | hsa-miR-7106-5p | 3.55E−05 | − |
| 76 | hsa-miR-6889-5p | 4.00E−05 | − |
| 77 | hsa-miR-6780b-5p | 4.32E−05 | + |
| 78 | hsa-miR-6090 | 5.02E−05 | + |
| 79 | hsa-miR-4534 | 1.36E−04 | − |
| 80 | hsa-miR-4449 | 1.63E−04 | + |
| 81 | hsa-miR-5195-3p | 1.70E−04 | − |
| 82 | hsa-miR-1202 | 1.83E−04 | − |
| 83 | hsa-miR-4467 | 7.51E−04 | + |
| 84 | hsa-miR-6515-3p | 8.23E−04 | + |
| 85 | hsa-miR-4281 | 8.83E−04 | − |
| 86 | hsa-miR-4505 | 8.88E−04 | − |
| 87 | hsa-miR-4484 | 9.98E−04 | + |
| 88 | hsa-miR-6805-3p | 1.04E−03 | + |
| 89 | hsa-miR-3135b | 1.11E−03 | − |
| 90 | hsa-miR-3162-5p | 1.26E−03 | − |
| 91 | hsa-miR-6768-5p | 1.45E−03 | − |
| 92 | hsa-miR-6721-5p | 1.57E−03 | + |
| 93 | hsa-miR-1227-5p | 1.65E−03 | + |
| 94 | hsa-miR-6722-3p | 1.66E−03 | + |
| 95 | hsa-miR-4286 | 1.73E−03 | − |
| 96 | hsa-miR-4746-3p | 1.83E−03 | + |
| 97 | hsa-miR-6727-5p | 3.32E−03 | − |
| 98 | hsa-miR-6816-5p | 4.09E−03 | + |
| 99 | hsa-miR-4741 | 4.57E−03 | + |
| 100 | hsa-miR-4508 | 6.50E−03 | + |
| 101 | hsa-miR-940 | 7.02E−03 | − |
| 102 | hsa-miR-4327 | 7.54E−03 | − |
| 103 | hsa-miR-4665-3p | 7.88E−03 | + |
| 104 | hsa-miR-718 | 9.73E−03 | + |
| 105 | hsa-miR-125a-3p | 2.01E−50 | − |
| 106 | hsa-miR-204-3p | 1.58E−30 | − |
| 107 | hsa-miR-1469 | 1.67E−28 | + |
| 108 | hsa-miR-575 | 1.50E−26 | − |
| 109 | hsa-miR-150-3p | 7.09E−23 | − |
| 110 | hsa-miR-423-5p | 4.74E−21 | − |
| 111 | hsa-miR-564 | 2.56E−10 | − |
| 112 | hsa-miR-3188 | 2.93E−09 | + |
| 113 | hsa-miR-1246 | 3.33E−08 | + |
| 114 | hsa-miR-602 | 1.67E−06 | + |
| 115 | hsa-miR-1290 | 3.00E−06 | + |
| 116 | hsa-miR-16-5p | 3.74E−06 | − |
| 117 | hsa-miR-451a | 1.28E−05 | − |
| 118 | hsa-miR-24-3p | 4.71E−05 | − |
| 119 | hsa-miR-187-5p | 1.11E−04 | − |
| 120 | hsa-miR-1908-5p | 4.29E−04 | + |
| 121 | hsa-miR-371a-5p | 1.56E−03 | − |
| 122 | hsa-miR-550a-5p | 8.60E−03 | + |

TABLE 3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 95.8 | 94 | 97 | 92.8 | 87.9 | 96 |
| 2 | 88.6 | 74.6 | 98 | 96.4 | 90.9 | 100 |
| 3 | 90.4 | 85.1 | 94 | 78.3 | 66.7 | 86 |
| 4 | 86.8 | 74.6 | 95 | 88 | 87.9 | 88 |
| 5 | 88 | 85.1 | 90 | 84.3 | 81.8 | 86 |
| 6 | 86.2 | 73.1 | 95 | 81.9 | 69.7 | 90 |
| 7 | 91.6 | 86.6 | 95 | 92.8 | 90.9 | 94 |
| 8 | 85 | 73.1 | 93 | 84.3 | 69.7 | 94 |
| 9 | 85 | 80.6 | 88 | 83.1 | 78.8 | 86 |
| 10 | 83.2 | 77.6 | 87 | 79.5 | 75.8 | 82 |
| 11 | 79 | 68.7 | 86 | 81.9 | 78.8 | 84 |
| 12 | 81.9 | 71.2 | 89 | 80.7 | 66.7 | 90 |
| 13 | 82 | 77.6 | 85 | 81.9 | 72.7 | 88 |
| 14 | 82 | 65.7 | 93 | 78.3 | 54.5 | 94 |
| 15 | 83.2 | 64.2 | 96 | 85.5 | 66.7 | 98 |
| 16 | 80.8 | 73.1 | 86 | 74.7 | 63.6 | 82 |
| 17 | 83.8 | 65.7 | 96 | 81.9 | 72.7 | 88 |
| 18 | 85 | 77.6 | 90 | 89.2 | 78.8 | 96 |
| 19 | 79.6 | 64.2 | 90 | 81.9 | 63.6 | 94 |
| 20 | 75.4 | 64.2 | 83 | 73.5 | 51.5 | 88 |
| 21 | 76.6 | 70.1 | 81 | 81.9 | 84.8 | 80 |
| 22 | 77.8 | 62.7 | 88 | 83.1 | 78.8 | 86 |
| 23 | 75.4 | 58.2 | 87 | 65.9 | 46.9 | 78 |
| 24 | 76 | 59.7 | 87 | 83.1 | 81.8 | 84 |
| 25 | 80.8 | 67.2 | 90 | 86.7 | 81.8 | 90 |
| 26 | 76.6 | 61.2 | 87 | 73.5 | 48.5 | 90 |
| 27 | 77.2 | 62.7 | 87 | 75.9 | 51.5 | 92 |
| 28 | 76 | 65.7 | 83 | 71.1 | 69.7 | 72 |
| 29 | 76 | 62.7 | 85 | 74.7 | 63.6 | 82 |
| 30 | 79.6 | 68.7 | 87 | 83.1 | 63.6 | 96 |
| 31 | 76 | 62.7 | 85 | 74.7 | 72.7 | 76 |
| 32 | 79 | 64.2 | 89 | 71.1 | 48.5 | 86 |
| 33 | 78.4 | 58.2 | 92 | 80.7 | 60.6 | 94 |
| 34 | 79 | 74.6 | 82 | 75.9 | 66.7 | 82 |
| 35 | 77.8 | 61.2 | 89 | 88 | 93.9 | 84 |
| 36 | 76 | 59.7 | 87 | 69.9 | 51.5 | 82 |
| 37 | 74.9 | 61.2 | 84 | 79.5 | 63.6 | 90 |

TABLE 3-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 38 | 77.8 | 52.2 | 95 | 78.3 | 51.5 | 96 |
| 39 | 74.9 | 52.2 | 90 | 83.1 | 66.7 | 94 |
| 40 | 79.6 | 56.7 | 95 | 75.9 | 54.5 | 90 |
| 41 | 76 | 56.7 | 89 | 75.9 | 45.5 | 96 |
| 42 | 78.4 | 53.7 | 95 | 78.3 | 66.7 | 86 |
| 43 | 75.4 | 61.2 | 85 | 68.7 | 36.4 | 90 |
| 44 | 77.8 | 61.2 | 89 | 75.9 | 57.6 | 88 |
| 45 | 71.9 | 59.7 | 80 | 69.9 | 54.5 | 80 |
| 46 | 75.4 | 62.7 | 84 | 84.3 | 81.8 | 86 |
| 47 | 71.3 | 50.7 | 85 | 68.7 | 45.5 | 84 |
| 48 | 75.4 | 56.7 | 88 | 73.5 | 48.5 | 90 |
| 49 | 72.5 | 53.7 | 85 | 66.3 | 39.4 | 84 |
| 50 | 68.9 | 49.3 | 82 | 75.6 | 68.8 | 80 |
| 51 | 77.2 | 62.7 | 87 | 78.3 | 66.7 | 86 |
| 52 | 78.4 | 70.1 | 84 | 72.3 | 63.6 | 78 |
| 53 | 74.9 | 55.2 | 88 | 73.5 | 51.5 | 88 |
| 54 | 74.9 | 53.7 | 89 | 72.3 | 51.5 | 86 |
| 55 | 73.7 | 56.7 | 85 | 74.7 | 63.6 | 82 |
| 56 | 72.5 | 56.7 | 83 | 67.5 | 54.5 | 76 |
| 57 | 74.9 | 47.8 | 93 | 78.3 | 54.5 | 94 |
| 58 | 75.4 | 56.7 | 88 | 81.9 | 72.7 | 88 |
| 59 | 75.4 | 55.2 | 89 | 75.9 | 57.6 | 88 |
| 60 | 74.3 | 46.3 | 93 | 71.1 | 39.4 | 92 |
| 61 | 74.3 | 52.2 | 89 | 72.3 | 42.4 | 92 |
| 62 | 71.3 | 64.2 | 76 | 69.9 | 57.6 | 78 |
| 63 | 67.1 | 47.8 | 80 | 61.4 | 42.4 | 74 |
| 64 | 74.3 | 59.7 | 84 | 74.7 | 66.7 | 80 |
| 65 | 71.9 | 55.2 | 83 | 79.5 | 66.7 | 88 |
| 66 | 77.8 | 64.2 | 87 | 81.9 | 75.8 | 86 |
| 67 | 70.1 | 47.8 | 85 | 75.9 | 69.7 | 80 |
| 68 | 69.5 | 46.3 | 85 | 68.7 | 45.5 | 84 |
| 69 | 74.9 | 62.7 | 83 | 63.9 | 54.5 | 70 |
| 70 | 77.2 | 59.7 | 89 | 71.1 | 60.6 | 78 |
| 71 | 70.7 | 46.3 | 87 | 72.3 | 42.4 | 92 |
| 72 | 70.7 | 50.7 | 84 | 65.9 | 39.4 | 83.7 |
| 73 | 72.5 | 47.8 | 89 | 69.9 | 33.3 | 94 |
| 74 | 71.3 | 44.8 | 89 | 71.1 | 45.5 | 88 |
| 75 | 71.9 | 50.7 | 86 | 78.3 | 69.7 | 84 |
| 76 | 65.3 | 37.3 | 84 | 65.1 | 30.3 | 88 |
| 77 | 71.9 | 50.7 | 86 | 75.3 | 58.1 | 86 |
| 78 | 68.3 | 56.7 | 76 | 68.7 | 66.7 | 70 |
| 79 | 74.9 | 53.7 | 89 | 79.5 | 69.7 | 86 |
| 80 | 70.1 | 43.3 | 88 | 75.9 | 54.5 | 90 |
| 81 | 71.7 | 51.5 | 85 | 75.9 | 57.6 | 88 |
| 82 | 65.3 | 40.3 | 82 | 74.7 | 60.6 | 84 |
| 83 | 65.9 | 38.8 | 84 | 77.1 | 63.6 | 86 |
| 84 | 66.5 | 43.3 | 82 | 60.2 | 36.4 | 76 |
| 85 | 66.5 | 46.3 | 80 | 74.7 | 45.5 | 94 |
| 86 | 71.9 | 44.8 | 90 | 67.5 | 36.4 | 88 |
| 87 | 64.7 | 41.8 | 80 | 65.1 | 36.4 | 84 |
| 88 | 64.7 | 40.3 | 81 | 67.5 | 45.5 | 82 |
| 89 | 71.9 | 47.8 | 88 | 77.1 | 57.6 | 90 |
| 90 | 70.7 | 41.8 | 90 | 72.3 | 45.5 | 90 |
| 91 | 70.7 | 43.3 | 89 | 69.9 | 42.4 | 88 |
| 92 | 68.9 | 50.7 | 81 | 68.7 | 57.6 | 76 |
| 93 | 62.9 | 38.8 | 79 | 69.9 | 51.5 | 82 |
| 94 | 68.3 | 35.8 | 90 | 78.3 | 63.6 | 88 |
| 95 | 66.5 | 41.8 | 83 | 60.2 | 27.3 | 82 |
| 96 | 70.1 | 44.8 | 87 | 79.5 | 60.6 | 78 |
| 97 | 73.7 | 49.3 | 90 | 69.9 | 45.5 | 84 |
| 98 | 75.3 | 57.6 | 87 | 77.1 | 60.6 | 86 |
| 99 | 67.7 | 43.3 | 84 | 73.5 | 54.5 | 82 |
| 100 | 64.1 | 28.4 | 88 | 63.9 | 39.4 | 90 |
| 101 | 62.9 | 31.3 | 84 | 62.7 | 27.3 | 94 |
| 102 | 68.9 | 43.3 | 86 | 66.3 | 24.2 | 84 |
| 103 | 72.5 | 46.3 | 90 | 74.7 | 63.6 | 82 |
| 104 | 70.1 | 44.8 | 87 | 68.7 | 45.5 | 86 |

TABLE 4

| SEQ ID NO: | Discriminant coefficient | Constant term |
|---|---|---|
| 1 | 2.460 | 19.714 |
| 2 | 2.382 | 21.068 |
| 3 | 3.095 | 21.899 |
| 4 | 2.352 | 23.243 |
| 5 | 7.904 | 99.660 |
| 6 | 1.427 | 9.523 |
| 7 | 2.999 | 26.661 |
| 8 | 1.567 | 13.180 |
| 9 | 4.320 | 34.683 |
| 10 | 2.347 | 21.497 |
| 11 | 1.240 | 8.775 |
| 12 | 2.099 | 24.008 |
| 13 | 2.507 | 16.240 |
| 14 | 2.542 | 16.656 |
| 15 | 3.003 | 30.919 |
| 16 | 5.690 | 56.064 |
| 17 | 1.236 | 6.777 |
| 18 | 1.762 | 12.038 |
| 19 | 2.603 | 19.023 |
| 20 | 1.993 | 19.451 |
| 21 | 5.292 | 39.055 |
| 22 | 4.377 | 43.459 |
| 23 | 2.108 | 26.455 |
| 24 | 3.957 | 28.165 |
| 25 | 2.128 | 15.182 |
| 26 | 1.961 | 18.889 |
| 27 | 4.907 | 58.675 |
| 28 | 4.501 | 38.362 |
| 29 | 3.320 | 21.613 |
| 30 | 1.615 | 9.456 |
| 31 | 5.158 | 53.443 |
| 32 | 3.419 | 32.836 |
| 33 | 4.112 | 44.623 |
| 34 | 3.556 | 26.261 |
| 35 | 3.089 | 20.506 |
| 36 | 2.763 | 26.001 |
| 37 | 4.150 | 28.312 |
| 38 | 2.643 | 17.528 |
| 39 | 5.818 | 74.782 |
| 40 | 1.432 | 9.710 |
| 41 | 1.548 | 12.083 |
| 42 | 3.016 | 17.886 |
| 43 | 2.295 | 15.780 |
| 44 | 3.562 | 24.535 |
| 45 | 4.999 | 52.068 |
| 46 | 4.621 | 55.322 |
| 47 | 5.752 | 65.582 |
| 48 | 3.690 | 28.014 |
| 49 | 2.300 | 13.896 |
| 50 | 3.446 | 30.899 |
| 51 | 2.754 | 19.334 |
| 52 | 3.342 | 26.922 |
| 53 | 2.877 | 17.377 |
| 54 | 2.361 | 24.174 |
| 55 | 3.775 | 37.577 |
| 56 | 4.572 | 35.653 |
| 57 | 2.278 | 22.355 |
| 58 | 1.996 | 14.097 |
| 59 | 1.651 | 10.003 |
| 60 | 2.120 | 16.586 |
| 61 | 2.027 | 16.365 |
| 62 | 4.550 | 49.932 |
| 63 | 3.688 | 22.416 |
| 64 | 4.384 | 27.791 |
| 65 | 5.587 | 39.777 |
| 66 | 2.642 | 23.269 |
| 67 | 4.993 | 56.756 |
| 68 | 2.773 | 24.275 |
| 69 | 6.973 | 96.404 |
| 70 | 4.314 | 53.140 |
| 71 | 2.482 | 17.866 |
| 72 | 3.669 | 22.882 |
| 73 | 3.449 | 25.517 |
| 74 | 2.141 | 18.183 |
| 75 | 2.787 | 16.795 |
| 76 | 2.574 | 18.040 |
| 77 | 3.025 | 26.735 |

TABLE 4-continued

| SEQ ID NO: | Discriminant coefficient | Constant term |
|---|---|---|
| 78 | 6.736 | 87.662 |
| 79 | 2.855 | 19.214 |
| 80 | 3.280 | 21.398 |
| 81 | 3.072 | 21.250 |
| 82 | 3.225 | 21.272 |
| 83 | 1.954 | 19.003 |
| 84 | 4.310 | 29.038 |
| 85 | 3.905 | 45.270 |
| 86 | 4.055 | 33.489 |
| 87 | 2.767 | 31.507 |
| 88 | 2.531 | 18.803 |
| 89 | 2.479 | 19.469 |
| 90 | 2.939 | 21.665 |
| 91 | 3.025 | 28.509 |
| 92 | 3.753 | 28.267 |
| 93 | 6.207 | 58.913 |
| 94 | 5.548 | 47.238 |
| 95 | 2.358 | 17.589 |
| 96 | 2.487 | 16.190 |
| 97 | 5.449 | 69.434 |
| 98 | 3.843 | 38.475 |
| 99 | 3.266 | 32.112 |
| 100 | 6.751 | 87.358 |
| 101 | 3.318 | 20.579 |
| 102 | 4.434 | 37.869 |
| 103 | 3.950 | 23.214 |
| 104 | 3.491 | 23.806 |

TABLE 5-1

| Training cohort | | | |
|---|---|---|---|
| Sample name | Cancer stage | CEA(ng/mL) | CA19-9(U/mL) |
| P01 | III | 5.6(+) | 202.7(+) |
| P05 | IV | 7.9(+) | 2535(+) |
| P06 | IV | 5.7(+) | 2381(+) |
| P07 | IB | 0.7(−) | 81.9(+) |
| P09 | IV | 1(−) | 48.6(+) |
| P10 | IIB | 3.3(−) | 85.4(+) |
| P11 | IV | 1.4(−) | 8.4(−) |
| P12 | IV | 23.6(+) | 0.5(−) |
| P13 | IV | 3.8(−) | 21.5(−) |
| P14 | IV | 39.2(+) | 248000(+) |
| P17 | IV | 282.1(+) | 77700(+) |
| P18 | IV | 14.8(+) | 7580(+) |
| P19 | IIB | 6.1(+) | 562(+) |
| P21 | III | 1.4(−) | 4690(+) |
| P25 | IV | 255.7(+) | 302.9(+) |
| P26 | IIB | 3.9(−) | 0.1(−) |
| P27 | III | 1(−) | 1304(+) |
| P29 | III | 5.9(+) | 883(+) |
| P33 | IV | 3.6(−) | 3.7(−) |
| P35 | IV | 3.8(−) | 8600(+) |
| P38 | IV | 26.7(+) | 9080(+) |
| P39 | IV | 31.2(+) | 299000(+) |
| P42 | IV | 4.8(−) | 14.1(−) |
| P43 | IV | 188.2(+) | 119700(+) |
| P44 | IV | 55.3(+) | 38620(+) |
| P46 | IV | 20.7(+) | 10.6(−) |
| P47 | IV | 5.6(+) | 107.9(+) |
| P48 | III | 3.4(−) | 285.6(+) |
| P49 | IIB | 3.6(−) | 338.8(+) |
| P50 | III | 11(+) | 2760(+) |
| P52 | IV | 13.6(+) | 9850(+) |
| P53 | III | 8.8(+) | 891(+) |
| P54 | III | 8.4(+) | 0.5(−) |
| P55 | IV | 8.1(+) | 8799(+) |
| P56 | IV | 202(+) | 337900(+) |
| P57 | IV | 1.8(−) | 110.7(+) |
| P59 | IV | 64.3(+) | 223.9(+) |
| P60 | IIB | 2.8(−) | 270.2(+) |
| P61 | IIB | 1(−) | 29.5(−) |
| P62 | III | 32.2(+) | 1490(+) |
| P66 | IIB | 1.5(−) | 0.1(−) |
| P68 | III | 5.7(+) | 236.9(+) |
| P71 | IIB | 6.2(+) | 742(+) |
| P72 | IIB | 3.2(−) | 81.4(+) |
| P73 | IV | 4.4(−) | 970(+) |
| P75 | III | 1.4(−) | 580(+) |
| P76 | III | 59.9(+) | 1279(+) |
| P79 | IV | 2.6(−) | 1297(+) |
| P80 | IV | 8.4(+) | 0.9(−) |
| P81 | IV | 4.1(−) | 882(+) |
| P83 | IV | 8.6(+) | 2.2(−) |
| P84 | IV | 2(−) | 1375(+) |
| P86 | III | 4.3(−) | 17640(+) |
| P87 | III | 6.6(+) | 374.3(+) |
| P88 | IV | 147.4(+) | 2695(+) |
| P89 | IV | 2.9(−) | 2274(+) |
| P90 | IV | 7.4(+) | 1986(+) |
| P93 | IV | 17.8(+) | 2771(+) |
| P94 | III | 2(−) | 116.1(+) |
| P95 | III | 3.5(−) | 132.9(+) |
| P96 | IV | 1.2(−) | 2.3(−) |
| P97 | IV | 338.1(+) | 42990(+) |
| P98 | IV | 1.5(−) | 57500(+) |
| P99 | IV | 74.1(+) | 89700(+) |
| B38 | IIB | 0.9(−) | 19(−) |
| B87 | III | 5.7(+) | 0.1(−) |
| P101 | IV | 43.2(+) | 91500(+) |
| Sensitivity (%) | | 55.2 | 77.6 |

TABLE 5-2

| Validation cohort | | | |
|---|---|---|---|
| Sample name | Cancer stage | CEA(ng/mL) | CA19-9(U/mL) |
| P02 | IV | 1.5(−) | 569(+) |
| P03 | III | 4(−) | 1116(+) |
| P04 | IV | 4.6(−) | 5.8(−) |
| P08 | III | 3.3(−) | 81.4(+) |
| P15 | IV | 12.8(+) | 47.1(+) |
| P16 | IV | 5.1(+) | 181.4(+) |
| P20 | III | 0.9(−) | 13.6(−) |
| P22 | III | 0.7(−) | 31.4(−) |
| P23 | IV | 7.7(+) | 17080(+) |
| P24 | III | 1.7(−) | 72.9(+) |
| P28 | IV | 25.1(+) | 2995(+) |
| P30 | IV | 4.3(−) | 5.7(−) |
| P31 | IV | 2.9(−) | 3375(+) |
| P32 | III | 12.2(+) | 2955(+) |
| P34 | IIA | 1.3(−) | 66(+) |
| P36 | III | 2.7(−) | 32.2(−) |
| P37 | III | 2(−) | 858(+) |
| P40 | III | 65.6(+) | 9.6(−) |
| P41 | IV | 11.4(+) | 128080(+) |
| P45 | III | 2(−) | 410.8(+) |
| P51 | IV | 26.1(+) | 5880(+) |
| P58 | IV | 80.3(+) | 6510(+) |
| P63 | IIB | 4.4(−) | 5490(+) |
| P65 | IB | 7(+) | 55.3(+) |
| P67 | IIB | 2.5(−) | 28.7(−) |
| P69 | IIB | 4.2(−) | 832(+) |
| P70 | IIB | 1.6(−) | 71.3(+) |
| P74 | IIA | 3.2(−) | 36.8(−) |
| P77 | IV | 9.5(+) | 6110(+) |
| P78 | IV | 417(+) | 971000(+) |
| P82 | III | 6.7(+) | 3730(+) |
| P85 | IV | 5.4(+) | 6960(+) |
| P100 | IV | 240(+) | 68500(+) |
| Sensitivity (%) | | 45.5 | 75.8 |

For CEA, 5 ng/ml or lower was indicated as "−", and, for CA19-9, 37 U/ml or lower was indicated as "−", while values exceeding these were indicated as "+".

TABLE 6

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 2_105 | 96.4 | 94 | 98 | 100 | 100 | 100 |
| 18_105 | 98.8 | 97 | 100 | 100 | 100 | 100 |
| 46_105 | 97.6 | 95.5 | 99 | 100 | 100 | 100 |
| 55_105 | 98.2 | 97 | 99 | 100 | 100 | 100 |
| 58_105 | 98.2 | 95.5 | 100 | 100 | 100 | 100 |
| 66_105 | 96.4 | 92.5 | 99 | 100 | 100 | 100 |
| 71_105 | 98.2 | 97 | 99 | 100 | 100 | 100 |
| 77_105 | 98.8 | 97 | 100 | 100 | 100 | 100 |
| 83_105 | 97 | 95.5 | 98 | 100 | 100 | 100 |
| 99_105 | 97 | 94 | 99 | 100 | 100 | 100 |
| 10_18 | 96.4 | 91 | 100 | 100 | 100 | 100 |
| 52_105 | 96.4 | 94 | 98 | 98.8 | 100 | 98 |
| 18_109 | 97.6 | 95.5 | 99 | 98.8 | 100 | 98 |
| 18_25 | 88.6 | 79.1 | 95 | 97.6 | 100 | 96 |
| 25_112 | 89.2 | 80.6 | 95 | 97.6 | 100 | 96 |
| 8_109 | 95.8 | 94 | 97 | 96.4 | 100 | 94 |
| 25_58 | 87.4 | 74.6 | 96 | 95.2 | 100 | 92 |
| 5_105 | 98.2 | 97 | 99 | 98.8 | 97 | 100 |
| 8_105 | 97.6 | 95.5 | 99 | 98.8 | 97 | 100 |
| 13_105 | 98.2 | 95.5 | 100 | 98.8 | 97 | 100 |
| 35_105 | 97.6 | 95.5 | 99 | 98.8 | 97 | 100 |
| 70_105 | 97 | 94 | 99 | 98.8 | 97 | 100 |
| 74_105 | 97 | 95.5 | 98 | 98.8 | 97 | 100 |
| 79_105 | 97.6 | 95.5 | 99 | 98.8 | 97 | 100 |
| 89_105 | 97 | 94 | 99 | 98.8 | 97 | 100 |
| 93_105 | 97 | 94 | 99 | 98.8 | 97 | 100 |
| 96_105 | 97 | 94 | 99 | 98.8 | 97 | 100 |
| 97_105 | 97.6 | 94 | 100 | 98.8 | 97 | 100 |
| 18_107 | 97 | 94 | 99 | 98.8 | 97 | 100 |
| 18_108 | 97.6 | 94 | 100 | 98.8 | 97 | 100 |
| 6_18 | 97.6 | 95.5 | 99 | 98.8 | 97 | 100 |
| 4_105 | 97 | 94 | 99 | 97.6 | 97 | 98 |
| 14_105 | 97.6 | 95.5 | 99 | 97.6 | 97 | 98 |
| 21_105 | 97 | 94 | 99 | 97.6 | 97 | 98 |
| 39_105 | 98.2 | 97 | 99 | 97.6 | 97 | 98 |
| 56_105 | 97 | 95.5 | 98 | 97.6 | 97 | 98 |
| 68_105 | 97.6 | 95.5 | 99 | 97.6 | 97 | 98 |
| 94_105 | 97 | 94 | 99 | 97.6 | 97 | 98 |
| 2_16 | 92.2 | 83.6 | 98 | 97.6 | 97 | 98 |
| 4_119 | 88 | 80.6 | 93 | 97.6 | 97 | 98 |
| 12_108 | 93.4 | 89.4 | 96 | 97.6 | 97 | 98 |
| 83_108 | 92.2 | 83.6 | 98 | 97.6 | 97 | 98 |
| 5_33 | 93.4 | 89.6 | 96 | 97.6 | 97 | 98 |
| 13_22 | 91.6 | 88.1 | 94 | 97.6 | 97 | 98 |
| 22_105 | 97 | 94 | 99 | 96.4 | 97 | 96 |
| 2_10 | 92.2 | 83.6 | 98 | 96.4 | 97 | 96 |
| 2_22 | 90.4 | 82.1 | 96 | 96.4 | 97 | 96 |
| 34_108 | 95.2 | 89.6 | 99 | 96.4 | 97 | 96 |
| 4_45 | 89.8 | 83.6 | 94 | 95.2 | 97 | 94 |
| 37_108 | 91.6 | 86.6 | 95 | 95.2 | 97 | 94 |
| 12_109 | 93.4 | 90.9 | 95 | 95.2 | 97 | 94 |
| 13_24 | 91.6 | 92.5 | 91 | 95.2 | 97 | 94 |
| 18_70 | 88 | 77.6 | 95 | 95.2 | 97 | 94 |
| 25_83 | 83.8 | 74.6 | 90 | 95.2 | 97 | 94 |
| 35_113 | 88.6 | 76.1 | 97 | 95.2 | 97 | 94 |
| 35_87 | 80.8 | 73.1 | 86 | 95.2 | 97 | 94 |
| 2_109 | 91.6 | 83.6 | 97 | 94 | 97 | 92 |
| 93_108 | 86.8 | 79.1 | 92 | 94 | 97 | 92 |
| 24_71 | 80.2 | 70.1 | 87 | 94 | 97 | 92 |
| 24_35 | 84.4 | 73.1 | 92 | 92.8 | 97 | 90 |
| 4_98 | 86.7 | 75.8 | 94 | 91.6 | 97 | 88 |
| 13_25 | 91 | 89.6 | 92 | 91.6 | 97 | 88 |
| 35_44 | 83.8 | 73.1 | 91 | 91.6 | 97 | 88 |
| 35_99 | 77.2 | 65.7 | 85 | 91.6 | 97 | 88 |
| 4_58 | 88 | 77.6 | 95 | 90.4 | 97 | 86 |
| 25_35 | 82 | 68.7 | 91 | 89.2 | 97 | 84 |
| 35_63 | 80.8 | 71.6 | 87 | 89.2 | 97 | 84 |
| 35_97 | 79.6 | 68.7 | 87 | 89.2 | 97 | 84 |
| 35_66 | 81.4 | 67.2 | 91 | 88 | 97 | 82 |
| 35_121 | 81.4 | 67.2 | 91 | 88 | 97 | 82 |
| 35_94 | 77.8 | 61.2 | 89 | 86.7 | 97 | 80 |
| 66_109 | 88 | 80.6 | 93 | 85.5 | 97 | 78 |
| 66_100 | 80.2 | 64.2 | 91 | 85.5 | 97 | 78 |
| 50_105 | 97 | 95.5 | 98 | 98.8 | 96.9 | 100 |
| 23_105 | 97 | 94 | 99 | 97.6 | 96.9 | 98 |
| 35_50 | 80.2 | 67.2 | 89 | 89 | 96.9 | 84 |
| 1_77 | 95.8 | 91 | 99 | 96.3 | 96.8 | 96 |
| 6_105 | 96.4 | 94 | 98 | 97.6 | 93.9 | 100 |
| 7_105 | 97 | 94 | 99 | 97.6 | 93.9 | 100 |
| 12_105 | 97.6 | 97 | 98 | 97.6 | 93.9 | 100 |
| 15_105 | 96.4 | 94 | 98 | 97.6 | 93.9 | 100 |
| 17_105 | 97 | 94 | 99 | 97.6 | 93.9 | 100 |
| 20_105 | 97.6 | 97 | 98 | 97.6 | 93.9 | 100 |
| 25_105 | 96.4 | 94 | 98 | 97.6 | 93.9 | 100 |
| 26_105 | 97.6 | 97 | 98 | 97.6 | 93.9 | 100 |
| 27_105 | 97 | 94 | 99 | 97.6 | 93.9 | 100 |
| 31_105 | 96.4 | 92.5 | 99 | 97.6 | 93.9 | 100 |
| 33_105 | 97 | 94 | 99 | 97.6 | 93.9 | 100 |
| 34_105 | 95.8 | 92.5 | 98 | 97.6 | 93.9 | 100 |
| 40_105 | 96.4 | 94 | 98 | 97.6 | 93.9 | 100 |
| 49_105 | 97 | 97 | 97 | 97.6 | 93.9 | 100 |
| 57_105 | 97 | 94 | 99 | 97.6 | 93.9 | 100 |
| 67_105 | 96.4 | 94 | 98 | 97.6 | 93.9 | 100 |
| 81_105 | 97.6 | 95.5 | 99 | 97.6 | 93.9 | 100 |
| 88_105 | 97 | 94 | 99 | 97.6 | 93.9 | 100 |
| 90_105 | 97.6 | 95.5 | 99 | 97.6 | 93.9 | 100 |
| 98_105 | 96.4 | 93.9 | 98 | 97.6 | 93.9 | 100 |
| 1_119 | 97 | 95.5 | 98 | 97.6 | 93.9 | 100 |
| 2_108 | 95.2 | 88.1 | 100 | 97.6 | 93.9 | 100 |
| 2_13 | 91.6 | 82.1 | 98 | 97.6 | 93.9 | 100 |
| 2_18 | 91 | 77.6 | 100 | 97.6 | 93.9 | 100 |
| 2_34 | 90.4 | 79.1 | 98 | 97.6 | 93.9 | 100 |
| 2_35 | 88.6 | 74.6 | 98 | 97.6 | 93.9 | 100 |
| 2_37 | 89.8 | 77.6 | 98 | 97.6 | 93.9 | 100 |
| 2_52 | 89.8 | 77.6 | 98 | 97.6 | 93.9 | 100 |
| 2_58 | 89.2 | 76.1 | 98 | 97.6 | 93.9 | 100 |
| 2_62 | 91 | 80.6 | 98 | 97.6 | 93.9 | 100 |
| 2_65 | 89.8 | 79.1 | 97 | 97.6 | 93.9 | 100 |
| 2_71 | 89.2 | 76.1 | 98 | 97.6 | 93.9 | 100 |
| 2_119 | 90.4 | 80.6 | 97 | 97.6 | 93.9 | 100 |
| 2_120 | 88 | 76.1 | 96 | 97.6 | 93.9 | 100 |
| 2_121 | 88 | 74.6 | 97 | 97.6 | 93.9 | 100 |
| 2_94 | 88.6 | 76.1 | 97 | 97.6 | 93.9 | 100 |
| 2_98 | 89.2 | 77.3 | 97 | 97.6 | 93.9 | 100 |
| 2_99 | 88.6 | 74.6 | 98 | 97.6 | 93.9 | 100 |
| 4_13 | 95.2 | 89.6 | 99 | 97.6 | 93.9 | 100 |
| 58_108 | 95.2 | 88.1 | 100 | 97.6 | 93.9 | 100 |
| 6_8 | 94.6 | 91 | 97 | 97.6 | 93.9 | 100 |
| 9_105 | 97 | 94 | 99 | 96.4 | 93.9 | 98 |
| 24_105 | 97 | 94 | 99 | 96.4 | 93.9 | 98 |
| 28_105 | 97 | 94 | 99 | 96.4 | 93.9 | 98 |
| 29_105 | 97 | 94 | 99 | 96.4 | 93.9 | 98 |
| 36_105 | 97 | 94 | 99 | 96.4 | 93.9 | 98 |
| 37_105 | 97.6 | 95.5 | 99 | 96.4 | 93.9 | 98 |
| 38_105 | 97 | 94 | 99 | 96.4 | 93.9 | 98 |
| 43_105 | 97 | 95.5 | 98 | 96.4 | 93.9 | 98 |
| 45_105 | 97 | 94 | 99 | 96.4 | 93.9 | 98 |
| 47_105 | 96.4 | 94 | 98 | 96.4 | 93.9 | 98 |
| 62_105 | 96.4 | 94 | 98 | 96.4 | 93.9 | 98 |
| 65_105 | 97.6 | 95.5 | 99 | 96.4 | 93.9 | 98 |
| 80_105 | 97 | 94 | 99 | 96.4 | 93.9 | 98 |
| 82_105 | 97 | 94 | 99 | 96.4 | 93.9 | 98 |
| 84_105 | 97 | 94 | 99 | 96.4 | 93.9 | 98 |
| 85_105 | 96.4 | 94 | 98 | 96.4 | 93.9 | 98 |
| 86_105 | 97 | 94 | 99 | 96.4 | 93.9 | 98 |
| 92_105 | 95.8 | 92.5 | 98 | 96.4 | 93.9 | 98 |
| 102_105 | 97 | 94 | 99 | 96.4 | 93.9 | 98 |
| 1_20 | 95.2 | 92.5 | 97 | 96.4 | 93.9 | 98 |
| 2_6 | 93.4 | 88.1 | 97 | 96.4 | 93.9 | 98 |
| 2_112 | 87.4 | 74.6 | 96 | 96.4 | 93.9 | 98 |
| 2_45 | 90.4 | 79.1 | 98 | 96.4 | 93.9 | 98 |
| 2_80 | 88.6 | 74.6 | 98 | 96.4 | 93.9 | 98 |
| 2_81 | 88.6 | 75.8 | 97 | 96.4 | 93.9 | 98 |
| 2_88 | 90.4 | 79.1 | 98 | 96.4 | 93.9 | 98 |
| 13_107 | 96.4 | 91 | 100 | 96.4 | 93.9 | 98 |
| 4_18 | 89.8 | 77.6 | 98 | 96.4 | 93.9 | 98 |
| 5_19 | 92.2 | 85.1 | 97 | 96.4 | 93.9 | 98 |
| 7_34 | 91.6 | 83.6 | 97 | 96.4 | 93.9 | 98 |

TABLE 6-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 16_105 | 97.6 | 95.5 | 99 | 95.2 | 93.9 | 96 |
| 51_105 | 97 | 94 | 99 | 95.2 | 93.9 | 96 |
| 75_105 | 97.6 | 95.5 | 99 | 95.2 | 93.9 | 96 |
| 78_105 | 97 | 94 | 99 | 95.2 | 93.9 | 96 |
| 100_105 | 97.6 | 95.5 | 99 | 95.2 | 93.9 | 96 |
| 104_105 | 97 | 94 | 99 | 95.2 | 93.9 | 96 |
| 1_2 | 96.4 | 92.5 | 99 | 95.2 | 93.9 | 96 |
| 1_12 | 95.8 | 92.4 | 98 | 95.2 | 93.9 | 96 |
| 1_37 | 95.2 | 94 | 96 | 95.2 | 93.9 | 96 |
| 2_21 | 90.4 | 77.6 | 99 | 95.2 | 93.9 | 96 |
| 2_67 | 89.2 | 77.6 | 97 | 95.2 | 93.9 | 96 |
| 2_78 | 89.2 | 79.1 | 96 | 95.2 | 93.9 | 96 |
| 2_103 | 89.8 | 77.6 | 98 | 95.2 | 93.9 | 96 |
| 37_107 | 92.2 | 86.6 | 96 | 95.2 | 93.9 | 96 |
| 35_108 | 92.2 | 82.1 | 99 | 95.2 | 93.9 | 96 |
| 71_108 | 94.6 | 89.6 | 98 | 95.2 | 93.9 | 96 |
| 5_44 | 91 | 86.6 | 94 | 95.2 | 93.9 | 96 |
| 5_57 | 91.6 | 83.6 | 97 | 95.2 | 93.9 | 96 |
| 7_12 | 91.6 | 87.9 | 94 | 95.2 | 93.9 | 96 |
| 7_94 | 92.2 | 83.6 | 98 | 95.2 | 93.9 | 96 |
| 18_24 | 88.6 | 80.6 | 94 | 95.2 | 93.9 | 96 |
| 25_98 | 84.3 | 75.8 | 90 | 95.2 | 93.9 | 96 |
| 30_35 | 86.2 | 80.6 | 90 | 95.2 | 93.9 | 96 |
| 3_105 | 95.8 | 94 | 97 | 94 | 93.9 | 94 |
| 2_54 | 89.2 | 77.6 | 97 | 94 | 93.9 | 94 |
| 5_107 | 94 | 91 | 96 | 94 | 93.9 | 94 |
| 4_112 | 88.6 | 76.1 | 97 | 94 | 93.9 | 94 |
| 74_108 | 91.6 | 86.6 | 95 | 94 | 93.9 | 94 |
| 5_18 | 91 | 80.6 | 98 | 94 | 93.9 | 94 |
| 5_30 | 95.8 | 94 | 97 | 94 | 93.9 | 94 |
| 7_18 | 93.4 | 86.6 | 98 | 94 | 93.9 | 94 |
| 7_37 | 90.4 | 83.6 | 95 | 94 | 93.9 | 94 |
| 13_42 | 89.8 | 85.1 | 93 | 94 | 93.9 | 94 |
| 22_24 | 86.8 | 82.1 | 90 | 94 | 93.9 | 94 |
| 35_115 | 82.6 | 70.1 | 91 | 94 | 93.9 | 94 |
| 12_107 | 95.2 | 93.9 | 96 | 92.8 | 93.9 | 92 |
| 4_12 | 91 | 84.8 | 95 | 92.8 | 93.9 | 92 |
| 4_44 | 88 | 76.1 | 96 | 92.8 | 93.9 | 92 |
| 4_75 | 84.4 | 73.1 | 92 | 92.8 | 93.9 | 92 |
| 4_120 | 86.8 | 76.1 | 94 | 92.8 | 93.9 | 92 |
| 4_97 | 89.2 | 82.1 | 94 | 92.8 | 93.9 | 92 |
| 13_108 | 93.4 | 89.6 | 96 | 92.8 | 93.9 | 92 |
| 97_108 | 95.2 | 94 | 96 | 92.8 | 93.9 | 92 |
| 5_31 | 91.6 | 88.1 | 94 | 92.8 | 93.9 | 92 |
| 5_66 | 91 | 86.6 | 94 | 92.8 | 93.9 | 92 |
| 5_80 | 86.8 | 73.1 | 96 | 92.8 | 93.9 | 92 |
| 6_112 | 93.4 | 91 | 95 | 92.8 | 93.9 | 92 |
| 7_119 | 91.6 | 86.6 | 95 | 92.8 | 93.9 | 92 |
| 9_35 | 83.8 | 73.1 | 91 | 92.8 | 93.9 | 92 |
| 10_13 | 90.4 | 88.1 | 92 | 92.8 | 93.9 | 92 |
| 18_35 | 84.4 | 73.1 | 92 | 92.8 | 93.9 | 92 |
| 22_120 | 83.8 | 73.1 | 91 | 92.8 | 93.9 | 92 |
| 25_81 | 81.9 | 71.2 | 89 | 92.8 | 93.9 | 92 |
| 35_112 | 79 | 65.7 | 88 | 92.8 | 93.9 | 92 |
| 4_26 | 88.6 | 79.1 | 95 | 91.6 | 93.9 | 90 |
| 4_49 | 90.4 | 82.1 | 96 | 91.6 | 93.9 | 90 |
| 4_63 | 88.6 | 80.6 | 94 | 91.6 | 93.9 | 90 |
| 4_71 | 88.6 | 79.1 | 95 | 91.6 | 93.9 | 90 |
| 37_109 | 89.2 | 80.6 | 95 | 91.6 | 93.9 | 90 |
| 7_13 | 93.4 | 92.5 | 94 | 91.6 | 93.9 | 90 |
| 10_112 | 94 | 89.6 | 97 | 91.6 | 93.9 | 90 |
| 13_35 | 88.6 | 82.1 | 93 | 91.6 | 93.9 | 90 |
| 18_22 | 87.4 | 82.1 | 91 | 91.6 | 93.9 | 90 |
| 22_98 | 84.9 | 77.3 | 90 | 91.6 | 93.9 | 90 |
| 24_93 | 82 | 73.1 | 88 | 91.6 | 93.9 | 90 |
| 25_120 | 88.6 | 83.6 | 92 | 91.6 | 93.9 | 90 |
| 35_47 | 80.2 | 70.1 | 87 | 91.6 | 93.9 | 90 |
| 35_65 | 80.2 | 70.1 | 87 | 91.6 | 93.9 | 90 |
| 34_107 | 91.6 | 91 | 92 | 90.4 | 93.9 | 88 |
| 4_20 | 91 | 83.6 | 96 | 90.4 | 93.9 | 88 |
| 4_34 | 87.4 | 80.6 | 92 | 90.4 | 93.9 | 88 |
| 4_46 | 88 | 76.1 | 96 | 90.4 | 93.9 | 88 |
| 4_65 | 89.8 | 82.1 | 95 | 90.4 | 93.9 | 88 |
| 4_89 | 89.8 | 80.6 | 96 | 90.4 | 93.9 | 88 |
| 13_66 | 86.8 | 82.1 | 90 | 90.4 | 93.9 | 88 |
| 24_112 | 87.4 | 80.6 | 92 | 90.4 | 93.9 | 88 |
| 24_83 | 80.2 | 67.2 | 89 | 90.4 | 93.9 | 88 |
| 24_96 | 82.6 | 73.1 | 89 | 90.4 | 93.9 | 88 |
| 25_119 | 84.4 | 79.1 | 88 | 90.4 | 93.9 | 88 |
| 25_96 | 82.6 | 68.7 | 92 | 90.4 | 93.9 | 88 |
| 31_119 | 84.4 | 76.1 | 90 | 90.4 | 93.9 | 88 |
| 35_53 | 79.6 | 64.2 | 90 | 90.4 | 93.9 | 88 |
| 35_55 | 79.6 | 59.7 | 93 | 90.4 | 93.9 | 88 |
| 35_119 | 80.8 | 68.7 | 89 | 90.4 | 93.9 | 88 |
| 35_98 | 82.5 | 69.7 | 91 | 90.4 | 93.9 | 88 |
| 4_109 | 88 | 77.6 | 95 | 89.2 | 93.9 | 86 |
| 20_109 | 94.6 | 92.5 | 96 | 89.2 | 93.9 | 86 |
| 22_35 | 83.2 | 74.6 | 89 | 89.2 | 93.9 | 86 |
| 22_58 | 83.2 | 71.6 | 91 | 89.2 | 93.9 | 86 |
| 22_100 | 83.2 | 74.6 | 89 | 89.2 | 93.9 | 86 |
| 35_89 | 82.6 | 70.1 | 91 | 89.2 | 93.9 | 86 |
| 35_92 | 80.8 | 64.2 | 92 | 89.2 | 93.9 | 86 |
| 4_52 | 86.8 | 76.1 | 94 | 88 | 93.9 | 84 |
| 10_35 | 89.8 | 83.6 | 94 | 88 | 93.9 | 84 |
| 25_52 | 88 | 79.1 | 94 | 88 | 93.9 | 84 |
| 35_80 | 80.8 | 65.7 | 91 | 88 | 93.9 | 84 |
| 35_83 | 77.8 | 59.7 | 90 | 88 | 93.9 | 84 |
| 35_72 | 80.2 | 65.7 | 90 | 87.8 | 93.9 | 83.7 |
| 26_109 | 92.8 | 89.6 | 95 | 86.7 | 93.9 | 82 |
| 22_83 | 82 | 70.1 | 90 | 86.7 | 93.9 | 82 |
| 25_99 | 83.2 | 71.6 | 91 | 86.7 | 93.9 | 82 |
| 35_79 | 79 | 64.2 | 89 | 86.7 | 93.9 | 82 |
| 10_52 | 90.4 | 86.6 | 93 | 85.5 | 93.9 | 80 |
| 25_79 | 81.4 | 68.7 | 90 | 85.5 | 93.9 | 80 |
| 1_23 | 97 | 95.5 | 98 | 96.3 | 93.8 | 98 |
| 4_50 | 86.2 | 73.1 | 95 | 90.2 | 93.8 | 88 |
| 3_77 | 92.2 | 83.6 | 98 | 95.1 | 93.5 | 96 |
| 11_105 | 97 | 94 | 99 | 96.4 | 90.9 | 100 |
| 19_105 | 95.8 | 94 | 97 | 96.4 | 90.9 | 100 |
| 30_105 | 97.6 | 95.5 | 99 | 96.4 | 90.9 | 100 |
| 41_105 | 96.4 | 94 | 98 | 96.4 | 90.9 | 100 |
| 44_105 | 97 | 94 | 99 | 96.4 | 90.9 | 100 |
| 48_105 | 97 | 94 | 99 | 96.4 | 90.9 | 100 |
| 60_105 | 97 | 94 | 99 | 96.4 | 90.9 | 100 |
| 73_105 | 96.4 | 94 | 98 | 96.4 | 90.9 | 100 |
| 87_105 | 97 | 94 | 99 | 96.4 | 90.9 | 100 |
| 1_13 | 97 | 94 | 99 | 96.4 | 90.9 | 100 |
| 1_61 | 97 | 95.5 | 98 | 96.4 | 90.9 | 100 |
| 2_7 | 92.8 | 83.6 | 99 | 96.4 | 90.9 | 100 |
| 2_15 | 94 | 86.6 | 99 | 96.4 | 90.9 | 100 |
| 2_19 | 92.2 | 83.6 | 98 | 96.4 | 90.9 | 100 |
| 2_24 | 91 | 82.1 | 97 | 96.4 | 90.9 | 100 |
| 2_25 | 90.4 | 80.6 | 97 | 96.4 | 90.9 | 100 |
| 2_30 | 90.4 | 82.1 | 96 | 96.4 | 90.9 | 100 |
| 2_44 | 89.8 | 79.1 | 97 | 96.4 | 90.9 | 100 |
| 2_46 | 88.6 | 74.6 | 98 | 96.4 | 90.9 | 100 |
| 2_53 | 91.6 | 80.6 | 99 | 96.4 | 90.9 | 100 |
| 2_55 | 88.6 | 74.6 | 98 | 96.4 | 90.9 | 100 |
| 2_63 | 91 | 80.6 | 98 | 96.4 | 90.9 | 100 |
| 2_66 | 88.6 | 74.6 | 98 | 96.4 | 90.9 | 100 |
| 2_70 | 88.6 | 74.6 | 98 | 96.4 | 90.9 | 100 |
| 2_73 | 90.4 | 80.6 | 97 | 96.4 | 90.9 | 100 |
| 2_74 | 89.2 | 77.6 | 97 | 96.4 | 90.9 | 100 |
| 2_118 | 89.2 | 77.6 | 97 | 96.4 | 90.9 | 100 |
| 2_85 | 88 | 74.6 | 97 | 96.4 | 90.9 | 100 |
| 2_87 | 89.8 | 80.6 | 96 | 96.4 | 90.9 | 100 |
| 2_89 | 89.8 | 77.6 | 98 | 96.4 | 90.9 | 100 |
| 2_90 | 89.2 | 76.1 | 98 | 96.4 | 90.9 | 100 |
| 2_92 | 88.6 | 74.6 | 98 | 96.4 | 90.9 | 100 |
| 2_93 | 88.6 | 74.6 | 98 | 96.4 | 90.9 | 100 |
| 2_96 | 88.6 | 76.1 | 97 | 96.4 | 90.9 | 100 |
| 2_100 | 88 | 74.6 | 97 | 96.4 | 90.9 | 100 |
| 32_105 | 95.8 | 92.5 | 98 | 95.2 | 90.9 | 98 |
| 42_105 | 97 | 94 | 99 | 95.2 | 90.9 | 98 |
| 53_105 | 96.4 | 94 | 98 | 95.2 | 90.9 | 98 |
| 54_105 | 96.4 | 94 | 98 | 95.2 | 90.9 | 98 |
| 63_105 | 97 | 94 | 99 | 95.2 | 90.9 | 98 |
| 64_105 | 96.4 | 94 | 98 | 95.2 | 90.9 | 98 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 69_105 | 97 | 94 | 99 | 95.2 | 90.9 | 98 |
| 76_105 | 97 | 94 | 99 | 95.2 | 90.9 | 98 |
| 91_105 | 97 | 94 | 99 | 95.2 | 90.9 | 98 |
| 103_105 | 97 | 94 | 99 | 95.2 | 90.9 | 98 |
| 1_108 | 97 | 95.5 | 98 | 95.2 | 90.9 | 98 |
| 1_18 | 97 | 92.5 | 100 | 95.2 | 90.9 | 98 |
| 1_30 | 95.2 | 91 | 98 | 95.2 | 90.9 | 98 |
| 1_36 | 96.4 | 94 | 98 | 95.2 | 90.9 | 98 |
| 1_120 | 96.4 | 94 | 98 | 95.2 | 90.9 | 98 |
| 2_5 | 91 | 80.6 | 98 | 95.2 | 90.9 | 98 |
| 2_14 | 92.8 | 83.6 | 99 | 95.2 | 90.9 | 98 |
| 2_28 | 93.4 | 85.1 | 99 | 95.2 | 90.9 | 98 |
| 2_41 | 91 | 82.1 | 97 | 95.2 | 90.9 | 98 |
| 2_116 | 89.2 | 77.6 | 97 | 95.2 | 90.9 | 98 |
| 2_117 | 89.2 | 77.6 | 97 | 95.2 | 90.9 | 98 |
| 2_82 | 90.4 | 77.6 | 99 | 95.2 | 90.9 | 98 |
| 2_84 | 91 | 80.6 | 98 | 95.2 | 90.9 | 98 |
| 2_104 | 91 | 80.6 | 98 | 95.2 | 90.9 | 98 |
| 4_30 | 88.6 | 77.6 | 96 | 95.2 | 90.9 | 98 |
| 4_87 | 91 | 79.1 | 99 | 95.2 | 90.9 | 98 |
| 8_108 | 96.4 | 92.5 | 99 | 95.2 | 90.9 | 98 |
| 98_108 | 95.2 | 87.9 | 100 | 95.2 | 90.9 | 98 |
| 5_13 | 92.2 | 86.6 | 96 | 95.2 | 90.9 | 98 |
| 7_52 | 91 | 82.1 | 97 | 95.2 | 90.9 | 98 |
| 8_10 | 94.6 | 89.6 | 98 | 95.2 | 90.9 | 98 |
| 18_110 | 95.8 | 94 | 97 | 95.2 | 90.9 | 98 |
| 18_111 | 89.2 | 79.1 | 96 | 95.2 | 90.9 | 98 |
| 19_35 | 86.8 | 77.6 | 93 | 95.2 | 90.9 | 98 |
| 19_58 | 89.8 | 83.6 | 94 | 95.2 | 90.9 | 98 |
| 72_105 | 96.4 | 94 | 98 | 95.1 | 90.9 | 98 |
| 1_4 | 95.8 | 94 | 97 | 94 | 90.9 | 96 |
| 1_8 | 96.4 | 94 | 98 | 94 | 90.9 | 96 |
| 1_110 | 96.4 | 94 | 98 | 94 | 90.9 | 96 |
| 1_14 | 97 | 94 | 99 | 94 | 90.9 | 96 |
| 1_22 | 95.8 | 95.5 | 96 | 94 | 90.9 | 96 |
| 1_25 | 95.8 | 94 | 97 | 94 | 90.9 | 96 |
| 1_26 | 94.6 | 91 | 97 | 94 | 90.9 | 96 |
| 1_35 | 97 | 95.5 | 98 | 94 | 90.9 | 96 |
| 1_40 | 96.4 | 94 | 98 | 94 | 90.9 | 96 |
| 1_112 | 95.8 | 91 | 99 | 94 | 90.9 | 96 |
| 1_43 | 95.2 | 91 | 98 | 94 | 90.9 | 96 |
| 1_49 | 95.8 | 92.5 | 98 | 94 | 90.9 | 96 |
| 1_113 | 95.8 | 92.5 | 98 | 94 | 90.9 | 96 |
| 1_52 | 97 | 94 | 99 | 94 | 90.9 | 96 |
| 1_55 | 96.4 | 94 | 98 | 94 | 90.9 | 96 |
| 1_56 | 96.4 | 95.5 | 97 | 94 | 90.9 | 96 |
| 1_58 | 95.8 | 92.5 | 98 | 94 | 90.9 | 96 |
| 1_65 | 96.4 | 94 | 98 | 94 | 90.9 | 96 |
| 1_66 | 94.6 | 91 | 97 | 94 | 90.9 | 96 |
| 1_69 | 97 | 94 | 99 | 94 | 90.9 | 96 |
| 1_71 | 98.2 | 98.5 | 98 | 94 | 90.9 | 96 |
| 1_74 | 95.8 | 92.5 | 98 | 94 | 90.9 | 96 |
| 1_79 | 96.4 | 95.5 | 97 | 94 | 90.9 | 96 |
| 1_81 | 97 | 93.9 | 99 | 94 | 90.9 | 96 |
| 1_83 | 96.4 | 94 | 98 | 94 | 90.9 | 96 |
| 1_99 | 97 | 94 | 99 | 94 | 90.9 | 96 |
| 1_102 | 97 | 95.5 | 98 | 94 | 90.9 | 96 |
| 8_106 | 94.6 | 88.1 | 99 | 94 | 90.9 | 96 |
| 2_107 | 93.4 | 86.6 | 98 | 94 | 90.9 | 96 |
| 2_4 | 89.2 | 79.1 | 96 | 94 | 90.9 | 96 |
| 2_9 | 92.8 | 85.1 | 98 | 94 | 90.9 | 96 |
| 2_12 | 91.6 | 81.8 | 98 | 94 | 90.9 | 96 |
| 2_111 | 92.2 | 83.6 | 98 | 94 | 90.9 | 96 |
| 2_39 | 88.6 | 74.6 | 98 | 94 | 90.9 | 96 |
| 2_114 | 89.2 | 74.6 | 99 | 94 | 90.9 | 96 |
| 2_69 | 90.4 | 80.6 | 97 | 94 | 90.9 | 96 |
| 2_95 | 89.2 | 77.6 | 97 | 94 | 90.9 | 96 |
| 4_7 | 92.2 | 83.6 | 98 | 94 | 90.9 | 96 |
| 4_41 | 88 | 77.6 | 95 | 94 | 90.9 | 96 |
| 5_108 | 95.2 | 91 | 98 | 94 | 90.9 | 96 |
| 21_108 | 92.2 | 85.1 | 97 | 94 | 90.9 | 96 |
| 49_108 | 92.8 | 86.6 | 97 | 94 | 90.9 | 96 |
| 65_108 | 91.6 | 88.1 | 94 | 94 | 90.9 | 96 |
| 96_108 | 93.4 | 88.1 | 97 | 94 | 90.9 | 96 |
| 99_108 | 94 | 86.6 | 99 | 94 | 90.9 | 96 |
| 13_109 | 94.6 | 89.6 | 98 | 94 | 90.9 | 96 |
| 7_67 | 91 | 83.6 | 96 | 94 | 90.9 | 96 |
| 7_70 | 92.8 | 86.6 | 97 | 94 | 90.9 | 96 |
| 9_119 | 87.4 | 83.6 | 90 | 94 | 90.9 | 96 |
| 10_12 | 91.6 | 89.4 | 93 | 94 | 90.9 | 96 |
| 13_16 | 94.6 | 98.5 | 92 | 94 | 90.9 | 96 |
| 14_18 | 94 | 88.1 | 98 | 94 | 90.9 | 96 |
| 35_41 | 83.2 | 73.1 | 90 | 94 | 90.9 | 96 |
| 66_85 | 83.2 | 68.7 | 93 | 94 | 90.9 | 96 |
| 1_21 | 96.4 | 95.5 | 97 | 92.8 | 90.9 | 94 |
| 1_29 | 96.4 | 94 | 98 | 92.8 | 90.9 | 94 |
| 1_39 | 97.6 | 97 | 98 | 92.8 | 90.9 | 94 |
| 1_70 | 97 | 94 | 99 | 92.8 | 90.9 | 94 |
| 1_75 | 97 | 94 | 99 | 92.8 | 90.9 | 94 |
| 4_107 | 90.4 | 85.1 | 94 | 92.8 | 90.9 | 94 |
| 14_107 | 92.2 | 80.6 | 100 | 92.8 | 90.9 | 94 |
| 58_107 | 92.8 | 88.1 | 96 | 92.8 | 90.9 | 94 |
| 66_107 | 90.4 | 80.6 | 97 | 92.8 | 90.9 | 94 |
| 94_107 | 90.4 | 83.6 | 95 | 92.8 | 90.9 | 94 |
| 99_107 | 89.8 | 80.6 | 96 | 92.8 | 90.9 | 94 |
| 3_119 | 91 | 89.6 | 92 | 92.8 | 90.9 | 94 |
| 4_14 | 90.4 | 82.1 | 96 | 92.8 | 90.9 | 94 |
| 4_113 | 90.4 | 80.6 | 97 | 92.8 | 90.9 | 94 |
| 4_115 | 89.8 | 79.1 | 97 | 92.8 | 90.9 | 94 |
| 43_108 | 93.4 | 91 | 95 | 92.8 | 90.9 | 94 |
| 5_7 | 95.2 | 94 | 96 | 92.8 | 90.9 | 94 |
| 5_12 | 91.6 | 84.8 | 96 | 92.8 | 90.9 | 94 |
| 5_24 | 93.4 | 91 | 95 | 92.8 | 90.9 | 94 |
| 5_112 | 87.4 | 79.1 | 93 | 92.8 | 90.9 | 94 |
| 5_89 | 90.4 | 83.6 | 95 | 92.8 | 90.9 | 94 |
| 7_9 | 90.4 | 89.6 | 91 | 92.8 | 90.9 | 94 |
| 7_16 | 90.4 | 88.1 | 92 | 92.8 | 90.9 | 94 |
| 7_22 | 91 | 83.6 | 96 | 92.8 | 90.9 | 94 |
| 7_51 | 91 | 85.1 | 95 | 92.8 | 90.9 | 94 |
| 7_62 | 91.6 | 85.1 | 96 | 92.8 | 90.9 | 94 |
| 7_114 | 89.8 | 83.6 | 94 | 92.8 | 90.9 | 94 |
| 7_80 | 92.2 | 85.1 | 97 | 92.8 | 90.9 | 94 |
| 7_83 | 91 | 80.6 | 98 | 92.8 | 90.9 | 94 |
| 7_103 | 91.6 | 86.6 | 95 | 92.8 | 90.9 | 94 |
| 10_20 | 89.8 | 85.1 | 93 | 92.8 | 90.9 | 94 |
| 10_58 | 94.6 | 91 | 97 | 92.8 | 90.9 | 94 |
| 13_27 | 91 | 86.6 | 94 | 92.8 | 90.9 | 94 |
| 18_30 | 86.8 | 80.6 | 91 | 92.8 | 90.9 | 94 |
| 18_41 | 85 | 77.6 | 90 | 92.8 | 90.9 | 94 |
| 18_66 | 85 | 74.6 | 92 | 92.8 | 90.9 | 94 |
| 22_85 | 86.2 | 77.6 | 92 | 92.8 | 90.9 | 94 |
| 24_37 | 85 | 74.6 | 92 | 92.8 | 90.9 | 94 |
| 24_119 | 82.6 | 76.1 | 87 | 92.8 | 90.9 | 94 |
| 25_39 | 86.2 | 74.6 | 94 | 92.8 | 90.9 | 94 |
| 25_45 | 88.6 | 76.1 | 97 | 92.8 | 90.9 | 94 |
| 25_46 | 85 | 73.1 | 93 | 92.8 | 90.9 | 94 |
| 1_121 | 98.2 | 97 | 99 | 91.6 | 90.9 | 92 |
| 20_107 | 95.2 | 92.5 | 97 | 91.6 | 90.9 | 92 |
| 26_107 | 95.8 | 94 | 97 | 91.6 | 90.9 | 92 |
| 49_107 | 94 | 91 | 96 | 91.6 | 90.9 | 92 |
| 3_58 | 94.6 | 91 | 97 | 91.6 | 90.9 | 92 |
| 4_5 | 91 | 83.6 | 96 | 91.6 | 90.9 | 92 |
| 4_6 | 90.4 | 80.6 | 97 | 91.6 | 90.9 | 92 |
| 4_10 | 91.6 | 86.6 | 95 | 91.6 | 90.9 | 92 |
| 4_24 | 87.4 | 76.1 | 95 | 91.6 | 90.9 | 92 |
| 4_48 | 89.2 | 79.1 | 96 | 91.6 | 90.9 | 92 |
| 4_55 | 88.6 | 79.1 | 95 | 91.6 | 90.9 | 92 |
| 4_88 | 86.2 | 77.6 | 92 | 91.6 | 90.9 | 92 |
| 4_102 | 89.2 | 80.6 | 95 | 91.6 | 90.9 | 92 |
| 55_108 | 91.6 | 83.6 | 97 | 91.6 | 90.9 | 92 |
| 5_25 | 91 | 86.6 | 94 | 91.6 | 90.9 | 92 |
| 5_42 | 91.6 | 86.6 | 95 | 91.6 | 90.9 | 92 |
| 5_56 | 91.6 | 88.1 | 94 | 91.6 | 90.9 | 92 |
| 7_21 | 90.4 | 85.1 | 94 | 91.6 | 90.9 | 92 |
| 7_35 | 89.8 | 79.1 | 97 | 91.6 | 90.9 | 92 |
| 7_112 | 93.4 | 86.6 | 98 | 91.6 | 90.9 | 92 |
| 7_65 | 91 | 86.6 | 94 | 91.6 | 90.9 | 92 |
| 7_66 | 91 | 85.1 | 95 | 91.6 | 90.9 | 92 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 7_79 | 89.8 | 83.6 | 94 | 91.6 | 90.9 | 92 |
| 7_120 | 91 | 83.6 | 96 | 91.6 | 90.9 | 92 |
| 7_87 | 91.6 | 85.1 | 96 | 91.6 | 90.9 | 92 |
| 7_88 | 90.4 | 86.6 | 93 | 91.6 | 90.9 | 92 |
| 7_104 | 91 | 86.6 | 94 | 91.6 | 90.9 | 92 |
| 10_120 | 91.6 | 85.1 | 96 | 91.6 | 90.9 | 92 |
| 13_21 | 89.8 | 86.6 | 92 | 91.6 | 90.9 | 92 |
| 18_46 | 83.2 | 74.6 | 89 | 91.6 | 90.9 | 92 |
| 22_96 | 80.8 | 70.1 | 88 | 91.6 | 90.9 | 92 |
| 24_79 | 82 | 68.7 | 91 | 91.6 | 90.9 | 92 |
| 25_94 | 82.6 | 68.7 | 92 | 91.6 | 90.9 | 92 |
| 35_90 | 79.6 | 65.7 | 89 | 91.6 | 90.9 | 92 |
| 54_107 | 92.2 | 88.1 | 95 | 90.4 | 90.9 | 90 |
| 3_21 | 91 | 88.1 | 93 | 90.4 | 90.9 | 90 |
| 3_35 | 94.6 | 95.5 | 94 | 90.4 | 90.9 | 90 |
| 4_9 | 88 | 77.6 | 95 | 90.4 | 90.9 | 90 |
| 4_37 | 85.6 | 74.6 | 93 | 90.4 | 90.9 | 90 |
| 4_43 | 86.8 | 74.6 | 95 | 90.4 | 90.9 | 90 |
| 4_47 | 89.2 | 79.1 | 96 | 90.4 | 90.9 | 90 |
| 4_56 | 88.6 | 79.1 | 95 | 90.4 | 90.9 | 90 |
| 4_74 | 86.8 | 74.6 | 95 | 90.4 | 90.9 | 90 |
| 47_108 | 91.6 | 83.6 | 97 | 90.4 | 90.9 | 90 |
| 94_108 | 91.6 | 82.1 | 98 | 90.4 | 90.9 | 90 |
| 5_11 | 91.6 | 86.6 | 95 | 90.4 | 90.9 | 90 |
| 5_21 | 91.6 | 85.1 | 96 | 90.4 | 90.9 | 90 |
| 5_75 | 88.6 | 83.6 | 92 | 90.4 | 90.9 | 90 |
| 7_109 | 93.4 | 86.6 | 98 | 90.4 | 90.9 | 90 |
| 7_44 | 92.2 | 85.1 | 97 | 90.4 | 90.9 | 90 |
| 7_58 | 89.8 | 77.6 | 98 | 90.4 | 90.9 | 90 |
| 7_71 | 89.2 | 82.1 | 94 | 90.4 | 90.9 | 90 |
| 7_121 | 91 | 88.1 | 93 | 90.4 | 90.9 | 90 |
| 7_99 | 88.6 | 80.6 | 94 | 90.4 | 90.9 | 90 |
| 9_24 | 89.2 | 83.6 | 93 | 90.4 | 90.9 | 90 |
| 9_58 | 88 | 80.6 | 93 | 90.4 | 90.9 | 90 |
| 10_34 | 91.6 | 88.1 | 94 | 90.4 | 90.9 | 90 |
| 10_119 | 91 | 88.1 | 93 | 90.4 | 90.9 | 90 |
| 18_67 | 88.6 | 80.6 | 94 | 90.4 | 90.9 | 90 |
| 18_79 | 85.6 | 76.1 | 92 | 90.4 | 90.9 | 90 |
| 21_25 | 84.4 | 73.1 | 92 | 90.4 | 90.9 | 90 |
| 22_46 | 83.2 | 73.1 | 90 | 90.4 | 90.9 | 90 |
| 22_88 | 83.8 | 77.6 | 88 | 90.4 | 90.9 | 90 |
| 24_55 | 85 | 70.1 | 95 | 90.4 | 90.9 | 90 |
| 24_80 | 77.8 | 64.2 | 87 | 90.4 | 90.9 | 90 |
| 24_81 | 84.9 | 77.3 | 90 | 90.4 | 90.9 | 90 |
| 24_90 | 83.2 | 71.6 | 91 | 90.4 | 90.9 | 90 |
| 25_34 | 89.8 | 80.6 | 96 | 90.4 | 90.9 | 90 |
| 35_37 | 79 | 68.7 | 86 | 90.4 | 90.9 | 90 |
| 66_98 | 79.5 | 63.6 | 90 | 90.4 | 90.9 | 90 |
| 52_107 | 92.2 | 89.6 | 94 | 89.2 | 90.9 | 88 |
| 4_25 | 88 | 79.1 | 94 | 89.2 | 90.9 | 88 |
| 4_80 | 86.8 | 74.6 | 95 | 89.2 | 90.9 | 88 |
| 4_81 | 86.7 | 75.8 | 94 | 89.2 | 90.9 | 88 |
| 4_82 | 86.8 | 74.6 | 95 | 89.2 | 90.9 | 88 |
| 4_83 | 86.8 | 74.6 | 95 | 89.2 | 90.9 | 88 |
| 4_85 | 88 | 76.1 | 96 | 89.2 | 90.9 | 88 |
| 4_90 | 87.4 | 76.1 | 95 | 89.2 | 90.9 | 88 |
| 4_91 | 85.6 | 73.1 | 94 | 89.2 | 90.9 | 88 |
| 4_94 | 87.4 | 74.6 | 96 | 89.2 | 90.9 | 88 |
| 49_109 | 89.8 | 89.6 | 90 | 89.2 | 90.9 | 88 |
| 10_81 | 89.2 | 81.8 | 94 | 89.2 | 90.9 | 88 |
| 10_83 | 89.2 | 82.1 | 94 | 89.2 | 90.9 | 88 |
| 10_121 | 89.2 | 83.6 | 93 | 89.2 | 90.9 | 88 |
| 22_80 | 83.2 | 74.6 | 89 | 89.2 | 90.9 | 88 |
| 24_31 | 83.2 | 68.7 | 93 | 89.2 | 90.9 | 88 |
| 24_118 | 83.2 | 74.6 | 89 | 89.2 | 90.9 | 88 |
| 25_66 | 80.8 | 67.2 | 90 | 89.2 | 90.9 | 88 |
| 25_70 | 82.6 | 68.7 | 92 | 89.2 | 90.9 | 88 |
| 25_75 | 82.6 | 73.1 | 89 | 89.2 | 90.9 | 88 |
| 25_80 | 84.4 | 73.1 | 92 | 89.2 | 90.9 | 88 |
| 28_35 | 82 | 71.6 | 89 | 89.2 | 90.9 | 88 |
| 4_11 | 86.8 | 79.1 | 92 | 88 | 90.9 | 86 |
| 4_16 | 88 | 77.6 | 95 | 88 | 90.9 | 86 |
| 4_21 | 87.4 | 76.1 | 95 | 88 | 90.9 | 86 |
| 4_39 | 89.2 | 79.1 | 96 | 88 | 90.9 | 86 |
| 4_76 | 86.8 | 73.1 | 96 | 88 | 90.9 | 86 |
| 4_92 | 85.6 | 73.1 | 94 | 88 | 90.9 | 86 |
| 4_96 | 88 | 76.1 | 96 | 88 | 90.9 | 86 |
| 4_99 | 85.6 | 71.6 | 95 | 88 | 90.9 | 86 |
| 9_109 | 88.6 | 79.1 | 95 | 88 | 90.9 | 86 |
| 54_109 | 88 | 83.6 | 91 | 88 | 90.9 | 86 |
| 9_46 | 88 | 85.1 | 90 | 88 | 90.9 | 86 |
| 13_67 | 83.2 | 74.6 | 89 | 88 | 90.9 | 86 |
| 13_79 | 84.4 | 82.1 | 86 | 88 | 90.9 | 86 |
| 16_83 | 83.8 | 82.1 | 85 | 88 | 90.9 | 86 |
| 22_55 | 81.4 | 73.1 | 87 | 88 | 90.9 | 86 |
| 24_121 | 83.2 | 73.1 | 90 | 88 | 90.9 | 86 |
| 25_92 | 82.6 | 71.6 | 90 | 88 | 90.9 | 86 |
| 35_71 | 78.4 | 62.7 | 89 | 88 | 90.9 | 86 |
| 35_93 | 77.8 | 61.2 | 89 | 88 | 90.9 | 86 |
| 4_84 | 87.4 | 79.1 | 93 | 86.7 | 90.9 | 84 |
| 4_121 | 86.8 | 76.1 | 94 | 86.7 | 90.9 | 84 |
| 81_109 | 84.9 | 80.3 | 88 | 86.7 | 90.9 | 84 |
| 21_35 | 80.8 | 70.1 | 88 | 86.7 | 90.9 | 84 |
| 21_75 | 80.2 | 70.1 | 87 | 86.7 | 90.9 | 84 |
| 21_83 | 80.8 | 74.6 | 85 | 86.7 | 90.9 | 84 |
| 21_89 | 79 | 70.1 | 85 | 86.7 | 90.9 | 84 |
| 21_97 | 81.4 | 71.6 | 88 | 86.7 | 90.9 | 84 |
| 22_66 | 77.2 | 67.2 | 84 | 86.7 | 90.9 | 84 |
| 22_119 | 83.8 | 80.6 | 86 | 86.7 | 90.9 | 84 |
| 24_58 | 81.4 | 71.6 | 88 | 86.7 | 90.9 | 84 |
| 24_120 | 83.2 | 76.1 | 88 | 86.7 | 90.9 | 84 |
| 31_112 | 82.6 | 73.1 | 89 | 86.7 | 90.9 | 84 |
| 35_118 | 81.4 | 67.2 | 91 | 86.7 | 90.9 | 84 |
| 35_120 | 79 | 64.2 | 89 | 86.7 | 90.9 | 84 |
| 35_96 | 78.4 | 62.7 | 89 | 86.7 | 90.9 | 84 |
| 66_70 | 81.4 | 68.7 | 90 | 86.7 | 90.9 | 84 |
| 66_119 | 79 | 70.1 | 85 | 86.7 | 90.9 | 84 |
| 21_109 | 91 | 85.1 | 95 | 85.5 | 90.9 | 82 |
| 21_55 | 79.6 | 65.7 | 89 | 85.5 | 90.9 | 82 |
| 21_56 | 80.8 | 68.7 | 89 | 85.5 | 90.9 | 82 |
| 22_78 | 78.4 | 68.7 | 85 | 85.5 | 90.9 | 82 |
| 35_42 | 82.6 | 65.7 | 94 | 85.5 | 90.9 | 82 |
| 35_81 | 77.1 | 63.6 | 86 | 85.5 | 90.9 | 82 |
| 35_82 | 77.2 | 62.7 | 87 | 85.5 | 90.9 | 82 |
| 35_100 | 77.8 | 64.2 | 87 | 85.5 | 90.9 | 82 |
| 35_103 | 80.8 | 65.7 | 91 | 85.5 | 90.9 | 82 |
| 39_109 | 84.4 | 76.1 | 90 | 84.3 | 90.9 | 80 |
| 31_58 | 82.6 | 73.1 | 89 | 84.3 | 90.9 | 80 |
| 35_75 | 77.8 | 59.7 | 90 | 84.3 | 90.9 | 80 |
| 9_100 | 88.6 | 91 | 87 | 83.1 | 90.9 | 78 |
| 10_94 | 85 | 79.1 | 89 | 83.1 | 90.9 | 78 |
| 21_71 | 80.8 | 71.6 | 87 | 83.1 | 90.9 | 78 |
| 79_109 | 85 | 73.1 | 93 | 81.9 | 90.9 | 76 |
| 99_109 | 85.6 | 80.6 | 89 | 81.9 | 90.9 | 76 |
| 31_109 | 85 | 73.1 | 93 | 80.7 | 90.9 | 74 |
| 2_50 | 91 | 79.1 | 99 | 96.3 | 90.6 | 100 |
| 1_50 | 96.4 | 94 | 98 | 93.9 | 90.6 | 96 |
| 7_50 | 91 | 83.6 | 96 | 93.9 | 90.6 | 96 |
| 2_23 | 91.6 | 82.1 | 98 | 92.7 | 90.6 | 94 |
| 18_23 | 89.8 | 82.1 | 95 | 92.7 | 90.6 | 94 |
| 5_50 | 91 | 83.6 | 96 | 91.5 | 90.6 | 92 |
| 24_50 | 81.4 | 74.6 | 86 | 91.5 | 90.6 | 92 |
| 4_23 | 86.8 | 74.6 | 95 | 87.8 | 90.6 | 86 |
| 22_50 | 83.2 | 76.1 | 88 | 87.8 | 90.6 | 86 |
| 50_109 | 88 | 82.1 | 92 | 80.5 | 90.6 | 74 |
| 2_77 | 88.6 | 74.6 | 98 | 96.3 | 90.3 | 100 |
| 7_77 | 88.6 | 82.1 | 93 | 95.1 | 90.3 | 98 |
| 4_77 | 88 | 76.1 | 96 | 92.6 | 90.3 | 94 |
| 21_77 | 80.8 | 76.1 | 84 | 87.7 | 90.3 | 86 |
| 1_105 | 97 | 94 | 99 | 95.2 | 87.9 | 100 |
| 61_105 | 97 | 94 | 99 | 95.2 | 87.9 | 100 |
| 1_19 | 95.2 | 91 | 98 | 95.2 | 87.9 | 100 |
| 1_87 | 98.2 | 97 | 99 | 95.2 | 87.9 | 100 |
| 13_106 | 94 | 85.1 | 100 | 95.2 | 87.9 | 100 |
| 2_11 | 91 | 82.1 | 97 | 95.2 | 87.9 | 100 |
| 2_17 | 92.2 | 83.6 | 98 | 95.2 | 87.9 | 100 |
| 2_29 | 91.6 | 82.1 | 98 | 95.2 | 87.9 | 100 |
| 2_33 | 92.8 | 85.1 | 98 | 95.2 | 87.9 | 100 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 2_38 | 92.8 | 85.1 | 98 | 95.2 | 87.9 | 100 |
| 2_47 | 88.6 | 76.1 | 97 | 95.2 | 87.9 | 100 |
| 2_49 | 88.6 | 77.6 | 96 | 95.2 | 87.9 | 100 |
| 2_113 | 91.6 | 82.1 | 98 | 95.2 | 87.9 | 100 |
| 2_56 | 91 | 82.1 | 97 | 95.2 | 87.9 | 100 |
| 2_57 | 88.6 | 76.1 | 97 | 95.2 | 87.9 | 100 |
| 2_60 | 90.4 | 80.6 | 97 | 95.2 | 87.9 | 100 |
| 2_64 | 91 | 80.6 | 98 | 95.2 | 87.9 | 100 |
| 2_68 | 90.4 | 79.1 | 98 | 95.2 | 87.9 | 100 |
| 2_115 | 91 | 80.6 | 98 | 95.2 | 87.9 | 100 |
| 2_79 | 88.6 | 74.6 | 98 | 95.2 | 87.9 | 100 |
| 2_91 | 89.2 | 76.1 | 98 | 95.2 | 87.9 | 100 |
| 2_101 | 89.2 | 76.1 | 98 | 95.2 | 87.9 | 100 |
| 37_111 | 84.4 | 71.6 | 93 | 95.2 | 87.9 | 100 |
| 2_72 | 89.8 | 80.6 | 96 | 95.1 | 87.9 | 100 |
| 10_105 | 97.6 | 95.5 | 99 | 94 | 87.9 | 98 |
| 95_105 | 97 | 95.5 | 98 | 94 | 87.9 | 98 |
| 1_5 | 97.6 | 97 | 98 | 94 | 87.9 | 98 |
| 1_7 | 97.6 | 94 | 100 | 94 | 87.9 | 98 |
| 1_41 | 95.8 | 92.5 | 98 | 94 | 87.9 | 98 |
| 1_54 | 95.8 | 92.5 | 98 | 94 | 87.9 | 98 |
| 1_97 | 96.4 | 94 | 98 | 94 | 87.9 | 98 |
| 1_101 | 96.4 | 94 | 98 | 94 | 87.9 | 98 |
| 18_106 | 95.8 | 91 | 99 | 94 | 87.9 | 98 |
| 30_106 | 92.8 | 82.1 | 100 | 94 | 87.9 | 98 |
| 2_3 | 96.4 | 91 | 100 | 94 | 87.9 | 98 |
| 2_26 | 88.6 | 76.1 | 97 | 94 | 87.9 | 98 |
| 2_27 | 89.8 | 79.1 | 97 | 94 | 87.9 | 98 |
| 2_31 | 88.6 | 74.6 | 98 | 94 | 87.9 | 98 |
| 2_32 | 92.2 | 82.1 | 99 | 94 | 87.9 | 98 |
| 2_40 | 92.2 | 82.1 | 99 | 94 | 87.9 | 98 |
| 2_51 | 91 | 80.6 | 98 | 94 | 87.9 | 98 |
| 2_83 | 90.4 | 77.6 | 99 | 94 | 87.9 | 98 |
| 3_12 | 92.8 | 89.4 | 95 | 94 | 87.9 | 98 |
| 3_18 | 95.2 | 89.6 | 99 | 94 | 87.9 | 98 |
| 4_19 | 89.2 | 77.6 | 97 | 94 | 87.9 | 98 |
| 7_108 | 92.8 | 85.1 | 98 | 94 | 87.9 | 98 |
| 26_108 | 92.8 | 89.6 | 95 | 94 | 87.9 | 98 |
| 46_108 | 92.2 | 85.1 | 97 | 94 | 87.9 | 98 |
| 89_108 | 89.2 | 82.1 | 94 | 94 | 87.9 | 98 |
| 5_15 | 92.2 | 83.6 | 98 | 94 | 87.9 | 98 |
| 5_38 | 91.6 | 83.6 | 97 | 94 | 87.9 | 98 |
| 6_37 | 89.8 | 82.1 | 95 | 94 | 87.9 | 98 |
| 7_45 | 92.2 | 83.6 | 98 | 94 | 87.9 | 98 |
| 7_74 | 93.4 | 89.6 | 96 | 94 | 87.9 | 98 |
| 7_85 | 92.8 | 85.1 | 98 | 94 | 87.9 | 98 |
| 7_96 | 91 | 80.6 | 98 | 94 | 87.9 | 98 |
| 18_38 | 89.8 | 80.6 | 96 | 94 | 87.9 | 98 |
| 18_59 | 92.2 | 85.1 | 97 | 94 | 87.9 | 98 |
| 19_46 | 90.4 | 85.1 | 94 | 94 | 87.9 | 98 |
| 59_105 | 97 | 95.5 | 98 | 92.8 | 87.9 | 96 |
| 101_105 | 97 | 95.5 | 98 | 92.8 | 87.9 | 96 |
| 1_106 | 95.8 | 94 | 97 | 92.8 | 87.9 | 96 |
| 1_3 | 96.4 | 94 | 98 | 92.8 | 87.9 | 96 |
| 1_6 | 95.8 | 94 | 97 | 92.8 | 87.9 | 96 |
| 1_9 | 96.4 | 94 | 98 | 92.8 | 87.9 | 96 |
| 1_10 | 97 | 94 | 99 | 92.8 | 87.9 | 96 |
| 1_11 | 95.8 | 94 | 97 | 92.8 | 87.9 | 96 |
| 1_16 | 97.6 | 97 | 98 | 92.8 | 87.9 | 96 |
| 1_17 | 95.8 | 94 | 97 | 92.8 | 87.9 | 96 |
| 1_24 | 97 | 95.5 | 98 | 92.8 | 87.9 | 96 |
| 1_28 | 96.4 | 94 | 98 | 92.8 | 87.9 | 96 |
| 1_31 | 97.6 | 95.5 | 99 | 92.8 | 87.9 | 96 |
| 1_32 | 96.4 | 94 | 98 | 92.8 | 87.9 | 96 |
| 1_33 | 95.8 | 94 | 97 | 92.8 | 87.9 | 96 |
| 1_34 | 97 | 94 | 99 | 92.8 | 87.9 | 96 |
| 1_38 | 95.8 | 92.5 | 98 | 92.8 | 87.9 | 96 |
| 1_42 | 95.8 | 94 | 97 | 92.8 | 87.9 | 96 |
| 1_44 | 95.8 | 94 | 97 | 92.8 | 87.9 | 96 |
| 1_45 | 96.4 | 92.5 | 99 | 92.8 | 87.9 | 96 |
| 1_46 | 96.4 | 92.5 | 99 | 92.8 | 87.9 | 96 |
| 1_47 | 97 | 97 | 97 | 92.8 | 87.9 | 96 |
| 1_48 | 97 | 94 | 99 | 92.8 | 87.9 | 96 |
| 1_51 | 95.8 | 94 | 97 | 92.8 | 87.9 | 96 |
| 1_53 | 95.2 | 92.5 | 97 | 92.8 | 87.9 | 96 |
| 1_57 | 95.8 | 94 | 97 | 92.8 | 87.9 | 96 |
| 1_60 | 95.8 | 94 | 97 | 92.8 | 87.9 | 96 |
| 1_62 | 96.4 | 94 | 98 | 92.8 | 87.9 | 96 |
| 1_63 | 95.8 | 94 | 97 | 92.8 | 87.9 | 96 |
| 1_64 | 95.8 | 94 | 97 | 92.8 | 87.9 | 96 |
| 1_114 | 95.2 | 91 | 98 | 92.8 | 87.9 | 96 |
| 1_67 | 96.4 | 94 | 98 | 92.8 | 87.9 | 96 |
| 1_68 | 95.8 | 94 | 97 | 92.8 | 87.9 | 96 |
| 1_115 | 95.8 | 94 | 97 | 92.8 | 87.9 | 96 |
| 1_117 | 95.8 | 92.5 | 98 | 92.8 | 87.9 | 96 |
| 1_73 | 97 | 95.5 | 98 | 92.8 | 87.9 | 96 |
| 1_76 | 95.8 | 94 | 97 | 92.8 | 87.9 | 96 |
| 1_118 | 97.6 | 95.5 | 99 | 92.8 | 87.9 | 96 |
| 1_78 | 95.8 | 94 | 97 | 92.8 | 87.9 | 96 |
| 1_80 | 96.4 | 95.5 | 97 | 92.8 | 87.9 | 96 |
| 1_84 | 95.8 | 94 | 97 | 92.8 | 87.9 | 96 |
| 1_85 | 95.8 | 94 | 97 | 92.8 | 87.9 | 96 |
| 1_86 | 97 | 95.5 | 98 | 92.8 | 87.9 | 96 |
| 1_88 | 95.8 | 92.5 | 98 | 92.8 | 87.9 | 96 |
| 1_89 | 97 | 94 | 99 | 92.8 | 87.9 | 96 |
| 1_90 | 97 | 97 | 97 | 92.8 | 87.9 | 96 |
| 1_91 | 95.8 | 94 | 97 | 92.8 | 87.9 | 96 |
| 1_92 | 95.2 | 92.5 | 97 | 92.8 | 87.9 | 96 |
| 1_94 | 96.4 | 94 | 98 | 92.8 | 87.9 | 96 |
| 1_95 | 96.4 | 94 | 98 | 92.8 | 87.9 | 96 |
| 1_98 | 97 | 93.9 | 99 | 92.8 | 87.9 | 96 |
| 1_100 | 95.8 | 94 | 97 | 92.8 | 87.9 | 96 |
| 1_103 | 96.4 | 95.5 | 97 | 92.8 | 87.9 | 96 |
| 1_104 | 95.8 | 94 | 97 | 92.8 | 87.9 | 96 |
| 2_20 | 90.4 | 79.1 | 98 | 92.8 | 87.9 | 96 |
| 2_36 | 91.6 | 82.1 | 98 | 92.8 | 87.9 | 96 |
| 2_42 | 91.6 | 83.6 | 97 | 92.8 | 87.9 | 96 |
| 2_59 | 91.6 | 82.1 | 98 | 92.8 | 87.9 | 96 |
| 35_107 | 88 | 79.1 | 94 | 92.8 | 87.9 | 96 |
| 98_107 | 90.4 | 81.8 | 96 | 92.8 | 87.9 | 96 |
| 3_13 | 92.8 | 88.1 | 96 | 92.8 | 87.9 | 96 |
| 3_120 | 90.4 | 85.1 | 94 | 92.8 | 87.9 | 96 |
| 3_99 | 92.2 | 86.6 | 96 | 92.8 | 87.9 | 96 |
| 5_17 | 91.6 | 86.6 | 95 | 92.8 | 87.9 | 96 |
| 5_26 | 91 | 85.1 | 95 | 92.8 | 87.9 | 96 |
| 5_115 | 91.6 | 91 | 92 | 92.8 | 87.9 | 96 |
| 5_97 | 91 | 83.6 | 96 | 92.8 | 87.9 | 96 |
| 7_10 | 92.2 | 86.6 | 96 | 92.8 | 87.9 | 96 |
| 7_20 | 91 | 86.6 | 94 | 92.8 | 87.9 | 96 |
| 7_24 | 92.8 | 88.1 | 96 | 92.8 | 87.9 | 96 |
| 7_54 | 88.6 | 82.1 | 93 | 92.8 | 87.9 | 96 |
| 7_76 | 89.8 | 83.6 | 94 | 92.8 | 87.9 | 96 |
| 7_118 | 93.4 | 86.6 | 98 | 92.8 | 87.9 | 96 |
| 7_91 | 91 | 83.6 | 96 | 92.8 | 87.9 | 96 |
| 7_102 | 92.8 | 88.1 | 96 | 92.8 | 87.9 | 96 |
| 9_18 | 91.6 | 85.1 | 96 | 92.8 | 87.9 | 96 |
| 9_120 | 83.2 | 79.1 | 86 | 92.8 | 87.9 | 96 |
| 11_18 | 88 | 83.6 | 91 | 92.8 | 87.9 | 96 |
| 12_24 | 86.1 | 80.3 | 90 | 92.8 | 87.9 | 96 |
| 13_30 | 89.2 | 89.6 | 89 | 92.8 | 87.9 | 96 |
| 13_53 | 85 | 85.1 | 85 | 92.8 | 87.9 | 96 |
| 13_60 | 86.8 | 79.1 | 92 | 92.8 | 87.9 | 96 |
| 14_24 | 88 | 77.6 | 95 | 92.8 | 87.9 | 96 |
| 18_19 | 88 | 80.6 | 93 | 92.8 | 87.9 | 96 |
| 42_119 | 79 | 65.7 | 88 | 92.8 | 87.9 | 96 |
| 1_72 | 95.8 | 94 | 97 | 92.7 | 87.9 | 95.9 |
| 1_109 | 97 | 95.5 | 98 | 91.6 | 87.9 | 94 |
| 1_59 | 95.2 | 91 | 98 | 91.6 | 87.9 | 94 |
| 1_116 | 95.8 | 92.5 | 98 | 91.6 | 87.9 | 94 |
| 1_93 | 97.6 | 95.5 | 99 | 91.6 | 87.9 | 94 |
| 2_106 | 93.4 | 85.1 | 99 | 91.6 | 87.9 | 94 |
| 9_106 | 92.2 | 83.6 | 98 | 91.6 | 87.9 | 94 |
| 9_107 | 93.4 | 86.6 | 98 | 91.6 | 87.9 | 94 |
| 39_107 | 91 | 85.1 | 95 | 91.6 | 87.9 | 94 |
| 44_107 | 95.2 | 91 | 98 | 91.6 | 87.9 | 94 |
| 55_107 | 92.8 | 85.1 | 98 | 91.6 | 87.9 | 94 |
| 3_5 | 97 | 95.5 | 98 | 91.6 | 87.9 | 94 |
| 3_71 | 98.2 | 98.5 | 98 | 91.6 | 87.9 | 94 |

TABLE 6-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 4_108 | 93.4 | 88.1 | 97 | 91.6 | 87.9 | 94 |
| 4_8 | 92.8 | 85.1 | 98 | 91.6 | 87.9 | 94 |
| 20_108 | 93.4 | 89.6 | 96 | 91.6 | 87.9 | 94 |
| 70_108 | 90.4 | 79.1 | 98 | 91.6 | 87.9 | 94 |
| 81_108 | 92.2 | 84.8 | 97 | 91.6 | 87.9 | 94 |
| 87_108 | 88 | 83.6 | 91 | 91.6 | 87.9 | 94 |
| 5_20 | 92.2 | 88.1 | 95 | 91.6 | 87.9 | 94 |
| 5_29 | 90.4 | 82.1 | 96 | 91.6 | 87.9 | 94 |
| 5_87 | 89.8 | 83.6 | 94 | 91.6 | 87.9 | 94 |
| 5_90 | 88 | 82.1 | 92 | 91.6 | 87.9 | 94 |
| 14_109 | 87.4 | 74.6 | 96 | 91.6 | 87.9 | 94 |
| 7_47 | 86.8 | 80.6 | 91 | 91.6 | 87.9 | 94 |
| 7_55 | 92.2 | 83.6 | 98 | 91.6 | 87.9 | 94 |
| 7_115 | 94 | 88.1 | 98 | 91.6 | 87.9 | 94 |
| 7_75 | 89.8 | 83.6 | 94 | 91.6 | 87.9 | 94 |
| 7_82 | 90.4 | 85.1 | 94 | 91.6 | 87.9 | 94 |
| 7_92 | 90.4 | 83.6 | 95 | 91.6 | 87.9 | 94 |
| 7_93 | 91 | 82.1 | 97 | 91.6 | 87.9 | 94 |
| 7_97 | 91 | 83.6 | 96 | 91.6 | 87.9 | 94 |
| 7_98 | 89.8 | 81.8 | 95 | 91.6 | 87.9 | 94 |
| 11_25 | 88 | 80.6 | 93 | 91.6 | 87.9 | 94 |
| 14_21 | 88.6 | 79.1 | 95 | 91.6 | 87.9 | 94 |
| 18_42 | 89.8 | 79.1 | 97 | 91.6 | 87.9 | 94 |
| 18_51 | 89.2 | 83.6 | 93 | 91.6 | 87.9 | 94 |
| 18_115 | 85.6 | 76.1 | 92 | 91.6 | 87.9 | 94 |
| 19_21 | 87.4 | 76.1 | 95 | 91.6 | 87.9 | 94 |
| 19_34 | 88.6 | 83.6 | 92 | 91.6 | 87.9 | 94 |
| 28_39 | 85.6 | 74.6 | 93 | 91.6 | 87.9 | 94 |
| 30_46 | 85 | 79.1 | 89 | 91.6 | 87.9 | 94 |
| 39_87 | 86.2 | 73.1 | 95 | 91.6 | 87.9 | 94 |
| 58_113 | 87.4 | 79.1 | 93 | 91.6 | 87.9 | 94 |
| 7_72 | 89.2 | 83.6 | 93 | 91.5 | 87.9 | 93.9 |
| 5_106 | 94 | 88.1 | 98 | 90.4 | 87.9 | 92 |
| 16_106 | 93.4 | 86.6 | 98 | 90.4 | 87.9 | 92 |
| 24_107 | 89.2 | 82.1 | 94 | 90.4 | 87.9 | 92 |
| 74_107 | 93.4 | 88.1 | 97 | 90.4 | 87.9 | 92 |
| 96_107 | 89.8 | 82.1 | 95 | 90.4 | 87.9 | 92 |
| 3_55 | 93.4 | 91 | 95 | 90.4 | 87.9 | 92 |
| 3_83 | 93.4 | 92.5 | 94 | 90.4 | 87.9 | 92 |
| 4_22 | 88 | 77.6 | 95 | 90.4 | 87.9 | 92 |
| 4_86 | 91 | 83.6 | 96 | 90.4 | 87.9 | 92 |
| 9_108 | 90.4 | 86.6 | 93 | 90.4 | 87.9 | 92 |
| 31_108 | 91 | 82.1 | 97 | 90.4 | 87.9 | 92 |
| 44_108 | 93.4 | 88.1 | 97 | 90.4 | 87.9 | 92 |
| 52_108 | 95.2 | 88.1 | 100 | 90.4 | 87.9 | 92 |
| 80_108 | 91 | 88.1 | 93 | 90.4 | 87.9 | 92 |
| 7_28 | 92.2 | 91 | 93 | 90.4 | 87.9 | 92 |
| 7_117 | 93.4 | 88.1 | 97 | 90.4 | 87.9 | 92 |
| 7_78 | 92.8 | 86.6 | 97 | 90.4 | 87.9 | 92 |
| 7_81 | 90.4 | 83.3 | 95 | 90.4 | 87.9 | 92 |
| 7_90 | 91 | 85.1 | 95 | 90.4 | 87.9 | 92 |
| 8_21 | 86.2 | 76.1 | 93 | 90.4 | 87.9 | 92 |
| 9_13 | 92.2 | 94 | 91 | 90.4 | 87.9 | 92 |
| 10_37 | 88 | 82.1 | 92 | 90.4 | 87.9 | 92 |
| 10_66 | 87.4 | 76.1 | 95 | 90.4 | 87.9 | 92 |
| 13_31 | 87.4 | 82.1 | 91 | 90.4 | 87.9 | 92 |
| 13_114 | 86.2 | 85.1 | 87 | 90.4 | 87.9 | 92 |
| 13_103 | 85.6 | 82.1 | 88 | 90.4 | 87.9 | 92 |
| 16_119 | 86.2 | 80.6 | 90 | 90.4 | 87.9 | 92 |
| 18_27 | 89.2 | 83.6 | 93 | 90.4 | 87.9 | 92 |
| 18_47 | 83.8 | 76.1 | 89 | 90.4 | 87.9 | 92 |
| 18_113 | 90.4 | 83.6 | 95 | 90.4 | 87.9 | 92 |
| 18_56 | 87.4 | 79.1 | 93 | 90.4 | 87.9 | 92 |
| 22_45 | 87.4 | 79.1 | 93 | 90.4 | 87.9 | 92 |
| 22_97 | 83.2 | 79.1 | 86 | 90.4 | 87.9 | 92 |
| 24_32 | 84.4 | 77.6 | 89 | 90.4 | 87.9 | 92 |
| 24_74 | 80.2 | 76.1 | 83 | 90.4 | 87.9 | 92 |
| 24_99 | 83.2 | 74.6 | 89 | 90.4 | 87.9 | 92 |
| 30_34 | 84.4 | 77.6 | 89 | 90.4 | 87.9 | 92 |
| 35_39 | 78.4 | 61.2 | 90 | 90.4 | 87.9 | 92 |
| 66_112 | 83.8 | 71.6 | 92 | 90.4 | 87.9 | 92 |
| 51_58 | 85.6 | 74.6 | 93 | 90.4 | 87.9 | 92 |
| 65_107 | 92.8 | 85.1 | 98 | 89.2 | 87.9 | 90 |
| 92_107 | 92.8 | 89.6 | 95 | 89.2 | 87.9 | 90 |
| 3_4 | 93.4 | 88.1 | 97 | 89.2 | 87.9 | 90 |
| 4_32 | 90.4 | 83.6 | 95 | 89.2 | 87.9 | 90 |
| 4_53 | 86.2 | 73.1 | 95 | 89.2 | 87.9 | 90 |
| 4_69 | 87.4 | 79.1 | 93 | 89.2 | 87.9 | 90 |
| 4_117 | 88.6 | 77.6 | 96 | 89.2 | 87.9 | 90 |
| 4_79 | 86.8 | 74.6 | 95 | 89.2 | 87.9 | 90 |
| 4_101 | 86.8 | 77.6 | 93 | 89.2 | 87.9 | 90 |
| 42_108 | 89.2 | 80.6 | 95 | 89.2 | 87.9 | 90 |
| 45_108 | 94.6 | 89.6 | 98 | 89.2 | 87.9 | 90 |
| 5_34 | 89.8 | 86.6 | 92 | 89.2 | 87.9 | 90 |
| 5_96 | 87.4 | 77.6 | 94 | 89.2 | 87.9 | 90 |
| 6_58 | 91.6 | 83.6 | 97 | 89.2 | 87.9 | 90 |
| 87_109 | 92.2 | 88.1 | 95 | 89.2 | 87.9 | 90 |
| 7_69 | 89.8 | 83.6 | 94 | 89.2 | 87.9 | 90 |
| 7_100 | 94 | 91 | 96 | 89.2 | 87.9 | 90 |
| 9_20 | 89.8 | 89.6 | 90 | 89.2 | 87.9 | 90 |
| 9_25 | 84.4 | 77.6 | 89 | 89.2 | 87.9 | 90 |
| 9_55 | 86.2 | 77.6 | 92 | 89.2 | 87.9 | 90 |
| 10_98 | 89.8 | 89.4 | 90 | 89.2 | 87.9 | 90 |
| 11_112 | 83.8 | 77.6 | 88 | 89.2 | 87.9 | 90 |
| 12_21 | 85.5 | 77.3 | 91 | 89.2 | 87.9 | 90 |
| 13_18 | 89.8 | 85.1 | 93 | 89.2 | 87.9 | 90 |
| 21_119 | 81.4 | 73.1 | 87 | 89.2 | 87.9 | 90 |
| 21_122 | 77.8 | 68.7 | 84 | 89.2 | 87.9 | 90 |
| 22_115 | 85 | 79.1 | 89 | 89.2 | 87.9 | 90 |
| 24_33 | 82 | 70.1 | 90 | 89.2 | 87.9 | 90 |
| 24_34 | 82.6 | 76.1 | 87 | 89.2 | 87.9 | 90 |
| 24_42 | 77.8 | 59.7 | 90 | 89.2 | 87.9 | 90 |
| 24_66 | 83.2 | 68.7 | 93 | 89.2 | 87.9 | 90 |
| 24_70 | 83.8 | 71.6 | 92 | 89.2 | 87.9 | 90 |
| 24_82 | 81.4 | 71.6 | 88 | 89.2 | 87.9 | 90 |
| 24_97 | 83.2 | 77.6 | 87 | 89.2 | 87.9 | 90 |
| 25_89 | 85 | 74.6 | 92 | 89.2 | 87.9 | 90 |
| 25_121 | 80.8 | 70.1 | 88 | 89.2 | 87.9 | 90 |
| 35_51 | 77.8 | 59.7 | 90 | 89.2 | 87.9 | 90 |
| 35_54 | 80.8 | 70.1 | 88 | 89.2 | 87.9 | 90 |
| 35_61 | 76 | 62.7 | 85 | 89.2 | 87.9 | 90 |
| 35_85 | 77.2 | 62.7 | 87 | 89.2 | 87.9 | 90 |
| 59_112 | 86.8 | 76.1 | 94 | 89.2 | 87.9 | 90 |
| 67_112 | 80.8 | 64.2 | 92 | 89.2 | 87.9 | 90 |
| 46_104 | 84.4 | 71.6 | 93 | 89.2 | 87.9 | 90 |
| 51_52 | 85 | 79.1 | 89 | 89.2 | 87.9 | 90 |
| 55_113 | 89.8 | 80.6 | 96 | 89.2 | 87.9 | 90 |
| 3_67 | 92.2 | 89.6 | 94 | 88 | 87.9 | 88 |
| 3_94 | 91.6 | 86.6 | 95 | 88 | 87.9 | 88 |
| 4_31 | 86.2 | 73.1 | 95 | 88 | 87.9 | 88 |
| 4_35 | 86.8 | 74.6 | 95 | 88 | 87.9 | 88 |
| 4_51 | 86.8 | 74.6 | 95 | 88 | 87.9 | 88 |
| 4_59 | 86.2 | 73.1 | 95 | 88 | 87.9 | 88 |
| 4_62 | 88 | 74.6 | 97 | 88 | 87.9 | 88 |
| 4_114 | 87.4 | 74.6 | 96 | 88 | 87.9 | 88 |
| 4_68 | 86.2 | 73.1 | 95 | 88 | 87.9 | 88 |
| 4_116 | 88.6 | 77.6 | 96 | 88 | 87.9 | 88 |
| 4_78 | 86.2 | 74.6 | 94 | 88 | 87.9 | 88 |
| 4_93 | 86.8 | 76.1 | 94 | 88 | 87.9 | 88 |
| 4_103 | 86.8 | 74.6 | 95 | 88 | 87.9 | 88 |
| 4_104 | 86.8 | 74.6 | 95 | 88 | 87.9 | 88 |
| 75_108 | 91.6 | 82.1 | 98 | 88 | 87.9 | 88 |
| 5_35 | 89.2 | 80.6 | 95 | 88 | 87.9 | 88 |
| 6_21 | 89.8 | 79.1 | 97 | 88 | 87.9 | 88 |
| 9_70 | 86.8 | 79.1 | 92 | 88 | 87.9 | 88 |
| 9_85 | 83.2 | 79.1 | 86 | 88 | 87.9 | 88 |
| 10_79 | 85 | 74.6 | 92 | 88 | 87.9 | 88 |
| 11_55 | 81.4 | 71.6 | 88 | 88 | 87.9 | 88 |
| 16_112 | 88 | 83.6 | 91 | 88 | 87.9 | 88 |
| 18_21 | 86.8 | 77.6 | 93 | 88 | 87.9 | 88 |
| 19_75 | 88.6 | 80.6 | 94 | 88 | 87.9 | 88 |
| 21_22 | 80.2 | 71.6 | 86 | 88 | 87.9 | 88 |
| 21_111 | 83.8 | 73.1 | 91 | 88 | 87.9 | 88 |
| 21_45 | 85.6 | 83.6 | 87 | 88 | 87.9 | 88 |
| 21_115 | 80.2 | 70.1 | 87 | 88 | 87.9 | 88 |
| 22_112 | 87.4 | 76.1 | 95 | 88 | 87.9 | 88 |
| 22_62 | 83.2 | 70.1 | 92 | 88 | 87.9 | 88 |
| 22_118 | 83.2 | 73.1 | 90 | 88 | 87.9 | 88 |

TABLE 6-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 24_64 | 77.2 | 62.7 | 87 | 88 | 87.9 | 88 |
| 24_65 | 83.2 | 76.1 | 88 | 88 | 87.9 | 88 |
| 24_75 | 81.4 | 70.1 | 89 | 88 | 87.9 | 88 |
| 25_93 | 83.2 | 73.1 | 90 | 88 | 87.9 | 88 |
| 27_120 | 82.6 | 77.6 | 86 | 88 | 87.9 | 88 |
| 35_46 | 78.4 | 62.7 | 89 | 88 | 87.9 | 88 |
| 35_91 | 80.2 | 67.2 | 89 | 88 | 87.9 | 88 |
| 35_122 | 79 | 67.2 | 87 | 88 | 87.9 | 88 |
| 42_58 | 83.2 | 71.6 | 91 | 88 | 87.9 | 88 |
| 70_112 | 82 | 67.2 | 92 | 88 | 87.9 | 88 |
| 79_112 | 80.8 | 67.2 | 90 | 88 | 87.9 | 88 |
| 4_72 | 89.2 | 82.1 | 94 | 87.8 | 87.9 | 87.8 |
| 21_106 | 93.4 | 85.1 | 99 | 86.7 | 87.9 | 86 |
| 4_64 | 85.6 | 74.6 | 93 | 86.7 | 87.9 | 86 |
| 4_66 | 88 | 77.6 | 95 | 86.7 | 87.9 | 86 |
| 4_118 | 89.8 | 82.1 | 95 | 86.7 | 87.9 | 86 |
| 5_78 | 88.6 | 82.1 | 93 | 86.7 | 87.9 | 86 |
| 5_82 | 89.8 | 85.1 | 93 | 86.7 | 87.9 | 86 |
| 9_56 | 83.2 | 77.6 | 87 | 86.7 | 87.9 | 86 |
| 9_71 | 86.2 | 79.1 | 91 | 86.7 | 87.9 | 86 |
| 9_94 | 85.6 | 77.6 | 91 | 86.7 | 87.9 | 86 |
| 11_35 | 80.8 | 70.1 | 88 | 86.7 | 87.9 | 86 |
| 16_35 | 85.6 | 80.6 | 89 | 86.7 | 87.9 | 86 |
| 21_24 | 85 | 74.6 | 92 | 86.7 | 87.9 | 86 |
| 21_39 | 82.6 | 73.1 | 89 | 86.7 | 87.9 | 86 |
| 21_46 | 82.6 | 71.6 | 90 | 86.7 | 87.9 | 86 |
| 21_49 | 83.2 | 74.6 | 89 | 86.7 | 87.9 | 86 |
| 21_57 | 84.4 | 76.1 | 90 | 86.7 | 87.9 | 86 |
| 21_85 | 80.2 | 68.7 | 88 | 86.7 | 87.9 | 86 |
| 22_52 | 84.4 | 77.6 | 89 | 86.7 | 87.9 | 86 |
| 22_65 | 86.8 | 82.1 | 90 | 86.7 | 87.9 | 86 |
| 22_114 | 82 | 77.6 | 85 | 86.7 | 87.9 | 86 |
| 22_94 | 81.4 | 71.6 | 88 | 86.7 | 87.9 | 86 |
| 22_99 | 83.8 | 74.6 | 90 | 86.7 | 87.9 | 86 |
| 25_44 | 83.2 | 71.6 | 91 | 86.7 | 87.9 | 86 |
| 25_65 | 86.2 | 80.6 | 90 | 86.7 | 87.9 | 86 |
| 25_67 | 80.8 | 70.1 | 88 | 86.7 | 87.9 | 86 |
| 29_31 | 85 | 74.6 | 92 | 86.7 | 87.9 | 86 |
| 35_58 | 82 | 68.7 | 91 | 86.7 | 87.9 | 86 |
| 35_70 | 79.6 | 61.2 | 92 | 86.7 | 87.9 | 86 |
| 35_84 | 79.6 | 67.2 | 88 | 86.7 | 87.9 | 86 |
| 55_115 | 83.2 | 71.6 | 91 | 86.7 | 87.9 | 86 |
| 58_79 | 79 | 64.2 | 89 | 86.7 | 87.9 | 86 |
| 66_83 | 80.8 | 67.2 | 90 | 86.7 | 87.9 | 86 |
| 67_80 | 76.6 | 65.7 | 84 | 86.7 | 87.9 | 86 |
| 79_98 | 77.1 | 60.6 | 88 | 86.7 | 87.9 | 86 |
| 83_104 | 79 | 64.2 | 89 | 86.7 | 87.9 | 86 |
| 4_36 | 87.4 | 76.1 | 95 | 85.5 | 87.9 | 84 |
| 4_100 | 86.8 | 74.6 | 95 | 85.5 | 87.9 | 84 |
| 5_109 | 93.4 | 89.6 | 96 | 85.5 | 87.9 | 84 |
| 16_109 | 90.4 | 86.6 | 93 | 85.5 | 87.9 | 84 |
| 25_109 | 85.6 | 76.1 | 92 | 85.5 | 87.9 | 84 |
| 58_110 | 88 | 83.6 | 91 | 85.5 | 87.9 | 84 |
| 11_71 | 80.8 | 74.6 | 85 | 85.5 | 87.9 | 84 |
| 21_65 | 79.6 | 70.1 | 86 | 85.5 | 87.9 | 84 |
| 21_68 | 81.4 | 70.1 | 89 | 85.5 | 87.9 | 84 |
| 21_74 | 83.2 | 71.6 | 91 | 85.5 | 87.9 | 84 |
| 21_118 | 84.4 | 79.1 | 88 | 85.5 | 87.9 | 84 |
| 21_90 | 77.2 | 71.6 | 81 | 85.5 | 87.9 | 84 |
| 22_104 | 79 | 73.1 | 83 | 85.5 | 87.9 | 84 |
| 24_52 | 81.4 | 71.6 | 88 | 85.5 | 87.9 | 84 |
| 24_67 | 82 | 73.1 | 88 | 85.5 | 87.9 | 84 |
| 24_92 | 80.2 | 70.1 | 87 | 85.5 | 87.9 | 84 |
| 34_75 | 80.2 | 76.1 | 83 | 85.5 | 87.9 | 84 |
| 35_104 | 79 | 62.7 | 90 | 85.5 | 87.9 | 84 |
| 81_104 | 80.1 | 65.2 | 90 | 85.5 | 87.9 | 84 |
| 35_109 | 85 | 73.1 | 93 | 84.3 | 87.9 | 82 |
| 104_109 | 88 | 80.6 | 93 | 84.3 | 87.9 | 82 |
| 10_99 | 88 | 82.1 | 92 | 84.3 | 87.9 | 82 |
| 21_31 | 78.4 | 65.7 | 87 | 84.3 | 87.9 | 82 |
| 21_98 | 78.9 | 69.7 | 85 | 84.3 | 87.9 | 82 |
| 24_98 | 84.9 | 77.3 | 90 | 84.3 | 87.9 | 82 |
| 24_100 | 77.2 | 61.2 | 88 | 84.3 | 87.9 | 82 |
| 25_100 | 82.6 | 71.6 | 90 | 84.3 | 87.9 | 82 |
| 31_34 | 84.4 | 76.1 | 90 | 84.3 | 87.9 | 82 |
| 31_120 | 82.6 | 74.6 | 88 | 84.3 | 87.9 | 82 |
| 35_52 | 79 | 65.7 | 88 | 84.3 | 87.9 | 82 |
| 35_114 | 79.6 | 65.7 | 89 | 84.3 | 87.9 | 82 |
| 35_69 | 83.8 | 73.1 | 91 | 84.3 | 87.9 | 82 |
| 58_67 | 79 | 58.2 | 93 | 84.3 | 87.9 | 82 |
| 65_78 | 74.9 | 65.7 | 81 | 84.3 | 87.9 | 82 |
| 66_94 | 77.8 | 56.7 | 92 | 84.3 | 87.9 | 82 |
| 29_109 | 83.8 | 73.1 | 91 | 83.1 | 87.9 | 80 |
| 90_109 | 88 | 80.6 | 93 | 83.1 | 87.9 | 80 |
| 21_34 | 83.8 | 74.6 | 90 | 83.1 | 87.9 | 80 |
| 21_52 | 80.8 | 71.6 | 87 | 83.1 | 87.9 | 80 |
| 21_121 | 82 | 74.6 | 87 | 83.1 | 87.9 | 80 |
| 21_94 | 79.6 | 70.1 | 86 | 83.1 | 87.9 | 80 |
| 21_102 | 78.4 | 71.6 | 83 | 83.1 | 87.9 | 80 |
| 31_98 | 78.9 | 68.2 | 86 | 83.1 | 87.9 | 80 |
| 66_93 | 77.8 | 59.7 | 90 | 83.1 | 87.9 | 80 |
| 34_109 | 88.6 | 91 | 87 | 81.9 | 87.9 | 78 |
| 80_109 | 87.4 | 80.6 | 92 | 81.9 | 87.9 | 78 |
| 21_100 | 81.4 | 71.6 | 88 | 81.9 | 87.9 | 78 |
| 35_78 | 76.6 | 59.7 | 88 | 81.9 | 87.9 | 78 |
| 42_109 | 85 | 77.6 | 90 | 80.7 | 87.9 | 76 |
| 75_109 | 83.8 | 76.1 | 89 | 80.7 | 87.9 | 76 |
| 96_109 | 85 | 80.6 | 88 | 80.7 | 87.9 | 76 |
| 103_109 | 86.8 | 80.6 | 91 | 80.7 | 87.9 | 76 |
| 10_92 | 89.2 | 86.6 | 91 | 80.7 | 87.9 | 76 |
| 52_109 | 88 | 85.1 | 90 | 79.5 | 87.9 | 74 |
| 50_79 | 74.3 | 56.7 | 86 | 86.6 | 87.5 | 86 |
| 23_35 | 81.4 | 67.2 | 91 | 85.4 | 87.5 | 84 |
| 10_50 | 90.4 | 83.6 | 95 | 84.1 | 87.5 | 82 |
| 50_67 | 74.3 | 61.2 | 83 | 82.9 | 87.5 | 80 |
| 77_108 | 90.4 | 77.6 | 99 | 95.1 | 87.1 | 100 |
| 24_77 | 80.8 | 74.6 | 85 | 88.9 | 87.1 | 90 |
| 9_77 | 83.8 | 76.1 | 89 | 87.7 | 87.1 | 88 |
| 19_106 | 93.4 | 86.6 | 98 | 94 | 84.8 | 100 |
| 87_106 | 92.2 | 83.6 | 98 | 94 | 84.8 | 100 |
| 2_8 | 92.2 | 85.1 | 97 | 94 | 84.8 | 100 |
| 2_75 | 88.6 | 76.1 | 97 | 94 | 84.8 | 100 |
| 2_97 | 88 | 74.6 | 97 | 94 | 84.8 | 100 |
| 2_102 | 92.8 | 82.1 | 100 | 94 | 84.8 | 100 |
| 2_122 | 89.2 | 77.6 | 97 | 94 | 84.8 | 100 |
| 6_119 | 91.6 | 83.6 | 97 | 94 | 84.8 | 100 |
| 7_8 | 93.4 | 85.1 | 99 | 94 | 84.8 | 100 |
| 7_32 | 91 | 82.1 | 97 | 94 | 84.8 | 100 |
| 8_17 | 90.4 | 79.1 | 98 | 94 | 84.8 | 100 |
| 12_15 | 92.8 | 86.4 | 97 | 94 | 84.8 | 100 |
| 17_18 | 91 | 82.1 | 97 | 94 | 84.8 | 100 |
| 1_107 | 95.8 | 92.5 | 98 | 92.8 | 84.8 | 98 |
| 1_122 | 96.4 | 94 | 98 | 92.8 | 84.8 | 98 |
| 2_110 | 92.2 | 85.1 | 97 | 92.8 | 84.8 | 98 |
| 2_48 | 91.6 | 80.6 | 99 | 92.8 | 84.8 | 98 |
| 2_61 | 89.8 | 76.1 | 99 | 92.8 | 84.8 | 98 |
| 2_76 | 91.6 | 80.6 | 99 | 92.8 | 84.8 | 98 |
| 8_107 | 97 | 94 | 99 | 92.8 | 84.8 | 98 |
| 3_66 | 92.8 | 86.6 | 97 | 92.8 | 84.8 | 98 |
| 90_108 | 88 | 80.6 | 93 | 92.8 | 84.8 | 98 |
| 5_113 | 93.4 | 94 | 93 | 92.8 | 84.8 | 98 |
| 5_53 | 91 | 85.1 | 95 | 92.8 | 84.8 | 98 |
| 6_12 | 92.2 | 83.3 | 98 | 92.8 | 84.8 | 98 |
| 6_13 | 94 | 86.6 | 99 | 92.8 | 84.8 | 98 |
| 6_20 | 91.6 | 86.6 | 95 | 92.8 | 84.8 | 98 |
| 6_26 | 91 | 83.6 | 96 | 92.8 | 84.8 | 98 |
| 7_111 | 88.6 | 77.6 | 96 | 92.8 | 84.8 | 98 |
| 7_57 | 89.8 | 79.1 | 97 | 92.8 | 84.8 | 98 |
| 7_101 | 91.6 | 88.1 | 94 | 92.8 | 84.8 | 98 |
| 8_9 | 92.2 | 89.6 | 94 | 92.8 | 84.8 | 98 |
| 13_17 | 89.2 | 79.1 | 96 | 92.8 | 84.8 | 98 |
| 14_55 | 92.8 | 82.1 | 100 | 92.8 | 84.8 | 98 |
| 17_20 | 89.2 | 79.1 | 96 | 92.8 | 84.8 | 98 |
| 18_69 | 86.8 | 76.1 | 94 | 92.8 | 84.8 | 98 |
| 1_15 | 96.4 | 94 | 98 | 91.6 | 84.8 | 96 |
| 1_27 | 97 | 95.5 | 98 | 91.6 | 84.8 | 96 |
| 1_111 | 96.4 | 95.5 | 97 | 91.6 | 84.8 | 96 |
| 1_82 | 96.4 | 95.5 | 97 | 91.6 | 84.8 | 96 |

TABLE 6-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 1_96 | 95.8 | 92.5 | 98 | 91.6 | 84.8 | 96 |
| 49_106 | 91.6 | 83.6 | 97 | 91.6 | 84.8 | 96 |
| 7_107 | 94.6 | 88.1 | 99 | 91.6 | 84.8 | 96 |
| 16_107 | 93.4 | 91 | 95 | 91.6 | 84.8 | 96 |
| 22_107 | 89.8 | 83.6 | 94 | 91.6 | 84.8 | 96 |
| 83_107 | 89.2 | 80.6 | 95 | 91.6 | 84.8 | 96 |
| 85_107 | 87.4 | 77.6 | 94 | 91.6 | 84.8 | 96 |
| 87_107 | 93.4 | 88.1 | 97 | 91.6 | 84.8 | 96 |
| 101_107 | 90.4 | 79.1 | 98 | 91.6 | 84.8 | 96 |
| 3_26 | 90.4 | 86.6 | 93 | 91.6 | 84.8 | 96 |
| 4_61 | 89.2 | 80.6 | 95 | 91.6 | 84.8 | 96 |
| 64_108 | 86.8 | 76.1 | 94 | 91.6 | 84.8 | 96 |
| 66_108 | 91.6 | 85.1 | 96 | 91.6 | 84.8 | 96 |
| 5_28 | 91.6 | 89.6 | 93 | 91.6 | 84.8 | 96 |
| 5_37 | 90.4 | 83.6 | 95 | 91.6 | 84.8 | 96 |
| 5_119 | 91 | 82.1 | 97 | 91.6 | 84.8 | 96 |
| 30_109 | 92.8 | 86.6 | 97 | 91.6 | 84.8 | 96 |
| 7_11 | 91.6 | 83.6 | 97 | 91.6 | 84.8 | 96 |
| 7_19 | 92.8 | 88.1 | 96 | 91.6 | 84.8 | 96 |
| 7_26 | 93.4 | 88.1 | 97 | 91.6 | 84.8 | 96 |
| 7_30 | 92.8 | 88.1 | 96 | 91.6 | 84.8 | 96 |
| 7_38 | 93.4 | 86.6 | 98 | 91.6 | 84.8 | 96 |
| 7_46 | 91 | 82.1 | 97 | 91.6 | 84.8 | 96 |
| 7_86 | 89.8 | 83.6 | 94 | 91.6 | 84.8 | 96 |
| 11_13 | 89.2 | 82.1 | 94 | 91.6 | 84.8 | 96 |
| 12_17 | 90.4 | 80.3 | 97 | 91.6 | 84.8 | 96 |
| 12_25 | 92.2 | 89.4 | 94 | 91.6 | 84.8 | 96 |
| 18_55 | 83.2 | 71.6 | 91 | 91.6 | 84.8 | 96 |
| 18_57 | 82.6 | 70.1 | 91 | 91.6 | 84.8 | 96 |
| 22_30 | 85 | 77.6 | 90 | 91.6 | 84.8 | 96 |
| 24_26 | 82.6 | 76.1 | 87 | 91.6 | 84.8 | 96 |
| 24_30 | 87.4 | 77.6 | 94 | 91.6 | 84.8 | 96 |
| 35_60 | 83.8 | 68.7 | 94 | 91.6 | 84.8 | 96 |
| 41_112 | 84.4 | 80.6 | 87 | 91.6 | 84.8 | 96 |
| 46_113 | 86.2 | 79.1 | 91 | 91.6 | 84.8 | 96 |
| 51_120 | 83.2 | 71.6 | 91 | 91.6 | 84.8 | 96 |
| 5_72 | 90.4 | 89.6 | 91 | 91.5 | 84.8 | 95.9 |
| 20_106 | 92.2 | 83.6 | 98 | 90.4 | 84.8 | 94 |
| 25_107 | 90.4 | 83.6 | 95 | 90.4 | 84.8 | 94 |
| 47_107 | 90.4 | 83.6 | 95 | 90.4 | 84.8 | 94 |
| 89_107 | 91 | 80.6 | 98 | 90.4 | 84.8 | 94 |
| 103_107 | 89.2 | 79.1 | 96 | 90.4 | 84.8 | 94 |
| 104_107 | 91 | 83.6 | 96 | 90.4 | 84.8 | 94 |
| 4_33 | 88 | 76.1 | 96 | 90.4 | 84.8 | 94 |
| 4_38 | 86.2 | 74.6 | 94 | 90.4 | 84.8 | 94 |
| 4_40 | 88.6 | 77.6 | 96 | 90.4 | 84.8 | 94 |
| 19_108 | 91.6 | 83.6 | 97 | 90.4 | 84.8 | 94 |
| 24_108 | 89.8 | 83.6 | 94 | 90.4 | 84.8 | 94 |
| 5_49 | 91 | 85.1 | 95 | 90.4 | 84.8 | 94 |
| 5_68 | 89.2 | 83.6 | 93 | 90.4 | 84.8 | 94 |
| 5_74 | 89.2 | 82.1 | 94 | 90.4 | 84.8 | 94 |
| 6_46 | 85.6 | 73.1 | 94 | 90.4 | 84.8 | 94 |
| 7_25 | 91 | 86.6 | 94 | 90.4 | 84.8 | 94 |
| 7_27 | 90.4 | 83.6 | 95 | 90.4 | 84.8 | 94 |
| 7_39 | 91 | 80.6 | 98 | 90.4 | 84.8 | 94 |
| 7_53 | 91 | 86.6 | 94 | 90.4 | 84.8 | 94 |
| 7_64 | 90.4 | 83.6 | 95 | 90.4 | 84.8 | 94 |
| 7_122 | 91.6 | 86.6 | 95 | 90.4 | 84.8 | 94 |
| 9_117 | 85.6 | 79.1 | 90 | 90.4 | 84.8 | 94 |
| 13_40 | 86.2 | 79.1 | 91 | 90.4 | 84.8 | 94 |
| 14_35 | 88 | 79.1 | 94 | 90.4 | 84.8 | 94 |
| 18_40 | 89.2 | 77.6 | 97 | 90.4 | 84.8 | 94 |
| 20_24 | 86.2 | 80.6 | 90 | 90.4 | 84.8 | 94 |
| 22_34 | 87.4 | 82.1 | 91 | 90.4 | 84.8 | 94 |
| 22_44 | 85.6 | 77.6 | 91 | 90.4 | 84.8 | 94 |
| 24_25 | 82 | 67.2 | 92 | 90.4 | 84.8 | 94 |
| 24_40 | 82 | 73.1 | 88 | 90.4 | 84.8 | 94 |
| 25_56 | 81.4 | 73.1 | 87 | 90.4 | 84.8 | 94 |
| 25_85 | 82 | 76.1 | 86 | 90.4 | 84.8 | 94 |
| 27_112 | 86.2 | 80.6 | 90 | 90.4 | 84.8 | 94 |
| 30_58 | 85 | 80.6 | 88 | 90.4 | 84.8 | 94 |
| 30_79 | 85 | 80.6 | 88 | 90.4 | 84.8 | 94 |
| 30_81 | 82.5 | 72.7 | 89 | 90.4 | 84.8 | 94 |
| 33_35 | 82.6 | 67.2 | 93 | 90.4 | 84.8 | 94 |
| 35_40 | 84.4 | 68.7 | 95 | 90.4 | 84.8 | 94 |
| 35_86 | 84.4 | 76.1 | 90 | 90.4 | 84.8 | 94 |
| 37_46 | 79.6 | 71.6 | 85 | 90.4 | 84.8 | 94 |
| 38_112 | 86.8 | 77.6 | 93 | 90.4 | 84.8 | 94 |
| 41_58 | 85.6 | 80.6 | 89 | 90.4 | 84.8 | 94 |
| 46_53 | 84.4 | 74.6 | 91 | 90.4 | 84.8 | 94 |
| 46_115 | 82.6 | 73.1 | 89 | 90.4 | 84.8 | 94 |
| 46_87 | 79.6 | 73.1 | 84 | 90.4 | 84.8 | 94 |
| 53_94 | 82 | 71.6 | 89 | 90.4 | 84.8 | 94 |
| 58_60 | 85 | 77.6 | 90 | 90.4 | 84.8 | 94 |
| 21_107 | 92.8 | 85.1 | 98 | 89.2 | 84.8 | 92 |
| 31_107 | 91 | 80.6 | 98 | 89.2 | 84.8 | 92 |
| 67_107 | 89.8 | 82.1 | 95 | 89.2 | 84.8 | 92 |
| 79_107 | 89.8 | 79.1 | 97 | 89.2 | 84.8 | 92 |
| 95_107 | 92.2 | 85.1 | 97 | 89.2 | 84.8 | 92 |
| 97_107 | 91 | 83.6 | 96 | 89.2 | 84.8 | 92 |
| 100_107 | 89.8 | 79.1 | 97 | 89.2 | 84.8 | 92 |
| 3_112 | 93.4 | 89.6 | 96 | 89.2 | 84.8 | 92 |
| 3_81 | 94.6 | 90.9 | 97 | 89.2 | 84.8 | 92 |
| 4_28 | 88 | 77.6 | 95 | 89.2 | 84.8 | 92 |
| 53_108 | 88 | 76.1 | 96 | 89.2 | 84.8 | 92 |
| 54_108 | 89.2 | 80.6 | 95 | 89.2 | 84.8 | 92 |
| 63_108 | 85.6 | 79.1 | 90 | 89.2 | 84.8 | 92 |
| 85_108 | 89.8 | 83.6 | 94 | 89.2 | 84.8 | 92 |
| 88_108 | 91 | 82.1 | 97 | 89.2 | 84.8 | 92 |
| 103_108 | 88.6 | 82.1 | 93 | 89.2 | 84.8 | 92 |
| 5_9 | 93.4 | 94 | 93 | 89.2 | 84.8 | 92 |
| 5_10 | 94 | 91 | 96 | 89.2 | 84.8 | 92 |
| 5_16 | 92.2 | 91 | 93 | 89.2 | 84.8 | 92 |
| 5_45 | 91 | 86.6 | 94 | 89.2 | 84.8 | 92 |
| 5_51 | 89.8 | 86.6 | 92 | 89.2 | 84.8 | 92 |
| 5_104 | 91 | 83.6 | 96 | 89.2 | 84.8 | 92 |
| 7_31 | 90.4 | 86.6 | 93 | 89.2 | 84.8 | 92 |
| 7_42 | 91 | 83.6 | 96 | 89.2 | 84.8 | 92 |
| 7_84 | 90.4 | 85.1 | 94 | 89.2 | 84.8 | 92 |
| 7_95 | 92.2 | 86.6 | 96 | 89.2 | 84.8 | 92 |
| 9_112 | 91 | 88.1 | 93 | 89.2 | 84.8 | 92 |
| 9_116 | 85 | 79.1 | 89 | 89.2 | 84.8 | 92 |
| 10_26 | 88.6 | 82.1 | 93 | 89.2 | 84.8 | 92 |
| 10_71 | 90.4 | 85.1 | 94 | 89.2 | 84.8 | 92 |
| 13_113 | 88 | 86.6 | 89 | 89.2 | 84.8 | 92 |
| 13_56 | 85.6 | 80.6 | 89 | 89.2 | 84.8 | 92 |
| 15_34 | 88 | 82.1 | 92 | 89.2 | 84.8 | 92 |
| 16_24 | 89.8 | 85.1 | 93 | 89.2 | 84.8 | 92 |
| 17_35 | 85.6 | 70.1 | 96 | 89.2 | 84.8 | 92 |
| 17_112 | 90.4 | 82.1 | 96 | 89.2 | 84.8 | 92 |
| 18_31 | 86.2 | 76.1 | 93 | 89.2 | 84.8 | 92 |
| 18_53 | 87.4 | 79.1 | 93 | 89.2 | 84.8 | 92 |
| 18_68 | 88.6 | 79.1 | 95 | 89.2 | 84.8 | 92 |
| 18_100 | 86.2 | 77.6 | 92 | 89.2 | 84.8 | 92 |
| 21_37 | 81.4 | 70.1 | 89 | 89.2 | 84.8 | 92 |
| 24_103 | 80.2 | 67.2 | 89 | 89.2 | 84.8 | 92 |
| 25_111 | 86.2 | 76.1 | 93 | 89.2 | 84.8 | 92 |
| 25_117 | 85 | 74.6 | 92 | 89.2 | 84.8 | 92 |
| 25_90 | 80.2 | 67.2 | 89 | 89.2 | 84.8 | 92 |
| 29_35 | 86.2 | 73.1 | 95 | 89.2 | 84.8 | 92 |
| 37_55 | 79 | 68.7 | 86 | 89.2 | 84.8 | 92 |
| 38_99 | 86.2 | 76.1 | 93 | 89.2 | 84.8 | 92 |
| 58_115 | 84.4 | 73.1 | 92 | 89.2 | 84.8 | 92 |
| 45_107 | 91 | 83.6 | 96 | 88 | 84.8 | 90 |
| 3_108 | 91.6 | 85.1 | 96 | 88 | 84.8 | 90 |
| 3_39 | 93.4 | 89.6 | 96 | 88 | 84.8 | 90 |
| 4_27 | 88.6 | 77.6 | 96 | 88 | 84.8 | 90 |
| 4_54 | 88.6 | 77.6 | 96 | 88 | 84.8 | 90 |
| 4_95 | 85.6 | 73.1 | 94 | 88 | 84.8 | 90 |
| 4_122 | 85.6 | 71.6 | 95 | 88 | 84.8 | 90 |
| 25_108 | 90.4 | 83.6 | 95 | 88 | 84.8 | 90 |
| 48_108 | 87.4 | 77.6 | 94 | 88 | 84.8 | 90 |
| 59_108 | 88 | 82.1 | 92 | 88 | 84.8 | 90 |
| 62_108 | 89.2 | 80.6 | 95 | 88 | 84.8 | 90 |
| 86_108 | 86.8 | 73.1 | 96 | 88 | 84.8 | 90 |
| 5_22 | 91 | 86.6 | 94 | 88 | 84.8 | 90 |
| 5_36 | 91.6 | 88.1 | 94 | 88 | 84.8 | 90 |
| 5_111 | 91.6 | 86.6 | 95 | 88 | 84.8 | 90 |

TABLE 6-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 5_39 | 89.2 | 80.6 | 95 | 88 | 84.8 | 90 |
| 5_52 | 90.4 | 82.1 | 96 | 88 | 84.8 | 90 |
| 5_79 | 88.6 | 83.6 | 92 | 88 | 84.8 | 90 |
| 9_12 | 91 | 87.9 | 93 | 88 | 84.8 | 90 |
| 9_21 | 84.4 | 77.6 | 89 | 88 | 84.8 | 90 |
| 9_22 | 83.8 | 79.1 | 87 | 88 | 84.8 | 90 |
| 9_89 | 87.4 | 82.1 | 91 | 88 | 84.8 | 90 |
| 10_89 | 88 | 80.6 | 93 | 88 | 84.8 | 90 |
| 11_37 | 86.2 | 82.1 | 89 | 88 | 84.8 | 90 |
| 13_46 | 84.4 | 76.1 | 90 | 88 | 84.8 | 90 |
| 13_121 | 83.2 | 77.6 | 87 | 88 | 84.8 | 90 |
| 16_18 | 88 | 83.6 | 91 | 88 | 84.8 | 90 |
| 18_34 | 86.2 | 80.6 | 90 | 88 | 84.8 | 90 |
| 18_75 | 85.6 | 82.1 | 88 | 88 | 84.8 | 90 |
| 18_81 | 85.5 | 78.8 | 90 | 88 | 84.8 | 90 |
| 20_35 | 83.8 | 74.6 | 90 | 88 | 84.8 | 90 |
| 21_41 | 81.4 | 73.1 | 87 | 88 | 84.8 | 90 |
| 21_113 | 82.6 | 73.1 | 89 | 88 | 84.8 | 90 |
| 24_39 | 82.6 | 70.1 | 91 | 88 | 84.8 | 90 |
| 28_46 | 86.8 | 77.6 | 93 | 88 | 84.8 | 90 |
| 34_41 | 83.2 | 79.1 | 86 | 88 | 84.8 | 90 |
| 34_113 | 85 | 74.6 | 92 | 88 | 84.8 | 90 |
| 35_48 | 86.8 | 79.1 | 92 | 88 | 84.8 | 90 |
| 35_102 | 80.8 | 70.1 | 88 | 88 | 84.8 | 90 |
| 44_111 | 79.6 | 62.7 | 91 | 88 | 84.8 | 90 |
| 46_112 | 76.6 | 62.7 | 86 | 88 | 84.8 | 90 |
| 47_112 | 81.4 | 76.1 | 85 | 88 | 84.8 | 90 |
| 46_70 | 75.4 | 61.2 | 85 | 88 | 84.8 | 90 |
| 46_89 | 78.4 | 65.7 | 87 | 88 | 84.8 | 90 |
| 55_65 | 83.2 | 67.2 | 94 | 88 | 84.8 | 90 |
| 58_70 | 77.8 | 62.7 | 88 | 88 | 84.8 | 90 |
| 66_75 | 78.4 | 62.7 | 89 | 88 | 84.8 | 90 |
| 80_83 | 72.5 | 53.7 | 85 | 88 | 84.8 | 90 |
| 25_106 | 88.6 | 79.1 | 95 | 86.7 | 84.8 | 88 |
| 34_106 | 89.2 | 80.6 | 95 | 86.7 | 84.8 | 88 |
| 3_34 | 91.6 | 86.6 | 95 | 86.7 | 84.8 | 88 |
| 3_121 | 94 | 92.5 | 95 | 86.7 | 84.8 | 88 |
| 3_96 | 93.4 | 89.6 | 96 | 86.7 | 84.8 | 88 |
| 4_42 | 86.8 | 76.1 | 94 | 86.7 | 84.8 | 88 |
| 4_57 | 88.6 | 79.1 | 95 | 86.7 | 84.8 | 88 |
| 4_67 | 86.8 | 74.6 | 95 | 86.7 | 84.8 | 88 |
| 4_70 | 86.8 | 73.1 | 96 | 86.7 | 84.8 | 88 |
| 79_108 | 90.4 | 79.1 | 98 | 86.7 | 84.8 | 88 |
| 6_52 | 87.4 | 80.6 | 92 | 86.7 | 84.8 | 88 |
| 6_99 | 86.8 | 79.1 | 92 | 86.7 | 84.8 | 88 |
| 40_109 | 86.8 | 77.6 | 93 | 86.7 | 84.8 | 88 |
| 9_11 | 88 | 80.6 | 93 | 86.7 | 84.8 | 88 |
| 9_37 | 85 | 79.1 | 89 | 86.7 | 84.8 | 88 |
| 9_45 | 86.8 | 83.6 | 89 | 86.7 | 84.8 | 88 |
| 9_98 | 84.3 | 80.3 | 87 | 86.7 | 84.8 | 88 |
| 10_22 | 84.4 | 77.6 | 89 | 86.7 | 84.8 | 88 |
| 10_55 | 86.8 | 83.6 | 89 | 86.7 | 84.8 | 88 |
| 11_39 | 79.6 | 71.6 | 85 | 86.7 | 84.8 | 88 |
| 11_46 | 79 | 68.7 | 86 | 86.7 | 84.8 | 88 |
| 11_75 | 81.4 | 73.1 | 87 | 86.7 | 84.8 | 88 |
| 13_63 | 88.6 | 91 | 87 | 86.7 | 84.8 | 88 |
| 13_81 | 84.3 | 81.8 | 86 | 86.7 | 84.8 | 88 |
| 16_46 | 84.4 | 82.1 | 86 | 86.7 | 84.8 | 88 |
| 16_58 | 84.4 | 82.1 | 86 | 86.7 | 84.8 | 88 |
| 16_120 | 84.4 | 77.6 | 89 | 86.7 | 84.8 | 88 |
| 17_34 | 84.4 | 73.1 | 92 | 86.7 | 84.8 | 88 |
| 18_78 | 82.6 | 76.1 | 87 | 86.7 | 84.8 | 88 |
| 18_84 | 88.6 | 79.1 | 95 | 86.7 | 84.8 | 88 |
| 21_26 | 83.2 | 70.1 | 92 | 86.7 | 84.8 | 88 |
| 21_33 | 82.6 | 74.6 | 88 | 86.7 | 84.8 | 88 |
| 21_42 | 85 | 71.6 | 94 | 86.7 | 84.8 | 88 |
| 21_43 | 82.6 | 71.6 | 90 | 86.7 | 84.8 | 88 |
| 22_25 | 82 | 76.1 | 86 | 86.7 | 84.8 | 88 |
| 22_75 | 80.2 | 68.7 | 88 | 86.7 | 84.8 | 88 |
| 22_89 | 82.6 | 76.1 | 87 | 86.7 | 84.8 | 88 |
| 22_121 | 82 | 70.1 | 90 | 86.7 | 84.8 | 88 |
| 24_44 | 81.4 | 70.1 | 89 | 86.7 | 84.8 | 88 |
| 24_46 | 82.6 | 74.6 | 88 | 86.7 | 84.8 | 88 |
| 25_118 | 84.4 | 74.6 | 91 | 86.7 | 84.8 | 88 |
| 34_35 | 79.6 | 70.1 | 86 | 86.7 | 84.8 | 88 |
| 35_49 | 84.4 | 77.6 | 89 | 86.7 | 84.8 | 88 |
| 51_83 | 82 | 67.2 | 92 | 86.7 | 84.8 | 88 |
| 56_66 | 83.8 | 74.6 | 90 | 86.7 | 84.8 | 88 |
| 58_66 | 83.8 | 68.7 | 94 | 86.7 | 84.8 | 88 |
| 70_104 | 79.6 | 67.2 | 88 | 86.7 | 84.8 | 88 |
| 24_72 | 79 | 65.7 | 88 | 86.6 | 84.8 | 87.8 |
| 31_106 | 89.8 | 77.6 | 98 | 85.5 | 84.8 | 86 |
| 71_106 | 89.8 | 79.1 | 97 | 85.5 | 84.8 | 86 |
| 99_106 | 89.8 | 77.6 | 98 | 85.5 | 84.8 | 86 |
| 76_108 | 85.6 | 79.1 | 90 | 85.5 | 84.8 | 86 |
| 21_110 | 89.2 | 85.1 | 92 | 85.5 | 84.8 | 86 |
| 9_34 | 86.8 | 80.6 | 91 | 85.5 | 84.8 | 86 |
| 9_83 | 83.8 | 74.6 | 90 | 85.5 | 84.8 | 86 |
| 9_102 | 86.2 | 80.6 | 90 | 85.5 | 84.8 | 86 |
| 10_39 | 91 | 86.6 | 94 | 85.5 | 84.8 | 86 |
| 11_24 | 83.2 | 76.1 | 88 | 85.5 | 84.8 | 86 |
| 11_31 | 83.8 | 73.1 | 91 | 85.5 | 84.8 | 86 |
| 11_66 | 80.8 | 68.7 | 89 | 85.5 | 84.8 | 86 |
| 11_85 | 79.6 | 70.1 | 86 | 85.5 | 84.8 | 86 |
| 11_88 | 77.2 | 71.6 | 81 | 85.5 | 84.8 | 86 |
| 13_47 | 89.8 | 85.1 | 93 | 85.5 | 84.8 | 86 |
| 16_89 | 85 | 79.1 | 89 | 85.5 | 84.8 | 86 |
| 21_48 | 82.6 | 74.6 | 88 | 85.5 | 84.8 | 86 |
| 22_39 | 83.2 | 73.1 | 90 | 85.5 | 84.8 | 86 |
| 22_51 | 82 | 76.1 | 86 | 85.5 | 84.8 | 86 |
| 22_67 | 79 | 64.2 | 89 | 85.5 | 84.8 | 86 |
| 22_71 | 81.4 | 70.1 | 89 | 85.5 | 84.8 | 86 |
| 22_103 | 78.4 | 70.1 | 84 | 85.5 | 84.8 | 86 |
| 24_45 | 84.4 | 74.6 | 91 | 85.5 | 84.8 | 86 |
| 24_85 | 76.6 | 64.2 | 85 | 85.5 | 84.8 | 86 |
| 24_89 | 83.2 | 80.6 | 85 | 85.5 | 84.8 | 86 |
| 25_55 | 85 | 71.6 | 94 | 85.5 | 84.8 | 86 |
| 25_57 | 86.2 | 77.6 | 92 | 85.5 | 84.8 | 86 |
| 25_71 | 83.2 | 70.1 | 92 | 85.5 | 84.8 | 86 |
| 25_104 | 81.4 | 71.6 | 88 | 85.5 | 84.8 | 86 |
| 28_71 | 86.8 | 80.6 | 91 | 85.5 | 84.8 | 86 |
| 31_39 | 82 | 70.1 | 90 | 85.5 | 84.8 | 86 |
| 34_111 | 80.8 | 73.1 | 86 | 85.5 | 84.8 | 86 |
| 35_117 | 77.8 | 58.2 | 91 | 85.5 | 84.8 | 86 |
| 35_76 | 81.4 | 65.7 | 92 | 85.5 | 84.8 | 86 |
| 44_46 | 79 | 68.7 | 86 | 85.5 | 84.8 | 86 |
| 46_80 | 78.4 | 61.2 | 90 | 85.5 | 84.8 | 86 |
| 66_78 | 76 | 61.2 | 86 | 85.5 | 84.8 | 86 |
| 66_88 | 79 | 65.7 | 88 | 85.5 | 84.8 | 86 |
| 70_119 | 75.4 | 62.7 | 84 | 85.5 | 84.8 | 86 |
| 70_98 | 80.7 | 63.6 | 92 | 85.5 | 84.8 | 86 |
| 79_89 | 80.8 | 65.7 | 91 | 85.5 | 84.8 | 86 |
| 103_106 | 89.2 | 79.1 | 96 | 84.3 | 84.8 | 84 |
| 3_78 | 88.6 | 83.6 | 92 | 84.3 | 84.8 | 84 |
| 32_109 | 87.4 | 77.6 | 94 | 84.3 | 84.8 | 84 |
| 35_110 | 85.6 | 74.6 | 93 | 84.3 | 84.8 | 84 |
| 9_75 | 83.8 | 76.1 | 89 | 84.3 | 84.8 | 84 |
| 10_74 | 86.2 | 80.6 | 90 | 84.3 | 84.8 | 84 |
| 11_79 | 80.2 | 70.1 | 87 | 84.3 | 84.8 | 84 |
| 11_98 | 81.9 | 74.2 | 87 | 84.3 | 84.8 | 84 |
| 16_21 | 85 | 77.6 | 90 | 84.3 | 84.8 | 84 |
| 20_67 | 84.4 | 77.6 | 89 | 84.3 | 84.8 | 84 |
| 21_59 | 82 | 74.6 | 87 | 84.3 | 84.8 | 84 |
| 21_120 | 79.6 | 71.6 | 85 | 84.3 | 84.8 | 84 |
| 21_86 | 79.6 | 73.1 | 84 | 84.3 | 84.8 | 84 |
| 21_96 | 77.2 | 68.7 | 83 | 84.3 | 84.8 | 84 |
| 21_99 | 82.6 | 77.6 | 86 | 84.3 | 84.8 | 84 |
| 22_92 | 86.2 | 82.1 | 89 | 84.3 | 84.8 | 84 |
| 22_93 | 82 | 68.7 | 91 | 84.3 | 84.8 | 84 |
| 24_94 | 79 | 62.7 | 90 | 84.3 | 84.8 | 84 |
| 31_35 | 77.2 | 61.2 | 88 | 84.3 | 84.8 | 84 |
| 32_35 | 84.4 | 74.6 | 91 | 84.3 | 84.8 | 84 |
| 34_42 | 79 | 70.1 | 85 | 84.3 | 84.8 | 84 |
| 35_57 | 79 | 58.2 | 93 | 84.3 | 84.8 | 84 |
| 42_94 | 77.8 | 55.2 | 93 | 84.3 | 84.8 | 84 |
| 44_70 | 83.8 | 73.1 | 91 | 84.3 | 84.8 | 84 |
| 55_67 | 81.4 | 64.2 | 93 | 84.3 | 84.8 | 84 |
| 66_99 | 75.4 | 58.2 | 87 | 84.3 | 84.8 | 84 |

TABLE 6-continued

| SEQ ID NO: | Training cohort | | | Validation cohort | | | SEQ ID NO: | Training cohort | | | Validation cohort | | |
|---|---|---|---|---|---|---|---|---|---|---|---|---|---|
| | Accuracy (%) | Sensitivity (%) | Specificity (%) | Accuracy (%) | Sensitivity (%) | Specificity (%) | | Accuracy (%) | Sensitivity (%) | Specificity (%) | Accuracy (%) | Sensitivity (%) | Specificity (%) |
| 79_94 | 76.6 | 59.7 | 88 | 84.3 | 84.8 | 84 | 50_108 | 89.8 | 80.6 | 96 | 87.8 | 84.4 | 90 |
| 82_83 | 72.5 | 52.2 | 86 | 84.3 | 84.8 | 84 | 50_107 | 89.8 | 80.6 | 96 | 86.6 | 84.4 | 88 |
| 93_106 | 89.2 | 76.1 | 98 | 83.1 | 84.8 | 82 | 5_23 | 91 | 86.6 | 94 | 85.4 | 84.4 | 86 |
| 51_109 | 86.8 | 76.1 | 94 | 83.1 | 84.8 | 82 | 50_112 | 76 | 62.7 | 85 | 85.4 | 84.4 | 86 |
| 53_109 | 91.6 | 88.1 | 94 | 83.1 | 84.8 | 82 | 50_71 | 77.2 | 65.7 | 85 | 85.4 | 84.4 | 86 |
| 58_109 | 86.2 | 80.6 | 90 | 83.1 | 84.8 | 82 | 16_50 | 84.4 | 79.1 | 88 | 84.1 | 84.4 | 84 |
| 10_44 | 87.4 | 82.1 | 91 | 83.1 | 84.8 | 82 | 21_50 | 82 | 74.6 | 87 | 84.1 | 84.4 | 84 |
| 10_96 | 90.4 | 88.1 | 92 | 83.1 | 84.8 | 82 | 50_100 | 74.9 | 59.7 | 85 | 82.9 | 84.4 | 82 |
| 11_21 | 81.4 | 74.6 | 86 | 83.1 | 84.8 | 82 | 50_70 | 77.2 | 62.7 | 87 | 81.7 | 84.4 | 80 |
| 11_70 | 79.6 | 68.7 | 87 | 83.1 | 84.8 | 82 | 50_55 | 78.4 | 62.7 | 89 | 80.5 | 84.4 | 78 |
| 11_83 | 79 | 68.7 | 86 | 83.1 | 84.8 | 82 | 10_77 | 89.8 | 79.1 | 97 | 92.6 | 83.9 | 98 |
| 21_44 | 82 | 71.6 | 89 | 83.1 | 84.8 | 82 | 77_106 | 92.2 | 82.1 | 99 | 91.4 | 83.9 | 96 |
| 21_58 | 81.4 | 70.1 | 89 | 83.1 | 84.8 | 82 | 22_77 | 85.6 | 77.6 | 91 | 90.1 | 83.9 | 94 |
| 21_70 | 80.8 | 68.7 | 89 | 83.1 | 84.8 | 82 | 25_77 | 85 | 73.1 | 93 | 90.1 | 83.9 | 94 |
| 24_56 | 81.4 | 77.6 | 84 | 83.1 | 84.8 | 82 | 35_77 | 77.2 | 64.2 | 86 | 88.9 | 83.9 | 92 |
| 25_31 | 80.8 | 65.7 | 91 | 83.1 | 84.8 | 82 | 77_109 | 86.2 | 82.1 | 89 | 86.4 | 83.9 | 88 |
| 25_103 | 82 | 70.1 | 90 | 83.1 | 84.8 | 82 | 28_77 | 82.6 | 76.1 | 87 | 86.4 | 83.9 | 88 |
| 27_34 | 83.8 | 77.6 | 88 | 83.1 | 84.8 | 82 | 5_77 | 88 | 85.1 | 90 | 85.2 | 83.9 | 86 |
| 35_64 | 79 | 65.7 | 88 | 83.1 | 84.8 | 82 | 6_7 | 91.6 | 82.1 | 98 | 92.8 | 81.8 | 100 |
| 44_79 | 82.6 | 65.7 | 94 | 83.1 | 84.8 | 82 | 6_49 | 89.8 | 86.6 | 92 | 92.8 | 81.8 | 100 |
| 55_79 | 78.4 | 62.7 | 89 | 83.1 | 84.8 | 82 | 7_17 | 89.8 | 77.6 | 98 | 92.8 | 81.8 | 100 |
| 55_103 | 77.2 | 64.2 | 86 | 83.1 | 84.8 | 82 | 8_111 | 90.4 | 79.1 | 98 | 92.8 | 81.8 | 100 |
| 67_89 | 73.1 | 52.2 | 87 | 83.1 | 84.8 | 82 | 13_15 | 88.6 | 82.1 | 93 | 92.8 | 81.8 | 100 |
| 70_94 | 76 | 61.2 | 86 | 83.1 | 84.8 | 82 | 15_20 | 88.6 | 83.6 | 92 | 92.8 | 81.8 | 100 |
| 79_119 | 75.4 | 64.2 | 83 | 83.1 | 84.8 | 82 | 15_112 | 89.8 | 82.1 | 95 | 92.8 | 81.8 | 100 |
| 83_103 | 71.3 | 50.7 | 85 | 83.1 | 84.8 | 82 | 17_119 | 87.4 | 74.6 | 96 | 92.8 | 81.8 | 100 |
| 3_109 | 92.2 | 89.6 | 94 | 81.9 | 84.8 | 80 | 17_87 | 86.2 | 71.6 | 96 | 92.8 | 81.8 | 100 |
| 100_108 | 89.8 | 83.6 | 94 | 81.9 | 84.8 | 80 | 2_43 | 88.6 | 77.6 | 96 | 91.6 | 81.8 | 98 |
| 22_109 | 86.2 | 77.6 | 92 | 81.9 | 84.8 | 80 | 5_14 | 93.4 | 88.1 | 97 | 91.6 | 81.8 | 98 |
| 24_109 | 84.4 | 79.1 | 88 | 81.9 | 84.8 | 80 | 7_14 | 93.4 | 88.1 | 97 | 91.6 | 81.8 | 98 |
| 46_109 | 83.8 | 73.1 | 91 | 81.9 | 84.8 | 80 | 7_33 | 91 | 82.1 | 97 | 91.6 | 81.8 | 98 |
| 55_109 | 83.8 | 76.1 | 89 | 81.9 | 84.8 | 80 | 7_48 | 90.4 | 85.1 | 94 | 91.6 | 81.8 | 98 |
| 85_109 | 83.2 | 77.6 | 87 | 81.9 | 84.8 | 80 | 7_59 | 90.4 | 82.1 | 96 | 91.6 | 81.8 | 98 |
| 11_16 | 89.2 | 83.6 | 93 | 81.9 | 84.8 | 80 | 7_89 | 91.6 | 83.6 | 97 | 91.6 | 81.8 | 98 |
| 11_78 | 79.6 | 71.6 | 85 | 81.9 | 84.8 | 80 | 8_110 | 93.4 | 89.6 | 96 | 91.6 | 81.8 | 98 |
| 11_121 | 80.2 | 70.1 | 87 | 81.9 | 84.8 | 80 | 8_14 | 89.8 | 77.6 | 98 | 91.6 | 81.8 | 98 |
| 11_92 | 78.4 | 68.7 | 85 | 81.9 | 84.8 | 80 | 11_87 | 86.8 | 74.6 | 95 | 91.6 | 81.8 | 98 |
| 11_103 | 79.6 | 67.2 | 88 | 81.9 | 84.8 | 80 | 13_19 | 90.4 | 88.1 | 92 | 91.6 | 81.8 | 98 |
| 21_63 | 83.2 | 74.6 | 89 | 81.9 | 84.8 | 80 | 13_96 | 86.2 | 74.6 | 94 | 91.6 | 81.8 | 98 |
| 21_67 | 81.4 | 68.7 | 90 | 81.9 | 84.8 | 80 | 14_66 | 82.6 | 65.7 | 94 | 91.6 | 81.8 | 98 |
| 21_79 | 80.2 | 73.1 | 85 | 81.9 | 84.8 | 80 | 14_80 | 85 | 68.7 | 96 | 91.6 | 81.8 | 98 |
| 21_81 | 80.1 | 72.7 | 85 | 81.9 | 84.8 | 80 | 14_96 | 86.8 | 77.6 | 93 | 91.6 | 81.8 | 98 |
| 21_84 | 83.2 | 73.1 | 90 | 81.9 | 84.8 | 80 | 15_25 | 87.4 | 73.1 | 97 | 91.6 | 81.8 | 98 |
| 21_92 | 80.2 | 71.6 | 86 | 81.9 | 84.8 | 80 | 15_65 | 86.2 | 76.1 | 93 | 91.6 | 81.8 | 98 |
| 21_93 | 78.4 | 71.6 | 83 | 81.9 | 84.8 | 80 | 17_26 | 88.6 | 79.1 | 95 | 91.6 | 81.8 | 98 |
| 28_75 | 81.4 | 73.1 | 87 | 81.9 | 84.8 | 80 | 18_76 | 92.8 | 91 | 94 | 91.6 | 81.8 | 98 |
| 42_52 | 79 | 59.7 | 92 | 81.9 | 84.8 | 80 | 19_45 | 85 | 71.6 | 94 | 91.6 | 81.8 | 98 |
| 81_94 | 75.9 | 57.6 | 88 | 81.9 | 84.8 | 80 | 19_70 | 88 | 82.1 | 92 | 91.6 | 81.8 | 98 |
| 94_121 | 72.5 | 53.7 | 85 | 81.9 | 84.8 | 80 | 19_83 | 86.2 | 82.1 | 89 | 91.6 | 81.8 | 98 |
| 21_72 | 79.6 | 70.1 | 86 | 81.7 | 84.8 | 79.6 | 24_117 | 83.8 | 67.2 | 95 | 91.6 | 81.8 | 98 |
| 47_109 | 85.6 | 79.1 | 90 | 80.7 | 84.8 | 78 | 12_106 | 94 | 86.4 | 99 | 90.4 | 81.8 | 96 |
| 56_109 | 82.6 | 76.1 | 87 | 80.7 | 84.8 | 78 | 38_106 | 90.4 | 80.6 | 97 | 90.4 | 81.8 | 96 |
| 62_109 | 86.8 | 77.6 | 93 | 80.7 | 84.8 | 78 | 28_107 | 93.4 | 86.6 | 98 | 90.4 | 81.8 | 96 |
| 82_109 | 85.6 | 76.1 | 92 | 80.7 | 84.8 | 78 | 36_107 | 88 | 76.1 | 96 | 90.4 | 81.8 | 96 |
| 88_109 | 85.6 | 83.6 | 87 | 80.7 | 84.8 | 78 | 38_107 | 91.6 | 82.1 | 98 | 90.4 | 81.8 | 96 |
| 89_109 | 85 | 77.6 | 90 | 80.7 | 84.8 | 78 | 41_107 | 91 | 83.6 | 96 | 90.4 | 81.8 | 96 |
| 13_104 | 88.6 | 89.6 | 88 | 80.7 | 84.8 | 78 | 51_107 | 88.6 | 77.6 | 96 | 90.4 | 81.8 | 96 |
| 29_75 | 82 | 74.6 | 87 | 80.7 | 84.8 | 78 | 59_107 | 88.6 | 77.6 | 96 | 90.4 | 81.8 | 96 |
| 29_79 | 83.2 | 74.6 | 89 | 80.7 | 84.8 | 78 | 68_107 | 88 | 76.1 | 96 | 90.4 | 81.8 | 96 |
| 31_45 | 85.6 | 79.1 | 90 | 80.7 | 84.8 | 78 | 70_107 | 88 | 76.1 | 96 | 90.4 | 81.8 | 96 |
| 79_99 | 74.3 | 55.2 | 87 | 80.7 | 84.8 | 78 | 75_107 | 89.8 | 77.6 | 96 | 90.4 | 81.8 | 96 |
| 104_121 | 77.8 | 67.2 | 85 | 80.7 | 84.8 | 78 | 82_107 | 89.2 | 79.1 | 96 | 90.4 | 81.8 | 96 |
| 67_109 | 84.4 | 74.6 | 91 | 79.5 | 84.8 | 76 | 3_8 | 94.6 | 92.5 | 96 | 90.4 | 81.8 | 96 |
| 94_109 | 82.6 | 76.1 | 87 | 79.5 | 84.8 | 76 | 3_20 | 91 | 86.6 | 94 | 90.4 | 81.9 | 96 |
| 98_109 | 88 | 84.8 | 90 | 79.5 | 84.8 | 76 | 14_108 | 88.6 | 77.6 | 96 | 90.4 | 81.8 | 96 |
| 31_78 | 80.2 | 67.2 | 89 | 79.5 | 84.8 | 76 | 39_108 | 94 | 89.6 | 97 | 90.4 | 81.8 | 96 |
| 83_109 | 83.8 | 76.1 | 89 | 78.3 | 84.8 | 74 | 5_40 | 91.6 | 88.1 | 94 | 90.4 | 81.8 | 96 |
| 79_80 | 75.4 | 58.2 | 87 | 78.3 | 84.8 | 74 | 5_41 | 94 | 89.6 | 97 | 90.4 | 81.8 | 96 |
| 92_109 | 85.6 | 83.6 | 87 | 77.1 | 84.8 | 72 | 5_60 | 92.2 | 89.6 | 94 | 90.4 | 81.8 | 96 |
| 31_100 | 79.6 | 70.1 | 86 | 77.1 | 84.8 | 72 | 6_16 | 88.6 | 82.1 | 93 | 90.4 | 81.8 | 96 |
| 25_50 | 85.6 | 74.6 | 93 | 91.5 | 84.4 | 96 | 6_38 | 88.6 | 74.6 | 98 | 90.4 | 81.8 | 96 |
| 23_107 | 88 | 77.6 | 95 | 90.2 | 84.4 | 94 | 6_74 | 87.4 | 76.1 | 95 | 90.4 | 81.8 | 96 |
| 7_23 | 91 | 85.1 | 95 | 90.2 | 84.4 | 94 | 6_120 | 88 | 79.1 | 94 | 90.4 | 81.8 | 96 |
| 14_50 | 86.2 | 73.1 | 95 | 90.2 | 84.4 | 94 | 7_29 | 92.8 | 85.1 | 98 | 90.4 | 81.8 | 96 |

TABLE 6-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 7_43 | 92.8 | 89.6 | 95 | 90.4 | 81.8 | 96 |
| 7_113 | 94.6 | 89.6 | 98 | 90.4 | 81.8 | 96 |
| 7_73 | 91 | 85.1 | 95 | 90.4 | 81.8 | 96 |
| 8_25 | 92.2 | 83.6 | 98 | 90.4 | 81.8 | 96 |
| 8_59 | 91 | 82.1 | 97 | 90.4 | 81.8 | 96 |
| 10_30 | 87.4 | 76.1 | 95 | 90.4 | 81.8 | 96 |
| 11_30 | 88 | 80.6 | 93 | 90.4 | 81.8 | 96 |
| 11_119 | 82.6 | 73.1 | 89 | 90.4 | 81.8 | 96 |
| 13_111 | 85.6 | 73.1 | 94 | 90.4 | 81.8 | 96 |
| 14_42 | 87.4 | 71.6 | 98 | 90.4 | 81.8 | 96 |
| 14_46 | 86.2 | 73.1 | 95 | 90.4 | 81.8 | 96 |
| 15_31 | 83.8 | 68.7 | 94 | 90.4 | 81.8 | 96 |
| 15_35 | 86.2 | 73.1 | 95 | 90.4 | 81.8 | 96 |
| 15_94 | 85 | 73.1 | 93 | 90.4 | 81.8 | 96 |
| 17_37 | 85.6 | 73.1 | 94 | 90.4 | 81.8 | 96 |
| 18_48 | 88.6 | 79.1 | 95 | 90.4 | 81.8 | 96 |
| 18_89 | 85.6 | 79.1 | 90 | 90.4 | 81.8 | 96 |
| 19_39 | 92.2 | 83.6 | 98 | 90.4 | 81.8 | 96 |
| 19_93 | 85 | 74.6 | 92 | 90.4 | 81.8 | 96 |
| 19_96 | 87.4 | 80.6 | 92 | 90.4 | 81.8 | 96 |
| 24_60 | 79.6 | 62.7 | 91 | 90.4 | 81.8 | 96 |
| 30_120 | 83.2 | 76.1 | 88 | 90.4 | 81.8 | 96 |
| 26_106 | 91.6 | 83.6 | 97 | 89.2 | 81.8 | 94 |
| 40_106 | 90.4 | 77.6 | 99 | 89.2 | 81.8 | 94 |
| 53_106 | 92.2 | 83.6 | 98 | 89.2 | 81.8 | 94 |
| 10_107 | 88.6 | 77.6 | 96 | 89.2 | 81.8 | 94 |
| 15_107 | 90.4 | 77.6 | 99 | 89.2 | 81.8 | 94 |
| 17_107 | 88.6 | 76.1 | 97 | 89.2 | 81.8 | 94 |
| 29_107 | 89.2 | 79.1 | 96 | 89.2 | 81.8 | 94 |
| 40_107 | 91.6 | 80.6 | 99 | 89.2 | 81.8 | 94 |
| 43_107 | 92.8 | 89.6 | 95 | 89.2 | 81.8 | 94 |
| 46_107 | 89.8 | 77.6 | 98 | 89.2 | 81.8 | 94 |
| 56_107 | 89.2 | 79.1 | 96 | 89.2 | 81.8 | 94 |
| 60_107 | 90.4 | 79.1 | 98 | 89.2 | 81.8 | 94 |
| 62_107 | 91.6 | 83.6 | 97 | 89.2 | 81.8 | 94 |
| 64_107 | 91 | 85.1 | 95 | 89.2 | 81.8 | 94 |
| 71_107 | 90.4 | 83.6 | 95 | 89.2 | 81.8 | 94 |
| 76_107 | 88.6 | 77.6 | 96 | 89.2 | 81.8 | 94 |
| 80_107 | 89.2 | 79.1 | 96 | 89.2 | 81.8 | 94 |
| 81_107 | 92.8 | 86.4 | 97 | 89.2 | 81.8 | 94 |
| 84_107 | 89.2 | 80.6 | 95 | 89.2 | 81.8 | 94 |
| 86_107 | 90.4 | 79.1 | 98 | 89.2 | 81.8 | 94 |
| 93_107 | 89.8 | 79.1 | 97 | 89.2 | 81.8 | 94 |
| 11_108 | 90.4 | 77.6 | 99 | 89.2 | 81.8 | 94 |
| 29_108 | 91 | 80.6 | 98 | 89.2 | 81.8 | 94 |
| 38_108 | 86.2 | 71.6 | 96 | 89.2 | 81.8 | 94 |
| 56_108 | 90.4 | 80.6 | 97 | 89.2 | 81.8 | 94 |
| 102_108 | 89.2 | 79.1 | 96 | 89.2 | 81.8 | 94 |
| 5_63 | 91 | 86.6 | 94 | 89.2 | 81.8 | 94 |
| 6_54 | 90.4 | 83.6 | 95 | 89.2 | 81.8 | 94 |
| 6_55 | 86.8 | 74.6 | 95 | 89.2 | 81.8 | 94 |
| 6_71 | 87.4 | 77.6 | 94 | 89.2 | 81.8 | 94 |
| 6_80 | 86.2 | 73.1 | 95 | 89.2 | 81.8 | 94 |
| 7_41 | 91.6 | 89.6 | 93 | 89.2 | 81.8 | 94 |
| 7_49 | 91 | 85.1 | 95 | 89.2 | 81.8 | 94 |
| 7_56 | 91.6 | 86.6 | 95 | 89.2 | 81.8 | 94 |
| 7_63 | 93.4 | 88.1 | 97 | 89.2 | 81.8 | 94 |
| 7_68 | 91.6 | 83.6 | 97 | 89.2 | 81.8 | 94 |
| 9_30 | 87.4 | 82.1 | 91 | 89.2 | 81.8 | 94 |
| 13_38 | 86.2 | 82.1 | 89 | 89.2 | 81.8 | 94 |
| 13_112 | 85.6 | 83.6 | 87 | 89.2 | 81.8 | 94 |
| 13_71 | 88 | 82.1 | 92 | 89.2 | 81.8 | 94 |
| 13_90 | 86.2 | 82.1 | 89 | 89.2 | 81.8 | 94 |
| 14_29 | 90.4 | 76.1 | 100 | 89.2 | 81.8 | 94 |
| 14_83 | 83.8 | 68.7 | 94 | 89.2 | 81.8 | 94 |
| 15_58 | 88 | 79.1 | 94 | 89.2 | 81.8 | 94 |
| 17_25 | 87.4 | 74.6 | 96 | 89.2 | 81.8 | 94 |
| 17_90 | 84.4 | 71.6 | 93 | 89.2 | 81.8 | 94 |
| 18_39 | 84.4 | 71.6 | 93 | 89.2 | 81.8 | 94 |
| 18_60 | 88.6 | 77.6 | 96 | 89.2 | 81.8 | 94 |
| 18_62 | 86.8 | 76.1 | 94 | 89.2 | 81.8 | 94 |
| 18_82 | 86.2 | 82.1 | 89 | 89.2 | 81.8 | 94 |
| 18_91 | 89.2 | 80.6 | 95 | 89.2 | 81.8 | 94 |
| 18_94 | 84.4 | 77.6 | 89 | 89.2 | 81.8 | 94 |
| 18_104 | 83.2 | 73.1 | 90 | 89.2 | 81.8 | 94 |
| 19_79 | 85 | 76.1 | 91 | 89.2 | 81.8 | 94 |
| 24_61 | 83.2 | 71.6 | 91 | 89.2 | 81.8 | 94 |
| 25_30 | 88.6 | 77.6 | 96 | 89.2 | 81.8 | 94 |
| 35_38 | 83.2 | 70.1 | 92 | 89.2 | 81.8 | 94 |
| 37_42 | 84.4 | 74.6 | 91 | 89.2 | 81.8 | 94 |
| 37_67 | 79.6 | 68.7 | 87 | 89.2 | 81.8 | 94 |
| 38_58 | 83.2 | 70.1 | 92 | 89.2 | 81.8 | 94 |
| 55_112 | 80.8 | 65.7 | 91 | 89.2 | 81.8 | 94 |
| 46_60 | 85.6 | 74.6 | 93 | 89.2 | 81.8 | 94 |
| 51_97 | 89.2 | 82.1 | 94 | 89.2 | 81.8 | 94 |
| 83_113 | 85 | 76.1 | 91 | 89.2 | 81.8 | 94 |
| 4_106 | 89.2 | 77.6 | 97 | 88 | 81.8 | 92 |
| 54_106 | 91.6 | 80.6 | 99 | 88 | 81.8 | 92 |
| 32_107 | 91 | 79.1 | 99 | 88 | 81.8 | 92 |
| 42_107 | 86.8 | 74.6 | 95 | 88 | 81.8 | 92 |
| 63_107 | 92.2 | 85.1 | 97 | 88 | 81.8 | 92 |
| 78_107 | 88 | 76.1 | 96 | 88 | 81.8 | 92 |
| 88_107 | 91 | 80.6 | 98 | 88 | 81.8 | 92 |
| 90_107 | 89.8 | 80.6 | 96 | 88 | 81.8 | 92 |
| 3_70 | 94 | 88.1 | 98 | 88 | 81.8 | 92 |
| 3_75 | 92.8 | 89.6 | 95 | 88 | 81.8 | 92 |
| 4_73 | 87.4 | 77.6 | 94 | 88 | 81.8 | 92 |
| 22_108 | 88 | 80.6 | 93 | 88 | 81.8 | 92 |
| 36_108 | 86.8 | 73.1 | 96 | 88 | 81.8 | 92 |
| 40_108 | 89.8 | 79.1 | 97 | 88 | 81.8 | 92 |
| 5_6 | 95.2 | 94 | 96 | 88 | 81.8 | 92 |
| 5_43 | 87.4 | 82.1 | 91 | 88 | 81.8 | 92 |
| 5_48 | 94 | 89.6 | 97 | 88 | 81.8 | 92 |
| 5_62 | 89.2 | 85.1 | 92 | 88 | 81.8 | 92 |
| 5_64 | 89.8 | 82.1 | 95 | 88 | 81.8 | 92 |
| 5_65 | 88 | 79.1 | 94 | 88 | 81.8 | 92 |
| 5_114 | 89.8 | 82.1 | 95 | 88 | 81.8 | 92 |
| 5_73 | 92.2 | 89.6 | 94 | 88 | 81.8 | 92 |
| 5_88 | 91 | 82.1 | 97 | 88 | 81.8 | 92 |
| 6_96 | 88.6 | 83.6 | 92 | 88 | 81.8 | 92 |
| 7_40 | 95.2 | 89.6 | 99 | 88 | 81.8 | 92 |
| 7_61 | 92.2 | 88.1 | 95 | 88 | 81.8 | 92 |
| 7_116 | 91 | 85.1 | 95 | 88 | 81.8 | 92 |
| 8_11 | 91.6 | 88.1 | 94 | 88 | 81.8 | 92 |
| 37_110 | 88 | 83.6 | 91 | 88 | 81.8 | 92 |
| 9_17 | 83.8 | 73.1 | 91 | 88 | 81.8 | 92 |
| 9_39 | 85 | 76.1 | 91 | 88 | 81.8 | 92 |
| 9_44 | 88 | 82.1 | 92 | 88 | 81.8 | 92 |
| 9_114 | 83.2 | 77.6 | 87 | 88 | 81.8 | 92 |
| 9_87 | 82.6 | 80.6 | 84 | 88 | 81.8 | 92 |
| 10_49 | 91 | 89.6 | 92 | 88 | 81.8 | 92 |
| 10_65 | 88 | 83.6 | 91 | 88 | 81.8 | 92 |
| 10_87 | 86.8 | 82.1 | 90 | 88 | 81.8 | 92 |
| 10_90 | 86.2 | 83.6 | 88 | 88 | 81.8 | 92 |
| 11_38 | 85.6 | 76.1 | 92 | 88 | 81.8 | 92 |
| 13_37 | 90.4 | 89.6 | 91 | 88 | 81.8 | 92 |
| 13_44 | 88 | 86.6 | 89 | 88 | 81.8 | 92 |
| 13_51 | 88.6 | 85.1 | 91 | 88 | 81.8 | 92 |
| 13_59 | 86.8 | 79.1 | 92 | 88 | 81.8 | 92 |
| 14_20 | 91 | 82.1 | 97 | 88 | 81.8 | 92 |
| 14_58 | 89.2 | 82.1 | 94 | 88 | 81.8 | 92 |
| 18_36 | 88.6 | 82.1 | 93 | 88 | 81.8 | 92 |
| 19_25 | 83.8 | 70.1 | 93 | 88 | 81.8 | 92 |
| 19_55 | 89.2 | 82.1 | 94 | 88 | 81.8 | 92 |
| 19_67 | 86.8 | 77.6 | 93 | 88 | 81.8 | 92 |
| 21_38 | 86.8 | 77.6 | 93 | 88 | 81.8 | 92 |
| 22_29 | 88 | 82.1 | 92 | 88 | 81.8 | 92 |
| 22_111 | 83.2 | 67.2 | 94 | 88 | 81.8 | 92 |
| 25_52 | 80.8 | 74.6 | 85 | 88 | 81.8 | 92 |
| 29_55 | 83.2 | 74.6 | 89 | 88 | 81.8 | 92 |
| 29_66 | 82.6 | 70.1 | 91 | 88 | 81.8 | 92 |
| 34_51 | 86.2 | 82.1 | 89 | 88 | 81.8 | 92 |
| 34_60 | 84.4 | 77.6 | 89 | 88 | 81.8 | 92 |
| 35_73 | 81.4 | 71.6 | 88 | 88 | 81.8 | 92 |
| 58_111 | 79 | 64.2 | 89 | 88 | 81.8 | 92 |
| 37_112 | 84.4 | 74.6 | 91 | 88 | 81.8 | 92 |
| 51_112 | 86.8 | 80.6 | 91 | 88 | 81.8 | 92 |
| 46_51 | 84.4 | 73.1 | 92 | 88 | 81.8 | 92 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 51_75 | 80.8 | 68.7 | 89 | 88 | 81.8 | 92 |
| 51_119 | 80.8 | 70.1 | 88 | 88 | 81.8 | 92 |
| 51_96 | 82 | 70.1 | 90 | 88 | 81.8 | 92 |
| 98_113 | 86.7 | 75.8 | 94 | 88 | 81.8 | 92 |
| 90_94 | 75.4 | 56.7 | 88 | 88 | 81.8 | 92 |
| 72_108 | 89.2 | 79.1 | 96 | 87.8 | 81.8 | 91.8 |
| 39_106 | 89.8 | 79.1 | 97 | 86.7 | 81.8 | 90 |
| 44_106 | 91 | 80.6 | 98 | 86.7 | 81.8 | 90 |
| 47_106 | 89.2 | 79.1 | 96 | 86.7 | 81.8 | 90 |
| 64_106 | 89.8 | 80.6 | 96 | 86.7 | 81.8 | 90 |
| 66_106 | 89.8 | 76.1 | 99 | 86.7 | 81.8 | 90 |
| 97_106 | 89.8 | 82.1 | 95 | 86.7 | 81.8 | 90 |
| 98_106 | 89.8 | 80.3 | 96 | 86.7 | 81.8 | 90 |
| 91_107 | 90.4 | 79.1 | 98 | 86.7 | 81.8 | 90 |
| 3_93 | 94.6 | 91 | 97 | 86.7 | 81.8 | 90 |
| 4_15 | 89.2 | 82.1 | 94 | 86.7 | 81.8 | 90 |
| 4_17 | 87.4 | 73.1 | 97 | 86.7 | 81.8 | 90 |
| 4_29 | 89.2 | 79.1 | 96 | 86.7 | 81.8 | 90 |
| 4_60 | 86.8 | 73.1 | 96 | 86.7 | 81.8 | 90 |
| 10_108 | 86.2 | 74.6 | 94 | 86.7 | 81.8 | 90 |
| 16_108 | 90.4 | 86.6 | 93 | 86.7 | 81.8 | 90 |
| 28_108 | 87.4 | 80.6 | 92 | 86.7 | 81.8 | 90 |
| 51_108 | 86.8 | 74.6 | 95 | 86.7 | 81.8 | 90 |
| 67_108 | 88.6 | 79.1 | 95 | 86.7 | 81.8 | 90 |
| 69_108 | 86.8 | 77.6 | 93 | 86.7 | 81.8 | 90 |
| 82_108 | 86.8 | 76.1 | 94 | 86.7 | 81.8 | 90 |
| 91_108 | 86.8 | 77.6 | 93 | 86.7 | 81.8 | 90 |
| 5_59 | 91 | 86.6 | 94 | 86.7 | 81.8 | 90 |
| 5_118 | 89.2 | 83.6 | 93 | 86.7 | 81.8 | 90 |
| 5_85 | 87.4 | 83.6 | 90 | 86.7 | 81.8 | 90 |
| 5_86 | 92.8 | 89.6 | 95 | 86.7 | 81.8 | 90 |
| 6_34 | 89.2 | 82.1 | 94 | 86.7 | 81.8 | 90 |
| 6_35 | 88.6 | 76.1 | 97 | 86.7 | 81.8 | 90 |
| 6_66 | 88.6 | 76.1 | 97 | 86.7 | 81.8 | 90 |
| 15_109 | 86.2 | 73.1 | 95 | 86.7 | 81.8 | 90 |
| 9_26 | 89.2 | 86.6 | 91 | 86.7 | 81.8 | 90 |
| 9_54 | 86.8 | 82.1 | 90 | 86.7 | 81.8 | 90 |
| 9_66 | 83.8 | 77.6 | 88 | 86.7 | 81.8 | 90 |
| 9_80 | 84.4 | 80.6 | 87 | 86.7 | 81.8 | 90 |
| 9_97 | 87.4 | 85.1 | 89 | 86.7 | 81.8 | 90 |
| 10_46 | 90.4 | 80.6 | 97 | 86.7 | 81.8 | 90 |
| 10_56 | 83.8 | 74.6 | 90 | 86.7 | 81.8 | 90 |
| 10_117 | 85 | 74.6 | 92 | 86.7 | 81.8 | 90 |
| 10_75 | 86.2 | 76.1 | 93 | 86.7 | 81.8 | 90 |
| 12_42 | 84.9 | 72.7 | 93 | 86.7 | 81.8 | 90 |
| 12_67 | 86.7 | 78.8 | 92 | 86.7 | 81.8 | 90 |
| 13_14 | 86.2 | 79.1 | 91 | 86.7 | 81.8 | 90 |
| 13_65 | 86.8 | 83.6 | 89 | 86.7 | 81.8 | 90 |
| 17_21 | 85.6 | 73.1 | 94 | 86.7 | 81.8 | 90 |
| 17_24 | 83.8 | 73.1 | 91 | 86.7 | 81.8 | 90 |
| 17_31 | 85.6 | 70.1 | 96 | 86.7 | 81.8 | 90 |
| 17_42 | 83.8 | 64.2 | 97 | 86.7 | 81.8 | 90 |
| 17_66 | 85.6 | 67.2 | 98 | 86.7 | 81.8 | 90 |
| 18_73 | 85 | 76.1 | 91 | 86.7 | 81.8 | 90 |
| 18_90 | 83.2 | 71.6 | 91 | 86.7 | 81.8 | 90 |
| 21_62 | 78.4 | 62.7 | 89 | 86.7 | 81.8 | 90 |
| 22_26 | 86.2 | 77.6 | 92 | 86.7 | 81.8 | 90 |
| 22_37 | 81.4 | 73.1 | 87 | 86.7 | 81.8 | 90 |
| 22_56 | 82 | 73.1 | 88 | 86.7 | 81.8 | 90 |
| 24_43 | 83.8 | 80.6 | 86 | 86.7 | 81.8 | 90 |
| 24_114 | 83.2 | 71.6 | 91 | 86.7 | 81.8 | 90 |
| 24_95 | 79.6 | 73.1 | 84 | 86.7 | 81.8 | 90 |
| 25_29 | 86.2 | 74.6 | 94 | 86.7 | 81.8 | 90 |
| 25_97 | 79.6 | 65.7 | 89 | 86.7 | 81.8 | 90 |
| 26_31 | 86.8 | 76.1 | 94 | 86.7 | 81.8 | 90 |
| 26_35 | 86.2 | 77.6 | 92 | 86.7 | 81.8 | 90 |
| 27_119 | 83.2 | 77.6 | 87 | 86.7 | 81.8 | 90 |
| 27_98 | 80.1 | 71.2 | 86 | 86.7 | 81.8 | 90 |
| 28_83 | 84.4 | 77.6 | 89 | 86.7 | 81.8 | 90 |
| 29_71 | 85.6 | 79.1 | 90 | 86.7 | 81.8 | 90 |
| 30_67 | 85.6 | 74.6 | 93 | 86.7 | 81.8 | 90 |
| 35_101 | 77.8 | 67.2 | 85 | 86.7 | 81.8 | 90 |
| 66_111 | 83.2 | 64.2 | 96 | 86.7 | 81.8 | 90 |
| 39_42 | 83.2 | 70.1 | 92 | 86.7 | 81.8 | 90 |
| 39_51 | 86.2 | 77.6 | 92 | 86.7 | 81.8 | 90 |
| 40_55 | 85.6 | 70.1 | 96 | 86.7 | 81.8 | 90 |
| 65_112 | 83.8 | 74.6 | 90 | 86.7 | 81.8 | 90 |
| 44_67 | 80.2 | 71.6 | 86 | 86.7 | 81.8 | 90 |
| 47_66 | 78.4 | 65.7 | 87 | 86.7 | 81.8 | 90 |
| 61_67 | 79 | 67.2 | 87 | 86.7 | 81.8 | 90 |
| 66_118 | 80.8 | 65.7 | 91 | 86.7 | 81.8 | 90 |
| 67_120 | 75.4 | 61.2 | 85 | 86.7 | 81.8 | 90 |
| 79_115 | 80.8 | 67.2 | 90 | 86.7 | 81.8 | 90 |
| 83_99 | 70.7 | 53.7 | 82 | 86.7 | 81.8 | 90 |
| 24_106 | 90.4 | 82.1 | 96 | 85.5 | 81.8 | 88 |
| 29_106 | 89.2 | 79.1 | 96 | 85.5 | 81.8 | 88 |
| 35_106 | 87.4 | 73.1 | 97 | 85.5 | 81.8 | 88 |
| 46_106 | 88.6 | 74.6 | 98 | 85.5 | 81.8 | 88 |
| 58_106 | 90.4 | 79.1 | 98 | 85.5 | 81.8 | 88 |
| 80_106 | 88.6 | 76.1 | 97 | 85.5 | 81.8 | 88 |
| 82_106 | 88.6 | 76.1 | 97 | 85.5 | 81.8 | 88 |
| 83_106 | 88.6 | 74.6 | 98 | 85.5 | 81.8 | 88 |
| 88_106 | 92.2 | 82.1 | 99 | 85.5 | 81.8 | 88 |
| 104_106 | 89.8 | 79.1 | 97 | 85.5 | 81.8 | 88 |
| 3_22 | 94 | 91 | 96 | 85.5 | 81.8 | 88 |
| 3_31 | 95.2 | 91 | 98 | 85.5 | 81.8 | 88 |
| 3_79 | 94 | 91 | 96 | 85.5 | 81.8 | 88 |
| 4_111 | 85.6 | 71.6 | 95 | 85.5 | 81.8 | 88 |
| 32_108 | 88.6 | 82.1 | 93 | 85.5 | 81.8 | 88 |
| 78_108 | 90.4 | 80.6 | 97 | 85.5 | 81.8 | 88 |
| 84_108 | 85.6 | 76.1 | 92 | 85.5 | 81.8 | 88 |
| 92_108 | 89.8 | 85.1 | 93 | 85.5 | 81.8 | 88 |
| 5_55 | 89.8 | 82.1 | 95 | 85.5 | 81.8 | 88 |
| 5_71 | 88 | 83.6 | 91 | 85.5 | 81.8 | 88 |
| 5_91 | 88.6 | 82.1 | 93 | 85.5 | 81.8 | 88 |
| 5_94 | 88.6 | 82.1 | 93 | 85.5 | 81.8 | 88 |
| 5_100 | 88 | 82.1 | 92 | 85.5 | 81.8 | 88 |
| 5_103 | 89.8 | 82.1 | 95 | 85.5 | 81.8 | 88 |
| 6_31 | 85.6 | 71.6 | 95 | 85.5 | 81.8 | 88 |
| 6_89 | 86.8 | 77.6 | 93 | 85.5 | 81.8 | 88 |
| 28_109 | 91 | 86.6 | 94 | 85.5 | 81.8 | 88 |
| 38_109 | 85 | 73.1 | 93 | 85.5 | 81.8 | 88 |
| 9_110 | 89.2 | 82.1 | 94 | 85.5 | 81.8 | 88 |
| 9_42 | 85 | 79.1 | 89 | 85.5 | 81.8 | 88 |
| 9_47 | 82.6 | 77.6 | 86 | 85.5 | 81.8 | 88 |
| 9_62 | 80.2 | 74.6 | 84 | 85.5 | 81.8 | 88 |
| 9_74 | 86.8 | 80.6 | 91 | 85.5 | 81.8 | 88 |
| 10_24 | 88 | 82.1 | 92 | 85.5 | 81.8 | 88 |
| 10_116 | 85.6 | 76.1 | 92 | 85.5 | 81.8 | 88 |
| 10_118 | 86.8 | 80.6 | 91 | 85.5 | 81.8 | 88 |
| 10_80 | 83.8 | 76.1 | 89 | 85.5 | 81.8 | 88 |
| 11_20 | 88 | 83.6 | 91 | 85.5 | 81.8 | 88 |
| 11_56 | 82.6 | 73.1 | 89 | 85.5 | 81.8 | 88 |
| 11_62 | 83.8 | 71.6 | 92 | 85.5 | 81.8 | 88 |
| 11_114 | 82.6 | 68.7 | 92 | 85.5 | 81.8 | 88 |
| 11_102 | 82 | 73.1 | 88 | 85.5 | 81.8 | 88 |
| 12_14 | 92.2 | 84.8 | 97 | 85.5 | 81.8 | 88 |
| 12_35 | 84.9 | 74.2 | 92 | 85.5 | 81.8 | 88 |
| 12_51 | 86.7 | 80.3 | 91 | 85.5 | 81.8 | 88 |
| 13_78 | 84.4 | 79.1 | 88 | 85.5 | 81.8 | 88 |
| 13_82 | 82.6 | 77.6 | 86 | 85.5 | 81.8 | 88 |
| 13_94 | 85.6 | 82.1 | 88 | 85.5 | 81.8 | 88 |
| 13_100 | 83.2 | 80.6 | 85 | 85.5 | 81.8 | 88 |
| 16_45 | 85 | 80.6 | 88 | 85.5 | 81.8 | 88 |
| 16_98 | 84.9 | 81.8 | 87 | 85.5 | 81.8 | 88 |
| 17_96 | 85 | 70.1 | 95 | 85.5 | 81.8 | 88 |
| 18_83 | 82 | 73.1 | 88 | 85.5 | 81.8 | 88 |
| 20_21 | 83.2 | 74.6 | 89 | 85.5 | 81.8 | 88 |
| 20_42 | 83.8 | 71.6 | 92 | 85.5 | 81.8 | 88 |
| 21_30 | 85 | 79.1 | 89 | 85.5 | 81.8 | 88 |
| 21_40 | 83.2 | 65.7 | 95 | 85.5 | 81.8 | 88 |
| 21_51 | 76 | 64.2 | 84 | 85.5 | 81.8 | 88 |
| 21_61 | 81.4 | 71.6 | 88 | 85.5 | 81.8 | 88 |
| 21_117 | 79 | 70.1 | 85 | 85.5 | 81.8 | 88 |
| 21_87 | 80.2 | 71.6 | 86 | 85.5 | 81.8 | 88 |
| 24_57 | 82.6 | 73.1 | 89 | 85.5 | 81.8 | 88 |
| 24_63 | 80.2 | 71.6 | 86 | 85.5 | 81.8 | 88 |
| 25_82 | 83.2 | 74.6 | 89 | 85.5 | 81.8 | 88 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 27_58 | 79 | 70.1 | 85 | 85.5 | 81.8 | 88 |
| 31_47 | 78.4 | 67.2 | 86 | 85.5 | 81.8 | 88 |
| 35_36 | 80.2 | 67.2 | 89 | 85.5 | 81.8 | 88 |
| 35_56 | 80.2 | 67.2 | 89 | 85.5 | 81.8 | 88 |
| 35_62 | 80.2 | 70.1 | 87 | 85.5 | 81.8 | 88 |
| 35_74 | 79 | 65.7 | 88 | 85.5 | 81.8 | 88 |
| 40_67 | 80.2 | 65.7 | 90 | 85.5 | 81.8 | 88 |
| 42_55 | 83.8 | 71.6 | 92 | 85.5 | 81.8 | 88 |
| 42_120 | 79 | 68.7 | 86 | 85.5 | 81.8 | 88 |
| 42_98 | 81.3 | 63.6 | 93 | 85.5 | 81.8 | 88 |
| 75_112 | 79.6 | 71.6 | 85 | 85.5 | 81.8 | 88 |
| 44_71 | 77.2 | 64.2 | 86 | 85.5 | 81.8 | 88 |
| 46_119 | 76 | 62.7 | 85 | 85.5 | 81.8 | 88 |
| 46_96 | 74.9 | 62.7 | 83 | 85.5 | 81.8 | 88 |
| 51_93 | 81.4 | 68.7 | 90 | 85.5 | 81.8 | 88 |
| 75_113 | 88 | 82.1 | 92 | 85.5 | 81.8 | 88 |
| 53_58 | 82.6 | 74.6 | 88 | 85.5 | 81.8 | 88 |
| 66_80 | 78.4 | 58.2 | 92 | 85.5 | 81.8 | 88 |
| 66_120 | 77.8 | 61.2 | 89 | 85.5 | 81.8 | 88 |
| 45_106 | 90.4 | 79.1 | 98 | 84.3 | 81.8 | 86 |
| 55_106 | 89.2 | 77.6 | 97 | 84.3 | 81.8 | 86 |
| 59_106 | 88 | 74.6 | 97 | 84.3 | 81.8 | 86 |
| 63_106 | 89.8 | 80.6 | 96 | 84.3 | 81.8 | 86 |
| 67_106 | 88 | 74.6 | 97 | 84.3 | 81.8 | 86 |
| 79_106 | 87.4 | 73.1 | 97 | 84.3 | 81.8 | 86 |
| 89_106 | 88 | 76.1 | 96 | 84.3 | 81.8 | 86 |
| 96_106 | 88 | 76.1 | 96 | 84.3 | 81.8 | 86 |
| 5_46 | 88 | 85.1 | 90 | 84.3 | 81.8 | 86 |
| 5_81 | 87.3 | 83.3 | 90 | 84.3 | 81.8 | 86 |
| 5_120 | 88 | 85.1 | 90 | 84.3 | 81.8 | 86 |
| 5_121 | 88 | 85.1 | 90 | 84.3 | 81.8 | 86 |
| 5_93 | 88 | 85.1 | 90 | 84.3 | 81.8 | 86 |
| 5_98 | 87.3 | 83.3 | 90 | 84.3 | 81.8 | 86 |
| 5_99 | 86.2 | 80.6 | 90 | 84.3 | 81.8 | 86 |
| 6_79 | 88.6 | 77.6 | 96 | 84.3 | 81.8 | 86 |
| 34_110 | 86.2 | 86.6 | 86 | 84.3 | 81.8 | 86 |
| 9_65 | 83.8 | 79.1 | 87 | 84.3 | 81.8 | 86 |
| 9_67 | 82 | 76.1 | 86 | 84.3 | 81.8 | 86 |
| 9_90 | 82.6 | 76.1 | 87 | 84.3 | 81.8 | 86 |
| 9_121 | 83.8 | 77.6 | 88 | 84.3 | 81.8 | 86 |
| 10_47 | 84.4 | 74.6 | 91 | 84.3 | 81.8 | 86 |
| 10_97 | 86.8 | 85.1 | 88 | 84.3 | 81.8 | 86 |
| 11_22 | 85.6 | 76.1 | 92 | 84.3 | 81.8 | 86 |
| 11_44 | 83.8 | 79.1 | 87 | 84.3 | 81.8 | 86 |
| 11_65 | 86.2 | 77.6 | 92 | 84.3 | 81.8 | 86 |
| 11_80 | 80.8 | 67.2 | 90 | 84.3 | 81.8 | 86 |
| 11_81 | 79.5 | 69.7 | 86 | 84.3 | 81.8 | 86 |
| 11_97 | 81.4 | 74.6 | 86 | 84.3 | 81.8 | 86 |
| 11_99 | 82.6 | 77.6 | 86 | 84.3 | 81.8 | 86 |
| 13_69 | 88 | 82.1 | 92 | 84.3 | 81.8 | 86 |
| 13_70 | 85.6 | 79.1 | 90 | 84.3 | 81.8 | 86 |
| 16_93 | 83.2 | 77.6 | 87 | 84.3 | 81.8 | 86 |
| 17_56 | 82.6 | 62.7 | 96 | 84.3 | 81.8 | 86 |
| 18_63 | 86.8 | 77.6 | 93 | 84.3 | 81.8 | 86 |
| 20_31 | 88 | 77.6 | 95 | 84.3 | 81.8 | 86 |
| 21_27 | 82 | 71.6 | 89 | 84.3 | 81.8 | 86 |
| 21_53 | 82 | 76.1 | 86 | 84.3 | 81.8 | 86 |
| 21_116 | 80.2 | 70.1 | 87 | 84.3 | 81.8 | 86 |
| 22_28 | 81.4 | 76.1 | 85 | 84.3 | 81.8 | 86 |
| 22_42 | 82.6 | 68.7 | 92 | 84.3 | 81.8 | 86 |
| 22_47 | 82.6 | 71.6 | 90 | 84.3 | 81.8 | 86 |
| 22_69 | 82 | 74.6 | 87 | 84.3 | 81.8 | 86 |
| 22_70 | 83.2 | 73.1 | 90 | 84.3 | 81.8 | 86 |
| 22_81 | 81.9 | 68.2 | 91 | 84.3 | 81.8 | 86 |
| 24_27 | 84.4 | 73.1 | 92 | 84.3 | 81.8 | 86 |
| 24_36 | 77.2 | 62.7 | 87 | 84.3 | 81.8 | 86 |
| 24_88 | 80.8 | 76.1 | 84 | 84.3 | 81.8 | 86 |
| 25_114 | 83.2 | 70.1 | 92 | 84.3 | 81.8 | 86 |
| 25_78 | 82.6 | 70.1 | 91 | 84.3 | 81.8 | 86 |
| 25_88 | 85 | 77.6 | 90 | 84.3 | 81.8 | 86 |
| 28_98 | 84.3 | 71.2 | 93 | 84.3 | 81.8 | 86 |
| 29_93 | 83.8 | 73.1 | 91 | 84.3 | 81.8 | 86 |
| 30_75 | 87.4 | 80.6 | 92 | 84.3 | 81.8 | 86 |
| 31_89 | 82.6 | 73.1 | 89 | 84.3 | 81.8 | 86 |
| 35_45 | 82.6 | 70.1 | 91 | 84.3 | 81.8 | 86 |
| 40_58 | 86.2 | 73.1 | 95 | 84.3 | 81.8 | 86 |
| 42_83 | 78.4 | 62.7 | 89 | 84.3 | 81.8 | 86 |
| 42_96 | 78.4 | 62.7 | 89 | 84.3 | 81.8 | 86 |
| 56_112 | 83.2 | 74.6 | 89 | 84.3 | 81.8 | 86 |
| 46_66 | 81.4 | 67.2 | 91 | 84.3 | 81.8 | 86 |
| 46_83 | 75.4 | 62.7 | 84 | 84.3 | 81.8 | 86 |
| 46_90 | 76.6 | 65.7 | 84 | 84.3 | 81.8 | 86 |
| 46_92 | 76 | 62.7 | 85 | 84.3 | 81.8 | 86 |
| 46_99 | 73.1 | 62.7 | 80 | 84.3 | 81.8 | 86 |
| 58_100 | 73.7 | 59.7 | 83 | 84.3 | 81.8 | 86 |
| 65_66 | 80.8 | 70.1 | 88 | 84.3 | 81.8 | 86 |
| 65_94 | 78.4 | 65.7 | 87 | 84.3 | 81.8 | 86 |
| 71_114 | 82 | 67.2 | 92 | 84.3 | 81.8 | 86 |
| 70_80 | 79.6 | 62.7 | 91 | 84.3 | 81.8 | 86 |
| 75_98 | 77.1 | 63.6 | 86 | 84.3 | 81.8 | 86 |
| 13_72 | 87.4 | 85.1 | 89 | 84.1 | 81.8 | 85.7 |
| 92_106 | 89.2 | 79.1 | 96 | 83.1 | 81.8 | 84 |
| 94_106 | 88 | 76.1 | 96 | 83.1 | 81.8 | 84 |
| 3_52 | 90.4 | 85.1 | 94 | 83.1 | 81.8 | 84 |
| 33_109 | 86.8 | 77.6 | 93 | 83.1 | 81.8 | 84 |
| 73_109 | 86.8 | 82.1 | 90 | 83.1 | 81.8 | 84 |
| 66_110 | 86.2 | 74.6 | 94 | 83.1 | 81.8 | 84 |
| 9_52 | 85 | 80.6 | 88 | 83.1 | 81.8 | 84 |
| 9_78 | 82.6 | 74.6 | 88 | 83.1 | 81.8 | 84 |
| 9_96 | 85 | 76.1 | 91 | 83.1 | 81.8 | 84 |
| 9_99 | 86.2 | 82.1 | 89 | 83.1 | 81.8 | 84 |
| 11_63 | 81.4 | 73.1 | 87 | 83.1 | 81.8 | 84 |
| 11_64 | 79.6 | 73.1 | 84 | 83.1 | 81.8 | 84 |
| 11_93 | 79 | 70.1 | 85 | 83.1 | 81.8 | 84 |
| 11_96 | 80.2 | 70.1 | 87 | 83.1 | 81.8 | 84 |
| 11_104 | 83.2 | 70.1 | 92 | 83.1 | 81.8 | 84 |
| 13_75 | 86.8 | 85.1 | 88 | 83.1 | 81.8 | 84 |
| 16_25 | 85 | 80.6 | 88 | 83.1 | 81.8 | 84 |
| 16_70 | 83.8 | 80.6 | 86 | 83.1 | 81.8 | 84 |
| 21_112 | 85.6 | 79.1 | 90 | 83.1 | 81.8 | 84 |
| 21_47 | 85 | 76.1 | 91 | 83.1 | 81.8 | 84 |
| 21_91 | 80.8 | 71.6 | 87 | 83.1 | 81.8 | 84 |
| 21_101 | 79 | 70.1 | 85 | 83.1 | 81.8 | 84 |
| 22_82 | 80.8 | 70.1 | 88 | 83.1 | 81.8 | 84 |
| 25_84 | 82 | 73.1 | 88 | 83.1 | 81.8 | 84 |
| 29_47 | 82 | 70.1 | 90 | 83.1 | 81.8 | 84 |
| 29_58 | 80.2 | 71.6 | 86 | 83.1 | 81.8 | 84 |
| 31_44 | 83.8 | 73.1 | 91 | 83.1 | 81.8 | 84 |
| 31_99 | 78.4 | 67.2 | 86 | 83.1 | 81.8 | 84 |
| 34_70 | 82.6 | 77.6 | 86 | 83.1 | 81.8 | 84 |
| 35_88 | 76.6 | 67.2 | 83 | 83.1 | 81.8 | 84 |
| 35_95 | 79 | 65.7 | 88 | 83.1 | 81.8 | 84 |
| 42_46 | 82 | 70.1 | 90 | 83.1 | 81.8 | 84 |
| 42_99 | 79 | 58.2 | 93 | 83.1 | 81.8 | 84 |
| 46_114 | 82 | 71.6 | 89 | 83.1 | 81.8 | 84 |
| 46_79 | 77.2 | 64.2 | 86 | 83.1 | 81.8 | 84 |
| 46_94 | 74.9 | 59.7 | 85 | 83.1 | 81.8 | 84 |
| 46_98 | 75.9 | 62.1 | 85 | 83.1 | 81.8 | 84 |
| 55_66 | 76.6 | 64.2 | 85 | 83.1 | 81.8 | 84 |
| 55_82 | 80.8 | 65.7 | 91 | 83.1 | 81.8 | 84 |
| 65_119 | 77.2 | 68.7 | 83 | 83.1 | 81.8 | 84 |
| 65_80 | 80.2 | 71.6 | 86 | 83.1 | 81.8 | 84 |
| 66_114 | 81.4 | 65.7 | 92 | 83.1 | 81.8 | 84 |
| 66_67 | 77.2 | 56.7 | 91 | 83.1 | 81.8 | 84 |
| 66_79 | 79 | 64.2 | 89 | 83.1 | 81.8 | 84 |
| 93_114 | 77.8 | 62.7 | 88 | 83.1 | 81.8 | 84 |
| 67_119 | 79 | 62.7 | 90 | 83.1 | 81.8 | 84 |
| 79_85 | 74.9 | 58.2 | 86 | 83.1 | 81.8 | 84 |
| 99_104 | 76 | 59.7 | 87 | 83.1 | 81.8 | 84 |
| 52_106 | 89.8 | 80.6 | 96 | 81.9 | 81.8 | 82 |
| 27_109 | 84.4 | 76.1 | 90 | 81.9 | 81.8 | 82 |
| 43_109 | 89.2 | 80.6 | 95 | 81.9 | 81.8 | 82 |
| 44_109 | 89.2 | 85.1 | 92 | 81.9 | 81.8 | 82 |
| 45_109 | 87.4 | 82.1 | 91 | 81.9 | 81.8 | 82 |
| 63_109 | 86.2 | 82.1 | 89 | 81.9 | 81.8 | 82 |
| 31_110 | 88 | 79.1 | 94 | 81.9 | 81.8 | 82 |
| 9_16 | 82.6 | 79.1 | 85 | 81.9 | 81.8 | 82 |
| 9_63 | 84.4 | 79.1 | 88 | 81.9 | 81.8 | 82 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 9_92 | 82.6 | 76.1 | 87 | 81.9 | 81.8 | 82 |
| 10_45 | 92.2 | 88.1 | 95 | 81.9 | 81.8 | 82 |
| 11_67 | 80.2 | 70.1 | 87 | 81.9 | 81.8 | 82 |
| 11_118 | 82 | 79.1 | 84 | 81.9 | 81.8 | 82 |
| 16_80 | 82.6 | 77.6 | 86 | 81.9 | 81.8 | 82 |
| 16_94 | 85.6 | 83.6 | 87 | 81.9 | 81.8 | 82 |
| 16_99 | 82 | 79.1 | 84 | 81.9 | 81.8 | 82 |
| 21_64 | 80.2 | 67.2 | 89 | 81.9 | 81.8 | 82 |
| 21_114 | 79.6 | 68.7 | 87 | 81.9 | 81.8 | 82 |
| 22_79 | 81.4 | 71.6 | 88 | 81.9 | 81.8 | 82 |
| 25_69 | 83.8 | 73.1 | 91 | 81.9 | 81.8 | 82 |
| 28_47 | 85 | 80.6 | 88 | 81.9 | 81.8 | 82 |
| 31_92 | 80.8 | 67.2 | 90 | 81.9 | 81.8 | 82 |
| 34_67 | 78.4 | 70.1 | 84 | 81.9 | 81.8 | 82 |
| 35_67 | 78.4 | 64.2 | 88 | 81.9 | 81.8 | 82 |
| 36_99 | 79 | 70.1 | 85 | 81.9 | 81.8 | 82 |
| 42_67 | 79.6 | 64.2 | 90 | 81.9 | 81.8 | 82 |
| 42_79 | 80.8 | 62.7 | 93 | 81.9 | 81.8 | 82 |
| 42_93 | 81.4 | 65.7 | 92 | 81.9 | 81.8 | 82 |
| 46_58 | 76 | 62.7 | 85 | 81.9 | 81.8 | 82 |
| 46_103 | 75.4 | 61.2 | 85 | 81.9 | 81.8 | 82 |
| 55_78 | 74.3 | 65.7 | 80 | 81.9 | 81.8 | 82 |
| 66_87 | 73.7 | 59.7 | 83 | 81.9 | 81.8 | 82 |
| 67_83 | 72.5 | 58.2 | 82 | 81.9 | 81.8 | 82 |
| 75_115 | 79.6 | 67.2 | 88 | 81.9 | 81.8 | 82 |
| 57_109 | 85.6 | 76.1 | 92 | 80.7 | 81.8 | 80 |
| 97_109 | 85 | 82.1 | 87 | 80.7 | 81.8 | 80 |
| 11_69 | 81.4 | 71.6 | 88 | 80.7 | 81.8 | 80 |
| 21_66 | 77.8 | 70.1 | 83 | 80.7 | 81.8 | 80 |
| 21_78 | 77.2 | 65.7 | 85 | 80.7 | 81.8 | 80 |
| 21_80 | 77.2 | 67.2 | 84 | 80.7 | 81.8 | 80 |
| 21_82 | 78.4 | 73.1 | 82 | 80.7 | 81.8 | 80 |
| 21_88 | 79 | 70.1 | 85 | 80.7 | 81.8 | 80 |
| 21_103 | 77.8 | 68.7 | 84 | 80.7 | 81.8 | 80 |
| 21_104 | 76 | 68.7 | 81 | 80.7 | 81.8 | 80 |
| 28_93 | 80.8 | 76.1 | 84 | 80.7 | 81.8 | 80 |
| 31_52 | 85 | 73.1 | 93 | 80.7 | 81.8 | 80 |
| 34_79 | 82 | 76.1 | 86 | 80.7 | 81.8 | 80 |
| 35_59 | 80.8 | 65.7 | 91 | 80.7 | 81.8 | 80 |
| 52_111 | 82 | 71.6 | 89 | 80.7 | 81.8 | 80 |
| 66_69 | 83.8 | 70.1 | 93 | 80.7 | 81.8 | 80 |
| 65_109 | 86.2 | 79.1 | 91 | 79.5 | 81.8 | 78 |
| 68_109 | 82.6 | 73.1 | 89 | 79.5 | 81.8 | 78 |
| 71_109 | 84.4 | 77.6 | 89 | 79.5 | 81.8 | 78 |
| 21_69 | 81.4 | 73.1 | 87 | 79.5 | 81.8 | 78 |
| 28_119 | 80.2 | 79.1 | 81 | 79.5 | 81.8 | 78 |
| 67_97 | 74.9 | 59.7 | 85 | 79.5 | 81.8 | 78 |
| 71_78 | 73.1 | 61.2 | 81 | 79.5 | 81.8 | 78 |
| 11_109 | 86.2 | 77.6 | 92 | 78.3 | 81.8 | 76 |
| 17_109 | 83.8 | 74.6 | 90 | 78.3 | 81.8 | 76 |
| 11_94 | 79.6 | 71.6 | 85 | 78.3 | 81.8 | 76 |
| 65_100 | 77.2 | 65.7 | 85 | 78.3 | 81.8 | 76 |
| 79_104 | 73.7 | 59.7 | 83 | 78.3 | 81.8 | 76 |
| 83_100 | 64.7 | 40.3 | 81 | 78.3 | 81.8 | 76 |
| 69_109 | 82.6 | 76.1 | 87 | 77.1 | 81.8 | 74 |
| 78_109 | 84.4 | 77.6 | 89 | 77.1 | 81.8 | 74 |
| 84_109 | 84.4 | 74.6 | 91 | 77.1 | 81.8 | 74 |
| 93_109 | 82.6 | 74.6 | 88 | 77.1 | 81.8 | 74 |
| 31_65 | 81.4 | 76.1 | 85 | 77.1 | 81.8 | 74 |
| 100_109 | 82 | 77.6 | 85 | 75.9 | 81.8 | 72 |
| 28_100 | 80.2 | 73.1 | 85 | 75.9 | 81.8 | 72 |
| 64_79 | 77.8 | 67.2 | 85 | 75.9 | 81.8 | 72 |
| 70_100 | 75.4 | 59.7 | 86 | 75.9 | 81.8 | 72 |
| 10_100 | 86.2 | 80.6 | 90 | 74.7 | 81.8 | 70 |
| 67_69 | 79.6 | 71.6 | 85 | 74.7 | 81.8 | 70 |
| 13_50 | 85 | 79.1 | 89 | 87.8 | 81.2 | 92 |
| 18_50 | 83.8 | 73.1 | 91 | 87.8 | 81.2 | 92 |
| 50_106 | 89.8 | 77.6 | 98 | 85.4 | 81.2 | 88 |
| 40_50 | 81.4 | 67.2 | 91 | 85.4 | 81.2 | 88 |
| 50_114 | 80.2 | 65.7 | 90 | 85.4 | 81.2 | 88 |
| 9_50 | 84.4 | 77.6 | 89 | 84.1 | 81.2 | 86 |
| 50_66 | 74.9 | 56.7 | 87 | 82.9 | 81.2 | 84 |
| 50_81 | 74.1 | 57.6 | 85 | 82.9 | 81.2 | 84 |
| 11_50 | 77.8 | 68.7 | 84 | 81.7 | 81.2 | 82 |
| 50_58 | 76 | 59.7 | 87 | 81.7 | 81.2 | 82 |
| 50_83 | 70.7 | 52.2 | 83 | 81.7 | 81.2 | 82 |
| 23_109 | 83.2 | 71.6 | 91 | 75.6 | 81.2 | 72 |
| 6_77 | 89.2 | 80.6 | 95 | 91.4 | 80.6 | 98 |
| 77_107 | 90.4 | 85.1 | 94 | 88.9 | 80.6 | 94 |
| 19_77 | 82.6 | 71.6 | 90 | 88.9 | 80.6 | 94 |
| 42_77 | 78.4 | 62.7 | 89 | 87.7 | 80.6 | 92 |
| 51_77 | 80.2 | 62.7 | 92 | 87.7 | 80.6 | 92 |
| 6_28 | 91.6 | 85.1 | 96 | 91.6 | 78.8 | 100 |
| 6_43 | 86.2 | 76.1 | 93 | 91.6 | 78.8 | 100 |
| 6_87 | 90.4 | 82.1 | 96 | 91.6 | 78.8 | 100 |
| 7_15 | 91 | 82.1 | 97 | 91.6 | 78.8 | 100 |
| 8_15 | 89.8 | 85.1 | 93 | 91.6 | 78.8 | 100 |
| 10_41 | 86.8 | 74.6 | 95 | 91.6 | 78.8 | 100 |
| 15_18 | 90.4 | 86.6 | 93 | 91.6 | 78.8 | 100 |
| 18_33 | 86.2 | 74.6 | 94 | 91.6 | 78.8 | 100 |
| 14_106 | 91 | 79.1 | 99 | 90.4 | 78.8 | 98 |
| 41_106 | 91.6 | 82.1 | 98 | 90.4 | 78.8 | 98 |
| 2_86 | 91 | 80.6 | 98 | 90.4 | 78.8 | 98 |
| 30_107 | 92.2 | 85.1 | 97 | 90.4 | 78.8 | 98 |
| 6_108 | 89.8 | 80.6 | 96 | 90.4 | 78.8 | 98 |
| 15_108 | 88 | 76.1 | 96 | 90.4 | 78.8 | 98 |
| 30_108 | 92.8 | 85.1 | 98 | 90.4 | 78.8 | 98 |
| 41_108 | 91 | 82.1 | 97 | 90.4 | 78.8 | 98 |
| 68_108 | 87.4 | 76.1 | 95 | 90.4 | 78.8 | 98 |
| 6_14 | 91 | 80.6 | 98 | 90.4 | 78.8 | 98 |
| 7_110 | 91.6 | 82.1 | 98 | 90.4 | 78.8 | 98 |
| 9_19 | 88 | 82.1 | 92 | 90.4 | 78.8 | 98 |
| 13_80 | 85 | 82.1 | 87 | 90.4 | 78.8 | 98 |
| 14_112 | 91.6 | 80.6 | 99 | 90.4 | 78.8 | 98 |
| 15_39 | 89.2 | 79.1 | 96 | 90.4 | 78.8 | 98 |
| 18_32 | 89.2 | 80.6 | 95 | 90.4 | 78.8 | 98 |
| 18_118 | 85.6 | 76.1 | 92 | 90.4 | 78.8 | 98 |
| 24_41 | 82.6 | 68.7 | 92 | 90.4 | 78.8 | 98 |
| 30_31 | 84.4 | 73.1 | 92 | 90.4 | 78.8 | 98 |
| 33_112 | 85.6 | 71.6 | 95 | 90.4 | 78.8 | 98 |
| 87_111 | 83.2 | 67.2 | 94 | 90.4 | 78.8 | 98 |
| 7_106 | 92.2 | 82.1 | 99 | 89.2 | 78.8 | 96 |
| 28_106 | 93.4 | 85.1 | 99 | 89.2 | 78.8 | 96 |
| 61_106 | 91.6 | 80.6 | 99 | 89.2 | 78.8 | 96 |
| 19_107 | 94 | 88.1 | 98 | 89.2 | 78.8 | 96 |
| 3_7 | 95.2 | 89.6 | 99 | 89.2 | 78.8 | 96 |
| 3_30 | 91 | 85.1 | 95 | 89.2 | 78.8 | 96 |
| 17_108 | 87.4 | 71.6 | 98 | 89.2 | 78.8 | 96 |
| 5_8 | 95.2 | 91 | 98 | 89.2 | 78.8 | 96 |
| 5_122 | 90.4 | 85.1 | 94 | 89.2 | 78.8 | 96 |
| 6_22 | 85.6 | 74.6 | 93 | 89.2 | 78.8 | 96 |
| 6_90 | 87.4 | 80.6 | 92 | 89.2 | 78.8 | 96 |
| 7_36 | 91.6 | 82.1 | 98 | 89.2 | 78.8 | 96 |
| 9_41 | 87.4 | 82.1 | 91 | 89.2 | 78.8 | 96 |
| 12_111 | 88 | 78.8 | 94 | 89.2 | 78.8 | 96 |
| 12_56 | 87.3 | 83.3 | 90 | 89.2 | 78.8 | 96 |
| 13_36 | 89.8 | 83.6 | 94 | 89.2 | 78.8 | 96 |
| 13_41 | 85.6 | 85.1 | 86 | 89.2 | 78.8 | 96 |
| 14_34 | 89.8 | 82.1 | 95 | 89.2 | 78.8 | 96 |
| 14_37 | 89.8 | 79.1 | 97 | 89.2 | 78.8 | 96 |
| 14_44 | 89.8 | 76.1 | 99 | 89.2 | 78.8 | 96 |
| 14_75 | 86.2 | 73.1 | 95 | 89.2 | 78.8 | 96 |
| 14_89 | 86.2 | 71.6 | 96 | 89.2 | 78.8 | 96 |
| 15_21 | 84.4 | 71.6 | 93 | 89.2 | 78.8 | 96 |
| 15_44 | 85 | 71.6 | 94 | 89.2 | 78.8 | 96 |
| 18_112 | 84.4 | 76.1 | 90 | 89.2 | 78.8 | 96 |
| 18_44 | 85.6 | 74.6 | 93 | 89.2 | 78.8 | 96 |
| 18_117 | 85 | 73.1 | 93 | 89.2 | 78.8 | 96 |
| 18_119 | 84.4 | 76.1 | 90 | 89.2 | 78.8 | 96 |
| 18_80 | 83.8 | 76.1 | 89 | 89.2 | 78.8 | 96 |
| 18_120 | 84.4 | 76.1 | 90 | 89.2 | 78.8 | 96 |
| 18_98 | 84.3 | 75.8 | 90 | 89.2 | 78.8 | 96 |
| 18_122 | 84.4 | 76.1 | 90 | 89.2 | 78.8 | 96 |
| 19_26 | 83.2 | 73.1 | 90 | 89.2 | 78.8 | 96 |
| 19_31 | 87.4 | 76.1 | 95 | 89.2 | 78.8 | 96 |
| 19_52 | 86.8 | 80.6 | 91 | 89.2 | 78.8 | 96 |
| 20_33 | 88 | 79.1 | 94 | 89.2 | 78.8 | 96 |
| 20_111 | 88.6 | 77.6 | 96 | 89.2 | 78.8 | 96 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 24_38 | 84.4 | 71.6 | 93 | 89.2 | 78.8 | 96 |
| 25_38 | 85 | 67.2 | 97 | 89.2 | 78.8 | 96 |
| 30_112 | 85 | 79.1 | 89 | 89.2 | 78.8 | 96 |
| 30_94 | 82.6 | 73.1 | 89 | 89.2 | 78.8 | 96 |
| 33_71 | 82.6 | 73.1 | 89 | 89.2 | 78.8 | 96 |
| 33_99 | 83.8 | 68.7 | 94 | 89.2 | 78.8 | 96 |
| 98_111 | 77.7 | 56.1 | 92 | 89.2 | 78.8 | 96 |
| 37_70 | 79 | 71.6 | 84 | 89.2 | 78.8 | 96 |
| 38_46 | 87.4 | 76.1 | 95 | 89.2 | 78.8 | 96 |
| 40_42 | 82.6 | 61.2 | 97 | 89.2 | 78.8 | 96 |
| 41_120 | 80.8 | 73.1 | 86 | 89.2 | 78.8 | 96 |
| 96_113 | 85 | 74.6 | 92 | 89.2 | 78.8 | 96 |
| 36_106 | 91 | 79.1 | 99 | 88 | 78.8 | 94 |
| 37_106 | 91 | 80.6 | 98 | 88 | 78.8 | 94 |
| 60_106 | 91.6 | 82.1 | 98 | 88 | 78.8 | 94 |
| 62_106 | 91 | 80.6 | 98 | 88 | 78.8 | 94 |
| 74_106 | 91 | 80.6 | 98 | 88 | 78.8 | 94 |
| 90_106 | 89.8 | 77.6 | 98 | 88 | 78.8 | 94 |
| 3_107 | 92.8 | 86.6 | 97 | 88 | 78.8 | 94 |
| 6_107 | 88 | 76.1 | 96 | 88 | 78.8 | 94 |
| 27_107 | 91 | 83.6 | 96 | 88 | 78.8 | 94 |
| 48_107 | 91 | 82.1 | 97 | 88 | 78.8 | 94 |
| 57_107 | 91 | 82.1 | 97 | 88 | 78.8 | 94 |
| 73_107 | 91 | 80.6 | 98 | 88 | 78.8 | 94 |
| 102_107 | 90.4 | 79.1 | 98 | 88 | 78.8 | 94 |
| 3_37 | 91.6 | 88.1 | 94 | 88 | 78.8 | 94 |
| 27_108 | 90.4 | 79.1 | 98 | 88 | 78.8 | 94 |
| 33_108 | 86.8 | 73.1 | 96 | 88 | 78.8 | 94 |
| 57_108 | 87.4 | 71.6 | 98 | 88 | 78.8 | 94 |
| 6_9 | 88.6 | 79.1 | 95 | 88 | 78.8 | 94 |
| 6_25 | 86.2 | 74.6 | 94 | 88 | 78.8 | 94 |
| 6_85 | 86.2 | 79.1 | 91 | 88 | 78.8 | 94 |
| 6_98 | 86.7 | 77.3 | 93 | 88 | 78.8 | 94 |
| 7_60 | 92.8 | 89.6 | 95 | 88 | 78.8 | 94 |
| 8_31 | 89.2 | 82.1 | 94 | 88 | 78.8 | 94 |
| 8_42 | 89.8 | 79.1 | 97 | 88 | 78.8 | 94 |
| 26_110 | 91 | 86.6 | 94 | 88 | 78.8 | 94 |
| 9_38 | 83.2 | 76.1 | 88 | 88 | 78.8 | 94 |
| 10_19 | 88.6 | 79.1 | 95 | 88 | 78.8 | 94 |
| 10_43 | 88 | 83.6 | 91 | 88 | 78.8 | 94 |
| 12_13 | 92.2 | 89.4 | 94 | 88 | 78.8 | 94 |
| 13_29 | 89.2 | 82.1 | 94 | 88 | 78.8 | 94 |
| 13_39 | 86.8 | 74.6 | 95 | 88 | 78.8 | 94 |
| 14_52 | 89.2 | 79.1 | 96 | 88 | 78.8 | 94 |
| 15_119 | 85 | 77.6 | 90 | 88 | 78.8 | 94 |
| 17_54 | 87.4 | 71.6 | 98 | 88 | 78.8 | 94 |
| 17_64 | 85 | 68.7 | 96 | 88 | 78.8 | 94 |
| 17_120 | 84.4 | 68.7 | 95 | 88 | 78.8 | 94 |
| 18_29 | 85 | 74.6 | 92 | 88 | 78.8 | 94 |
| 18_114 | 85 | 74.6 | 92 | 88 | 78.8 | 94 |
| 18_71 | 80.2 | 70.1 | 87 | 88 | 78.8 | 94 |
| 18_86 | 86.2 | 77.6 | 92 | 88 | 78.8 | 94 |
| 18_92 | 84.4 | 76.1 | 90 | 88 | 78.8 | 94 |
| 18_99 | 83.8 | 74.6 | 90 | 88 | 78.8 | 94 |
| 20_25 | 89.8 | 83.6 | 94 | 88 | 78.8 | 94 |
| 24_49 | 83.8 | 79.1 | 87 | 88 | 78.8 | 94 |
| 24_116 | 82.6 | 67.2 | 93 | 88 | 78.8 | 94 |
| 24_87 | 82.6 | 68.7 | 92 | 88 | 78.8 | 94 |
| 30_39 | 89.8 | 82.1 | 95 | 88 | 78.8 | 94 |
| 30_70 | 85.6 | 74.6 | 93 | 88 | 78.8 | 94 |
| 34_38 | 85 | 74.6 | 92 | 88 | 78.8 | 94 |
| 38_98 | 82.5 | 65.2 | 94 | 88 | 78.8 | 94 |
| 39_113 | 87.4 | 76.1 | 95 | 88 | 78.8 | 94 |
| 39_60 | 88 | 74.6 | 97 | 88 | 78.8 | 94 |
| 40_46 | 85 | 74.6 | 92 | 88 | 78.8 | 94 |
| 41_66 | 79.6 | 62.7 | 91 | 88 | 78.8 | 94 |
| 41_83 | 79 | 65.7 | 88 | 88 | 78.8 | 94 |
| 71_112 | 79.6 | 65.7 | 89 | 88 | 78.8 | 94 |
| 83_112 | 77.2 | 64.2 | 86 | 88 | 78.8 | 94 |
| 46_62 | 80.2 | 70.1 | 87 | 88 | 78.8 | 94 |
| 58_73 | 80.8 | 71.6 | 87 | 88 | 78.8 | 94 |
| 59_119 | 82 | 64.2 | 94 | 88 | 78.8 | 94 |
| 67_115 | 78.4 | 68.7 | 85 | 88 | 78.8 | 94 |
| 83_115 | 83.8 | 73.1 | 91 | 88 | 78.8 | 94 |
| 70_120 | 76 | 59.7 | 87 | 88 | 78.8 | 94 |
| 72_107 | 89.2 | 79.1 | 96 | 87.8 | 78.8 | 93.9 |
| 22_106 | 89.2 | 79.1 | 96 | 86.7 | 78.8 | 92 |
| 32_106 | 91 | 77.6 | 100 | 86.7 | 78.8 | 92 |
| 33_106 | 90.4 | 80.6 | 97 | 86.7 | 78.8 | 92 |
| 11_107 | 89.8 | 80.6 | 96 | 86.7 | 78.8 | 92 |
| 3_98 | 90.4 | 86.4 | 93 | 86.7 | 78.8 | 92 |
| 5_61 | 89.8 | 86.6 | 92 | 86.7 | 78.8 | 92 |
| 5_70 | 87.4 | 80.6 | 92 | 86.7 | 78.8 | 92 |
| 5_101 | 87.4 | 80.6 | 92 | 86.7 | 78.8 | 92 |
| 6_83 | 85.6 | 76.1 | 92 | 86.7 | 78.8 | 92 |
| 41_109 | 89.2 | 83.6 | 93 | 86.7 | 78.8 | 92 |
| 9_111 | 83.8 | 71.6 | 92 | 86.7 | 78.8 | 92 |
| 9_43 | 88.6 | 85.1 | 91 | 86.7 | 78.8 | 92 |
| 9_113 | 86.8 | 79.1 | 92 | 86.7 | 78.8 | 92 |
| 9_115 | 85 | 79.1 | 89 | 86.7 | 78.8 | 92 |
| 10_14 | 87.4 | 76.1 | 95 | 86.7 | 78.8 | 92 |
| 10_21 | 89.8 | 82.1 | 95 | 86.7 | 78.8 | 92 |
| 10_33 | 85 | 73.1 | 93 | 86.7 | 78.8 | 92 |
| 11_28 | 86.8 | 76.1 | 94 | 86.7 | 78.8 | 92 |
| 11_113 | 86.8 | 77.6 | 93 | 86.7 | 78.8 | 92 |
| 13_58 | 85 | 76.1 | 91 | 86.7 | 78.8 | 92 |
| 13_68 | 87.4 | 79.1 | 93 | 86.7 | 78.8 | 92 |
| 13_115 | 85.6 | 82.1 | 88 | 86.7 | 78.8 | 92 |
| 14_26 | 89.2 | 76.1 | 98 | 86.7 | 78.8 | 92 |
| 14_31 | 84.4 | 70.1 | 94 | 86.7 | 78.8 | 92 |
| 14_119 | 88 | 76.1 | 96 | 86.7 | 78.8 | 92 |
| 15_42 | 85 | 68.7 | 96 | 86.7 | 78.8 | 92 |
| 17_22 | 85 | 71.6 | 94 | 86.7 | 78.8 | 92 |
| 17_46 | 84.4 | 71.6 | 93 | 86.7 | 78.8 | 92 |
| 17_55 | 88 | 74.6 | 97 | 86.7 | 78.8 | 92 |
| 17_58 | 85 | 73.1 | 93 | 86.7 | 78.8 | 92 |
| 17_65 | 85 | 70.1 | 95 | 86.7 | 78.8 | 92 |
| 17_94 | 83.2 | 68.7 | 93 | 86.7 | 78.8 | 92 |
| 18_28 | 89.8 | 82.1 | 95 | 86.7 | 78.8 | 92 |
| 18_61 | 85.6 | 76.1 | 92 | 86.7 | 78.8 | 92 |
| 18_121 | 83.8 | 77.6 | 88 | 86.7 | 78.8 | 92 |
| 19_81 | 86.1 | 80.3 | 90 | 86.7 | 78.8 | 92 |
| 22_113 | 87.4 | 80.6 | 92 | 86.7 | 78.8 | 92 |
| 24_113 | 83.2 | 73.1 | 90 | 86.7 | 78.8 | 92 |
| 25_40 | 86.2 | 73.1 | 95 | 86.7 | 78.8 | 92 |
| 25_42 | 84.4 | 71.6 | 93 | 86.7 | 78.8 | 92 |
| 25_116 | 84.4 | 74.6 | 91 | 86.7 | 78.8 | 92 |
| 26_29 | 85 | 74.6 | 92 | 86.7 | 78.8 | 92 |
| 29_70 | 82 | 71.6 | 89 | 86.7 | 78.8 | 92 |
| 30_119 | 80.2 | 74.6 | 84 | 86.7 | 78.8 | 92 |
| 33_55 | 83.2 | 67.2 | 94 | 86.7 | 78.8 | 92 |
| 36_119 | 80.8 | 71.6 | 87 | 86.7 | 78.8 | 92 |
| 55_111 | 81.4 | 67.2 | 91 | 86.7 | 78.8 | 92 |
| 37_66 | 79 | 68.7 | 86 | 86.7 | 78.8 | 92 |
| 39_46 | 77.8 | 65.7 | 86 | 86.7 | 78.8 | 92 |
| 39_70 | 78.4 | 64.2 | 88 | 86.7 | 78.8 | 92 |
| 39_75 | 77.8 | 65.7 | 86 | 86.7 | 78.8 | 92 |
| 40_112 | 86.8 | 74.6 | 95 | 86.7 | 78.8 | 92 |
| 41_67 | 80.2 | 64.2 | 91 | 86.7 | 78.8 | 92 |
| 91_112 | 82.6 | 65.7 | 94 | 86.7 | 78.8 | 92 |
| 93_112 | 77.8 | 65.7 | 86 | 86.7 | 78.8 | 92 |
| 46_55 | 79 | 64.2 | 89 | 86.7 | 78.8 | 92 |
| 66_113 | 83.8 | 68.7 | 94 | 86.7 | 78.8 | 92 |
| 79_113 | 84.4 | 73.1 | 92 | 86.7 | 78.8 | 92 |
| 52_53 | 84.4 | 79.1 | 88 | 86.7 | 78.8 | 92 |
| 58_119 | 75.4 | 62.7 | 84 | 86.7 | 78.8 | 92 |
| 58_87 | 82 | 74.6 | 87 | 86.7 | 78.8 | 92 |
| 98_115 | 81.9 | 65.2 | 93 | 86.7 | 78.8 | 92 |
| 15_106 | 89.8 | 77.6 | 98 | 85.5 | 78.8 | 90 |
| 65_106 | 93.4 | 86.6 | 98 | 85.5 | 78.8 | 90 |
| 81_106 | 91 | 80.3 | 98 | 85.5 | 78.8 | 90 |
| 85_106 | 88.6 | 79.1 | 95 | 85.5 | 78.8 | 90 |
| 69_107 | 87.4 | 77.6 | 94 | 85.5 | 78.8 | 90 |
| 3_9 | 93.4 | 88.1 | 97 | 85.5 | 78.8 | 90 |
| 3_45 | 92.8 | 86.6 | 97 | 85.5 | 78.8 | 90 |
| 3_46 | 93.4 | 88.1 | 97 | 85.5 | 78.8 | 90 |
| 61_108 | 91.6 | 86.6 | 95 | 85.5 | 78.8 | 90 |
| 73_108 | 86.2 | 73.1 | 95 | 85.5 | 78.8 | 90 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 5_58 | 86.8 | 77.6 | 93 | 85.5 | 78.8 | 90 |
| 5_69 | 90.4 | 83.6 | 95 | 85.5 | 78.8 | 90 |
| 5_76 | 90.4 | 83.6 | 95 | 85.5 | 78.8 | 90 |
| 5_84 | 89.2 | 85.1 | 92 | 85.5 | 78.8 | 90 |
| 5_92 | 88.6 | 85.1 | 91 | 85.5 | 78.8 | 90 |
| 5_95 | 89.8 | 83.6 | 94 | 85.5 | 78.8 | 90 |
| 6_11 | 85.6 | 74.6 | 93 | 85.5 | 78.8 | 90 |
| 8_35 | 89.2 | 82.1 | 94 | 85.5 | 78.8 | 90 |
| 8_40 | 87.4 | 76.1 | 95 | 85.5 | 78.8 | 90 |
| 9_10 | 86.8 | 82.1 | 90 | 85.5 | 78.8 | 90 |
| 9_32 | 84.4 | 79.1 | 88 | 85.5 | 78.8 | 90 |
| 9_48 | 84.4 | 80.6 | 87 | 85.5 | 78.8 | 90 |
| 10_25 | 82.6 | 73.1 | 89 | 85.5 | 78.8 | 90 |
| 10_70 | 88 | 77.6 | 95 | 85.5 | 78.8 | 90 |
| 12_66 | 82.5 | 72.7 | 89 | 85.5 | 78.8 | 90 |
| 12_95 | 85.5 | 78.8 | 90 | 85.5 | 78.8 | 90 |
| 13_34 | 91 | 85.1 | 95 | 85.5 | 78.8 | 90 |
| 13_52 | 89.2 | 82.1 | 94 | 85.5 | 78.8 | 90 |
| 13_99 | 84.4 | 80.6 | 87 | 85.5 | 78.8 | 90 |
| 15_52 | 88 | 82.1 | 92 | 85.5 | 78.8 | 90 |
| 16_55 | 84.4 | 79.1 | 88 | 85.5 | 78.8 | 90 |
| 17_45 | 85.6 | 73.1 | 94 | 85.5 | 78.8 | 90 |
| 17_118 | 83.8 | 70.1 | 93 | 85.5 | 78.8 | 90 |
| 17_83 | 83.2 | 67.2 | 94 | 85.5 | 78.8 | 90 |
| 17_85 | 83.8 | 67.2 | 95 | 85.5 | 78.8 | 90 |
| 17_88 | 82 | 67.2 | 92 | 85.5 | 78.8 | 90 |
| 17_97 | 83.2 | 70.1 | 92 | 85.5 | 78.8 | 90 |
| 18_65 | 86.2 | 76.1 | 93 | 85.5 | 78.8 | 90 |
| 21_32 | 84.4 | 80.6 | 87 | 85.5 | 78.8 | 90 |
| 21_73 | 79.6 | 76.1 | 82 | 85.5 | 78.8 | 90 |
| 22_40 | 87.4 | 76.1 | 95 | 85.5 | 78.8 | 90 |
| 22_57 | 86.8 | 79.1 | 92 | 85.5 | 78.8 | 90 |
| 22_76 | 77.8 | 64.2 | 87 | 85.5 | 78.8 | 90 |
| 24_28 | 85 | 79.1 | 89 | 85.5 | 78.8 | 90 |
| 24_111 | 83.8 | 73.1 | 91 | 85.5 | 78.8 | 90 |
| 24_47 | 77.8 | 65.7 | 86 | 85.5 | 78.8 | 90 |
| 24_62 | 82.6 | 68.7 | 92 | 85.5 | 78.8 | 90 |
| 25_43 | 85 | 76.1 | 91 | 85.5 | 78.8 | 90 |
| 25_51 | 83.2 | 71.6 | 91 | 85.5 | 78.8 | 90 |
| 25_113 | 83.2 | 68.7 | 93 | 85.5 | 78.8 | 90 |
| 25_115 | 82.6 | 68.7 | 92 | 85.5 | 78.8 | 90 |
| 28_55 | 87.4 | 76.1 | 95 | 85.5 | 78.8 | 90 |
| 28_58 | 87.4 | 79.1 | 93 | 85.5 | 78.8 | 90 |
| 29_119 | 83.8 | 80.6 | 86 | 85.5 | 78.8 | 90 |
| 34_115 | 82.6 | 73.1 | 89 | 85.5 | 78.8 | 90 |
| 99_111 | 81.4 | 62.7 | 94 | 85.5 | 78.8 | 90 |
| 38_55 | 88 | 73.1 | 98 | 85.5 | 78.8 | 90 |
| 39_104 | 80.2 | 65.7 | 90 | 85.5 | 78.8 | 90 |
| 40_81 | 80.7 | 68.2 | 89 | 85.5 | 78.8 | 90 |
| 41_79 | 81.4 | 68.7 | 90 | 85.5 | 78.8 | 90 |
| 42_112 | 82 | 67.2 | 92 | 85.5 | 78.8 | 90 |
| 42_56 | 82 | 71.6 | 89 | 85.5 | 78.8 | 90 |
| 68_112 | 82.6 | 70.1 | 91 | 85.5 | 78.8 | 90 |
| 45_66 | 79 | 68.7 | 86 | 85.5 | 78.8 | 90 |
| 51_81 | 77.7 | 66.7 | 85 | 85.5 | 78.8 | 90 |
| 51_98 | 80.7 | 72.7 | 86 | 85.5 | 78.8 | 90 |
| 94_113 | 84.4 | 70.1 | 94 | 85.5 | 78.8 | 90 |
| 58_117 | 78.4 | 61.2 | 90 | 85.5 | 78.8 | 90 |
| 58_80 | 78.4 | 62.7 | 89 | 85.5 | 78.8 | 90 |
| 58_99 | 76.6 | 61.2 | 87 | 85.5 | 78.8 | 90 |
| 62_66 | 79 | 64.2 | 89 | 85.5 | 78.8 | 90 |
| 99_114 | 79 | 67.2 | 87 | 85.5 | 78.8 | 90 |
| 81_115 | 78.3 | 66.7 | 86 | 85.5 | 78.8 | 90 |
| 76_98 | 80.7 | 69.7 | 88 | 85.5 | 78.8 | 90 |
| 27_106 | 89.2 | 76.1 | 98 | 84.3 | 78.8 | 88 |
| 68_106 | 89.8 | 79.1 | 97 | 84.3 | 78.8 | 88 |
| 75_106 | 88 | 74.6 | 97 | 84.3 | 78.8 | 88 |
| 84_106 | 89.2 | 79.1 | 96 | 84.3 | 78.8 | 88 |
| 91_106 | 89.8 | 79.1 | 97 | 84.3 | 78.8 | 88 |
| 3_111 | 88.6 | 79.1 | 95 | 84.3 | 78.8 | 88 |
| 3_103 | 91.6 | 86.6 | 95 | 84.3 | 78.8 | 88 |
| 4_110 | 91 | 86.6 | 94 | 84.3 | 78.8 | 88 |
| 95_108 | 89.8 | 85.1 | 93 | 84.3 | 78.8 | 88 |
| 104_108 | 88 | 79.1 | 94 | 84.3 | 78.8 | 88 |
| 5_110 | 95.2 | 91 | 98 | 84.3 | 78.8 | 88 |
| 5_27 | 88.6 | 83.6 | 92 | 84.3 | 78.8 | 88 |
| 6_39 | 89.8 | 85.1 | 93 | 84.3 | 78.8 | 88 |
| 6_45 | 90.4 | 80.6 | 97 | 84.3 | 78.8 | 88 |
| 6_67 | 87.4 | 74.6 | 96 | 84.3 | 78.8 | 88 |
| 6_93 | 87.4 | 76.1 | 95 | 84.3 | 78.8 | 88 |
| 9_59 | 86.8 | 79.1 | 92 | 84.3 | 78.8 | 88 |
| 9_86 | 85.6 | 80.6 | 89 | 84.3 | 78.8 | 88 |
| 9_88 | 83.8 | 79.1 | 87 | 84.3 | 78.8 | 88 |
| 9_103 | 82.6 | 74.6 | 88 | 84.3 | 78.8 | 88 |
| 9_104 | 81.4 | 76.1 | 85 | 84.3 | 78.8 | 88 |
| 10_60 | 83.8 | 71.6 | 92 | 84.3 | 78.8 | 88 |
| 11_47 | 83.8 | 74.6 | 90 | 84.3 | 78.8 | 88 |
| 11_76 | 82 | 71.6 | 89 | 84.3 | 78.8 | 88 |
| 11_120 | 79.6 | 68.7 | 87 | 84.3 | 78.8 | 88 |
| 12_16 | 88 | 89.4 | 87 | 84.3 | 78.8 | 88 |
| 12_31 | 87.3 | 80.3 | 92 | 84.3 | 78.8 | 88 |
| 12_78 | 85.5 | 80.3 | 89 | 84.3 | 78.8 | 88 |
| 13_62 | 83.2 | 82.1 | 84 | 84.3 | 78.8 | 88 |
| 13_93 | 83.8 | 82.1 | 85 | 84.3 | 78.8 | 88 |
| 14_100 | 85.6 | 71.6 | 95 | 84.3 | 78.8 | 88 |
| 16_34 | 88 | 85.1 | 90 | 84.3 | 78.8 | 88 |
| 16_39 | 89.2 | 86.6 | 91 | 84.3 | 78.8 | 88 |
| 16_97 | 84.4 | 85.1 | 84 | 84.3 | 78.8 | 88 |
| 17_27 | 85 | 70.1 | 95 | 84.3 | 78.8 | 88 |
| 17_39 | 84.4 | 74.6 | 91 | 84.3 | 78.8 | 88 |
| 17_44 | 85 | 70.1 | 95 | 84.3 | 78.8 | 88 |
| 17_121 | 83.2 | 67.2 | 94 | 84.3 | 78.8 | 88 |
| 22_74 | 83.2 | 77.6 | 87 | 84.3 | 78.8 | 88 |
| 24_84 | 79.6 | 68.7 | 87 | 84.3 | 78.8 | 88 |
| 25_32 | 84.4 | 73.1 | 92 | 84.3 | 78.8 | 88 |
| 25_74 | 83.8 | 74.6 | 90 | 84.3 | 78.8 | 88 |
| 25_76 | 80.8 | 67.2 | 90 | 84.3 | 78.8 | 88 |
| 25_91 | 81.4 | 67.2 | 91 | 84.3 | 78.8 | 88 |
| 27_28 | 83.2 | 74.6 | 89 | 84.3 | 78.8 | 88 |
| 28_94 | 82 | 73.1 | 88 | 84.3 | 78.8 | 88 |
| 28_96 | 86.2 | 76.1 | 93 | 84.3 | 78.8 | 88 |
| 29_42 | 80.2 | 64.2 | 91 | 84.3 | 78.8 | 88 |
| 29_96 | 78.4 | 70.1 | 84 | 84.3 | 78.8 | 88 |
| 31_115 | 80.8 | 67.2 | 90 | 84.3 | 78.8 | 88 |
| 32_46 | 85 | 77.6 | 90 | 84.3 | 78.8 | 88 |
| 32_55 | 86.8 | 82.1 | 90 | 84.3 | 78.8 | 88 |
| 35_111 | 82 | 65.7 | 93 | 84.3 | 78.8 | 88 |
| 35_86 | 78.4 | 64.2 | 88 | 84.3 | 78.8 | 88 |
| 37_100 | 79 | 67.2 | 87 | 84.3 | 78.8 | 88 |
| 39_44 | 80.2 | 67.2 | 89 | 84.3 | 78.8 | 88 |
| 40_66 | 81.4 | 61.2 | 95 | 84.3 | 78.8 | 88 |
| 42_66 | 80.2 | 59.7 | 94 | 84.3 | 78.8 | 88 |
| 76_112 | 88 | 80.6 | 93 | 84.3 | 78.8 | 88 |
| 78_112 | 77.2 | 61.2 | 88 | 84.3 | 78.8 | 88 |
| 81_112 | 77.7 | 62.1 | 88 | 84.3 | 78.8 | 88 |
| 44_78 | 79.6 | 68.7 | 87 | 84.3 | 78.8 | 88 |
| 46_75 | 75.4 | 67.2 | 81 | 84.3 | 78.8 | 88 |
| 46_85 | 76.6 | 61.2 | 87 | 84.3 | 78.8 | 88 |
| 46_93 | 74.9 | 59.7 | 85 | 84.3 | 78.8 | 88 |
| 51_55 | 79 | 67.2 | 87 | 84.3 | 78.8 | 88 |
| 53_67 | 77.2 | 67.2 | 84 | 84.3 | 78.8 | 88 |
| 53_75 | 81.4 | 70.1 | 89 | 84.3 | 78.8 | 88 |
| 53_83 | 76.6 | 62.7 | 86 | 84.3 | 78.8 | 88 |
| 55_62 | 83.8 | 70.1 | 93 | 84.3 | 78.8 | 88 |
| 56_58 | 79 | 64.2 | 89 | 84.3 | 78.8 | 88 |
| 56_114 | 79 | 70.1 | 85 | 84.3 | 78.8 | 88 |
| 56_119 | 77.8 | 65.7 | 86 | 84.3 | 78.8 | 88 |
| 62_70 | 80.2 | 64.2 | 91 | 84.3 | 78.8 | 88 |
| 65_70 | 83.2 | 70.1 | 92 | 84.3 | 78.8 | 88 |
| 65_98 | 76.5 | 62.1 | 86 | 84.3 | 78.8 | 88 |
| 66_71 | 80.2 | 67.2 | 89 | 84.3 | 78.8 | 88 |
| 66_74 | 80.8 | 67.2 | 90 | 84.3 | 78.8 | 88 |
| 66_81 | 77.7 | 62.1 | 88 | 84.3 | 78.8 | 88 |
| 66_89 | 80.2 | 68.7 | 88 | 84.3 | 78.8 | 88 |
| 75_114 | 81.4 | 70.1 | 89 | 84.3 | 78.8 | 88 |
| 71_104 | 80.8 | 65.7 | 91 | 84.3 | 78.8 | 88 |
| 81_89 | 77.1 | 62.1 | 87 | 84.3 | 78.8 | 88 |
| 90_98 | 74.1 | 57.6 | 85 | 84.3 | 78.8 | 88 |

TABLE 6-continued

| SEQ ID NO: | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 72_106 | 89.2 | 79.1 | 96 | 84.1 | 78.8 | 87.8 |
| 9_72 | 85 | 79.1 | 89 | 84.1 | 78.8 | 87.8 |
| 18_72 | 87.4 | 80.6 | 92 | 84.1 | 78.8 | 87.8 |
| 6_106 | 89.8 | 79.1 | 97 | 83.1 | 78.8 | 86 |
| 10_106 | 88 | 76.1 | 96 | 83.1 | 78.8 | 86 |
| 11_106 | 89.2 | 77.6 | 97 | 83.1 | 78.8 | 86 |
| 42_106 | 89.2 | 77.6 | 97 | 83.1 | 78.8 | 86 |
| 57_106 | 89.2 | 76.1 | 98 | 83.1 | 78.8 | 86 |
| 69_106 | 89.2 | 77.6 | 97 | 83.1 | 78.8 | 86 |
| 76_106 | 89.2 | 77.6 | 97 | 83.1 | 78.8 | 86 |
| 3_56 | 91.6 | 85.1 | 96 | 83.1 | 78.8 | 86 |
| 5_67 | 87.4 | 82.1 | 91 | 83.1 | 78.8 | 86 |
| 6_121 | 86.8 | 76.1 | 94 | 83.1 | 78.8 | 86 |
| 46_110 | 83.8 | 77.6 | 88 | 83.1 | 78.8 | 86 |
| 9_28 | 86.2 | 86.6 | 86 | 83.1 | 78.8 | 86 |
| 9_64 | 82.6 | 74.6 | 88 | 83.1 | 78.8 | 86 |
| 9_76 | 83.8 | 77.6 | 88 | 83.1 | 78.8 | 86 |
| 9_79 | 85.6 | 79.1 | 90 | 83.1 | 78.8 | 86 |
| 9_82 | 84.4 | 79.1 | 88 | 83.1 | 78.8 | 86 |
| 9_95 | 86.8 | 80.6 | 91 | 83.1 | 78.8 | 86 |
| 9_101 | 85.6 | 83.6 | 87 | 83.1 | 78.8 | 86 |
| 10_11 | 85.6 | 74.6 | 93 | 83.1 | 78.8 | 86 |
| 10_111 | 82 | 68.7 | 91 | 83.1 | 78.8 | 86 |
| 10_40 | 85.6 | 74.6 | 93 | 83.1 | 78.8 | 86 |
| 11_59 | 80.8 | 73.1 | 86 | 83.1 | 78.8 | 86 |
| 11_68 | 79 | 71.6 | 84 | 83.1 | 78.8 | 86 |
| 11_117 | 80.2 | 70.1 | 87 | 83.1 | 78.8 | 86 |
| 11_74 | 81.4 | 74.6 | 86 | 83.1 | 78.8 | 86 |
| 11_90 | 79.6 | 73.1 | 84 | 83.1 | 78.8 | 86 |
| 13_55 | 90.4 | 83.6 | 95 | 83.1 | 78.8 | 86 |
| 16_44 | 82.6 | 76.1 | 87 | 83.1 | 78.8 | 86 |
| 16_65 | 82.6 | 80.6 | 84 | 83.1 | 78.8 | 86 |
| 16_66 | 80.8 | 73.1 | 86 | 83.1 | 78.8 | 86 |
| 16_71 | 83.8 | 77.6 | 88 | 83.1 | 78.8 | 86 |
| 17_52 | 84.4 | 71.6 | 93 | 83.1 | 78.8 | 86 |
| 17_98 | 84.3 | 68.2 | 95 | 83.1 | 78.8 | 86 |
| 21_76 | 79 | 73.1 | 83 | 83.1 | 78.8 | 86 |
| 22_31 | 80.2 | 68.7 | 88 | 83.1 | 78.8 | 86 |
| 22_43 | 86.2 | 76.1 | 93 | 83.1 | 78.8 | 86 |
| 22_90 | 79.6 | 70.1 | 86 | 83.1 | 78.8 | 86 |
| 22_91 | 77.8 | 67.2 | 85 | 83.1 | 78.8 | 86 |
| 26_67 | 83.2 | 74.6 | 89 | 83.1 | 78.8 | 86 |
| 28_34 | 88.6 | 79.1 | 95 | 83.1 | 78.8 | 86 |
| 28_52 | 87.4 | 80.6 | 92 | 83.1 | 78.8 | 86 |
| 29_111 | 80.2 | 65.7 | 90 | 83.1 | 78.8 | 86 |
| 29_112 | 83.8 | 73.1 | 91 | 83.1 | 78.8 | 86 |
| 29_45 | 85 | 79.1 | 89 | 83.1 | 78.8 | 86 |
| 29_46 | 81.4 | 73.1 | 87 | 83.1 | 78.8 | 86 |
| 31_40 | 82 | 67.2 | 92 | 83.1 | 78.8 | 86 |
| 31_46 | 77.8 | 65.7 | 86 | 83.1 | 78.8 | 86 |
| 32_66 | 82.6 | 71.6 | 90 | 83.1 | 78.8 | 86 |
| 32_98 | 86.1 | 80.3 | 90 | 83.1 | 78.8 | 86 |
| 34_66 | 83.2 | 74.6 | 89 | 83.1 | 78.8 | 86 |
| 35_116 | 77.2 | 59.7 | 89 | 83.1 | 78.8 | 86 |
| 39_66 | 78.4 | 64.2 | 88 | 83.1 | 78.8 | 86 |
| 42_71 | 81.4 | 65.7 | 92 | 83.1 | 78.8 | 86 |
| 42_81 | 84.3 | 72.7 | 92 | 83.1 | 78.8 | 86 |
| 44_83 | 76.6 | 61.2 | 87 | 83.1 | 78.8 | 86 |
| 44_93 | 77.8 | 67.2 | 85 | 83.1 | 78.8 | 86 |
| 46_120 | 73.7 | 59.7 | 83 | 83.1 | 78.8 | 86 |
| 51_65 | 82 | 74.6 | 87 | 83.1 | 78.8 | 86 |
| 51_66 | 79.6 | 64.2 | 90 | 83.1 | 78.8 | 86 |
| 51_94 | 80.2 | 67.2 | 89 | 83.1 | 78.8 | 86 |
| 54_56 | 85.6 | 83.6 | 87 | 83.1 | 78.8 | 86 |
| 55_75 | 77.8 | 62.7 | 88 | 83.1 | 78.8 | 86 |
| 55_94 | 75.4 | 59.7 | 86 | 83.1 | 78.8 | 86 |
| 55_98 | 73.5 | 56.1 | 85 | 83.1 | 78.8 | 86 |
| 58_82 | 77.2 | 59.7 | 89 | 83.1 | 78.8 | 86 |
| 58_93 | 74.9 | 58.2 | 86 | 83.1 | 78.8 | 86 |
| 62_81 | 70.5 | 57.6 | 79 | 83.1 | 78.8 | 86 |
| 64_67 | 82.6 | 73.1 | 89 | 83.1 | 78.8 | 86 |
| 66_96 | 77.2 | 61.2 | 88 | 83.1 | 78.8 | 86 |
| 67_98 | 76.5 | 60.6 | 87 | 83.1 | 78.8 | 86 |
| 17_106 | 89.8 | 79.1 | 97 | 81.9 | 78.8 | 84 |
| 70_106 | 88.6 | 74.6 | 98 | 81.9 | 78.8 | 84 |
| 64_109 | 86.2 | 80.6 | 90 | 81.9 | 78.8 | 84 |
| 39_110 | 87.4 | 83.6 | 90 | 81.9 | 78.8 | 84 |
| 9_31 | 83.8 | 76.1 | 89 | 81.9 | 78.8 | 84 |
| 9_81 | 85.5 | 80.3 | 89 | 81.9 | 78.8 | 84 |
| 10_31 | 85.6 | 79.1 | 90 | 81.9 | 78.8 | 84 |
| 10_63 | 83.8 | 79.1 | 87 | 81.9 | 78.8 | 84 |
| 10_114 | 87.4 | 77.6 | 94 | 81.9 | 78.8 | 84 |
| 10_67 | 84.4 | 76.1 | 90 | 81.9 | 78.8 | 84 |
| 10_88 | 88.6 | 79.1 | 95 | 81.9 | 78.8 | 84 |
| 11_36 | 79.6 | 70.1 | 86 | 81.9 | 78.8 | 84 |
| 11_57 | 79 | 68.7 | 86 | 81.9 | 78.8 | 84 |
| 11_58 | 80.8 | 71.6 | 87 | 81.9 | 78.8 | 84 |
| 11_82 | 80.8 | 68.7 | 89 | 81.9 | 78.8 | 84 |
| 11_89 | 80.2 | 70.1 | 87 | 81.9 | 78.8 | 84 |
| 11_91 | 79.6 | 68.7 | 87 | 81.9 | 78.8 | 84 |
| 12_22 | 90.4 | 84.8 | 94 | 81.9 | 78.8 | 84 |
| 16_22 | 82 | 76.1 | 86 | 81.9 | 78.8 | 84 |
| 16_96 | 80.8 | 73.1 | 86 | 81.9 | 78.8 | 84 |
| 17_75 | 83.8 | 67.2 | 95 | 81.9 | 78.8 | 84 |
| 17_100 | 83.2 | 71.6 | 91 | 81.9 | 78.8 | 84 |
| 22_54 | 84.4 | 77.6 | 89 | 81.9 | 78.8 | 84 |
| 27_29 | 83.8 | 74.6 | 90 | 81.9 | 78.8 | 84 |
| 28_66 | 83.2 | 76.1 | 88 | 81.9 | 78.8 | 84 |
| 28_70 | 83.8 | 74.6 | 90 | 81.9 | 78.8 | 84 |
| 28_120 | 85 | 76.1 | 91 | 81.9 | 78.8 | 84 |
| 29_34 | 81.4 | 74.6 | 86 | 81.9 | 78.8 | 84 |
| 31_32 | 86.2 | 79.1 | 91 | 81.9 | 78.8 | 84 |
| 31_66 | 76 | 64.2 | 84 | 81.9 | 78.8 | 84 |
| 31_85 | 77.2 | 67.2 | 84 | 81.9 | 78.8 | 84 |
| 31_87 | 79 | 71.6 | 84 | 81.9 | 78.8 | 84 |
| 31_94 | 79 | 65.7 | 88 | 81.9 | 78.8 | 84 |
| 31_96 | 80.2 | 71.6 | 86 | 81.9 | 78.8 | 84 |
| 34_82 | 79 | 74.6 | 82 | 81.9 | 78.8 | 84 |
| 44_99 | 76 | 58.2 | 88 | 81.9 | 78.8 | 84 |
| 44_103 | 81.4 | 64.2 | 93 | 81.9 | 78.8 | 84 |
| 45_46 | 77.2 | 67.2 | 84 | 81.9 | 78.8 | 84 |
| 46_82 | 73.7 | 61.2 | 82 | 81.9 | 78.8 | 84 |
| 47_51 | 80.2 | 67.2 | 89 | 81.9 | 78.8 | 84 |
| 47_120 | 76.6 | 68.7 | 82 | 81.9 | 78.8 | 84 |
| 51_71 | 82.6 | 73.1 | 89 | 81.9 | 78.8 | 84 |
| 55_117 | 78.4 | 59.7 | 91 | 81.9 | 78.8 | 84 |
| 55_99 | 77.8 | 65.7 | 86 | 81.9 | 78.8 | 84 |
| 58_75 | 76 | 64.2 | 84 | 81.9 | 78.8 | 84 |
| 58_94 | 76.6 | 58.2 | 89 | 81.9 | 78.8 | 84 |
| 83_114 | 82.6 | 65.7 | 94 | 81.9 | 78.8 | 84 |
| 94_114 | 78.4 | 64.2 | 88 | 81.9 | 78.8 | 84 |
| 67_118 | 73.7 | 52.2 | 88 | 81.9 | 78.8 | 84 |
| 67_121 | 75.4 | 64.2 | 83 | 81.9 | 78.8 | 84 |
| 78_119 | 73.1 | 56.7 | 84 | 81.9 | 78.8 | 84 |
| 81_98 | 74.5 | 60 | 84 | 81.9 | 78.8 | 84 |
| 93_98 | 74.1 | 56.1 | 86 | 81.9 | 78.8 | 84 |
| 78_106 | 89.2 | 77.6 | 97 | 80.7 | 78.8 | 82 |
| 100_106 | 89.2 | 80.6 | 95 | 80.7 | 78.8 | 82 |
| 10_109 | 86.2 | 77.6 | 92 | 80.7 | 78.8 | 82 |
| 74_109 | 89.2 | 82.1 | 94 | 80.7 | 78.8 | 82 |
| 102_109 | 84.4 | 73.1 | 92 | 80.7 | 78.8 | 82 |
| 79_110 | 86.8 | 76.1 | 94 | 80.7 | 78.8 | 82 |
| 96_110 | 86.2 | 85.1 | 87 | 80.7 | 78.8 | 82 |
| 9_69 | 82.6 | 80.6 | 84 | 80.7 | 78.8 | 82 |
| 9_84 | 82 | 77.6 | 85 | 80.7 | 78.8 | 82 |
| 9_93 | 82.6 | 74.6 | 88 | 80.7 | 78.8 | 82 |
| 10_78 | 85.6 | 77.6 | 91 | 80.7 | 78.8 | 82 |
| 10_93 | 83.8 | 77.6 | 88 | 80.7 | 78.8 | 82 |
| 10_103 | 85 | 77.6 | 90 | 80.7 | 78.8 | 82 |
| 11_42 | 83.2 | 76.1 | 88 | 80.7 | 78.8 | 82 |
| 11_95 | 78.4 | 68.7 | 85 | 80.7 | 78.8 | 82 |
| 11_100 | 78.4 | 68.7 | 85 | 80.7 | 78.8 | 82 |
| 24_78 | 79 | 64.2 | 89 | 80.7 | 78.8 | 82 |
| 25_28 | 82 | 74.6 | 87 | 80.7 | 78.8 | 82 |
| 25_63 | 83.8 | 76.1 | 89 | 80.7 | 78.8 | 82 |
| 28_42 | 82 | 70.1 | 90 | 80.7 | 78.8 | 82 |
| 29_56 | 80.2 | 70.1 | 87 | 80.7 | 78.8 | 82 |
| 31_111 | 81.4 | 65.7 | 92 | 80.7 | 78.8 | 82 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 32_79 | 81.4 | 73.1 | 87 | 80.7 | 78.8 | 82 |
| 92_111 | 77.2 | 62.7 | 87 | 80.7 | 78.8 | 82 |
| 39_100 | 74.9 | 61.2 | 84 | 80.7 | 78.8 | 82 |
| 42_57 | 79 | 58.2 | 93 | 80.7 | 78.8 | 82 |
| 42_121 | 81.4 | 70.1 | 89 | 80.7 | 78.8 | 82 |
| 44_100 | 76 | 61.2 | 86 | 80.7 | 78.8 | 82 |
| 100_113 | 84.4 | 74.6 | 91 | 80.7 | 78.8 | 82 |
| 55_118 | 82 | 67.2 | 92 | 80.7 | 78.8 | 82 |
| 55_81 | 76.5 | 54.5 | 91 | 80.7 | 78.8 | 82 |
| 55_87 | 77.2 | 65.7 | 85 | 80.7 | 78.8 | 82 |
| 62_93 | 77.2 | 65.7 | 85 | 80.7 | 78.8 | 82 |
| 78_114 | 77.2 | 65.7 | 85 | 80.7 | 78.8 | 82 |
| 70_96 | 74.3 | 62.7 | 82 | 80.7 | 78.8 | 82 |
| 70_103 | 80.2 | 65.7 | 90 | 80.7 | 78.8 | 82 |
| 78_80 | 74.9 | 59.7 | 85 | 80.7 | 78.8 | 82 |
| 46_72 | 79 | 71.6 | 84 | 80.5 | 78.8 | 81.6 |
| 101_109 | 86.8 | 79.1 | 92 | 79.5 | 78.8 | 80 |
| 10_95 | 82.6 | 74.6 | 88 | 79.5 | 78.8 | 80 |
| 16_78 | 82 | 76.1 | 86 | 79.5 | 78.8 | 80 |
| 21_29 | 82 | 73.1 | 88 | 79.5 | 78.8 | 80 |
| 21_95 | 81.4 | 67.2 | 91 | 79.5 | 78.8 | 80 |
| 27_45 | 83.2 | 80.6 | 85 | 79.5 | 78.8 | 80 |
| 28_45 | 89.2 | 86.6 | 91 | 79.5 | 78.8 | 80 |
| 31_114 | 81.4 | 68.7 | 90 | 79.5 | 78.8 | 80 |
| 31_80 | 79.6 | 62.7 | 91 | 79.5 | 78.8 | 80 |
| 31_88 | 79.6 | 71.6 | 85 | 79.5 | 78.8 | 80 |
| 31_97 | 82 | 73.1 | 88 | 79.5 | 78.8 | 80 |
| 42_100 | 77.8 | 56.7 | 92 | 79.5 | 78.8 | 80 |
| 45_79 | 78.4 | 67.2 | 86 | 79.5 | 78.8 | 80 |
| 46_121 | 75.4 | 61.2 | 85 | 79.5 | 78.8 | 80 |
| 46_100 | 74.9 | 64.2 | 82 | 79.5 | 78.8 | 80 |
| 55_100 | 76.6 | 59.7 | 88 | 79.5 | 78.8 | 80 |
| 56_98 | 74.7 | 60.6 | 84 | 79.5 | 78.8 | 80 |
| 58_78 | 76 | 62.7 | 85 | 79.5 | 78.8 | 80 |
| 65_79 | 79 | 62.7 | 90 | 79.5 | 78.8 | 80 |
| 65_104 | 77.8 | 67.2 | 85 | 79.5 | 78.8 | 80 |
| 67_99 | 74.9 | 58.2 | 86 | 79.5 | 78.8 | 80 |
| 78_81 | 72.3 | 59.1 | 81 | 79.5 | 78.8 | 80 |
| 78_90 | 74.3 | 61.2 | 83 | 79.5 | 78.8 | 80 |
| 79_96 | 76 | 62.7 | 85 | 79.5 | 78.8 | 80 |
| 80_121 | 74.9 | 62.7 | 83 | 79.5 | 78.8 | 80 |
| 94_99 | 71.9 | 53.7 | 84 | 79.5 | 78.8 | 80 |
| 3_92 | 92.8 | 89.6 | 95 | 78.3 | 78.8 | 78 |
| 6_109 | 86.2 | 77.6 | 92 | 78.3 | 78.8 | 78 |
| 52_110 | 85.6 | 85.1 | 86 | 78.3 | 78.8 | 78 |
| 10_42 | 84.4 | 76.1 | 90 | 78.3 | 78.8 | 78 |
| 29_67 | 82.6 | 73.1 | 89 | 78.3 | 78.8 | 78 |
| 31_83 | 78.4 | 64.2 | 88 | 78.3 | 78.8 | 78 |
| 46_52 | 79 | 70.1 | 85 | 78.3 | 78.8 | 78 |
| 67_79 | 74.9 | 56.7 | 87 | 78.3 | 78.8 | 78 |
| 67_93 | 73.1 | 53.7 | 86 | 78.3 | 78.8 | 78 |
| 67_103 | 76 | 58.2 | 88 | 78.3 | 78.8 | 78 |
| 70_92 | 75.4 | 62.7 | 84 | 78.3 | 78.8 | 78 |
| 59_109 | 83.8 | 74.6 | 90 | 77.1 | 78.8 | 76 |
| 70_109 | 83.2 | 74.6 | 89 | 77.1 | 78.8 | 76 |
| 76_109 | 82.6 | 73.1 | 89 | 77.1 | 78.8 | 76 |
| 95_109 | 86.2 | 79.1 | 91 | 77.1 | 78.8 | 76 |
| 31_42 | 81.4 | 67.2 | 91 | 77.1 | 78.8 | 76 |
| 31_55 | 83.2 | 70.1 | 92 | 77.1 | 78.8 | 76 |
| 34_55 | 80.2 | 73.1 | 85 | 77.1 | 78.8 | 76 |
| 42_78 | 76 | 59.7 | 87 | 77.1 | 78.8 | 76 |
| 67_85 | 71.3 | 56.7 | 81 | 77.1 | 78.8 | 76 |
| 78_85 | 72.5 | 55.2 | 84 | 77.1 | 78.8 | 76 |
| 79_92 | 72.5 | 52.2 | 86 | 77.1 | 78.8 | 76 |
| 94_103 | 73.7 | 50.7 | 89 | 77.1 | 78.8 | 76 |
| 99_100 | 71.9 | 52.2 | 85 | 77.1 | 78.8 | 76 |
| 36_109 | 83.8 | 74.6 | 90 | 75.9 | 78.8 | 74 |
| 91_109 | 84.4 | 76.1 | 90 | 75.9 | 78.8 | 74 |
| 46_78 | 76 | 62.7 | 85 | 75.9 | 78.8 | 74 |
| 52_67 | 76 | 65.7 | 83 | 75.9 | 78.8 | 74 |
| 63_78 | 78.4 | 74.6 | 81 | 75.9 | 78.8 | 74 |
| 67_70 | 77.8 | 61.2 | 89 | 75.9 | 78.8 | 74 |
| 69_79 | 80.2 | 71.6 | 86 | 75.9 | 78.8 | 74 |
| 31_104 | 77.8 | 65.7 | 86 | 74.7 | 78.8 | 72 |
| 63_79 | 79 | 68.7 | 86 | 74.7 | 78.8 | 72 |
| 67_92 | 73.1 | 56.7 | 84 | 74.7 | 78.8 | 72 |
| 75_78 | 76.6 | 65.7 | 84 | 74.7 | 78.8 | 72 |
| 69_78 | 74.9 | 61.2 | 84 | 73.5 | 78.8 | 70 |
| 79_100 | 74.3 | 59.7 | 84 | 73.5 | 78.8 | 70 |
| 13_23 | 91 | 82.1 | 97 | 90.2 | 78.1 | 98 |
| 23_108 | 89.2 | 80.6 | 95 | 87.8 | 78.1 | 94 |
| 8_23 | 88.6 | 79.1 | 95 | 87.8 | 78.1 | 94 |
| 41_50 | 81.4 | 67.2 | 91 | 86.6 | 78.1 | 92 |
| 50_51 | 79 | 64.2 | 89 | 85.4 | 78.1 | 90 |
| 50_87 | 78.4 | 62.7 | 89 | 85.4 | 78.1 | 90 |
| 37_50 | 82.6 | 71.6 | 90 | 84.1 | 78.1 | 88 |
| 9_23 | 87.4 | 82.1 | 91 | 82.9 | 78.1 | 86 |
| 50_68 | 79.6 | 64.2 | 90 | 82.9 | 78.1 | 86 |
| 23_106 | 89.2 | 76.1 | 98 | 81.7 | 78.1 | 84 |
| 46_50 | 76.6 | 67.2 | 83 | 81.7 | 78.1 | 84 |
| 50_75 | 76 | 64.2 | 84 | 81.7 | 78.1 | 84 |
| 50_111 | 79 | 61.2 | 91 | 80.5 | 78.1 | 82 |
| 31_50 | 82.6 | 70.1 | 91 | 78 | 78.1 | 78 |
| 50_78 | 73.7 | 62.7 | 81 | 74.4 | 78.1 | 72 |
| 77_110 | 84.4 | 76.1 | 90 | 88.9 | 77.4 | 96 |
| 18_77 | 83.2 | 74.6 | 89 | 86.4 | 77.4 | 92 |
| 77_115 | 79 | 67.2 | 87 | 86.4 | 77.4 | 92 |
| 16_77 | 85.6 | 82.1 | 88 | 85.2 | 77.4 | 90 |
| 29_77 | 83.2 | 76.1 | 88 | 85.2 | 77.4 | 90 |
| 58_77 | 74.3 | 56.7 | 86 | 85.2 | 77.4 | 90 |
| 66_77 | 76.6 | 59.7 | 88 | 85.2 | 77.4 | 90 |
| 77_104 | 79.6 | 62.7 | 91 | 84 | 77.4 | 88 |
| 11_77 | 80.2 | 71.6 | 86 | 82.7 | 77.4 | 86 |

Example 3

<Selection of Gene Markers Using all Samples and Method for Evaluating Pancreatic Cancer Discriminant Performance of Acquired Gene Markers>

In this Example, the samples of the training cohort and the validation cohort used in Examples 1 and 2 were integrated, and selection of a gene marker and evaluation of its pancreatic cancer discriminant performance were conducted using all of the samples.

Specifically, the miRNA expression levels in the sera of the 100 pancreatic cancer patients and the 150 healthy subjects obtained in the preceding Reference Examples were normalized by quantile normalization. In order to acquire diagnosis markers with higher reliability, only genes having a gene expression level of $2^6$ or higher in 50% or more of the samples in either of the pancreatic cancer patient group or the healthy subject group were selected in the gene marker selection. In order to further acquire statistical significance for discriminating a pancreatic cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant and described in Table 7 In this way, hsa-miR-4417, hsa-miR-4707-5p, hsa-miR-7847-3p, hsa-miR-2861, hsa-miR-4513, hsa-miR-6777-5p, hsa-miR-7113-3p, hsa-miR-4648, hsa-miR-3184-5p, hsa-miR-4271, hsa-miR-6791-5p, hsa-miR-642a-3p, hsa-miR-7108-5p, hsa-miR-128-1-5p, hsa-miR-5196-5p, hsa-miR-3178, hsa-miR-3656, hsa-miR-92a-2-5p, hsa-miR-6769b-5p, hsa-miR-4689, hsa-miR-6076, hsa-miR-92h-5p, hsa-miR-6774-5p, hsa-miR-486-3p, hsa-miR-6806-5p, hsa-miR-6716-5p, hsa-miR-557, hsa-miR-4673, hsa-miR-4674, hsa-miR-4442, hsa-miR-1915-3p, hsa-miR-4687-3p, and hsa-mniR-92b-3p genes, and the nucleotide sequences of SEQ ID NOs: 349 to 383 related thereto were found in addition to the genes described in Table 2. As with the nucleotide sequences of SEQ ID NOs: 1 to 122, the results obtained about the polynucleotides shown in SEQ ID NOs: 349 to 383 also showed that the measurement values were significantly lower (−) or higher (+) in the pancreatic cancer patient group than in the healthy subject group (Table 7). These results were able to be validated in the validation cohort. Thus, the presence or absence of pancreatic cancer in the newly obtained samples can be determined by the methods described in Examples 1 and 2 by using, alone or in combination, the gene expression level measurement values described in Table 7.

TABLE 7

| SEQ ID NO: | Name | p. value | Expression level in pancreatic cancer patient relative to healthy subject |
|---|---|---|---|
| 105 | hsa-miR-125a-3p | 7.05E−72 | − |
| 1 | hsa-miR-6893-5p | 4.14E−64 | − |
| 2 | hsa-miR-6075 | 1.06E−49 | + |
| 4 | hsa-miR-4294 | 5.56E−43 | − |
| 107 | hsa-miR-1469 | 1.06E−42 | + |
| 106 | hsa-miR-204-3p | 6.17E−42 | − |
| 108 | hsa-miR-575 | 1.26E−39 | − |
| 5 | hsa-miR-6729-5p | 1.24E−38 | + |
| 6 | hsa-miR-4476 | 2.46E−36 | − |
| 3 | hsa-miR-6820-5p | 1.80E−34 | − |
| 8 | hsa-miR-6765-3p | 3.08E−32 | − |
| 109 | hsa-miR-150-3p | 7.57E−31 | − |
| 7 | hsa-miR-6836-3p | 1.12E−29 | + |
| 18 | hsa-miR-4792 | 4.50E−29 | + |
| 9 | hsa-miR-6799-5p | 3.91E−28 | − |
| 10 | hsa-miR-4530 | 6.27E−27 | − |
| 13 | hsa-miR-615-5p | 2.79E−26 | − |
| 12 | hsa-miR-4454 | 4.13E−26 | − |
| 17 | hsa-miR-4450 | 6.27E−26 | − |
| 11 | hsa-miR-7641 | 1.99E−25 | − |
| 110 | hsa-miR-423-5p | 3.69E−25 | − |
| 24 | hsa-miR-6877-5p | 4.17E−25 | − |
| 19 | hsa-miR-665 | 6.54E−25 | + |
| 14 | hsa-miR-8073 | 3.32E−24 | + |
| 35 | hsa-miR-1231 | 4.73E−23 | + |
| 25 | hsa-miR-6880-5p | 4.77E−23 | − |
| 22 | hsa-miR-6789-5p | 1.52E−22 | + |
| 16 | hsa-miR-4634 | 3.85E−22 | + |
| 30 | hsa-miR-5585-3p | 8.16E−22 | + |
| 20 | hsa-miR-7975 | 1.73E−20 | − |
| 33 | hsa-miR-4651 | 3.57E−19 | − |
| 31 | hsa-miR-6085 | 3.92E−19 | − |
| 26 | hsa-miR-7977 | 4.07E−19 | − |
| 29 | hsa-miR-8089 | 2.29E−18 | − |
| 112 | hsa-miR-3188 | 3.55E−18 | + |
| 34 | hsa-miR-4433-3p | 6.97E−18 | + |
| 27 | hsa-miR-4734 | 8.43E−18 | + |
| 111 | hsa-miR-564 | 8.77E−18 | − |
| 46 | hsa-miR-6125 | 4.60E−17 | + |
| 21 | hsa-miR-7109-5p | 4.84E−17 | − |
| 23 | hsa-miR-4497 | 1.63E−16 | − |
| 41 | hsa-miR-619-5p | 2.74E−16 | + |
| 37 | hsa-miR-7114-5p | 2.89E−16 | − |
| 42 | hsa-miR-3622a-5p | 4.11E−16 | − |
| 39 | hsa-miR-8069 | 1.67E−15 | + |
| 58 | hsa-miR-3185 | 2.47E−15 | + |
| 66 | hsa-miR-4723-5p | 2.57E−15 | − |
| 38 | hsa-miR-1238-5p | 2.84E−15 | + |
| 44 | hsa-miR-6741-5p | 3.06E−15 | − |
| 40 | hsa-miR-4732-5p | 4.29E−15 | + |
| 32 | hsa-miR-6845-5p | 1.09E−14 | + |
| 55 | hsa-miR-6724-5p | 1.51E−14 | + |
| 28 | hsa-miR-6821-5p | 2.47E−14 | − |
| 50 | hsa-miR-6875-5p | 7.80E−14 | + |
| 113 | hsa-miR-1246 | 1.34E−13 | + |

TABLE 7-continued

| SEQ ID NO: | Name | p. value | Expression level in pancreatic cancer patient relative to healthy subject |
|---|---|---|---|
| 53 | hsa-miR-4736 | 2.22E−13 | + |
| 47 | hsa-miR-6805-5p | 2.32E−13 | + |
| 36 | hsa-miR-4665-5p | 5.61E−13 | − |
| 114 | hsa-miR-602 | 7.01E−13 | + |
| 45 | hsa-miR-6781-5p | 1.70E−12 | + |
| 15 | hsa-miR-663a | 1.70E−12 | + |
| 57 | hsa-miR-6726-5p | 2.61E−12 | − |
| 67 | hsa-miR-6850-5p | 4.31E−12 | + |
| 56 | hsa-miR-7107-5p | 7.43E−12 | − |
| 52 | hsa-miR-4433b-3p | 7.79E−12 | + |
| 71 | hsa-miR-4486 | 8.29E−12 | + |
| 65 | hsa-miR-6779-5p | 1.76E−11 | − |
| 115 | hsa-miR-1290 | 1.99E−11 | + |
| 51 | hsa-miR-1908-3p | 2.20E−11 | + |
| 70 | hsa-miR-8072 | 2.98E−11 | + |
| 60 | hsa-miR-1273g-3p | 6.69E−11 | + |
| 43 | hsa-miR-1260a | 1.14E−10 | − |
| 79 | hsa-miR-4534 | 2.20E−10 | − |
| 80 | hsa-miR-4449 | 2.54E−10 | + |
| 77 | hsa-miR-6780b-5p | 2.77E−10 | + |
| 49 | hsa-miR-6872-3p | 3.55E−10 | − |
| 119 | hsa-miR-187-5p | 3.74E−10 | − |
| 75 | hsa-miR-7106-5p | 4.23E−10 | − |
| 54 | hsa-miR-5100 | 5.83E−10 | − |
| 83 | hsa-miR-4467 | 6.44E−10 | + |
| 59 | hsa-miR-4638-5p | 9.61E−10 | − |
| 81 | hsa-miR-5195-3p | 1.12E−09 | − |
| 62 | hsa-miR-328-5p | 1.36E−09 | − |
| 68 | hsa-miR-760 | 2.30E−09 | − |
| 78 | hsa-miR-6090 | 2.36E−09 | + |
| 90 | hsa-miR-3162-5p | 3.27E−09 | − |
| 48 | hsa-miR-6132 | 4.46E−09 | − |
| 120 | hsa-miR-1908-5p | 4.47E−09 | + |
| 61 | hsa-miR-6778-5p | 6.12E−09 | + |
| 98 | hsa-miR-6816-5p | 9.29E−09 | + |
| 94 | hsa-miR-6722-3p | 9.46E−09 | + |
| 82 | hsa-miR-1202 | 1.14E−08 | − |
| 117 | hsa-miR-451a | 2.71E−08 | − |
| 118 | hsa-miR-24-3p | 3.63E−08 | − |
| 74 | hsa-miR-1260b | 6.21E−08 | − |
| 73 | hsa-miR-4656 | 6.81E−08 | + |
| 85 | hsa-miR-4281 | 6.81E−08 | − |
| 99 | hsa-miR-4741 | 9.33E−08 | + |
| 116 | hsa-miR-16-5p | 9.82E−08 | − |
| 121 | hsa-miR-371a-5p | 1.38E−07 | − |
| 93 | hsa-miR-1227-5p | 1.43E−07 | + |
| 63 | hsa-miR-3679-3p | 1.83E−07 | + |
| 72 | hsa-miR-1913 | 3.84E−07 | + |
| 69 | hsa-miR-7704 | 1.35E−06 | − |
| 87 | hsa-miR-4484 | 1.46E−06 | + |
| 89 | hsa-miR-3135b | 1.72E−06 | − |
| 103 | hsa-miR-4665-3p | 3.01E−06 | + |
| 349 | hsa-miR-4417 | 3.10E−06 | + |
| 350 | hsa-miR-4707-5p | 3.58E−06 | + |
| 88 | hsa-miR-6805-3p | 4.95E−06 | + |
| 351 | hsa-miR-7847-3p | 5.06E−06 | − |
| 352 | hsa-miR-2861 | 6.22E−06 | − |
| 104 | hsa-miR-718 | 7.23E−06 | + |
| 353 | hsa-miR-4513 | 7.71E−06 | − |
| 76 | hsa-miR-6889-5p | 1.88E−05 | − |
| 92 | hsa-miR-6721-5p | 2.26E−05 | + |
| 354 | hsa-miR-7111-5p | 2.67E−05 | − |
| 355 | hsa-miR-6777-5p | 3.00E−05 | − |
| 91 | hsa-miR-6768-5p | 3.39E−05 | − |
| 356 | hsa-miR-7113-3p | 3.47E−05 | + |
| 97 | hsa-miR-6727-5p | 3.73E−05 | − |
| 357 | hsa-miR-4648 | 4.03E−05 | + |
| 100 | hsa-miR-4508 | 4.48E−05 | + |
| 358 | hsa-miR-3184-5p | 4.67E−05 | + |
| 359 | hsa-miR-4271 | 4.87E−05 | − |
| 96 | hsa-miR-4746-3p | 4.91E−05 | + |
| 360 | hsa-miR-6791-5p | 7.71E−05 | + |
| 361 | hsa-miR-642a-3p | 2.26E−04 | − |
| 362 | hsa-miR-7108-5p | 2.56E−04 | + |
| 363 | hsa-miR-128-1-5p | 2.70E−04 | + |

TABLE 7-continued

| SEQ ID NO: | Name | p. value | Expression level in pancreatic cancer patient relative to healthy subject |
|---|---|---|---|
| 364 | hsa-miR-5196-5p | 2.85E-04 | − |
| 365 | hsa-miR-3178 | 6.64E-04 | + |
| 366 | hsa-miR-3656 | 7.51E-04 | + |
| 367 | hsa-miR-92a-2-5p | 1.04E-03 | − |
| 368 | hsa-miR-6769b-5p | 1.06E-03 | − |
| 369 | hsa-miR-4689 | 1.17E-03 | − |
| 370 | hsa-miR-6076 | 1.29E-03 | − |
| 371 | hsa-miR-92b-5p | 1.68E-03 | + |
| 122 | hsa-miR-550a-5p | 1.80E-03 | + |
| 372 | hsa-miR-6774-5p | 1.81E-03 | + |
| 373 | hsa-miR-486-3p | 2.00E-03 | + |
| 374 | hsa-miR-6806-5p | 2.02E-03 | + |
| 64 | hsa-miR-1228-3p | 2.28E-03 | + |
| 375 | hsa-miR-6842-5p | 2.35E-03 | + |
| 102 | hsa-miR-4327 | 2.57E-03 | − |
| 376 | hsa-miR-6716-5p | 2.70E-03 | + |
| 377 | hsa-miR-557 | 2.87E-03 | + |
| 378 | hsa-miR-4673 | 3.26E-03 | + |
| 379 | hsa-miR-4674 | 3.91E-03 | + |
| 95 | hsa-miR-4286 | 4.47E-03 | − |
| 86 | hsa-miR-4505 | 5.22E-03 | − |
| 380 | hsa-miR-4442 | 5.97E-03 | − |
| 381 | hsa-miR-1915-3p | 6.28E-03 | + |
| 382 | hsa-miR-4687-3p | 6.36E-03 | − |
| 383 | hsa-miR-92b-3p | 7.44E-03 | + |

Example 4

<Method for Evaluating Pancreatic Cancer-Specific Discriminant Performance by Combination of Plurality of Gene Markers Using Samples of Validation Cohort>

In this Example, gene expression levels of miRNAs in sera were compared between pancreatic cancer patients and a control group consisting of healthy subjects, colorectal cancer patients, stomach cancer patients, esophageal cancer patients, liver cancer patients, and benign pancreaticohiliary disease patients in the same way as the method described in Example 1 with respect to the training cohort as the sample group described in Reference Example 2 to select an additional gene marker for diagnosis. The additional gene marker for diagnosis (at least one of SEQ ID NOs: 464 to 473 and 492 to 494) thus selected was combined with the gene markers selected in Example 1 to study a method for evaluating pancreatic cancer-specific discriminant performance.

Specifically, first, the miRNA expression levels of the training cohort and the validation cohort obtained in Reference Example 2 mentioned above were combined and normalized by quantile normalization. Next. Fisher's discriminant analysis was conducted as to combinations of 1 to 4 expression level measurement values comprising at least one or more of the expression level measurement values of the newly found polynucleotides consisting of the nucleotide sequences represented by SEQ ID NOs: 1 to 104, 349 to 383, 464 to 473, and 492 to 494 among the polynucleotides consisting of the nucleotide sequences represented by SEQ ID NOs: 1 to 122, 349 to 383, 464 to 473, and 492 to 494, and the polynucleotides consisting of the nucleotide sequences represented by SEQ ID NOs: 105 and 108, to construct a discriminant for determining the presence or absence of pancreatic cancer. Next, accuracy, sensitivity, and specificity in the validation cohort were calculated using the discriminant thus prepared, with the pancreatic cancer patient group as a positive sample group and the healthy subject group, the colorectal cancer patient group, the stomach cancer patient group, the esophageal cancer patient group, the liver cancer patient group, and the benign pancreaticobiliary disease patient group as negative sample groups. The discriminant performance of the selected polynucleotides was validated using independent samples.

Most of polynucleotides consisting of the nucleotide sequences represented by these SEQ ID NOs (SEQ ID NOs: 1 to 122, 349 to 383, 464 to 473, and 492 to 494 corresponding to the miRNA markers of Table 1) or complementary sequences thereof mentioned above were able to provide relatively high accuracy, sensitivity, and specificity in the determination of the presence or absence of pancreatic cancer, and furthermore, were able to specifically discriminate pancreatic cancer from the other cancers. For example, among the combinations of multiple polynucleotides selected from the group consisting of polynucleotides consisting of the nucleotide sequences represented by SEQ ID NOs: 2, 4, 6, 7, 9, 10, 25, 28, 30, 31, 38, 48, 82, 103, 105, 108, and 464 or complementary sequences thereof (the cancer type-specific polynucleotide group 1) as polynucleotides capable of specifically binding to target markers, combinations comprising at least one or more polynucleotides preferably selected from the group consisting of polynucleotides consisting of the nucleotide sequences represented by SEQ ID NOs: 2, 4, 7, 10, and 25 or complementary sequences thereof (the cancer type-specific polynucleotide group 2) included in the cancer type-specific polynucleotide group 1 were able to specifically discriminate pancreatic cancer from the other cancers with high accuracy.

The number of the polynucleotides with cancer type specificity in the combination mentioned above can be 1, 2, 3, 4, 5, 6, 7, 8, 9, 10 or more for the combination. The combinations of 4 or more of these polynucleotides were able to exhibit discrimination accuracy of 80% or higher.

The probes used in the measurement were the above-defined nucleic acids capable of specifically binding to each polynucleotide as a target marker.

Specifically, the following results were obtained as the discrimination accuracy of the measurement using the polynucleotide consisting of the nucleotide sequence represented by SEQ II7 NO: 2 or a complementary sequence thereof as a target marker.

The measurement using one polynucleotide consisting of the nucleotide sequence represented by SEQ ID NO: 2 or a complementary sequence thereof exhibited accuracy of 91.1% in the training cohort and the highest accuracy of 85.3% in the validation cohort (Table 8). Also, for example, the measurement using the combinations of two polynucleotides comprising at least one polynucleotide consisting of the nucleotide sequence represented by SEQ ID NO: 2 or a complementary sequence thereof exhibited the highest accuracy of 93.0% in the training cohort and the highest accuracy of 91.7% in the validation cohort (Table 9). Furthermore, for example, the measurement using the combinations of three polynucleotides comprising at least one polynucleotide consisting of the nucleotide sequence represented by SEQ ID NO: 2 or a complementary sequence thereof exhibited the highest accuracy of 92.7% in the training cohort and the highest accuracy of 93.6% in the validation cohort (Table 10). Furthermore, for example, the measurement using the combinations of four polynucleotides comprising at least one polynucleotide consisting of the nucleotide sequence represented by SEQ ID NO: 2 or a complementary sequence thereof exhibited the highest accuracy of 93.3% in the training cohort and the highest accuracy of 96.2% in the validation cohort (Table 11).

Specifically, the following results were obtained as the discrimination accuracy of the measurement using the polynucleotide consisting of the nucleotide sequence represented by SEQ ID NO: 4 or a complementary sequence thereof as a target marker.

The measurement using one polynucleotide consisting of the nucleotide sequence represented by SEQ ID NO: 4 or a complementary sequence thereof exhibited accuracy of 77.1% in the training cohort and the highest accuracy of 78.8% in the validation cohort (Table 8). Also, for example, the measurement using the combinations of two polynucleotides comprising at least one polynucleotide consisting of the nucleotide sequence represented by SEQ ID NO: 4 or a complementary sequence thereof exhibited the highest accuracy of 89.8% in the training cohort and the highest accuracy of 88.5% in the validation cohort (Table 9). Furthermore, for example, the measurement using the combinations of three polynucleotides comprising at least one polynucleotide consisting of the nucleotide sequence represented by SEQ ID NO: 4 or a complementary sequence thereof exhibited the highest accuracy of 92.7% in the training cohort and the highest accuracy of 91.7% in the validation cohort (Table 10). Furthermore, for example, the measurement using the combinations of four polynucleotides comprising at least one polynucleotide consisting of the nucleotide sequence represented by SEQ ID NO: 4 or a complementary sequence thereof exhibited the highest accuracy of 92.7% in the training cohort and the highest accuracy of 93.6% in the validation cohort (Table 11).

Specifically, the following results were obtained as the discrimination accuracy of the measurement using the polynucleotide consisting of the nucleotide sequence represented by SEQ ID NO: 7 or a complementary sequence thereof as a target marker.

The measurement using one polynucleotide consisting of the nucleotide sequence represented by SEQ ID NO: 7 or a complementary sequence thereof exhibited accuracy of 86.7% in the training cohort and the highest accuracy of 82.1% in the validation cohort (Table 8). Also, for example, the measurement using the combinations of two polynucleotides comprising at least one polynucleotide consisting of the nucleotide sequence represented by SEQ ID NO: 7 or a complementary sequence thereof exhibited the highest accuracy of 90.2% in the training cohort and the highest accuracy of 89.1% in the validation cohort (Table 9). Furthermore, for example, the measurement using the combinations of three polynucleotides comprising at least one polynucleotide consisting of the nucleotide sequence represented by SEQ ID NO: 7 or a complementary sequence thereof exhibited the highest accuracy of 92.7% in the training cohort and the highest accuracy of 93.6% in the validation cohort (Table 10). Furthermore, for example, the measurement using the combinations of four polynucleotides comprising at least one polynucleotide consisting of the nucleotide sequence represented by SEQ ID NO: 7 or a complementary sequence thereof exhibited the highest accuracy of 93.3% in the training cohort and the highest accuracy of 96.2% in the validation cohort (Table 11).

Specifically, the following results were obtained as the discrimination accuracy of the measurement using the polynucleotide consisting of the nucleotide sequence represented by SEQ ID NO: 10 or a complementary sequence thereof as a target marker.

The measurement using one polynucleotide consisting of the nucleotide sequence represented by SEQ ID NO: 10 or a complementary sequence thereof exhibited accuracy of 77.1% in the training cohort and the highest accuracy of 68.6% in the validation cohort (Table 8). Also, for example, the measurement using the combinations of two polynucleotides comprising at least one polynucleotide consisting of the nucleotide sequence represented by SEQ ID NO: 10 or a complementary sequence thereof exhibited the highest accuracy of 90.8% in the training cohort and the highest accuracy of 89.7% in the validation cohort (Table 9). Furthermore, for example, the measurement using the combinations of three polynucleotides comprising at least one polynucleotide consisting of the nucleotide sequence represented by SEQ ID NO: 10 or a complementary sequence thereof exhibited the highest accuracy of 93.0% in the training cohort and the highest accuracy of 91.7% in the validation cohort (Table 10). Furthermore, for example, the measurement using the combinations of four polynucleotides comprising at least one polynucleotide consisting of the nucleotide sequence represented by SEQ ID NO: 10 or a complementary sequence thereof exhibited the highest accuracy of 93.7% in the training cohort and the highest accuracy of 93.6% in the validation cohort (Table 11).

Specifically, the following results were obtained as the discrimination accuracy of the measurement using the polynucleotide consisting of the nucleotide sequence represented by SEQ ID NO: 25 or a complementary sequence thereof as a target marker.

The measurement using one polynucleotide consisting of the nucleotide sequence represented by SEQ ID NO: 25 or a complementary sequence thereof exhibited accuracy of 82.2% in the training cohort and the highest accuracy of 75.6% in the validation cohort (Table 8). Also, for example, the measurement using the combinations of two polynucleotides comprising at least one polynucleotide consisting of the nucleotide sequence represented by SEQ ID NO: 25 or a complementary sequence thereof exhibited the highest accuracy of 90.8% in the training cohort and the highest accuracy of 87.8% in the validation cohort (Table 9). Furthermore, for example, the measurement using the combinations of three polynucleotides comprising at least one polynucleotide consisting of the nucleotide sequence represented by SEQ ID NO: 25 or a complementary sequence thereof exhibited the highest accuracy of 91.1% in the training cohort and the highest accuracy of 91.0% in the validation cohort (Table 10). Furthermore, for example, the measurement using the combinations of four polynucleotides comprising at least one polynucleotide consisting of the nucleotide sequence represented by SEQ ID NO: 25 or a complementary sequence thereof exhibited the highest accuracy of 92.7% in the training cohort and the highest accuracy of 93.6% in the validation cohort (Table 11).

Figure 4:
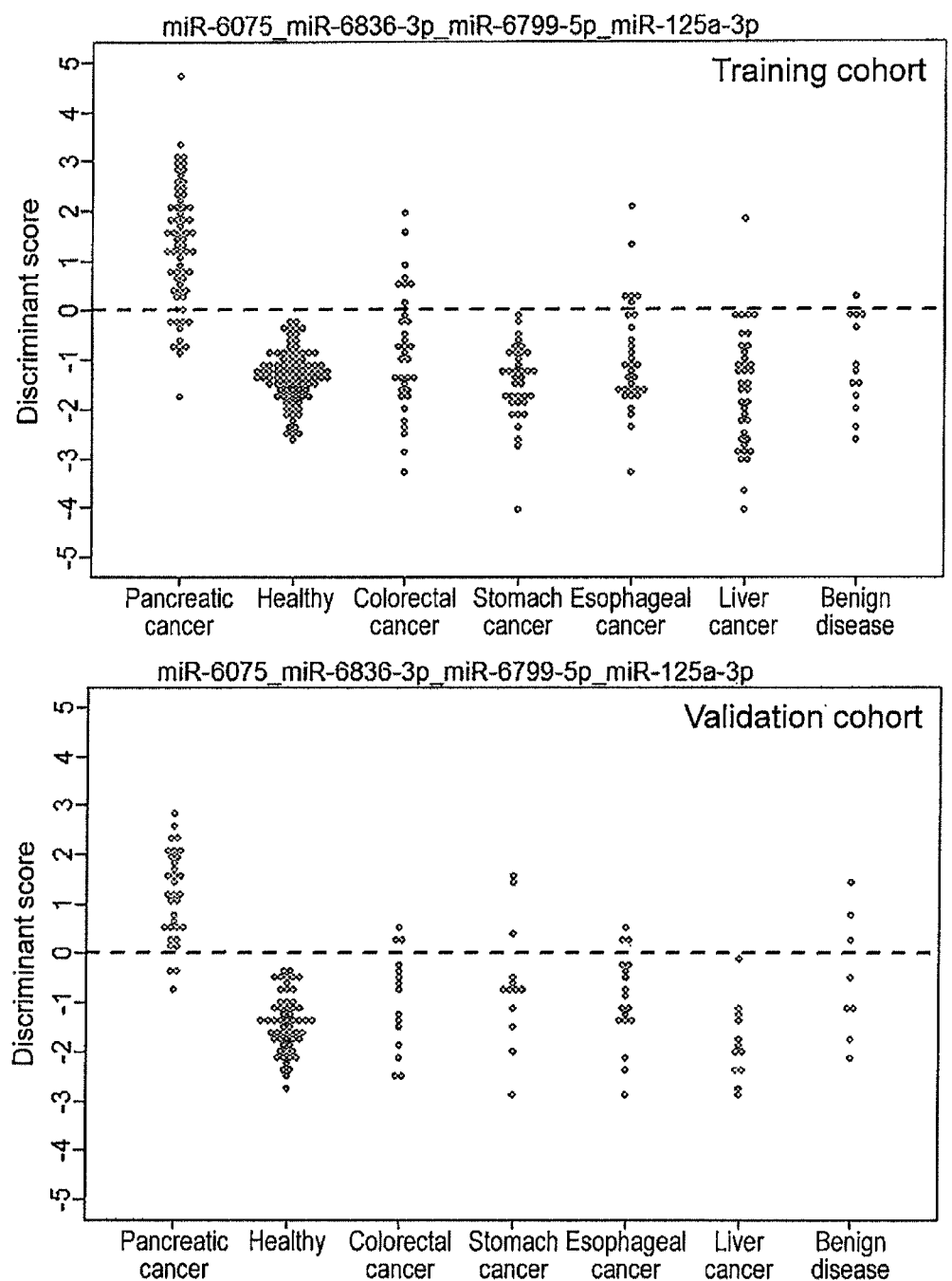
FIG. 4 Upper diagram: a discriminant (1.64×hsa-miR-6075+1.02×hsa-miR-6836-3p-0.35×hsa-miR-6799-5p-0.06×hsa-miR-125a-3p-20.67) was prepared by use of Fisher's discriminant analysis from the expression level measurement values of hsa-miR-6075 (SEQ ID NO: 2), hsa-miR-6836-3p (SEQ II) NO: 7), hsa-miR-6799-5p (SEQ ID NO: 9), and hsa-miR-125a-3p (SEQ ID NO: 105) in 67 pancreatic cancer patients, 93 healthy subjects, 35 colorectal cancer patients, 37 stomach cancer patients, 32 esophageal cancer patients, 38 liver cancer patients, and 13 benign pancreaticobiliary disease patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared from the training cohort as to the expression level measurement values of hsa-miR-6075 (SEQ ID NO: 2), hsa-miR-6799-5p (SEQ ID NO: 9), hsa-miR-125a-3p (SEQ ID NO: 105), and lisa-miR-6836-3p (SEQ ID NO: 7) in 33 pancreatic cancer patients, 57 healthy subjects, 15 colorectal cancer patients, 13 stomach cancer patients, 18 esophageal cancer patients, 12 liver cancer patients, and 8 benign pancreaticobiliary disease patients selected as a validation cohort were plotted on the ordinate against the sample groups on the abscissa. The dotted line in the diagram depicts the discriminant boundary that offered a discriminant score of 0 and discriminated between both of the groups.

The expression level measurement values of the nucleotide sequences represented by SEQ ID NOs: 2, 7, 9, and 105 were compared among 67 pancreatic cancer patients, 93 healthy subjects, 35 colorectal cancer patients, 37 stomach cancer patients, 32 esophageal cancer patients, 38 liver cancer patients, and 13 benign pancreaticobiliary disease patients in the training cohort. As a result, a scatter diagram that significantly separated the discriminant score of the pancreatic cancer patient group from the other discriminant scores was obtained in the training cohort (see the upper diagram of FIG. 4). These results were also reproducible in the validation cohort (see the lower diagram of FIG. 4).

Tables 8, 9, 10, and 11 mentioned above are as follows.

TABLE 8

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2 | 91.1 | 83.6 | 93.1 | 85.3 | 69.7 | 89.4 |
| 4 | 77.1 | 77.6 | 77 | 78.8 | 81.8 | 78 |
| 6 | 81 | 76.1 | 82.3 | 75 | 60.6 | 78.9 |
| 7 | 86.7 | 89.6 | 85.9 | 82.1 | 87.9 | 80.5 |
| 9 | 78.4 | 85.1 | 76.6 | 75 | 90.9 | 70.7 |
| 10 | 77.1 | 82.1 | 75.8 | 68.6 | 75.8 | 66.7 |
| 25 | 82.2 | 86.6 | 81 | 75.6 | 72.7 | 76.4 |
| 28 | 68.9 | 74.6 | 67.3 | 67.9 | 69.7 | 67.5 |
| 30 | 70.2 | 70.1 | 70.2 | 76.3 | 72.7 | 77.2 |
| 31 | 75.6 | 68.7 | 77.4 | 74.4 | 69.7 | 75.6 |
| 38 | 77.1 | 67.2 | 79.8 | 73.7 | 63.6 | 76.4 |
| 48 | 74 | 77.6 | 73 | 74.4 | 66.7 | 76.4 |
| 82 | 57.5 | 59.7 | 56.9 | 62.2 | 63.6 | 61.8 |
| 103 | 58.1 | 49.3 | 60.5 | 52.6 | 48.5 | 53.7 |
| 108 | 74.6 | 70.1 | 75.8 | 71.2 | 69.7 | 71.5 |
| 464 | 68.3 | 53.7 | 72.2 | 67.3 | 57.6 | 69.9 |

TABLE 9

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_48 | 93 | 83.6 | 95.6 | 91.7 | 81.8 | 94.3 |
| 2_10 | 90.8 | 86.6 | 91.9 | 89.7 | 87.9 | 90.2 |
| 2_465 | 89.5 | 83.6 | 91.1 | 89.7 | 87.9 | 90.2 |
| 2_9 | 90.5 | 85.1 | 91.9 | 89.7 | 84.8 | 91.1 |
| 2_30 | 91.7 | 85.1 | 93.5 | 89.7 | 81.8 | 91.9 |
| 2_61 | 89.8 | 79.1 | 92.7 | 89.7 | 81.8 | 91.9 |
| 2_101 | 90.5 | 82.1 | 92.7 | 89.7 | 78.8 | 92.7 |
| 2_7 | 90.2 | 80.6 | 92.7 | 89.1 | 84.8 | 90.2 |
| 2_28 | 90.5 | 83.6 | 92.3 | 89.1 | 84.8 | 90.2 |
| 2_4 | 89.8 | 83.6 | 91.5 | 88.5 | 81.8 | 90.2 |
| 2_68 | 90.8 | 85.1 | 92.3 | 88.5 | 81.8 | 90.2 |
| 2_25 | 90.8 | 86.6 | 91.9 | 87.8 | 81.8 | 89.4 |

TABLE 10

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_7_101 | 92.7 | 86.6 | 94.4 | 93.6 | 93.9 | 93.5 |
| 2_48_68 | 93.7 | 83.6 | 96.4 | 93.6 | 78.8 | 97.6 |
| 2_7_82 | 92.7 | 82.1 | 95.6 | 92.9 | 87.9 | 94.3 |
| 2_6_48 | 93.7 | 85.1 | 96 | 92.9 | 87.9 | 94.3 |
| 2_48_17 | 92.7 | 83.6 | 95.2 | 92.9 | 84.8 | 95.1 |
| 2_48_101 | 93.3 | 85.1 | 95.6 | 92.9 | 84.8 | 95.1 |
| 2_465_467 | 90.8 | 82.1 | 93.1 | 92.3 | 93.9 | 91.9 |
| 2_7_48 | 92.4 | 83.6 | 94.8 | 92.3 | 84.8 | 94.3 |
| 2_48_38 | 92.7 | 82.1 | 95.6 | 92.3 | 84.8 | 94.3 |
| 2_48_22 | 92.7 | 85.1 | 94.8 | 92.3 | 84.8 | 94.3 |
| 2_48_30 | 94.3 | 88.1 | 96 | 92.3 | 84.8 | 94.3 |
| 2_48_53 | 93.3 | 83.6 | 96 | 92.3 | 84.8 | 94.3 |
| 2_48_47 | 93 | 85.1 | 95.2 | 92.3 | 84.8 | 94.3 |
| 2_48_365 | 93 | 85.1 | 95.2 | 92.3 | 84.8 | 94.3 |
| 2_38_101 | 91.4 | 85.1 | 93.1 | 92.3 | 84.8 | 94.3 |
| 2_31_101 | 91.7 | 82.1 | 94.4 | 92.3 | 81.8 | 95.1 |
| 2_48_82 | 93 | 83.6 | 95.6 | 92.3 | 81.8 | 95.1 |
| 2_9_103 | 91.4 | 83.6 | 93.5 | 91.7 | 93.9 | 91.1 |
| 2_9_469 | 90.2 | 85.1 | 91.5 | 91.7 | 93.9 | 91.1 |
| 2_38_465 | 91.7 | 85.1 | 93.5 | 91.7 | 87.9 | 92.7 |
| 2_465_373 | 89.8 | 83.6 | 91.5 | 91.7 | 87.9 | 92.7 |
| 2_61_365 | 88.9 | 79.1 | 91.5 | 91.7 | 87.9 | 92.7 |
| 2_31_48 | 93.7 | 86.6 | 95.6 | 91.7 | 84.8 | 93.5 |
| 2_6_101 | 91.7 | 85.1 | 93.5 | 91.7 | 84.8 | 93.5 |
| 2_48_103 | 93.3 | 85.1 | 95.6 | 91.7 | 84.8 | 93.5 |
| 2_68_101 | 91.7 | 85.1 | 93.5 | 91.7 | 84.8 | 93.5 |
| 2_465_101 | 90.8 | 82.1 | 93.1 | 91.7 | 84.8 | 93.5 |
| 2_61_101 | 90.5 | 80.6 | 93.1 | 91.7 | 84.8 | 93.5 |
| 2_4_48 | 92.7 | 82.1 | 95.6 | 91.7 | 81.8 | 94.3 |
| 2_10_48 | 93 | 85.1 | 95.2 | 91.7 | 81.8 | 94.3 |
| 2_9_48 | 93.3 | 85.1 | 95.6 | 91.7 | 81.8 | 94.3 |
| 2_48_51 | 93 | 83.6 | 95.6 | 91.7 | 81.8 | 94.3 |
| 2_48_465 | 93 | 83.6 | 95.6 | 91.7 | 81.8 | 94.3 |
| 2_48_108 | 93 | 82.1 | 96 | 91.7 | 81.8 | 94.3 |
| 2_48_28 | 93 | 83.6 | 95.6 | 91.7 | 81.8 | 94.3 |
| 2_48_373 | 93 | 80.6 | 96.4 | 91.7 | 81.8 | 94.3 |
| 2_48_466 | 92.7 | 82.1 | 95.6 | 91.7 | 81.8 | 94.3 |
| 2_48_61 | 93 | 83.6 | 95.6 | 91.7 | 81.8 | 94.3 |
| 2_48_467 | 93.3 | 82.1 | 96.4 | 91.7 | 81.8 | 94.3 |
| 2_48_464 | 93 | 83.6 | 95.6 | 91.7 | 81.8 | 94.3 |
| 2_48_382 | 92.7 | 83.3 | 95.2 | 91.7 | 81.8 | 94.3 |
| 2_48_370 | 93 | 82.1 | 96 | 91.7 | 81.8 | 94.3 |
| 2_101_365 | 90.5 | 79.1 | 93.5 | 91.7 | 81.8 | 94.3 |
| 2_10_365 | 89.5 | 83.6 | 91.1 | 91 | 93.9 | 90.2 |
| 2_7_465 | 91.1 | 82.1 | 93.5 | 91 | 90.9 | 91.1 |
| 2_7_61 | 90.2 | 82.1 | 92.3 | 91 | 90.9 | 91.1 |
| 2_9_467 | 90.5 | 85.1 | 91.9 | 91 | 90.9 | 91.1 |
| 2_465_469 | 89.2 | 83.6 | 90.7 | 91 | 90.9 | 91.1 |
| 2_25_30 | 91.1 | 86.6 | 92.3 | 91 | 87.9 | 91.9 |
| 2_7_466 | 90.2 | 80.6 | 92.7 | 91 | 87.9 | 91.9 |
| 2_7_47 | 89.8 | 82.1 | 91.9 | 91 | 87.9 | 91.9 |
| 2_10_82 | 90.8 | 88.1 | 91.5 | 91 | 87.9 | 91.9 |
| 2_9_47 | 90.8 | 85.1 | 92.3 | 91 | 87.9 | 91.9 |
| 2_7_68 | 92.4 | 85.1 | 94.4 | 91 | 84.8 | 92.7 |
| 2_7_22 | 91.7 | 83.6 | 94 | 91 | 84.8 | 92.7 |
| 2_7_100 | 90.2 | 80.6 | 92.7 | 91 | 84.8 | 92.7 |
| 2_10_101 | 92.7 | 86.6 | 94.4 | 91 | 84.8 | 92.7 |
| 2_9_101 | 92.4 | 85.1 | 94.4 | 91 | 84.8 | 92.7 |
| 2_48_359 | 93 | 82.1 | 96 | 91 | 84.8 | 92.7 |
| 2_38_103 | 91.4 | 85.1 | 93.1 | 91 | 84.8 | 92.7 |
| 2_465_82 | 90.5 | 85.1 | 91.9 | 91 | 84.8 | 92.7 |
| 2_28_382 | 91.1 | 83.3 | 93.1 | 91 | 84.8 | 92.7 |
| 2_28_82 | 91.7 | 85.1 | 93.5 | 91 | 84.8 | 92.7 |
| 2_30_101 | 92.1 | 83.6 | 94.4 | 91 | 84.8 | 92.7 |
| 2_25_48 | 93 | 85.1 | 95.2 | 91 | 81.8 | 93.5 |
| 2_48_90 | 94 | 88.1 | 95.6 | 91 | 81.8 | 93.5 |
| 2_48_468 | 93 | 83.6 | 95.6 | 91 | 81.8 | 93.5 |
| 2_48_118 | 92.4 | 85.1 | 94.4 | 91 | 81.8 | 93.5 |
| 2_51_101 | 90.8 | 83.6 | 92.7 | 91 | 81.8 | 93.5 |
| 2_38_30 | 90.8 | 82.1 | 93.1 | 91 | 81.8 | 93.5 |
| 2_61_469 | 90.5 | 80.6 | 93.1 | 91 | 81.8 | 93.5 |
| 2_53_101 | 91.1 | 83.6 | 93.1 | 91 | 81.8 | 93.5 |
| 2_101_464 | 90.2 | 80.6 | 92.7 | 91 | 81.8 | 93.5 |
| 2_101_118 | 90.2 | 82.1 | 92.3 | 91 | 81.8 | 93.5 |
| 2_101_469 | 90.5 | 82.1 | 92.7 | 91 | 81.8 | 93.5 |
| 2_101_47 | 91.4 | 83.6 | 93.5 | 91 | 78.8 | 94.3 |
| 2_101_100 | 90.5 | 82.1 | 92.7 | 91 | 78.8 | 94.3 |
| 2_465_365 | 88.9 | 82.1 | 90.7 | 90.4 | 93.9 | 89.4 |
| 2_7_9 | 91.4 | 83.6 | 93.5 | 90.4 | 90.9 | 90.2 |
| 2_7_28 | 91.1 | 82.1 | 93.5 | 90.4 | 90.9 | 90.2 |
| 2_7_53 | 91.1 | 83.6 | 93.1 | 90.4 | 90.9 | 90.2 |
| 2_7_365 | 89.8 | 80.6 | 92.3 | 90.4 | 90.9 | 90.2 |
| 2_10_9 | 91.1 | 86.6 | 92.3 | 90.4 | 90.9 | 90.2 |
| 2_9_365 | 89.5 | 83.6 | 91.1 | 90.4 | 90.9 | 90.2 |
| 2_9_82 | 92.1 | 86.6 | 93.5 | 90.4 | 90.9 | 90.2 |
| 2_465_47 | 89.8 | 83.6 | 91.5 | 90.4 | 90.9 | 90.2 |
| 2_25_61 | 91.1 | 85.1 | 92.7 | 90.4 | 87.9 | 91.1 |
| 2_7_17 | 90.5 | 80.6 | 93.1 | 90.4 | 87.9 | 91.1 |
| 2_7_464 | 89.2 | 79.1 | 91.9 | 90.4 | 87.9 | 91.1 |
| 2_7_103 | 92.4 | 85.1 | 94.4 | 90.4 | 87.9 | 91.1 |
| 2_7_469 | 90.2 | 80.6 | 92.7 | 90.4 | 87.9 | 91.1 |
| 2_10_30 | 91.7 | 88.1 | 92.7 | 90.4 | 87.9 | 91.1 |
| 2_10_61 | 90.5 | 85.1 | 91.9 | 90.4 | 87.9 | 91.1 |
| 2_9_31 | 90.2 | 85.1 | 91.5 | 90.4 | 87.9 | 91.1 |
| 2_9_28 | 91.1 | 83.6 | 93.1 | 90.4 | 87.9 | 91.1 |
| 2_9_468 | 90.2 | 85.1 | 91.5 | 90.4 | 87.9 | 91.1 |
| 2_9_370 | 90.8 | 85.1 | 92.3 | 90.4 | 87.9 | 91.1 |

TABLE 10-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 2_9_100 | 89.8 | 85.1 | 91.1 | 90.4 | 87.9 | 91.1 |
| 2_38_61 | 90.8 | 83.6 | 92.7 | 90.4 | 87.9 | 91.1 |
| 2_7_382 | 92 | 81.8 | 94.8 | 90.4 | 84.8 | 91.9 |
| 2_9_61 | 90.5 | 83.6 | 92.3 | 90.4 | 84.8 | 91.9 |
| 2_48_100 | 93.7 | 85.1 | 96 | 90.4 | 84.8 | 91.9 |
| 2_48_469 | 93 | 82.1 | 96 | 90.4 | 84.8 | 91.9 |
| 2_51_30 | 91.7 | 86.6 | 93.1 | 90.4 | 84.8 | 91.9 |
| 2_68_28 | 92.1 | 83.6 | 94.4 | 90.4 | 84.8 | 91.9 |
| 2_465_30 | 91.1 | 85.1 | 92.7 | 90.4 | 84.8 | 91.9 |
| 2_465_61 | 90.8 | 85.1 | 92.3 | 90.4 | 84.8 | 91.9 |
| 2_28_30 | 92.4 | 85.1 | 94.4 | 90.4 | 84.8 | 91.9 |
| 2_28_47 | 90.2 | 83.6 | 91.9 | 90.4 | 84.8 | 91.9 |
| 2_28_370 | 91.1 | 83.6 | 93.1 | 90.4 | 84.8 | 91.9 |
| 2_22_61 | 90.5 | 80.6 | 93.1 | 90.4 | 84.8 | 91.9 |
| 2_30_365 | 90.5 | 82.1 | 92.7 | 90.4 | 84.8 | 91.9 |
| 2_30_100 | 91.4 | 85.1 | 93.1 | 90.4 | 84.8 | 91.9 |
| 2_61_467 | 89.5 | 80.6 | 91.9 | 90.4 | 84.8 | 91.9 |
| 2_61_464 | 89.5 | 77.6 | 92.7 | 90.4 | 84.8 | 91.9 |
| 2_25_101 | 91.1 | 85.1 | 92.7 | 90.4 | 81.8 | 92.7 |
| 2_4_101 | 90.5 | 80.6 | 93.1 | 90.4 | 81.8 | 92.7 |
| 2_28_101 | 91.7 | 83.6 | 94 | 90.4 | 81.8 | 92.7 |
| 2_22_101 | 90.2 | 80.6 | 92.7 | 90.4 | 81.8 | 92.7 |
| 2_30_53 | 90.8 | 82.1 | 93.1 | 90.4 | 81.8 | 92.7 |
| 2_61_47 | 88.9 | 80.6 | 91.1 | 90.4 | 81.8 | 92.7 |
| 2_108_101 | 91.1 | 82.1 | 93.5 | 90.4 | 78.8 | 93.5 |
| 2_28_17 | 92.1 | 85.1 | 94 | 90.4 | 78.8 | 93.5 |
| 2_373_101 | 90.5 | 82.1 | 92.7 | 90.4 | 78.8 | 93.5 |
| 2_466_101 | 90.8 | 82.1 | 93.1 | 90.4 | 78.8 | 93.5 |
| 2_101_468 | 90.5 | 82.1 | 92.7 | 90.4 | 78.8 | 93.5 |
| 2_101_370 | 89.8 | 79.1 | 92.7 | 90.4 | 78.8 | 93.5 |
| 2_101_82 | 91.1 | 82.1 | 93.5 | 90.4 | 78.8 | 93.5 |
| 2_7_10 | 91.7 | 85.1 | 93.5 | 89.7 | 90.9 | 89.4 |
| 2_9_38 | 91.7 | 86.6 | 93.1 | 89.7 | 90.9 | 89.4 |
| 2_25_465 | 89.2 | 85.1 | 90.3 | 89.7 | 87.9 | 90.2 |
| 2_25_28 | 90.8 | 85.1 | 92.3 | 89.7 | 87.9 | 90.2 |
| 2_7_38 | 92.4 | 82.1 | 95.2 | 89.7 | 87.9 | 90.2 |
| 2_7_108 | 90.2 | 80.6 | 92.7 | 89.7 | 87.9 | 90.2 |
| 2_7_118 | 89.5 | 83.6 | 91.1 | 89.7 | 87.9 | 90.2 |
| 2_4_465 | 89.5 | 83.6 | 91.1 | 89.7 | 87.9 | 90.2 |
| 2_10_465 | 91.7 | 86.6 | 93.1 | 89.7 | 87.9 | 90.2 |
| 2_10_28 | 91.1 | 86.6 | 92.3 | 89.7 | 87.9 | 90.2 |
| 2_10_466 | 90.8 | 86.6 | 91.9 | 89.7 | 87.9 | 90.2 |
| 2_10_370 | 91.1 | 86.6 | 92.3 | 89.7 | 87.9 | 90.2 |
| 2_10_359 | 90.8 | 86.6 | 91.9 | 89.7 | 87.9 | 90.2 |
| 2_10_469 | 91.7 | 86.6 | 93.1 | 89.7 | 87.9 | 90.2 |
| 2_9_6 | 89.8 | 86.6 | 90.7 | 89.7 | 87.9 | 90.2 |
| 2_9_465 | 90.5 | 83.6 | 92.3 | 89.7 | 87.9 | 90.2 |
| 2_9_382 | 90.8 | 84.8 | 92.3 | 89.7 | 87.9 | 90.2 |
| 2_6_365 | 89.5 | 83.6 | 91.1 | 89.7 | 87.9 | 90.2 |
| 2_51_465 | 89.5 | 83.6 | 91.1 | 89.7 | 87.9 | 90.2 |
| 2_465_108 | 89.8 | 83.6 | 91.5 | 89.7 | 87.9 | 90.2 |
| 2_465_28 | 90.8 | 85.1 | 92.3 | 89.7 | 87.9 | 90.2 |
| 2_465_22 | 89.2 | 83.6 | 90.7 | 89.7 | 87.9 | 90.2 |
| 2_465_17 | 89.5 | 83.6 | 91.1 | 89.7 | 87.9 | 90.2 |
| 2_465_466 | 89.8 | 83.6 | 91.5 | 89.7 | 87.9 | 90.2 |
| 2_465_464 | 89.8 | 85.1 | 91.1 | 89.7 | 87.9 | 90.2 |
| 2_465_368 | 89.5 | 83.6 | 91.1 | 89.7 | 87.9 | 90.2 |
| 2_465_359 | 89.5 | 83.6 | 91.1 | 89.7 | 87.9 | 90.2 |
| 2_465_100 | 89.8 | 85.1 | 91.1 | 89.7 | 87.9 | 90.2 |
| 2_25_47 | 89.8 | 85.1 | 91.1 | 89.7 | 84.8 | 91.1 |
| 2_7_4 | 90.2 | 80.6 | 92.7 | 89.7 | 84.8 | 91.1 |
| 2_7_31 | 90.2 | 80.6 | 92.7 | 89.7 | 84.8 | 91.1 |
| 2_7_373 | 89.8 | 79.1 | 92.7 | 89.7 | 84.8 | 91.1 |
| 2_7_370 | 90.5 | 80.6 | 93.1 | 89.7 | 84.8 | 91.1 |
| 2_4_61 | 89.8 | 80.6 | 92.3 | 89.7 | 84.8 | 91.1 |
| 2_10_108 | 90.8 | 86.6 | 91.9 | 89.7 | 84.8 | 91.1 |
| 2_10_118 | 90.5 | 86.6 | 91.5 | 89.7 | 84.8 | 91.1 |
| 2_9_108 | 90.5 | 85.1 | 91.9 | 89.7 | 84.8 | 91.1 |
| 2_9_22 | 90.5 | 85.1 | 91.9 | 89.7 | 84.8 | 91.1 |
| 2_9_30 | 91.7 | 85.1 | 93.5 | 89.7 | 84.8 | 91.1 |
| 2_9_466 | 90.5 | 85.1 | 91.9 | 89.7 | 84.8 | 91.1 |
| 2_9_368 | 90.5 | 85.1 | 91.9 | 89.7 | 84.8 | 91.1 |
| 2_51_61 | 90.8 | 83.6 | 92.7 | 89.7 | 84.8 | 91.1 |
| 2_38_382 | 91.1 | 84.8 | 92.7 | 89.7 | 84.8 | 91.1 |
| 2_465_53 | 90.5 | 85.1 | 91.9 | 89.7 | 84.8 | 91.1 |
| 2_108_61 | 89.8 | 82.1 | 91.9 | 89.7 | 84.8 | 91.1 |
| 2_28_467 | 91.4 | 85.1 | 93.1 | 89.7 | 84.8 | 91.1 |
| 2_28_468 | 91.4 | 85.1 | 93.1 | 89.7 | 84.8 | 91.1 |
| 2_28_469 | 91.1 | 83.6 | 93.1 | 89.7 | 84.8 | 91.1 |
| 2_22_103 | 89.8 | 83.6 | 91.5 | 89.7 | 84.8 | 91.1 |
| 2_466_61 | 90.5 | 82.1 | 92.7 | 89.7 | 84.8 | 91.1 |
| 2_7_30 | 92.1 | 88.1 | 93.1 | 89.7 | 81.8 | 91.9 |
| 2_4_30 | 91.1 | 82.1 | 93.5 | 89.7 | 81.8 | 91.9 |
| 2_9_373 | 90.2 | 85.1 | 91.5 | 89.7 | 81.8 | 91.9 |
| 2_9_464 | 90.5 | 85.1 | 91.9 | 89.7 | 81.8 | 91.9 |
| 2_31_465 | 89.8 | 83.6 | 91.5 | 89.7 | 81.8 | 91.9 |
| 2_31_61 | 89.8 | 79.1 | 92.7 | 89.7 | 81.8 | 91.9 |
| 2_68_38 | 92.1 | 85.1 | 94 | 89.7 | 81.8 | 91.9 |
| 2_465_103 | 91.1 | 83.6 | 93.1 | 89.7 | 81.8 | 91.9 |
| 2_28_373 | 91.7 | 85.1 | 93.5 | 89.7 | 81.8 | 91.9 |
| 2_28_61 | 90.8 | 85.1 | 92.3 | 89.7 | 81.8 | 91.9 |
| 2_28_368 | 91.4 | 85.1 | 93.1 | 89.7 | 81.8 | 91.9 |
| 2_28_118 | 90.2 | 85.1 | 91.5 | 89.7 | 81.8 | 91.9 |
| 2_373_61 | 90.2 | 80.6 | 92.7 | 89.7 | 81.8 | 91.9 |
| 2_22_30 | 91.4 | 85.1 | 93.1 | 89.7 | 81.8 | 91.9 |
| 2_30_17 | 91.7 | 85.1 | 93.5 | 89.7 | 81.8 | 91.9 |
| 2_30_61 | 91.7 | 85.1 | 93.5 | 89.7 | 81.8 | 91.9 |
| 2_30_368 | 91.4 | 83.6 | 93.5 | 89.7 | 81.8 | 91.9 |
| 2_30_118 | 92.1 | 85.1 | 94 | 89.7 | 81.8 | 91.9 |
| 2_30_359 | 91.7 | 85.1 | 93.5 | 89.7 | 81.8 | 91.9 |
| 2_30_103 | 92.4 | 83.6 | 94.8 | 89.7 | 81.8 | 91.9 |
| 2_17_61 | 89.8 | 79.1 | 92.7 | 89.7 | 81.8 | 91.9 |
| 2_61_370 | 89.8 | 79.1 | 92.7 | 89.7 | 81.8 | 91.9 |
| 2_61_368 | 89.8 | 77.6 | 93.1 | 89.7 | 81.8 | 91.9 |
| 2_61_118 | 90.2 | 80.6 | 92.7 | 89.7 | 81.8 | 91.9 |
| 2_61_82 | 89.8 | 76.1 | 93.5 | 89.7 | 81.8 | 91.9 |
| 2_17_101 | 90.5 | 82.1 | 92.7 | 89.7 | 78.8 | 92.7 |
| 2_467_101 | 90.5 | 82.1 | 92.7 | 89.7 | 78.8 | 92.7 |
| 2_101_382 | 91.1 | 81.8 | 93.5 | 89.7 | 78.8 | 92.7 |
| 2_101_368 | 90.5 | 82.1 | 92.7 | 89.7 | 78.8 | 92.7 |
| 2_101_359 | 90.5 | 82.1 | 92.7 | 89.7 | 78.8 | 92.7 |
| 2_101_103 | 90.5 | 82.1 | 92.7 | 89.7 | 78.8 | 92.7 |
| 2_90_101 | 90.8 | 82.1 | 93.1 | 89.7 | 75.8 | 93.5 |
| 2_25_9 | 90.2 | 85.1 | 91.5 | 89.1 | 87.9 | 89.4 |
| 2_25_53 | 89.8 | 85.1 | 91.1 | 89.1 | 87.9 | 89.4 |
| 2_7_6 | 90.8 | 85.1 | 92.3 | 89.1 | 87.9 | 89.4 |
| 2_10_22 | 90.8 | 86.6 | 91.9 | 89.1 | 87.9 | 89.4 |
| 2_10_53 | 90.8 | 86.6 | 91.9 | 89.1 | 87.9 | 89.4 |
| 2_10_47 | 89.8 | 86.6 | 90.7 | 89.1 | 87.9 | 89.4 |
| 2_9_51 | 90.5 | 85.1 | 91.9 | 89.1 | 87.9 | 89.4 |
| 2_25_7 | 91.4 | 83.6 | 93.5 | 89.1 | 84.8 | 90.2 |
| 2_25_68 | 91.4 | 86.6 | 92.7 | 89.1 | 84.8 | 90.2 |
| 2_25_17 | 90.5 | 86.6 | 91.5 | 89.1 | 84.8 | 90.2 |
| 2_25_365 | 89.5 | 83.6 | 91.1 | 89.1 | 84.8 | 90.2 |
| 2_7_467 | 90.8 | 80.6 | 93.5 | 89.1 | 84.8 | 90.2 |
| 2_7_468 | 90.5 | 80.6 | 93.1 | 89.1 | 84.8 | 90.2 |
| 2_7_368 | 90.2 | 80.6 | 92.7 | 89.1 | 84.8 | 90.2 |
| 2_7_359 | 90.8 | 83.6 | 92.7 | 89.1 | 84.8 | 90.2 |
| 2_4_10 | 90.8 | 86.6 | 91.9 | 89.1 | 84.8 | 90.2 |
| 2_4_9 | 90.5 | 85.1 | 91.9 | 89.1 | 84.8 | 90.2 |
| 2_4_28 | 90.5 | 83.6 | 92.3 | 89.1 | 84.8 | 90.2 |
| 2_4_90 | 90.5 | 82.1 | 92.7 | 89.1 | 84.8 | 90.2 |
| 2_10_31 | 91.1 | 86.6 | 92.3 | 89.1 | 84.8 | 90.2 |
| 2_10_51 | 90.8 | 86.6 | 91.9 | 89.1 | 84.8 | 90.2 |
| 2_10_382 | 90.4 | 86.4 | 91.5 | 89.1 | 84.8 | 90.2 |
| 2_9_53 | 91.1 | 85.1 | 92.7 | 89.1 | 84.8 | 90.2 |
| 2_9_359 | 90.5 | 85.1 | 91.9 | 89.1 | 84.8 | 90.2 |
| 2_51_28 | 90.8 | 83.6 | 92.7 | 89.1 | 84.8 | 90.2 |
| 2_51_90 | 90.8 | 80.6 | 93.5 | 89.1 | 84.8 | 90.2 |
| 2_68_61 | 91.4 | 82.1 | 94 | 89.1 | 84.8 | 90.2 |
| 2_38_28 | 90.8 | 85.1 | 92.3 | 89.1 | 84.8 | 90.2 |
| 2_108_30 | 91.7 | 88.1 | 92.7 | 89.1 | 84.8 | 90.2 |
| 2_28_466 | 90.5 | 83.6 | 92.3 | 89.1 | 84.8 | 90.2 |
| 2_28_359 | 90.8 | 83.6 | 92.7 | 89.1 | 84.8 | 90.2 |
| 2_28_100 | 90.8 | 85.1 | 92.3 | 89.1 | 84.8 | 90.2 |
| 2_30_464 | 91.4 | 82.1 | 94 | 89.1 | 84.8 | 90.2 |
| 2_468_365 | 88.9 | 80.6 | 91.1 | 89.1 | 84.8 | 90.2 |
| 2_25_82 | 90.8 | 86.6 | 91.9 | 89.1 | 81.8 | 91.1 |

TABLE 10-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 2_7_51 | 89.2 | 77.6 | 92.3 | 89.1 | 81.8 | 91.1 |
| 2_4_103 | 91.1 | 82.1 | 93.5 | 89.1 | 81.8 | 91.1 |
| 2_31_68 | 90.2 | 83.6 | 91.9 | 89.1 | 81.8 | 91.1 |
| 2_31_30 | 91.1 | 82.1 | 93.5 | 89.1 | 81.8 | 91.1 |
| 2_6_30 | 91.7 | 88.1 | 92.7 | 89.1 | 81.8 | 91.1 |
| 2_48_368 | 93 | 85.1 | 95.2 | 89.1 | 81.8 | 91.1 |
| 2_51_373 | 89.8 | 83.6 | 91.5 | 89.1 | 81.8 | 91.1 |
| 2_68_47 | 90.5 | 85.1 | 91.9 | 89.1 | 81.8 | 91.1 |
| 2_68_368 | 91.4 | 85.1 | 93.1 | 89.1 | 81.8 | 91.1 |
| 2_68_100 | 91.1 | 85.1 | 92.7 | 89.1 | 81.8 | 91.1 |
| 2_68_103 | 90.8 | 85.1 | 92.3 | 89.1 | 81.8 | 91.1 |
| 2_38_82 | 90.5 | 85.1 | 91.9 | 89.1 | 81.8 | 91.1 |
| 2_108_28 | 91.1 | 83.6 | 93.1 | 89.1 | 81.8 | 91.1 |
| 2_108_17 | 91.4 | 83.6 | 93.5 | 89.1 | 81.8 | 91.1 |
| 2_373_30 | 92.4 | 86.6 | 94 | 89.1 | 81.8 | 91.1 |
| 2_30_466 | 90.8 | 85.1 | 92.3 | 89.1 | 81.8 | 91.1 |
| 2_30_370 | 91.7 | 85.1 | 93.5 | 89.1 | 81.8 | 91.1 |
| 2_30_82 | 91.4 | 85.1 | 93.1 | 89.1 | 81.8 | 91.1 |
| 2_466_103 | 91.4 | 85.1 | 93.1 | 89.1 | 81.8 | 91.1 |
| 2_61_53 | 91.1 | 82.1 | 93.5 | 89.1 | 81.8 | 91.1 |
| 2_61_468 | 89.8 | 79.1 | 92.7 | 89.1 | 81.8 | 91.1 |
| 2_61_359 | 89.8 | 79.1 | 92.7 | 89.1 | 81.8 | 91.1 |
| 2_9_17 | 90.5 | 85.1 | 91.9 | 89.1 | 78.8 | 91.9 |
| 2_28_103 | 91.4 | 83.6 | 93.5 | 89.1 | 78.8 | 91.9 |
| 2_90_100 | 90.5 | 80.6 | 93.1 | 89.1 | 78.8 | 91.9 |
| 2_61_382 | 90.1 | 80.3 | 92.7 | 89.1 | 78.8 | 91.9 |
| 2_100_103 | 90.8 | 83.6 | 92.7 | 89.1 | 75.8 | 92.7 |
| 2_25_10 | 90.2 | 88.1 | 90.7 | 88.5 | 84.8 | 89.4 |
| 2_25_464 | 90.5 | 86.6 | 91.5 | 88.5 | 84.8 | 89.4 |
| 2_4_82 | 90.5 | 85.1 | 91.9 | 88.5 | 84.8 | 89.4 |
| 2_10_467 | 90.8 | 86.6 | 91.9 | 88.5 | 84.8 | 89.4 |
| 2_10_464 | 91.1 | 86.6 | 92.3 | 88.5 | 84.8 | 89.4 |
| 2_10_368 | 90.8 | 86.6 | 91.9 | 88.5 | 84.8 | 89.4 |
| 2_9_68 | 92.1 | 86.6 | 93.5 | 88.5 | 84.8 | 89.4 |
| 2_6_51 | 89.8 | 85.1 | 91.1 | 88.5 | 84.8 | 89.4 |
| 2_6_61 | 88.9 | 83.6 | 90.3 | 88.5 | 84.8 | 89.4 |
| 2_6_464 | 89.5 | 85.1 | 90.7 | 88.5 | 84.8 | 89.4 |
| 2_6_100 | 90.2 | 85.1 | 91.5 | 88.5 | 84.8 | 89.4 |
| 2_51_365 | 89.5 | 83.6 | 91.1 | 88.5 | 84.8 | 89.4 |
| 2_38_90 | 90.8 | 80.6 | 93.5 | 88.5 | 84.8 | 89.4 |
| 2_38_365 | 88.6 | 82.1 | 90.3 | 88.5 | 84.8 | 89.4 |
| 2_108_365 | 89.2 | 83.6 | 90.7 | 88.5 | 84.8 | 89.4 |
| 2_108_82 | 91.1 | 85.1 | 92.7 | 88.5 | 84.8 | 89.4 |
| 2_28_365 | 89.2 | 83.6 | 90.7 | 88.5 | 84.8 | 89.4 |
| 2_22_467 | 89.8 | 85.1 | 91.1 | 88.5 | 84.8 | 89.4 |
| 2_22_382 | 89.8 | 83.3 | 91.5 | 88.5 | 84.8 | 89.4 |
| 2_22_82 | 90.5 | 85.1 | 91.9 | 88.5 | 84.8 | 89.4 |
| 2_466_365 | 89.2 | 83.6 | 90.7 | 88.5 | 84.8 | 89.4 |
| 2_25_38 | 91.4 | 86.6 | 92.7 | 88.5 | 81.8 | 90.2 |
| 2_25_373 | 90.5 | 86.6 | 91.5 | 88.5 | 81.8 | 90.2 |
| 2_25_468 | 90.8 | 85.1 | 92.3 | 88.5 | 81.8 | 90.2 |
| 2_4_464 | 90.2 | 83.6 | 91.9 | 88.5 | 81.8 | 90.2 |
| 2_4_468 | 89.8 | 83.6 | 91.5 | 88.5 | 81.8 | 90.2 |
| 2_4_47 | 90.2 | 83.6 | 91.9 | 88.5 | 81.8 | 90.2 |
| 2_10_373 | 90.2 | 86.6 | 91.1 | 88.5 | 81.8 | 90.2 |
| 2_10_468 | 90.8 | 86.6 | 91.9 | 88.5 | 81.8 | 90.2 |
| 2_9_90 | 90.5 | 82.1 | 92.7 | 88.5 | 81.8 | 90.2 |
| 2_9_118 | 90.5 | 85.1 | 91.9 | 88.5 | 81.8 | 90.2 |
| 2_31_38 | 90.2 | 85.1 | 91.5 | 88.5 | 81.8 | 90.2 |
| 2_6_68 | 91.7 | 85.1 | 93.5 | 88.5 | 81.8 | 90.2 |
| 2_51_82 | 90.2 | 83.6 | 91.9 | 88.5 | 81.8 | 90.2 |
| 2_68_373 | 90.8 | 85.1 | 92.3 | 88.5 | 81.8 | 90.2 |
| 2_68_464 | 89.8 | 83.6 | 91.5 | 88.5 | 81.8 | 90.2 |
| 2_38_464 | 90.2 | 85.1 | 91.5 | 88.5 | 81.8 | 90.2 |
| 2_38_359 | 91.4 | 85.1 | 93.1 | 88.5 | 81.8 | 90.2 |
| 2_465_90 | 90.2 | 80.6 | 92.7 | 88.5 | 81.8 | 90.2 |
| 2_465_468 | 90.2 | 83.6 | 91.9 | 88.5 | 81.8 | 90.2 |
| 2_465_370 | 89.8 | 82.1 | 91.9 | 88.5 | 81.8 | 90.2 |
| 2_465_118 | 90.8 | 86.6 | 91.9 | 88.5 | 81.8 | 90.2 |
| 2_28_464 | 91.1 | 85.1 | 92.7 | 88.5 | 81.8 | 90.2 |
| 2_22_90 | 90.2 | 80.6 | 92.7 | 88.5 | 81.8 | 90.2 |
| 2_22_118 | 90.8 | 83.6 | 92.7 | 88.5 | 81.8 | 90.2 |
| 2_30_467 | 91.7 | 85.1 | 93.5 | 88.5 | 81.8 | 90.2 |
| 2_30_468 | 92.1 | 85.1 | 94 | 88.5 | 81.8 | 90.2 |
| 2_30_47 | 92.1 | 86.6 | 93.5 | 88.5 | 81.8 | 90.2 |
| 2_61_103 | 90.2 | 77.6 | 93.5 | 88.5 | 81.8 | 90.2 |
| 2_467_365 | 87.9 | 80.6 | 89.9 | 88.5 | 81.8 | 90.2 |
| 2_53_365 | 88.9 | 80.6 | 91.1 | 88.5 | 81.8 | 90.2 |
| 2_53_103 | 91.1 | 82.1 | 93.5 | 88.5 | 81.8 | 90.2 |
| 2_31_382 | 89.5 | 80.3 | 91.9 | 88.5 | 78.8 | 91.1 |
| 2_31_103 | 89.5 | 79.1 | 92.3 | 88.5 | 78.8 | 91.1 |
| 2_68_30 | 92.4 | 85.1 | 94.4 | 88.5 | 78.8 | 91.1 |
| 2_68_370 | 90.2 | 83.6 | 91.9 | 88.5 | 78.8 | 91.1 |
| 2_68_82 | 91.4 | 85.1 | 93.1 | 88.5 | 78.8 | 91.1 |
| 2_38_17 | 90.5 | 85.1 | 91.9 | 88.5 | 78.8 | 91.1 |
| 2_38_100 | 90.2 | 85.1 | 91.5 | 88.5 | 78.8 | 91.1 |
| 2_90_61 | 90.5 | 79.1 | 93.5 | 88.5 | 78.8 | 91.1 |
| 2_90_464 | 90.5 | 80.6 | 93.1 | 88.5 | 78.8 | 91.1 |
| 2_90_370 | 90.8 | 80.6 | 93.5 | 88.5 | 78.8 | 91.1 |
| 2_30_382 | 91.1 | 81.8 | 93.5 | 88.5 | 78.8 | 91.1 |
| 2_30_469 | 91.1 | 83.6 | 93.1 | 88.5 | 78.8 | 91.1 |
| 2_61_100 | 89.8 | 80.6 | 92.3 | 88.5 | 78.8 | 91.1 |
| 2_368_82 | 90.8 | 83.6 | 92.7 | 88.5 | 78.8 | 91.1 |
| 2_100_82 | 90.2 | 83.6 | 91.9 | 88.5 | 78.8 | 91.1 |
| 2_90_368 | 90.8 | 80.6 | 93.5 | 88.5 | 75.8 | 91.9 |
| 2_90_118 | 90.2 | 80.6 | 92.7 | 88.5 | 75.8 | 91.9 |
| 7_4_82 | 90.2 | 85.1 | 91.5 | 90.4 | 90.9 | 90.2 |
| 7_68_61 | 89.8 | 88.1 | 90.3 | 89.7 | 87.9 | 90.2 |
| 7_38_101 | 90.2 | 86.6 | 91.1 | 89.7 | 87.9 | 90.2 |
| 7_30_101 | 87.6 | 89.6 | 87.1 | 89.1 | 90.9 | 88.6 |
| 7_30_82 | 87.9 | 89.6 | 87.5 | 89.1 | 87.9 | 89.4 |
| 2_25_7 | 91.4 | 83.6 | 93.5 | 89.1 | 84.8 | 90.2 |
| 7_68_28 | 89.2 | 85.1 | 90.3 | 89.1 | 84.8 | 90.2 |
| 7_4_103 | 88.9 | 88.1 | 89.1 | 88.5 | 87.9 | 88.6 |
| 7_10_31 | 86.3 | 79.1 | 88.3 | 88.5 | 87.9 | 88.6 |
| 7_68_38 | 90.5 | 86.6 | 91.5 | 88.5 | 84.8 | 89.4 |
| 7_68_47 | 88.6 | 85.1 | 89.5 | 88.5 | 84.8 | 89.4 |
| 7_30_103 | 87.9 | 89.6 | 87.5 | 88.5 | 81.8 | 90.2 |
| 25_7_47 | 87.9 | 86.6 | 88.3 | 90.4 | 87.9 | 91.1 |
| 25_7_373 | 89.2 | 91 | 88.7 | 89.1 | 93.9 | 87.8 |
| 25_7_61 | 87.6 | 89.6 | 87.1 | 89.1 | 93.9 | 87.8 |
| 25_7_48 | 89.2 | 88.1 | 89.5 | 89.1 | 87.9 | 89.4 |
| 25_7_467 | 89.2 | 89.6 | 89.1 | 88.5 | 90.9 | 87.8 |
| 25_7_464 | 87.9 | 91 | 87.1 | 88.5 | 90.9 | 87.8 |
| 25_7_118 | 88.9 | 91 | 88.3 | 88.5 | 90.9 | 87.8 |

TABLE 11

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 2_7_61_82 | 93.3 | 85.1 | 95.6 | 96.2 | 97 | 95.9 |
| 2_7_82_103 | 93 | 83.6 | 95.6 | 95.5 | 87.9 | 97.6 |
| 2_7_47_82 | 92.4 | 83.6 | 94.8 | 94.9 | 93.9 | 95.1 |
| 2_7_82_101 | 94.6 | 88.1 | 96.4 | 94.9 | 87.9 | 96.7 |
| 2_7_9_101 | 92.7 | 86.6 | 94.4 | 94.2 | 93.9 | 94.3 |
| 2_7_31_101 | 93 | 86.6 | 94.8 | 94.2 | 93.9 | 94.3 |

TABLE 11-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_7_51_101 | 92.4 | 83.6 | 94.8 | 94.2 | 93.9 | 94.3 |
| 2_38_53_465 | 92.1 | 85.1 | 94 | 94.2 | 93.9 | 94.3 |
| 2_7_9_82 | 93 | 85.1 | 95.2 | 94.2 | 90.9 | 95.1 |
| 2_7_48_103 | 93.7 | 85.1 | 96 | 94.2 | 90.9 | 95.1 |
| 2_7_101_466 | 92.1 | 82.1 | 94.8 | 94.2 | 90.9 | 95.1 |
| 2_7_47_101 | 92.4 | 85.1 | 94.4 | 94.2 | 90.9 | 95.1 |
| 2_7_48_51 | 93 | 86.6 | 94.8 | 94.2 | 87.9 | 95.9 |
| 2_7_48_469 | 92.7 | 83.6 | 95.2 | 94.2 | 87.9 | 95.9 |
| 2_38_82_101 | 91.4 | 83.6 | 93.5 | 94.2 | 87.9 | 95.9 |
| 2_7_48_82 | 94 | 83.6 | 96.8 | 94.2 | 84.8 | 96.7 |
| 2_48_68_467 | 94 | 85.1 | 96.4 | 94.2 | 81.8 | 97.6 |
| 2_48_68_370 | 93.3 | 83.6 | 96 | 94.2 | 81.8 | 97.6 |
| 2_7_25_101 | 92.7 | 86.6 | 94.4 | 93.6 | 93.9 | 93.5 |
| 2_7_101_465 | 92.7 | 86.6 | 94.4 | 93.6 | 93.9 | 93.5 |
| 2_7_61_101 | 92.7 | 86.6 | 94.4 | 93.6 | 93.9 | 93.5 |
| 2_7_61_103 | 92.7 | 83.6 | 95.2 | 93.6 | 93.9 | 93.5 |
| 2_7_101_368 | 92.4 | 85.1 | 94.4 | 93.6 | 93.9 | 93.5 |
| 2_7_101_365 | 92.7 | 85.1 | 94.8 | 93.6 | 93.9 | 93.5 |
| 2_38_51_465 | 91.1 | 85.1 | 92.7 | 93.6 | 93.9 | 93.5 |
| 2_28_465_467 | 92.7 | 86.6 | 94.4 | 93.6 | 93.9 | 93.5 |
| 2_365_373_465 | 90.2 | 83.6 | 91.9 | 93.6 | 93.9 | 93.5 |
| 2_100_465_467 | 91.4 | 85.1 | 93.1 | 93.6 | 93.9 | 93.5 |
| 2_7_10_82 | 93.7 | 83.6 | 96.4 | 93.6 | 90.9 | 94.3 |
| 2_7_38_48 | 93.3 | 83.6 | 96 | 93.6 | 90.9 | 94.3 |
| 2_7_48_359 | 93.3 | 83.6 | 96 | 93.6 | 90.9 | 94.3 |
| 2_7_101_373 | 92.7 | 85.1 | 94.8 | 93.6 | 90.9 | 94.3 |
| 2_7_82_118 | 92.4 | 83.6 | 94.8 | 93.6 | 90.9 | 94.3 |
| 2_7_82_365 | 92.1 | 80.6 | 95.2 | 93.6 | 90.9 | 94.3 |
| 2_6_48_359 | 93.7 | 83.6 | 96.4 | 93.6 | 90.9 | 94.3 |
| 2_38_82_465 | 92.1 | 85.1 | 94 | 93.6 | 90.9 | 94.3 |
| 2_38_101_365 | 92.1 | 83.6 | 94.4 | 93.6 | 90.9 | 94.3 |
| 2_7_25_82 | 93.7 | 85.1 | 96 | 93.6 | 87.9 | 95.1 |
| 2_7_48_466 | 92.4 | 85.1 | 94.4 | 93.6 | 87.9 | 95.1 |
| 2_7_48_467 | 93 | 83.6 | 95.6 | 93.6 | 87.9 | 95.1 |
| 2_7_82_465 | 92.7 | 82.1 | 95.6 | 93.6 | 87.9 | 95.1 |
| 2_7_30_82 | 93 | 85.1 | 95.2 | 93.6 | 87.9 | 95.1 |
| 2_7_101_382 | 93.3 | 84.8 | 95.6 | 93.6 | 87.9 | 95.1 |
| 2_30_31_48 | 94.6 | 89.6 | 96 | 93.6 | 87.9 | 95.1 |
| 2_31_48_53 | 93.7 | 86.6 | 95.6 | 93.6 | 87.9 | 95.1 |
| 2_31_48_82 | 93.3 | 86.6 | 95.2 | 93.6 | 87.9 | 95.1 |
| 2_31_53_101 | 91.4 | 80.6 | 94.4 | 93.6 | 87.9 | 95.1 |
| 2_38_48_101 | 92.7 | 83.6 | 95.2 | 93.6 | 87.9 | 95.1 |
| 2_48_465_467 | 93.3 | 83.6 | 96 | 93.6 | 87.9 | 95.1 |
| 2_17_48_365 | 92.7 | 83.6 | 95.2 | 93.6 | 87.9 | 95.1 |
| 2_28_68_101 | 93.3 | 86.6 | 95.2 | 93.6 | 87.9 | 95.1 |
| 2_30_38_101 | 93 | 86.6 | 94.8 | 93.6 | 87.9 | 95.1 |
| 2_17_25_48 | 92.7 | 83.6 | 95.2 | 93.6 | 84.8 | 95.9 |
| 2_7_47_68 | 91.7 | 83.6 | 94 | 93.6 | 84.8 | 95.9 |
| 2_7_28_82 | 93.7 | 85.1 | 96 | 93.6 | 84.8 | 95.9 |
| 2_7_382_82 | 92.7 | 81.8 | 95.6 | 93.6 | 84.8 | 95.9 |
| 2_4_38_48 | 92.7 | 82.1 | 95.6 | 93.6 | 84.8 | 95.9 |
| 2_48_465_466 | 93 | 83.6 | 95.6 | 93.6 | 84.8 | 95.9 |
| 2_48_101_108 | 93 | 83.6 | 95.6 | 93.6 | 84.8 | 95.9 |
| 2_22_48_82 | 92.4 | 85.1 | 94.4 | 93.6 | 84.8 | 95.9 |
| 2_30_48_467 | 93.3 | 82.1 | 96.4 | 93.6 | 84.8 | 95.9 |
| 2_30_48_82 | 94.6 | 89.6 | 96 | 93.6 | 84.8 | 95.9 |
| 2_17_48_101 | 92.7 | 83.6 | 95.2 | 93.6 | 84.8 | 95.9 |
| 2_48_82_101 | 93.3 | 85.1 | 95.6 | 93.6 | 84.8 | 95.9 |
| 2_38_101_359 | 91.7 | 85.1 | 93.5 | 93.6 | 84.8 | 95.9 |
| 2_82_101_108 | 91.4 | 82.1 | 94 | 93.6 | 84.8 | 95.9 |
| 2_31_48_68 | 94 | 86.6 | 96 | 93.6 | 81.8 | 96.7 |
| 2_6_48_68 | 94.3 | 85.1 | 96.8 | 93.6 | 81.8 | 96.7 |
| 2_38_48_68 | 93.3 | 83.6 | 96 | 93.6 | 81.8 | 96.7 |
| 2_48_68_90 | 94 | 86.6 | 96 | 93.6 | 81.8 | 96.7 |
| 2_25_48_68 | 93.7 | 83.6 | 96.4 | 93.6 | 78.8 | 97.6 |
| 2_4_48_68 | 93.7 | 83.6 | 96.4 | 93.6 | 78.8 | 97.6 |
| 2_48_51_68 | 93.7 | 83.6 | 96.4 | 93.6 | 78.8 | 97.6 |
| 2_48_68_465 | 93.7 | 83.6 | 96.4 | 93.6 | 78.8 | 97.6 |
| 2_48_68_108 | 93.7 | 83.6 | 96.4 | 93.6 | 78.8 | 97.6 |
| 2_48_68_373 | 94 | 83.6 | 96.8 | 93.6 | 78.8 | 97.6 |
| 2_48_68_466 | 93.7 | 83.6 | 96.4 | 93.6 | 78.8 | 97.6 |
| 2_48_68_101 | 94 | 85.1 | 96.4 | 93.6 | 78.8 | 97.6 |
| 2_48_68_103 | 93.7 | 83.6 | 96.4 | 93.6 | 78.8 | 97.6 |
| 2_7_61_365 | 89.8 | 79.1 | 92.7 | 92.9 | 97 | 91.9 |
| 2_10_82_365 | 91.1 | 85.1 | 92.7 | 92.9 | 97 | 91.9 |

TABLE 11-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_9_82_467 | 92.7 | 88.1 | 94 | 92.9 | 97 | 91.9 |
| 2_7_10_101 | 93.3 | 86.6 | 95.2 | 92.9 | 93.9 | 92.7 |
| 2_7_38_101 | 93.3 | 86.6 | 95.2 | 92.9 | 93.9 | 92.7 |
| 2_7_61_466 | 90.5 | 80.6 | 93.1 | 92.9 | 93.9 | 92.7 |
| 2_51_465_467 | 90.8 | 82.1 | 93.1 | 92.9 | 93.9 | 92.7 |
| 2_38_465_466 | 91.4 | 83.6 | 93.5 | 92.9 | 93.9 | 92.7 |
| 2_38_365_465 | 91.1 | 83.6 | 93.1 | 92.9 | 93.9 | 92.7 |
| 2_47_465_467 | 90.8 | 80.6 | 93.5 | 92.9 | 93.9 | 92.7 |
| 2_368_465_467 | 90.8 | 82.1 | 93.1 | 92.9 | 93.9 | 92.7 |
| 2_25_61_101 | 90.8 | 82.1 | 93.1 | 92.9 | 90.9 | 93.5 |
| 2_7_47_465 | 90.2 | 82.1 | 92.3 | 92.9 | 90.9 | 93.5 |
| 2_7_28_47 | 90.8 | 82.1 | 93.1 | 92.9 | 90.9 | 93.5 |
| 2_7_30_101 | 93.3 | 88.1 | 94.8 | 92.9 | 90.9 | 93.5 |
| 2_7_53_101 | 93 | 88.1 | 94.4 | 92.9 | 90.9 | 93.5 |
| 2_7_101_359 | 92.7 | 85.1 | 94.8 | 92.9 | 90.9 | 93.5 |
| 2_10_82_90 | 94 | 89.6 | 95.2 | 92.9 | 90.9 | 93.5 |
| 2_9_31_101 | 91.4 | 82.1 | 94 | 92.9 | 90.9 | 93.5 |
| 2_31_38_48 | 93 | 85.1 | 95.2 | 92.9 | 84.8 | 95.1 |
| 2_28_31_48 | 93.7 | 86.6 | 95.6 | 92.3 | 87.9 | 93.5 |
| 4_7_82_101 | 92.4 | 91 | 92.7 | 92.3 | 93.9 | 91.9 |
| 4_7_38_82 | 91.1 | 85.1 | 92.7 | 92.3 | 90.9 | 92.7 |
| 6_7_61_68 | 92.1 | 89.6 | 92.7 | 92.3 | 84.8 | 94.3 |
| 7_25_47_466 | 87.3 | 83.6 | 88.3 | 92.3 | 87.9 | 93.5 |
| 7_25_48_466 | 89.8 | 85.1 | 91.1 | 92.3 | 84.8 | 94.3 |
| 4_7_82_103 | 92.4 | 89.6 | 93.1 | 91.7 | 90.9 | 91.9 |
| 4_7_47_82 | 89.2 | 86.6 | 89.9 | 91.7 | 90.9 | 91.9 |
| 7_25_28_466 | 91.7 | 86.6 | 93.1 | 91.7 | 90.9 | 91.9 |
| 7_25_30_466 | 89.2 | 89.6 | 89.1 | 91.7 | 90.9 | 91.9 |
| 7_25_31_47 | 88.9 | 89.6 | 88.7 | 91.7 | 90.9 | 91.9 |
| 4_7_31_82 | 88.6 | 83.6 | 89.9 | 91 | 87.9 | 91.9 |
| 2_7_9_105 | 91.4 | 83.6 | 93.5 | 90.4 | 90.9 | 90.2 |
| 2_7_108_464 | 89.2 | 80.6 | 91.5 | 90.4 | 87.9 | 91.1 |
| 2_10_25_105 | 90.2 | 88.1 | 90.7 | 89.1 | 87.9 | 89.4 |
| 4_28_31_82 | 87.6 | 82.1 | 89.1 | 89.1 | 87.9 | 89.4 |
| 10_47_90_101 | 91.1 | 92.5 | 90.7 | 88.5 | 90.9 | 87.8 |
| 10_30_103_365 | 86.3 | 85.1 | 86.7 | 88.5 | 84.8 | 89.4 |
| 9_10_61_68 | 90.5 | 86.6 | 91.5 | 88.5 | 78.8 | 91.1 |
| 10_48_68_90 | 93.7 | 89.6 | 94.8 | 88.5 | 75.8 | 91.9 |
| 10_30_68_365 | 91.1 | 82.1 | 93.5 | 88.5 | 75.8 | 91.9 |
| 4_7_10_82 | 88.9 | 86.6 | 89.5 | 87.8 | 84.8 | 88.6 |
| 4_6_10_105 | 81 | 83.6 | 80.2 | 78.8 | 78.8 | 78.9 |

Example 5

<Method B for Evaluating Pancreatic Cancer Discriminant Performance by Combination of Multiple Gene Markers Using Samples in the Validation Cohort>

Example 2 showed that discriminant performance was improved by using a combination of the multiple gene markers selected in Example 1, as compared with using one of the gene marker. Thus, in this Example, even the gene markers that were not selected in Example 1 were studied as to whether high pancreatic cancer discriminant performance is obtained by combinations with the gene markers selected in Example 1.

Specifically, among the genes having a gene expression level of $2^6$ or higher in 50% or more of the samples in either of the pancreatic cancer patient group in the training cohort or the healthy subject group in the training cohort, genes that showed statistical significance for discriminating a pancreatic cancer patient group from a healthy subject group with the P value smaller than 0.5 calculated by two-tailed t-test assuming equal variance as to each gene expression level and corrected by the Bonferroni method, were examined. As a result, 161 genes containing the 122 genes selected in Example 1 were found. Fisher's discriminant analysis was conducted as to 13,042 combinations using one or two of these 161 genes, to construct a discriminant for determining the presence or absence of pancreatic cancer. The discriminant performance of the selected combinations of 1 or 2 of the genes was validated in the same way as the method of Example 2.

As a result, some combinations of these genes exhibited accuracy of 85% or higher in both of the training cohort and the validation cohort and are shown in Table 12. For example, the newly found polynucleotide consisting of the nucleotide sequence represented by SEQ ID NO: 492, 493, or 494 discriminated the pancreatic cancer patients from the healthy subjects with high discriminant performance when used in combination of two polynucleotides comprising any of the polynucleotides consisting of the nucleotide sequences represented by SEQ ID NOs: 1 to 122. More specifically, the polynucleotide consisting of the nucleotide sequence represented by SEQ ID NO: 492, 493, or 494 was able to exhibit discrimination accuracy of 85% or higher between the pancreatic cancer patients and the healthy subjects in both of the training cohort and the validation cohort when used in combination of two polynucleotides comprising any of the polynucleotides consisting of the nucleotide sequences represented by SEQ ID NOs: 1, 2, 4, 7, 15, 24, 105, 107, and 108. Examples of such combinations of two genes include combinations of SEQ ID NOs: 105 and 492, SEQ ID NOs: 105 and 493, SEQ ID NOs: 1 and 492, SEQ ID NOs: 105 and 494, SEQ ID NOs: 1 and 493, SEQ ID NOs: 1 and 494, SEQ ID NOs: 107 and 493, SEQ ID NOs: 2 and 493, SEQ ID NOs: 7 and 493, SEQ ID NOs: 4 and 493, SEQ ID NOs: 2 and 492, SEQ ID NOs: 108 and 492, SEQ ID NOs: 2 and 494, SEQ ID NOs: 7 and 492, SEQ ID NOs: 7 and 494, SEQ ID NOs: 108 and 494, SEQ ID NOs: 4 and 492, SEQ ID NOs: 107 and 492, SEQ ID NOs: 107 and 494, SEQ ID NOs: 108 and 493, SEQ ID NOs: 15 and 492, SEQ ID NOs: 24 and 493, and SEQ ID NOs: 15 and 494.

As one example, an attempt was made to discriminate the pancreatic cancer patients from the healthy subjects using the expression level measurement V ues of the nucleotide sequences represented by SEQ ID NO: 105 and SEQ ID NO: 492. As a result, discriminant performance as high as 97.6% accuracy, 95.5% sensitivity, and 99.0% specificity in the training cohort and 96.4% accuracy, 93.9% sensitivity, and 98.0% specificity in the validation cohort was obtained.

From these results, it can be concluded that all of the polynucleotides consisting of the nucleotide sequences represented by SEQ ID NOs: 492 to 494 are also excellent diagnostic markers.

Table 12 mentioned above is as follows.

TABLE 12

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 105_492 | 97.6 | 95.5 | 99.0 | 96.4 | 93.9 | 98.0 |
| 105_493 | 97.6 | 95.5 | 99.0 | 96.4 | 93.9 | 98.0 |
| 1_492 | 97.6 | 97.0 | 98.0 | 94.0 | 90.9 | 96.0 |
| 105_494 | 96.4 | 94.0 | 98.0 | 96.4 | 93.9 | 98.0 |
| 1_493 | 95.8 | 92.5 | 98.0 | 92.8 | 87.9 | 96.0 |
| 1_494 | 95.8 | 94.0 | 97.0 | 92.8 | 87.9 | 96.0 |
| 107_493 | 94.0 | 88.1 | 98.0 | 89.2 | 84.8 | 92.0 |
| 2_493 | 92.2 | 83.6 | 98.0 | 95.2 | 90.9 | 98.0 |
| 7_493 | 91.0 | 89.6 | 92.0 | 90.4 | 90.9 | 90.0 |
| 4_493 | 91.0 | 85.1 | 95.0 | 88.0 | 87.9 | 88.0 |
| 2_492 | 90.4 | 79.1 | 98.0 | 96.4 | 93.9 | 98.0 |
| 108_492 | 89.8 | 86.6 | 92.0 | 89.2 | 87.9 | 90.0 |
| 2_494 | 89.2 | 79.1 | 96.0 | 95.2 | 93.9 | 96.0 |
| 7_492 | 88.6 | 89.6 | 88.0 | 86.7 | 90.9 | 84.0 |
| 7_494 | 88.6 | 85.1 | 91.0 | 90.4 | 90.9 | 90.0 |
| 108_494 | 88.6 | 83.6 | 92.0 | 88.0 | 87.9 | 88.0 |
| 4_492 | 88.0 | 79.1 | 94.0 | 89.2 | 90.9 | 88.0 |
| 107_492 | 88.0 | 83.6 | 91.0 | 85.5 | 84.8 | 86.0 |
| 107_494 | 87.4 | 83.6 | 90.0 | 86.7 | 84.8 | 88.0 |
| 108_493 | 86.8 | 83.6 | 89.0 | 86.7 | 84.8 | 88.0 |
| 15_492 | 85.6 | 76.1 | 92.0 | 88.0 | 84.8 | 90.0 |
| 24_493 | 85.6 | 83.6 | 87.0 | 86.7 | 84.8 | 88.0 |
| 15_494 | 85.6 | 74.6 | 93.0 | 86.7 | 78.8 | 92.0 |

Comparative Example 1

<Pancreatic Cancer Discriminant Performance of Existing Tumor Markers in Blood>

The concentrations of the existing tumor markers CEA and CA19-9 in blood were measured in the training cohort and the validation cohort obtained in the preceding Reference Examples. When the concentrations of these tumor markers in blood are higher than the reference values described in Non-Patent Literature 3 above (CEA: 5 ng/mL, CA19-9: 37 U/mL), subjects are usually suspected of having cancer. Thus, whether or not the concentrations of CEA and CA19-9 in blood exceeded their reference values was confirmed for each sample to assess the ability of these tumor markers to detect cancer in pancreatic cancer patients. The sensitivity of each existing marker in the training cohort and the validation cohort was calculated. The results are shown in Table 5. The sensitivity of CEA and CA19-9 was as low as 55.2% and 77.6%, respectively, in the training cohort, and was as low as 45.5% and 75.8%, respectively, in the validation cohort, demonstrating that neither of the markers are useful in the detection of pancreatic cancer (Table 5).

On the other hand, as shown above in Tables 3 and 6 of Examples 1 and 2, it can be concluded that in all of the polynucleotides consisting of the nucleotide sequences represented by SEQ ID NOs: 1 to 122, combinations of 1, 2 or more polynucleotides exhibiting sensitivity beyond the existing pancreatic cancer markers are present, and thus such polynucleotides serve as excellent diagnosis markers.

As shown in these Examples and Comparative Example, the kit and the method of the present invention can detect pancreatic cancer with higher sensitivity than the existing tumor markers and therefore permit early decision to carry out the surgical resection of a cancer site. As a result, improvement in 5-year survival rate and reduction in the rate of recurrence can be achieved.

INDUSTRIAL APPLICABILITY

According to the present invention, pancreatic cancer can be effectively detected by a simple and inexpensive method. This enables early detection, diagnosis and treatment of pancreatic cancer. The method of the present invention can detect pancreatic cancer with limited invasiveness using the blood of a patient and therefore allows pancreatic cancer to be detected conveniently and rapidly.

All publications, patents, and patent applications cited herein are incorporated herein by reference in their entirety.

The invention claimed is:
1. A kit for the detection of pancreatic cancer, comprising nucleic acids capable of specifically binding to polynucleotides of pancreatic cancer markers: miR-6836-3p and miR-6799-5p.
2. The kit according to claim 1, wherein miR-6836-3p is hsa-miR-6836-3p, and miR-6799-5p is hsa-miR-6799-5p.
3. The kit according to claim 1, wherein the nucleic acids are: a polynucleotide(s) selected from the group consisting of the following polynucleotides (a1) to (e1):
   (a1) a polynucleotide consisting of a nucleotide sequence represented by SEQ ID NO: 7 or a nucleotide sequence derived from the nucleotide sequence by the replacement of u with t, a variant thereof, a derivative thereof, or a fragment thereof comprising 15 or more consecutive nucleotides;
   (b1) a polynucleotide comprising a nucleotide sequence represented by SEQ ID NO: 7;
   (c1) a polynucleotide consisting of a nucleotide sequence complementary to a nucleotide sequence represented by SEQ ID NO: 7 or a nucleotide sequence derived from the nucleotide sequence by the replacement of u with t, a variant thereof, a derivative thereof, or a fragment thereof comprising 15 or more consecutive nucleotides;
   (d1) a polynucleotide comprising a nucleotide sequence complementary to a nucleotide sequence represented by SEQ ID NO: 7 or a nucleotide sequence derived from the nucleotide sequence by the replacement of u with t; and
   (e1) a polynucleotide hybridizing under stringent conditions to any of the polynucleotides (a1) to (d1); and
a polynucleotide(s) selected from the group consisting of the following polynucleotides (a2) to (e2):
   (a2) a polynucleotide consisting of a nucleotide sequence represented by SEQ ID NO: 9 or a nucleotide sequence derived from the nucleotide sequence by the replacement of u with t, a variant thereof, a derivative thereof, or a fragment thereof comprising 15 or more consecutive nucleotides;
   (b2) a polynucleotide comprising a nucleotide sequence represented by SEQ ID NO: 9;
   (c2) a polynucleotide consisting of a nucleotide sequence complementary to a nucleotide sequence represented by SEQ ID NO: 9 or a nucleotide sequence derived from the nucleotide sequence by the replacement of u with t, a variant thereof, a derivative thereof, or a fragment thereof comprising 15 or more consecutive nucleotides;
   (d2) a polynucleotide comprising a nucleotide sequence complementary to a nucleotide sequence represented by SEQ ID NO: 9 or a nucleotide sequence derived from the nucleotide sequence by the replacement of u with t; and
   (e2) a polynucleotide hybridizing under stringent conditions to any of the polynucleotides (a2) to (d2).
4. A kit according to claim 1, further comprising a nucleic acid(s) capable of specifically binding to at least one or more-polynucleotides selected from the group consisting of the following of pancreatic cancer markers: miR-6893-5p, miR-6075, miR-6820-5p, miR-4294, miR-6729-5p, miR-4476, miR-6765-3p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231, miR-4665-5p, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-4508, miR-940, miR-4327, miR-4665-3p, miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p.
5. The kit according to claim 4, wherein miR-6893-5p is hsa-miR-6893-5p, miR-6075 is hsa-miR-6075, miR-6820-5p is hsa-miR-6820-5p, miR-4294 is hsa-miR-4294, miR-6729-5p is hsa-miR-6729-5p, miR-4476 is hsa-miR-4476, miR-6765-3p is hsa-miR-6765-3p, miR-4530 is hsa-miR-4530, miR-7641 is hsa-miR-7641, miR-4454 is hsa-miR-4454, miR-615-5p is hsa-miR-615-5p, miR-8073 is hsa-miR-8073, miR-663a is hsa-miR-663a, miR-4634 is hsa-miR-4634, miR-4450 is hsa-miR-4450, miR-4792 is hsa-miR-4792, miR-665 is hsa-miR-665, miR-7975 is hsa-miR-7975, miR-7109-5p is hsa-miR-7109-5p, miR-6789-5p is hsa-miR-6789-5p, miR-4497 is hsa-miR-4497, miR-6877-5p is hsa-miR-6877-5p, miR-6880-5p is hsa-miR-6880-5p, miR-7977 is hsa-miR-7977, miR-4734 is hsa-miR-4734, miR-6821-5p is hsa-miR-6821-5p, miR-8089 is hsa-miR-8089, miR-5585-3p is hsa-miR-5585-3p, miR-6085 is hsa-miR-6085, miR-6845-5p is hsa-miR-6845-5p, miR-4651 is hsa-miR-4651, miR-4433-3p is hsa-miR-4433-3p, miR-1231 is hsa-miR-1231, miR-4665-5p is hsa-miR-4665-5p, miR-7114-5p is hsa-miR-7114-5p, miR-1238-5p is hsa-miR-1238-5p, miR-8069 is hsa-miR-8069, miR-4732-5p is hsa-miR-4732-5p, miR-619-5p is hsa-miR-619-5p, miR-3622a-5p is hsa-miR-3622a-5p, miR-1260a is hsa-miR-1260a, miR-6741-5p is hsa-miR-6741-5p, miR-6781-5p is hsa-miR-6781-5p, miR-6125 is hsa-miR-6125, miR-6805-5p is hsa-miR-6805-5p, miR-6132 is hsa-miR-6132, miR-6872-3p is hsa-miR-6872-3p, miR-6875-5p is hsa-miR-6875-5p, miR-1908-3p is hsa-miR-1908-3p, miR-4433b-3p is hsa-miR-4433b-3p, miR-4736 is hsa-miR-4736, miR-5100 is hsa-miR-5100, miR-6724-5p is hsa-miR-6724-5p, miR-7107-5p is hsa-miR-7107-5p, miR-6726-5p is hsa-miR-6726-5p, miR-3185 is hsa-miR-3185, miR-4638-5p is hsa-miR-4638-5p, miR-1273g-3p is hsa-miR-1273g-3p, miR-6778-5p is hsa-miR-6778-5p, miR-328-5p is hsa-miR-328-5p, miR-3679-3p is hsa-miR-3679-3p, miR-1228-3p is hsa-miR-1228-3p, miR-6779-5p is hsa-miR-6779-5p, miR-4723-5p is hsa-miR-4723-5p, miR-6850-5p is hsa-miR-6850-5p, miR-760 is hsa-miR-760, miR-7704 is hsa-miR-7704, miR-8072 is hsa-miR-8072, miR-4486 is hsa-miR-4486, miR-1913 is hsa-miR-1913, miR-4656 is hsa-miR-4656, miR-1260b is hsa-miR-1260b, miR-7106-5p is hsa-miR-7106-5p, miR-6889-5p is hsa-miR-6889-5p, miR-6780b-5p is hsa-miR-6780b-5p, miR-6090 is hsa-miR-6090, miR-4534 is hsa-miR-4534, miR-4449 is hsa-miR-4449, miR-5195-3p is hsa-miR-5195-3p, miR-1202 is hsa-miR-1202, miR-4467 is hsa-miR-4467, miR-6515-3p is hsa-miR-6515-3p, miR-4281 is hsa-miR-4281, miR-4505 is hsa-miR-4505, miR-4484 is hsa-miR-4484, miR-6805-3p is hsa-miR-

6805-3p, miR-3135b is hsa-miR-3135b, miR-3162-5p is hsa-miR-3162-5p, miR-6768-5p is hsa-miR-6768-5p, miR-6721-5p is hsa-miR-6721-5p, miR-1227-5p is hsa-miR-1227-5p, miR-6722-3p is hsa-miR-6722-3p, miR-4286 is hsa-miR-4286, miR-4746-3p is hsa-miR-4746-3p, miR-6727-5p is hsa-miR-6727-5p, miR-6816-5p is hsa-miR-6816-5p, miR-4741 is hsa-miR-4741, miR-4508 is hsa-miR-4508, miR-940 is hsa-miR-940, miR-4327 is hsa-miR-4327, miR-4665-3p is hsa-miR-4665-3p, miR-718 is hsa-miR-718, miR-1203 is hsa-miR-1203, miR-663b is hsa-miR-663b, miR-4258 is hsa-miR-4258, miR-4649-5p is hsa-miR-4649-5p, miR-4516 is hsa-miR-4516, miR-3619-3p is hsa-miR-3619-3p, miR-6826-5p is hsa-miR-6826-5p, miR-6757-5p is hsa-miR-6757-5p, miR-3131 is hsa-miR-3131, miR-1343-3p is hsa-miR-1343-3p, miR-6775-5p is hsa-miR-6775-5p, miR-6813-5p is hsa-miR-6813-5p, and miR-3940-5p is hsa-miR-3940-5p.

6. The kit according to claim 4, wherein the nucleic acid(s) is a polynucleotide(s) selected from the group consisting of the following polynucleotides (a3) to (e3):

(a3) a polynucleotide consisting of a nucleotide sequence represented by any of SEQ ID NOs: 1 to 6, 8, 10 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;

(b3) a polynucleotide comprising a nucleotide sequence represented by any of SEQ ID NOs: 1 to 6, 8 to 104, 464 to 473, and 492 to 494;

(c)3 a polynucleotide consisting of a nucleotide sequence complementary to a nucleotide sequence represented by any of SEQ ID NOs: 1 to 6, 8, 10 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;

(d3) a polynucleotide comprising a nucleotide sequence complementary to a nucleotide sequence represented by any of SEQ ID NOs: 1 to 6, 8, 10 to 104, 464 to 473, and 492 to 494 or a nucleotide sequence derived from the nucleotide sequence by the replacement of u with t; and (e3) a polynucleotide hybridizing under stringent conditions to any of the polynucleotides (a3) to (d3).

* * * * *

SEQUENCE LISTING

<160> NUMBER OF SEQ ID NOS: 499

<210> SEQ ID NO 1
<211> LENGTH: 21
<212> TYPE: RNA
<213> ORGANISM: Homo sapiens

<400> SEQUENCE: 1
caggcaggug uaggguggag c                                            21

<210> SEQ ID NO 2
<211> LENGTH: 21
<212> TYPE: RNA

<213> ORGANISM: Homo sapiens

<400> SEQUENCE: 2
acggcccagg cggcauuggu g    21

<210> SEQ ID NO 3
<211> LENGTH: 19
<212> TYPE: RNA
<213> ORGANISM: Homo sapiens

<400> SEQUENCE: 3
ugcggcagag cugggguca    19

<210> SEQ ID NO 4
<211> LENGTH: 17
<212> TYPE: RNA
<213> ORGANISM: Homo sapiens

<400> SEQUENCE: 4
gggagucuac agcaggg    17

<210> SEQ ID NO 5
<211> LENGTH: 22
<212> TYPE: RNA
<213> ORGANISM: Homo sapiens

<400> SEQUENCE: 5
ugggcgaggg cggcugagcg gc    22

<210> SEQ ID NO 6
<211> LENGTH: 22
<212> TYPE: RNA
<213> ORGANISM: Homo sapiens

<400> SEQUENCE: 6
caggaaggau uuagggacag gc    22

<210> SEQ ID NO 7
<211> LENGTH: 21
<212> TYPE: RNA
<213> ORGANISM: Homo sapiens

<400> SEQUENCE: 7
augccucccc cggccccgca g    21

<210> SEQ ID NO 8
<211> LENGTH: 21
<212> TYPE: RNA
<213> ORGANISM: Homo sapiens

<400> SEQUENCE: 8
ucaccuggcu ggcccgccca g    21

<210> SEQ ID NO 9
<211> LENGTH: 20
<212> TYPE: RNA
<213> ORGANISM: Homo sapiens

<400> SEQUENCE: 9
ggggaggugu gcagggcugg    20

<210> SEQ ID NO 10
<211> LENGTH: 18

```
<212> TYPE: RNA
<213> ORGANISM: Homo sapiens

<400> SEQUENCE: 10
cccagcagga cgggagcg                                                 18

<210> SEQ ID NO 11
<211> LENGTH: 19
<212> TYPE: RNA
<213> ORGANISM: Homo sapiens

<400> SEQUENCE: 11
uugaucucgg aagcuaagc                                                19

<210> SEQ ID NO 12
<211> LENGTH: 20
<212> TYPE: RNA
<213> ORGANISM: Homo sapiens

<400> SEQUENCE: 12
ggauccgagu cacggcacca                                               20

<210> SEQ ID NO 13
<211> LENGTH: 22
<212> TYPE: RNA
<213> ORGANISM: Homo sapiens

<400> SEQUENCE: 13
gggggucccc ggugcucgga uc                                            22

<210> SEQ ID NO 14
<211> LENGTH: 22
<212> TYPE: RNA
<213> ORGANISM: Homo sapiens

<400> SEQUENCE: 14
accuggcagc agggagcguc gu                                            22

<210> SEQ ID NO 15
<211> LENGTH: 22
<212> TYPE: RNA
<213> ORGANISM: Homo sapiens

<400> SEQUENCE: 15
aggcggggcg ccgcgggacc gc                                            22

<210> SEQ ID NO 16
<211> LENGTH: 19
<212> TYPE: RNA
<213> ORGANISM: Homo sapiens

<400> SEQUENCE: 16
cggcgcgacc ggcccgggg                                                19

<210> SEQ ID NO 17
<211> LENGTH: 22
<212> TYPE: RNA
<213> ORGANISM: Homo sapiens

<400> SEQUENCE: 17
uggggauuug gagaaguggu ga                                            22

<210> SEQ ID NO 18
```

-continued

```
<211> LENGTH: 18
<212> TYPE: RNA
<213> ORGANISM: Homo sapiens

<400> SEQUENCE: 18
cggugagcgc ucgcuggc                                                       18

<210> SEQ ID NO 19
<211> LENGTH: 20
<212> TYPE: RNA
<213> ORGANISM: Homo sapiens

<400> SEQUENCE: 19
accaggaggc ugaggccccu                                                     20

<210> SEQ ID NO 20
<211> LENGTH: 18
<212> TYPE: RNA
<213> ORGANISM: Homo sapiens

<400> SEQUENCE: 20
auccuaguca cggcacca                                                       18

<210> SEQ ID NO 21
<211> LENGTH: 21
<212> TYPE: RNA
<213> ORGANISM: Homo sapiens

<400> SEQUENCE: 21
cuggggggag gagacccugc u                                                   21

<210> SEQ ID NO 22
<211> LENGTH: 24
<212> TYPE: RNA
<213> ORGANISM: Homo sapiens

<400> SEQUENCE: 22 guagggcgu cccgggcgcg cggg                                                 24

<210> SEQ ID NO 23
<211> LENGTH: 17
<212> TYPE: RNA
<213> ORGANISM: Homo sapiens

<400> SEQUENCE: 23
cuccgggacg gcugggc                                                        17

<210> SEQ ID NO 24
<211> LENGTH: 22
<212> TYPE: RNA
<213> ORGANISM: Homo sapiens

<400> SEQUENCE: 24
agggccgaag gguggaagcu gc                                                  22

<210> SEQ ID NO 25
<211> LENGTH: 22
<212> TYPE: RNA
<213> ORGANISM: Homo sapiens

<400> SEQUENCE: 25
ugguggagga agagggcagc uc                                                  22
```

```
<210> SEQ ID NO 26
<211> LENGTH: 18
<212> TYPE: RNA
<213> ORGANISM: Homo sapiens

<400> SEQUENCE: 26
uucccagcca acgcacca                                                 18

<210> SEQ ID NO 27
<211> LENGTH: 22
<212> TYPE: RNA
<213> ORGANISM: Homo sapiens

<400> SEQUENCE: 27
gcugcgggcu gcggucaggg cg                                            22

<210> SEQ ID NO 28
<211> LENGTH: 23
<212> TYPE: RNA
<213> ORGANISM: Homo sapiens

<400> SEQUENCE: 28
gugcguggug gcucgaggcg ggg                                           23

<210> SEQ ID NO 29
<211> LENGTH: 24
<212> TYPE: RNA
<213> ORGANISM: Homo sapiens

<400> SEQUENCE: 29
ccuggggaca ggggauuggg gcag                                          24

<210> SEQ ID NO 30
<211> LENGTH: 22
<212> TYPE: RNA
<213> ORGANISM: Homo sapiens

<400> SEQUENCE: 30
cugaauagcu gggacuacag gu                                            22

<210> SEQ ID NO 31
<211> LENGTH: 19
<212> TYPE: RNA
<213> ORGANISM: Homo sapiens

<400> SEQUENCE: 31
aaggggcugg gggagcaca                                                19

<210> SEQ ID NO 32
<211> LENGTH: 19
<212> TYPE: RNA
<213> ORGANISM: Homo sapiens

<400> SEQUENCE: 32
cggggccaga gcagagagc                                                19

<210> SEQ ID NO 33
<211> LENGTH: 20
<212> TYPE: RNA
<213> ORGANISM: Homo sapiens

<400> SEQUENCE: 33
cggggugggu gaggucgggc                                               20
```

<210> SEQ ID NO 34
<211> LENGTH: 21
<212> TYPE: RNA
<213> ORGANISM: Homo sapiens

<400> SEQUENCE: 34
acaggagugg ggugggaca u                                          21

<210> SEQ ID NO 35
<211> LENGTH: 20
<212> TYPE: RNA
<213> ORGANISM: Homo sapiens

<400> SEQUENCE: 35
gugucugggc ggacagcugc                                           20

<210> SEQ ID NO 36
<211> LENGTH: 23
<212> TYPE: RNA
<213> ORGANISM: Homo sapiens

<400> SEQUENCE: 36 cuggggacg cgugagcgcg agc                                        23

<210> SEQ ID NO 37
<211> LENGTH: 21
<212> TYPE: RNA
<213> ORGANISM: Homo sapiens

<400> SEQUENCE: 37
ucuguggagu ggggugccug u                                         21

<210> SEQ ID NO 38
<211> LENGTH: 23
<212> TYPE: RNA
<213> ORGANISM: Homo sapiens

<400> SEQUENCE: 38
gugaguggga gccccagugu gug                                       23

<210> SEQ ID NO 39
<211> LENGTH: 23
<212> TYPE: RNA
<213> ORGANISM: Homo sapiens

<400> SEQUENCE: 39
ggaugguugg gggcggucgg cgu                                       23

<210> SEQ ID NO 40
<211> LENGTH: 23
<212> TYPE: RNA
<213> ORGANISM: Homo sapiens

<400> SEQUENCE: 40
uguagagcag ggagcaggaa gcu                                       23

<210> SEQ ID NO 41
<211> LENGTH: 22
<212> TYPE: RNA
<213> ORGANISM: Homo sapiens

<400> SEQUENCE: 41
gcugggauua caggcaugag cc                                        22

```
<210> SEQ ID NO 42
<211> LENGTH: 22
<212> TYPE: RNA
<213> ORGANISM: Homo sapiens

<400> SEQUENCE: 42
caggcacggg agcucaggug ag                                              22

<210> SEQ ID NO 43
<211> LENGTH: 18
<212> TYPE: RNA
<213> ORGANISM: Homo sapiens

<400> SEQUENCE: 43
aucccaccuc ugccacca                                                   18

<210> SEQ ID NO 44
<211> LENGTH: 22
<212> TYPE: RNA
<213> ORGANISM: Homo sapiens

<400> SEQUENCE: 44
gugggugcug gugggagccg ug                                              22

<210> SEQ ID NO 45
<211> LENGTH: 21
<212> TYPE: RNA
<213> ORGANISM: Homo sapiens

<400> SEQUENCE: 45
cgggccggag gucaagggcg u                                               21

<210> SEQ ID NO 46
<211> LENGTH: 20
<212> TYPE: RNA
<213> ORGANISM: Homo sapiens

<400> SEQUENCE: 46
gcggaaggcg gagcggcgga                                                 20

<210> SEQ ID NO 47
<211> LENGTH: 22
<212> TYPE: RNA
<213> ORGANISM: Homo sapiens

<400> SEQUENCE: 47 uaggggcgg cuuguggagu gu                                               22

<210> SEQ ID NO 48
<211> LENGTH: 19
<212> TYPE: RNA
<213> ORGANISM: Homo sapiens

<400> SEQUENCE: 48
agcagggcug gggauugca                                                  19

<210> SEQ ID NO 49
<211> LENGTH: 21
<212> TYPE: RNA
<213> ORGANISM: Homo sapiens

<400> SEQUENCE: 49
```
cccaugccuc cugccgcggu c                                              21

<210> SEQ ID NO 50
<211> LENGTH: 21
<212> TYPE: RNA
<213> ORGANISM: Homo sapiens

<400> SEQUENCE: 50
ugagggaccc aggacaggag a                                              21

<210> SEQ ID NO 51
<211> LENGTH: 21
<212> TYPE: RNA
<213> ORGANISM: Homo sapiens

<400> SEQUENCE: 51
ccggccgccg gcuccgcccc g                                              21

<210> SEQ ID NO 52
<211> LENGTH: 21
<212> TYPE: RNA
<213> ORGANISM: Homo sapiens

<400> SEQUENCE: 52
caggaguggg ggugggacg u                                               21

<210> SEQ ID NO 53
<211> LENGTH: 19
<212> TYPE: RNA
<213> ORGANISM: Homo sapiens

<400> SEQUENCE: 53
aggcagguua ucugggcug                                                 19

<210> SEQ ID NO 54
<211> LENGTH: 22
<212> TYPE: RNA
<213> ORGANISM: Homo sapiens

<400> SEQUENCE: 54
uucagauccc agcggugccu cu                                             22

<210> SEQ ID NO 55
<211> LENGTH: 23
<212> TYPE: RNA
<213> ORGANISM: Homo sapiens

<400> SEQUENCE: 55
cugggcccgc ggcgggcgug ggg                                            23

<210> SEQ ID NO 56
<211> LENGTH: 22
<212> TYPE: RNA
<213> ORGANISM: Homo sapiens

<400> SEQUENCE: 56
ucggccuggg gaggaggaag gg                                             22

<210> SEQ ID NO 57
<211> LENGTH: 21
<212> TYPE: RNA
<213> ORGANISM: Homo sapiens

<400> SEQUENCE: 57

```
cgggagcugg ggucugcagg u                                           21

<210> SEQ ID NO 58
<211> LENGTH: 23
<212> TYPE: RNA
<213> ORGANISM: Homo sapiens

<400> SEQUENCE: 58
agaagaaggc ggucggucug cgg                                         23

<210> SEQ ID NO 59
<211> LENGTH: 21
<212> TYPE: RNA
<213> ORGANISM: Homo sapiens

<400> SEQUENCE: 59
acucggcugc gguggacaag u                                           21

<210> SEQ ID NO 60
<211> LENGTH: 21
<212> TYPE: RNA
<213> ORGANISM: Homo sapiens

<400> SEQUENCE: 60
accacugcac uccagccuga g                                           21

<210> SEQ ID NO 61
<211> LENGTH: 22
<212> TYPE: RNA
<213> ORGANISM: Homo sapiens

<400> SEQUENCE: 61
agugggagga caggaggcag gu                                          22

<210> SEQ ID NO 62
<211> LENGTH: 23
<212> TYPE: RNA
<213> ORGANISM: Homo sapiens

<400> SEQUENCE: 62
gggggggcag gaggggcuca ggg                                         23

<210> SEQ ID NO 63
<211> LENGTH: 22
<212> TYPE: RNA
<213> ORGANISM: Homo sapiens

<400> SEQUENCE: 63 cuuccccca guaaucuuca uc                                           22

<210> SEQ ID NO 64
<211> LENGTH: 20
<212> TYPE: RNA
<213> ORGANISM: Homo sapiens

<400> SEQUENCE: 64
ucacaccugc cucgccccc                                              20

<210> SEQ ID NO 65
<211> LENGTH: 21
<212> TYPE: RNA
<213> ORGANISM: Homo sapiens
```

<400> SEQUENCE: 65
cugggagggg cuggguuugg c                                            21

<210> SEQ ID NO 66
<211> LENGTH: 24
<212> TYPE: RNA
<213> ORGANISM: Homo sapiens

<400> SEQUENCE: 66 uggggagcc augagauaag agca                                          24

<210> SEQ ID NO 67
<211> LENGTH: 22
<212> TYPE: RNA
<213> ORGANISM: Homo sapiens

<400> SEQUENCE: 67
gugcggaacg cuggccgggg cg                                           22

<210> SEQ ID NO 68
<211> LENGTH: 20
<212> TYPE: RNA
<213> ORGANISM: Homo sapiens

<400> SEQUENCE: 68
cggcucuggg ucugugggga                                              20

<210> SEQ ID NO 69
<211> LENGTH: 19
<212> TYPE: RNA
<213> ORGANISM: Homo sapiens

<400> SEQUENCE: 69
cggggucggc ggcgacgug                                               19

<210> SEQ ID NO 70
<211> LENGTH: 20
<212> TYPE: RNA
<213> ORGANISM: Homo sapiens

<400> SEQUENCE: 70
ggcggcgggg agguaggcag                                              20

<210> SEQ ID NO 71
<211> LENGTH: 17
<212> TYPE: RNA
<213> ORGANISM: Homo sapiens

<400> SEQUENCE: 71
gcugggcgag gcuggca                                                 17

<210> SEQ ID NO 72
<211> LENGTH: 22
<212> TYPE: RNA
<213> ORGANISM: Homo sapiens

<400> SEQUENCE: 72
ucugcccccu ccgcugcugc ca                                           22

<210> SEQ ID NO 73
<211> LENGTH: 23
<212> TYPE: RNA
<213> ORGANISM: Homo sapiens

```
<400> SEQUENCE: 73
ugggcugagg gcaggaggcc ugu                                          23

<210> SEQ ID NO 74
<211> LENGTH: 19
<212> TYPE: RNA
<213> ORGANISM: Homo sapiens

<400> SEQUENCE: 74
aucccaccac ugccaccau                                               19

<210> SEQ ID NO 75
<211> LENGTH: 20
<212> TYPE: RNA
<213> ORGANISM: Homo sapiens

<400> SEQUENCE: 75
ugggaggagg ggaucuuggg                                              20

<210> SEQ ID NO 76
<211> LENGTH: 23
<212> TYPE: RNA
<213> ORGANISM: Homo sapiens

<400> SEQUENCE: 76
ucggggaguc uggggguccgg aau                                         23

<210> SEQ ID NO 77
<211> LENGTH: 23
<212> TYPE: RNA
<213> ORGANISM: Homo sapiens

<400> SEQUENCE: 77
uggggaaggc uuggcaggga aga                                          23

<210> SEQ ID NO 78
<211> LENGTH: 19
<212> TYPE: RNA
<213> ORGANISM: Homo sapiens

<400> SEQUENCE: 78
ggggagcgag gggcggggc                                               19

<210> SEQ ID NO 79
<211> LENGTH: 17
<212> TYPE: RNA
<213> ORGANISM: Homo sapiens

<400> SEQUENCE: 79
ggauggagga gggucu                                                  17

<210> SEQ ID NO 80
<211> LENGTH: 22
<212> TYPE: RNA
<213> ORGANISM: Homo sapiens

<400> SEQUENCE: 80
cgucccgggg cugcgcgagg ca                                           22

<210> SEQ ID NO 81
<211> LENGTH: 21
<212> TYPE: RNA
```

```
<213> ORGANISM: Homo sapiens

<400> SEQUENCE: 81
auccaguucu cugagggggc u                                              21

<210> SEQ ID NO 82
<211> LENGTH: 21
<212> TYPE: RNA
<213> ORGANISM: Homo sapiens

<400> SEQUENCE: 82
gugccagcug cagugggga g                                               21

<210> SEQ ID NO 83
<211> LENGTH: 22
<212> TYPE: RNA
<213> ORGANISM: Homo sapiens

<400> SEQUENCE: 83
uggcggcggu aguuaugggc uu                                             22

<210> SEQ ID NO 84
<211> LENGTH: 20
<212> TYPE: RNA
<213> ORGANISM: Homo sapiens

<400> SEQUENCE: 84
ucucuucauc uaccccccag                                                20

<210> SEQ ID NO 85
<211> LENGTH: 18
<212> TYPE: RNA
<213> ORGANISM: Homo sapiens

<400> SEQUENCE: 85
gggucccggg gagggggg                                                  18

<210> SEQ ID NO 86
<211> LENGTH: 18
<212> TYPE: RNA
<213> ORGANISM: Homo sapiens

<400> SEQUENCE: 86
aggcugggcu gggacgga                                                  18

<210> SEQ ID NO 87
<211> LENGTH: 20
<212> TYPE: RNA
<213> ORGANISM: Homo sapiens

<400> SEQUENCE: 87
aaaaggcggg agaagcccca                                                20

<210> SEQ ID NO 88
<211> LENGTH: 23
<212> TYPE: RNA
<213> ORGANISM: Homo sapiens

<400> SEQUENCE: 88
uugcucugcu cccccgcccc cag                                            23

<210> SEQ ID NO 89
<211> LENGTH: 22
```

<212> TYPE: RNA
<213> ORGANISM: Homo sapiens

<400> SEQUENCE: 89
ggcuggagcg agugcagugg ug                                      22

<210> SEQ ID NO 90
<211> LENGTH: 23
<212> TYPE: RNA
<213> ORGANISM: Homo sapiens

<400> SEQUENCE: 90
uuagggagua aagggugggg gag                                     23

<210> SEQ ID NO 91
<211> LENGTH: 23
<212> TYPE: RNA
<213> ORGANISM: Homo sapiens

<400> SEQUENCE: 91
cacacaggaa aagcggggcc cug                                     23

<210> SEQ ID NO 92
<211> LENGTH: 23
<212> TYPE: RNA
<213> ORGANISM: Homo sapiens

<400> SEQUENCE: 92
ugggcagggg cuuauuguag gag                                     23

<210> SEQ ID NO 93
<211> LENGTH: 17
<212> TYPE: RNA
<213> ORGANISM: Homo sapiens

<400> SEQUENCE: 93 gugggggccag gcggugg                                           17

<210> SEQ ID NO 94
<211> LENGTH: 22
<212> TYPE: RNA
<213> ORGANISM: Homo sapiens

<400> SEQUENCE: 94
ugcagggguc ggugggcca gg                                       22

<210> SEQ ID NO 95
<211> LENGTH: 17
<212> TYPE: RNA
<213> ORGANISM: Homo sapiens

<400> SEQUENCE: 95
accccacucc ugguacc                                            17

<210> SEQ ID NO 96
<211> LENGTH: 21
<212> TYPE: RNA
<213> ORGANISM: Homo sapiens

<400> SEQUENCE: 96
agcggugcuc cugcgggccg a                                       21

<210> SEQ ID NO 97

```
<211> LENGTH: 23
<212> TYPE: RNA
<213> ORGANISM: Homo sapiens

<400> SEQUENCE: 97
cucggggcag gcggcuggga gcg                                            23

<210> SEQ ID NO 98
<211> LENGTH: 21
<212> TYPE: RNA
<213> ORGANISM: Homo sapiens

<400> SEQUENCE: 98 ugggggcgggg caggucccug c                                             21

<210> SEQ ID NO 99
<211> LENGTH: 23
<212> TYPE: RNA
<213> ORGANISM: Homo sapiens

<400> SEQUENCE: 99
cgggcugucc ggaggggucg gcu                                            23

<210> SEQ ID NO 100
<211> LENGTH: 17
<212> TYPE: RNA
<213> ORGANISM: Homo sapiens

<400> SEQUENCE: 100
gcggggcugg gcgcgcg                                                   17

<210> SEQ ID NO 101
<211> LENGTH: 21
<212> TYPE: RNA
<213> ORGANISM: Homo sapiens

<400> SEQUENCE: 101
aaggcagggc ccccgcuccc c                                              21

<210> SEQ ID NO 102
<211> LENGTH: 19
<212> TYPE: RNA
<213> ORGANISM: Homo sapiens

<400> SEQUENCE: 102
ggcuugcaug ggggacugg                                                 19

<210> SEQ ID NO 103
<211> LENGTH: 26
<212> TYPE: RNA
<213> ORGANISM: Homo sapiens

<400> SEQUENCE: 103
cucggccgcg gcgcguagcc cccgcc                                         26

<210> SEQ ID NO 104
<211> LENGTH: 21
<212> TYPE: RNA
<213> ORGANISM: Homo sapiens

<400> SEQUENCE: 104
cuuccgcccc gccgggcguc g                                              21
```

-continued

```
<210> SEQ ID NO 105
<211> LENGTH: 22
<212> TYPE: RNA
<213> ORGANISM: Homo sapiens

<400> SEQUENCE: 105
acaggugagg uucuugggag cc                                              22

<210> SEQ ID NO 106
<211> LENGTH: 21
<212> TYPE: RNA
<213> ORGANISM: Homo sapiens

<400> SEQUENCE: 106
gcugggaagg caaagggacg u                                               21

<210> SEQ ID NO 107
<211> LENGTH: 22
<212> TYPE: RNA
<213> ORGANISM: Homo sapiens

<400> SEQUENCE: 107
cucggcgcgg ggcgcgggcu cc                                              22

<210> SEQ ID NO 108
<211> LENGTH: 19
<212> TYPE: RNA
<213> ORGANISM: Homo sapiens

<400> SEQUENCE: 108
gagccaguug gacaggagc                                                  19

<210> SEQ ID NO 109
<211> LENGTH: 22
<212> TYPE: RNA
<213> ORGANISM: Homo sapiens

<400> SEQUENCE: 109
cugguacagg ccuggggac ag                                               22

<210> SEQ ID NO 110
<211> LENGTH: 23
<212> TYPE: RNA
<213> ORGANISM: Homo sapiens

<400> SEQUENCE: 110
ugaggggcag agagcgagac uuu                                             23

<210> SEQ ID NO 111
<211> LENGTH: 19
<212> TYPE: RNA
<213> ORGANISM: Homo sapiens

<400> SEQUENCE: 111
aggcacggug ucagcaggc                                                  19

<210> SEQ ID NO 112
<211> LENGTH: 23
<212> TYPE: RNA
<213> ORGANISM: Homo sapiens

<400> SEQUENCE: 112
agaggcuuug ugcggauacg ggg                                             23
```

<210> SEQ ID NO 113
<211> LENGTH: 19
<212> TYPE: RNA
<213> ORGANISM: Homo sapiens

<400> SEQUENCE: 113
aauggauuuu uggagcagg                                          19

<210> SEQ ID NO 114
<211> LENGTH: 23
<212> TYPE: RNA
<213> ORGANISM: Homo sapiens

<400> SEQUENCE: 114
gacacgggcg acagcugcgg ccc                                     23

<210> SEQ ID NO 115
<211> LENGTH: 19
<212> TYPE: RNA
<213> ORGANISM: Homo sapiens

<400> SEQUENCE: 115
uggauuuuug gaucaggga                                          19

<210> SEQ ID NO 116
<211> LENGTH: 22
<212> TYPE: RNA
<213> ORGANISM: Homo sapiens

<400> SEQUENCE: 116
uagcagcacg uaaauauugg cg                                      22

<210> SEQ ID NO 117
<211> LENGTH: 22
<212> TYPE: RNA
<213> ORGANISM: Homo sapiens

<400> SEQUENCE: 117
aaaccguuac cauuacugag uu                                      22

<210> SEQ ID NO 118
<211> LENGTH: 22
<212> TYPE: RNA
<213> ORGANISM: Homo sapiens

<400> SEQUENCE: 118
uggcucaguu cagcaggaac ag                                      22

<210> SEQ ID NO 119
<211> LENGTH: 22
<212> TYPE: RNA
<213> ORGANISM: Homo sapiens

<400> SEQUENCE: 119
ggcuacaaca caggacccgg gc                                      22

<210> SEQ ID NO 120
<211> LENGTH: 21
<212> TYPE: RNA
<213> ORGANISM: Homo sapiens

<400> SEQUENCE: 120
cggcggggac ggcgauuggu c                                       21

<210> SEQ ID NO 121
<211> LENGTH: 20
<212> TYPE: RNA
<213> ORGANISM: Homo sapiens

<400> SEQUENCE: 121
acucaaacug uggggggcacu                                                  20

<210> SEQ ID NO 122
<211> LENGTH: 23
<212> TYPE: RNA
<213> ORGANISM: Homo sapiens

<400> SEQUENCE: 122
agugccugag ggaguaagag ccc                                               23

<210> SEQ ID NO 123
<211> LENGTH: 69
<212> TYPE: RNA
<213> ORGANISM: Homo sapiens

<400> SEQUENCE: 123
ccgggcaggc aggguagggg uggagcccac uguggcuccu gacucagccc ugcugccuuc       60
accugccag                                                               69

<210> SEQ ID NO 124
<211> LENGTH: 95
<212> TYPE: RNA
<213> ORGANISM: Homo sapiens

<400> SEQUENCE: 124
gacaccacau gcuccuccag gccugccugc ccuccagguc auguuccagu gucccacaga       60
ugcagcacca cggcccaggc ggcauuggug ucacc                                  95

<210> SEQ ID NO 125
<211> LENGTH: 62
<212> TYPE: RNA
<213> ORGANISM: Homo sapiens

<400> SEQUENCE: 125
ccuucugcgg cagagcuggg gucaccagcc cucauguacu gugacuucu ccccugccac        60 ag                                                                      62

<210> SEQ ID NO 126
<211> LENGTH: 76
<212> TYPE: RNA
<213> ORGANISM: Homo sapiens

<400> SEQUENCE: 126
ccgaugccuc gggagucuac agcagggcca ugucugugag ggcccaaggg ugcauguguc       60
ucccagguuu cggugc                                                       76

<210> SEQ ID NO 127
<211> LENGTH: 65
<212> TYPE: RNA
<213> ORGANISM: Homo sapiens

<400> SEQUENCE: 127 gaggguggc gagggcggcu gagcggcucc auccccggc cugcucaucc cccucgcccu         60
cucag                                                                65

<210> SEQ ID NO 128
<211> LENGTH: 70
<212> TYPE: RNA
<213> ORGANISM: Homo sapiens

<400> SEQUENCE: 128
aaaagccugu cccuaagucc cucccagccu uccagaguug gugccaggaa ggauuuaggg    60
acaggcuuug                                                           70

<210> SEQ ID NO 129
<211> LENGTH: 63
<212> TYPE: RNA
<213> ORGANISM: Homo sapiens

<400> SEQUENCE: 129
ggcuccgcag ggcccuggcg caggcaucca gacagcgggc gaaugccucc cccggccccg    60
cag                                                                  63

<210> SEQ ID NO 130
<211> LENGTH: 87
<212> TYPE: RNA
<213> ORGANISM: Homo sapiens

<400> SEQUENCE: 130
gugaggcggg gccaggaggg uguguggcgu gggugcugcg gggccgucag ggugccugcg    60
ggacgcucac cuggcuggcc cgcccag                                        87

<210> SEQ ID NO 131
<211> LENGTH: 69
<212> TYPE: RNA
<213> ORGANISM: Homo sapiens

<400> SEQUENCE: 131
gaggagggga ggugugcagg gcuggggggca cugacucugc uuccccugcc cugcaugaug    60
uccccacag                                                            69

<210> SEQ ID NO 132
<211> LENGTH: 56
<212> TYPE: RNA
<213> ORGANISM: Homo sapiens

<400> SEQUENCE: 132
cgaccgcacc cgcccgaagc ugggucaagg agcccagcag gacgggagcg cggcgc        56

<210> SEQ ID NO 133
<211> LENGTH: 61
<212> TYPE: RNA
<213> ORGANISM: Homo sapiens

<400> SEQUENCE: 133
ucucguuuga ucucggaagc uaagcagggu ugggccuggu aguacuugg augggaaacu     60 u                                                                    61

<210> SEQ ID NO 134
<211> LENGTH: 53
<212> TYPE: RNA
<213> ORGANISM: Homo sapiens

<400> SEQUENCE: 134
guuugaucuc ggaagcuaag cagggucggg ccugguuagu acuuggaugg gag       53

<210> SEQ ID NO 135
<211> LENGTH: 55
<212> TYPE: RNA
<213> ORGANISM: Homo sapiens

<400> SEQUENCE: 135
ccggauccga gucacggcac caaauuucau gcguguccgu gugaagagac cacca     55

<210> SEQ ID NO 136
<211> LENGTH: 96
<212> TYPE: RNA
<213> ORGANISM: Homo sapiens

<400> SEQUENCE: 136
cucgggaggg gcgggagggg gguccccggu gcucggaucu cgagggugcu auuguucgg  60 uccgagccug ggucucccuc uuccccccaa cccccc                          96

<210> SEQ ID NO 137
<211> LENGTH: 72
<212> TYPE: RNA
<213> ORGANISM: Homo sapiens

<400> SEQUENCE: 137
gauuucagug accuggcagc agggagcguc gucaguguuu gacuguuuau ggaugucag  60 ggagcugguu cc                                                    72

<210> SEQ ID NO 138
<211> LENGTH: 93
<212> TYPE: RNA
<213> ORGANISM: Homo sapiens

<400> SEQUENCE: 138
ccuuccggcg ucccaggcgg ggcgccgcgg gaccgcccuc gugucugugg cgguggrauc  60
ccgcggccgu guuuccugg uggcccggcc aug                              93

<210> SEQ ID NO 139
<211> LENGTH: 54
<212> TYPE: RNA
<213> ORGANISM: Homo sapiens

<400> SEQUENCE: 139
ggacaagggc ggcgcgaccg gcccggggcu cuugggcggc cgcguuuccc cucc       54

<210> SEQ ID NO 140
<211> LENGTH: 65
<212> TYPE: RNA
<213> ORGANISM: Homo sapiens

<400> SEQUENCE: 140
ugucugggga uuuggagaag uggugagcgc aggucuuugg caccaucucc ccuggucccu  60
uggcu                                                            65

<210> SEQ ID NO 141
<211> LENGTH: 74
<212> TYPE: RNA
<213> ORGANISM: Homo sapiens

<400> SEQUENCE: 141

```
gcagcccggu gagcgcucgc uggccuggca gucgucgga agaacagggc ggguggggcc      60
gcgcacaucu cugc                                                      74

<210> SEQ ID NO 142
<211> LENGTH: 72
<212> TYPE: RNA
<213> ORGANISM: Homo sapiens

<400> SEQUENCE: 142
ucuccucgag gggucucugc cucuacccag gacucuuuca ugaccaggag gcugaggccc      60
cucacaggcg gc                                                        72

<210> SEQ ID NO 143
<211> LENGTH: 68
<212> TYPE: RNA
<213> ORGANISM: Homo sapiens

<400> SEQUENCE: 143
gugcaaagag caggaggaca ggggauuuau cucccaaggg aggucccug auccuaguca      60 cggcacca                                                             68

<210> SEQ ID NO 144
<211> LENGTH: 65
<212> TYPE: RNA
<213> ORGANISM: Homo sapiens

<400> SEQUENCE: 144
gucuccuggg gggaggagac ccugcucucc cuggcagcaa gccucuccug cccuuccaga      60
uuagc                                                                65

<210> SEQ ID NO 145
<211> LENGTH: 98
<212> TYPE: RNA
<213> ORGANISM: Homo sapiens

<400> SEQUENCE: 145
cgagguaggg gcgucccggg cgcgcgggcg gguccaggc ugggcccuc ggaggccggg       60 ugcucacugc cccgucccgg cgcccguguc uccuccag                            98

<210> SEQ ID NO 146
<211> LENGTH: 89
<212> TYPE: RNA
<213> ORGANISM: Homo sapiens

<400> SEQUENCE: 146
accuccggga cggcugggcg ccggcggccg ggagauccgc gcuuccugaa ucccggccgg      60
cccgcccggc gcccguccgc ccgcggguc                                      89

<210> SEQ ID NO 147
<211> LENGTH: 64
<212> TYPE: RNA
<213> ORGANISM: Homo sapiens

<400> SEQUENCE: 147
aguucagggc cgaagggugg aagcugcugg ugcucaucuc agccucugcc cuuggccucc      60
ccag                                                                 64

<210> SEQ ID NO 148
<211> LENGTH: 62
```

<212> TYPE: RNA
<213> ORGANISM: Homo sapiens

<400> SEQUENCE: 148
gaggguggug gaggaagagg gcagcuccca ugacugccug accgccuucu cuccuccccc    60
ag    62

<210> SEQ ID NO 149
<211> LENGTH: 49
<212> TYPE: RNA
<213> ORGANISM: Homo sapiens

<400> SEQUENCE: 149
uucccagcca acgcaccaaa aaugauaugg gucuguuguc uggagaaac    49

<210> SEQ ID NO 150
<211> LENGTH: 70
<212> TYPE: RNA
<213> ORGANISM: Homo sapiens

<400> SEQUENCE: 150
cucgggcccg accgcgccgg cccgcaccuc ccggcccgga gcugcgggcu gcggucaggg    60
cgaucccggg    70

<210> SEQ ID NO 151
<211> LENGTH: 74
<212> TYPE: RNA
<213> ORGANISM: Homo sapiens

<400> SEQUENCE: 151
gugcguggug gcucgaggcg gggugggggg ccucgcccug cuugggcccu cccugaccuc    60
uccgcuccgc acag    74

<210> SEQ ID NO 152
<211> LENGTH: 82
<212> TYPE: RNA
<213> ORGANISM: Homo sapiens

<400> SEQUENCE: 152
aaggagcacu cacuccaauu ucccuggacu gggggcaggc ugccaccucc uggggacagg    60
ggauuggggc aggauguucc ag    82

<210> SEQ ID NO 153
<211> LENGTH: 59
<212> TYPE: RNA
<213> ORGANISM: Homo sapiens

<400> SEQUENCE: 153
ugaaguacca gcuacucgag aggucagagg auugcuccug aauagcuggg acuacaggu    59

<210> SEQ ID NO 154
<211> LENGTH: 110
<212> TYPE: RNA
<213> ORGANISM: Homo sapiens

<400> SEQUENCE: 154
gucuaccagg ugugggccca gcuuuacaua guucaugcug aggccgggau uucaugcaga    60
aaacugguug caaaaggugc ugaaggggcu gggggagcac aagggagaag    110

<210> SEQ ID NO 155

<211> LENGTH: 61
<212> TYPE: RNA
<213> ORGANISM: Homo sapiens

<400> SEQUENCE: 155
aacugcgggg ccagagcaga gagcccuugc acaccaccag ccucuccucc cugugcccca    60
g    61

<210> SEQ ID NO 156
<211> LENGTH: 73
<212> TYPE: RNA
<213> ORGANISM: Homo sapiens

<400> SEQUENCE: 156
cggcgacggc ggggugggug aggucgggcc ccaagacucg ggguuugccg ggcgccucag    60
uucaccgcgg ccg    73

<210> SEQ ID NO 157
<211> LENGTH: 81
<212> TYPE: RNA
<213> ORGANISM: Homo sapiens

<400> SEQUENCE: 157
cauccuccuu acgucccacc ccccacuccu guuucuggug aaauauucaa acaggagugg    60 ggguggggaca uaaggaggau a    81

<210> SEQ ID NO 158
<211> LENGTH: 92
<212> TYPE: RNA
<213> ORGANISM: Homo sapiens

<400> SEQUENCE: 158
gucagugucu gggcggacag cugcaggaaa gggaagacca aggcuugcug ucuguccagu    60
cugccacccu acccugucug uucuugccac ag    92

<210> SEQ ID NO 159
<211> LENGTH: 79
<212> TYPE: RNA
<213> ORGANISM: Homo sapiens

<400> SEQUENCE: 159
cucgaggugc uggggacgc gugagcgcga gccgcuuccu cacggcucgg ccgcggcgcg    60 uagccccgc cacaucggg    79

<210> SEQ ID NO 160
<211> LENGTH: 61
<212> TYPE: RNA
<213> ORGANISM: Homo sapiens

<400> SEQUENCE: 160
uccgcucugu ggaguggggu gccuguccccc ugccacuggg ugacccaccc cucuccacca    60
g    61

<210> SEQ ID NO 161
<211> LENGTH: 83
<212> TYPE: RNA
<213> ORGANISM: Homo sapiens

<400> SEQUENCE: 161
gugaguggga gccccagugu gugguugggg ccauggcggg ugggcagccc agccucugag    60
ccuuccucgu cugucugccc cag                                             83

<210> SEQ ID NO 162
<211> LENGTH: 86
<212> TYPE: RNA
<213> ORGANISM: Homo sapiens

<400> SEQUENCE: 162
cgccugagcg ugcagcagga caucuuccug accugguaau aauuagguga gaaggauggu    60 uggggcggu cggcguaacu caggga                                          86

<210> SEQ ID NO 163
<211> LENGTH: 76
<212> TYPE: RNA
<213> ORGANISM: Homo sapiens

<400> SEQUENCE: 163
gagggagcug uagagcaggg agcaggaagc ugugugaguc cagcccugac cguccuguu    60 cugcccccag ccccuc                                                    76

<210> SEQ ID NO 164
<211> LENGTH: 99
<212> TYPE: RNA
<213> ORGANISM: Homo sapiens

<400> SEQUENCE: 164
cgcccaccuc agccucccaa aaugcuggga uuacaggcau gagccacugc ggucgaccau    60
gaccuggaca uguuugugcc caguacuguc aguuugcag                          99

<210> SEQ ID NO 165
<211> LENGTH: 83
<212> TYPE: RNA
<213> ORGANISM: Homo sapiens

<400> SEQUENCE: 165
aauagagggu gcacaggcac gggagcucag gugaggcagg gagcugagcu caccugaccu    60
cccaugccug ugcacccucu auu                                            83

<210> SEQ ID NO 166
<211> LENGTH: 73
<212> TYPE: RNA
<213> ORGANISM: Homo sapiens

<400> SEQUENCE: 166 accuuccag cucaucccac cucugccacc aaaacacuca ucgcggguc agagggagug      60 ccaaaaaagg uaa                                                       73

<210> SEQ ID NO 167
<211> LENGTH: 63
<212> TYPE: RNA
<213> ORGANISM: Homo sapiens

<400> SEQUENCE: 167 aaugggguggg ugcugguggg agccgugccc uggccacuca uucggcucuc ucccucaccc   60
uag                                                                  63

<210> SEQ ID NO 168
<211> LENGTH: 64
<212> TYPE: RNA

<213> ORGANISM: Homo sapiens

<400> SEQUENCE: 168
aaccccgggc cggaggucaa gggcgucgcu ucucccuaau guugccucuu uuccacggcc    60
ucag    64

<210> SEQ ID NO 169
<211> LENGTH: 96
<212> TYPE: RNA
<213> ORGANISM: Homo sapiens

<400> SEQUENCE: 169
gcucuggggc gugccgccgc cgucgcugcc accuccccua ccgcuagugg aagaagaugg    60
cggaaggcgg agcggcggau cuggacaccc agcggu    96

<210> SEQ ID NO 170
<211> LENGTH: 62
<212> TYPE: RNA
<213> ORGANISM: Homo sapiens

<400> SEQUENCE: 170
uggccuaggg ggcggcuugu ggaguguaug ggcugagccu ugcucugcuc ccccgccccc    60
ag    62

<210> SEQ ID NO 171
<211> LENGTH: 109
<212> TYPE: RNA
<213> ORGANISM: Homo sapiens

<400> SEQUENCE: 171
ugcuauuguc uuacugcuac agcagggcug gggauugcag uauccgcugu ugcugcugcu    60
cccaguccug ccccugcugc uaccuagucc agccucaccg caucccaga    109

<210> SEQ ID NO 172
<211> LENGTH: 62
<212> TYPE: RNA
<213> ORGANISM: Homo sapiens

<400> SEQUENCE: 172
gugggucucg caucaggagg caaggccagg acccgcugac ccaugccucc ugccgcgguc    60
ag    62

<210> SEQ ID NO 173
<211> LENGTH: 72
<212> TYPE: RNA
<213> ORGANISM: Homo sapiens

<400> SEQUENCE: 173
gagucugagg gacccaggac aggagaaggc cuauggugau uugcauucuu ccugcccugg    60
cuccauccuc ag    72

<210> SEQ ID NO 174
<211> LENGTH: 80
<212> TYPE: RNA
<213> ORGANISM: Homo sapiens

<400> SEQUENCE: 174
cgggaaugcc gcggcgggga cggcgauugg uccguaugug ggugccacc ggccgccggc    60 uccgccccgg ccccccgccc    80

<210> SEQ ID NO 175
<211> LENGTH: 102
<212> TYPE: RNA
<213> ORGANISM: Homo sapiens

<400> SEQUENCE: 175
uguuuccccu auccuccuua ugcccaccc ccacuccugu uugaauauuu caccagaaac    60
aggagugggg ggugggacgu aaggaggaug ggggaaagaa ca                      102

<210> SEQ ID NO 176
<211> LENGTH: 47
<212> TYPE: RNA
<213> ORGANISM: Homo sapiens

<400> SEQUENCE: 176
aggcagguua ucugggcugc caucucccac uggcugcuug ccugccu                 47

<210> SEQ ID NO 177
<211> LENGTH: 119
<212> TYPE: RNA
<213> ORGANISM: Homo sapiens

<400> SEQUENCE: 177
ccaugaggag cuggcagugg gauggccugg ggguaggagc guggcuucug gagcuagacc   60 acaugggguuc agaucccagc ggugccucua acuggccaca ggaccuuggg cagucagcu  119

<210> SEQ ID NO 178
<211> LENGTH: 92
<212> TYPE: RNA
<213> ORGANISM: Homo sapiens

<400> SEQUENCE: 178
cgcugcgcuu cugggcccgc ggcgggcgug gggcugcccg ggccggucga ccagcgcgcc   60
guagcucccg aggcccgagc cgcgacccgc gg                                 92

<210> SEQ ID NO 179
<211> LENGTH: 80
<212> TYPE: RNA
<213> ORGANISM: Homo sapiens

<400> SEQUENCE: 179
ugccgucggc cuggggagga ggaagggcaa guccaaaggu auacaguugg ucuguucauu   60
cucucuuuuu ggccuacaag                                               80

<210> SEQ ID NO 180
<211> LENGTH: 61
<212> TYPE: RNA
<213> ORGANISM: Homo sapiens

<400> SEQUENCE: 180
gggggcggga gcuggggucu gcagguucgc acugaugccu gcucgcccug ucuccgcua    60 g                                                                   61

<210> SEQ ID NO 181
<211> LENGTH: 68
<212> TYPE: RNA
<213> ORGANISM: Homo sapiens

<400> SEQUENCE: 181

```
gaauggaaga agaaggcggu cggucugcgg gagccaggcc gcagagccau ccgccuucug    60
uccauguc                                                              68

<210> SEQ ID NO 182
<211> LENGTH: 68
<212> TYPE: RNA
<213> ORGANISM: Homo sapiens

<400> SEQUENCE: 182
gacucggcug cgguggacaa guccggcucc agaaccugga caccgcucag ccggccgcgg    60
cagggguc                                                              68

<210> SEQ ID NO 183
<211> LENGTH: 100
<212> TYPE: RNA
<213> ORGANISM: Homo sapiens

<400> SEQUENCE: 183
gaggugggag gauugcuuga gucagggugg uugaggcugc aguaaguugu gaucauacca    60
cugcacucca gccugaguga cagagcaaga ccuugucuca                          100

<210> SEQ ID NO 184
<211> LENGTH: 73
<212> TYPE: RNA
<213> ORGANISM: Homo sapiens

<400> SEQUENCE: 184
guucaagugg gaggacagga ggcaggugug guuggaggaa gcagccugaa ccugccuccc    60
ugacauucca cag                                                       73

<210> SEQ ID NO 185
<211> LENGTH: 75
<212> TYPE: RNA
<213> ORGANISM: Homo sapiens

<400> SEQUENCE: 185
uggagugggg gggcaggagg ggcucaggga gaaagugcau acagcccug gcccucucug     60 cccuuccguc cccug                                                     75

<210> SEQ ID NO 186
<211> LENGTH: 68
<212> TYPE: RNA
<213> ORGANISM: Homo sapiens

<400> SEQUENCE: 186
cguggugagg auauggcagg gaagggagu uucccucuau ucccuucccc ccaguaaucu     60
ucaucaug                                                              68

<210> SEQ ID NO 187
<211> LENGTH: 73
<212> TYPE: RNA
<213> ORGANISM: Homo sapiens

<400> SEQUENCE: 187
gugggcgggg gcaggugugu gguggugguu ggccugcggu gagcagggcc cucacaccug    60
ccucgccccc cag                                                       73

<210> SEQ ID NO 188
<211> LENGTH: 64
```

```
<212> TYPE: RNA
<213> ORGANISM: Homo sapiens

<400> SEQUENCE: 188
gagcucuggg aggggcuggg uuuggcagga caguuuccaa gcccugucuc cucccaucuu     60
ccag                                                                 64

<210> SEQ ID NO 189
<211> LENGTH: 81
<212> TYPE: RNA
<213> ORGANISM: Homo sapiens

<400> SEQUENCE: 189
aguugguggg ggagccauga gauaagagca ccuccuagag aauguugaac uaaaggugcc     60
cucucuggcu ccuccccaaa g                                              81

<210> SEQ ID NO 190
<211> LENGTH: 61
<212> TYPE: RNA
<213> ORGANISM: Homo sapiens

<400> SEQUENCE: 190
gugcggaacg cuggccgggg cgggagggga agggacgccc ggccggaacg ccgcacucac     60
g                                                                    61

<210> SEQ ID NO 191
<211> LENGTH: 80
<212> TYPE: RNA
<213> ORGANISM: Homo sapiens

<400> SEQUENCE: 191
ggcgcgucgc cccccucagu ccaccagagc ccggauaccu cagaaauucg gcucugguc     60 uguggggagc gaaaugcaac                                                80

<210> SEQ ID NO 192
<211> LENGTH: 59
<212> TYPE: RNA
<213> ORGANISM: Homo sapiens

<400> SEQUENCE: 192
cggggucggc ggcgacgugc ucagcuuggc acccaaguuc ugccgcuccg acgcccggc      59

<210> SEQ ID NO 193
<211> LENGTH: 80
<212> TYPE: RNA
<213> ORGANISM: Homo sapiens

<400> SEQUENCE: 193
gcgucaagau ggcggcgggg agguaggcag agcaggacgc cgcugcugcc gccgccaccg    60
ccgccuccgc uccagucgcc                                                80

<210> SEQ ID NO 194
<211> LENGTH: 63
<212> TYPE: RNA
<213> ORGANISM: Homo sapiens

<400> SEQUENCE: 194
gcaugcuggg cgaggcuggc aucuagcaca ggcgguagau gcuugcucuu gccauugcaa     60
uga                                                                  63
```

```
<210> SEQ ID NO 195
<211> LENGTH: 80
<212> TYPE: RNA
<213> ORGANISM: Homo sapiens

<400> SEQUENCE: 195
accucuaccu cccggcagag gaggcugcag aggcuggcuu uccaaaacuc ugccccucc      60 gcugcugcca aguggcuggu                                                80

<210> SEQ ID NO 196
<211> LENGTH: 75
<212> TYPE: RNA
<213> ORGANISM: Homo sapiens

<400> SEQUENCE: 196
aggcuggcgu gggcugaggg caggaggccu guggccgguc ccaggccucc ugcuuccugg     60
gcucaggcuc gguuu                                                     75

<210> SEQ ID NO 197
<211> LENGTH: 89
<212> TYPE: RNA
<213> ORGANISM: Homo sapiens

<400> SEQUENCE: 197
ucuccguuua ucccaccacu gccaccauua uugcuacugu ucagcaggug cugcuggugg     60
ugauggugau agucuggugg gggcggugg                                      89

<210> SEQ ID NO 198
<211> LENGTH: 65
<212> TYPE: RNA
<213> ORGANISM: Homo sapiens

<400> SEQUENCE: 198
gcuucuggga ggagggggauc uugggaguga ucccaacagc ugagcucccu gaaucccugu    60
cccag                                                                65

<210> SEQ ID NO 199
<211> LENGTH: 59
<212> TYPE: RNA
<213> ORGANISM: Homo sapiens

<400> SEQUENCE: 199
cugugucggg gagucugggg uccggaauuc uccagagccu cugugccccu acuucccag      59

<210> SEQ ID NO 200
<211> LENGTH: 79
<212> TYPE: RNA
<213> ORGANISM: Homo sapiens

<400> SEQUENCE: 200
cagccugggg aaggcuuggc agggaagaca caugagcagu gccuccacuu cacgccucuc     60 ccugucucc uuucccuag                                                  79

<210> SEQ ID NO 201
<211> LENGTH: 60
<212> TYPE: RNA
<213> ORGANISM: Homo sapiens

<400> SEQUENCE: 201
cgcuggguuc gcgcgcccug ggccgggcga uguccgcuug ggggagcgag gggcggggcg     60
```

```
<210> SEQ ID NO 202
<211> LENGTH: 60
<212> TYPE: RNA
<213> ORGANISM: Homo sapiens

<400> SEQUENCE: 202
ugugaaugac ccccuuccag agccaaaauc accagggaug gaggaggggu cuugggacu      60

<210> SEQ ID NO 203
<211> LENGTH: 66
<212> TYPE: RNA
<213> ORGANISM: Homo sapiens

<400> SEQUENCE: 203
agcagcccuc ggcggcccgg ggggcgggcg gcggugcccg ucccggggcu gcgcgaggca      60
caggcg                                                                66

<210> SEQ ID NO 204
<211> LENGTH: 115
<212> TYPE: RNA
<213> ORGANISM: Homo sapiens

<400> SEQUENCE: 204
gagcaaaaac cagagaacaa caugggagcg uuccuaaccc cuaaggcaac uggaugggag      60
accugaccca uccaguucuc ugaggggcu cuugugyguu cacaagguu guuca            115

<210> SEQ ID NO 205
<211> LENGTH: 83
<212> TYPE: RNA
<213> ORGANISM: Homo sapiens

<400> SEQUENCE: 205
ccugcugcag aggugccagc ugcagugggg gaggcacugc cagggcugcc cacucugcuu      60
agccagcagg ugccaagaac agg                                             83

<210> SEQ ID NO 206
<211> LENGTH: 63
<212> TYPE: RNA
<213> ORGANISM: Homo sapiens

<400> SEQUENCE: 206
ugguggcggc gguaguuaug ggcuucucuu ucucaccagc agccccuggg ccgccgccuc      60
ccu                                                                   63

<210> SEQ ID NO 207
<211> LENGTH: 57
<212> TYPE: RNA
<213> ORGANISM: Homo sapiens

<400> SEQUENCE: 207
cauuggaggg uguggaagac aucugggcca acucugaucu cuucaucuac ccccag         57

<210> SEQ ID NO 208
<211> LENGTH: 62
<212> TYPE: RNA
<213> ORGANISM: Homo sapiens

<400> SEQUENCE: 208
gcuggggguc ccccgacagu guggagcugg ggccgggucc cggggagggg gguucugggc      60
``` ag                                                                          62

<210> SEQ ID NO 209
<211> LENGTH: 73
<212> TYPE: RNA
<213> ORGANISM: Homo sapiens

<400> SEQUENCE: 209
ggaggcuggg cuggacgga cacccggccu ccacuuucug uggcagguac cuccuccaug    60
ucggcccgcc uug                                                     73

<210> SEQ ID NO 210
<211> LENGTH: 83
<212> TYPE: RNA
<213> ORGANISM: Homo sapiens

<400> SEQUENCE: 210
ggguucccuc ugccuuuuuu uccaaugaaa auaacgaaac cuguuauuuc ccauugaggg    60
ggaaaaaggc gggagaagcc cca                                           83

<210> SEQ ID NO 211
<211> LENGTH: 62
<212> TYPE: RNA
<213> ORGANISM: Homo sapiens

<400> SEQUENCE: 211
uggccuaggg ggcggcuugu ggaguguaug ggcugagccu ugcucugcuc ccccgccccc    60
ag                                                                  62

<210> SEQ ID NO 212
<211> LENGTH: 68
<212> TYPE: RNA
<213> ORGANISM: Homo sapiens

<400> SEQUENCE: 212
ugcccaggcu ggagcgagug caguggugca gucaguccua gcucacugca gccucgaacu    60
ccugggcu                                                            68

<210> SEQ ID NO 213
<211> LENGTH: 82
<212> TYPE: RNA
<213> ORGANISM: Homo sapiens

<400> SEQUENCE: 213
cugacuuuuu uagggaguag aaggguggg agcaugaaca auguuucuca cucccuaccc    60
cuccacuccc caaaaaaguc ag                                            82

<210> SEQ ID NO 214
<211> LENGTH: 72
<212> TYPE: RNA
<213> ORGANISM: Homo sapiens

<400> SEQUENCE: 214
ccaggcacac aggaaaagcg gggcccuggg uucggcugcu accccaaagg ccacauucuc    60
cugugcacac ag                                                       72

<210> SEQ ID NO 215
<211> LENGTH: 87
<212> TYPE: RNA
<213> ORGANISM: Homo sapiens

```
<400> SEQUENCE: 215
cccucaucuc ugggcagggg cuuauuguag gagucucuga agagagcugu ggacugaccu     60
gcuuuaaccc uucccaggu ucccauu                                         87

<210> SEQ ID NO 216
<211> LENGTH: 88
<212> TYPE: RNA
<213> ORGANISM: Homo sapiens

<400> SEQUENCE: 216 gugggggccag gcgguggugg gcacugcugg gguggggcaca gcagccaugc agagcgggca   60
uuugaccccg ugccacccuu uuccccag                                       88

<210> SEQ ID NO 217
<211> LENGTH: 78
<212> TYPE: RNA
<213> ORGANISM: Homo sapiens

<400> SEQUENCE: 217
ggccucaggc aggcgcaccc gaccacaugc auggcuggug gcggcgugca ggggucgggu     60
gggccaggcu gugggggcg                                                 78

<210> SEQ ID NO 218
<211> LENGTH: 93
<212> TYPE: RNA
<213> ORGANISM: Homo sapiens

<400> SEQUENCE: 218
uacuuauggc accccacucc ugguaccaua gucauaaguu aggagauguu agagcuguga    60
guaccaugac uuaagugugg uggcuuaaac aug                                 93

<210> SEQ ID NO 219
<211> LENGTH: 71
<212> TYPE: RNA
<213> ORGANISM: Homo sapiens

<400> SEQUENCE: 219
gugucugugc cggucccagg agaaccugca gaggcaucgg gucagcggug cuccugcggg     60
ccgacacuca c                                                         71

<210> SEQ ID NO 220
<211> LENGTH: 65
<212> TYPE: RNA
<213> ORGANISM: Homo sapiens

<400> SEQUENCE: 220
gggugcucgg ggcaggcggc ugggagcggc ccucacauug auggcuccug ccaccuccuc     60
cgcag                                                                65

<210> SEQ ID NO 221
<211> LENGTH: 66
<212> TYPE: RNA
<213> ORGANISM: Homo sapiens

<400> SEQUENCE: 221
ccgagugggg cggggcaggu cccugcaggg acugugacac ugaaggaccu gcaccuucgc     60
ccacag                                                               66
```

```
<210> SEQ ID NO 222
<211> LENGTH: 90
<212> TYPE: RNA
<213> ORGANISM: Homo sapiens

<400> SEQUENCE: 222
cgggcggggc ggguccggcc gccuccgagc ccggccggca gcccccggcc uuaaagcgcg      60
ggcuguccgg aggggucggc uuucccaccg                                      90

<210> SEQ ID NO 223
<211> LENGTH: 70
<212> TYPE: RNA
<213> ORGANISM: Homo sapiens

<400> SEQUENCE: 223
aggacccagc ggggcugggc gcgcggagca gcgcugggug cagcgccugc gccggcagcu      60
gcaagggccg                                                            70

<210> SEQ ID NO 224
<211> LENGTH: 94
<212> TYPE: RNA
<213> ORGANISM: Homo sapiens

<400> SEQUENCE: 224
gugaggugug ggcccggccc caggagcggg gccugggcag ccccgugugu ugaggaagga      60
aggcagggcc cccgcucccc gggccugacc ccac                                 94

<210> SEQ ID NO 225
<211> LENGTH: 85
<212> TYPE: RNA
<213> ORGANISM: Homo sapiens

<400> SEQUENCE: 225
ggccugggua ggcuugcaug ggggacuggg aagagaccau gaacagguua guccagggag      60
uucucaucaa gccuuuacuc aguag                                           85

<210> SEQ ID NO 226
<211> LENGTH: 70
<212> TYPE: RNA
<213> ORGANISM: Homo sapiens

<400> SEQUENCE: 226
ggccgcggcg cgcaagaugg cggcgggccc gggcaccgcc ccuuccgccc cgccgggcgu      60
cgcacgaggc                                                            70

<210> SEQ ID NO 227
<211> LENGTH: 86
<212> TYPE: RNA
<213> ORGANISM: Homo sapiens

<400> SEQUENCE: 227
ugccagucuc uagguccug agacccuuua accugugagg acauccaggg ucacagguga      60
gguucuuggg agccuggcgu cuggcc                                          86

<210> SEQ ID NO 228
<211> LENGTH: 110
<212> TYPE: RNA
<213> ORGANISM: Homo sapiens

<400> SEQUENCE: 228
```

```
ggcuacaguc uuucuucaug ugacucgugg acuucccuuu gucauccuau gccugagaau    60
auaugaagga ggcugggaag gcaaagggac guucaauugu caucacuggc              110

<210> SEQ ID NO 229
<211> LENGTH: 47
<212> TYPE: RNA
<213> ORGANISM: Homo sapiens

<400> SEQUENCE: 229
cucggcgcgg ggcgcgggcu ccggguuggg gcgagccaac gccgggg                 47

<210> SEQ ID NO 230
<211> LENGTH: 94
<212> TYPE: RNA
<213> ORGANISM: Homo sapiens

<400> SEQUENCE: 230
aauucagccc ugccacuggc uuaugucaug accuugggcu acucaggcug ucugcacaau    60
gagccaguug gacaggagca gugccacuca acuc                               94

<210> SEQ ID NO 231
<211> LENGTH: 84
<212> TYPE: RNA
<213> ORGANISM: Homo sapiens

<400> SEQUENCE: 231
cuccccaugg cccugucucc caacccuugu accagugcug ggcucagacc cugguacagg    60 ccuggggac agggaccugg ggac                                           84

<210> SEQ ID NO 232
<211> LENGTH: 94
<212> TYPE: RNA
<213> ORGANISM: Homo sapiens

<400> SEQUENCE: 232
auaaaggaag uuaggcugag gggcagagag cgagacuuuu cuauuuucca aaagcucggu    60
cugaggcccc ucagucuugc uuccuaaccc gcgc                               94

<210> SEQ ID NO 233
<211> LENGTH: 94
<212> TYPE: RNA
<213> ORGANISM: Homo sapiens

<400> SEQUENCE: 233
cgggcagcgg gugccaggca cggugucagc aggcaacaug gccgagaggc cggggccucc    60
gggcggcgcc gguccgcga ccgcguaccc ugac                                94

<210> SEQ ID NO 234
<211> LENGTH: 85
<212> TYPE: RNA
<213> ORGANISM: Homo sapiens

<400> SEQUENCE: 234
ggcgccuccu gcucugcugu gccgccaggg ccuccccuag cgcgccuucu ggagaggcuu    60
ugugcggaua cggggcugga ggccu                                         85

<210> SEQ ID NO 235
<211> LENGTH: 73
<212> TYPE: RNA
```

<213> ORGANISM: Homo sapiens

<400> SEQUENCE: 235
uguauccuug aauggauuuu uggagcagga guggacaccu gacccaaagg aaaucaaucc    60
auaggcuagc aau    73

<210> SEQ ID NO 236
<211> LENGTH: 98
<212> TYPE: RNA
<213> ORGANISM: Homo sapiens

<400> SEQUENCE: 236
uucucacccc cgccugacac gggcgacagc ugcggcccgc uguguucacu cgggccgagu    60
gcgucuccug ucaggcaagg gagagcagag cccccug    98

<210> SEQ ID NO 237
<211> LENGTH: 78
<212> TYPE: RNA
<213> ORGANISM: Homo sapiens

<400> SEQUENCE: 237
gagcgucacg uugacacuca aaaguuuca gauuuggaa cauucggau uuggauuuu    60 uggaucaggg augcucaa    78

<210> SEQ ID NO 238
<211> LENGTH: 89
<212> TYPE: RNA
<213> ORGANISM: Homo sapiens

<400> SEQUENCE: 238
gucagcagug ccuuagcagc acguaaauau uggcguuaag auucuaaaau uaucuccagu    60
auuaacugug cugcugaagu aagguugac    89

<210> SEQ ID NO 239
<211> LENGTH: 81
<212> TYPE: RNA
<213> ORGANISM: Homo sapiens

<400> SEQUENCE: 239
guuccacucu agcagcacgu aaauauuggc guagugaaau auauauuaaa caccaauauu    60
acugugcugc uuuaguguga c    81

<210> SEQ ID NO 240
<211> LENGTH: 72
<212> TYPE: RNA
<213> ORGANISM: Homo sapiens

<400> SEQUENCE: 240
cuugggaaug gcaaggaaac cguuaccauu acugaguuua guaaugguaa ugguucucuu    60
gcuauaccca ga    72

<210> SEQ ID NO 241
<211> LENGTH: 68
<212> TYPE: RNA
<213> ORGANISM: Homo sapiens

<400> SEQUENCE: 241
cuccggugcc uacugagcug auaucaguuc ucauuuuaca cacuggcuca guucagcagg    60
aacaggag    68

```
<210> SEQ ID NO 242
<211> LENGTH: 73
<212> TYPE: RNA
<213> ORGANISM: Homo sapiens

<400> SEQUENCE: 242
cucugccucc cgugccuacu gagcugaaac acaguugguu uguguacacu ggcucaguuc      60
agcaggaaca ggg                                                        73

<210> SEQ ID NO 243
<211> LENGTH: 109
<212> TYPE: RNA
<213> ORGANISM: Homo sapiens

<400> SEQUENCE: 243
ggucgggcuc accaugacac agugugagac cucgggcuac aacacaggac ccgggcgcug      60
cucugacccc ucgugucuug uguugcagcc ggagggacgc agguccgca                 109

<210> SEQ ID NO 244
<211> LENGTH: 80
<212> TYPE: RNA
<213> ORGANISM: Homo sapiens

<400> SEQUENCE: 244
cgggaaugcc gcggcgggga cggcgauugg uccguaugug uggugccacc ggccgccggc      60
uccgccccgg cccccgcccc                                                 80

<210> SEQ ID NO 245
<211> LENGTH: 67
<212> TYPE: RNA
<213> ORGANISM: Homo sapiens

<400> SEQUENCE: 245
guggcacuca aacugugggg gcacuuucug cucucuggug aaagugccgc caucuuuuga      60
guguuac                                                               67

<210> SEQ ID NO 246
<211> LENGTH: 97
<212> TYPE: RNA
<213> ORGANISM: Homo sapiens

<400> SEQUENCE: 246
ugaugcuuug cuggcuggug cagugccuga gggaguaaga gcccuguugu uguaagauag      60
ugucuuacuc cccucaggcac aucuccaaca agucucu                             97

<210> SEQ ID NO 247
<211> LENGTH: 97
<212> TYPE: RNA
<213> ORGANISM: Homo sapiens

<400> SEQUENCE: 247
ugaugcuuug cuggcuggug cagugccuga gggaguaaga gcccuguugu ugucagauag      60
ugucuuacuc ccucaggcac aucuccagcg agucucu                              97

<210> SEQ ID NO 248
<211> LENGTH: 22
<212> TYPE: RNA
<213> ORGANISM: Homo sapiens
```

```
<400> SEQUENCE: 248
aaggauuuag ggacaggcuu ug                                          22

<210> SEQ ID NO 249
<211> LENGTH: 19
<212> TYPE: RNA
<213> ORGANISM: Homo sapiens

<400> SEQUENCE: 249
caggaaggau uuagggaca                                              19

<210> SEQ ID NO 250
<211> LENGTH: 20
<212> TYPE: RNA
<213> ORGANISM: Homo sapiens

<400> SEQUENCE: 250
cagcaggacg ggagcgcggc                                             20

<210> SEQ ID NO 251
<211> LENGTH: 21
<212> TYPE: RNA
<213> ORGANISM: Homo sapiens

<400> SEQUENCE: 251
cggauccgag ucacggcacc a                                           21

<210> SEQ ID NO 252
<211> LENGTH: 15
<212> TYPE: RNA
<213> ORGANISM: Homo sapiens

<400> SEQUENCE: 252
uccgagucac ggcac                                                  15

<210> SEQ ID NO 253
<211> LENGTH: 23
<212> TYPE: RNA
<213> ORGANISM: Homo sapiens

<400> SEQUENCE: 253
gggggucccc ggugcucgga ucu                                         23

<210> SEQ ID NO 254
<211> LENGTH: 20
<212> TYPE: RNA
<213> ORGANISM: Homo sapiens

<400> SEQUENCE: 254
gggggucccc ggugcucgga                                             20

<210> SEQ ID NO 255
<211> LENGTH: 22
<212> TYPE: RNA
<213> ORGANISM: Homo sapiens

<400> SEQUENCE: 255
ggcgucccag gcggggcgcc gc                                          22

<210> SEQ ID NO 256
<211> LENGTH: 15
<212> TYPE: RNA
<213> ORGANISM: Homo sapiens
```

```
<400> SEQUENCE: 256
gcgccgcggg accgc                                                  15

<210> SEQ ID NO 257
<211> LENGTH: 15
<212> TYPE: RNA
<213> ORGANISM: Homo sapiens

<400> SEQUENCE: 257
gagcgcucgc uggcc                                                  15

<210> SEQ ID NO 258
<211> LENGTH: 15
<212> TYPE: RNA
<213> ORGANISM: Homo sapiens

<400> SEQUENCE: 258
cggugagcgc ucgcu                                                  15

<210> SEQ ID NO 259
<211> LENGTH: 22
<212> TYPE: RNA
<213> ORGANISM: Homo sapiens

<400> SEQUENCE: 259
accaggaggc ugaggcccct ca                                          22

<210> SEQ ID NO 260
<211> LENGTH: 15
<212> TYPE: RNA
<213> ORGANISM: Homo sapiens

<400> SEQUENCE: 260
accaggaggc ugagg                                                  15

<210> SEQ ID NO 261
<211> LENGTH: 17
<212> TYPE: RNA
<213> ORGANISM: Homo sapiens

<400> SEQUENCE: 261
uccuagucac ggcacca                                                17

<210> SEQ ID NO 262
<211> LENGTH: 17
<212> TYPE: RNA
<213> ORGANISM: Homo sapiens

<400> SEQUENCE: 262
ccuccgggac ggcuggg                                                17

<210> SEQ ID NO 263
<211> LENGTH: 15
<212> TYPE: RNA
<213> ORGANISM: Homo sapiens

<400> SEQUENCE: 263
ccgggacggc uggc                                                   15

<210> SEQ ID NO 264
<211> LENGTH: 20
<212> TYPE: RNA
```

```
<213> ORGANISM: Homo sapiens

<400> SEQUENCE: 264
gcugcgggcu gcggucaggg                                              20

<210> SEQ ID NO 265
<211> LENGTH: 18
<212> TYPE: RNA
<213> ORGANISM: Homo sapiens

<400> SEQUENCE: 265
gcuccugaau agcuggga                                                18

<210> SEQ ID NO 266
<211> LENGTH: 16
<212> TYPE: RNA
<213> ORGANISM: Homo sapiens

<400> SEQUENCE: 266
ugaauagcug ggacua                                                  16

<210> SEQ ID NO 267
<211> LENGTH: 23
<212> TYPE: RNA
<213> ORGANISM: Homo sapiens

<400> SEQUENCE: 267
ggugggugag gucgggcccc aag                                          23

<210> SEQ ID NO 268
<211> LENGTH: 23
<212> TYPE: RNA
<213> ORGANISM: Homo sapiens

<400> SEQUENCE: 268
acaggagugg ggugggaca uaa                                           23

<210> SEQ ID NO 269
<211> LENGTH: 20
<212> TYPE: RNA
<213> ORGANISM: Homo sapiens

<400> SEQUENCE: 269
acaggagugg ggugggaca                                               20

<210> SEQ ID NO 270
<211> LENGTH: 21
<212> TYPE: RNA
<213> ORGANISM: Homo sapiens

<400> SEQUENCE: 270 cuggggacg cgugagcgcg a                                             21

<210> SEQ ID NO 271
<211> LENGTH: 15
<212> TYPE: RNA
<213> ORGANISM: Homo sapiens

<400> SEQUENCE: 271
cagggagcag gaagc                                                   15

<210> SEQ ID NO 272
<211> LENGTH: 22
```

```
<212> TYPE: RNA
<213> ORGANISM: Homo sapiens

<400> SEQUENCE: 272
gcugggauua caggcaugag cc                                              22

<210> SEQ ID NO 273
<211> LENGTH: 15
<212> TYPE: RNA
<213> ORGANISM: Homo sapiens

<400> SEQUENCE: 273
gauuacaggc augag                                                      15

<210> SEQ ID NO 274
<211> LENGTH: 18
<212> TYPE: RNA
<213> ORGANISM: Homo sapiens

<400> SEQUENCE: 274
gcacgggagc ucagguga                                                   18

<210> SEQ ID NO 275
<211> LENGTH: 20
<212> TYPE: RNA
<213> ORGANISM: Homo sapiens

<400> SEQUENCE: 275
aucccaccuc ugccaccaaa                                                 20

<210> SEQ ID NO 276
<211> LENGTH: 16
<212> TYPE: RNA
<213> ORGANISM: Homo sapiens

<400> SEQUENCE: 276
ucccaccucu gccacc                                                     16

<210> SEQ ID NO 277
<211> LENGTH: 16
<212> TYPE: RNA
<213> ORGANISM: Homo sapiens

<400> SEQUENCE: 277
ggagcggcgg aucugg                                                     16

<210> SEQ ID NO 278
<211> LENGTH: 23
<212> TYPE: RNA
<213> ORGANISM: Homo sapiens

<400> SEQUENCE: 278
acagcagggc uggggauugc agu                                             23

<210> SEQ ID NO 279
<211> LENGTH: 20
<212> TYPE: RNA
<213> ORGANISM: Homo sapiens

<400> SEQUENCE: 279
accggccgcc ggcuccgccc                                                 20

<210> SEQ ID NO 280
```

```
<211> LENGTH: 17
<212> TYPE: RNA
<213> ORGANISM: Homo sapiens

<400> SEQUENCE: 280
ccggccgccg gcuccgc                                                  17

<210> SEQ ID NO 281
<211> LENGTH: 15
<212> TYPE: RNA
<213> ORGANISM: Homo sapiens

<400> SEQUENCE: 281
ucccagcggu gccuc                                                    15

<210> SEQ ID NO 282
<211> LENGTH: 25
<212> TYPE: RNA
<213> ORGANISM: Homo sapiens

<400> SEQUENCE: 282 uucuggpccc gcggcgggcg ugggg                                         25

<210> SEQ ID NO 283
<211> LENGTH: 15
<212> TYPE: RNA
<213> ORGANISM: Homo sapiens

<400> SEQUENCE: 283
cgcggcgggc guggg                                                    15

<210> SEQ ID NO 284
<211> LENGTH: 21
<212> TYPE: RNA
<213> ORGANISM: Homo sapiens

<400> SEQUENCE: 284
aagaaggcgg ucggucugcg g                                             21

<210> SEQ ID NO 285
<211> LENGTH: 22
<212> TYPE: RNA
<213> ORGANISM: Homo sapiens

<400> SEQUENCE: 285
acucggcugc gguggacaag uc                                            22

<210> SEQ ID NO 286
<211> LENGTH: 20
<212> TYPE: RNA
<213> ORGANISM: Homo sapiens

<400> SEQUENCE: 286
cucggcugcg guggacaagu                                               20

<210> SEQ ID NO 287
<211> LENGTH: 19
<212> TYPE: RNA
<213> ORGANISM: Homo sapiens

<400> SEQUENCE: 287
cuccagccug agugacaga                                                19
```

```
<210> SEQ ID NO 288
<211> LENGTH: 15
<212> TYPE: RNA
<213> ORGANISM: Homo sapiens

<400> SEQUENCE: 288
acugcacucc agccu                                                    15

<210> SEQ ID NO 289
<211> LENGTH: 16
<212> TYPE: RNA
<213> ORGANISM: Homo sapiens

<400> SEQUENCE: 289 guggggggc aggagg                                                    16

<210> SEQ ID NO 290
<211> LENGTH: 19
<212> TYPE: RNA
<213> ORGANISM: Homo sapiens

<400> SEQUENCE: 290 gggggcagg aggggcuca                                                 19

<210> SEQ ID NO 291
<211> LENGTH: 21
<212> TYPE: RNA
<213> ORGANISM: Homo sapiens

<400> SEQUENCE: 291
cuucccccca guaaucuuca u                                             21

<210> SEQ ID NO 292
<211> LENGTH: 22
<212> TYPE: RNA
<213> ORGANISM: Homo sapiens

<400> SEQUENCE: 292
ccucacaccu gccucgcccc cc                                            22

<210> SEQ ID NO 293
<211> LENGTH: 15
<212> TYPE: RNA
<213> ORGANISM: Homo sapiens

<400> SEQUENCE: 293
ucacaccugc cucgc                                                    15

<210> SEQ ID NO 294
<211> LENGTH: 22
<212> TYPE: RNA
<213> ORGANISM: Homo sapiens

<400> SEQUENCE: 294
guuggugggg gagccaugag au                                            22

<210> SEQ ID NO 295
<211> LENGTH: 22
<212> TYPE: RNA
<213> ORGANISM: Homo sapiens

<400> SEQUENCE: 295
ggggagccau gagauaagag ca                                            22
```

```
<210> SEQ ID NO 296
<211> LENGTH: 22
<212> TYPE: RNA
<213> ORGANISM: Homo sapiens

<400> SEQUENCE: 296
ucggcucugg gucugugggg ag                                    22

<210> SEQ ID NO 297
<211> LENGTH: 17
<212> TYPE: RNA
<213> ORGANISM: Homo sapiens

<400> SEQUENCE: 297
cggcucuggg ucugugg                                          17

<210> SEQ ID NO 298
<211> LENGTH: 19
<212> TYPE: RNA
<213> ORGANISM: Homo sapiens

<400> SEQUENCE: 298
gcugggcgag gcuggcauc                                        19

<210> SEQ ID NO 299
<211> LENGTH: 20
<212> TYPE: RNA
<213> ORGANISM: Homo sapiens

<400> SEQUENCE: 299
ucugcccccu ccgcugcugc                                       20

<210> SEQ ID NO 300
<211> LENGTH: 20
<212> TYPE: RNA
<213> ORGANISM: Homo sapiens

<400> SEQUENCE: 300
aucccaccac ugccaccauu                                       20

<210> SEQ ID NO 301
<211> LENGTH: 30
<212> TYPE: RNA
<213> ORGANISM: Homo sapiens

<400> SEQUENCE: 301
ccaccaccca ccacugccac caugccacca                            30

<210> SEQ ID NO 302
<211> LENGTH: 24
<212> TYPE: RNA
<213> ORGANISM: Homo sapiens

<400> SEQUENCE: 302
gugcccgucc cggggcugcg cgag                                  24

<210> SEQ ID NO 303
<211> LENGTH: 17
<212> TYPE: RNA
<213> ORGANISM: Homo sapiens

<400> SEQUENCE: 303
ccggggcugc gcgaggc                                          17
```

<210> SEQ ID NO 304
<211> LENGTH: 15
<212> TYPE: RNA
<213> ORGANISM: Homo sapiens

<400> SEQUENCE: 304
gcugcagugg gggag                                                    15

<210> SEQ ID NO 305
<211> LENGTH: 25
<212> TYPE: RNA
<213> ORGANISM: Homo sapiens

<400> SEQUENCE: 305
uggcggcggu aguuaugggc uucuc                                         25

<210> SEQ ID NO 306
<211> LENGTH: 30
<212> TYPE: RNA
<213> ORGANISM: Homo sapiens

<400> SEQUENCE: 306
gcugggcugg gacggacacc cggccuccac                                    30

<210> SEQ ID NO 307
<211> LENGTH: 20
<212> TYPE: RNA
<213> ORGANISM: Homo sapiens

<400> SEQUENCE: 307
ggaaaaaggc gggagaagcc                                               20

<210> SEQ ID NO 308
<211> LENGTH: 15
<212> TYPE: RNA
<213> ORGANISM: Homo sapiens

<400> SEQUENCE: 308
ggcgggagaa gcccc                                                    15

<210> SEQ ID NO 309
<211> LENGTH: 21
<212> TYPE: RNA
<213> ORGANISM: Homo sapiens

<400> SEQUENCE: 309
cccaggcugg agcgagugca g                                             21

<210> SEQ ID NO 310
<211> LENGTH: 23
<212> TYPE: RNA
<213> ORGANISM: Homo sapiens

<400> SEQUENCE: 310
agggaguaga agggugggga gca                                           23

<210> SEQ ID NO 311
<211> LENGTH: 16
<212> TYPE: RNA
<213> ORGANISM: Homo sapiens

<400> SEQUENCE: 311

-continued uagggaguag aagggu					16

<210> SEQ ID NO 312
<211> LENGTH: 25
<212> TYPE: RNA
<213> ORGANISM: Homo sapiens

<400> SEQUENCE: 312
ugggcagggg cuuauuguag gaguc			25

<210> SEQ ID NO 313
<211> LENGTH: 21
<212> TYPE: RNA
<213> ORGANISM: Homo sapiens

<400> SEQUENCE: 313
gggcaggggc uuauuguagg a				21

<210> SEQ ID NO 314
<211> LENGTH: 20
<212> TYPE: RNA
<213> ORGANISM: Homo sapiens

<400> SEQUENCE: 314
caccccacuc cugguaccau				20

<210> SEQ ID NO 315
<211> LENGTH: 15
<212> TYPE: RNA
<213> ORGANISM: Homo sapiens

<400> SEQUENCE: 315
ccccacuccu gguac				15

<210> SEQ ID NO 316
<211> LENGTH: 26
<212> TYPE: RNA
<213> ORGANISM: Homo sapiens

<400> SEQUENCE: 316
gcgggcuguc cggagggguc ggcuuu			26

<210> SEQ ID NO 317
<211> LENGTH: 16
<212> TYPE: RNA
<213> ORGANISM: Homo sapiens

<400> SEQUENCE: 317
gcuguccgga gggguc				16

<210> SEQ ID NO 318
<211> LENGTH: 18
<212> TYPE: RNA
<213> ORGANISM: Homo sapiens

<400> SEQUENCE: 318
cagcggggcu gggcgcgc				18

<210> SEQ ID NO 319
<211> LENGTH: 15
<212> TYPE: RNA
<213> ORGANISM: Homo sapiens

<400> SEQUENCE: 319

```
cggggcuggg cgcgc                                                  15

<210> SEQ ID NO 320
<211> LENGTH: 23
<212> TYPE: RNA
<213> ORGANISM: Homo sapiens

<400> SEQUENCE: 320
aggaaggaag gcagggcccc cgc                                         23

<210> SEQ ID NO 321
<211> LENGTH: 15
<212> TYPE: RNA
<213> ORGANISM: Homo sapiens

<400> SEQUENCE: 321 gggccccccgc uccccc                                                15

<210> SEQ ID NO 322
<211> LENGTH: 23
<212> TYPE: RNA
<213> ORGANISM: Homo sapiens

<400> SEQUENCE: 322
cacaggugag guucuuggga gcc                                         23

<210> SEQ ID NO 323
<211> LENGTH: 15
<212> TYPE: RNA
<213> ORGANISM: Homo sapiens

<400> SEQUENCE: 323
gagguucuug ggagc                                                  15

<210> SEQ ID NO 324
<211> LENGTH: 24
<212> TYPE: RNA
<213> ORGANISM: Homo sapiens

<400> SEQUENCE: 324
gaggcuggga aggcaaaggg acgu                                        24

<210> SEQ ID NO 325
<211> LENGTH: 15
<212> TYPE: RNA
<213> ORGANISM: Homo sapiens

<400> SEQUENCE: 325
cugggaaggc aaagg                                                  15

<210> SEQ ID NO 326
<211> LENGTH: 24
<212> TYPE: RNA
<213> ORGANISM: Homo sapiens

<400> SEQUENCE: 326
ugguacaggc cuggggggaca ggga                                       24

<210> SEQ ID NO 327
<211> LENGTH: 19
<212> TYPE: RNA
<213> ORGANISM: Homo sapiens
```

```
<400> SEQUENCE: 327
gguacaggcc uggggggaca                                               19

<210> SEQ ID NO 328
<211> LENGTH: 30
<212> TYPE: RNA
<213> ORGANISM: Homo sapiens

<400> SEQUENCE: 328
ugaggggcag agagcgagac uuuucuauuu                                    30

<210> SEQ ID NO 329
<211> LENGTH: 15
<212> TYPE: RNA
<213> ORGANISM: Homo sapiens

<400> SEQUENCE: 329
cagagagcga gacuu                                                    15

<210> SEQ ID NO 330
<211> LENGTH: 25
<212> TYPE: RNA
<213> ORGANISM: Homo sapiens

<400> SEQUENCE: 330
cuuugugcgg auacggggcu ggagg                                         25

<210> SEQ ID NO 331
<211> LENGTH: 19
<212> TYPE: RNA
<213> ORGANISM: Homo sapiens

<400> SEQUENCE: 331
agaggcuuug ugcggauac                                                19

<210> SEQ ID NO 332
<211> LENGTH: 21
<212> TYPE: RNA
<213> ORGANISM: Homo sapiens

<400> SEQUENCE: 332
gaauggauuu uuggagcagg a                                             21

<210> SEQ ID NO 333
<211> LENGTH: 15
<212> TYPE: RNA
<213> ORGANISM: Homo sapiens

<400> SEQUENCE: 333
ggauuuuugg agcag                                                    15

<210> SEQ ID NO 334
<211> LENGTH: 20
<212> TYPE: RNA
<213> ORGANISM: Homo sapiens

<400> SEQUENCE: 334
ggauuuuugg aucagggaug                                               20

<210> SEQ ID NO 335
<211> LENGTH: 15
<212> TYPE: RNA
<213> ORGANISM: Homo sapiens
```

```
<400> SEQUENCE: 335
uuuuuggauc aggga                                              15

<210> SEQ ID NO 336
<211> LENGTH: 27
<212> TYPE: RNA
<213> ORGANISM: Homo sapiens

<400> SEQUENCE: 336
uagcagcacg uaaauauugg cguuaag                                 27

<210> SEQ ID NO 337
<211> LENGTH: 26
<212> TYPE: RNA
<213> ORGANISM: Homo sapiens

<400> SEQUENCE: 337
uagcagcacg uaaauauugg cguagu                                  26

<210> SEQ ID NO 338
<211> LENGTH: 15
<212> TYPE: RNA
<213> ORGANISM: Homo sapiens

<400> SEQUENCE: 338
cacguaaaua uuggc                                              15

<210> SEQ ID NO 339
<211> LENGTH: 27
<212> TYPE: RNA
<213> ORGANISM: Homo sapiens

<400> SEQUENCE: 339
aaaccguuac cauuacugag uuuagua                                 27

<210> SEQ ID NO 340
<211> LENGTH: 15
<212> TYPE: RNA
<213> ORGANISM: Homo sapiens

<400> SEQUENCE: 340
uaccauuacu gaguu                                              15

<210> SEQ ID NO 341
<211> LENGTH: 24
<212> TYPE: RNA
<213> ORGANISM: Homo sapiens

<400> SEQUENCE: 341
uggcucaguu cagcaggaac agga                                    24

<210> SEQ ID NO 342
<211> LENGTH: 24
<212> TYPE: RNA
<213> ORGANISM: Homo sapiens

<400> SEQUENCE: 342
cuggcucagu ucagcaggaa cagg                                    24

<210> SEQ ID NO 343
<211> LENGTH: 15
<212> TYPE: RNA
```

```
<213> ORGANISM: Homo sapiens

<400> SEQUENCE: 343
aguucagcag gaaca                                                    15

<210> SEQ ID NO 344
<211> LENGTH: 22
<212> TYPE: RNA
<213> ORGANISM: Homo sapiens

<400> SEQUENCE: 344
gggcuacaac acaggacccg gg                                            22

<210> SEQ ID NO 345
<211> LENGTH: 22
<212> TYPE: RNA
<213> ORGANISM: Homo sapiens

<400> SEQUENCE: 345
gcuacaacac aggacccggg cg                                            22

<210> SEQ ID NO 346
<211> LENGTH: 22
<212> TYPE: RNA
<213> ORGANISM: Homo sapiens

<400> SEQUENCE: 346
acucaaacug uggggggcacu uu                                            22

<210> SEQ ID NO 347
<211> LENGTH: 19
<212> TYPE: RNA
<213> ORGANISM: Homo sapiens

<400> SEQUENCE: 347
acucaaacug uggggggcac                                                19

<210> SEQ ID NO 348
<211> LENGTH: 15
<212> TYPE: RNA
<213> ORGANISM: Homo sapiens

<400> SEQUENCE: 348
gagggaguaa gagcc                                                    15

<210> SEQ ID NO 349
<211> LENGTH: 18
<212> TYPE: RNA
<213> ORGANISM: Homo sapiens

<400> SEQUENCE: 349 gguggggcuuc ccggaggg                                                 18

<210> SEQ ID NO 350
<211> LENGTH: 23
<212> TYPE: RNA
<213> ORGANISM: Homo sapiens

<400> SEQUENCE: 350
gccccggcgc gggcggguuc ugg                                           23

<210> SEQ ID NO 351
<211> LENGTH: 21
```

```
<212> TYPE: RNA
<213> ORGANISM: Homo sapiens

<400> SEQUENCE: 351
cguggaggac gaggaggagg c                                          21

<210> SEQ ID NO 352
<211> LENGTH: 19
<212> TYPE: RNA
<213> ORGANISM: Homo sapiens

<400> SEQUENCE: 352
ggggccuggc gguggggcgg                                            19

<210> SEQ ID NO 353
<211> LENGTH: 22
<212> TYPE: RNA
<213> ORGANISM: Homo sapiens

<400> SEQUENCE: 353
agacugacgg cuggaggccc au                                         22

<210> SEQ ID NO 354
<211> LENGTH: 22
<212> TYPE: RNA
<213> ORGANISM: Homo sapiens

<400> SEQUENCE: 354 uggggggagga aggacaggcc au                                        22

<210> SEQ ID NO 355
<211> LENGTH: 23
<212> TYPE: RNA
<213> ORGANISM: Homo sapiens

<400> SEQUENCE: 355
acggggaguc aggcaguggu gga                                        23

<210> SEQ ID NO 356
<211> LENGTH: 23
<212> TYPE: RNA
<213> ORGANISM: Homo sapiens

<400> SEQUENCE: 356
ccucccugcc cgccucucug cag                                        23

<210> SEQ ID NO 357
<211> LENGTH: 20
<212> TYPE: RNA
<213> ORGANISM: Homo sapiens

<400> SEQUENCE: 357 uguggggacug caaaugggag                                           20

<210> SEQ ID NO 358
<211> LENGTH: 24
<212> TYPE: RNA
<213> ORGANISM: Homo sapiens

<400> SEQUENCE: 358
ugaggggccu cagaccgagc uuuu                                       24

<210> SEQ ID NO 359
```

```
<211> LENGTH: 19
<212> TYPE: RNA
<213> ORGANISM: Homo sapiens

<400> SEQUENCE: 359
gggggaagaa aaggugggg                                                  19

<210> SEQ ID NO 360
<211> LENGTH: 22
<212> TYPE: RNA
<213> ORGANISM: Homo sapiens

<400> SEQUENCE: 360
ccccuggggc ugggcaggcg ga                                              22

<210> SEQ ID NO 361
<211> LENGTH: 22
<212> TYPE: RNA
<213> ORGANISM: Homo sapiens

<400> SEQUENCE: 361
agacacauuu ggagagggaa cc                                              22

<210> SEQ ID NO 362
<211> LENGTH: 21
<212> TYPE: RNA
<213> ORGANISM: Homo sapiens

<400> SEQUENCE: 362
guguggccgg caggcgggug g                                               21

<210> SEQ ID NO 363
<211> LENGTH: 23
<212> TYPE: RNA
<213> ORGANISM: Homo sapiens

<400> SEQUENCE: 363
cggggccgua gcacugucug aga                                             23

<210> SEQ ID NO 364
<211> LENGTH: 22
<212> TYPE: RNA
<213> ORGANISM: Homo sapiens

<400> SEQUENCE: 364
agggaagggg acgaggguug gg                                              22

<210> SEQ ID NO 365
<211> LENGTH: 17
<212> TYPE: RNA
<213> ORGANISM: Homo sapiens

<400> SEQUENCE: 365
ggggcgcggc cggaucg                                                    17

<210> SEQ ID NO 366
<211> LENGTH: 17
<212> TYPE: RNA
<213> ORGANISM: Homo sapiens

<400> SEQUENCE: 366
ggcgggugcg ggggugg                                                    17
```

-continued

```
<210> SEQ ID NO 367
<211> LENGTH: 22
<212> TYPE: RNA
<213> ORGANISM: Homo sapiens

<400> SEQUENCE: 367 gggugggau uguugcauu ac                                          22

<210> SEQ ID NO 368
<211> LENGTH: 23
<212> TYPE: RNA
<213> ORGANISM: Homo sapiens

<400> SEQUENCE: 368 ugguggugg ggaggagaag ugc                                        23

<210> SEQ ID NO 369
<211> LENGTH: 22
<212> TYPE: RNA
<213> ORGANISM: Homo sapiens

<400> SEQUENCE: 369
uugaggagac augguggggg cc                                        22

<210> SEQ ID NO 370
<211> LENGTH: 21
<212> TYPE: RNA
<213> ORGANISM: Homo sapiens

<400> SEQUENCE: 370
agcaugacag aggagaggug g                                         21

<210> SEQ ID NO 371
<211> LENGTH: 22
<212> TYPE: RNA
<213> ORGANISM: Homo sapiens

<400> SEQUENCE: 371
agggacggga cgcggugcag ug                                        22

<210> SEQ ID NO 372
<211> LENGTH: 25
<212> TYPE: RNA
<213> ORGANISM: Homo sapiens

<400> SEQUENCE: 372
acuugggcag gagggacccu guaug                                     25

<210> SEQ ID NO 373
<211> LENGTH: 21
<212> TYPE: RNA
<213> ORGANISM: Homo sapiens

<400> SEQUENCE: 373
cggggcagcu caguacagga u                                         21

<210> SEQ ID NO 374
<211> LENGTH: 24
<212> TYPE: RNA
<213> ORGANISM: Homo sapiens

<400> SEQUENCE: 374
uguaggcaug aggcagggcc cagg                                      24
```

<210> SEQ ID NO 375
<211> LENGTH: 22
<212> TYPE: RNA
<213> ORGANISM: Homo sapiens

<400> SEQUENCE: 375
uggggguggu cucuagccaa gg                                           22

<210> SEQ ID NO 376
<211> LENGTH: 20
<212> TYPE: RNA
<213> ORGANISM: Homo sapiens

<400> SEQUENCE: 376
ugggaauggg gguaagggcc                                              20

<210> SEQ ID NO 377
<211> LENGTH: 23
<212> TYPE: RNA
<213> ORGANISM: Homo sapiens

<400> SEQUENCE: 377
guuugcacgg gugggccuug ucu                                          23

<210> SEQ ID NO 378
<211> LENGTH: 22
<212> TYPE: RNA
<213> ORGANISM: Homo sapiens

<400> SEQUENCE: 378
uccaggcagg agccggacug ga                                           22

<210> SEQ ID NO 379
<211> LENGTH: 21
<212> TYPE: RNA
<213> ORGANISM: Homo sapiens

<400> SEQUENCE: 379
cugggcucgg gacgcgcggc u                                            21

<210> SEQ ID NO 380
<211> LENGTH: 17
<212> TYPE: RNA
<213> ORGANISM: Homo sapiens

<400> SEQUENCE: 380
gccggacaag agggagg                                                 17

<210> SEQ ID NO 381
<211> LENGTH: 20
<212> TYPE: RNA
<213> ORGANISM: Homo sapiens

<400> SEQUENCE: 381
ccccagggcg acgcggcggg                                              20

<210> SEQ ID NO 382
<211> LENGTH: 21
<212> TYPE: RNA
<213> ORGANISM: Homo sapiens

<400> SEQUENCE: 382
uggcuguugg aggggcagg c                                             21

<210> SEQ ID NO 383
<211> LENGTH: 22
<212> TYPE: RNA
<213> ORGANISM: Homo sapiens

<400> SEQUENCE: 383
uauugcacuc gucccggccu cc                                             22

<210> SEQ ID NO 384
<211> LENGTH: 73
<212> TYPE: RNA
<213> ORGANISM: Homo sapiens

<400> SEQUENCE: 384
gaaaacaacc aggugggcuu cccggagggc ggaacaccca gccccagcau ccagggcuca    60
ccuaccacgu uug                                                       73

<210> SEQ ID NO 385
<211> LENGTH: 80
<212> TYPE: RNA
<213> ORGANISM: Homo sapiens

<400> SEQUENCE: 385
gguuccggag ccccggcgcg ggcggguucu ggguguaga cgcugcuggc cagcccgccc     60
cagccgaggu ucucggcacc                                                80

<210> SEQ ID NO 386
<211> LENGTH: 103
<212> TYPE: RNA
<213> ORGANISM: Homo sapiens

<400> SEQUENCE: 386
gugucggcug uggcgugacu gucccucugu gucccccacu aggcccacug cucaguggag    60
cguggaggac gaggaggagg ccguccacga gcaaugccag cau                     103

<210> SEQ ID NO 387
<211> LENGTH: 90
<212> TYPE: RNA
<213> ORGANISM: Homo sapiens

<400> SEQUENCE: 387
ggcgccucug cagcuccggc uccccuggc cucucgggaa cuacaagucc caggggccu      60 ggcggugggc ggcgggcgga agaggcgggg                                     90

<210> SEQ ID NO 388
<211> LENGTH: 86
<212> TYPE: RNA
<213> ORGANISM: Homo sapiens

<400> SEQUENCE: 388
auucuaggug gggagacuga cggcuggagg cccauaagcu gucuaaaacu ucggccccca    60
gauuucuggu cuccccacuu cagaac                                         86

<210> SEQ ID NO 389
<211> LENGTH: 72
<212> TYPE: RNA
<213> ORGANISM: Homo sapiens

<400> SEQUENCE: 389

```
cuggggagg aaggacaggc caucugcuau ucguccacca accugacuug auccucucuu        60
cccuccuccc ag                                                           72
```

<210> SEQ ID NO 390
<211> LENGTH: 66
<212> TYPE: RNA
<213> ORGANISM: Homo sapiens

<400> SEQUENCE: 390

```
ucaagacggg gagucaggca gugguggaga uggagagccc ugagccucca cucuccuggc        60
ccccag                                                                  66
```

<210> SEQ ID NO 391
<211> LENGTH: 59
<212> TYPE: RNA
<213> ORGANISM: Homo sapiens

<400> SEQUENCE: 391

```
cuccagggag acagugugug aggccucuug ccauggccuc ccugcccgcc ucucugcag         59
```

<210> SEQ ID NO 392
<211> LENGTH: 72
<212> TYPE: RNA
<213> ORGANISM: Homo sapiens

<400> SEQUENCE: 392

```
uguggacug caaaugggag cucagcaccu gccugccacc cacgcagacc agccccugcu         60 cguucccac ag                                                            72
```

<210> SEQ ID NO 393
<211> LENGTH: 75
<212> TYPE: RNA
<213> ORGANISM: Homo sapiens

<400> SEQUENCE: 393

```
aagcaagacu gaggggccuc agaccgagcu uuuggaaaau agaaaagucu cgcucucugc        60
cccucagccu aacuu                                                        75
```

<210> SEQ ID NO 394
<211> LENGTH: 67
<212> TYPE: RNA
<213> ORGANISM: Homo sapiens

<400> SEQUENCE: 394

```
aaaucucucu ccauaucuuu ccugcagccc ccagguggg gggaagaaaa ggugggaau         60 uagauuc                                                                 67
```

<210> SEQ ID NO 395
<211> LENGTH: 67
<212> TYPE: RNA
<213> ORGANISM: Homo sapiens

<400> SEQUENCE: 395

```
ccagacccu ggggcugggc aggcggaaag aggucugaac ugccucugcc uccuuggucu        60
ccggcag                                                                 67
```

<210> SEQ ID NO 396
<211> LENGTH: 97
<212> TYPE: RNA
<213> ORGANISM: Homo sapiens

```
<400> SEQUENCE: 396
aucugaguug ggagggucec ucuccaaaug ugucuugggg uggggauca agacacauuu    60 ggagagggaa ccucccaacu cggccucugc caucauu                           97

<210> SEQ ID NO 397
<211> LENGTH: 87
<212> TYPE: RNA
<213> ORGANISM: Homo sapiens

<400> SEQUENCE: 397
guguggccgg caggcggguq ggcggggqcg gccgguggga accccgcccc gccccgcgcc    60
cgcacucacc cgcccgucuc cccacag                                      87

<210> SEQ ID NO 398
<211> LENGTH: 82
<212> TYPE: RNA
<213> ORGANISM: Homo sapiens

<400> SEQUENCE: 398
ugagcuguug gauucggggc cguagcacug ucugagaggu uuacauuucu cacagugaac    60
cggucucuuu uucagcugcu uc                                           82

<210> SEQ ID NO 399
<211> LENGTH: 115
<212> TYPE: RNA
<213> ORGANISM: Homo sapiens

<400> SEQUENCE: 399
ucugaggaga ccugggcugu cagaggccag ggaaggggac gagqguuggg gaacaggugg    60 uuagcacuuc auccucgucu ccucccagg uuagaagggc ccccucucu gaagg        115

<210> SEQ ID NO 400
<211> LENGTH: 84
<212> TYPE: RNA
<213> ORGANISM: Homo sapiens

<400> SEQUENCE: 400
gaggcugggc ggggcgcggc cggaucgguc gagagcgucc uggcugauga cggucucccg    60
ugcccacgcc ccaaacgcag ucuc                                         84

<210> SEQ ID NO 401
<211> LENGTH: 69
<212> TYPE: RNA
<213> ORGANISM: Homo sapiens

<400> SEQUENCE: 401
cuuucggcca gcgggacggc auccgaggug ggcuaggcuc gggcccgugg cgggugcggg    60
ggugggagg                                                          69

<210> SEQ ID NO 402
<211> LENGTH: 75
<212> TYPE: RNA
<213> ORGANISM: Homo sapiens

<400> SEQUENCE: 402
ucaucccugg gugggauuu guugcauuac uuguguucua uauaaaguau ugcacuuguc    60
ccggccugug gaaga                                                   75
```

<210> SEQ ID NO 403
<211> LENGTH: 62
<212> TYPE: RNA
<213> ORGANISM: Homo sapiens

<400> SEQUENCE: 403
cuuccuggug ggugggagg agaagugccg uccucaugag ccccucucug ucccacccau    60
ag                                                                  62

<210> SEQ ID NO 404
<211> LENGTH: 70
<212> TYPE: RNA
<213> ORGANISM: Homo sapiens

<400> SEQUENCE: 404
gguuucuccu ugaggagaca uggugggggc cggucaggca gcccaugcca uguguccuca    60
uggagaggcc                                                          70

<210> SEQ ID NO 405
<211> LENGTH: 113
<212> TYPE: RNA
<213> ORGANISM: Homo sapiens

<400> SEQUENCE: 405
agcaugacag aggagaggug gagguaggcg agaguaauau aauuucucca ggagaacauc    60
ugagagggga aguugcuuuc cugcccuggc ccuuucaccc uccugaguuu ggg          113

<210> SEQ ID NO 406
<211> LENGTH: 96
<212> TYPE: RNA
<213> ORGANISM: Homo sapiens

<400> SEQUENCE: 406
cgggccccgg gcgggcggga gggacgggac gcggugcagu guuguuuuuu ccccgccaa    60 uauugcacuc gucccggccu ccggccccccc cggccc                            96

<210> SEQ ID NO 407
<211> LENGTH: 70
<212> TYPE: RNA
<213> ORGANISM: Homo sapiens

<400> SEQUENCE: 407
ugugcacuug ggcaggaggg acccuguaug ucuccccgca gcaccgucau cguguccuc    60 uuguccacag                                                          70

<210> SEQ ID NO 408
<211> LENGTH: 68
<212> TYPE: RNA
<213> ORGANISM: Homo sapiens

<400> SEQUENCE: 408
gcauccugua cugagcugcc ccgaggcccu ucaugcugcc cagcucgggg cagcucagua    60
caggauac                                                            68

<210> SEQ ID NO 409
<211> LENGTH: 64
<212> TYPE: RNA
<213> ORGANISM: Homo sapiens

<400> SEQUENCE: 409

```
uccuguacug agcugccccg agcugggcag caugaagggc cucgggggcag cucaguacag    60 gaug                                                                 64

<210> SEQ ID NO 410
<211> LENGTH: 64
<212> TYPE: RNA
<213> ORGANISM: Homo sapiens

<400> SEQUENCE: 410
ugcucuguag gcaugaggca gggcccaggu uccaugugau gcugaagcuc ugacauuccu    60
gcag                                                                 64

<210> SEQ ID NO 411
<211> LENGTH: 65
<212> TYPE: RNA
<213> ORGANISM: Homo sapiens

<400> SEQUENCE: 411
agcccugggg guggucucua gccaaggcuc uggggucuca cccuuggcug gucucugcuc    60
cgcag                                                                65

<210> SEQ ID NO 412
<211> LENGTH: 80
<212> TYPE: RNA
<213> ORGANISM: Homo sapiens

<400> SEQUENCE: 412
gagaggccaa gaccuuggga auggggguaa gggccuucug agcccagguc cgaacucucc    60
auuccucugc agagcgcucu                                                80

<210> SEQ ID NO 413
<211> LENGTH: 98
<212> TYPE: RNA
<213> ORGANISM: Homo sapiens

<400> SEQUENCE: 413
agaaugggca aaugaacagu aaauuuggag gccuggggcc cucccugcug cuggagaagu    60
guuugcacgg gugggccuug ucuuugaaag gaggugga                            98

<210> SEQ ID NO 414
<211> LENGTH: 59
<212> TYPE: RNA
<213> ORGANISM: Homo sapiens

<400> SEQUENCE: 414
guccaggcag gagccggacu ggaccucagg gaagaggcug acccggcccc ucuugcggc     59

<210> SEQ ID NO 415
<211> LENGTH: 87
<212> TYPE: RNA
<213> ORGANISM: Homo sapiens

<400> SEQUENCE: 415
cccaggcgcc cgcucccgac ccacgccgcg ccgccgdgguc ccuccucccc ggagaggcug   60
ggcucgggac gcgcggcuca gcucggg                                        87

<210> SEQ ID NO 416
<211> LENGTH: 67
<212> TYPE: RNA
```

```
<213> ORGANISM: Homo sapiens

<400> SEQUENCE: 416
gcgcccuccc ucucuccccg gugugcaaau gugugugugc gguguuaugc cggacaagag    60
ggaggug                                                              67

<210> SEQ ID NO 417
<211> LENGTH: 80
<212> TYPE: RNA
<213> ORGANISM: Homo sapiens

<400> SEQUENCE: 417
ugagaggccg caccuugccu ugcugcccgg gccgugcacc cgugggcccc agggcgacgc    60 ggcggggggcg gcccuagcga                                                80

<210> SEQ ID NO 418
<211> LENGTH: 80
<212> TYPE: RNA
<213> ORGANISM: Homo sapiens

<400> SEQUENCE: 418
accugaggag ccagcccucc ucccgcaccc aaacuuggag cacuugaccu uuggcuguug    60 gaggggggcag gcucgcgggu                                                80

<210> SEQ ID NO 419
<211> LENGTH: 96
<212> TYPE: RNA
<213> ORGANISM: Homo sapiens

<400> SEQUENCE: 419
cgggccccgg gcgggcggga gggacgggac gcggugcagu guuguuuuuu ccccccgccaa    60 uauugcacuc guccggccu ccggcccccc cggccc                                96

<210> SEQ ID NO 420
<211> LENGTH: 18
<212> TYPE: RNA
<213> ORGANISM: Homo sapiens

<400> SEQUENCE: 420
ggugggcuuc ccggaggg                                                  18

<210> SEQ ID NO 421
<211> LENGTH: 15
<212> TYPE: RNA
<213> ORGANISM: Homo sapiens

<400> SEQUENCE: 421
ggugggcuuc ccgga                                                     15

<210> SEQ ID NO 422
<211> LENGTH: 23
<212> TYPE: RNA
<213> ORGANISM: Homo sapiens

<400> SEQUENCE: 422
gccccggcgc gggcggguuc ugg                                            23

<210> SEQ ID NO 423
<211> LENGTH: 16
<212> TYPE: RNA
<213> ORGANISM: Homo sapiens
```

-continued

<400> SEQUENCE: 423
ggagccccgg cgcggg                                                     16

<210> SEQ ID NO 424
<211> LENGTH: 16
<212> TYPE: RNA
<213> ORGANISM: Homo sapiens

<400> SEQUENCE: 424 ggcgguggggc ggcggg                                                    16

<210> SEQ ID NO 425
<211> LENGTH: 15
<212> TYPE: RNA
<213> ORGANISM: Homo sapiens

<400> SEQUENCE: 425
ggccucucgg gaacu                                                      15

<210> SEQ ID NO 426
<211> LENGTH: 18
<212> TYPE: RNA
<213> ORGANISM: Homo sapiens

<400> SEQUENCE: 426 ucuaggguggg gagacuga                                                  18

<210> SEQ ID NO 427
<211> LENGTH: 16
<212> TYPE: RNA
<213> ORGANISM: Homo sapiens

<400> SEQUENCE: 427
guggggagac ugacgg                                                     16

<210> SEQ ID NO 428
<211> LENGTH: 22
<212> TYPE: RNA
<213> ORGANISM: Homo sapiens

<400> SEQUENCE: 428
ugugggacug caaaugggag cu                                              22

<210> SEQ ID NO 429
<211> LENGTH: 22
<212> TYPE: RNA
<213> ORGANISM: Homo sapiens

<400> SEQUENCE: 429
ugugggacug caaaugggag cu                                              22

<210> SEQ ID NO 430
<211> LENGTH: 16
<212> TYPE: RNA
<213> ORGANISM: Homo sapiens

<400> SEQUENCE: 430 uggggggaa gaaaag                                                      16

<210> SEQ ID NO 431
<211> LENGTH: 16
<212> TYPE: RNA

```
<213> ORGANISM: Homo sapiens

<400> SEQUENCE: 431
ugggggggaa gaaaag                                                         16

<210> SEQ ID NO 432
<211> LENGTH: 24
<212> TYPE: RNA
<213> ORGANISM: Homo sapiens

<400> SEQUENCE: 432
agacacauuu ggagagggaa ccuc                                                24

<210> SEQ ID NO 433
<211> LENGTH: 16
<212> TYPE: RNA
<213> ORGANISM: Homo sapiens

<400> SEQUENCE: 433
agacacauuu ggagag                                                         16

<210> SEQ ID NO 434
<211> LENGTH: 23
<212> TYPE: RNA
<213> ORGANISM: Homo sapiens

<400> SEQUENCE: 434
cggggccgua gcacugucug aga                                                 23

<210> SEQ ID NO 435
<211> LENGTH: 20
<212> TYPE: RNA
<213> ORGANISM: Homo sapiens

<400> SEQUENCE: 435
cggggccgua gcacugucug                                                     20

<210> SEQ ID NO 436
<211> LENGTH: 25
<212> TYPE: RNA
<213> ORGANISM: Homo sapiens

<400> SEQUENCE: 436
gggacgaggg uugggaaca ggugg                                                25

<210> SEQ ID NO 437
<211> LENGTH: 15
<212> TYPE: RNA
<213> ORGANISM: Homo sapiens

<400> SEQUENCE: 437
uggggaacag guggu                                                          15

<210> SEQ ID NO 438
<211> LENGTH: 24
<212> TYPE: RNA
<213> ORGANISM: Homo sapiens

<400> SEQUENCE: 438
gaucggucga gagcguccug gcug                                                24

<210> SEQ ID NO 439
<211> LENGTH: 15
```

```
<212> TYPE: RNA
<213> ORGANISM: Homo sapiens

<400> SEQUENCE: 439
gcugggcggg gcgcg                                                     15

<210> SEQ ID NO 440
<211> LENGTH: 19
<212> TYPE: RNA
<213> ORGANISM: Homo sapiens

<400> SEQUENCE: 440 uggcggguge gggggaggg                                                 19

<210> SEQ ID NO 441
<211> LENGTH: 15
<212> TYPE: RNA
<213> ORGANISM: Homo sapiens

<400> SEQUENCE: 441 uggcggguge ggggg                                                     15

<210> SEQ ID NO 442
<211> LENGTH: 25
<212> TYPE: RNA
<213> ORGANISM: Homo sapiens

<400> SEQUENCE: 442
ggguggggau uuguugcauu acuug                                          25

<210> SEQ ID NO 443
<211> LENGTH: 20
<212> TYPE: RNA
<213> ORGANISM: Homo sapiens

<400> SEQUENCE: 443
ggguggggau uuguugcauu                                                20

<210> SEQ ID NO 444
<211> LENGTH: 21
<212> TYPE: RNA
<213> ORGANISM: Homo sapiens

<400> SEQUENCE: 444
uugaggagac auggugggggg c                                             21

<210> SEQ ID NO 445
<211> LENGTH: 15
<212> TYPE: RNA
<213> ORGANISM: Homo sapiens

<400> SEQUENCE: 445
uugaggagac auggu                                                     15

<210> SEQ ID NO 446
<211> LENGTH: 26
<212> TYPE: RNA
<213> ORGANISM: Homo sapiens

<400> SEQUENCE: 446
agggacggga cgcggugcag uguugu                                         26

<210> SEQ ID NO 447
```

```
<211> LENGTH: 15
<212> TYPE: RNA
<213> ORGANISM: Homo sapiens

<400> SEQUENCE: 447
ggcgggcggg aggga                                                    15

<210> SEQ ID NO 448
<211> LENGTH: 23
<212> TYPE: RNA
<213> ORGANISM: Homo sapiens

<400> SEQUENCE: 448
cggggcagcu caguacagga uac                                           23

<210> SEQ ID NO 449
<211> LENGTH: 15
<212> TYPE: RNA
<213> ORGANISM: Homo sapiens

<400> SEQUENCE: 449
agcucaguac aggau                                                    15

<210> SEQ ID NO 450
<211> LENGTH: 21
<212> TYPE: RNA
<213> ORGANISM: Homo sapiens

<400> SEQUENCE: 450
ugggaauggg gguaagggcc u                                             21

<210> SEQ ID NO 451
<211> LENGTH: 15
<212> TYPE: RNA
<213> ORGANISM: Homo sapiens

<400> SEQUENCE: 451
cuucugagcc caggu                                                    15

<210> SEQ ID NO 452
<211> LENGTH: 24
<212> TYPE: RNA
<213> ORGANISM: Homo sapiens

<400> SEQUENCE: 452
caggcaggag ccggacugga ccuc                                          24

<210> SEQ ID NO 453
<211> LENGTH: 21
<212> TYPE: RNA
<213> ORGANISM: Homo sapiens

<400> SEQUENCE: 453
uccaggcagg agccggacug g                                             21

<210> SEQ ID NO 454
<211> LENGTH: 22
<212> TYPE: RNA
<213> ORGANISM: Homo sapiens

<400> SEQUENCE: 454
cugggcucgg gacgcgcggc uc                                            22
```

```
<210> SEQ ID NO 455
<211> LENGTH: 19
<212> TYPE: RNA
<213> ORGANISM: Homo sapiens

<400> SEQUENCE: 455
cugggcucgg gacgcgcgg                                              19

<210> SEQ ID NO 456
<211> LENGTH: 20
<212> TYPE: RNA
<213> ORGANISM: Homo sapiens

<400> SEQUENCE: 456
cuccccggug ugcaaaugug                                             20

<210> SEQ ID NO 457
<211> LENGTH: 15
<212> TYPE: RNA
<213> ORGANISM: Homo sapiens

<400> SEQUENCE: 457
gugugcggug uuaug                                                  15

<210> SEQ ID NO 458
<211> LENGTH: 20
<212> TYPE: RNA
<213> ORGANISM: Homo sapiens

<400> SEQUENCE: 458
ccccagggcg acgcggcggg                                             20

<210> SEQ ID NO 459
<211> LENGTH: 15
<212> TYPE: RNA
<213> ORGANISM: Homo sapiens

<400> SEQUENCE: 459
cgcggcgggg gcggc                                                  15

<210> SEQ ID NO 460
<211> LENGTH: 20
<212> TYPE: RNA
<213> ORGANISM: Homo sapiens

<400> SEQUENCE: 460
uggcuguugg aggggcagg                                              20

<210> SEQ ID NO 461
<211> LENGTH: 15
<212> TYPE: RNA
<213> ORGANISM: Homo sapiens

<400> SEQUENCE: 461 ggaggggca ggcuc                                                   15

<210> SEQ ID NO 462
<211> LENGTH: 24
<212> TYPE: RNA
<213> ORGANISM: Homo sapiens

<400> SEQUENCE: 462
aauauugcac ucgucccggc cucc                                        24
```

```
<210> SEQ ID NO 463
<211> LENGTH: 15
<212> TYPE: RNA
<213> ORGANISM: Homo sapiens

<400> SEQUENCE: 463
uauugcacuc guccc                                                    15

<210> SEQ ID NO 464
<211> LENGTH: 21
<212> TYPE: RNA
<213> ORGANISM: Homo sapiens

<400> SEQUENCE: 464
cccggagcca ggaugcagcu c                                             21

<210> SEQ ID NO 465
<211> LENGTH: 22
<212> TYPE: RNA
<213> ORGANISM: Homo sapiens

<400> SEQUENCE: 465
gguggcccgg ccgugccuga gg                                            22

<210> SEQ ID NO 466
<211> LENGTH: 17
<212> TYPE: RNA
<213> ORGANISM: Homo sapiens

<400> SEQUENCE: 466
ccccgccacc gccuugg                                                  17

<210> SEQ ID NO 467
<211> LENGTH: 24
<212> TYPE: RNA
<213> ORGANISM: Homo sapiens

<400> SEQUENCE: 467
ugggcgaggg gugggcucuc agag                                          24

<210> SEQ ID NO 468
<211> LENGTH: 17
<212> TYPE: RNA
<213> ORGANISM: Homo sapiens

<400> SEQUENCE: 468
gggagaaggg ucggggc                                                  17

<210> SEQ ID NO 469
<211> LENGTH: 22
<212> TYPE: RNA
<213> ORGANISM: Homo sapiens

<400> SEQUENCE: 469
gggaccaucc ugccugcugu gg                                            22

<210> SEQ ID NO 470
<211> LENGTH: 23
<212> TYPE: RNA
<213> ORGANISM: Homo sapiens

<400> SEQUENCE: 470
ucaauaggaa agagguggga ccu                                           23
```

```
<210> SEQ ID NO 471
<211> LENGTH: 22
<212> TYPE: RNA
<213> ORGANISM: Homo sapiens

<400> SEQUENCE: 471
uagggauggg aggccaggau ga                                              22

<210> SEQ ID NO 472
<211> LENGTH: 23
<212> TYPE: RNA
<213> ORGANISM: Homo sapiens

<400> SEQUENCE: 472
ucgaggacug guggaagggc cuu                                             23

<210> SEQ ID NO 473
<211> LENGTH: 22
<212> TYPE: RNA
<213> ORGANISM: Homo sapiens

<400> SEQUENCE: 473
cuccuggggc ccgcacucuc gc                                              22

<210> SEQ ID NO 474
<211> LENGTH: 85
<212> TYPE: RNA
<213> ORGANISM: Homo sapiens

<400> SEQUENCE: 474
uccuccccgg agccaggaug cagcucaagc cacagcaggg uguuuagcgc ucuucagugg     60
cuccagauug uggcgcuggu gcagg                                           85

<210> SEQ ID NO 475
<211> LENGTH: 115
<212> TYPE: RNA
<213> ORGANISM: Homo sapiens

<400> SEQUENCE: 475
ggugccgagg gccguccggc auccuaggcg ggucgcugcg guaccucccu ccugucugug     60 gcgguggau cccguggccg uguuuuccug guggcccggc cgugccgag guuuc            115

<210> SEQ ID NO 476
<211> LENGTH: 91
<212> TYPE: RNA
<213> ORGANISM: Homo sapiens

<400> SEQUENCE: 476
acgccccccg ccccgccacc gccuuggagg cugaccucuu acuuucgguc ggucuucuuc     60
ccugggcuug guuuggggc gggggagugu c                                     91

<210> SEQ ID NO 477
<211> LENGTH: 64
<212> TYPE: RNA
<213> ORGANISM: Homo sapiens

<400> SEQUENCE: 477
ucugggcgag ggugggcuc ucagagggggc uggcaguacu gcucugaggc cugccucucc     60
ccag                                                                  64
```

```
<210> SEQ ID NO 478
<211> LENGTH: 86
<212> TYPE: RNA
<213> ORGANISM: Homo sapiens

<400> SEQUENCE: 478
agggagaagg gucggggcag ggagggcagg gcaggcucug gggugggggg ucugugaguc       60
agccacggcu cugcccacgu cuccccc                                          86

<210> SEQ ID NO 479
<211> LENGTH: 83
<212> TYPE: RNA
<213> ORGANISM: Homo sapiens

<400> SEQUENCE: 479
acggcaucuu ugcacucagc aggcaggcug gugcagcccg guggggga ccauccugcc        60 ugcugugggg uaaggacggc ugu                                              83

<210> SEQ ID NO 480
<211> LENGTH: 98
<212> TYPE: RNA
<213> ORGANISM: Homo sapiens

<400> SEQUENCE: 480
cuuggucaau aggaaagagg ugggaccucc uggcuuuucc ucugcagcau ggcucggacc       60
uagugcaaug uuuaagcucc ccucucuuuc cuguucag                              98

<210> SEQ ID NO 481
<211> LENGTH: 69
<212> TYPE: RNA
<213> ORGANISM: Homo sapiens

<400> SEQUENCE: 481
gggcuuaggg augggaggcc aggaugaaga uuaauccccua auccccaaca cuggccuugc      60
uaucccccag                                                             69

<210> SEQ ID NO 482
<211> LENGTH: 63
<212> TYPE: RNA
<213> ORGANISM: Homo sapiens

<400> SEQUENCE: 482
gagucgagga cugguggaag ggccuuuccc cucagaccaa ggcccuggcc ccagcuucuu       60
cuc                                                                    63

<210> SEQ ID NO 483
<211> LENGTH: 84
<212> TYPE: RNA
<213> ORGANISM: Homo sapiens

<400> SEQUENCE: 483
gcuggcgucg gugcugggga gcggccccg gguggccuc ugcucuggcc ccuccugggg        60
cccgcacucu cgcucugggc ccgc                                             84

<210> SEQ ID NO 484
<211> LENGTH: 23
<212> TYPE: RNA
<213> ORGANISM: Homo sapiens

<400> SEQUENCE: 484
```
ggcccggccg ugccugaggu uuc                                              23

<210> SEQ ID NO 485
<211> LENGTH: 15
<212> TYPE: RNA
<213> ORGANISM: Homo sapiens

<400> SEQUENCE: 485 uguuuccug guggc                                                        15

<210> SEQ ID NO 486
<211> LENGTH: 23
<212> TYPE: RNA
<213> ORGANISM: Homo sapiens

<400> SEQUENCE: 486
agggucgggg cagggagggc agg                                              23

<210> SEQ ID NO 487
<211> LENGTH: 15
<212> TYPE: RNA
<213> ORGANISM: Homo sapiens

<400> SEQUENCE: 487
ggagaagggu cgggg                                                       15

<210> SEQ ID NO 488
<211> LENGTH: 24
<212> TYPE: RNA
<213> ORGANISM: Homo sapiens

<400> SEQUENCE: 488
ucgaggacug guggaagggc cuuu                                             24

<210> SEQ ID NO 489
<211> LENGTH: 17
<212> TYPE: RNA
<213> ORGANISM: Homo sapiens

<400> SEQUENCE: 489
acugguggaa gggccuu                                                     17

<210> SEQ ID NO 490
<211> LENGTH: 23
<212> TYPE: RNA
<213> ORGANISM: Homo sapiens

<400> SEQUENCE: 490
cuccuggggc ccgcacucuc gcu                                              23

<210> SEQ ID NO 491
<211> LENGTH: 18
<212> TYPE: RNA
<213> ORGANISM: Homo sapiens

<400> SEQUENCE: 491
cuccuggggc ccgcacuc                                                    18

<210> SEQ ID NO 492
<211> LENGTH: 25
<212> TYPE: RNA
<213> ORGANISM: Homo sapiens

```
<400> SEQUENCE: 492
ucggggcaug gggagggag gcugg                                           25

<210> SEQ ID NO 493
<211> LENGTH: 23
<212> TYPE: RNA
<213> ORGANISM: Homo sapiens

<400> SEQUENCE: 493 cagggcugg gguucaggu ucu                                              23

<210> SEQ ID NO 494
<211> LENGTH: 20
<212> TYPE: RNA
<213> ORGANISM: Homo sapiens

<400> SEQUENCE: 494
guggguuggg gcgggcucug                                                20

<210> SEQ ID NO 495
<211> LENGTH: 69
<212> TYPE: RNA
<213> ORGANISM: Homo sapiens

<400> SEQUENCE: 495
gaaccucggg gcauggggga gggaggcugg acaggagagg gcucacccag gcccuguccu    60
cugccccag                                                            69

<210> SEQ ID NO 496
<211> LENGTH: 56
<212> TYPE: RNA
<213> ORGANISM: Homo sapiens

<400> SEQUENCE: 496
guaggcaggg gcuggguuu cagguucuca gucagaaccu uggccccucu ccccag         56

<210> SEQ ID NO 497
<211> LENGTH: 102
<212> TYPE: RNA
<213> ORGANISM: Homo sapiens

<400> SEQUENCE: 497
gcuuaucgag gaaaagaucg agguggguug gggcgggcuc uggggauuug gucucacagc    60
ccggauccca gcccacuuac cuugguuacu cuccuuccuu cu                       102

<210> SEQ ID NO 498
<211> LENGTH: 19
<212> TYPE: RNA
<213> ORGANISM: Homo sapiens

<400> SEQUENCE: 498
guggguuggg gcgggcucu                                                 19

<210> SEQ ID NO 499
<211> LENGTH: 19
<212> TYPE: RNA
<213> ORGANISM: Homo sapiens

<400> SEQUENCE: 499
guggguuggg gcgggcucu                                                 19
```